United States Patent
Wang et al.

(10) Patent No.: US 11,168,055 B2
(45) Date of Patent: Nov. 9, 2021

(54) ENDOCYCLIC THIAMIDINOAMIDE-ARYLAMIDE COMPOUND AND USE THEREOF FOR TREATING HEPATITIS B

(71) Applicant: SHANGHAI LONGWOOD BIOPHARMACEUTICALS CO., LTD., Shanghai (CN)

(72) Inventors: Zhe Wang, Shanghai (CN); Xiaoguang Wang, Shanghai (CN); Sai Yang, Shanghai (CN); Zhihong Zeng, Shanghai (CN)

(73) Assignee: SHANGHAI LONGWOOD BIOPHARMACEUTICALS CO., LTD., Shanghai (CN)

( * ) Notice: Subject to any disclaimer, the term of this patent is extended or adjusted under 35 U.S.C. 154(b) by 0 days.

(21) Appl. No.: 16/630,729

(22) PCT Filed: Jul. 13, 2018

(86) PCT No.: PCT/CN2018/095614
§ 371 (c)(1),
(2) Date: Jan. 13, 2020

(87) PCT Pub. No.: WO2019/011323
PCT Pub. Date: Jan. 17, 2019

(65) Prior Publication Data
US 2020/0399216 A1 Dec. 24, 2020

(30) Foreign Application Priority Data

Jul. 14, 2017 (CN) .......................... 201710576102.1

(51) Int. Cl.
*C07D 207/36* (2006.01)
*C07D 513/04* (2006.01)
*A61P 31/20* (2006.01)

(52) U.S. Cl.
CPC ............ *C07D 207/36* (2013.01); *A61P 31/20* (2018.01); *C07D 513/04* (2013.01)

(58) Field of Classification Search
CPC ...... C07D 207/36; C07D 513/04; A61P 31/20
See application file for complete search history.

(56) References Cited

U.S. PATENT DOCUMENTS 9,399,619 B2 * 7/2016 Guo .................... C07D 295/26

FOREIGN PATENT DOCUMENTS

| CN | 108250121 A | 7/2018 |
| CN | 108250122 A | 7/2018 |
| CN | 108264520 A | 7/2018 |
| WO | 2013/006394 A1 | 1/2013 |

OTHER PUBLICATIONS

English Translation of the International Search Report corresponding to PCT/CN2018/095614 dated Oct. 9, 2018; 2 pages.
Weber, O. et al., "Inhibition of human hepatitis B virus (HBV) by a novel non-nucleosidic compound in a transgenic mouse model," *Antiviral Research* (Dec. 31, 2002); 54:69-78.

* cited by examiner

*Primary Examiner* — Timothy R Rozof
(74) *Attorney, Agent, or Firm* — Mintz Levin Cohn Ferris Glovsky and Popeo PC

(57) ABSTRACT

Disclosed are an endocyclic thiamidinoamide-arylamide compound and a pharmaceutical composition comprising the compound described above, and the use of the compound or pharmaceutical composition in the treatment of hepatitis B. In particular, disclosed is a compound that can be used as an HBV replication inhibitor and has the structure as shown in chemical formula (L), or a stereoisomer or tautomer thereof, or a pharmaceutically acceptable salt, hydrate or solvate thereof.

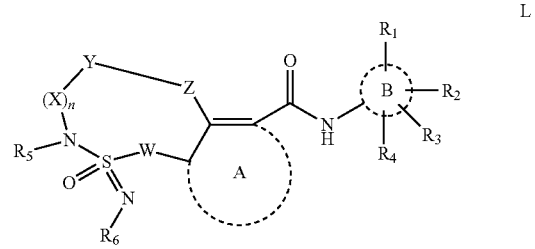

17 Claims, No Drawings

ENDOCYCLIC THIAMIDINOAMIDE-ARYLAMIDE COMPOUND AND USE THEREOF FOR TREATING HEPATITIS B

FIELD OF INVENTION

The present invention belongs to the field of medicine, and in particular, the present invention relates to a class of cyclic sulfonimidamide-arylamide compounds and the use as a medicine for treating hepatitis B thereof.

BACKGROUND OF THE INVENTION

Hepatitis B virus (HBV) is an enveloped virus of hepatotropic virus DNA family (Hepadnaviridae) with partially double-stranded DNA (dsDNA). The genome thereof contains 4 overlapped reading frames: precore/core gene, polymerase gene, UM and S genes (which encode three envelope proteins), and X gene. In the early stage of infection, the partially double-stranded DNA genome (open-loop DNA, rcDNA) in the host cell nucleus is transformed into covalently closed circular DNA (cccDNA) and transcribed into virus mRNA. Once encapsulated, the pre-genome RNA (pgRNA) (which encodes the core protein and Pol) serves as a template for reverse transcription, which regenerates this partial dsDNA genome (rcDNA) in the nucleocapsid.

HBV causes epidemics in certain areas of Asia and Africa, and is endemic in China. HBV has infected about 2 billion people worldwide, of which about 350 million people have developed into chronic infectious diseases. The virus causes hepatitis B disease and chronic infectious diseases are associated with a highly increased risk of development of cirrhosis and liver cancer.

The spread of hepatitis B virus is caused by exposure to infectious blood or body fluid, and the virus is detected in the saliva, tears, and urine of chronic carriers with high DNA titers in the serum.

Although there is currently an effective and well tolerated vaccine, the option of direct treatment is currently limited to interferon and the following antiviral drugs: tenofovir, lamivudine, adefovir, entecavir and telbivudine.

Additionally, heteroaryldihydropyrimidines (HAPs) are identified as a class of HBV inhibitors in tissue cultivation and animal models (Weber et al., Antiviral Res. 54: 69-78).

WO2013/006394 (published on Jan. 10, 2013) and WO 2013/096744 (published on Jun. 27, 2013) also disclosed sulfamoyl-arylamides having anti-HBV activity.

However, problems encountered in these direct HBV antiviral drugs are toxicity, mutagenicity, lack of selectivity, poor efficacy, poor bioavailability, and difficulty in synthesis.

Therefore, in order to overcome the above defects, it is necessary to develop HBV inhibitors with advantages such as high potency and lower toxicity.

SUMMARY OF INVENTION

An object of the present invention is to provide a class of structurally novel compounds useful as HBV inhibitors.

In the first aspect of the invention, a compound of the formula L, or a stereoisomer thereof, or a tautomer thereof, or a pharmaceutically acceptable salt, hydrate or solvate thereof is provided,

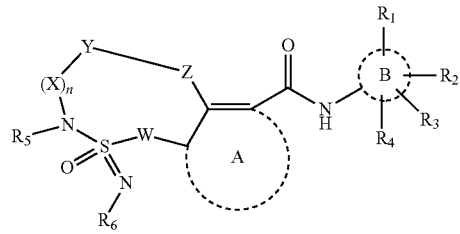

wherein n is 1, 2, 3, 4, 5, 6, 7, 8, 9, or 10;

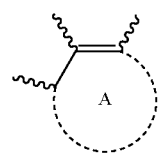

is a substituted or unsubstituted five or six membered ring, wherein the five or six membered ring optionally contains one or more heteroatoms selected from the group consisting of O, S, N and P; the substituted means that the hydrogen atoms on the group are substituted by one or more substituents selected from the group consisting of C1-C3 alkyl (especially methyl), C3-C4 cycloalkyl, cyano, or halogen;

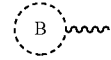

is a substituted or unsubstituted five- or six-membered aromatic ring, or a substituted or unsubstituted five- or six-membered heteroaromatic ring;

X is —CR$^a$R$^b$—;

Y is substituted or unsubstituted C1-C7 alkylene, or substituted or unsubstituted C2-C7 alkenylene, wherein the substituent is selected from the group consisting of C1-C4 alkyl, hydroxyl;

Z is selected from the group consisting of O, S, N, or P, or Z is a C—C single bond (i.e., Z is none);

W is NRc or none;

R$^1$, R$^2$, R$^3$ and R$^4$ are each independently selected from the group consisting of H, halogen, cyano, substituted or unsubstituted C3-C4 cycloalkyl, substituted or unsubstituted C1-C4 alkyl, substituted or unsubstituted C1-C4 alkoxy; wherein the substituted means that hydrogen atoms on the group are substituted by one or more substituents selected from the group consisting of halogen, C1-C4 alkyl (such as difluoromethyl, difluoroethyl, monofluoromethyl, trifluoromethyl, trifluoromethoxy);

R$^5$, R$^6$ are each independently selected from the group consisting of H, halogen, —CN, hydroxyl, amino, carboxyl, —(C=O)-substituted or unsubstituted $C_1$-$C_8$ alkyl, substituted or unsubstituted $C_1$-$C_8$ alkyl, substituted or unsubstituted $C_2$-$C_6$ alkenyl, substituted or unsubstituted $C_2$-$C_6$ alkynyl, substituted or unsubstituted $C_1$-$C_8$ alkylamino, substituted or unsubstituted $C_1$-$C_8$ alkoxy, substituted or unsubstituted $C_3$-$C_{10}$ cycloalkyl, substituted or unsubstituted 3-10 membered heterocycloalkyl having 1-3 heteroatoms selected from the group consisting of N, S and O, substituted or unsubstituted $C_6$-$C_{10}$ aryl, and substituted or unsubstituted 5-10 membered heteroaryl having 1-3 heteroatoms selected from the group consisting of N, S and O;

$R^a$ and $R^b$ are each independently H, halogen, —CN, hydroxyl, amino, carboxyl, —(C═O)-substituted or unsubstituted $C_1$-$C_8$ alkyl, substituted or unsubstituted $C_1$-$C_8$ alkyl, substituted or unsubstituted $C_2$-$C_6$ alkenyl, substituted or unsubstituted $C_2$-$C_6$ alkynyl, substituted or unsubstituted $C_1$-$C_8$ alkylamino, substituted or unsubstituted $C_1$-$C_8$ alkoxy, substituted or unsubstituted $C_1$-$C_6$ alkoxy-alkyl, substituted or unsubstituted $C_3$-$C_{10}$ cycloalkyl, substituted or unsubstituted 3-10 membered heterocycloalkyl having 1-3 heteroatoms selected from the group consisting of N, S and O, substituted or unsubstituted $C_6$-$C_{10}$ aryl, and substituted or unsubstituted 5-10 membered heteroaryl having 1-3 heteroatoms selected from the group consisting of N, S and O;

Rc is H, halogen, —CN, hydroxyl, amino, carboxyl, —(C═O)-substituted or unsubstituted $C_1$-$C_8$ alkyl, substituted or unsubstituted $C_1$-$C_8$ alkyl, substituted or unsubstituted $C_2$-$C_6$ alkenyl, substituted or unsubstituted $C_2$-$C_6$ alkynyl, substituted or unsubstituted $C_1$-$C_8$ alkylamino, substituted or unsubstituted $C_1$-$C_8$ alkoxy, substituted or unsubstituted $C_3$-$C_{10}$ cycloalkyl, substituted or unsubstituted 3-10 membered heterocycloalkyl having 1-3 heteroatoms selected from the group consisting of N, S and O, substituted or unsubstituted $C_6$-$C_{10}$ aryl, and substituted or unsubstituted 5-10 membered heteroaryl having 1-3 heteroatoms selected from the group consisting of N, S and O;

unless otherwise specified, "substituted" means that the group substituted by one or more (such as 2, 3, 4, etc.) substituents selected from the group consisting of halogen, C1-C6 alkyl, halogenated C1-C6 alkyl, C1-C6 alkoxy, halogenated C1-C6 alkoxy, C3-C8 cycloalkyl, halogenated C3-C8 cycloalkyl, oxo, —CN, hydroxyl, amino, carboxyl, and the following groups unsubstituted or substituted by one or more substituents: C6-C10 aryl, halogenated C6-C10 aryl, 5-10 membered heteroaryl having 1-3 heteroatoms selected from the group consisting of N, S and O, halogenated 5-10 membered heteroaryl having 1-3 heteroatoms selected from N, S and O; and the substituent is selected from the group consisting of halogen and C1-C6 alkoxy.

In another preferred embodiment, the Y is selected from the group consisting of C1-C4 alkylene and substituted or unsubstituted C2-C4 alkenylene.

In another preferred embodiment, the Ra and Rb are each independently substituted or unsubstituted $C_1$-$C_8$ alkyl, substituted or unsubstituted $C_1$-$C_8$ alkoxy; wherein the substituent is selected from the group consisting of halogen, hydroxyl, and cyano.

In another preferred embodiment, the compound has a structure selected from the group consisting of the following formulas L-1, L-2, L-3, and L-4:

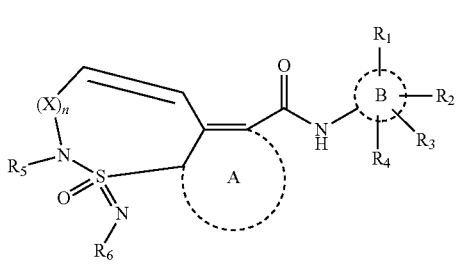

L-1

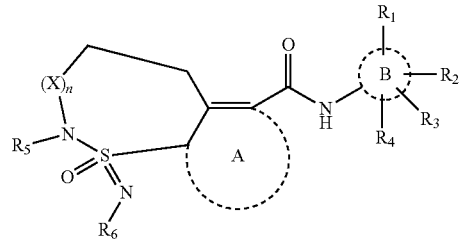

L-2

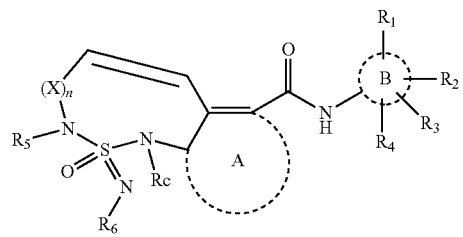

L-3

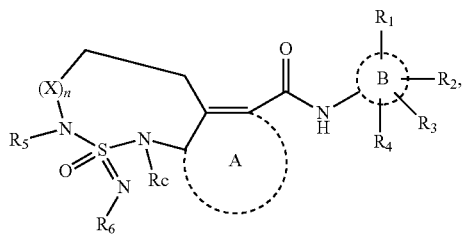

L-4

In each formula, n is 1, 2, 3, 4, 5, 6, 7, 8, 9, or 10;

the definitions of ring A, ring B, X, $R_1$, $R_2$, $R_3$, $R_4$, $R_5$ and $R_6$ are as described in the first aspect of the present invention.

In another preferred embodiment, the Ra and Rb are each independently substituted or unsubstituted $C_1$-$C_8$ alkyl, substituted or unsubstituted $C_1$-$C_8$ alkoxy; wherein the substituent is selected from the group consisting of halogen, hydroxyl, and cyano.

In another preferred embodiment, the formula I compound has the structure shown by the following formula II:

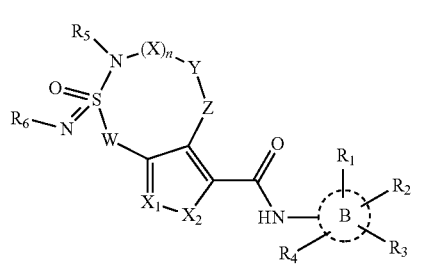

II wherein $X_1$ is —CR═ or —N═, $X_2$ is —NR—; and R is H or C1-C4 alkyl.

In another preferred embodiment, the $X_2$ is —$NCH_3$—.

In another preferred embodiment, the compound of formula I has the following structure:

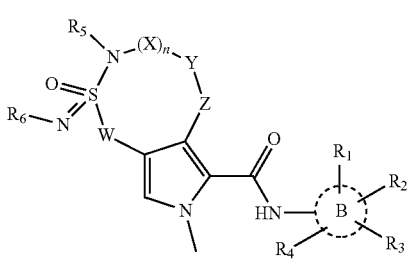

In another preferred embodiment, the compound of formula I has a structure represented by the following formula IV-1 or IV-2:

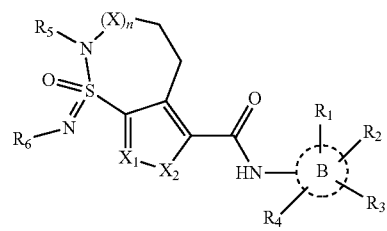

In another preferred embodiment, n is 1.

In another preferred embodiment, Ra is selected from the group consisting of substituted or unsubstituted $C_1$-$C_8$ alkyl, substituted or unsubstituted $C_1$-$C_8$ alkoxy, and substituted or unsubstituted C1-C6 alkoxy-alkyl;

Rb is H.

In another preferred embodiment, the Ra is selected from the group consisting of substituted or unsubstituted $C_1$-$C_8$ alkyl; wherein the substituted means that one or more hydrogen atoms on the group are substituted by substituent selected from the group consisting of C1-C4 alkoxy, hydroxyl, C6-C10 aryl unsubstituted or substituted with one or more substituents selected from the group consisting of halogen and C1-C6 alkoxy.

In another preferred embodiment, the B ring is a benzene ring or a pyridine ring.

In another preferred embodiment, the A ring is a pyrrole ring.

In another preferred embodiment, said

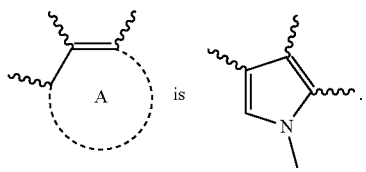

In another preferred embodiment, the $R_1$, $R_2$, $R_3$ and $R_4$ are each independently selected from the group consisting of H, halogen, and cyano.

In another preferred embodiment, the $R_5$ is selected from the group consisting of H, substituted or unsubstituted $C_1$-$C_8$ alkyl, and substituted or unsubstituted $C_3$-$C_{10}$ cycloalkyl.

In another preferred embodiment, the $R_6$ is selected from the group consisting of H, substituted or unsubstituted $C_1$-$C_8$ alkyl, and substituted or unsubstituted $C_3$-$C_{10}$ cycloalkyl.

In another preferred embodiment, the compound is the compound 10a1-60y2 as described in Table 1, wherein Peak 1 and Peak 2 refer to the order of the enantiomers' peaks in reversed-phase HPLC, wherein Peak 1 is the first peak in the enantiomer, and Peak 2 is the latter peak of the enantiomer.

In another preferred embodiment, in the above table, HPLC is reversed-phase HPLC, where peak 1 refers to a compound of greater polarity, and peak 2 refers to a compound of less polarity.

In the second aspect of the invention, a method for preparing compound of the formula I, or a stereoisomer thereof, or a tautomer thereof, or a pharmaceutically acceptable salt, hydrate or solvate thereof of the first aspect of the present invention is provided, which comprising the following steps:

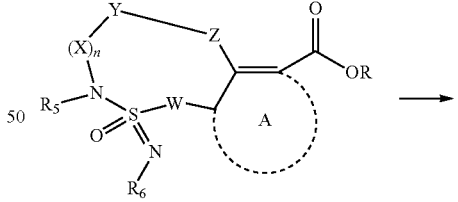

L1

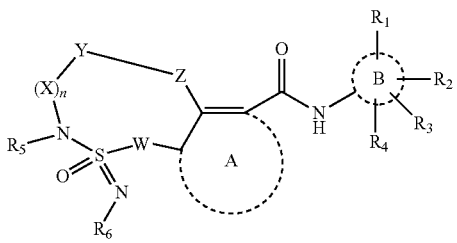

L in an inert solvent, reacting formula L1 compound with

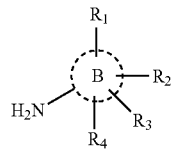

to provide compound L;

wherein, R is a leaving group, and the definitions of the remaining groups are as described in the first aspect of the present invention.

In another preferred embodiment, the compound of formula L is a compound of formula VII-1, and the method comprises the following steps:

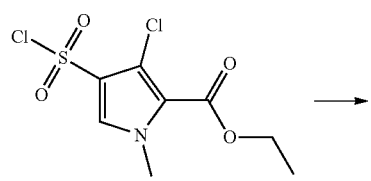

I-1

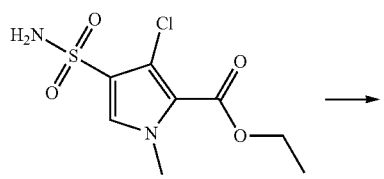

II-1

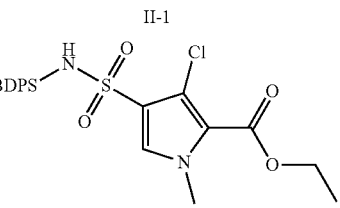

III-1

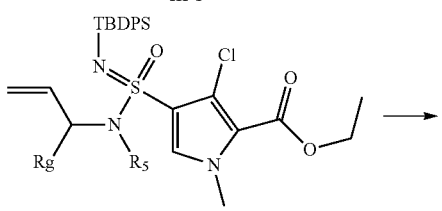

IV-1

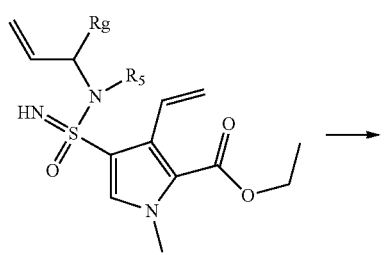

V-1

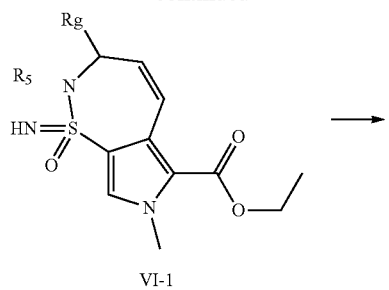

VI-1

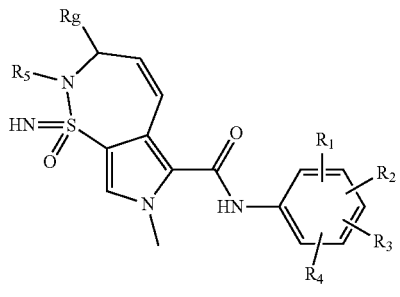

VII-1 wherein Rg is selected from the group consisting of H, halogen, —CN, hydroxyl, amino, carboxyl, —(C=O)-substituted or unsubstituted $C_1$-$C_8$ alkyl, substituted or unsubstituted $C_1$-$C_8$ alkyl, substituted or unsubstituted $C_2$-$C_6$ alkenyl, substituted or unsubstituted $C_2$-$C_6$ alkynyl, substituted or unsubstituted $C_1$-$C_8$ alkylamino, substituted or unsubstituted $C_1$-$C_8$ alkoxy, substituted or unsubstituted $C_3$-$C_{10}$ cycloalkyl, substituted or unsubstituted 3-10 membered heterocycloalkyl having 1-3 heteroatoms selected from the group consisting of N, S and O, substituted or unsubstituted $C_6$-$C_{10}$ aryl, and substituted or unsubstituted 5-10 membered heteroaryl having 1-3 heteroatoms selected from the group consisting of N, S and O;

the definition of each group is as set forth above.

In another preferred embodiment, the compound of formula L is a compound of formula II-2, and the method comprises the following steps:

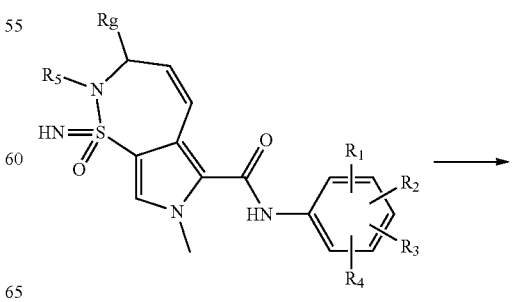

I-2

-continued

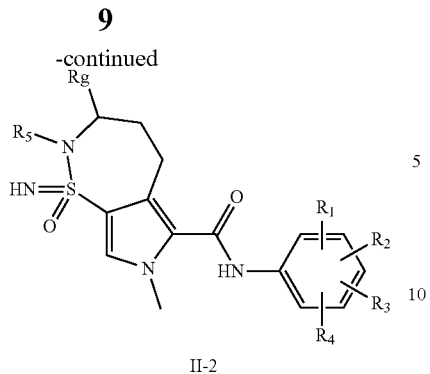

II-2

In each formula, the definition of each group is as set forth above.

In another preferred embodiment, the compound of formula L is a compound of formula VII-3, and the method comprises the following steps:

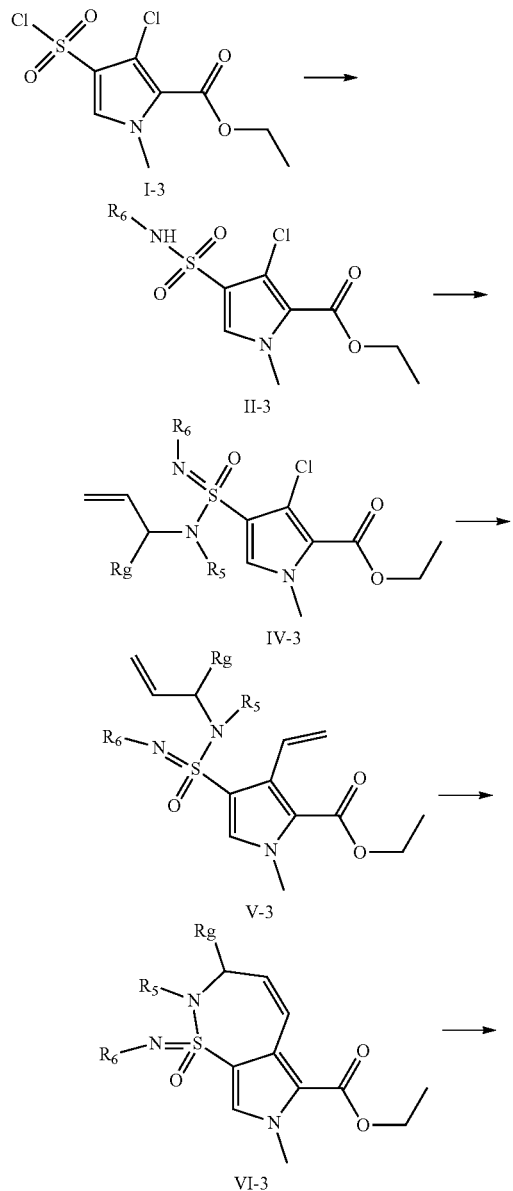

-continued

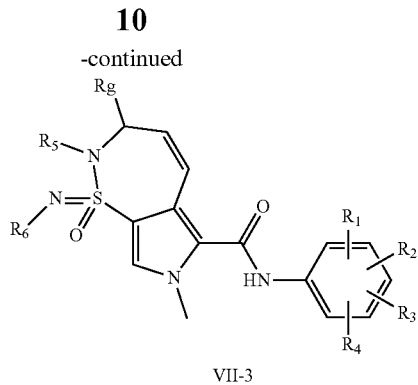

VII-3

In each formula, the definition of each group is as set forth above.

In another preferred embodiment, the compound of formula L is a compound of formula II-4, and the method comprises the following steps:

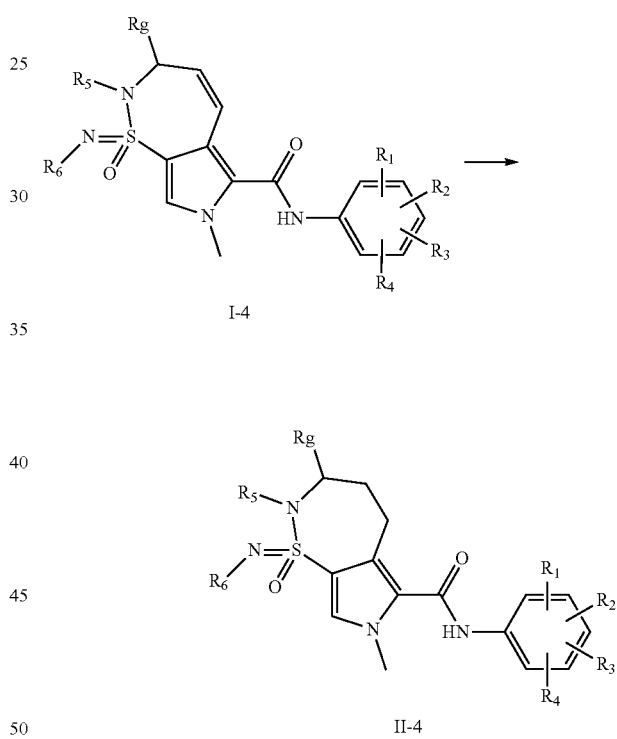

In each formula, the definition of each group is as set forth above.

In the third aspect of the present invention, a compound selected from the following group is provided:

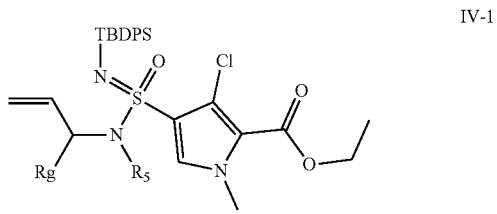

IV-1

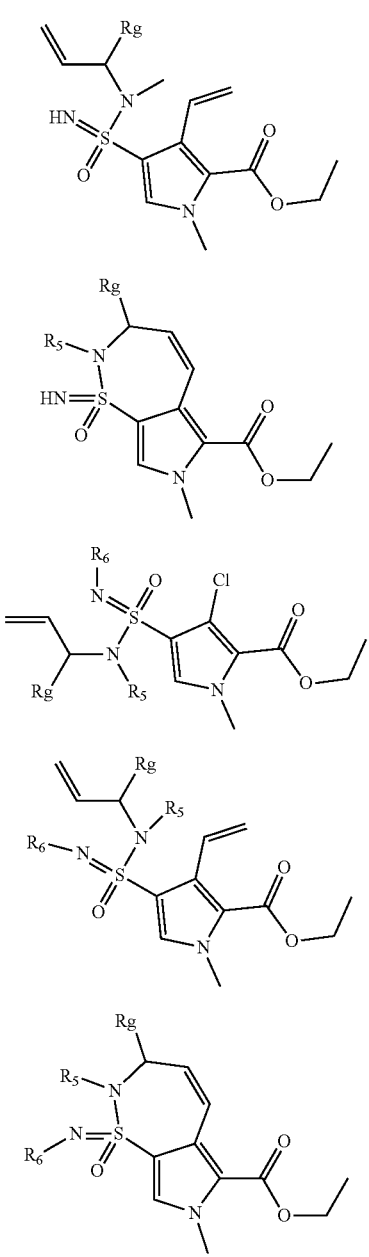

in each formula, Rg is selected from the group consisting of H, halogen, —CN, hydroxyl, amino, carboxyl, —(C=O)-substituted or unsubstituted $C_1$-$C_8$ alkyl, substituted or unsubstituted $C_1$-$C_8$ alkyl, substituted or unsubstituted $C_2$-$C_6$ alkenyl, substituted or unsubstituted $C_2$-$C_6$ alkynyl, substituted or unsubstituted $C_1$-$C_8$ alkylamino, substituted or unsubstituted $C_1$-$C_8$ alkoxy, substituted or unsubstituted $C_3$-$C_{10}$ cycloalkyl, substituted or unsubstituted 3-10 membered heterocycloalkyl having 1-3 heteroatoms selected from the group consisting of N, S and O, substituted or unsubstituted $C_6$-$C_{10}$ aryl, and substituted or unsubstituted 5-10 membered heteroaryl having 1-3 heteroatoms selected from the group consisting of N, S and O;

while each group is defined as in the first aspect of the present invention.

In the fourth aspect of the invention, a pharmaceutical composition is provided, which comprising (1) a compound, or a stereoisomer or tautomer thereof, or a pharmaceutically acceptable salt, hydrate or solvate thereof according to the first aspect of the invention; and (2) pharmaceutically acceptable carriers.

In the fifth aspect of the invention, a use of compound, or a stereoisomer or tautomer thereof, or a pharmaceutically acceptable salt, hydrate or solvate thereof according to the first aspect of the invention, or a use of the pharmaceutical composition according to the fourth aspect of the invention is provided, which is used for the preparation of medicine for the prevention and/or treatment of Hepatitis B.

In the sixth aspect of the invention, an inhibitor of hepatitis B virus is provided, which comprises the compound of the formula I, or a stereoisomer thereof, or a tautomer thereof, or a pharmaceutically acceptable salt, hydrate or solvate thereof of the first aspect of the present invention.

In the seventh aspect of the invention, a method for the prevention and/or treatment of hepatitis B is provided, which comprises the steps: administrating the compound, or a stereoisomer or tautomer thereof, or a pharmaceutically acceptable salt, hydrate or solvate thereof of the first aspect of the invention, or the pharmaceutical composition of the fourth aspect of the invention to a subject in need thereof.

In the eighth aspect of the invention, a method for in inhibiting replication of hepatitis B virus is provided, which comprises the steps: contacting the compound, or a stereoisomer or tautomer thereof, or a pharmaceutically acceptable salt, hydrate or solvate thereof of the first aspect of the invention with hepatitis B virus, thus inhibiting the replication of hepatitis B.

It should be understood that, in the present invention, each of the technical features specifically described above and below (such as those in the Examples) can be combined with each other, thereby constituting new or preferred technical solutions which are not necessarily specified one by one herein.

EMBODIMENTS FOR CARRYING OUT THE INVENTION

After extensive and intensive research, the inventors have found a novel class of compounds having excellent therapeutic effects on hepatitis B. The inventors have completed the present invention on this basis.

Definitions

As used herein, the term "alkyl" includes straight or branched alkyl groups. For example, $C_1$-$C_8$ alkyl refers to straight or branched alkyls having from 1-8 carbon atoms, such as methyl, ethyl, propyl, isopropyl, butyl, isobutyl, tert-butyl, and the like.

As used herein, the term "alkenyl" includes straight or branched alkenyl groups. For example, $C_2$-$C_6$ alkenyl refers to straight or branched alkenyls having 2-6 carbon atoms, such as vinyl, allyl, 1-propenyl, isopropenyl, 1-butenyl, 2-butenyl, and the like.

As used herein, the term "alkynyl" includes straight or branched alkynyl groups. For example, "$C_2$-$C_6$ alkynyl" refers to straight or branched alkynyl having 2-6 carbon atoms, such as ethynyl, propynyl, butynyl, and the like.

As used herein, the term "$C_3$-$C_{10}$ cycloalkyl" refers to cycloalkyl groups having 3 to 10 carbon atoms. It may be a monocyclic ring, such as cyclopropyl, cyclobutyl, cyclopentyl, cyclohexyl, and the like. It may also be of bicyclic form, such as bridged or spiro ring form.

As used herein, the term "$C_1$-$C_8$ alkylamino" refers to amine groups substituted by $C_1$-$C_8$ alkyl, which may be monosubstituted or disubstituted; such as methylamino, ethylamino, propylamino, isopropylamino, butylamino, isobutylamino, tert-butylamino, dimethylamino, diethylamino, dipropylamino, diisopropylamino, dibutylamino, diisobutylamino, di(tert-butyl)amino, and the like.

As used herein, the term "C$_1$-C$_8$ alkoxy" refers to straight or branched alkoxy groups having 1-8 carbon atoms; such as methoxy, ethoxy, propoxy, isopropoxy, butoxy, isobutoxy, tert-butoxy, and the like.

As used herein, the term "3-10 membered heterocycloalkyl having 1-3 heteroatoms selected from the group consisting of N, S and O" refers to a saturated or partially saturated cyclic group having 3-10 atoms, wherein 1-3 atoms are heteroatoms selected from the group consisting of N, S and O. It may be a monocyclic ring or bicyclic form, such as bridged or spiro ring form. Specific examples may be oxetane, azetidine, tetrahydro-2H-pyranyl, piperidinyl, tetrahydrofuranyl, morpholinyl and pyrrolidinyl, and the like.

As used herein, the term "C$_6$-C$_{10}$ aryl" refers to aryl groups having 6 to 10 carbon atoms, such as phenyl, naphthyl, and the like.

As used herein, the term "5-10 membered heteroaryl having 1-3 heteroatoms selected from the group consisting of N, S and O" refers to cyclic aromatic groups having 5-10 atoms, of which 1-3 is selected from the group consisting of N, S and O. It may be a monocyclic ring or fused ring form. Specific examples may be pyridyl, pyridazinyl, pyrimidinyl, pyrazinyl, triazinyl, pyrrolyl, pyrazolyl, imidazolyl, (1,2,3)-triazolyl and (1,2,4)-triazolyl, tetrazyl, furyl, thienyl, isoxazolyl, thiazolyl, oxazolyl, etc.

Unless otherwise specified as "substituted or unsubstituted", all the groups described in the present invention may be substituted with substituents selected from the group consisting of halogen, cyano, nitro, hydroxy, amino, C$_1$-C$_6$ alkyl-amino, C$_1$-C$_6$ alkyl, C$_2$-C$_6$ alkenyl, C$_2$-C$_6$ alkynyl, C$_1$-C$_6$ alkoxy, halogenated C$_1$-C$_6$ alkyl, halogenated C$_2$-C$_6$ alkenyl, halogenated C$_2$-C$_6$ alkynyl, halogenated C$_1$-C$_6$ alkoxy, allyl, benzyl, C$_6$-C$_{12}$ aryl, C$_1$-C$_6$ alkoxy-C$_1$-C$_6$ alkyl, C$_1$-C$_6$ alkoxy-carbonyl, phenoxycarbonyl, C$_2$-C$_6$ alkynyl-carbonyl, C$_2$-C$_6$ alkenyl-carbonyl, C$_3$-C$_6$ cycloalkyl-carbonyl, C$_1$-C$_6$ alkyl-sulfonyl, etc.

As used herein, "halogen" or "halogen atom" refers to F, Cl, Br, and I. More preferably, the halogen or halogen atom is selected from F, C or Br. "Halogenated" means substitution by atom(s) selected from the group consisting of F, Cl, Br, and I.

Unless otherwise specified, the structural formula described herein are intended to include all isomeric forms (such as enantiomeric, diastereomeric, and geometric isomers (or conformational isomers)): for example, R, S configuration having asymmetrical centers, (Z), (E) isomers of double bonds, etc. Therefore, the single stereo chemical isomers or enantiomers, diastereomers or geometric isomers (or conformers) of the compounds of the invention, or mixtures thereof all fall within the scope of the invention.

As used herein, the term "tautomer" means that structural isomers having different energies can exceed the low energy barrier and thereby transform between each other. For example, proton tautomers (proton shift) includes interconversion by proton transfer, such as 1H-carbazole and 2H-carbazole. Valence tautomers include interconversion through some bonding electron recombination.

As used herein, the term "solvate" refers to a complex of specific ratio formed by a compound of the invention coordinating to a solvent molecule.

As used herein, the term "hydrate" refers to a complex formed by the coordination of a compound of the invention with water.

Active Ingredients

As used herein, "compound of the invention" refers to the compound of formula L, as well as various crystal forms of the compound of formula L, or the pharmaceutically acceptable salts, hydrate or solvates thereof.

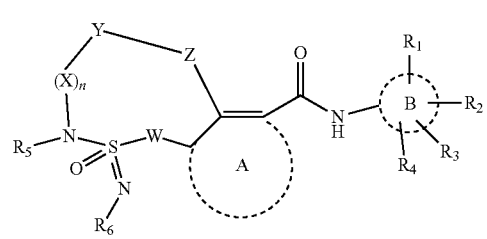

L

As used herein, the "pharmaceutically acceptable salts" refers to salts suitable for use in pharmaceutical which is formed by a compound of the present invention with an acid or base. The pharmaceutically acceptable salts include inorganic and organic salts. Preferred type of salts are salts formed by the compounds of the present invention and acid. Suitable salt-forming acids include, but are not limited to: inorganic acids such as hydrochloric acid, hydro bromic acid, hydrofluoric acid, sulfuric acid, nitric acid, phosphoric acid and the like; organic acids such as formic acid, acetic acid, propionic acid, oxalic acid, malonic acid, succinic acid, fumaric acid, maleic acid, lactic acid, malic acid, tartaric acid, citric acid, picric acid, methane sulfonic acid, toluene sulfonic acid, benzene sulfonic acid and the like; and acidic amino acids such as aspartic acid, glutamic acid.

In another preferred embodiment, said ring A, ring B, R$_1$, R$_2$, R$_3$, R$_4$, R$_5$ and R$_6$ are each independently the corresponding group of each compound in Table 1.

Preferred compounds of the invention are shown in Table 1:

TABLE 1

| No. | Structure | Mass Spectrum ESI-MS, (M + H) | Remark |
|---|---|---|---|
| 10a1 | 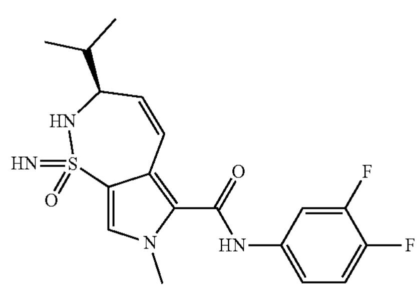 [SMILES: CC(C)[C@H]1C=Cc2c(cn(C)c2C(=O)Nc2ccc(F)c(F)c2)S(=N)(=O)N1] | 395 | Peak1 (HPLC) |

TABLE 1-continued

| No. | Structure | Mass Spectrum ESI-MS, (M + H) | Remark |
| --- | --- | --- | --- |
| 10a2 | 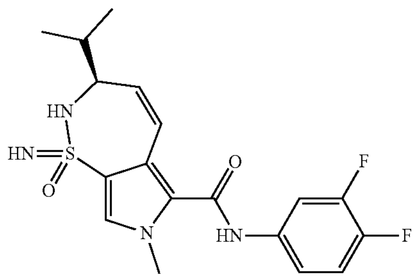 [SMILES: CC(C)[C@H]1C=Cc2c(cn(C)c2C(=O)Nc2ccc(F)c(F)c2)S(=N)(=O)N1] | 395 | Peak2 (HPLC) |
| 10b1 | 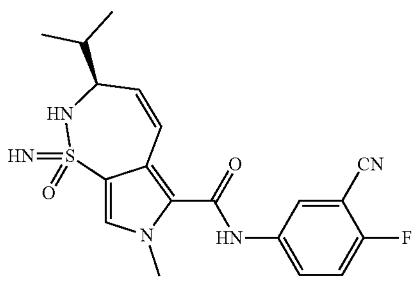 | 402 | Peak1 (HPLC) |
| 10b2 | 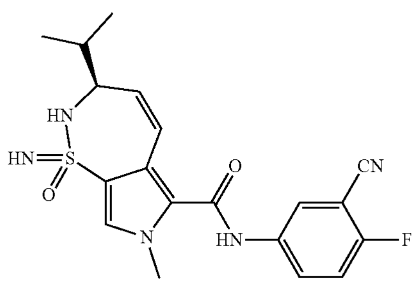 | 402 | Peak2 (HPLC) |
| 10c1 | 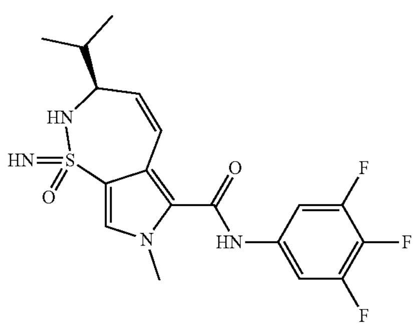 [SMILES: CC(C)[C@H]1C=Cc2c(cn(C)c2C(=O)Nc2cc(F)c(F)c(F)c2)S(=N)(=O)N1] | 413 | Peak1 (HPLC) |
| 10c2 | 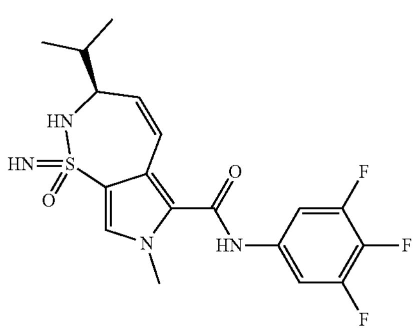 [SMILES: CC(C)[C@H]1C=Cc2c(cn(C)c2C(=O)Nc2cc(F)c(F)c(F)c2)S(=N)(=O)N1] | 413 | Peak2 (HPLC) |

TABLE 1-continued

| No. | Structure | Mass Spectrum ESI-MS, (M + H) | Remark |
|---|---|---|---|
| 10d1 | 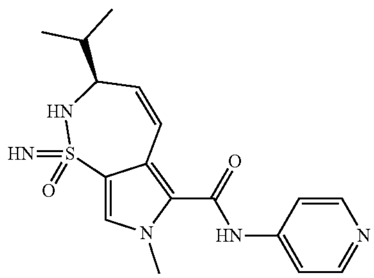 [SMILES: CC(C)[C@H]1C=Cc2c(cn(C)c2C(=O)Nc2ccncc2)S(=N)(=O)N1] | 360 | Peak1 (HPLC) |
| 10d2 | 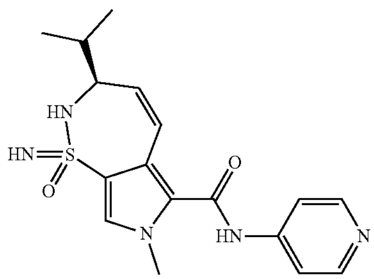 [SMILES: CC(C)[C@H]1C=Cc2c(cn(C)c2C(=O)Nc2ccncc2)S(=N)(=O)N1] | 360 | Peak2 (HPLC) |
| 10e1 | 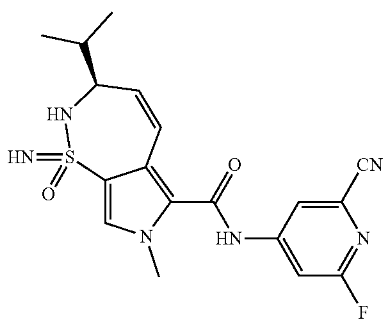 [SMILES: CC(C)[C@H]1C=Cc2c(cn(C)c2C(=O)Nc2cc(F)nc(C#N)c2)S(=N)(=O)N1] | 403 | Peak1 (HPLC) |
| 10e2 | 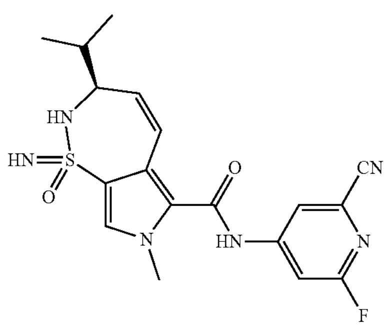 [SMILES: CC(C)[C@H]1C=Cc2c(cn(C)c2C(=O)Nc2cc(F)nc(C#N)c2)S(=N)(=O)N1] | 403 | Peak2 (HPLC) |
| 10f1 | 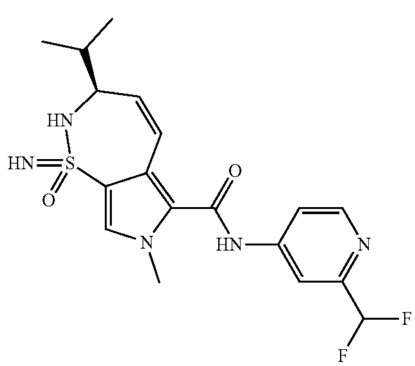 [SMILES: CC(C)[C@H]1C=Cc2c(cn(C)c2C(=O)Nc2ccnc(C(F)F)c2)S(=N)(=O)N1] | 410 | Peak1 (HPLC) |

TABLE 1-continued

| No. | Structure | Mass Spectrum ESI-MS, (M + H) | Remark |
|---|---|---|---|
| 10f2 | 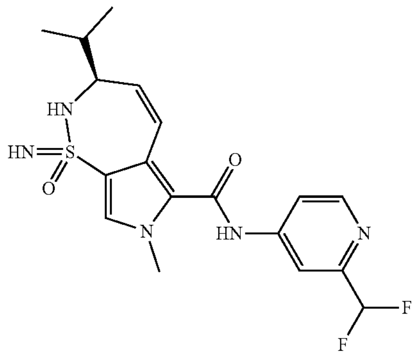 [SMILES: CC(C)[C@H]1C=Cc2c(cn(C)c2C(=O)Nc2ccnc(C(F)F)c2)S(=N)(=O)N1] | 410 | Peak2 (HPLC) |
| 10g1 | 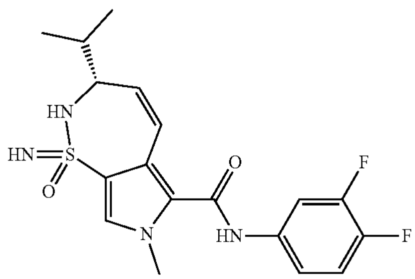 [SMILES: CC(C)[C@@H]1C=Cc2c(cn(C)c2C(=O)Nc2ccc(F)c(F)c2)S(=N)(=O)N1] | 395 | Peak1 (HPLC) |
| 10g2 | 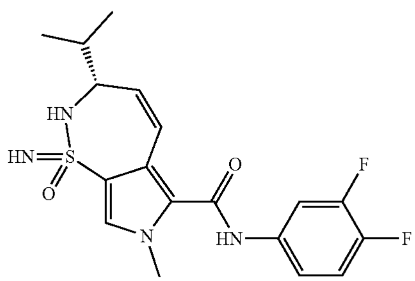 [SMILES: CC(C)[C@@H]1C=Cc2c(cn(C)c2C(=O)Nc2ccc(F)c(F)c2)S(=N)(=O)N1] | 395 | Peak2 (HPLC) |
| 10h1 | 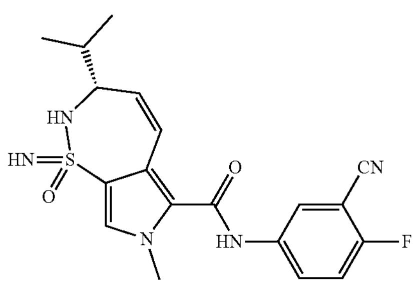 [SMILES: CC(C)[C@@H]1C=Cc2c(cn(C)c2C(=O)Nc2ccc(F)c(C#N)c2)S(=N)(=O)N1] | 402 | Peak1 (HPLC) |
| 10h2 | 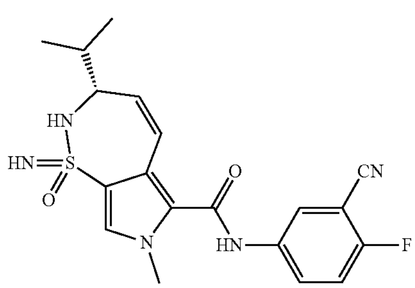 [SMILES: CC(C)[C@@H]1C=Cc2c(cn(C)c2C(=O)Nc2ccc(F)c(C#N)c2)S(=N)(=O)N1] | 402 | Peak2 (HPLC) |

TABLE 1-continued

| No. | Structure | Mass Spectrum ESI-MS, (M + H) | Remark |
|---|---|---|---|
| 10i1 | 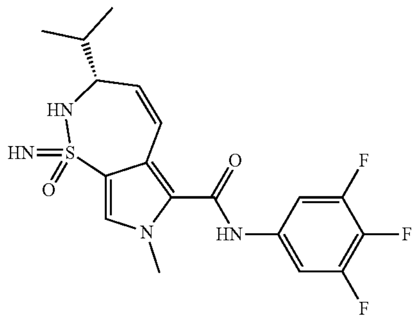 [SMILES: CC(C)[C@@H]1C=Cc2c(cn(C)c2C(=O)Nc2cc(F)c(F)c(F)c2)S(=N)(=O)N1] | 413 | Peak1 (HPLC) |
| 10i2 | 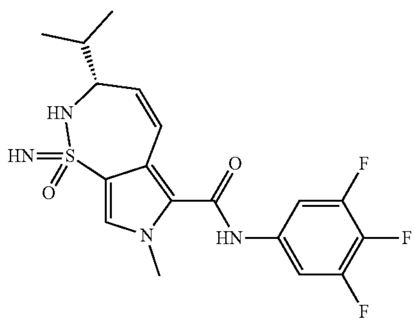 [SMILES: CC(C)[C@@H]1C=Cc2c(cn(C)c2C(=O)Nc2cc(F)c(F)c(F)c2)S(=N)(=O)N1] | 413 | Peak2 (HPLC) |
| 10j1 | 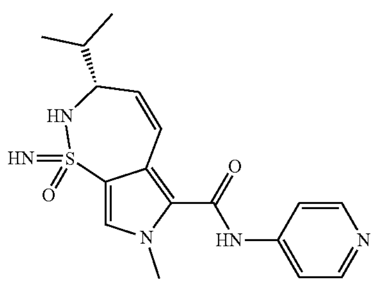 [SMILES: CC(C)[C@@H]1C=Cc2c(cn(C)c2C(=O)Nc2ccncc2)S(=N)(=O)N1] | 360 | Peak1 (HPLC) |
| 10j2 | 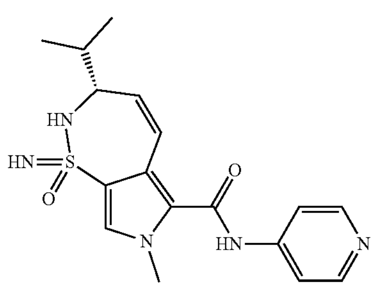 [SMILES: CC(C)[C@@H]1C=Cc2c(cn(C)c2C(=O)Nc2ccncc2)S(=N)(=O)N1] | 360 | Peak2 (HPLC) |
| 10k1 | 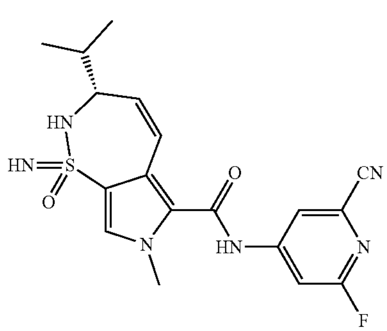 [SMILES: CC(C)[C@@H]1C=Cc2c(cn(C)c2C(=O)Nc2cc(F)nc(C#N)c2)S(=N)(=O)N1] | 403 | Peak1 (HPLC) |

TABLE 1-continued

| No. | Structure | Mass Spectrum ESI-MS, (M + H) | Remark |
|---|---|---|---|
| 10k2 | 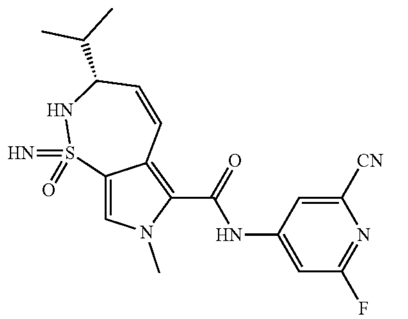 [SMILES: CC(C)[C@@H]1C=Cc2c(cn(C)c2C(=O)Nc2cc(F)nc(C#N)c2)S(=N)(=O)N1] | 403 | Peak2 (HPLC) |
| 10m1 | 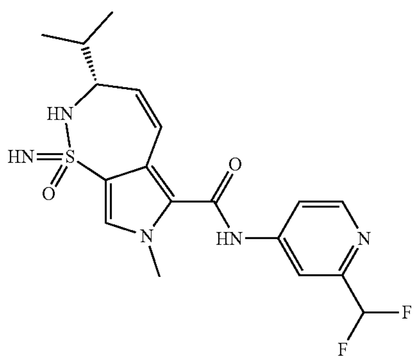 [SMILES: CC(C)[C@@H]1C=Cc2c(cn(C)c2C(=O)Nc2ccnc(C(F)F)c2)S(=N)(=O)N1] | 410 | Peak1 (HPLC) |
| 10m2 | 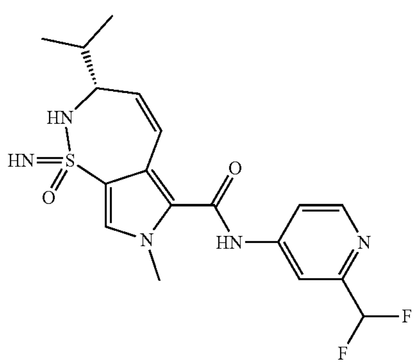 [SMILES: CC(C)[C@@H]1C=Cc2c(cn(C)c2C(=O)Nc2ccnc(C(F)F)c2)S(=N)(=O)N1] | 410 | Peak2 (HPLC) |
| 10n1 | 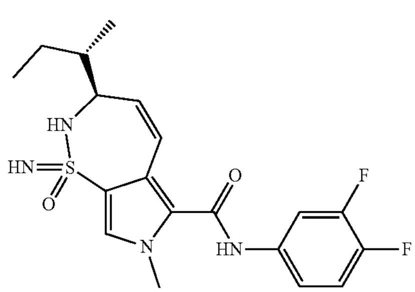 | 409 | Peak1 (HPLC) |

TABLE 1-continued

| No. | Structure | Mass Spectrum ESI-MS, (M + H) | Remark |
|---|---|---|---|
| 10n2 | 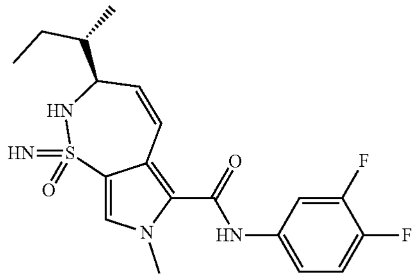 [SMILES: CC[C@H](C)[C@H]1C=Cc2c(cn(C)c2C(=O)Nc2ccc(F)c(F)c2)S(=N)(=O)N1] | 409 | Peak2 (HPLC) |
| 10o1 | 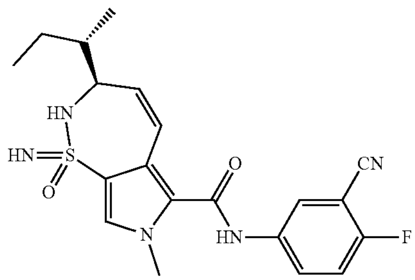 [SMILES: CC[C@H](C)[C@H]1C=Cc2c(cn(C)c2C(=O)Nc2ccc(F)c(C#N)c2)S(=N)(=O)N1] | 416 | Peak1 (HPLC) |
| 10o2 | 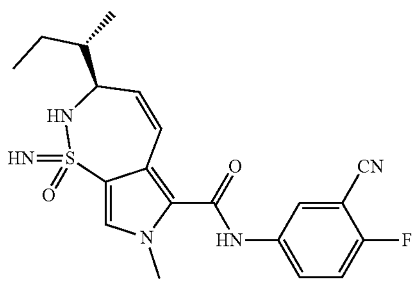 [SMILES: CC[C@H](C)[C@H]1C=Cc2c(cn(C)c2C(=O)Nc2ccc(F)c(C#N)c2)S(=N)(=O)N1] | 416 | Peak2 (HPLC) |
| 10p1 | 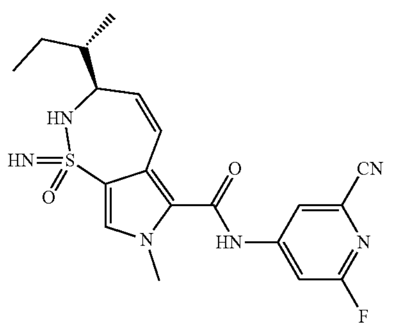 [SMILES: CC[C@H](C)[C@H]1C=Cc2c(cn(C)c2C(=O)Nc2cc(F)nc(C#N)c2)S(=N)(=O)N1] | 417 | Peak1 (HPLC) |
| 10p2 | 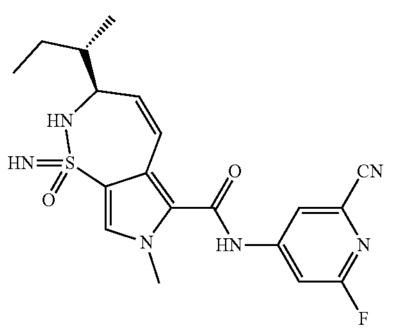 [SMILES: CC[C@H](C)[C@H]1C=Cc2c(cn(C)c2C(=O)Nc2cc(F)nc(C#N)c2)S(=N)(=O)N1] | 417 | Peak2 (HPLC) |

TABLE 1-continued

| No. | Structure | Mass Spectrum ESI-MS, (M + H) | Remark |
| --- | --- | --- | --- |
| 10q1 | 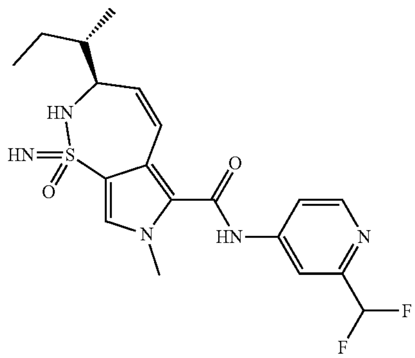 [SMILES: CC[C@H](C)[C@H]1C=Cc2c(cn(C)c2C(=O)Nc2ccnc(C(F)F)c2)S(=N)(=O)N1] | 424 | Peak1 (HPLC) |
| 10q2 | 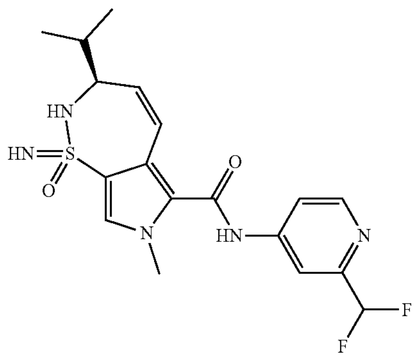 [SMILES: CC(C)[C@H]1C=Cc2c(cn(C)c2C(=O)Nc2ccnc(C(F)F)c2)S(=N)(=O)N1] | 424 | Peak2 (HPLC) |
| 10r1 | 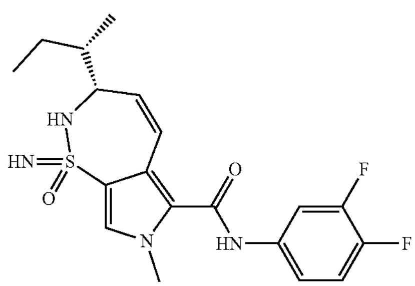 [SMILES: CC[C@H](C)[C@@H]1C=Cc2c(cn(C)c2C(=O)Nc2ccc(F)c(F)c2)S(=N)(=O)N1] | 409 | Peak1 (HPLC) |
| 10r2 | 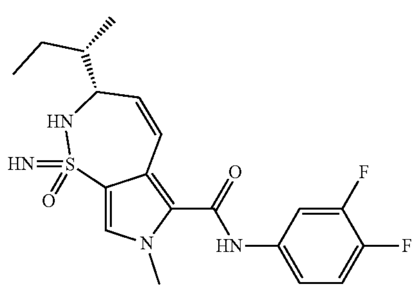 [SMILES: CC[C@H](C)[C@@H]1C=Cc2c(cn(C)c2C(=O)Nc2ccc(F)c(F)c2)S(=N)(=O)N1] | 409 | Peak2 (HPLC) |
| 10s1 | 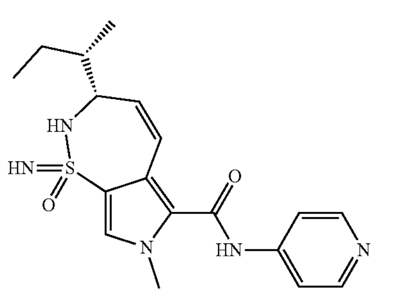 [SMILES: CC[C@H](C)[C@@H]1C=Cc2c(cn(C)c2C(=O)Nc2ccncc2)S(=N)(=O)N1] | 374 | Peak1 (HPLC) |

TABLE 1-continued

| No. | Structure | Mass Spectrum ESI-MS, (M + H) | Remark |
|---|---|---|---|
| 10s2 | 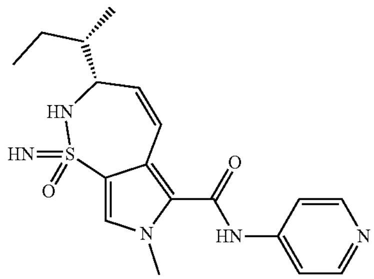 [SMILES: CC[C@H](C)[C@@H]1C=Cc2c(cn(C)c2C(=O)Nc2ccncc2)S(=N)(=O)N1] | 374 | Peak2 (HPLC) |
| 10t1 | 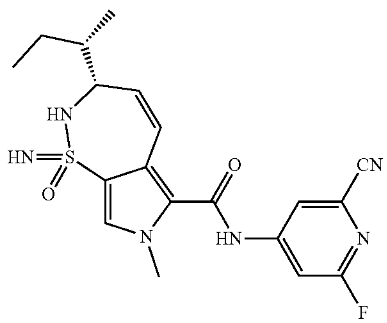 [SMILES: CC[C@H](C)[C@@H]1C=Cc2c(cn(C)c2C(=O)Nc2cc(F)nc(C#N)c2)S(=N)(=O)N1] | 417 | Peak1 (HPLC) |
| 10t2 | 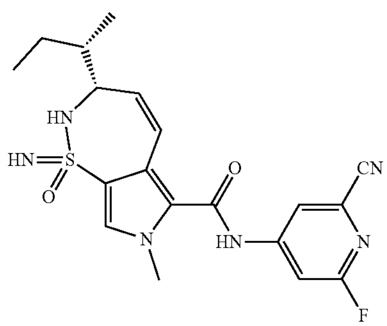 [SMILES: CC[C@H](C)[C@@H]1C=Cc2c(cn(C)c2C(=O)Nc2cc(F)nc(C#N)c2)S(=N)(=O)N1] | 417 | Peak2 (HPLC) |
| 10u1 | 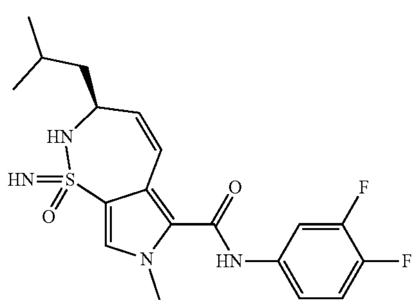 [SMILES: CC(C)C[C@H]1C=Cc2c(cn(C)c2C(=O)Nc2ccc(F)c(F)c2)S(=N)(=O)N1] | 409 | Peak1 (HPLC) |
| 10u2 | 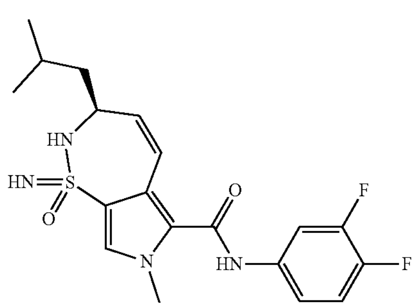 | 409 | Peak2 (HPLC) |

TABLE 1-continued

| No. | Structure | Mass Spectrum ESI-MS, (M + H) | Remark |
| --- | --- | --- | --- |
| 10v1 | 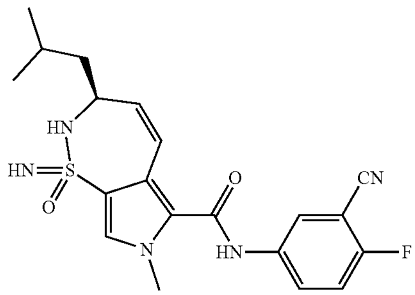 [SMILES: CC(C)C[C@H]1C=Cc2c(cn(C)c2C(=O)Nc2ccc(F)c(C#N)c2)S(=N)(=O)N1] | 416 | Peak1 (HPLC) |
| 10v2 | 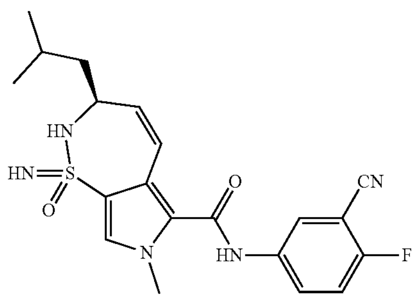 [SMILES: CC(C)C[C@H]1C=Cc2c(cn(C)c2C(=O)Nc2ccc(F)c(C#N)c2)S(=N)(=O)N1] | 416 | Peak2 (HPLC) |
| 10w1 | 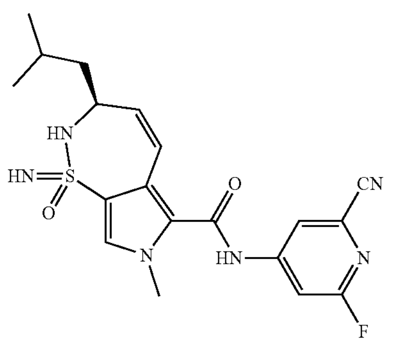 [SMILES: CC(C)C[C@H]1C=Cc2c(cn(C)c2C(=O)Nc2cc(F)nc(C#N)c2)S(=N)(=O)N1] | 417 | Peak1 (HPLC) |
| 10w2 | 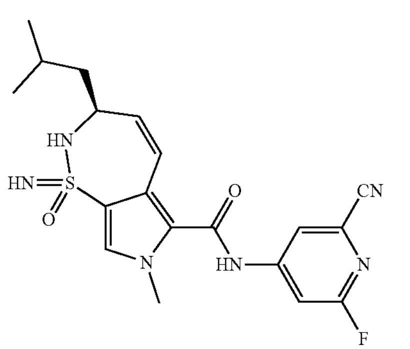 [SMILES: CC(C)C[C@H]1C=Cc2c(cn(C)c2C(=O)Nc2cc(F)nc(C#N)c2)S(=N)(=O)N1] | 417 | Peak2 (HPLC) |

TABLE 1-continued

| No. | Structure | Mass Spectrum ESI-MS, (M + H) | Remark |
| --- | --- | --- | --- |
| 10x1 | 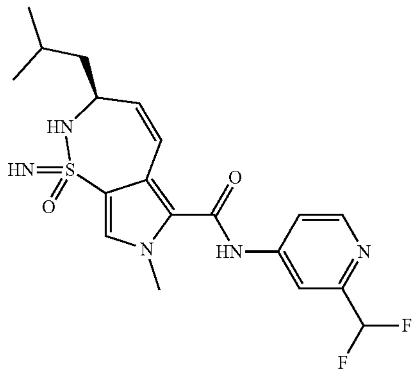 [SMILES: CC(C)C[C@H]1C=Cc2c(cn(C)c2C(=O)Nc2ccnc(C(F)F)c2)S(=N)(=O)N1] | 424 | Peak1 (HPLC) |
| 10x2 | 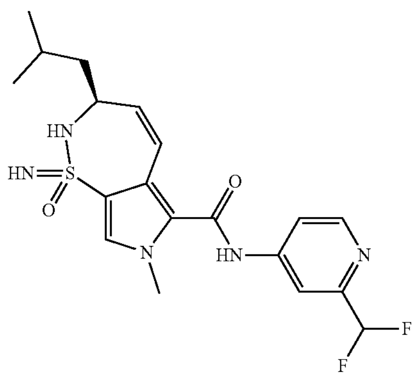 [SMILES: CC(C)C[C@H]1C=Cc2c(cn(C)c2C(=O)Nc2ccnc(C(F)F)c2)S(=N)(=O)N1] | 424 | Peak2 (HPLC) |
| 10y1 | 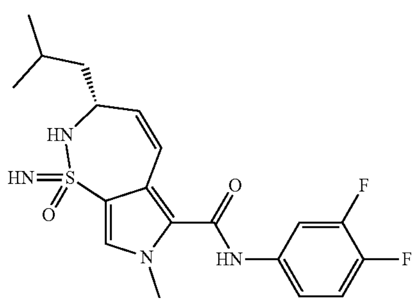 [SMILES: CC(C)C[C@@H]1C=Cc2c(cn(C)c2C(=O)Nc2ccc(F)c(F)c2)S(=N)(=O)N1] | 409 | Peak1 (HPLC) |
| 10y2 | 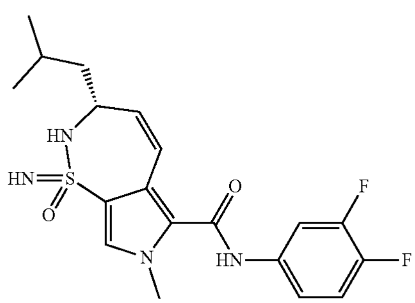 [SMILES: CC(C)C[C@@H]1C=Cc2c(cn(C)c2C(=O)Nc2ccc(F)c(F)c2)S(=N)(=O)N1] | 409 | Peak2 (HPLC) |

TABLE 1-continued

| No. | Structure | Mass Spectrum ESI-MS, (M + H) | Remark |
|---|---|---|---|
| 10z1 | 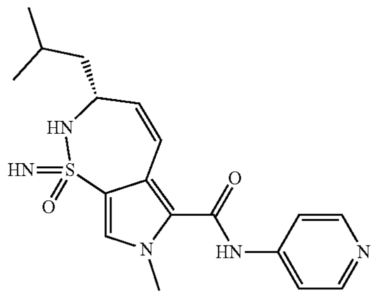 [SMILES: CC(C)C[C@@H]1C=Cc2c(cn(C)c2C(=O)Nc2ccncc2)S(=N)(=O)N1] | 374 | Peak1 (HPLC) |
| 10z2 | 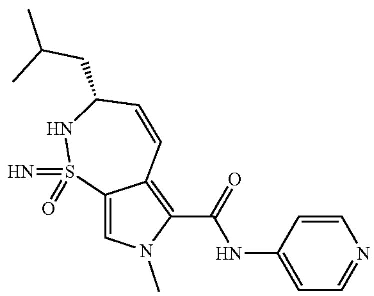 [SMILES: CC(C)C[C@@H]1C=Cc2c(cn(C)c2C(=O)Nc2ccncc2)S(=N)(=O)N1] | 374 | Peak2 (HPLC) |
| 10aa1 | 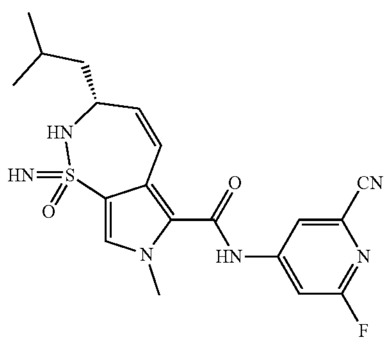 [SMILES: CC(C)C[C@@H]1C=Cc2c(cn(C)c2C(=O)Nc2cc(F)nc(C#N)c2)S(=N)(=O)N1] | 417 | Peak1 (HPLC) |
| 10aa2 | 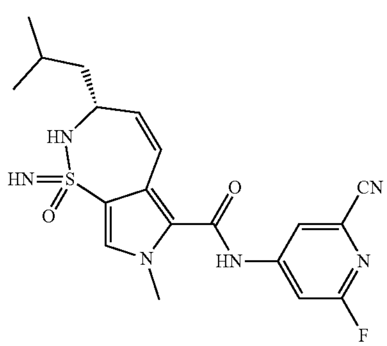 [SMILES: CC(C)C[C@@H]1C=Cc2c(cn(C)c2C(=O)Nc2cc(F)nc(C#N)c2)S(=N)(=O)N1] | 417 | Peak2 (HPLC) |

TABLE 1-continued
| No. | Structure | Mass Spectrum ESI-MS, (M + H) | Remark |
|---|---|---|---|
| 10bb1 | 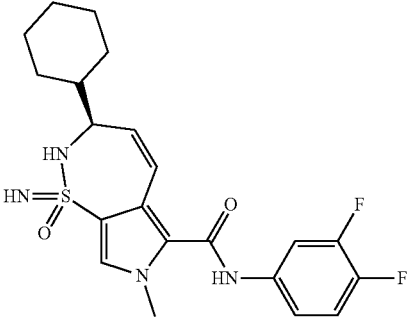 [SMILES: Cn1cc2c(c1C(=O)Nc1ccc(F)c(F)c1)C=C[C@H](C1CCCCC1)NS2(=N)=O] | 435 | Peak1 (HPLC) |
| 10bb2 | 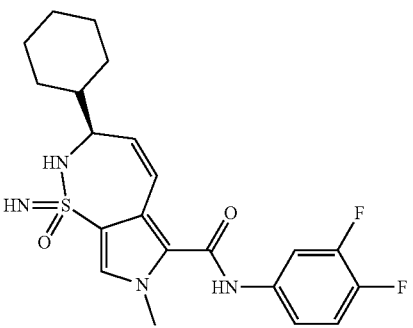 [SMILES: Cn1cc2c(c1C(=O)Nc1ccc(F)c(F)c1)C=C[C@H](C1CCCCC1)NS2(=N)=O] | 435 | Peak2 (HPLC) |
| 10cc1 | 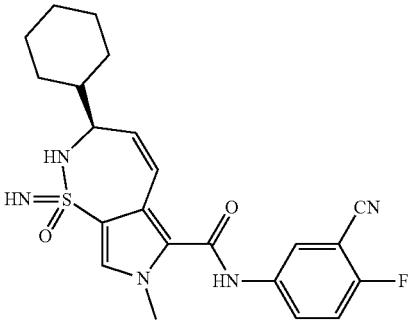 [SMILES: Cn1cc2c(c1C(=O)Nc1ccc(F)c(C#N)c1)C=C[C@H](C1CCCCC1)NS2(=N)=O] | 442 | Peak1 (HPLC) |
| 10cc2 | 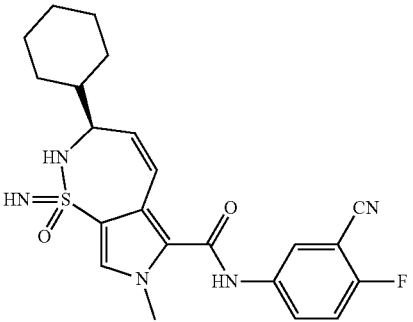 | 442 | Peak2 (HPLC) |

TABLE 1-continued

| No. | Structure | Mass Spectrum ESI-MS, (M + H) | Remark |
|---|---|---|---|
| 10dd1 | 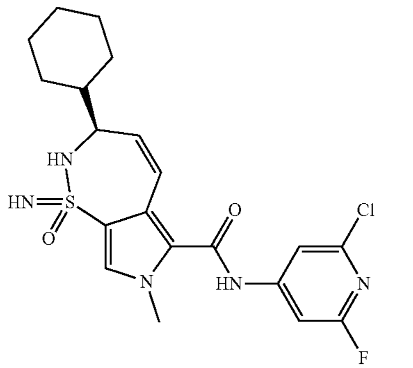 [SMILES: Cn1cc2c(c1C(=O)Nc1cc(F)nc(Cl)c1)C=C[C@H](C1CCCCC1)NS2(=N)=O] | 443 | Peak1 (HPLC) |
| 10dd2 | 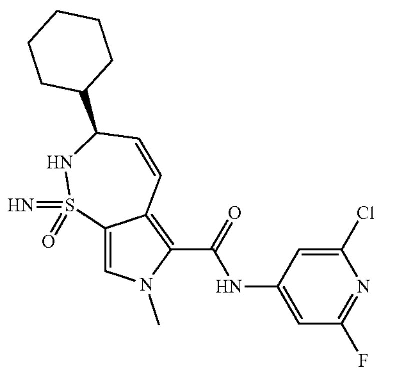 [SMILES: Cn1cc2c(c1C(=O)Nc1cc(F)nc(Cl)c1)C=C[C@H](C1CCCCC1)NS2(=N)=O] | 443 | Peak2 (HPLC) |
| 10ee1 | 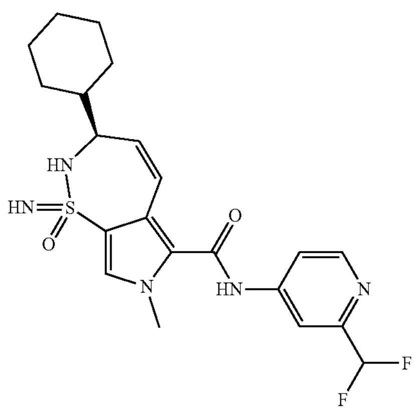 [SMILES: Cn1cc2c(c1C(=O)Nc1ccnc(C(F)F)c1)C=C[C@H](C1CCCCC1)NS2(=N)=O] | 450 | Peak1 (HPLC) |
| 10ee2 | 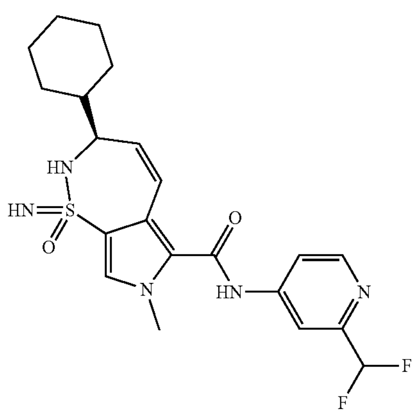 [SMILES: Cn1cc2c(c1C(=O)Nc1ccnc(C(F)F)c1)C=C[C@H](C1CCCCC1)NS2(=N)=O] | 450 | Peak2 (HPLC) |

TABLE 1-continued

| No. | Structure | Mass Spectrum ESI-MS, (M + H) | Remark |
|---|---|---|---|
| 10ff1 | 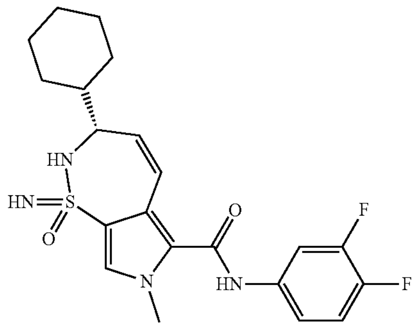 | 435 | Peak1 (HPLC) |
| 10ff2 | 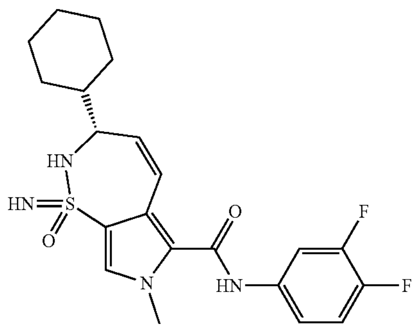 [SMILES: Cn1cc2c(c1C(=O)Nc1ccc(F)c(F)c1)C=C[C@@H](C1CCCCC1)NS2(=N)=O] | 435 | Peak2 (HPLC) |
| 10gg1 | 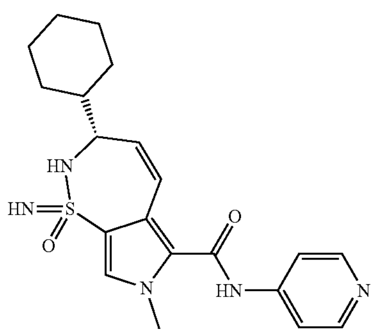 [SMILES: Cn1cc2c(c1C(=O)Nc1ccncc1)C=C[C@@H](C1CCCCC1)NS2(=N)=O] | 400 | Peak1 (HPLC) |
| 10gg2 | 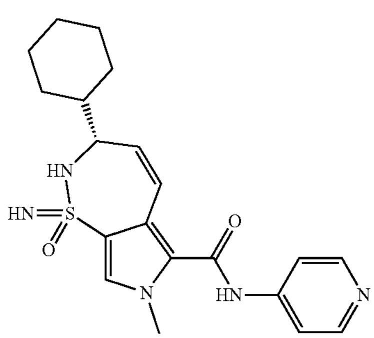 | 400 | Peak2 (HPLC) |

TABLE 1-continued

| No. | Structure | Mass Spectrum ESI-MS, (M + H) | Remark |
|---|---|---|---|
| 10hh1 | 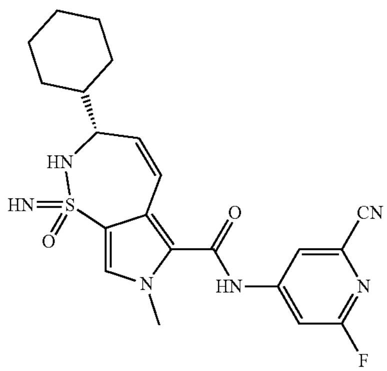 [SMILES: Cn1cc2c(c1C(=O)Nc1cc(F)nc(C#N)c1)C=C[C@@H](C1CCCCC1)NS2(=N)=O] | 443 | Peak1 (HPLC) |
| 10hh2 | 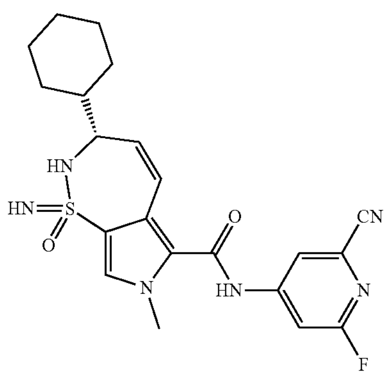 [SMILES: Cn1cc2c(c1C(=O)Nc1cc(F)nc(C#N)c1)C=C[C@@H](C1CCCCC1)NS2(=N)=O] | 443 | Peak2 (HPLC) |
| 10ii1 | 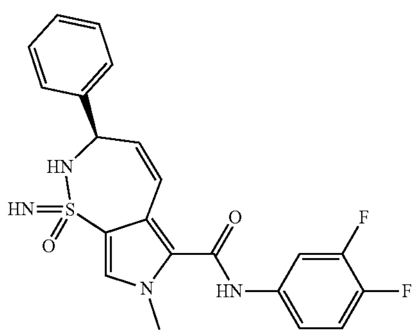 | 429 | Peak1 (HPLC) |
| 10ii2 | 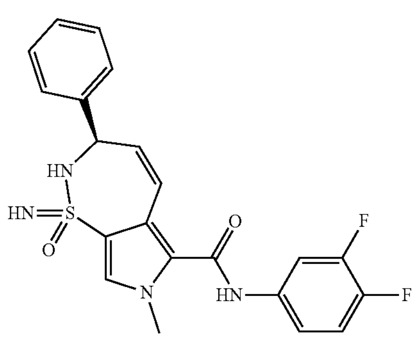 | 429 | Peak2 (HPLC) |

TABLE 1-continued

| No. | Structure | Mass Spectrum ESI-MS, (M + H) | Remark |
|---|---|---|---|
| 10jj1 | 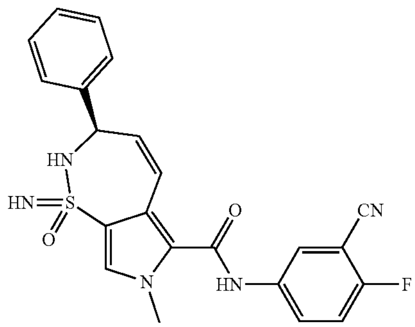 [SMILES: Cn1cc2c(c1C(=O)Nc1ccc(F)c(C#N)c1)C=C[C@H](c1ccccc1)NS2(=N)=O] | 436 | Peak1 (HPLC) |
| 10jj2 | 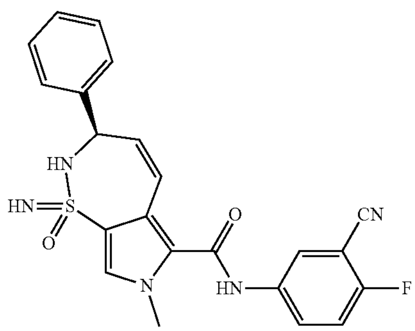 | 436 | Peak2 (HPLC) |
| 10kk1 | 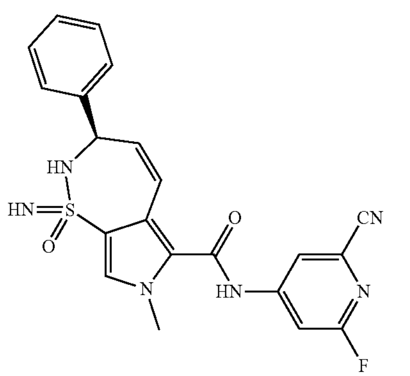 [SMILES: Cn1cc2c(c1C(=O)Nc1cc(F)nc(C#N)c1)C=C[C@H](c1ccccc1)NS2(=N)=O] | 437 | Peak1 (HPLC) |
| 10kk2 | 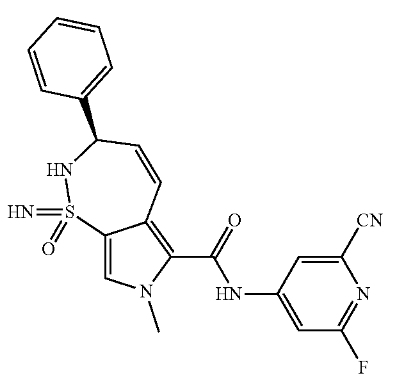 [SMILES: Cn1cc2c(c1C(=O)Nc1cc(F)nc(C#N)c1)C=C[C@H](c1ccccc1)NS2(=N)=O] | 437 | Peak2 (HPLC) |

TABLE 1-continued

| No. | Structure | Mass Spectrum ESI-MS, (M + H) | Remark |
|---|---|---|---|
| 10mm1 | 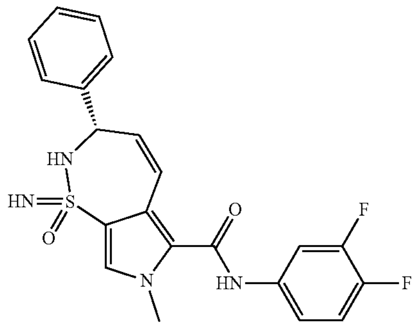 | 429 | Peak1 (HPLC) |
| 10mm2 | 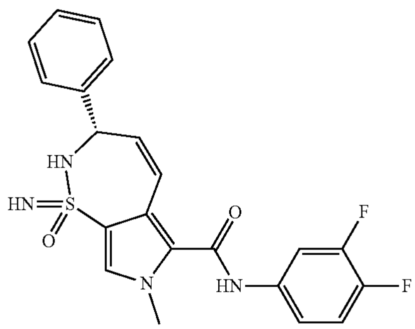 [SMILES: Cn1cc2c(c1C(=O)Nc1ccc(F)c(F)c1)C=C[C@@H](c1ccccc1)NS2(=N)=O] | 429 | Peak2 (HPLC) |
| 10nn1 | 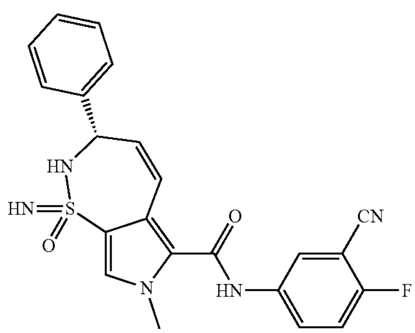 [SMILES: Cn1cc2c(c1C(=O)Nc1ccc(F)c(C#N)c1)C=C[C@@H](c1ccccc1)NS2(=N)=O] | 436 | Peak1 (HPLC) |
| 10nn2 | 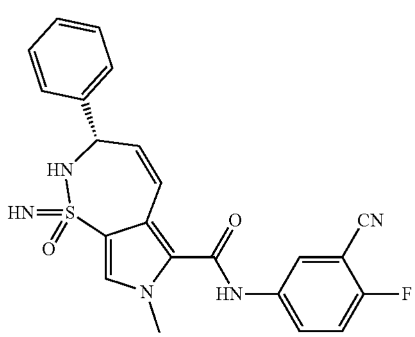 | 436 | Peak2 (HPLC) |

TABLE 1-continued

| No. | Structure | Mass Spectrum ESI-MS, (M + H) | Remark |
|---|---|---|---|
| 10oo1 | 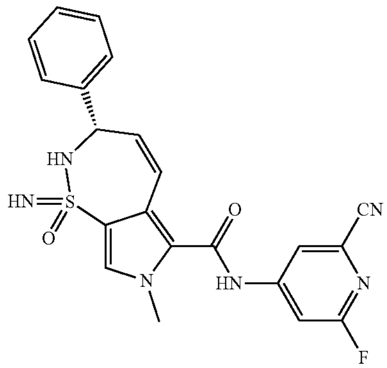 [SMILES: Cn1cc2c(c1C(=O)Nc1cc(F)nc(C#N)c1)C=C[C@@H](c1ccccc1)NS2(=N)=O] | 437 | Peak1 (HPLC) |
| 10oo2 | 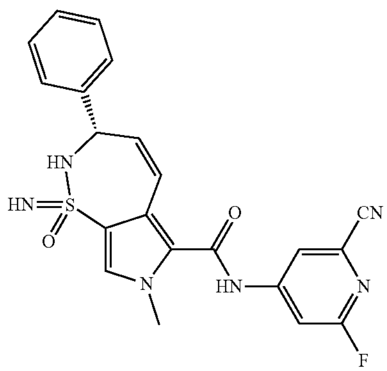 [SMILES: Cn1cc2c(c1C(=O)Nc1cc(F)nc(C#N)c1)C=C[C@@H](c1ccccc1)NS2(=N)=O] | 437 | Peak2 (HPLC) |
| 10pp1 | 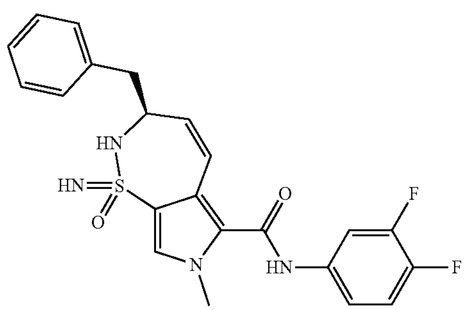 [SMILES: Cn1cc2c(c1C(=O)Nc1ccc(F)c(F)c1)C=C[C@H](Cc1ccccc1)NS2(=N)=O] | 443 | Peak1 (HPLC) |
| 10pp2 | 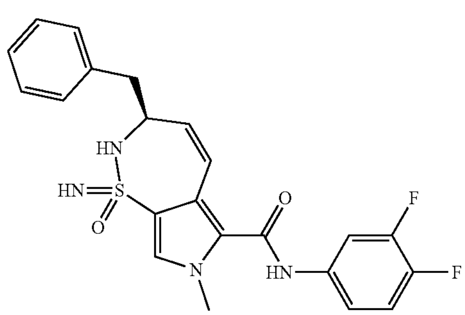 [SMILES: Cn1cc2c(c1C(=O)Nc1ccc(F)c(F)c1)C=C[C@H](Cc1ccccc1)NS2(=N)=O] | 443 | Peak2 (HPLC) |

TABLE 1-continued

| No. | Structure | Mass Spectrum ESI-MS, (M + H) | Remark |
|---|---|---|---|
| 10qq1 | 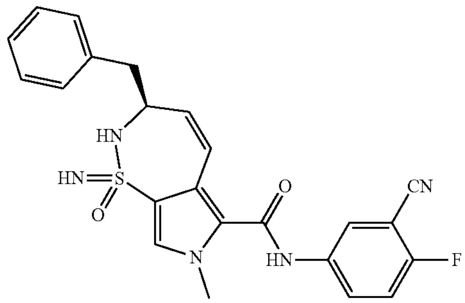 [SMILES: Cn1cc2c(c1C(=O)Nc1ccc(F)c(C#N)c1)C=C[C@H](Cc1ccccc1)NS2(=N)=O] | 450 | Peak1 (HPLC) |
| 10qq2 | 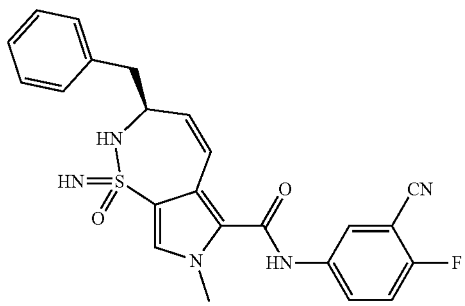 [SMILES: Cn1cc2c(c1C(=O)Nc1ccc(F)c(C#N)c1)C=C[C@H](Cc1ccccc1)NS2(=N)=O] | 450 | Peak2 (HPLC) |
| 10rr1 | 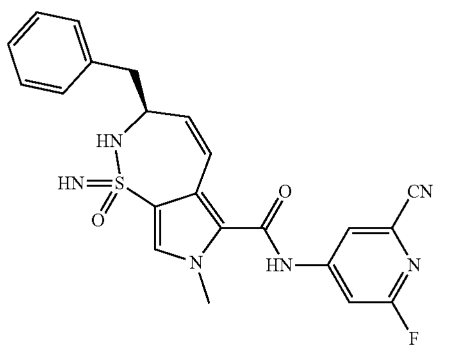 [SMILES: Cn1cc2c(c1C(=O)Nc1cc(F)nc(C#N)c1)C=C[C@H](Cc1ccccc1)NS2(=N)=O] | 451 | Peak1 (HPLC) |
| 10rr2 | 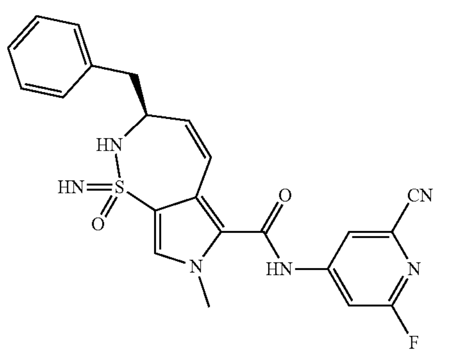 [SMILES: Cn1cc2c(c1C(=O)Nc1cc(F)nc(C#N)c1)C=C[C@H](Cc1ccccc1)NS2(=N)=O] | 451 | Peak2 (HPLC) |

TABLE 1-continued

| No. | Structure | Mass Spectrum ESI-MS, (M + H) | Remark |
|---|---|---|---|
| 10ss1 | 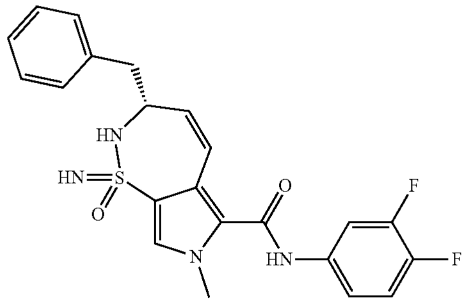 [SMILES: Cn1cc2c(c1C(=O)Nc1ccc(F)c(F)c1)C=C[C@@H](Cc1ccccc1)NS2(=N)=O] | 443 | Peak1 (HPLC) |
| 10ss2 | 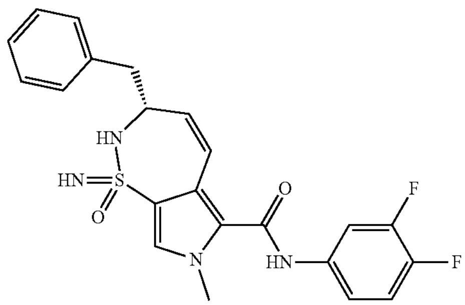 [SMILES: Cn1cc2c(c1C(=O)Nc1ccc(F)c(F)c1)C=C[C@@H](Cc1ccccc1)NS2(=N)=O] | 443 | Peak2 (HPLC) |
| 10tt1 | 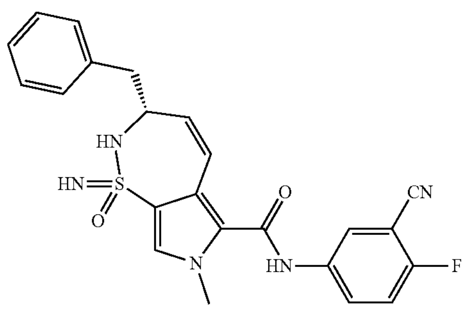 [SMILES: Cn1cc2c(c1C(=O)Nc1ccc(F)c(C#N)c1)C=C[C@@H](Cc1ccccc1)NS2(=N)=O] | 450 | Peak1 (HPLC) |
| 10tt2 | 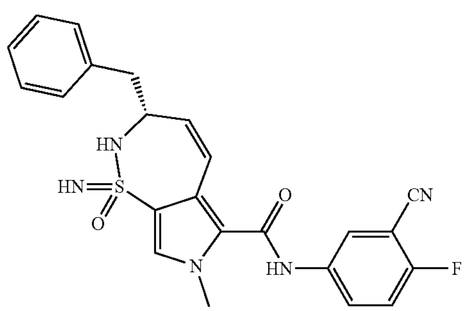 [SMILES: Cn1cc2c(c1C(=O)Nc1ccc(F)c(C#N)c1)C=C[C@@H](Cc1ccccc1)NS2(=N)=O] | 450 | Peak2 (HPLC) |
| 10uu1 | 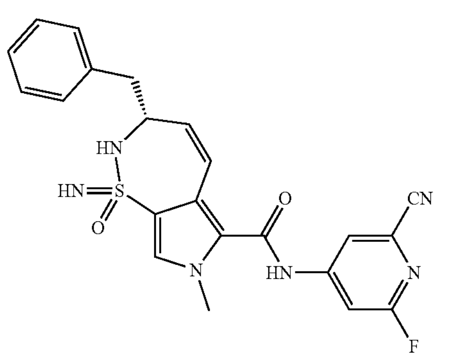 [SMILES: Cn1cc2c(c1C(=O)Nc1cc(F)nc(C#N)c1)C=C[C@@H](Cc1ccccc1)NS2(=N)=O] | 451 | Peak1 (HPLC) |

TABLE 1-continued
| No. | Structure | Mass Spectrum ESI-MS, (M + H) | Remark |
|---|---|---|---|
| 10uu2 | 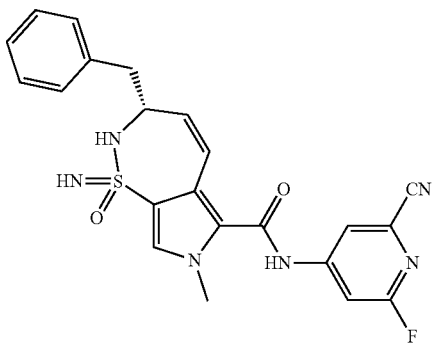 [SMILES: Cn1cc2c(c1C(=O)Nc1cc(F)nc(C#N)c1)C=C[C@@H](Cc1ccccc1)NS2(=N)=O] | 451 | Peak2 (HPLC) |
| 10vv1 | 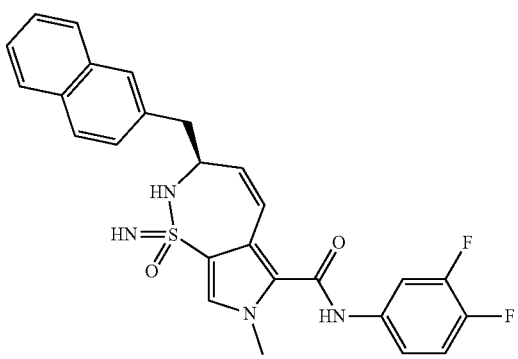 | 493 | Peak1 (HPLC) |
| 10vv2 | 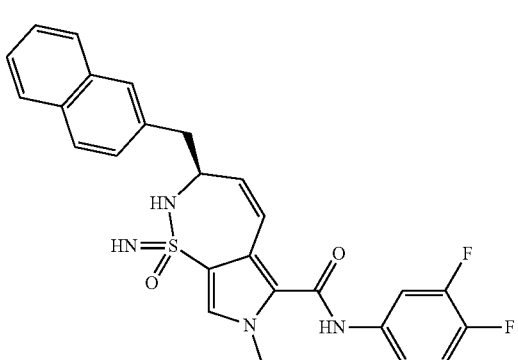 | 493 | Peak2 (HPLC) |
| 10ww1 | 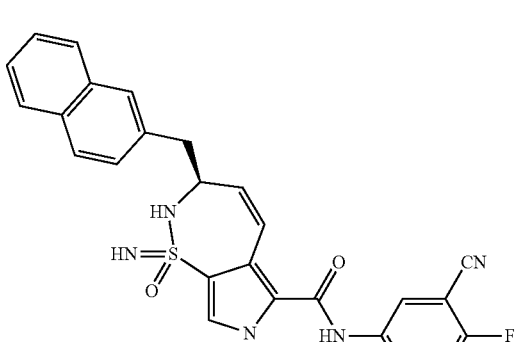 | 500 | Peak1 (HPLC) |

TABLE 1-continued
| No. | Structure | Mass Spectrum ESI-MS, (M + H) | Remark |
| --- | --- | --- | --- |
| 10ww2 | 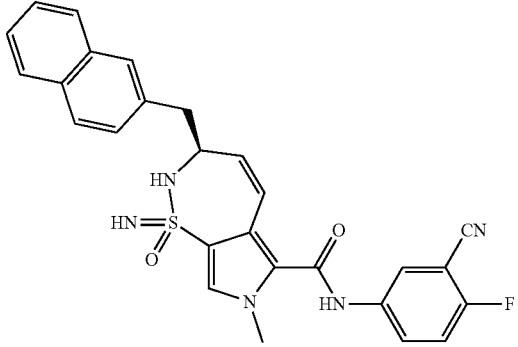 | 500 | Peak2 (HPLC) |
| 10xx1 | 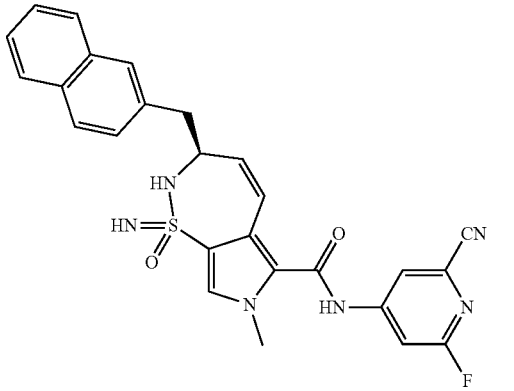 [SMILES: Cn1cc2c(c1C(=O)Nc1cc(F)nc(C#N)c1)C=C[C@H](Cc1ccc3ccccc3c1)NS2(=N)=O] | 501 | Peak1 (HPLC) |
| 10xx2 | 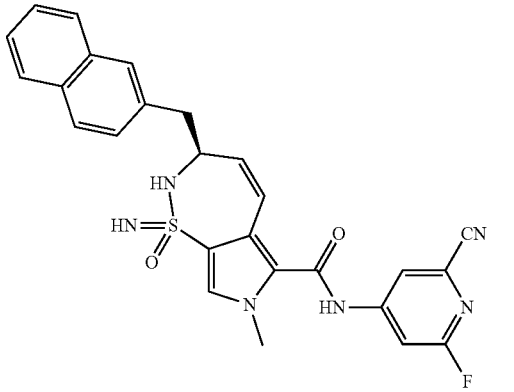 [SMILES: Cn1cc2c(c1C(=O)Nc1cc(F)nc(C#N)c1)C=C[C@H](Cc1ccc3ccccc3c1)NS2(=N)=O] | 501 | Peak2 (HPLC) |
| 10yy1 | 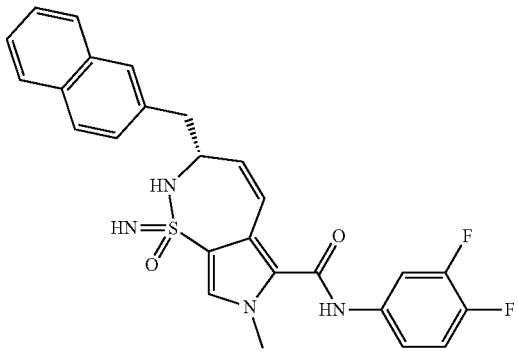 [SMILES: Cn1cc2c(c1C(=O)Nc1ccc(F)c(F)c1)C=C[C@@H](Cc1ccc3ccccc3c1)NS2(=N)=O] | 493 | Peak1 (HPLC) |

TABLE 1-continued
| No. | Structure | Mass Spectrum ESI-MS, (M + H) | Remark |
|---|---|---|---|
| 10yy2 | 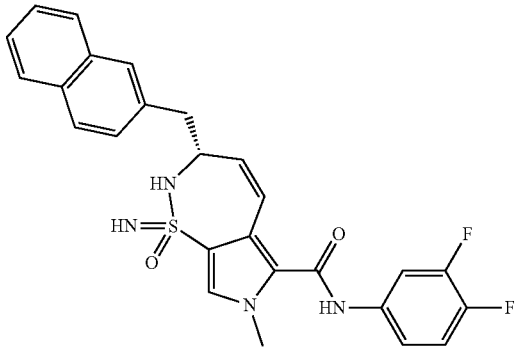 [SMILES: Cn1cc2c(c1C(=O)Nc1ccc(F)c(F)c1)C=C[C@@H](Cc1ccc3ccccc3c1)NS2(=N)=O] | 493 | Peak2 (HPLC) |
| 10zz1 | 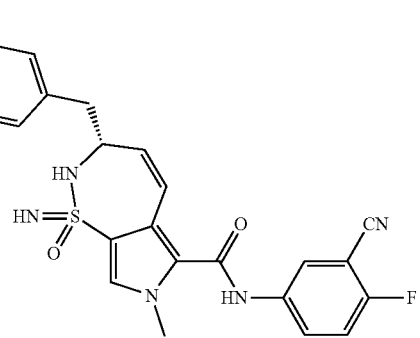 | 500 | Peak1 (HPLC) |
| 10zz2 | 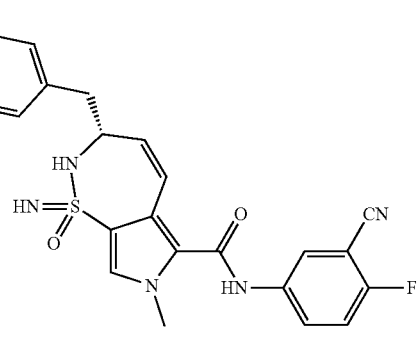 | 500 | Peak2 (HPLC) |
| 10aaa1 | 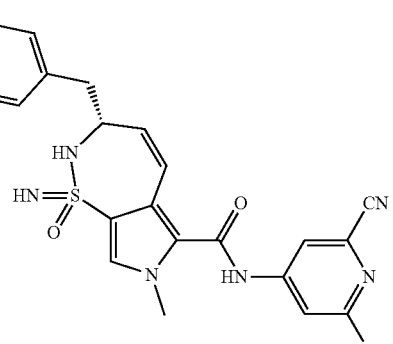 | 501 | Peak1 (HPLC) |

TABLE 1-continued
| No. | Structure | Mass Spectrum ESI-MS, (M + H) | Remark |
|---|---|---|---|
| 10aaa2 | 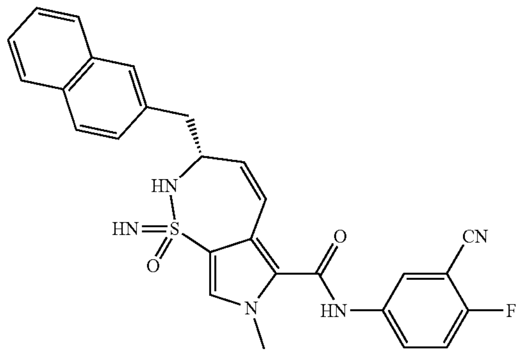 [SMILES: Cn1cc2c(c1C(=O)Nc1ccc(F)c(C#N)c1)C=C[C@@H](Cc1ccc3ccccc3c1)NS2(=N)=O] | 501 | Peak2 (HPLC) |
| 10bbb1 | 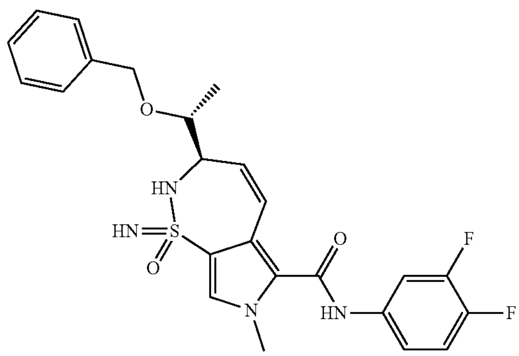 [SMILES: C[C@@H](OCc1ccccc1)[C@H]1C=Cc2c(cn(C)c2C(=O)Nc2ccc(F)c(F)c2)S(=N)(=O)N1] | 487 | Peak1 (HPLC) |
| 10bbb2 | 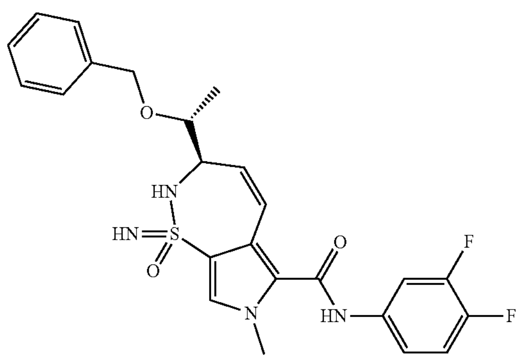 | 487 | Peak2 (HPLC) |
| 10ccc1 | 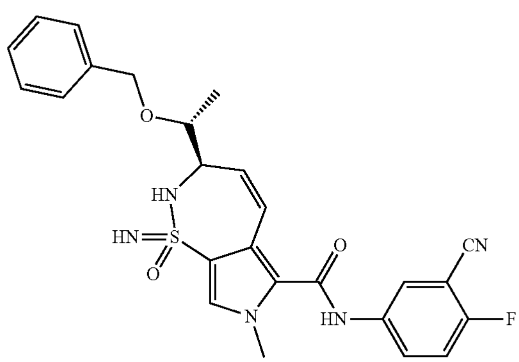 | 494 | Peak1 (HPLC) |

TABLE 1-continued
| No. | Structure | Mass Spectrum ESI-MS, (M + H) | Remark |
|---|---|---|---|
| 10ccc2 | 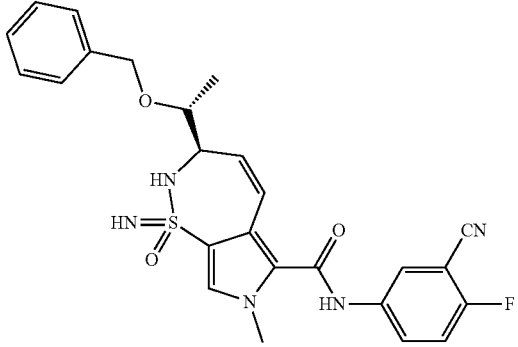 | 494 | Peak2 (HPLC) |
| 10ddd1 | 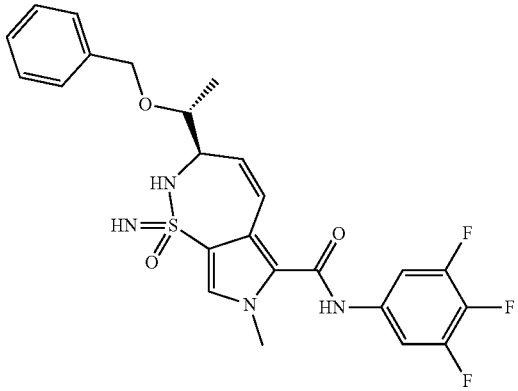 [SMILES: C[C@@H](OCc1ccccc1)[C@H]1C=Cc2c(cn(C)c2C(=O)Nc2cc(F)c(F)c(F)c2)S(=N)(=O)N1] | 505 | Peak1 (HPLC) |
| 10ddd2 | 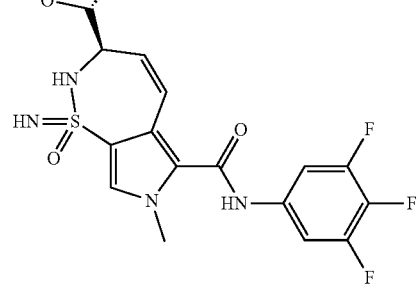 | 505 | Peak2 (HPLC) |
| 10eee1 | 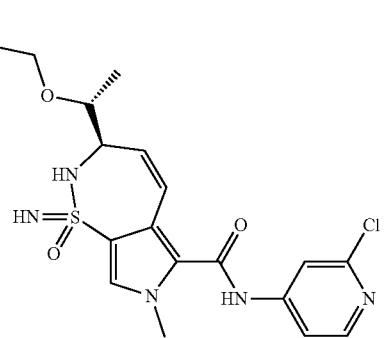 | 486 | Peak1 (HPLC) |

TABLE 1-continued
| No. | Structure | Mass Spectrum ESI-MS, (M + H) | Remark |
|---|---|---|---|
| 10eee2 | 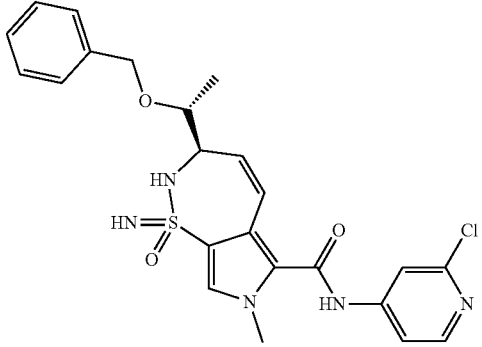 [SMILES: C[C@@H](OCc1ccccc1)[C@H]1C=Cc2c(cn(C)c2C(=O)Nc2ccnc(Cl)c2)S(=N)(=O)N1] | 486 | Peak2 (HPLC) |
| 10fff1 | 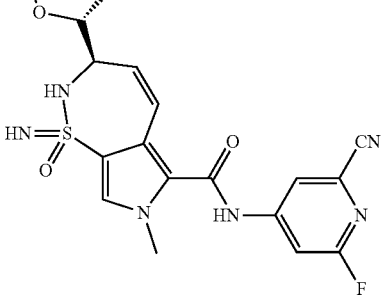 | 495 | Peak1 (HPLC) |
| 10fff2 | 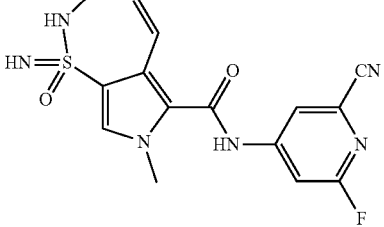 | 495 | Peak2 (HPLC) |
| 10ggg1 | 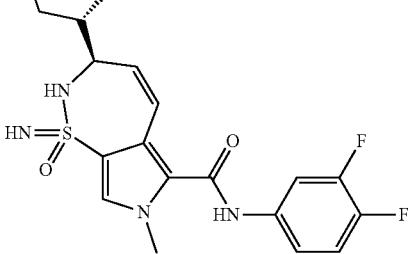 | 485 | Peak1 (HPLC) |

TABLE 1-continued
| No. | Structure | Mass Spectrum ESI-MS, (M + H) | Remark |
| --- | --- | --- | --- |
| 10ggg2 | 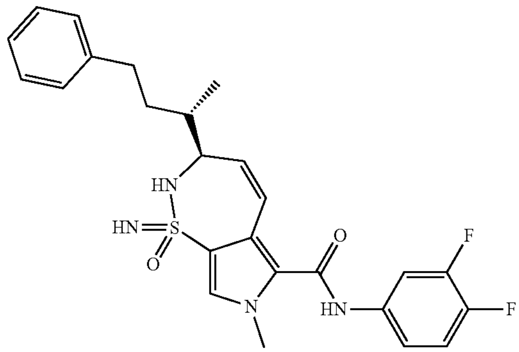 | 485 | Peak2 (HPLC) |
| 10hhh1 | 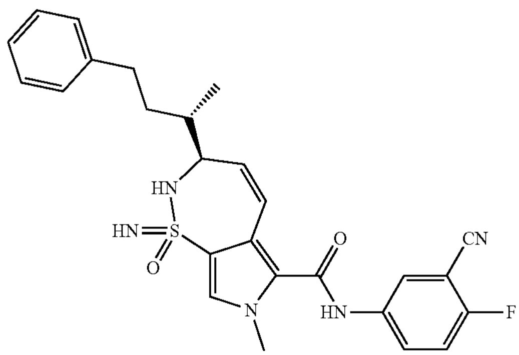 [SMILES: C[C@@H](CCc1ccccc1)[C@H]1C=Cc2c(cn(C)c2C(=O)Nc2ccc(F)c(C#N)c2)S(=N)(=O)N1] | 492 | Peak1 (HPLC) |
| 10hhh2 | 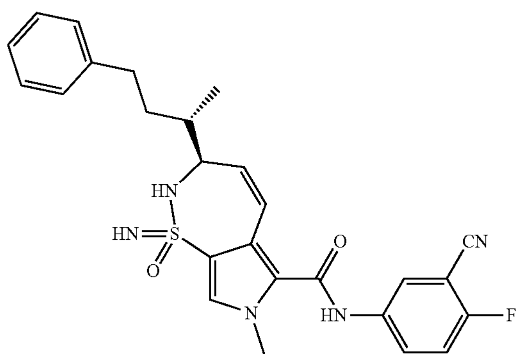 [SMILES: C[C@@H](CCc1ccccc1)[C@H]1C=Cc2c(cn(C)c2C(=O)Nc2ccc(F)c(C#N)c2)S(=N)(=O)N1] | 492 | Peak2 (HPLC) |
| 10iii1 | 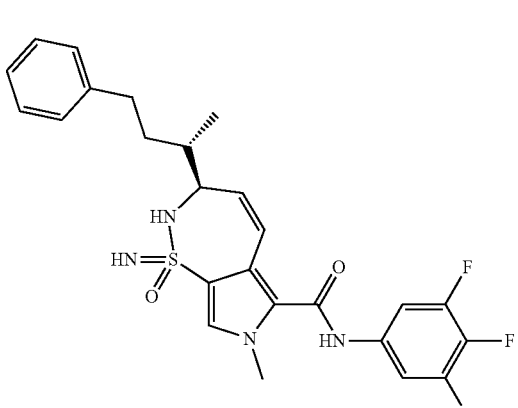 | 503 | Peak1 (HPLC) |

TABLE 1-continued
| No. | Structure | Mass Spectrum ESI-MS, (M + H) | Remark |
|---|---|---|---|
| 10iii2 | 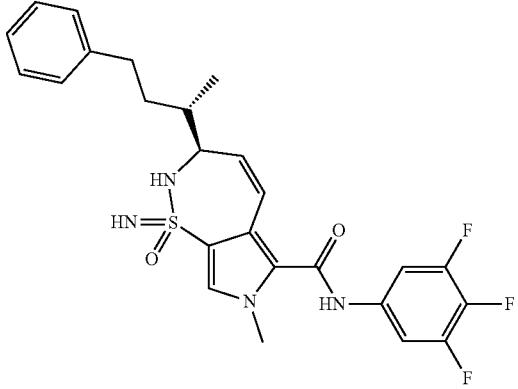 [SMILES: C[C@@H](CCc1ccccc1)[C@H]1C=Cc2c(cn(C)c2C(=O)Nc2cc(F)c(F)c(F)c2)S(=N)(=O)N1] | 503 | Peak2 (HPLC) |
| 10jjj1 | 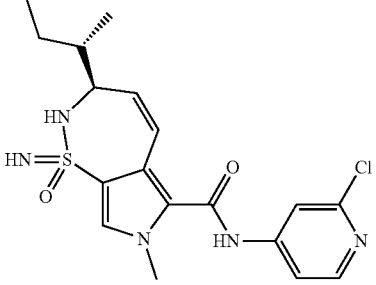 | 484 | Peak1 (HPLC) |
| 10jjj2 | 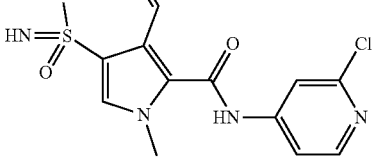 | 484 | Peak2 (HPLC) |
| 10kkk1 | 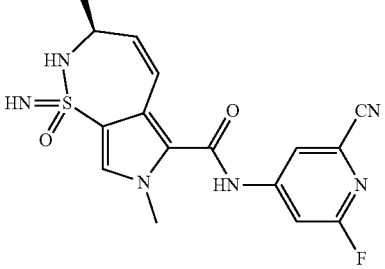 | 493 | Peak1 (HPLC) |

TABLE 1-continued

| No. | Structure | Mass Spectrum ESI-MS, (M + H) | Remark |
|---|---|---|---|
| 10kkk2 | 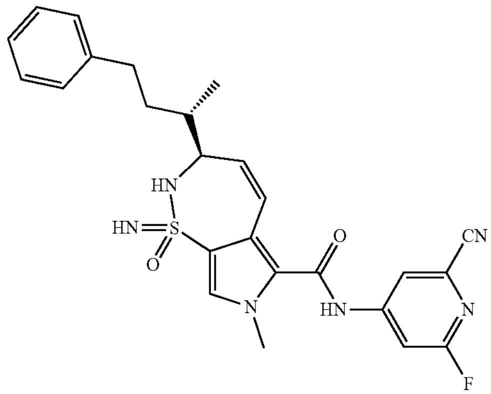 [SMILES: C[C@@H](CCc1ccccc1)[C@H]1C=Cc2c(cn(C)c2C(=O)Nc2cc(F)nc(C#N)c2)S(=N)(=O)N1] | 493 | Peak2 (HPLC) |
| 10mmm1 | 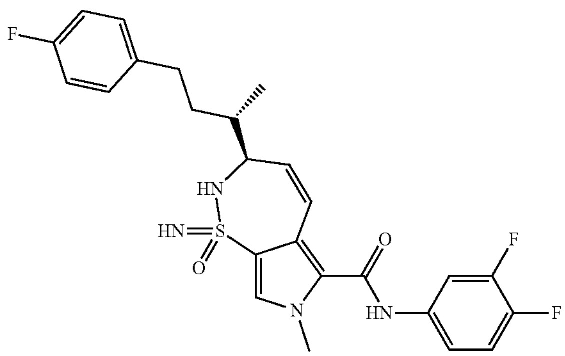 [SMILES: C[C@@H](CCc1ccc(F)cc1)[C@H]1C=Cc2c(cn(C)c2C(=O)Nc2ccc(F)c(F)c2)S(=N)(=O)N1] | 503 | Peak1 (HPLC) |
| 10mmm2 | 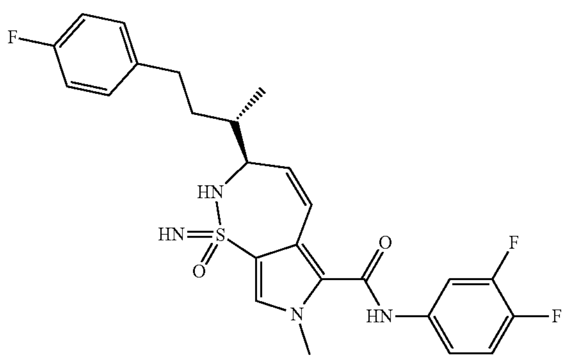 [SMILES: C[C@@H](CCc1ccc(F)cc1)[C@H]1C=Cc2c(cn(C)c2C(=O)Nc2ccc(F)c(F)c2)S(=N)(=O)N1] | 503 | Peak2 (HPLC) |
| 10nnn1 | 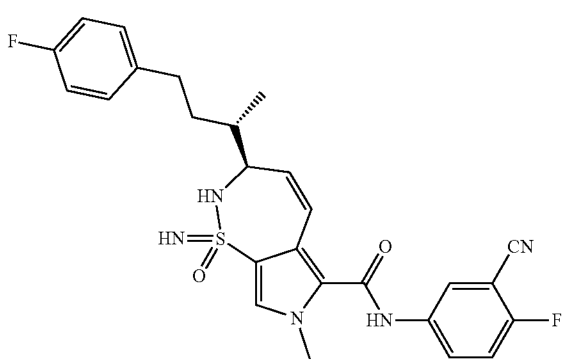 [SMILES: C[C@@H](CCc1ccc(F)cc1)[C@H]1C=Cc2c(cn(C)c2C(=O)Nc2ccc(F)c(C#N)c2)S(=N)(=O)N1] | 510 | Peak1 (HPLC) |

TABLE 1-continued

| No. | Structure | Mass Spectrum ESI-MS, (M + H) | Remark |
| --- | --- | --- | --- |
| 10nnn2 | 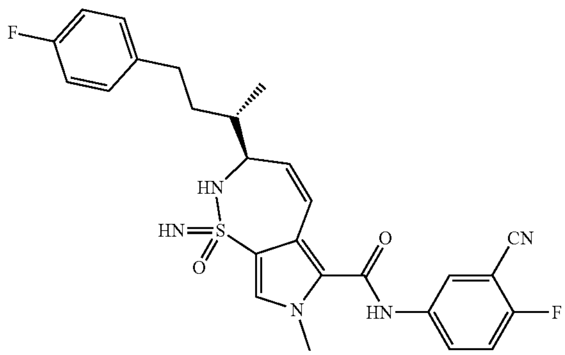 [SMILES: C[C@@H](CCc1ccc(F)cc1)[C@H]1C=Cc2c(cn(C)c2C(=O)Nc2ccc(F)c(C#N)c2)S(=N)(=O)N1] | 510 | Peak2 (HPLC) |
| 10ooo1 | 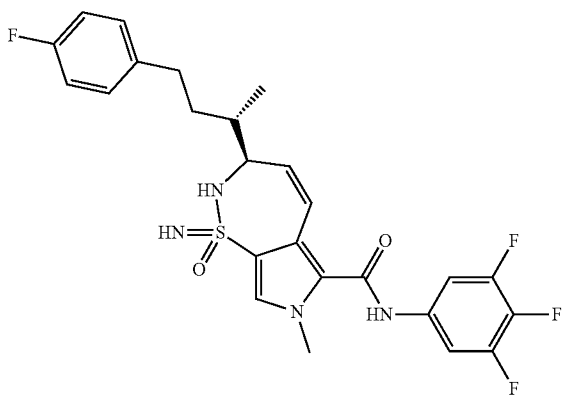 | 521 | Peak1 (HPLC) |
| 10ooo2 | 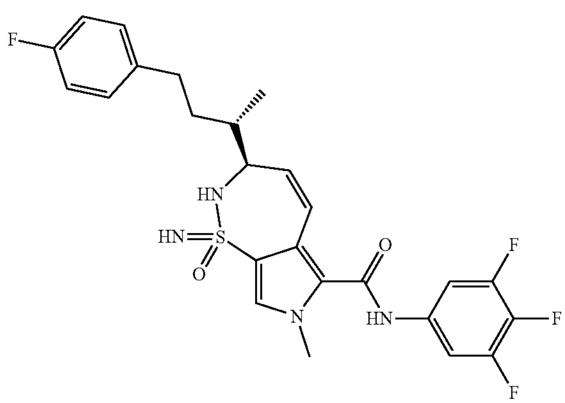 | 521 | Peak2 (HPLC) |
| 10ppp1 | 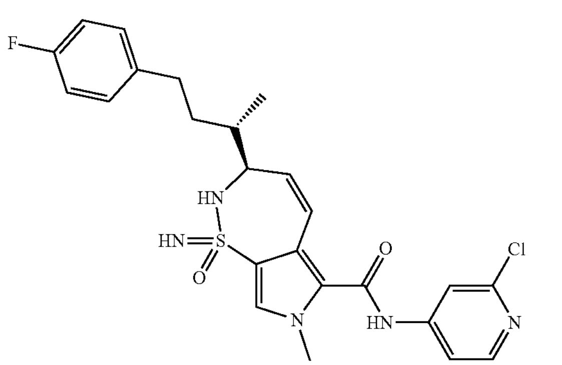 [SMILES: C[C@@H](CCc1ccc(F)cc1)[C@H]1C=Cc2c(cn(C)c2C(=O)Nc2ccnc(Cl)c2)S(=N)(=O)N1] | 502 | Peak1 (HPLC) |

TABLE 1-continued

| No. | Structure | Mass Spectrum ESI-MS, (M + H) | Remark |
|---|---|---|---|
| 10ppp2 | 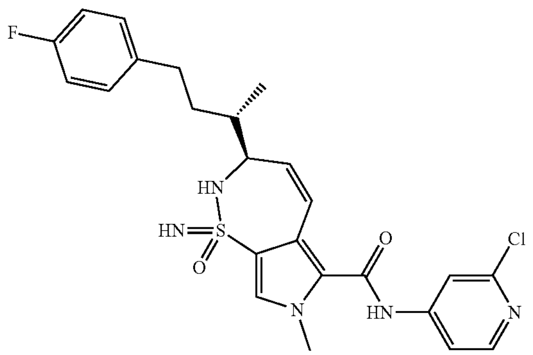 [SMILES: C[C@@H](CCc1ccc(F)cc1)[C@H]1C=Cc2c(cn(C)c2C(=O)Nc2ccnc(Cl)c2)S(=N)(=O)N1] | 502 | Peak2 (HPLC) |
| 10qqq1 | 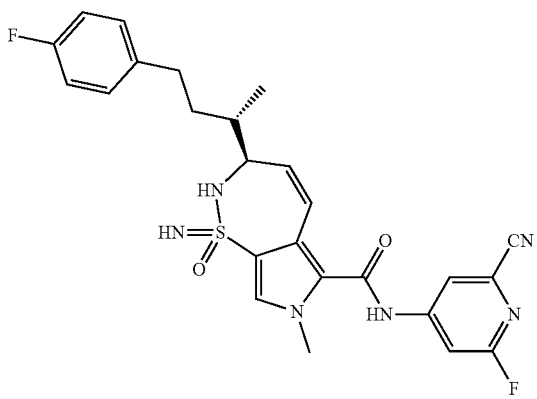 [SMILES: C[C@@H](CCc1ccc(F)cc1)[C@H]1C=Cc2c(cn(C)c2C(=O)Nc2cc(F)nc(C#N)c2)S(=N)(=O)N1] | 511 | Peak1 (HPLC) |
| 10qqq2 | 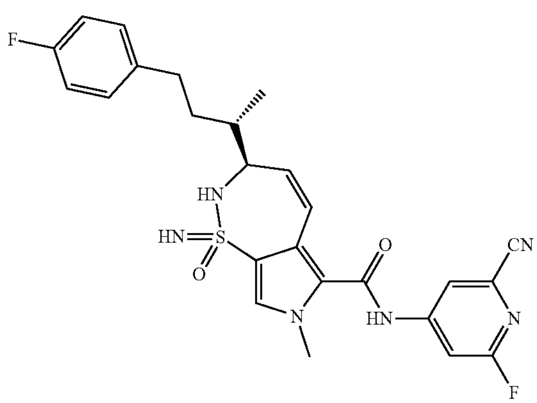 [SMILES: C[C@@H](CCc1ccc(F)cc1)[C@H]1C=Cc2c(cn(C)c2C(=O)Nc2cc(F)nc(C#N)c2)S(=N)(=O)N1] | 511 | Peak2 (HPLC) |
| 10rrr1 | 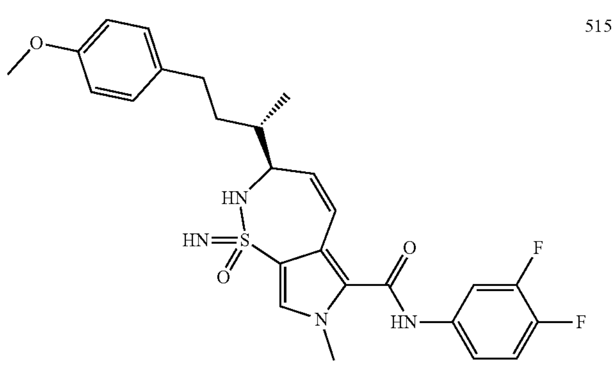 | 515 | Peak1 (HPLC) |

TABLE 1-continued
| No. | Structure | Mass Spectrum ESI-MS, (M + H) | Remark |
|---|---|---|---|
| 10rrr2 | 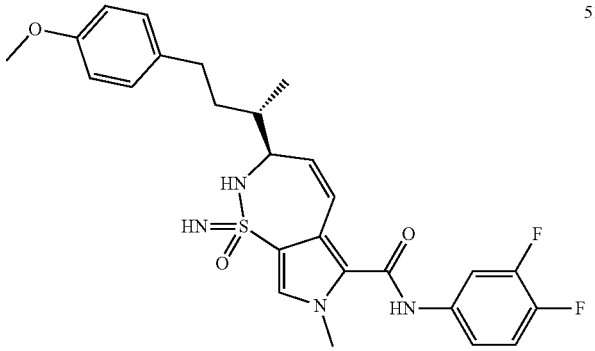 | 515 | Peak2 (HPLC) |
| 10sss1 | 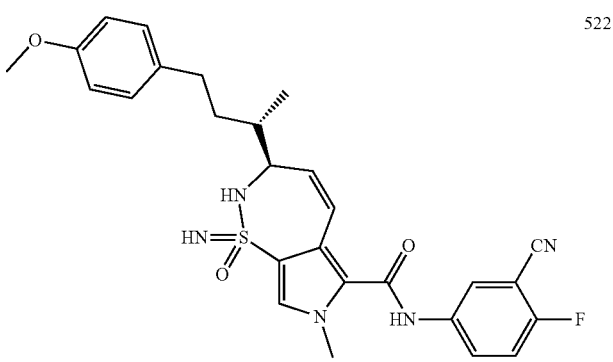 | 522 | Peak1 (HPLC) |
| 10sss2 | 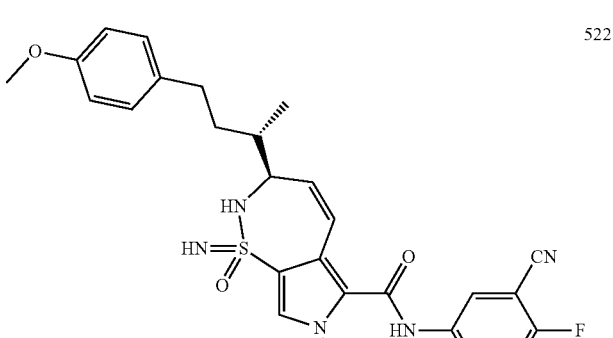 | 522 | Peak2 (HPLC) |
| 10ttt1 | 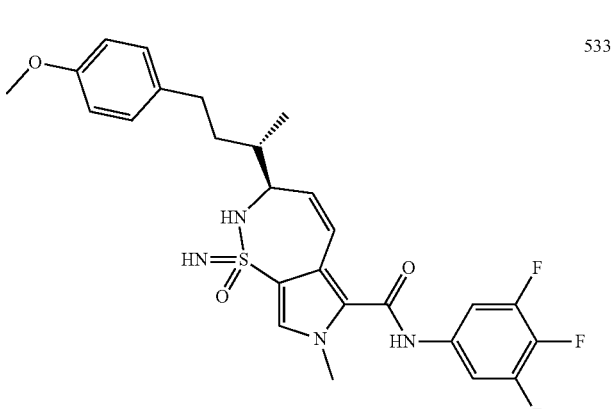 | 533 | Peak1 (HPLC) |

TABLE 1-continued
| No. | Structure | Mass Spectrum ESI-MS, (M + H) | Remark |
|---|---|---|---|
| 10ttt2 | 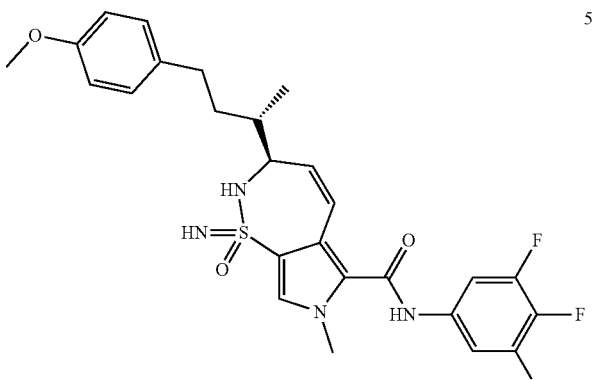 | 533 | Peak2 (HPLC) |
| 10uuu1 | 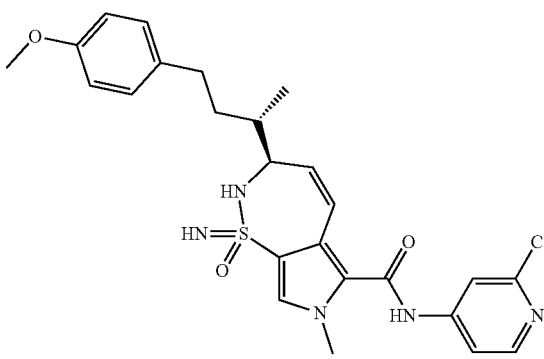 | 514 | Peak1 (HPLC) |
| 10uuu2 | 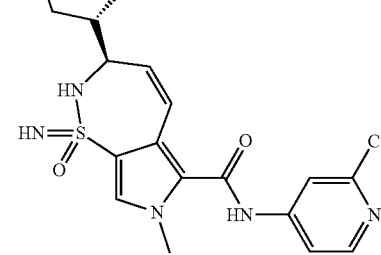 | 514 | Peak2 (HPLC) |
| 10vvv1 | 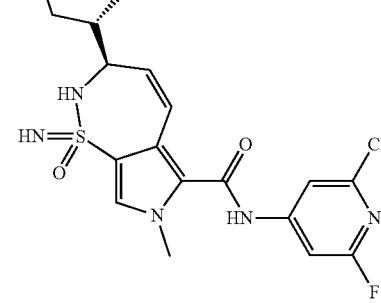 | 523 | Peak1 (HPLC) |

US 11,168,055 B2
81 82
TABLE 1-continued
| No. | Structure | Mass Spectrum ESI-MS, (M + H) | Remark |
|---|---|---|---|
| 10vvv2 | 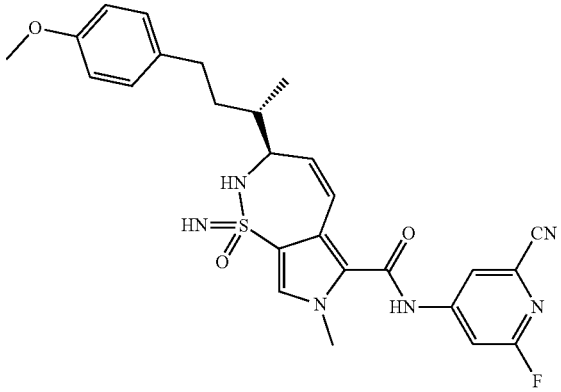 [SMILES: COc1ccc(CC[C@H](C)[C@H]2C=Cc3c(cn(C)c3C(=O)Nc3cc(F)nc(C#N)c3)S(=N)(=O)N2)cc1] | 523 | Peak2 (HPLC) |
| 10www1 | 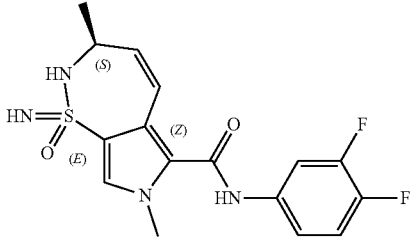 | 367 | Peak1 (HPLC) |
| 10www2 | 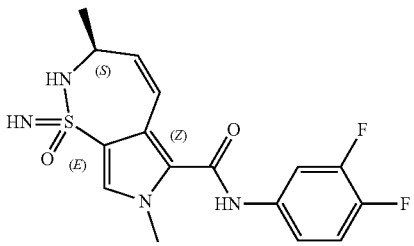 | 367 | Peak2 (HPLC) |
| 10xxx1 | 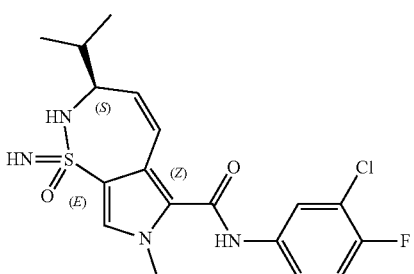 | 411 | Peak1 (HPLC) |
| 10xxx2 | 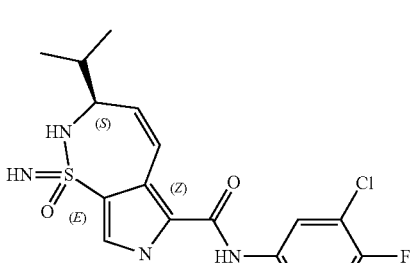 | 411 | Peak2 (HPLC) |

TABLE 1-continued

| No. | Structure | Mass Spectrum ESI-MS, (M + H) | Remark |
|---|---|---|---|
| 20a1 | 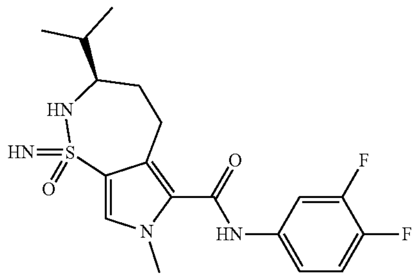 [SMILES: CC(C)[C@H]1CCc2c(cn(C)c2C(=O)Nc2ccc(F)c(F)c2)S(=N)(=O)N1] | 397 | Peak1 (HPLC) |
| 20a2 | 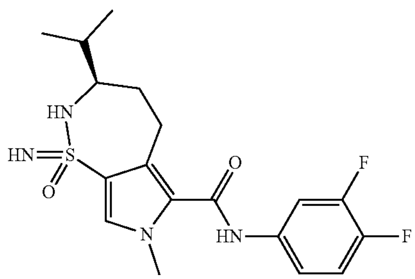 [SMILES: CC(C)[C@H]1CCc2c(cn(C)c2C(=O)Nc2ccc(F)c(F)c2)S(=N)(=O)N1] | 397 | Peak2 (HPLC) |
| 20b1 | 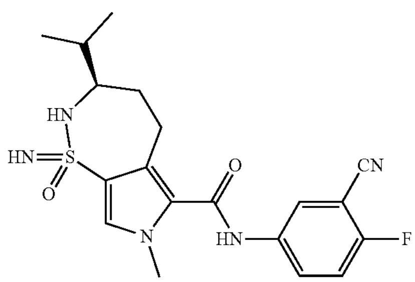 [SMILES: CC(C)[C@H]1CCc2c(cn(C)c2C(=O)Nc2ccc(F)c(C#N)c2)S(=N)(=O)N1] | 404 | Peak1 (HPLC) |
| 20b2 | 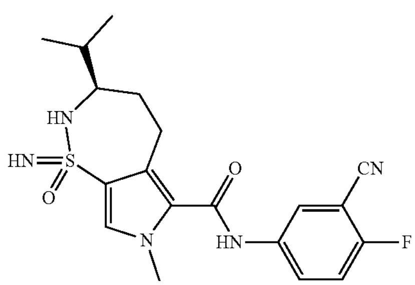 [SMILES: CC(C)[C@H]1CCc2c(cn(C)c2C(=O)Nc2ccc(F)c(C#N)c2)S(=N)(=O)N1] | 404 | Peak2 (HPLC) |
| 20c1 | 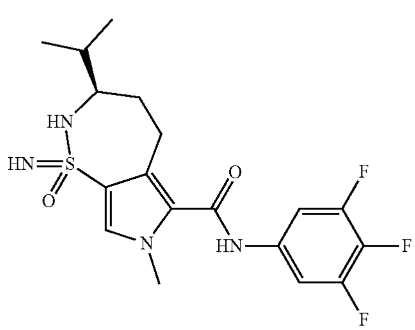 [SMILES: CC(C)[C@H]1CCc2c(cn(C)c2C(=O)Nc2cc(F)c(F)c(F)c2)S(=N)(=O)N1] | 415 | Peak1 (HPLC) |

TABLE 1-continued

| No. | Structure | Mass Spectrum ESI-MS, (M + H) | Remark |
|---|---|---|---|
| 20c2 | 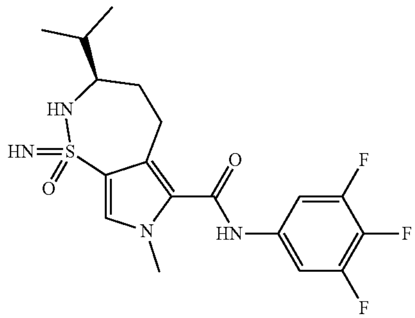 [SMILES: CC(C)[C@H]1CCc2c(cn(C)c2C(=O)Nc2cc(F)c(F)c(F)c2)S(=N)(=O)N1] | 415 | Peak2 (HPLC) |
| 20d1 | 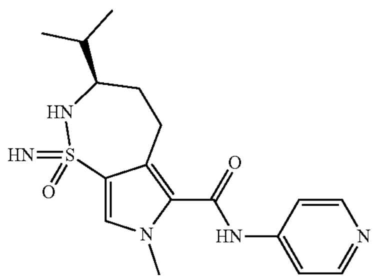 [SMILES: CC(C)[C@H]1CCc2c(cn(C)c2C(=O)Nc2ccncc2)S(=N)(=O)N1] | 362 | Peak1 (HPLC) |
| 20d2 | 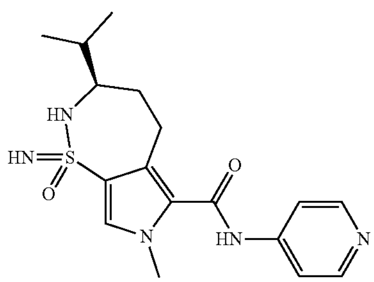 [SMILES: CC(C)[C@H]1CCc2c(cn(C)c2C(=O)Nc2ccncc2)S(=N)(=O)N1] | 362 | Peak2 (HPLC) |
| 20e1 | 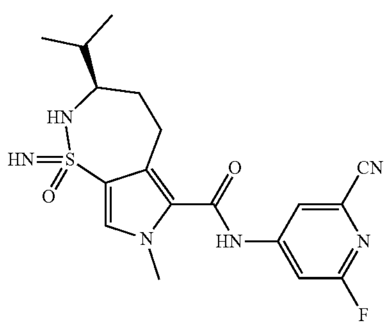 [SMILES: CC(C)[C@H]1CCc2c(cn(C)c2C(=O)Nc2cc(F)nc(C#N)c2)S(=N)(=O)N1] | 405 | Peak1 (HPLC) |
| 20e2 | 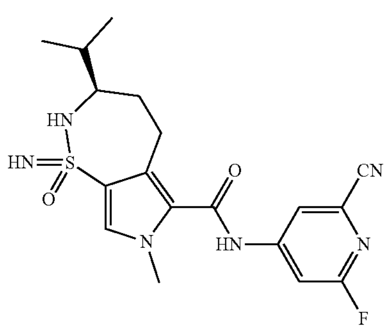 [SMILES: CC(C)[C@H]1CCc2c(cn(C)c2C(=O)Nc2cc(F)nc(C#N)c2)S(=N)(=O)N1] | 405 | Peak2 (HPLC) |

TABLE 1-continued

| No. | Structure | Mass Spectrum ESI-MS, (M + H) | Remark |
|---|---|---|---|
| 20f1 | 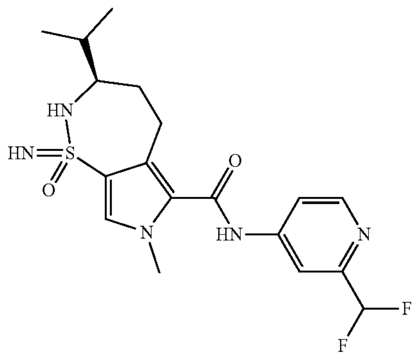 [SMILES: CC(C)[C@H]1CCc2c(cn(C)c2C(=O)Nc2ccnc(C(F)F)c2)S(=N)(=O)N1] | 412 | Peak1 (HPLC) |
| 20f2 | 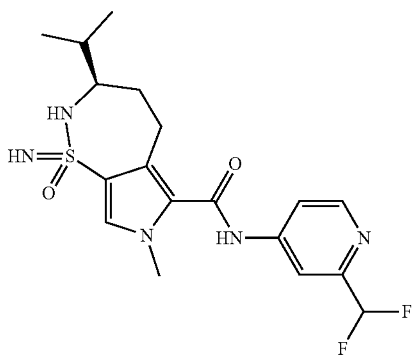 [SMILES: CC(C)[C@H]1CCc2c(cn(C)c2C(=O)Nc2ccnc(C(F)F)c2)S(=N)(=O)N1] | 412 | Peak2 (HPLC) |
| 20g1 | 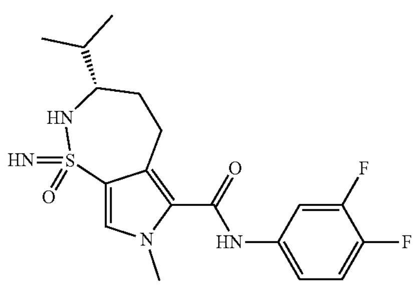 [SMILES: CC(C)[C@@H]1CCc2c(cn(C)c2C(=O)Nc2ccc(F)c(F)c2)S(=N)(=O)N1] | 397 | Peak1 (HPLC) |
| 20g2 | 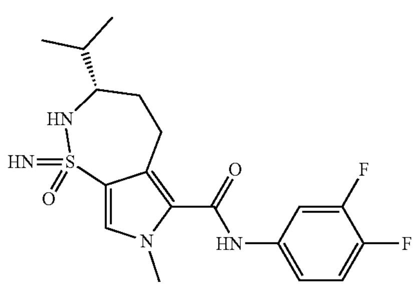 [SMILES: CC(C)[C@@H]1CCc2c(cn(C)c2C(=O)Nc2ccc(F)c(F)c2)S(=N)(=O)N1] | 397 | Peak2 (HPLC) |
| 20h1 | 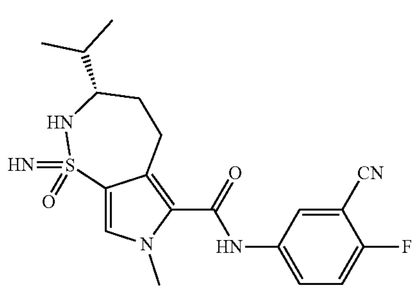 [SMILES: CC(C)[C@@H]1CCc2c(cn(C)c2C(=O)Nc2ccc(F)c(C#N)c2)S(=N)(=O)N1] | 404 | Peak1 (HPLC) |

TABLE 1-continued

| No. | Structure | Mass Spectrum ESI-MS, (M + H) | Remark |
|---|---|---|---|
| 20h2 | 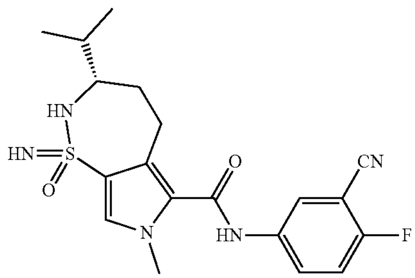 [SMILES: CC(C)[C@@H]1CCc2c(cn(C)c2C(=O)Nc2ccc(F)c(C#N)c2)S(=N)(=O)N1] | 404 | Peak2 (HPLC) |
| 20i1 | 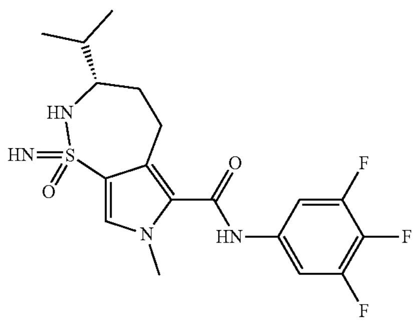 [SMILES: CC(C)[C@@H]1CCc2c(cn(C)c2C(=O)Nc2cc(F)c(F)c(F)c2)S(=N)(=O)N1] | 415 | Peak1 (HPLC) |
| 20i2 | 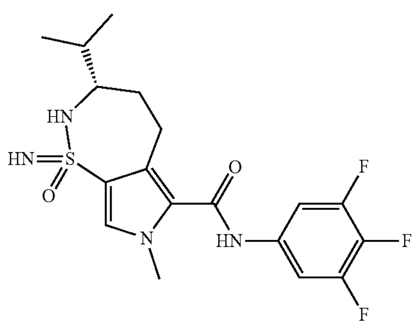 [SMILES: CC(C)[C@@H]1CCc2c(cn(C)c2C(=O)Nc2cc(F)c(F)c(F)c2)S(=N)(=O)N1] | 415 | Peak2 (HPLC) |
| 20j1 | 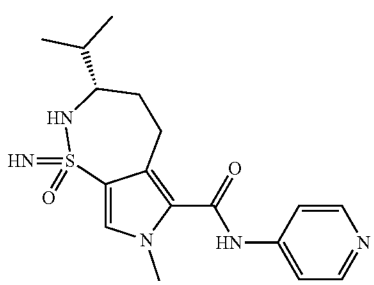 [SMILES: CC(C)[C@@H]1CCc2c(cn(C)c2C(=O)Nc2ccncc2)S(=N)(=O)N1] | 362 | Peak1 (HPLC) |
| 20j2 | 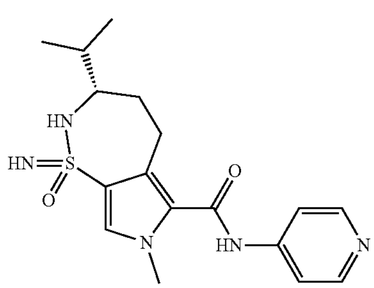 [SMILES: CC(C)[C@@H]1CCc2c(cn(C)c2C(=O)Nc2ccncc2)S(=N)(=O)N1] | 362 | Peak2 (HPLC) |

TABLE 1-continued
| No. | Structure | Mass Spectrum ESI-MS, (M + H) | Remark |
|---|---|---|---|
| 20k1 | 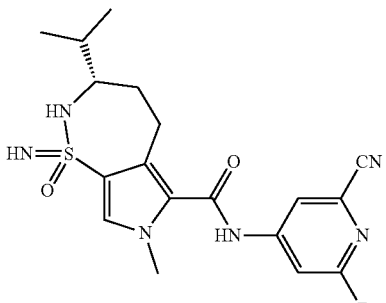 | 405 | Peak1 (HPLC) |
| 20k2 | 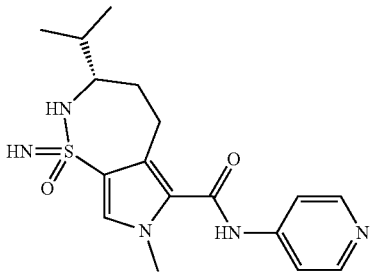 [SMILES: CC(C)[C@@H]1CCc2c(cn(C)c2C(=O)Nc2ccncc2)S(=N)(=O)N1] | 405 | Peak2 (HPLC) |
| 20m1 | 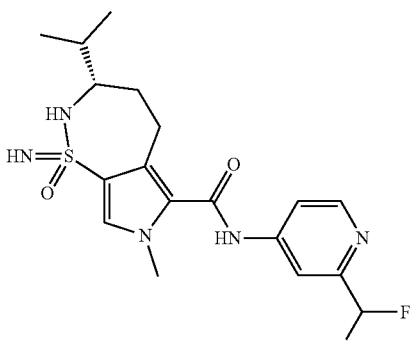 | 412 | Peak1 (HPLC) |
| 10m2 | 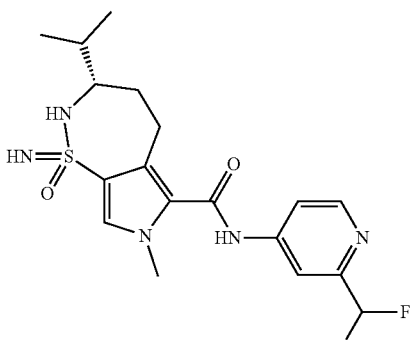 | 412 | Peak2 (HPLC) |

TABLE 1-continued

| No. | Structure | Mass Spectrum ESI-MS, (M + H) | Remark |
|---|---|---|---|
| 20n1 | 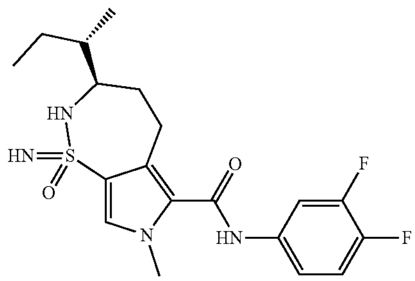 [SMILES: CC[C@H](C)[C@H]1CCc2c(cn(C)c2C(=O)Nc2ccc(F)c(F)c2)S(=N)(=O)N1] | 411 | Peak1 (HPLC) |
| 20n2 | 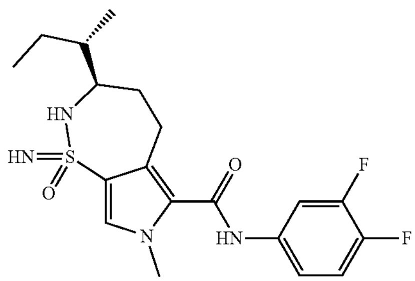 [SMILES: CC[C@H](C)[C@H]1CCc2c(cn(C)c2C(=O)Nc2ccc(F)c(F)c2)S(=N)(=O)N1] | 411 | Peak2 (HPLC) |
| 20o1 | 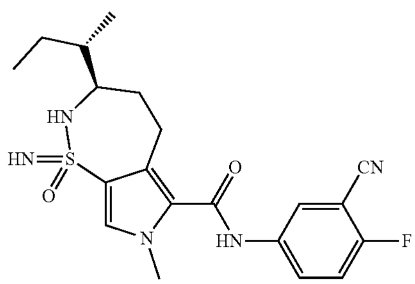 [SMILES: CC[C@H](C)[C@H]1CCc2c(cn(C)c2C(=O)Nc2ccc(F)c(C#N)c2)S(=N)(=O)N1] | 418 | Peak1 (HPLC) |
| 20o2 | 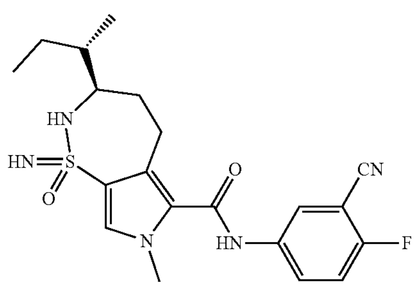 [SMILES: CC[C@H](C)[C@H]1CCc2c(cn(C)c2C(=O)Nc2ccc(F)c(C#N)c2)S(=N)(=O)N1] | 418 | Peak2 (HPLC) |
| 20p1 | 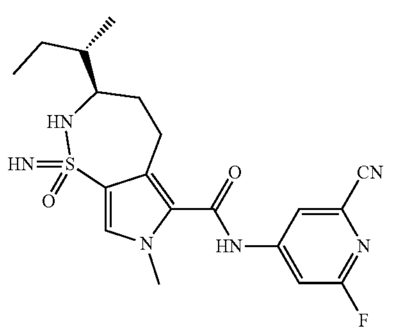 [SMILES: CC[C@H](C)[C@H]1CCc2c(cn(C)c2C(=O)Nc2cc(F)nc(C#N)c2)S(=N)(=O)N1] | 419 | Peak1 (HPLC) |

TABLE 1-continued

| No. | Structure | Mass Spectrum ESI-MS, (M + H) | Remark |
|---|---|---|---|
| 20p2 | 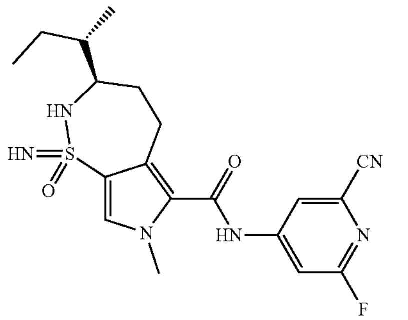 [SMILES: CC[C@H](C)[C@H]1CCc2c(cn(C)c2C(=O)Nc2cc(F)nc(C#N)c2)S(=N)(=O)N1] | 419 | Peak2 (HPLC) |
| 20q1 | 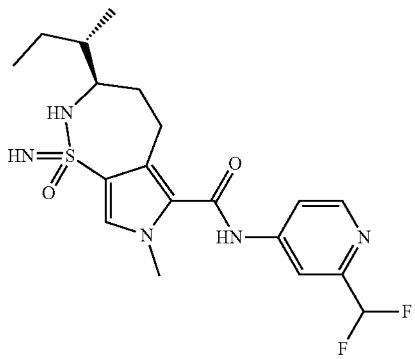 | 426 | Peak1 (HPLC) |
| 20q2 | 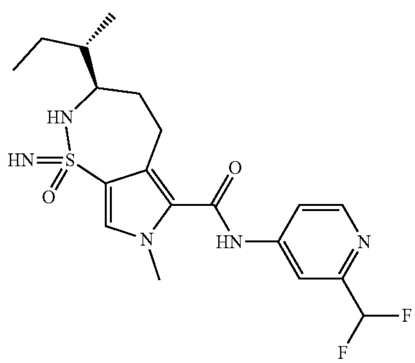 [SMILES: CC[C@H](C)[C@H]1CCc2c(cn(C)c2C(=O)Nc2ccnc(C(F)F)c2)S(=N)(=O)N1] | 426 | Peak2 (HPLC) |
| 20r1 | 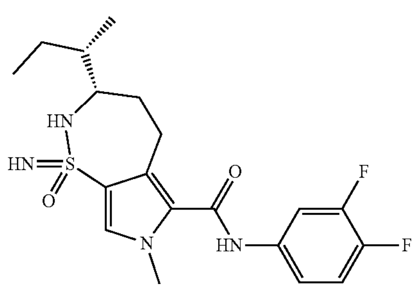 [SMILES: CC[C@H](C)[C@@H]1CCc2c(cn(C)c2C(=O)Nc2ccc(F)c(F)c2)S(=N)(=O)N1] | 411 | Peak1 (HPLC) |

TABLE 1-continued

| No. | Structure | Mass Spectrum ESI-MS, (M + H) | Remark |
|---|---|---|---|
| 20r2 | 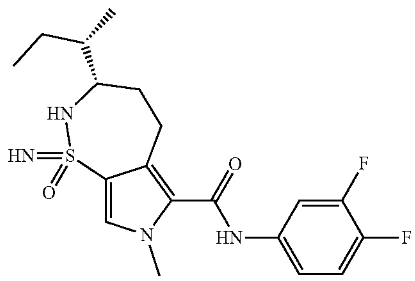 [SMILES: CC[C@H](C)[C@@H]1CCc2c(cn(C)c2C(=O)Nc2ccc(F)c(F)c2)S(=N)(=O)N1] | 411 | Peak2 (HPLC) |
| 20s1 | 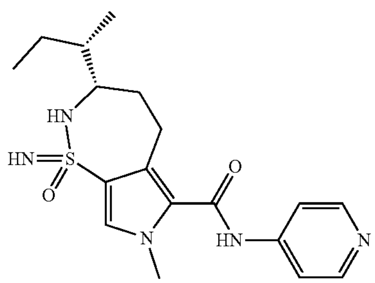 [SMILES: CC[C@H](C)[C@@H]1CCc2c(cn(C)c2C(=O)Nc2ccncc2)S(=N)(=O)N1] | 376 | Peak1 (HPLC) |
| 20s2 | 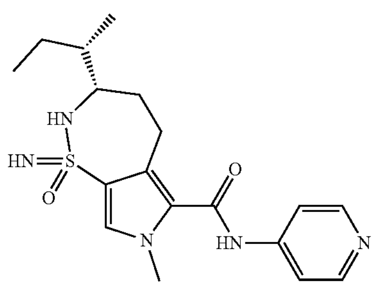 [SMILES: CC[C@H](C)[C@@H]1CCc2c(cn(C)c2C(=O)Nc2ccncc2)S(=N)(=O)N1] | 376 | Peak2 (HPLC) |
| 20t1 | 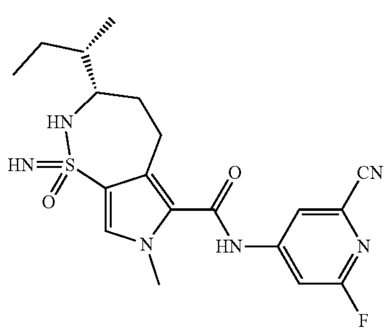 [SMILES: CC[C@H](C)[C@@H]1CCc2c(cn(C)c2C(=O)Nc2cc(F)nc(C#N)c2)S(=N)(=O)N1] | 419 | Peak1 (HPLC) |
| 20t2 | 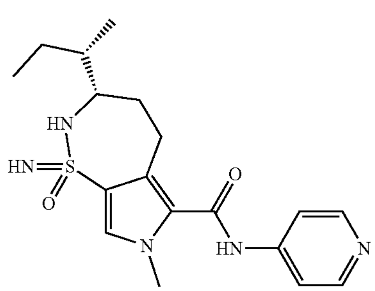 [SMILES: CC[C@H](C)[C@@H]1CCc2c(cn(C)c2C(=O)Nc2ccncc2)S(=N)(=O)N1] | 419 | Peak2 (HPLC) |

TABLE 1-continued

| No. | Structure | Mass Spectrum ESI-MS, (M + H) | Remark |
|---|---|---|---|
| 20u1 | 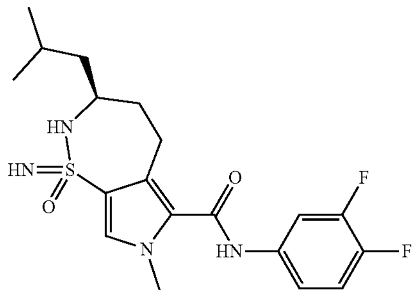 [SMILES: CC(C)C[C@H]1CCc2c(cn(C)c2C(=O)Nc2ccc(F)c(F)c2)S(=N)(=O)N1] | 411 | Peak1 (HPLC) |
| 20u2 | 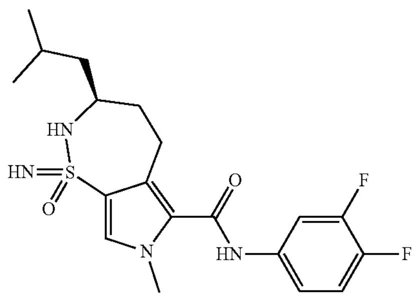 [SMILES: CC(C)C[C@H]1CCc2c(cn(C)c2C(=O)Nc2ccc(F)c(F)c2)S(=N)(=O)N1] | 411 | Peak2 (HPLC) |
| 20v1 | 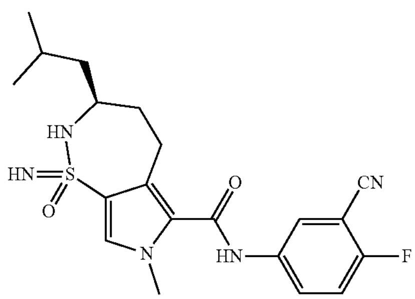 [SMILES: CC(C)C[C@H]1CCc2c(cn(C)c2C(=O)Nc2ccc(F)c(C#N)c2)S(=N)(=O)N1] | 418 | Peak1 (HPLC) |
| 20v2 | 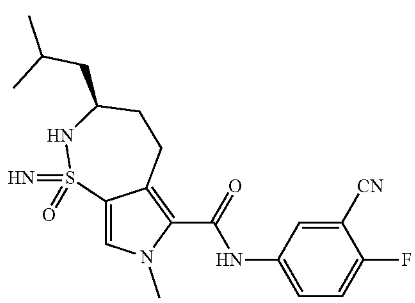 [SMILES: CC(C)C[C@H]1CCc2c(cn(C)c2C(=O)Nc2ccc(F)c(C#N)c2)S(=N)(=O)N1] | 418 | Peak2 (HPLC) |
| 20w1 | 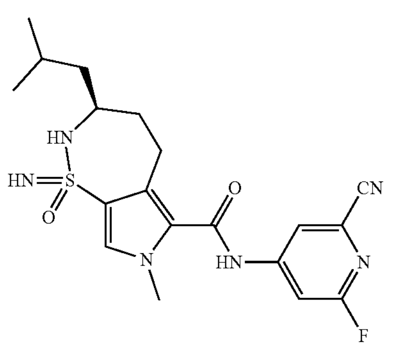 [SMILES: CC(C)C[C@H]1CCc2c(cn(C)c2C(=O)Nc2cc(F)nc(C#N)c2)S(=N)(=O)N1] | 419 | Peak1 (HPLC) |

TABLE 1-continued
| No. | Structure | Mass Spectrum ESI-MS, (M + H) | Remark |
|---|---|---|---|
| 20w2 | 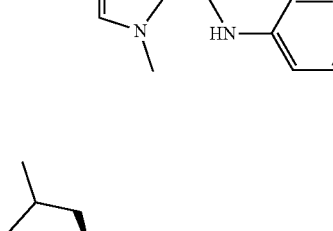 | 419 | Peak2 (HPLC) |
| 20x1 | 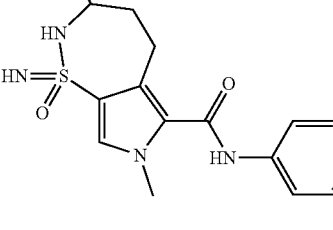 | 426 | Peak1 (HPLC) |
| 20x2 | 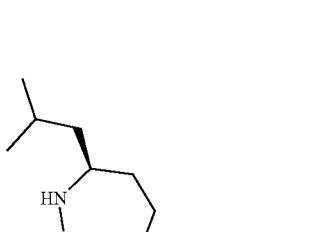 | 426 | Peak2 (HPLC) |
| 20y1 | 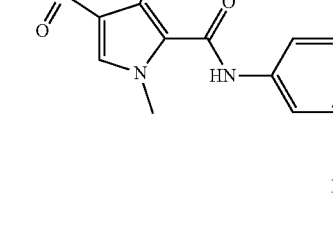 | 411 | Peak1 (HPLC) |

TABLE 1-continued

| No. | Structure | Mass Spectrum ESI-MS, (M + H) | Remark |
|---|---|---|---|
| 20y2 | 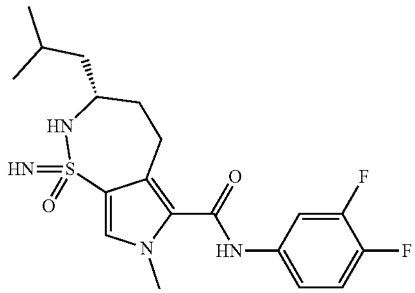 [SMILES: CC(C)C[C@@H]1CCc2c(cn(C)c2C(=O)Nc2ccc(F)c(F)c2)S(=N)(=O)N1] | 411 | Peak2 (HPLC) |
| 20z1 | 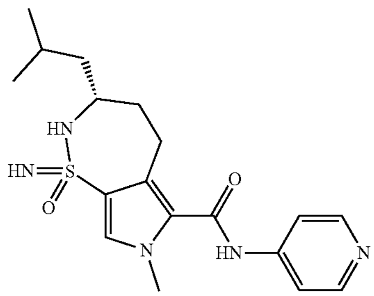 [SMILES: CC(C)C[C@@H]1CCc2c(cn(C)c2C(=O)Nc2ccncc2)S(=N)(=O)N1] | 376 | Peak1 (HPLC) |
| 20z2 | 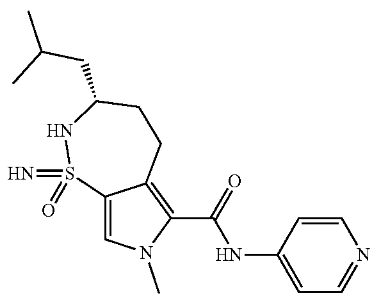 [SMILES: CC(C)C[C@@H]1CCc2c(cn(C)c2C(=O)Nc2ccncc2)S(=N)(=O)N1] | 376 | Peak2 (HPLC) |
| 20aa1 | 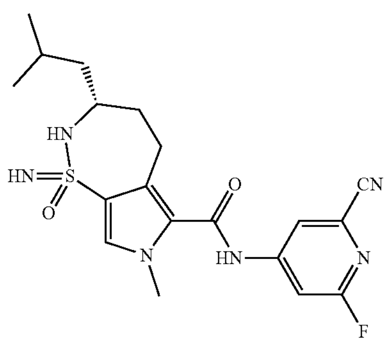 [SMILES: CC(C)C[C@@H]1CCc2c(cn(C)c2C(=O)Nc2cc(F)nc(C#N)c2)S(=N)(=O)N1] | 419 | Peak1 (HPLC) |
| 20aa2 | 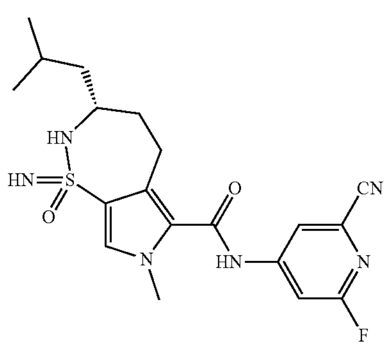 [SMILES: CC(C)C[C@@H]1CCc2c(cn(C)c2C(=O)Nc2cc(F)nc(C#N)c2)S(=N)(=O)N1] | 419 | Peak2 (HPLC) |

TABLE 1-continued

| No. | Structure | Mass Spectrum ESI-MS, (M + H) | Remark |
|---|---|---|---|
| 20bb1 | 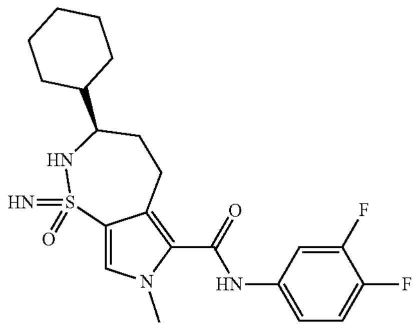 [SMILES: Cn1cc2c(c1C(=O)Nc1ccc(F)c(F)c1)CC[C@H](C1CCCCC1)NS2(=N)=O] | 437 | Peak1 (HPLC) |
| 20bb2 | 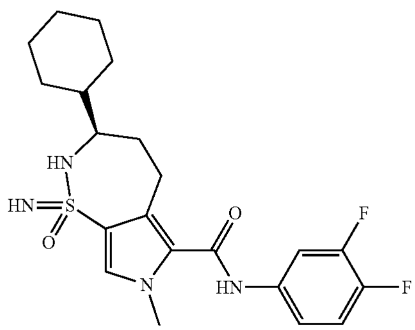 [SMILES: Cn1cc2c(c1C(=O)Nc1ccc(F)c(F)c1)CC[C@H](C1CCCCC1)NS2(=N)=O] | 437 | Peak2 (HPLC) |
| 20cc1 | 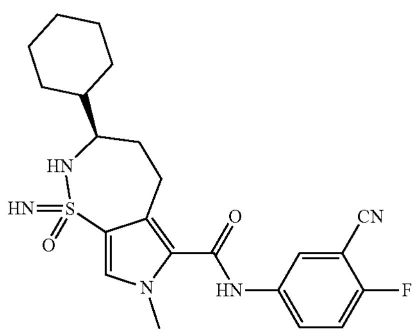 [SMILES: Cn1cc2c(c1C(=O)Nc1ccc(F)c(C#N)c1)CC[C@H](C1CCCCC1)NS2(=N)=O] | 444 | Peak1 (HPLC) |
| 20cc2 | 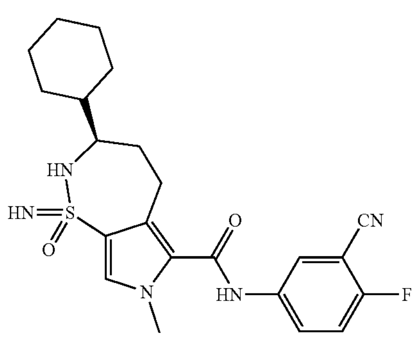 [SMILES: Cn1cc2c(c1C(=O)Nc1ccc(F)c(C#N)c1)CC[C@H](C1CCCCC1)NS2(=N)=O] | 444 | Peak2 (HPLC) |

TABLE 1-continued

| No. | Structure | Mass Spectrum ESI-MS, (M + H) | Remark |
|---|---|---|---|
| 20dd1 | 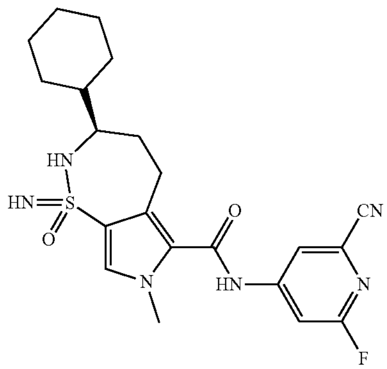 [SMILES: Cn1cc2c(c1C(=O)Nc1cc(F)nc(C#N)c1)CC[C@H](C1CCCCC1)NS2(=N)=O] | 445 | Peak1 (HPLC) |
| 20dd2 | 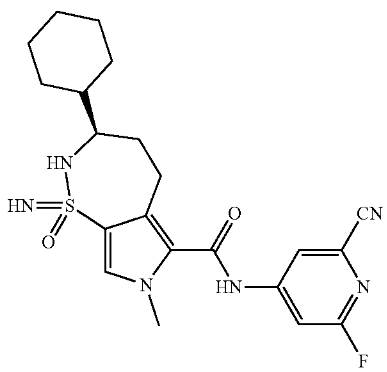 [SMILES: Cn1cc2c(c1C(=O)Nc1cc(F)nc(C#N)c1)CC[C@H](C1CCCCC1)NS2(=N)=O] | 445 | Peak2 (HPLC) |
| 20ee1 | 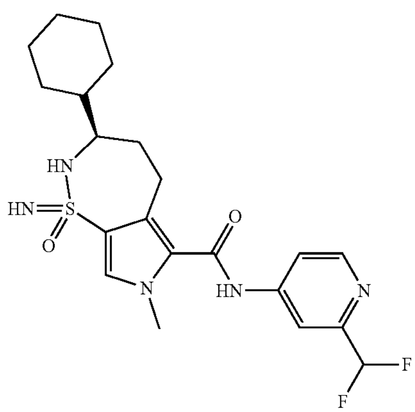 [SMILES: Cn1cc2c(c1C(=O)Nc1ccnc(C(F)F)c1)CC[C@H](C1CCCCC1)NS2(=N)=O] | 452 | Peak1 (HPLC) |
| 20ee2 | 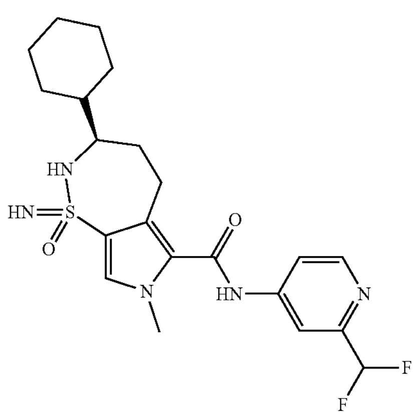 [SMILES: Cn1cc2c(c1C(=O)Nc1ccnc(C(F)F)c1)CC[C@H](C1CCCCC1)NS2(=N)=O] | 452 | Peak2 (HPLC) |

TABLE 1-continued

| No. | Structure | Mass Spectrum ESI-MS, (M + H) | Remark |
|---|---|---|---|
| 20ff1 | 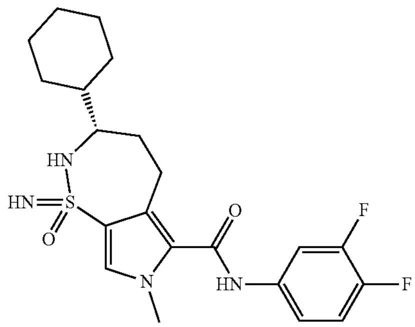 [SMILES: Cn1cc2c(c1C(=O)Nc1ccc(F)c(F)c1)CC[C@@H](C1CCCCC1)NS2(=N)=O] | 437 | Peak1 (HPLC) |
| 20ff2 | 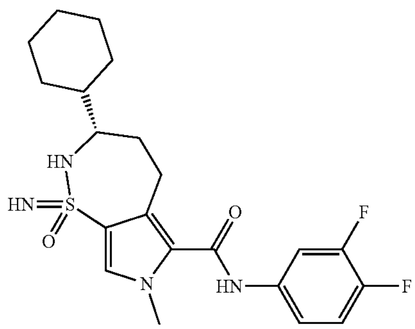 [SMILES: Cn1cc2c(c1C(=O)Nc1ccc(F)c(F)c1)CC[C@@H](C1CCCCC1)NS2(=N)=O] | 437 | Peak2 (HPLC) |
| 20gg1 | 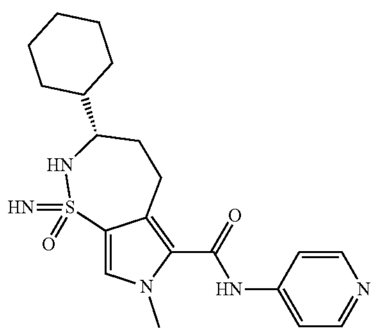 [SMILES: Cn1cc2c(c1C(=O)Nc1ccncc1)CC[C@@H](C1CCCCC1)NS2(=N)=O] | 402 | Peak1 (HPLC) |
| 20gg2 | 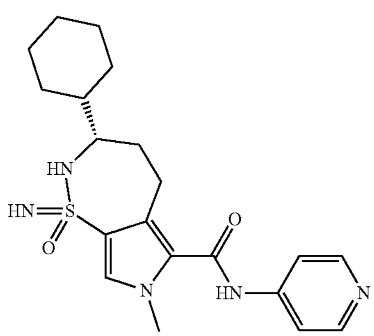 [SMILES: Cn1cc2c(c1C(=O)Nc1ccncc1)CC[C@@H](C1CCCCC1)NS2(=N)=O] | 402 | Peak2 (HPLC) |

TABLE 1-continued

| No. | Structure | Mass Spectrum ESI-MS, (M + H) | Remark |
|---|---|---|---|
| 20hh1 | 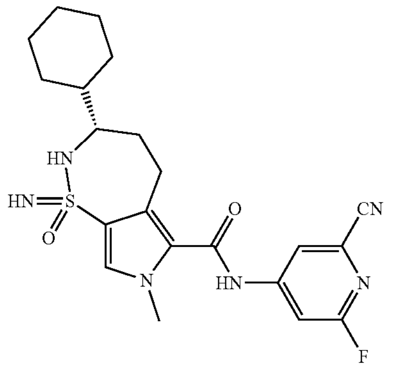 [SMILES: Cn1cc2c(c1C(=O)Nc1cc(F)nc(C#N)c1)CC[C@@H](C1CCCCC1)NS2(=N)=O] | 445 | Peak1 (HPLC) |
| 20hh2 | 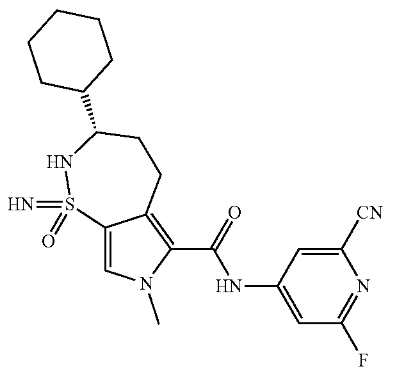 [SMILES: Cn1cc2c(c1C(=O)Nc1cc(F)nc(C#N)c1)CC[C@@H](C1CCCCC1)NS2(=N)=O] | 445 | Peak2 (HPLC) |
| 20ii1 | 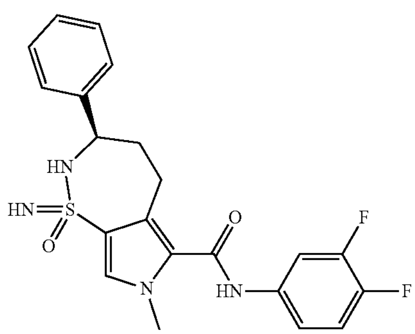 [SMILES: Cn1cc2c(c1C(=O)Nc1ccc(F)c(F)c1)CC[C@H](c1ccccc1)NS2(=N)=O] | 431 | Peak1 (HPLC) |
| 20ii2 | 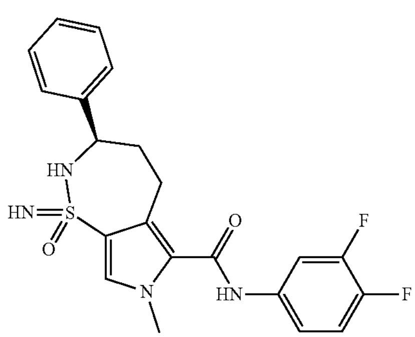 | 431 | Peak2 (HPLC) |

TABLE 1-continued

| No. | Structure | Mass Spectrum ESI-MS, (M + H) | Remark |
|---|---|---|---|
| 20jj1 | 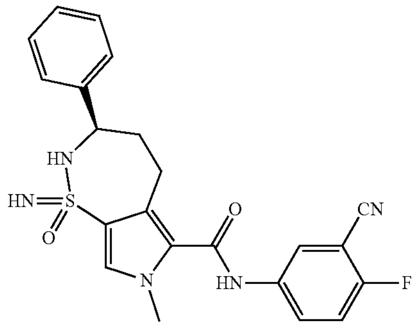 [SMILES: Cn1cc2c(c1C(=O)Nc1ccc(F)c(C#N)c1)CC[C@H](c1ccccc1)NS2(=N)=O] | 438 | Peak1 (HPLC) |
| 20jj2 | 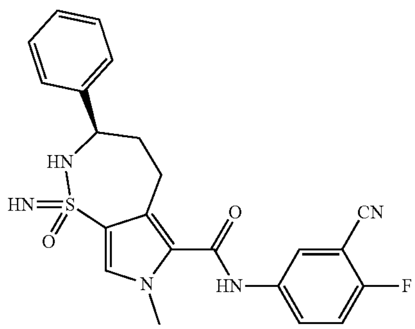 [SMILES: Cn1cc2c(c1C(=O)Nc1ccc(F)c(C#N)c1)CC[C@H](c1ccccc1)NS2(=N)=O] | 438 | Peak2 (HPLC) |
| 20kk1 | 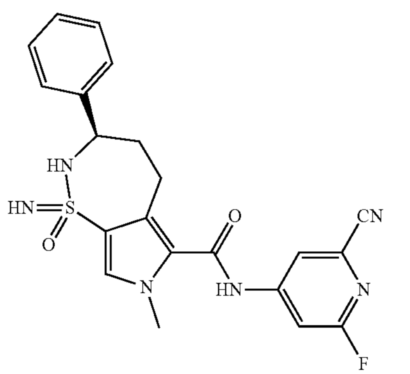 [SMILES: Cn1cc2c(c1C(=O)Nc1cc(F)nc(C#N)c1)CC[C@H](c1ccccc1)NS2(=N)=O] | 439 | Peak1 (HPLC) |
| 20kk2 | 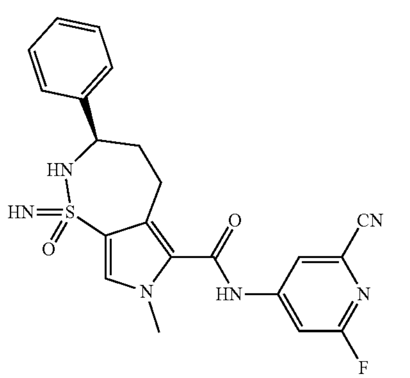 [SMILES: Cn1cc2c(c1C(=O)Nc1cc(F)nc(C#N)c1)CC[C@H](c1ccccc1)NS2(=N)=O] | 439 | Peak2 (HPLC) |

TABLE 1-continued

| No. | Structure | Mass Spectrum ESI-MS, (M + H) | Remark |
|---|---|---|---|
| 20mm1 | 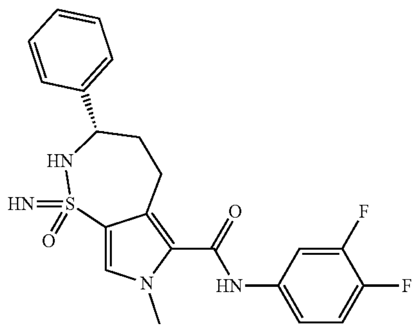 [SMILES: Cn1cc2c(c1C(=O)Nc1ccc(F)c(F)c1)CC[C@@H](c1ccccc1)NS2(=N)=O] | 431 | Peak1 (HPLC) |
| 20mm2 | 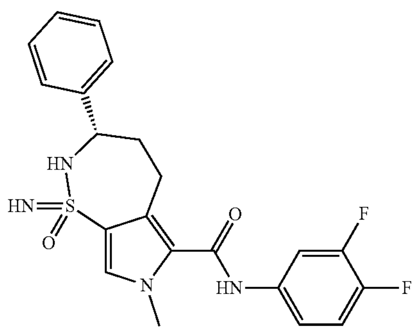 [SMILES: Cn1cc2c(c1C(=O)Nc1ccc(F)c(F)c1)CC[C@@H](c1ccccc1)NS2(=N)=O] | 431 | Peak2 (HPLC) |
| 20nn1 | 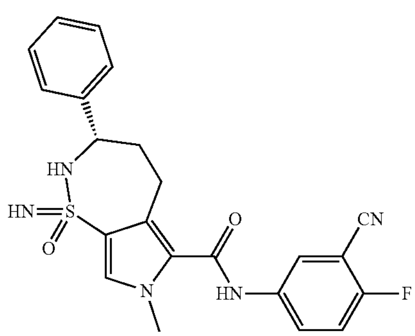 | 438 | Peak1 (HPLC) |
| 20nn2 | 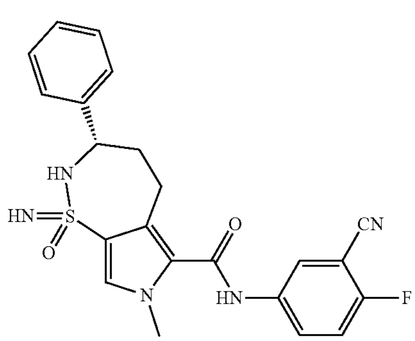 [SMILES: Cn1cc2c(c1C(=O)Nc1ccc(F)c(C#N)c1)CC[C@@H](c1ccccc1)NS2(=N)=O] | 438 | Peak2 (HPLC) |

TABLE 1-continued

| No. | Structure | Mass Spectrum ESI-MS, (M + H) | Remark |
|---|---|---|---|
| 20oo1 | 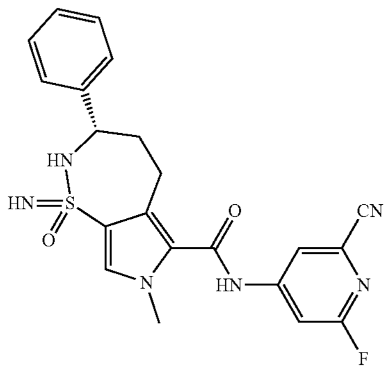 [SMILES: Cn1cc2c(c1C(=O)Nc1cc(F)nc(C#N)c1)CC[C@@H](c1ccccc1)NS2(=N)=O] | 439 | Peak1 (HPLC) |
| 20oo2 | 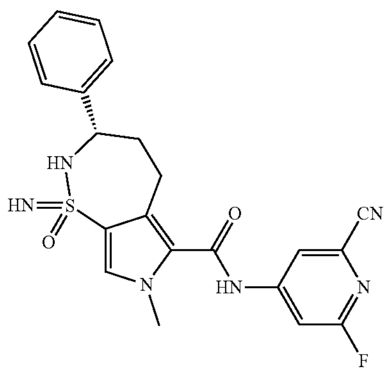 | 439 | Peak2 (HPLC) |
| 20pp1 | 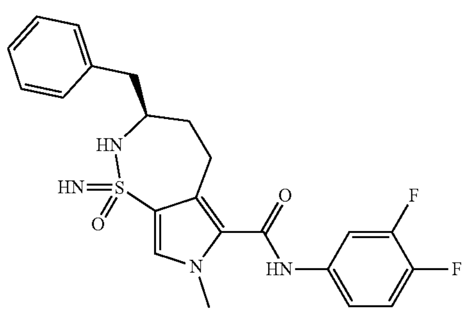 [SMILES: Cn1cc2c(c1C(=O)Nc1ccc(F)c(F)c1)CC[C@H](Cc1ccccc1)NS2(=N)=O] | 445 | Peak1 (HPLC) |
| 20pp2 | 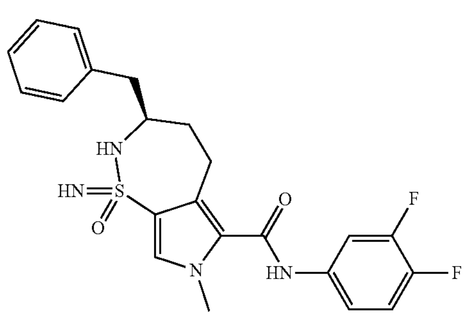 [SMILES: Cn1cc2c(c1C(=O)Nc1ccc(F)c(F)c1)CC[C@H](Cc1ccccc1)NS2(=N)=O] | 445 | Peak2 (HPLC) |

TABLE 1-continued
| No. | Structure | Mass Spectrum ESI-MS, (M + H) | Remark |
| --- | --- | --- | --- |
| 20qq1 | 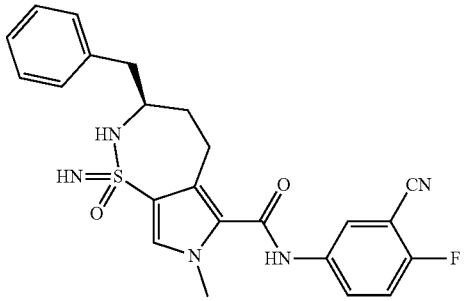 [SMILES: Cn1cc2c(c1C(=O)Nc1ccc(F)c(C#N)c1)CC[C@H](Cc1ccccc1)NS2(=N)=O] | 452 | Peak1 (HPLC) |
| 20qq2 | 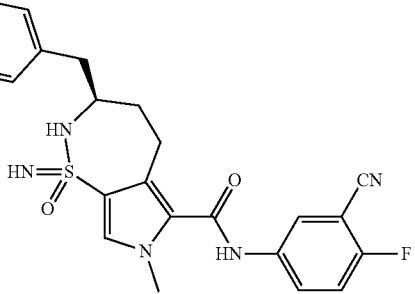 | 452 | Peak2 (HPLC) |
| 20rr1 | 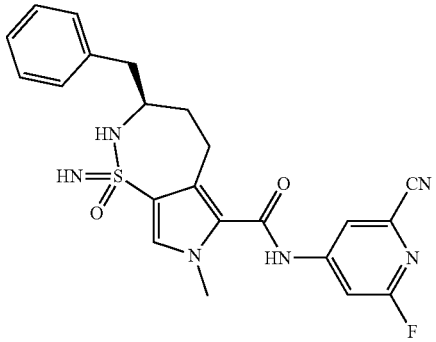 [SMILES: Cn1cc2c(c1C(=O)Nc1cc(F)nc(C#N)c1)CC[C@H](Cc1ccccc1)NS2(=N)=O] | 453 | Peak1 (HPLC) |
| 20rr2 | 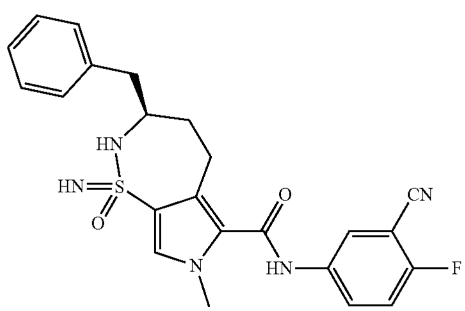 [SMILES: Cn1cc2c(c1C(=O)Nc1ccc(F)c(C#N)c1)CC[C@H](Cc1ccccc1)NS2(=N)=O] | 453 | Peak2 (HPLC) |
| 20ss1 | 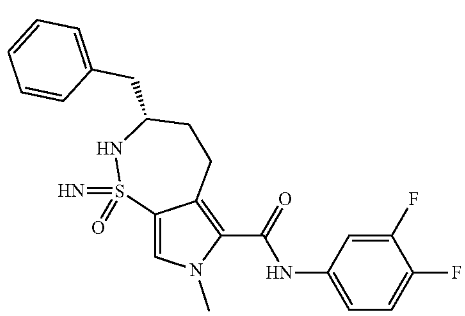 [SMILES: Cn1cc2c(c1C(=O)Nc1ccc(F)c(F)c1)CC[C@@H](Cc1ccccc1)NS2(=N)=O] | 445 | Peak1 (HPLC) |

TABLE 1-continued

| No. | Structure | Mass Spectrum ESI-MS, (M + H) | Remark |
|---|---|---|---|
| 20ss2 | 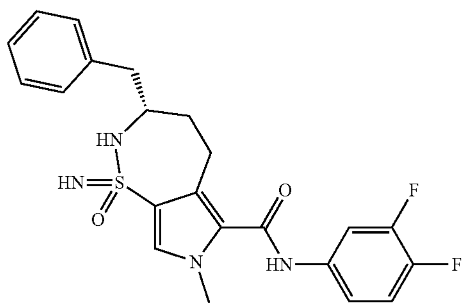 [SMILES: Cn1cc2c(c1C(=O)Nc1ccc(F)c(F)c1)CC[C@@H](Cc1ccccc1)NS2(=N)=O] | 445 | Peak2 (HPLC) |
| 20tt1 | 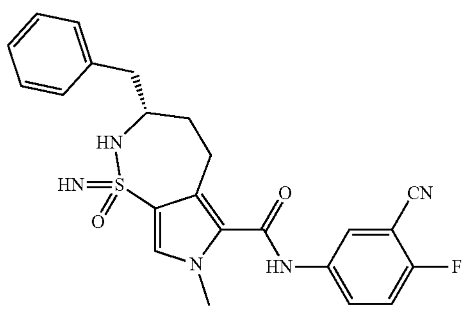 [SMILES: Cn1cc2c(c1C(=O)Nc1ccc(F)c(C#N)c1)CC[C@@H](Cc1ccccc1)NS2(=N)=O] | 452 | Peak1 (HPLC) |
| 20tt2 | 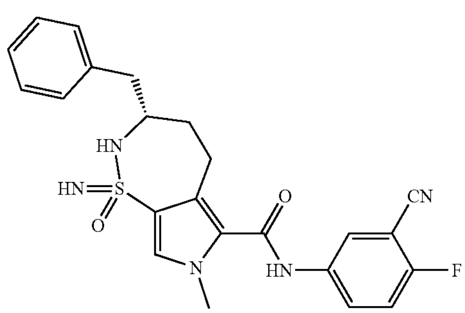 [SMILES: Cn1cc2c(c1C(=O)Nc1ccc(F)c(C#N)c1)CC[C@@H](Cc1ccccc1)NS2(=N)=O] | 452 | Peak2 (HPLC) |
| 20uu1 | 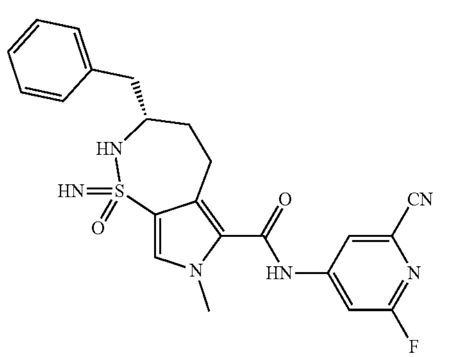 [SMILES: Cn1cc2c(c1C(=O)Nc1cc(F)nc(C#N)c1)CC[C@@H](Cc1ccccc1)NS2(=N)=O] | 453 | Peak1 (HPLC) |

TABLE 1-continued

| No. | Structure | Mass Spectrum ESI-MS, (M + H) | Remark |
|---|---|---|---|
| 20uu2 | 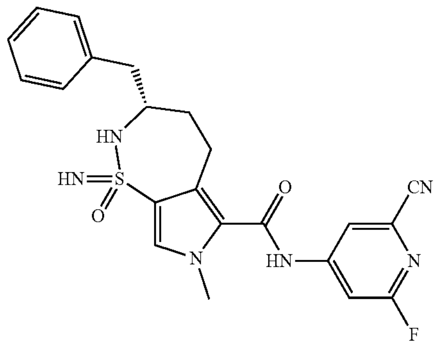 [SMILES: Cn1cc2c(c1C(=O)Nc1cc(F)nc(C#N)c1)CC[C@@H](Cc1ccccc1)NS2(=N)=O] | 453 | Peak2 (HPLC) |
| 20vv1 | 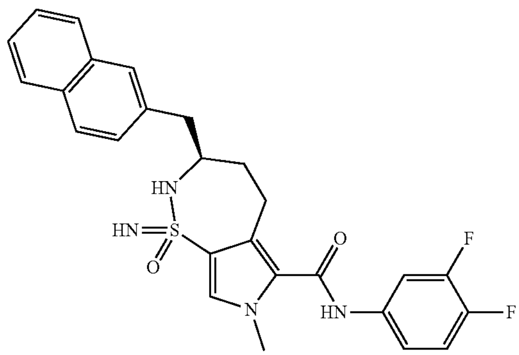 [SMILES: Cn1cc2c(c1C(=O)Nc1ccc(F)c(F)c1)CC[C@H](Cc1ccc3ccccc3c1)NS2(=N)=O] | 495 | Peak1 (HPLC) |
| 20vv2 | 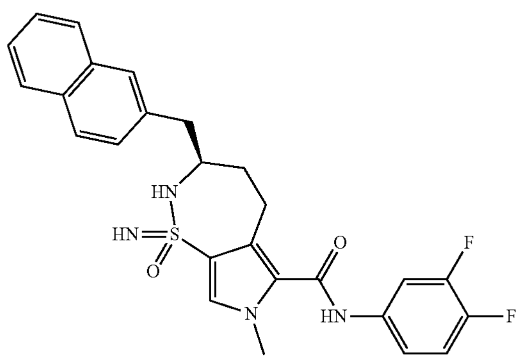 [SMILES: Cn1cc2c(c1C(=O)Nc1ccc(F)c(F)c1)CC[C@H](Cc1ccc3ccccc3c1)NS2(=N)=O] | 495 | Peak2 (HPLC) |
| 20ww1 | 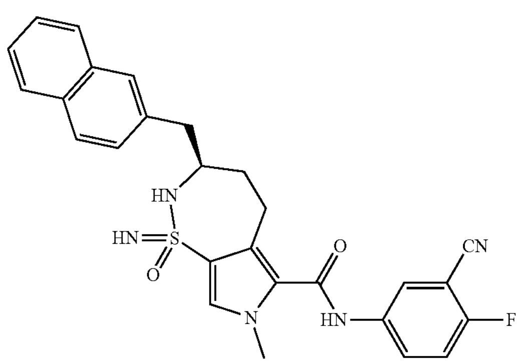 [SMILES: Cn1cc2c(c1C(=O)Nc1ccc(F)c(C#N)c1)CC[C@H](Cc1ccc3ccccc3c1)NS2(=N)=O] | 502 | Peak1 (HPLC) |

TABLE 1-continued

| No. | Structure | Mass Spectrum ESI-MS, (M + H) | Remark |
|---|---|---|---|
| 20ww2 | 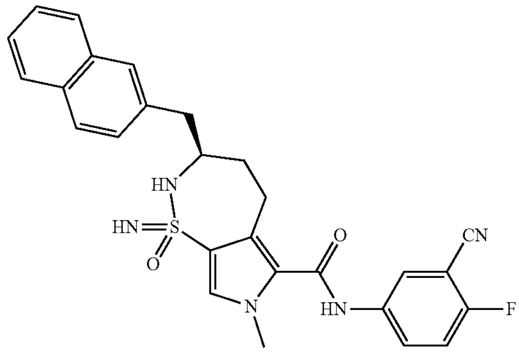 [SMILES: Cn1cc2c(c1C(=O)Nc1ccc(F)c(C#N)c1)CC[C@H](Cc1ccc3ccccc3c1)NS2(=N)=O] | 502 | Peak2 (HPLC) |
| 20xx1 | 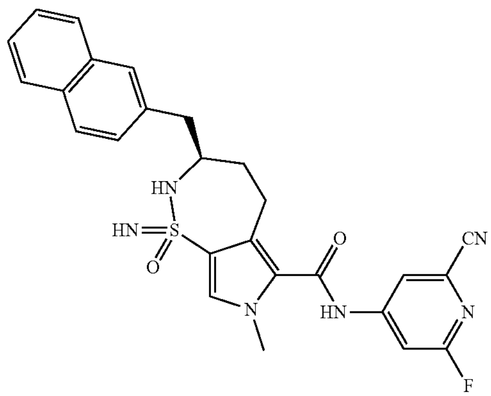 [SMILES: Cn1cc2c(c1C(=O)Nc1cc(F)nc(C#N)c1)CC[C@H](Cc1ccc3ccccc3c1)NS2(=N)=O] | 503 | Peak1 (HPLC) |
| 20xx2 | 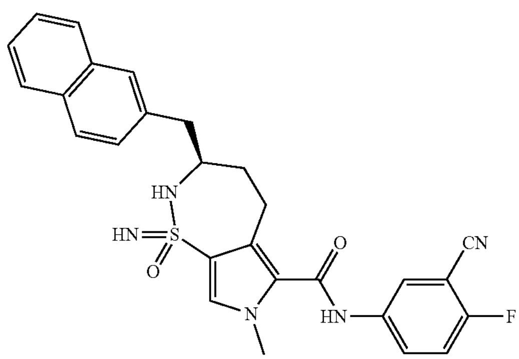 [SMILES: Cn1cc2c(c1C(=O)Nc1ccc(F)c(C#N)c1)CC[C@H](Cc1ccc3ccccc3c1)NS2(=N)=O] | 503 | Peak2 (HPLC) |
| 20yy1 | 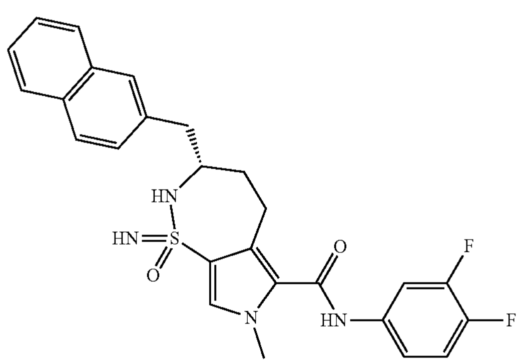 [SMILES: Cn1cc2c(c1C(=O)Nc1ccc(F)c(F)c1)CC[C@@H](Cc1ccc3ccccc3c1)NS2(=N)=O] | 495 | Peak1 (HPLC) |

TABLE 1-continued

| No. | Structure | Mass Spectrum ESI-MS, (M + H) | Remark |
|---|---|---|---|
| 20yy2 | 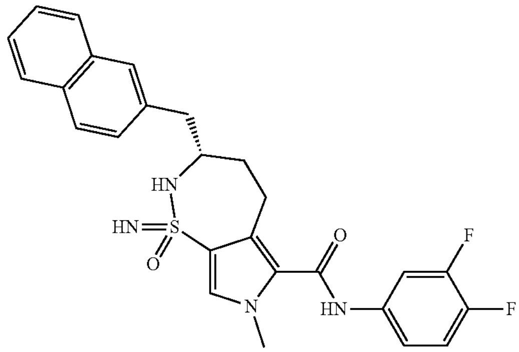 [SMILES: Cn1cc2c(c1C(=O)Nc1ccc(F)c(F)c1)CC[C@@H](Cc1ccc3ccccc3c1)NS2(=N)=O] | 495 | Peak2 (HPLC) |
| 20zz1 | 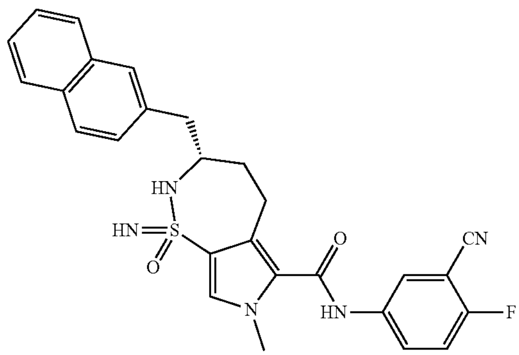 [SMILES: Cn1cc2c(c1C(=O)Nc1ccc(F)c(C#N)c1)CC[C@@H](Cc1ccc3ccccc3c1)NS2(=N)=O] | 502 | Peak1 (HPLC) |
| 20zz2 | 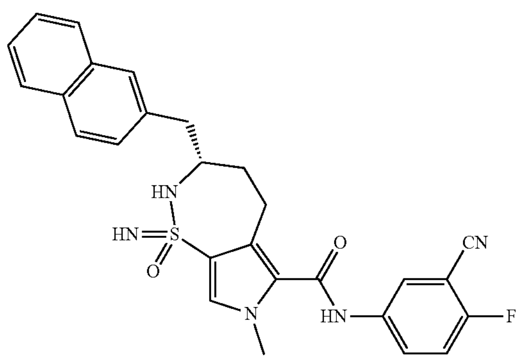 [SMILES: Cn1cc2c(c1C(=O)Nc1ccc(F)c(C#N)c1)CC[C@@H](Cc1ccc3ccccc3c1)NS2(=N)=O] | 502 | Peak2 (HPLC) |
| 20aaa1 | 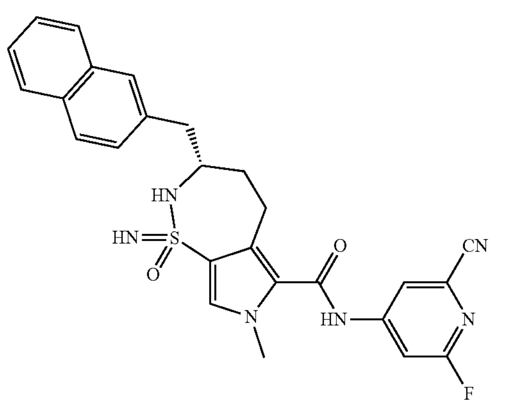 [SMILES: Cn1cc2c(c1C(=O)Nc1cc(F)nc(C#N)c1)CC[C@@H](Cc1ccc3ccccc3c1)NS2(=N)=O] | 503 | Peak1 (HPLC) |

TABLE 1-continued

| No. | Structure | Mass Spectrum ESI-MS, (M + H) | Remark |
|---|---|---|---|
| 20aaa2 | 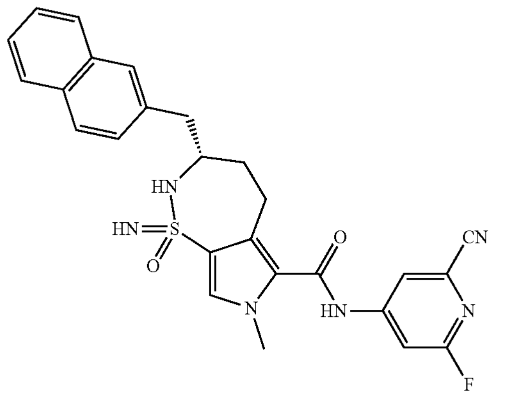 [SMILES: Cn1cc2c(c1C(=O)Nc1cc(F)nc(C#N)c1)CC[C@@H](Cc1ccc3ccccc3c1)NS2(=N)=O] | 503 | Peak2 (HPLC) |
| 20bbb1 | 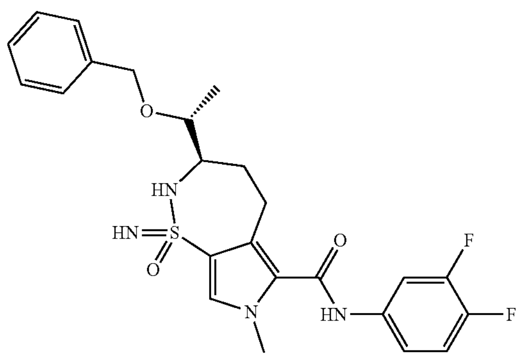 | 489 | Peak1 (HPLC) |
| 20bbb2 | 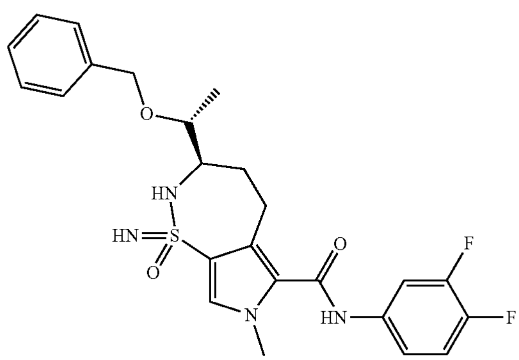 | 489 | Peak2 (HPLC) |
| 20ccc1 | 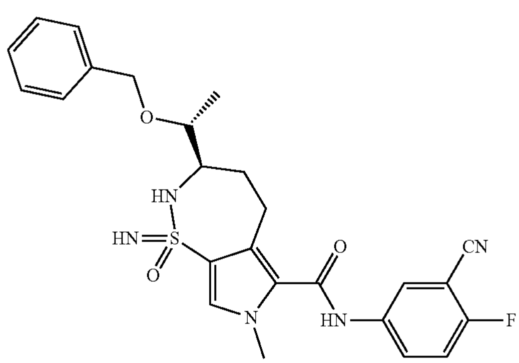 | 496 | Peak1 (HPLC) |

TABLE 1-continued

| No. | Structure | Mass Spectrum ESI-MS, (M + H) | Remark |
|---|---|---|---|
| 20ccc2 | 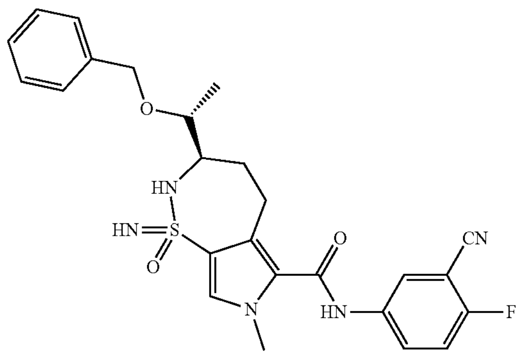 | 496 | Peak2 (HPLC) |
| 20ddd1 | 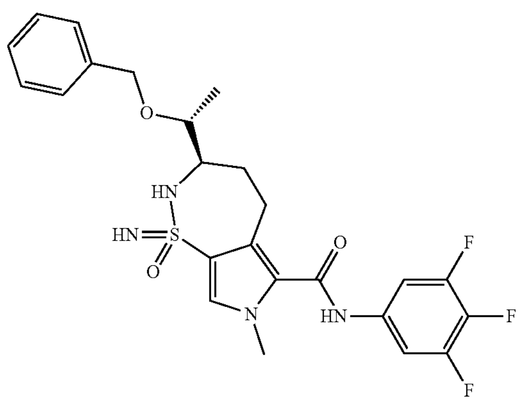 [SMILES: C[C@@H](OCc1ccccc1)[C@H]1CCc2c(cn(C)c2C(=O)Nc2cc(F)c(F)c(F)c2)S(=N)(=O)N1] | 507 | Peak1 (HPLC) |
| 20ddd2 | 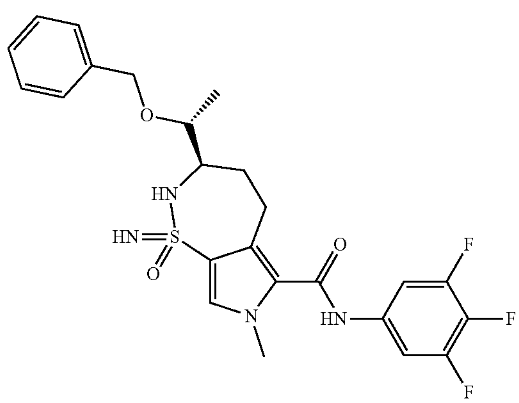 [SMILES: C[C@@H](OCc1ccccc1)[C@H]1CCc2c(cn(C)c2C(=O)Nc2cc(F)c(F)c(F)c2)S(=N)(=O)N1] | 507 | Peak2 (HPLC) |
| 20eee1 | 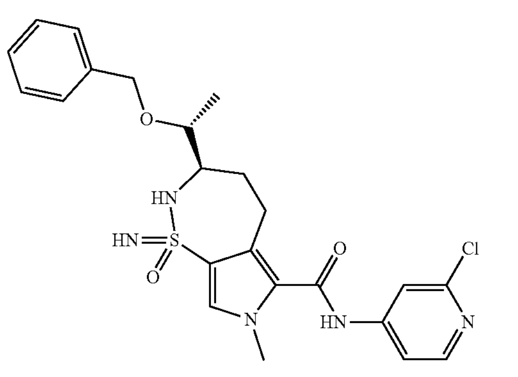 | 488 | Peak1 (HPLC) |

TABLE 1-continued

| No. | Structure | Mass Spectrum ESI-MS, (M + H) | Remark |
|---|---|---|---|
| 20eee2 | 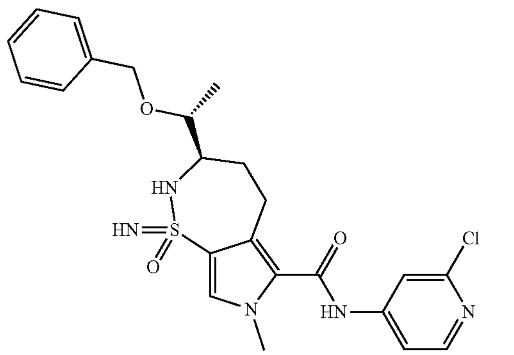 | 488 | Peak2 (HPLC) |
| 20fff1 | 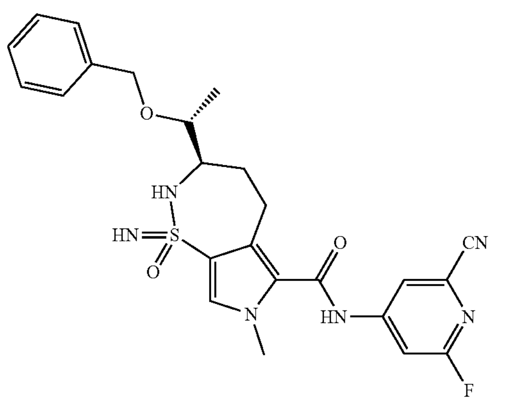 [SMILES: C[C@@H](OCc1ccccc1)[C@H]1CCc2c(cn(C)c2C(=O)Nc2cc(F)nc(C#N)c2)S(=N)(=O)N1] | 497 | Peak1 (HPLC) |
| 20fff2 | 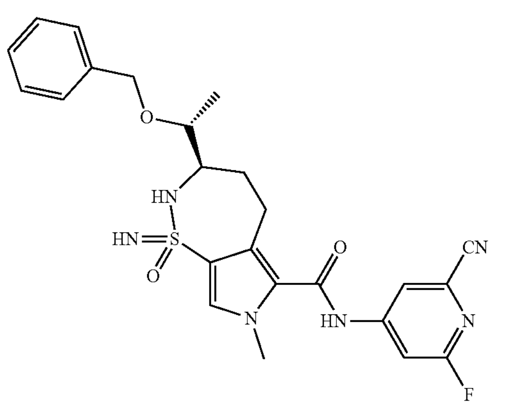 | 497 | Peak2 (HPLC) |
| 20ggg1 | 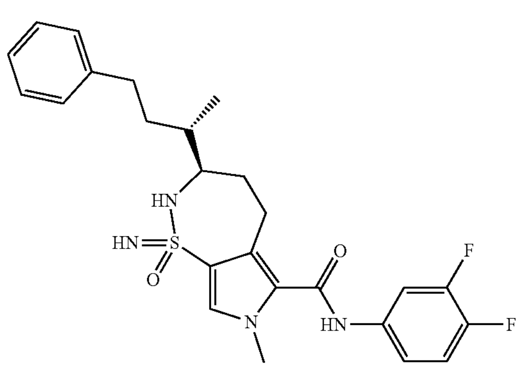 [SMILES: C[C@@H](CCc1ccccc1)[C@H]1CCc2c(cn(C)c2C(=O)Nc2ccc(F)c(F)c2)S(=N)(=O)N1] | 486 | Peak1 (HPLC) |

TABLE 1-continued

| No. | Structure | Mass Spectrum ESI-MS, (M + H) | Remark |
|---|---|---|---|
| 20ggg2 | 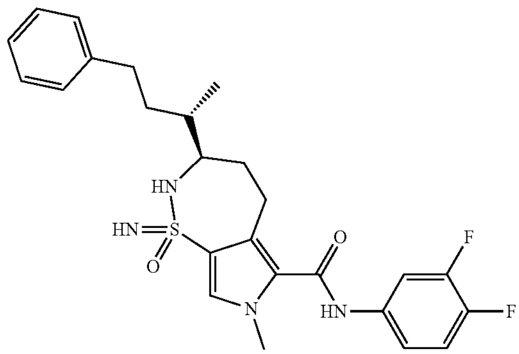 [SMILES: C[C@@H](CCc1ccccc1)[C@H]1CCc2c(cn(C)c2C(=O)Nc2ccc(F)c(F)c2)S(=N)(=O)N1] | 486 | Peak2 (HPLC) |
| 20hhh1 | 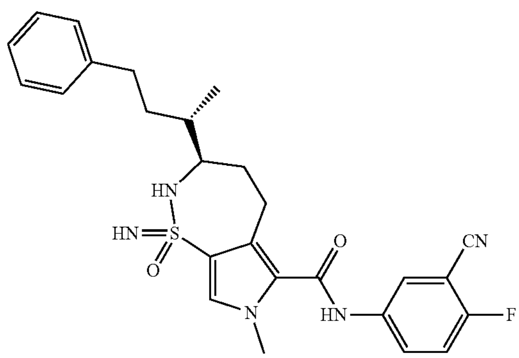 [SMILES: C[C@@H](CCc1ccccc1)[C@H]1CCc2c(cn(C)c2C(=O)Nc2ccc(F)c(C#N)c2)S(=N)(=O)N1] | 494 | Peak1 (HPLC) |
| 20hhh2 | 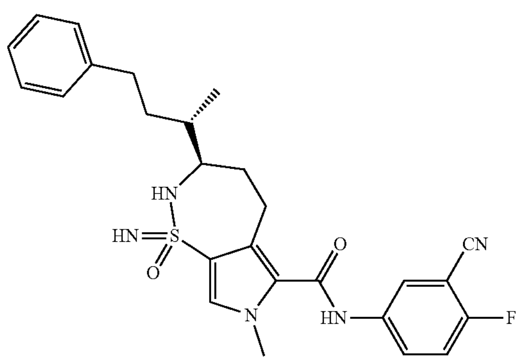 [SMILES: C[C@@H](CCc1ccccc1)[C@H]1CCc2c(cn(C)c2C(=O)Nc2ccc(F)c(C#N)c2)S(=N)(=O)N1] | 494 | Peak2 (HPLC) |
| 20iii1 | 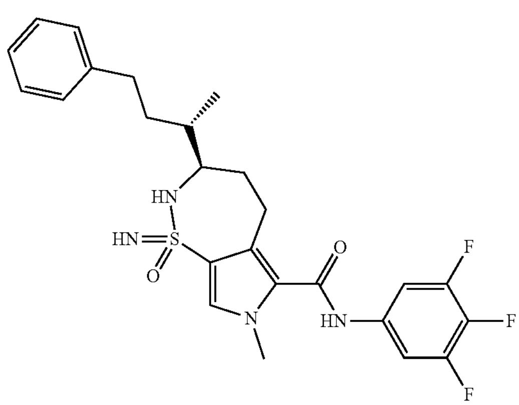 [SMILES: C[C@@H](CCc1ccccc1)[C@H]1CCc2c(cn(C)c2C(=O)Nc2cc(F)c(F)c(F)c2)S(=N)(=O)N1] | 505 | Peak1 (HPLC) |

US 11,168,055 B2

137                                                                 138

TABLE 1-continued

| No. | Structure | Mass Spectrum ESI-MS, (M + H) | Remark |
|---|---|---|---|
| 20iii2 | 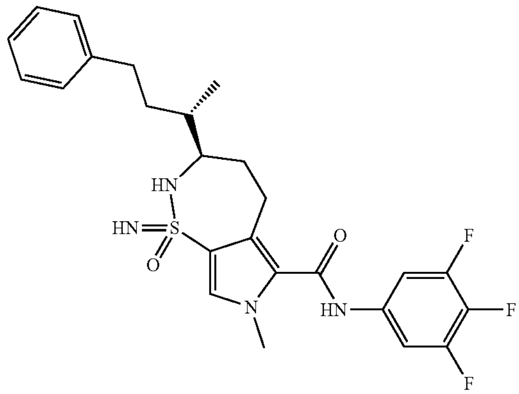 [SMILES: C[C@@H](CCc1ccccc1)[C@H]1CCc2c(cn(C)c2C(=O)Nc2cc(F)c(F)c(F)c2)S(=N)(=O)N1] | 505 | Peak2 (HPLC) |
| 20jjj1 | 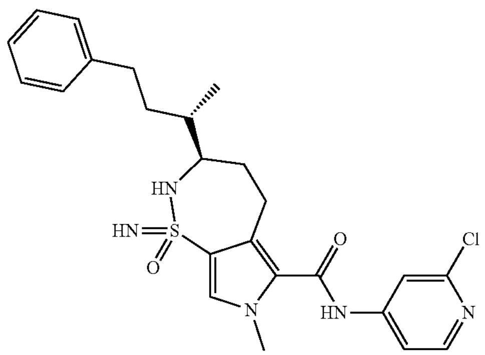 | 486 | Peak1 (HPLC) |
| 20jjj2 | 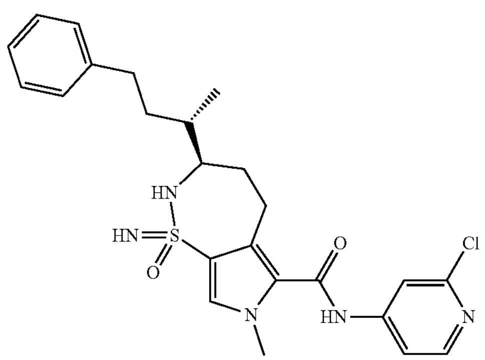 [SMILES: C[C@@H](CCc1ccccc1)[C@H]1CCc2c(cn(C)c2C(=O)Nc2ccnc(Cl)c2)S(=N)(=O)N1] | 486 | Peak2 (HPLC) |
| 20kkk1 | 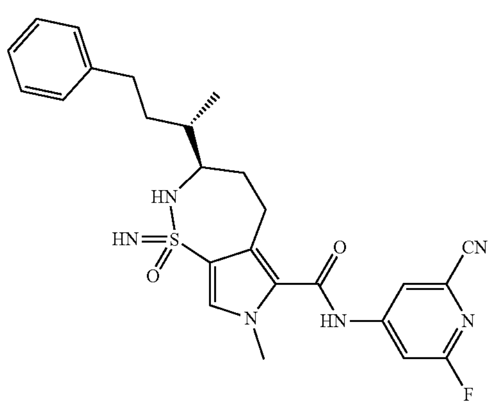 [SMILES: C[C@@H](CCc1ccccc1)[C@H]1CCc2c(cn(C)c2C(=O)Nc2cc(F)nc(C#N)c2)S(=N)(=O)N1] | 495 | Peak1 (HPLC) |

TABLE 1-continued

| No. | Structure | Mass Spectrum ESI-MS, (M + H) | Remark |
|---|---|---|---|
| 20kkk2 | 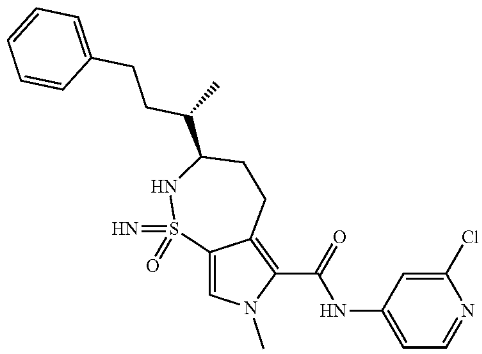 [SMILES: C[C@@H](CCc1ccccc1)[C@H]1CCc2c(cn(C)c2C(=O)Nc2ccnc(Cl)c2)S(=N)(=O)N1] | 495 | Peak2 (HPLC) |
| 20mmm1 | 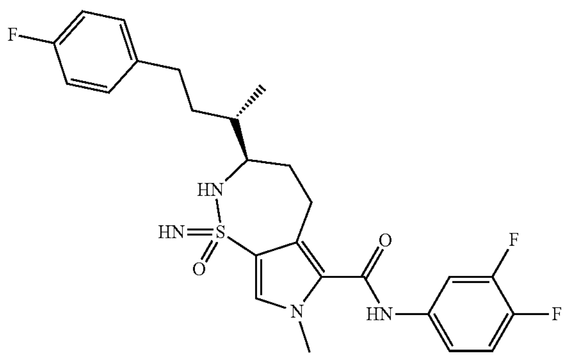 [SMILES: C[C@@H](CCc1ccc(F)cc1)[C@H]1CCc2c(cn(C)c2C(=O)Nc2ccc(F)c(F)c2)S(=N)(=O)N1] | 505 | Peak1 (HPLC) |
| 20mmm2 | 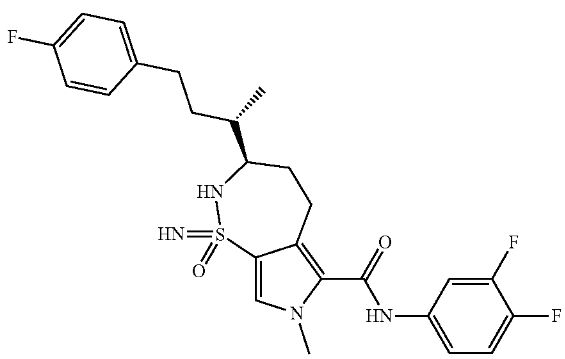 [SMILES: C[C@@H](CCc1ccc(F)cc1)[C@H]1CCc2c(cn(C)c2C(=O)Nc2ccc(F)c(F)c2)S(=N)(=O)N1] | 505 | Peak2 (HPLC) |
| 20nnn1 | 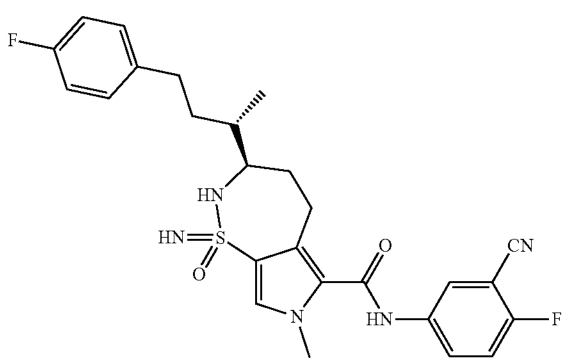 [SMILES: C[C@@H](CCc1ccc(F)cc1)[C@H]1CCc2c(cn(C)c2C(=O)Nc2ccc(F)c(C#N)c2)S(=N)(=O)N1] | 512 | Peak1 (HPLC) |

TABLE 1-continued

| No. | Structure | Mass Spectrum ESI-MS, (M + H) | Remark |
|---|---|---|---|
| 20nnn2 | 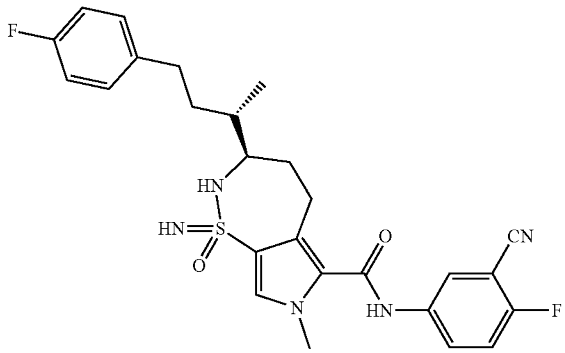 [SMILES: C[C@@H](CCc1ccc(F)cc1)[C@H]1CCc2c(cn(C)c2C(=O)Nc2ccc(F)c(C#N)c2)S(=N)(=O)N1] | 512 | Peak2 (HPLC) |
| 20ooo1 | 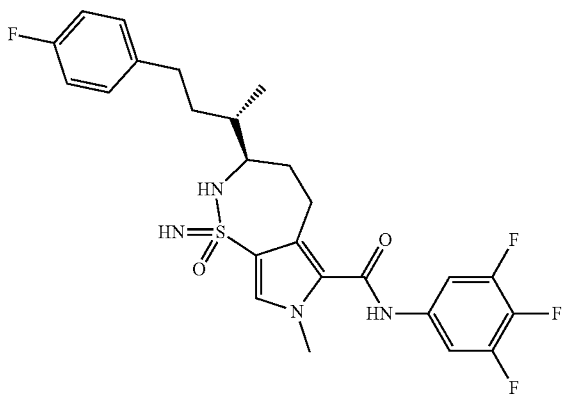 [SMILES: C[C@@H](CCc1ccc(F)cc1)[C@H]1CCc2c(cn(C)c2C(=O)Nc2cc(F)c(F)c(F)c2)S(=N)(=O)N1] | 523 | Peak1 (HPLC) |
| 20ooo2 | 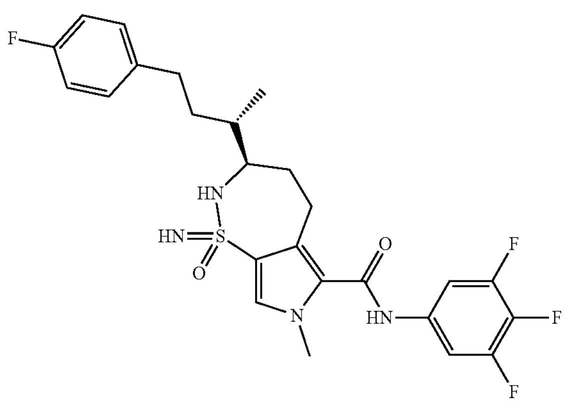 [SMILES: C[C@@H](CCc1ccc(F)cc1)[C@H]1CCc2c(cn(C)c2C(=O)Nc2cc(F)c(F)c(F)c2)S(=N)(=O)N1] | 523 | Peak2 (HPLC) |
| 20ppp1 | 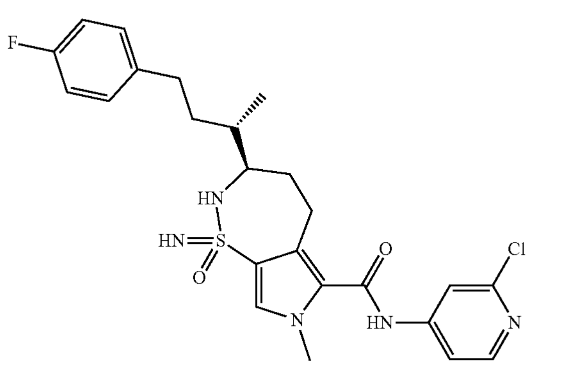 [SMILES: C[C@@H](CCc1ccc(F)cc1)[C@H]1CCc2c(cn(C)c2C(=O)Nc2ccnc(Cl)c2)S(=N)(=O)N1] | 504 | Peak1 (HPLC) |

TABLE 1-continued

| No. | Structure | Mass Spectrum ESI-MS, (M + H) | Remark |
|---|---|---|---|
| 20ppp2 | 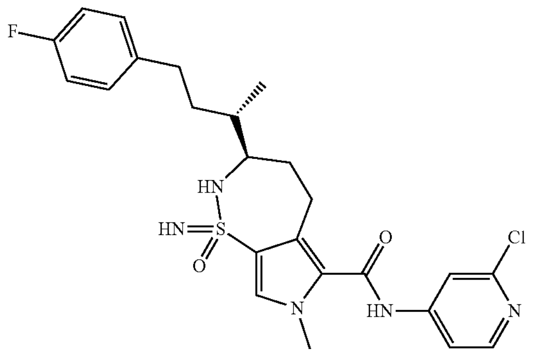 | 504 | Peak2 (HPLC) |
| 20qqq1 | 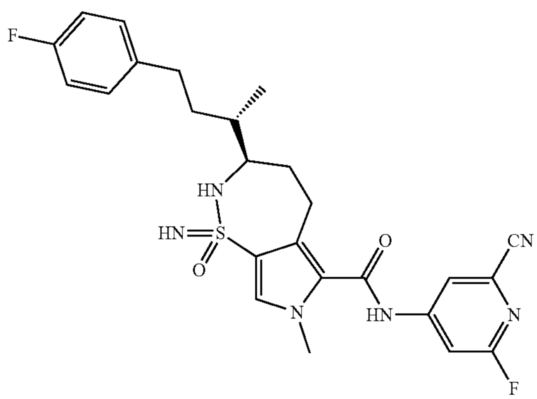 [SMILES: C[C@@H](CCc1ccc(F)cc1)[C@H]1CCc2c(cn(C)c2C(=O)Nc2cc(F)nc(C#N)c2)S(=N)(=O)N1] | 513 | Peak1 (HPLC) |
| 20qqq2 | 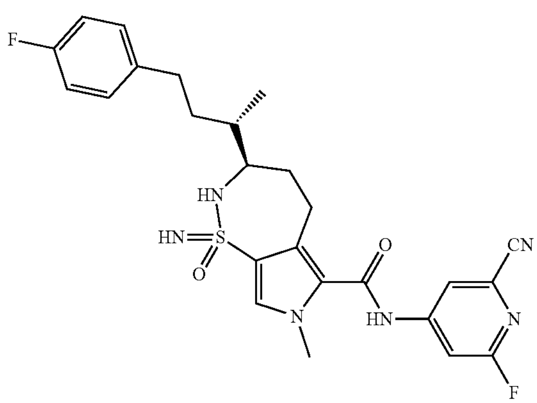 | 513 | Peak2 (HPLC) |
| 20rrr1 | 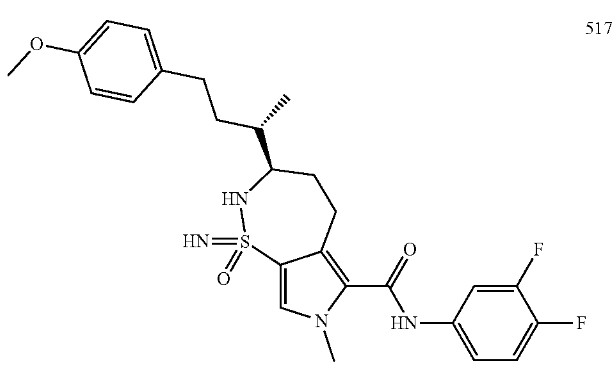 | 517 | Peak1 (HPLC) |

TABLE 1-continued

| No. | Structure | Mass Spectrum ESI-MS, (M + H) | Remark |
|---|---|---|---|
| 20rrr2 | 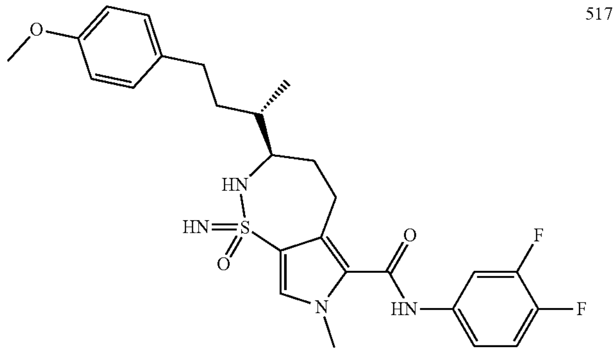 | 517 | Peak2 (HPLC) |
| 20sss1 | 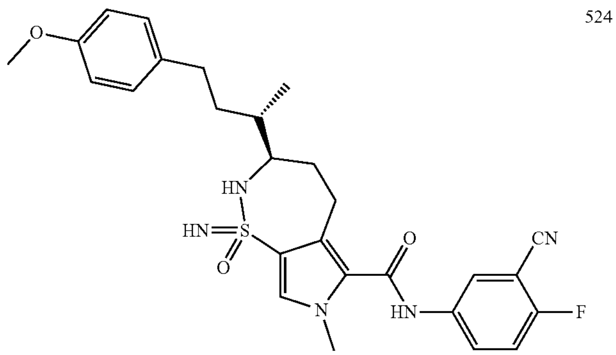 | 524 | Peak1 (HPLC) |
| 20sss2 | 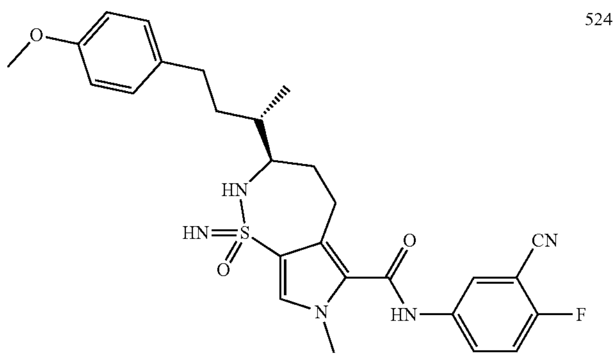 | 524 | Peak2 (HPLC) |
| 20ttt1 | 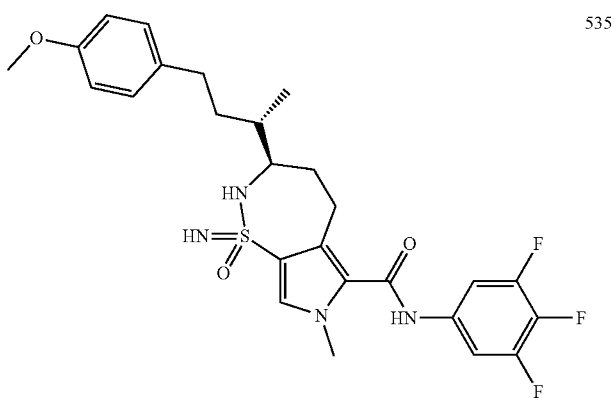 | 535 | Peak1 (HPLC) |

TABLE 1-continued
| No. | Structure | Mass Spectrum ESI-MS, (M + H) | Remark |
|---|---|---|---|
| 20ttt2 | 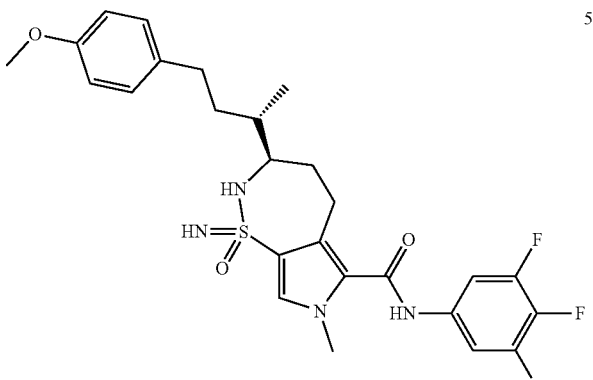 | 535 | Peak2 (HPLC) |
| 20uuu1 | 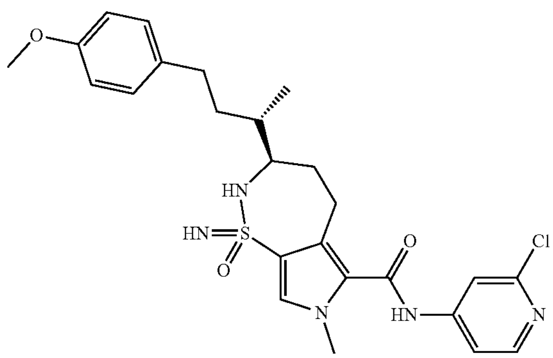 [SMILES: COc1ccc(CC[C@H](C)[C@H]2CCc3c(cn(C)c3C(=O)Nc3ccnc(Cl)c3)S(=N)(=O)N2)cc1] | 516 | Peak1 (HPLC) |
| 20uuu2 | 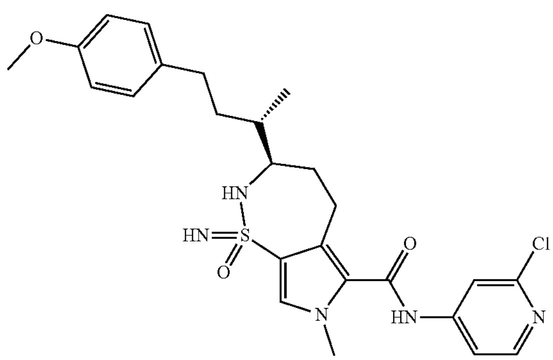 [SMILES: COc1ccc(CC[C@H](C)[C@H]2CCc3c(cn(C)c3C(=O)Nc3ccnc(Cl)c3)S(=N)(=O)N2)cc1] | 516 | Peak2 (HPLC) |
| 20vvv1 | 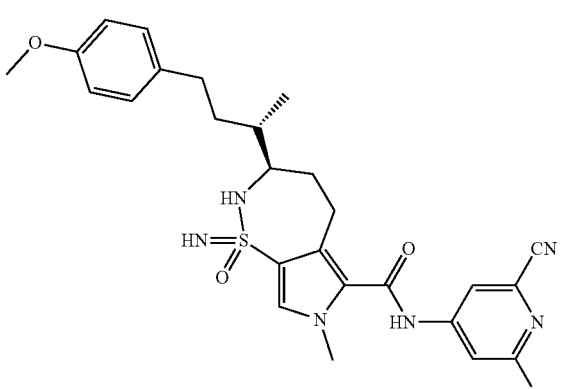 | 525 | Peak1 (HPLC) |

TABLE 1-continued

| No. | Structure | Mass Spectrum ESI-MS, (M + H) | Remark |
|---|---|---|---|
| 20vvv2 | 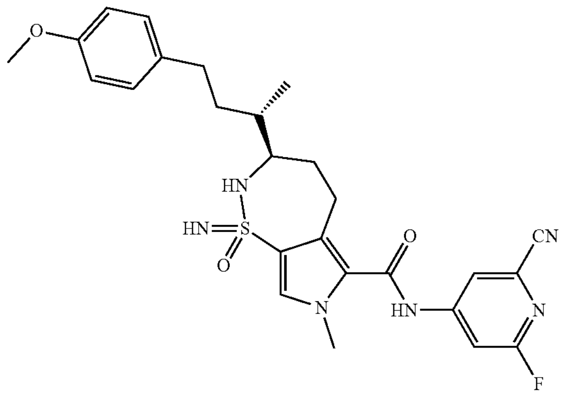 [SMILES: COc1ccc(CC[C@H](C)[C@H]2CCc3c(cn(C)c3C(=O)Nc3cc(F)nc(C#N)c3)S(=N)(=O)N2)cc1] | 525 | Peak2 (HPLC) |
| 20www1 | 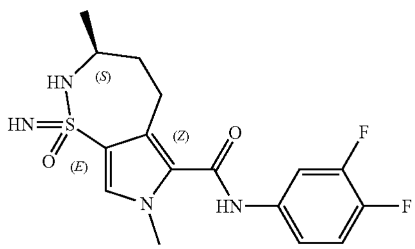 | 369 | Peak1 (HPLC) |
| 20www2 | 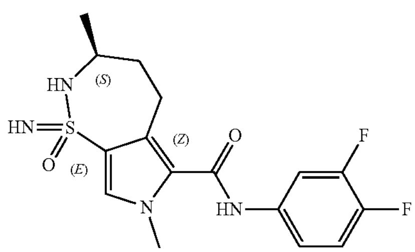 | 369 | Peak2 (HPLC) |
| 20xxx1 | 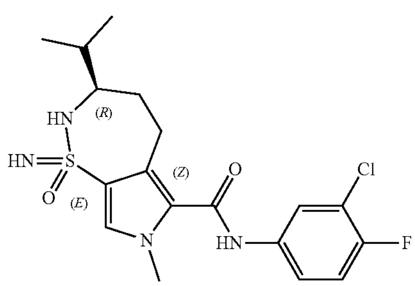 | 413 | Peak1 (HPLC) |
| 20xxx2 | 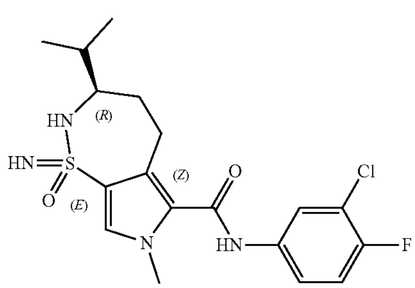 | 413 | Peak2 (HPLC) |

TABLE 1-continued

| No. | Structure | Mass Spectrum ESI-MS, (M + H) | Remark |
|---|---|---|---|
| 30a1 | 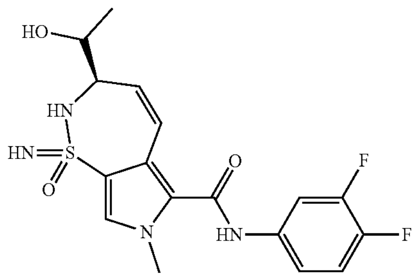 [SMILES: CC(O)[C@H]1C=Cc2c(cn(C)c2C(=O)Nc2ccc(F)c(F)c2)S(=N)(=O)N1] | 397 | Peak1 (HPLC) |
| 30a2 | 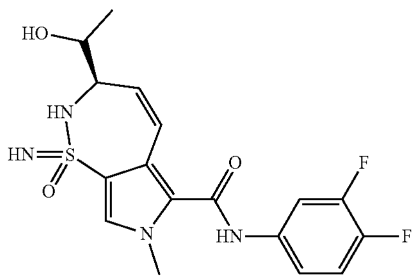 [SMILES: CC(O)[C@H]1C=Cc2c(cn(C)c2C(=O)Nc2ccc(F)c(F)c2)S(=N)(=O)N1] | 397 | Peak2 (HPLC) |
| 30b1 | 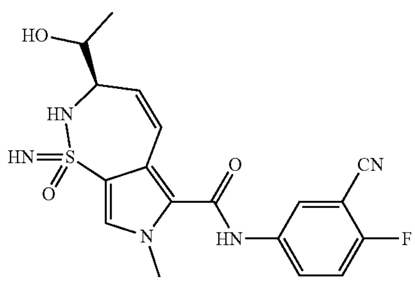 [SMILES: CC(O)[C@H]1C=Cc2c(cn(C)c2C(=O)Nc2ccc(F)c(C#N)c2)S(=N)(=O)N1] | 404 | Peak1 (HPLC) |
| 30b2 | 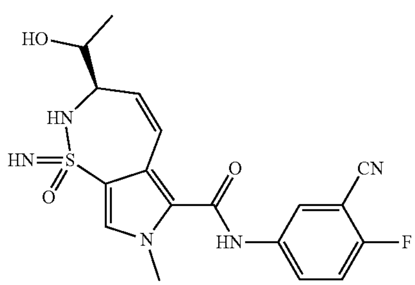 [SMILES: CC(O)[C@H]1C=Cc2c(cn(C)c2C(=O)Nc2ccc(F)c(C#N)c2)S(=N)(=O)N1] | 404 | Peak2 (HPLC) |
| 30c1 | 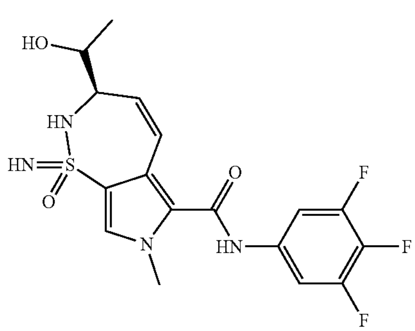 [SMILES: CC(O)[C@H]1C=Cc2c(cn(C)c2C(=O)Nc2cc(F)c(F)c(F)c2)S(=N)(=O)N1] | 415 | Peak1 (HPLC) |

TABLE 1-continued
| No. | Structure | Mass Spectrum ESI-MS, (M + H) | Remark |
|---|---|---|---|
| 30c2 | 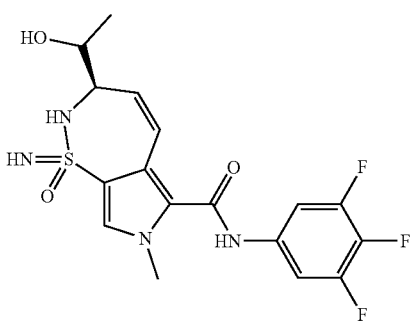 | 415 | Peak2 (HPLC) |
| 30d1 | 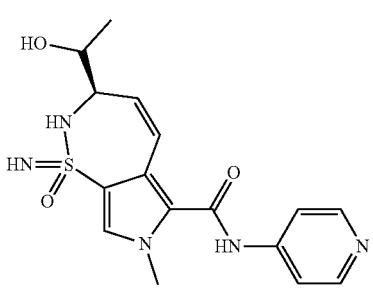 | 362 | Peak1 (HPLC) |
| 30d2 | 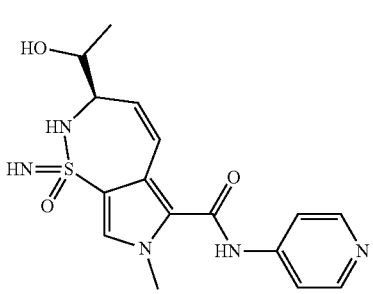 [SMILES: CC(O)[C@H]1C=Cc2c(cn(C)c2C(=O)Nc2ccncc2)S(=N)(=O)N1] | 362 | Peak2 (HPLC) |
| 30e1 | 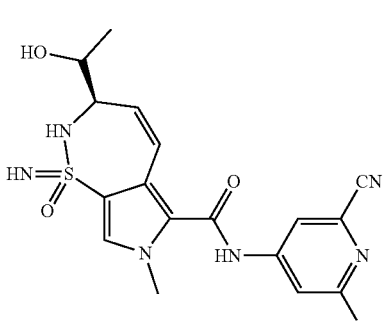 | 405 | Peak1 (HPLC) |
| 30e2 | 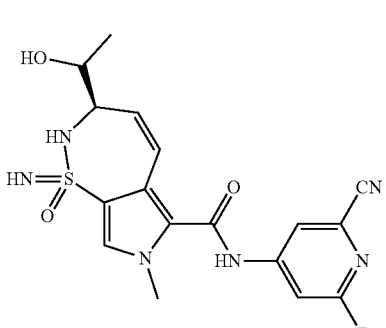 | 405 | Peak2 (HPLC) |

TABLE 1-continued

| No. | Structure | Mass Spectrum ESI-MS, (M + H) | Remark |
|---|---|---|---|
| 30f1 | 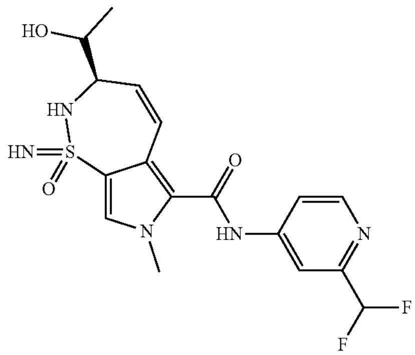 [SMILES: CC(O)[C@H]1C=Cc2c(cn(C)c2C(=O)Nc2ccnc(C(F)F)c2)S(=N)(=O)N1] | 412 | Peak1 (HPLC) |
| 30f2 | 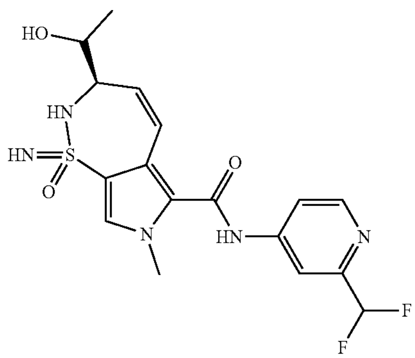 [SMILES: CC(O)[C@H]1C=Cc2c(cn(C)c2C(=O)Nc2ccnc(C(F)F)c2)S(=N)(=O)N1] | 412 | Peak2 (HPLC) |
| 30g1 | 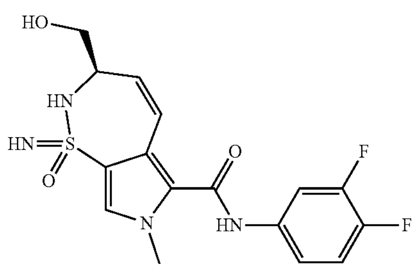 [SMILES: Cn1cc2c(c1C(=O)Nc1ccc(F)c(F)c1)C=C[C@H](CO)NS2(=N)=O] | 383 | Peak1 (HPLC) |
| 30g2 | 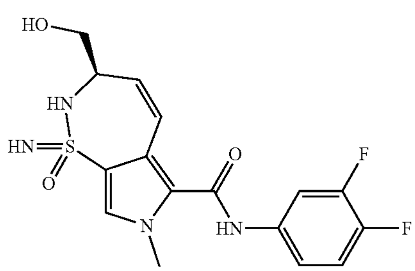 | 383 | Peak2 (HPLC) |
| 30h1 | 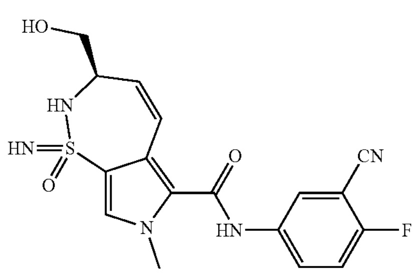 [SMILES: Cn1cc2c(c1C(=O)Nc1ccc(F)c(C#N)c1)C=C[C@H](CO)NS2(=N)=O] | 390 | Peak1 (HPLC) |

TABLE 1-continued

| No. | Structure | Mass Spectrum ESI-MS, (M + H) | Remark |
|---|---|---|---|
| 30h2 | 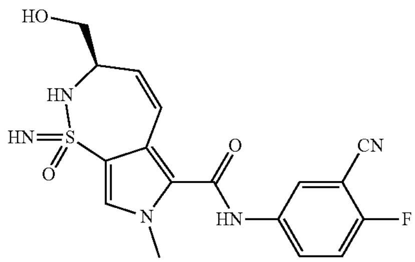 | 390 | Peak2 (HPLC) |
| 30i1 | 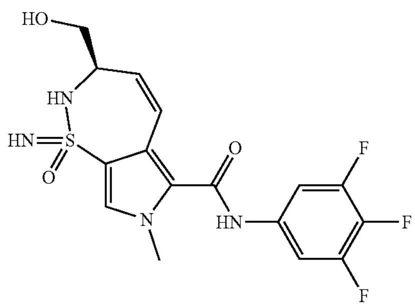 [SMILES: Cn1cc2c(c1C(=O)Nc1cc(F)c(F)c(F)c1)C=C[C@H](CO)NS2(=N)=O] | 401 | Peak1 (HPLC) |
| 30i2 | 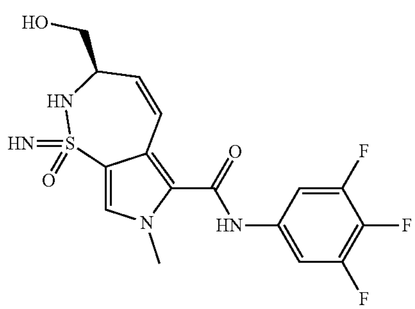 [SMILES: Cn1cc2c(c1C(=O)Nc1cc(F)c(F)c(F)c1)C=C[C@H](CO)NS2(=N)=O] | 401 | Peak2 (HPLC) |
| 30j1 | 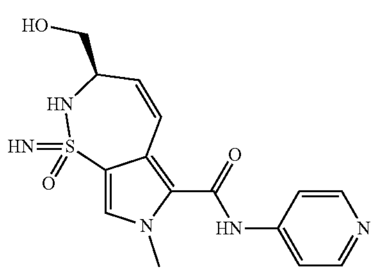 [SMILES: Cn1cc2c(c1C(=O)Nc1ccncc1)C=C[C@H](CO)NS2(=N)=O] | 348 | Peak1 (HPLC) |
| 30j2 | 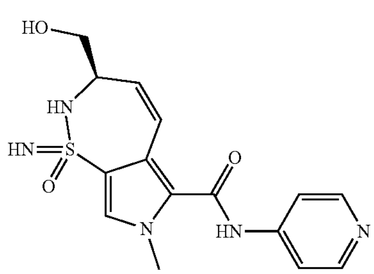 [SMILES: Cn1cc2c(c1C(=O)Nc1ccncc1)C=C[C@H](CO)NS2(=N)=O] | 348 | Peak2 (HPLC) |

TABLE 1-continued

| No. | Structure | Mass Spectrum ESI-MS, (M + H) | Remark |
|---|---|---|---|
| 30k1 | 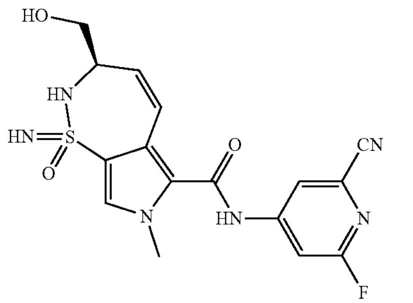 [SMILES: Cn1cc2c(c1C(=O)Nc1cc(F)nc(C#N)c1)C=C[C@H](CO)NS2(=N)=O] | 391 | Peak1 (HPLC) |
| 30k2 | 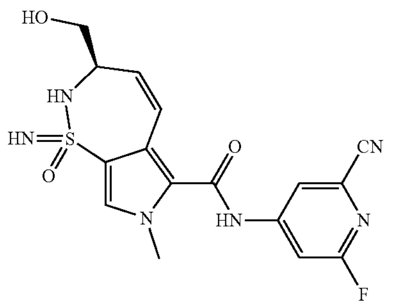 [SMILES: Cn1cc2c(c1C(=O)Nc1cc(F)nc(C#N)c1)C=C[C@H](CO)NS2(=N)=O] | 391 | Peak2 (HPLC) |
| 30m1 | 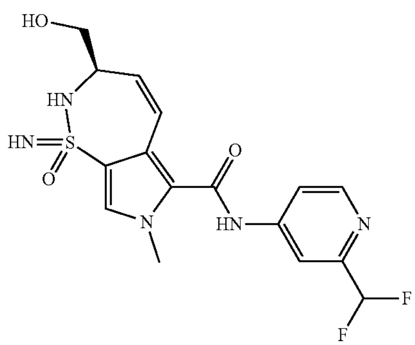 [SMILES: Cn1cc2c(c1C(=O)Nc1ccnc(C(F)F)c1)C=C[C@H](CO)NS2(=N)=O] | 398 | Peak1 (HPLC) |
| 30m2 | 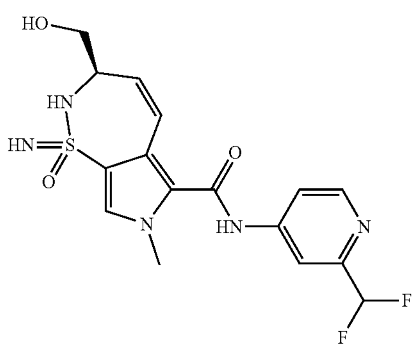 [SMILES: Cn1cc2c(c1C(=O)Nc1ccnc(C(F)F)c1)C=C[C@H](CO)NS2(=N)=O] | 398 | Peak2 (HPLC) |
| 40a1 | 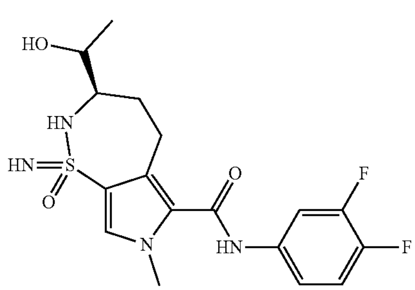 [SMILES: CC(O)[C@H]1CCc2c(cn(C)c2C(=O)Nc2ccc(F)c(F)c2)S(=N)(=O)N1] | 399 | Peak1 (HPLC) |

TABLE 1-continued

| No. | Structure | Mass Spectrum ESI-MS, (M + H) | Remark |
|---|---|---|---|
| 40a2 | 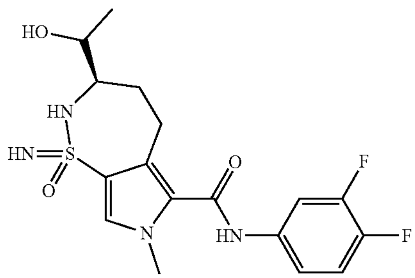 [SMILES: CC(O)[C@H]1CCc2c(cn(C)c2C(=O)Nc2ccc(F)c(F)c2)S(=N)(=O)N1] | 399 | Peak2 (HPLC) |
| 40b1 | 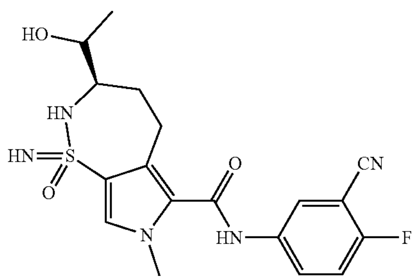 | 406 | Peak1 (HPLC) |
| 40b2 | 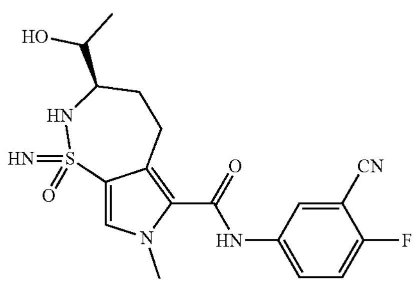 | 406 | Peak2 (HPLC) |
| 40c1 | 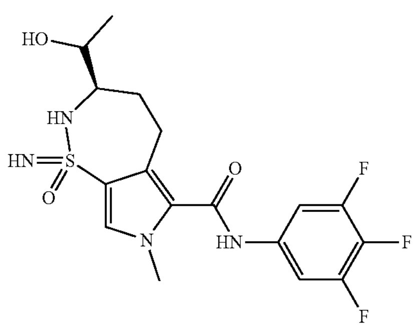 [SMILES: CC(O)[C@H]1CCc2c(cn(C)c2C(=O)Nc2cc(F)c(F)c(F)c2)S(=N)(=O)N1] | 417 | Peak1 (HPLC) |
| 40c2 | 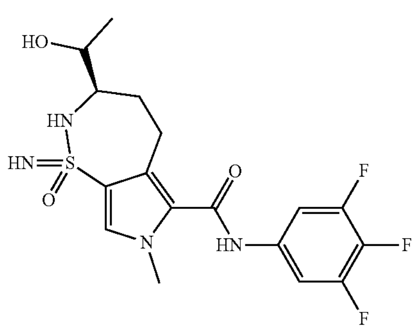 [SMILES: CC(O)[C@H]1CCc2c(cn(C)c2C(=O)Nc2cc(F)c(F)c(F)c2)S(=N)(=O)N1] | 417 | Peak2 (HPLC) |

TABLE 1-continued

| No. | Structure | Mass Spectrum ESI-MS, (M + H) | Remark |
|---|---|---|---|
| 40d1 | 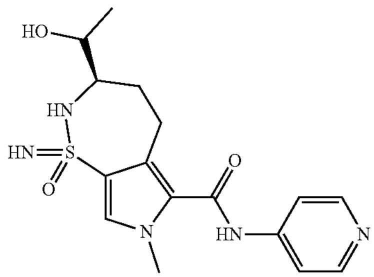 [SMILES: CC(O)[C@H]1CCc2c(cn(C)c2C(=O)Nc2ccncc2)S(=N)(=O)N1] | 364 | Peak1 (HPLC) |
| 40d2 | 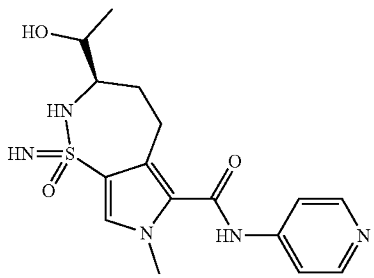 [SMILES: CC(O)[C@H]1CCc2c(cn(C)c2C(=O)Nc2ccncc2)S(=N)(=O)N1] | 364 | Peak2 (HPLC) |
| 40e1 | 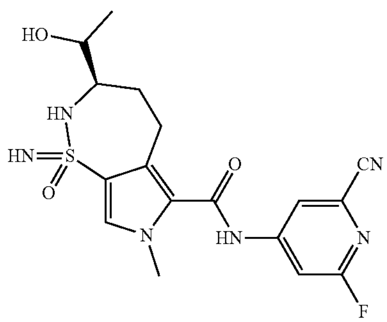 [SMILES: CC(O)[C@H]1CCc2c(cn(C)c2C(=O)Nc2cc(F)nc(C#N)c2)S(=N)(=O)N1] | 407 | Peak1 (HPLC) |
| 40e2 | 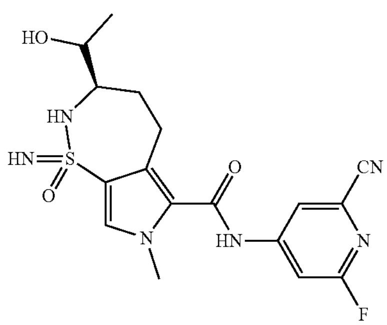 [SMILES: CC(O)[C@H]1CCc2c(cn(C)c2C(=O)Nc2cc(F)nc(C#N)c2)S(=N)(=O)N1] | 407 | Peak2 (HPLC) |
| 40f1 | 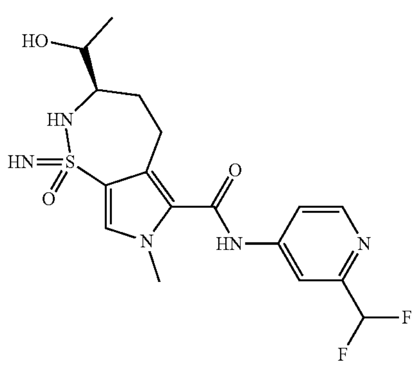 [SMILES: CC(O)[C@H]1CCc2c(cn(C)c2C(=O)Nc2ccnc(C(F)F)c2)S(=N)(=O)N1] | 414 | Peak1 (HPLC) |

TABLE 1-continued
| No. | Structure | Mass Spectrum ESI-MS, (M + H) | Remark |
|---|---|---|---|
| 40f2 | 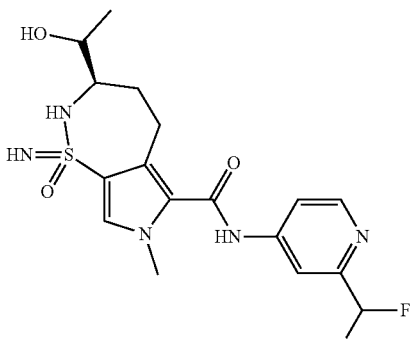 | 414 | Peak2 (HPLC) |
| 40g1 | 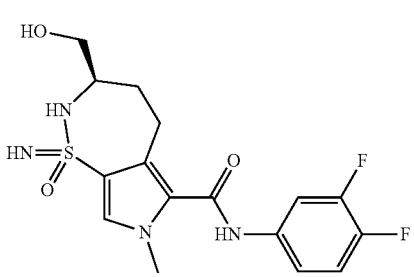 | 385 | Peak1 (HPLC) |
| 40g2 | 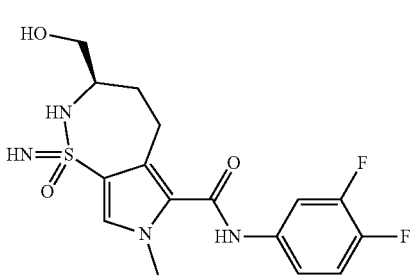 | 385 | Peak2 (HPLC) |
| 40h1 | 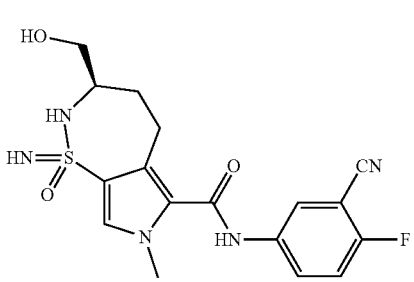 [SMILES: Cn1cc2c(c1C(=O)Nc1ccc(F)c(C#N)c1)CC[C@H](CO)NS2(=N)=O] | 392 | Peak1 (HPLC) |
| 40h2 | 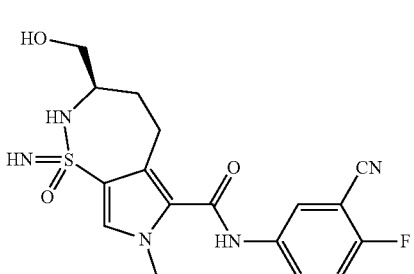 | 392 | Peak2 (HPLC) |

TABLE 1-continued

| No. | Structure | Mass Spectrum ESI-MS, (M + H) | Remark |
|---|---|---|---|
| 40i1 | 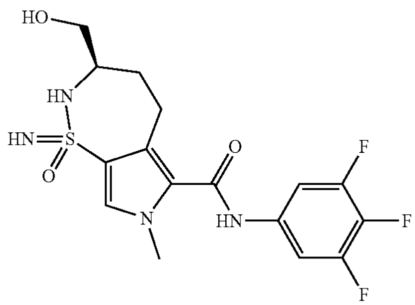 [SMILES: Cn1cc2c(c1C(=O)Nc1cc(F)c(F)c(F)c1)CC[C@H](CO)NS2(=N)=O] | 403 | Peak1 (HPLC) |
| 40i2 | 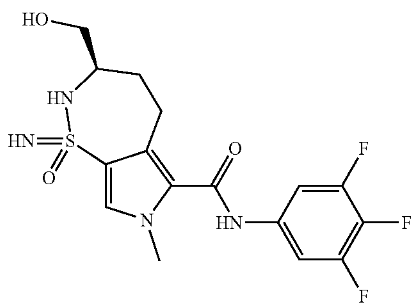 [SMILES: Cn1cc2c(c1C(=O)Nc1cc(F)c(F)c(F)c1)CC[C@H](CO)NS2(=N)=O] | 403 | Peak2 (HPLC) |
| 40j1 | 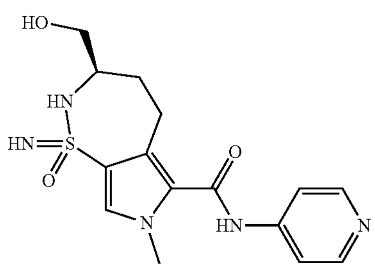 [SMILES: Cn1cc2c(c1C(=O)Nc1ccncc1)CC[C@H](CO)NS2(=N)=O] | 350 | Peak1 (HPLC) |
| 40j2 | 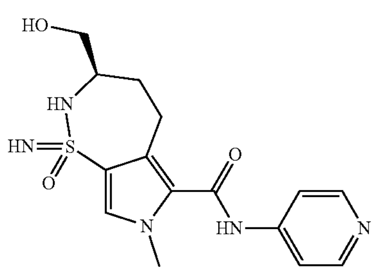 [SMILES: Cn1cc2c(c1C(=O)Nc1ccncc1)CC[C@H](CO)NS2(=N)=O] | 350 | Peak2 (HPLC) |
| 40k1 | 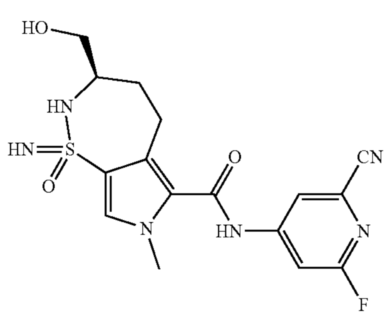 [SMILES: Cn1cc2c(c1C(=O)Nc1cc(F)nc(C#N)c1)CC[C@H](CO)NS2(=N)=O] | 393 | Peak1 (HPLC) |

TABLE 1-continued

| No. | Structure | Mass Spectrum ESI-MS, (M + H) | Remark |
|---|---|---|---|
| 40k2 | 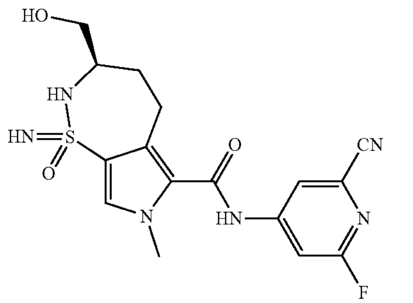 [SMILES: Cn1cc2c(c1C(=O)Nc1cc(F)nc(C#N)c1)CC[C@H](CO)NS2(=N)=O] | 393 | Peak2 (HPLC) |
| 40m1 | 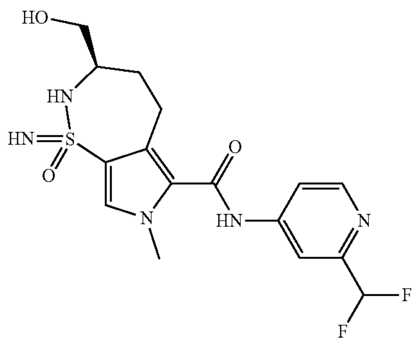 [SMILES: Cn1cc2c(c1C(=O)Nc1ccnc(C(F)F)c1)CC[C@H](CO)NS2(=N)=O] | 400 | Peak1 (HPLC) |
| 40m2 | 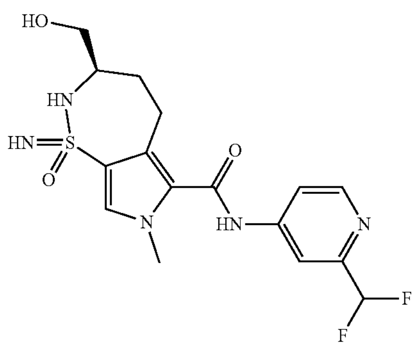 [SMILES: Cn1cc2c(c1C(=O)Nc1ccnc(C(F)F)c1)CC[C@H](CO)NS2(=N)=O] | 400 | Peak2 (HPLC) |
| 50a1 | 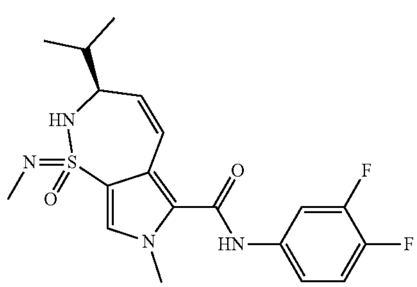 [SMILES: CN=S1(=O)N[C@@H](C(C)C)C=Cc2c1cn(C)c2C(=O)Nc1ccc(F)c(F)c1] | 409 | Peak1 (HPLC) |
| 50a2 | 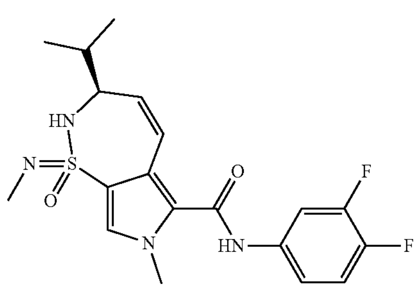 [SMILES: CN=S1(=O)N[C@@H](C(C)C)C=Cc2c1cn(C)c2C(=O)Nc1ccc(F)c(F)c1] | 409 | Peak2 (HPLC) |

TABLE 1-continued

| No. | Structure | Mass Spectrum ESI-MS, (M + H) | Remark |
|---|---|---|---|
| 50b1 | 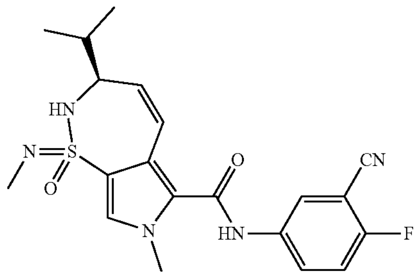 [SMILES: CN=S1(=O)N[C@@H](C(C)C)C=Cc2c1cn(C)c2C(=O)Nc1ccc(F)c(C#N)c1] | 416 | Peak1 (HPLC) |
| 50b2 | 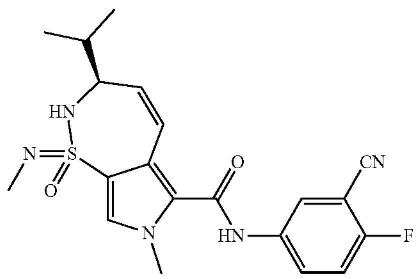 [SMILES: CN=S1(=O)N[C@@H](C(C)C)C=Cc2c1cn(C)c2C(=O)Nc1ccc(F)c(C#N)c1] | 416 | Peak2 (HPLC) |
| 50c1 | 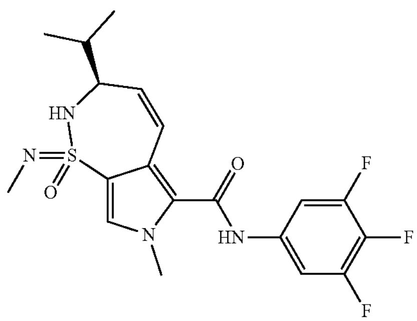 [SMILES: CN=S1(=O)N[C@@H](C(C)C)C=Cc2c1cn(C)c2C(=O)Nc1cc(F)c(F)c(F)c1] | 413 | Peak1 (HPLC) |
| 50c2 | 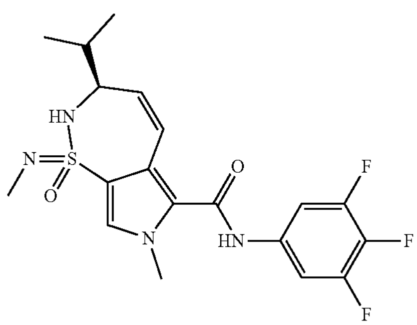 [SMILES: CN=S1(=O)N[C@@H](C(C)C)C=Cc2c1cn(C)c2C(=O)Nc1cc(F)c(F)c(F)c1] | 427 | Peak2 (HPLC) |
| 50d1 | 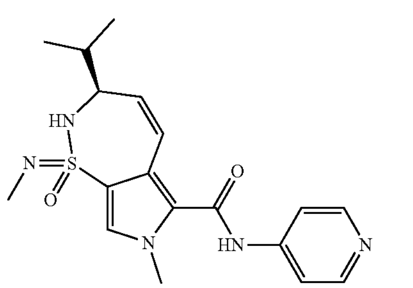 [SMILES: CN=S1(=O)N[C@@H](C(C)C)C=Cc2c1cn(C)c2C(=O)Nc1ccncc1] | 374 | Peak1 (HPLC) |

TABLE 1-continued

| No. | Structure | Mass Spectrum ESI-MS, (M + H) | Remark |
|---|---|---|---|
| 50d2 | 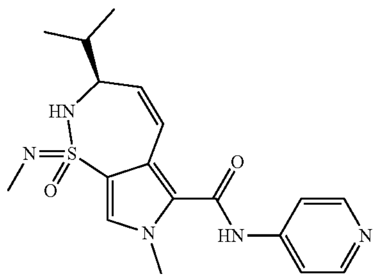 [SMILES: CN=S1(=O)N[C@@H](C(C)C)C=Cc2c1cn(C)c2C(=O)Nc1ccncc1] | 360 | Peak2 (HPLC) |
| 50e1 | 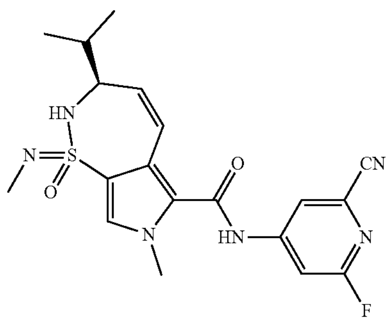 [SMILES: CN=S1(=O)N[C@@H](C(C)C)C=Cc2c1cn(C)c2C(=O)Nc1cc(F)nc(C#N)c1] | 417 | Peak1 (HPLC) |
| 50e2 | 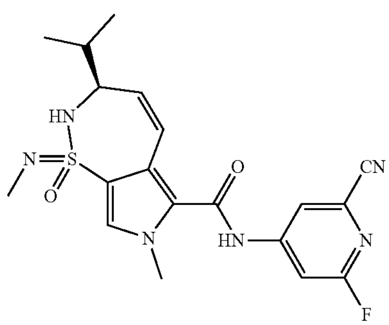 [SMILES: CN=S1(=O)N[C@@H](C(C)C)C=Cc2c1cn(C)c2C(=O)Nc1cc(F)nc(C#N)c1] | 417 | Peak2 (HPLC) |
| 50f1 | 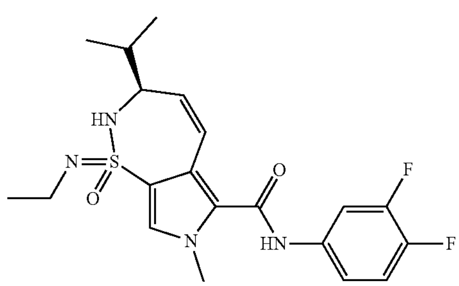 [SMILES: CCN=S1(=O)N[C@@H](C(C)C)C=Cc2c1cn(C)c2C(=O)Nc1ccc(F)c(F)c1] | 423 | Peak1 (HPLC) |
| 50f2 | 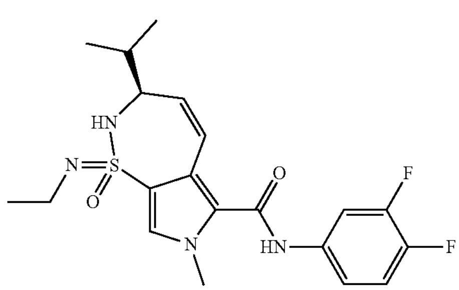 [SMILES: CCN=S1(=O)N[C@@H](C(C)C)C=Cc2c1cn(C)c2C(=O)Nc1ccc(F)c(F)c1] | 423 | Peak2 (HPLC) |

TABLE 1-continued

| No. | Structure | Mass Spectrum ESI-MS, (M + H) | Remark |
|---|---|---|---|
| 50g1 | 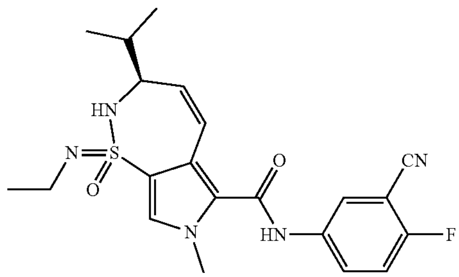 [SMILES: CCN=S1(=O)N[C@@H](C(C)C)C=Cc2c1cn(C)c2C(=O)Nc1ccc(F)c(C#N)c1] | 430 | Peak1 (HPLC) |
| 50g2 | 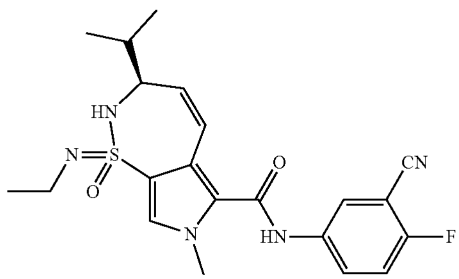 [SMILES: CCN=S1(=O)N[C@@H](C(C)C)C=Cc2c1cn(C)c2C(=O)Nc1ccc(F)c(C#N)c1] | 430 | Peak2 (HPLC) |
| 50h1 | 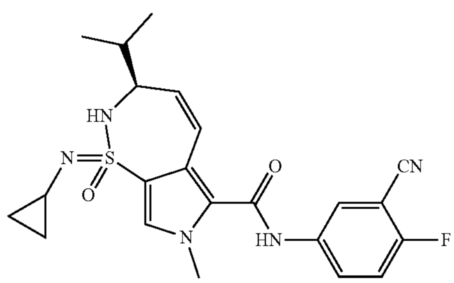 [SMILES: CC(C)[C@H]1C=Cc2c(cn(C)c2C(=O)Nc2ccc(F)c(C#N)c2)S(=O)(=NC2CC2)N1] | 442 | Peak1 (HPLC) |
| 50h2 | 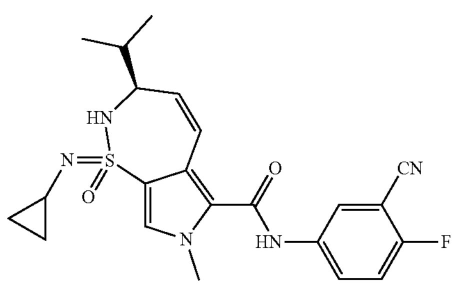 [SMILES: CC(C)[C@H]1C=Cc2c(cn(C)c2C(=O)Nc2ccc(F)c(C#N)c2)S(=O)(=NC2CC2)N1] | 442 | Peak2 (HPLC) |
| 50i1 | 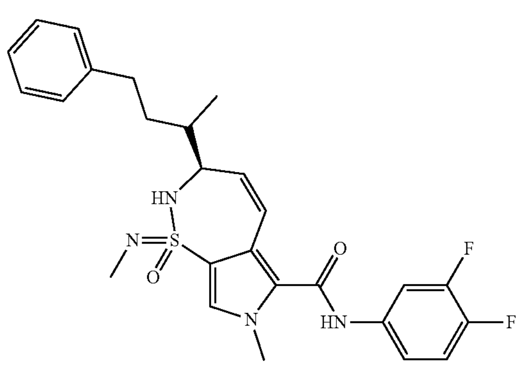 [SMILES: CN=S1(=O)N[C@@H](C(C)CCc2ccccc2)C=Cc2c1cn(C)c2C(=O)Nc1ccc(F)c(F)c1] | 499 | Peak1 (HPLC) |

TABLE 1-continued

| No. | Structure | Mass Spectrum ESI-MS, (M + H) | Remark |
|---|---|---|---|
| 50i2 | 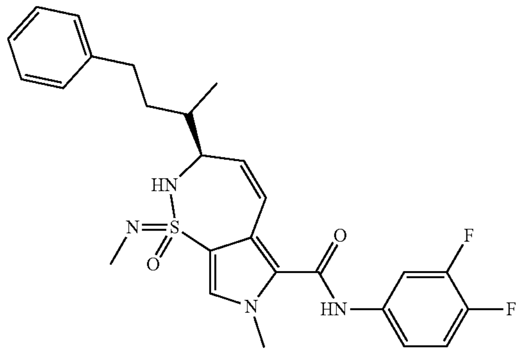 [SMILES: CN=S1(=O)N[C@@H](C(C)CCc2ccccc2)C=Cc2c1cn(C)c2C(=O)Nc1ccc(F)c(F)c1] | 499 | Peak2 (HPLC) |
| 50j1 | 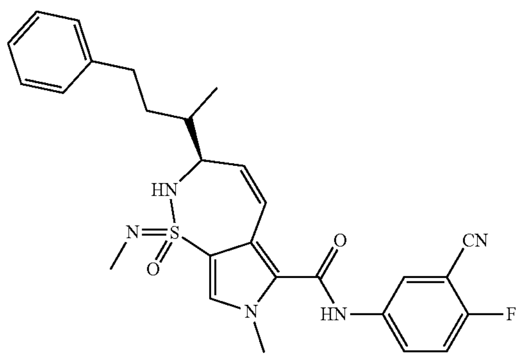 [SMILES: CN=S1(=O)N[C@@H](C(C)CCc2ccccc2)C=Cc2c1cn(C)c2C(=O)Nc1ccc(F)c(C#N)c1] | 506 | Peak1 (HPLC) |
| 50j2 | 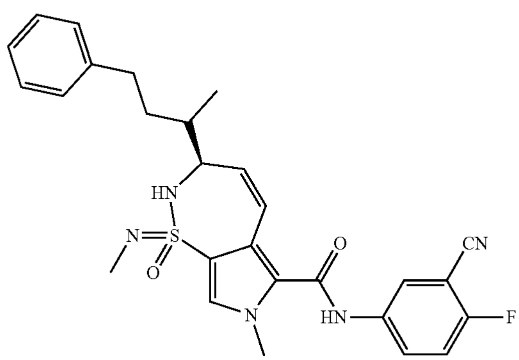 [SMILES: CN=S1(=O)N[C@@H](C(C)CCc2ccccc2)C=Cc2c1cn(C)c2C(=O)Nc1ccc(F)c(C#N)c1] | 506 | Peak2 (HPLC) |
| 50k1 | 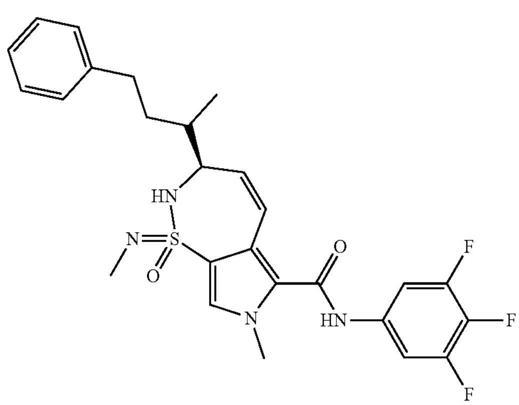 [SMILES: CN=S1(=O)N[C@@H](C(C)CCc2ccccc2)C=Cc2c1cn(C)c2C(=O)Nc1cc(F)c(F)c(F)c1] | 517 | Peak1 (HPLC) |

TABLE 1-continued

| No. | Structure | Mass Spectrum ESI-MS, (M + H) | Remark |
|---|---|---|---|
| 50k2 | 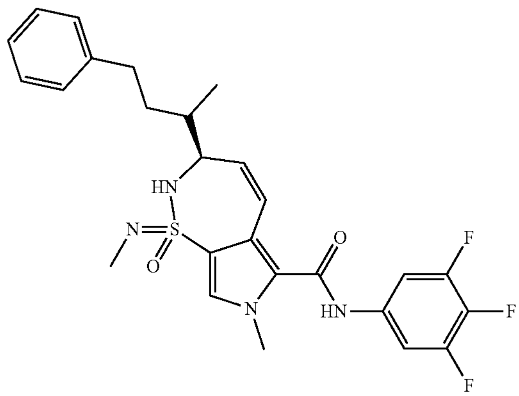 [SMILES: CN=S1(=O)N[C@@H](C(C)CCc2ccccc2)C=Cc2c1cn(C)c2C(=O)Nc1cc(F)c(F)c(F)c1] | 427 | Peak2 (HPLC) |
| 50m1 | 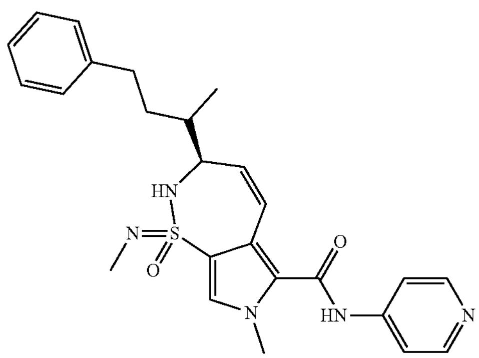 [SMILES: CN=S1(=O)N[C@@H](C(C)CCc2ccccc2)C=Cc2c1cn(C)c2C(=O)Nc1ccncc1] | 464 | Peak1 (HPLC) |
| 50m2 | 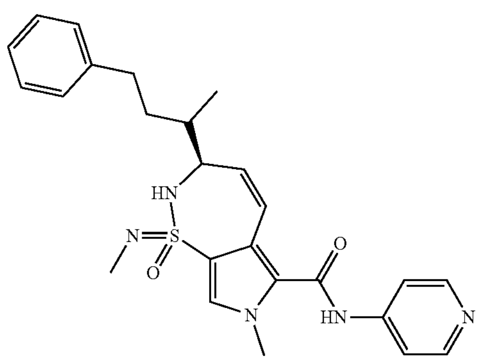 [SMILES: CN=S1(=O)N[C@@H](C(C)CCc2ccccc2)C=Cc2c1cn(C)c2C(=O)Nc1ccncc1] | 464 | Peak2 (HPLC) |
| 50n1 | 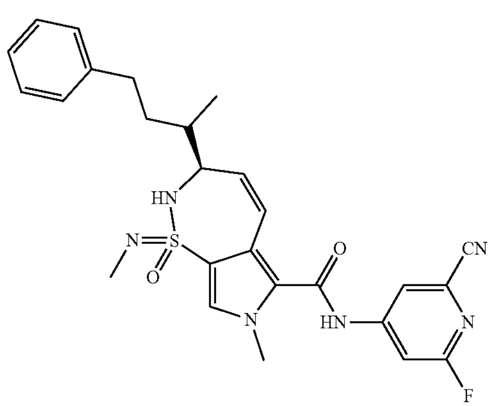 [SMILES: CN=S1(=O)N[C@@H](C(C)CCc2ccccc2)C=Cc2c1cn(C)c2C(=O)Nc1cc(F)nc(C#N)c1] | 507 | Peak1 (HPLC) |

TABLE 1-continued

| No. | Structure | Mass Spectrum ESI-MS, (M + H) | Remark |
|---|---|---|---|
| 50n2 | 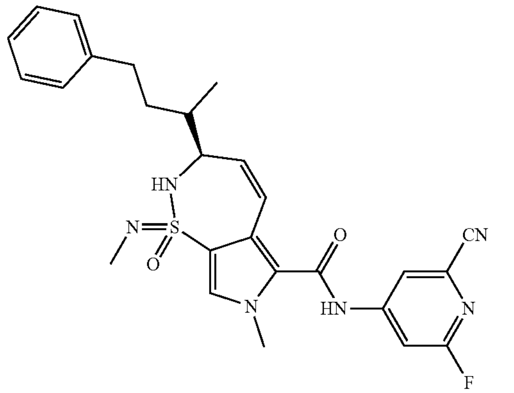 [SMILES: CN=S1(=O)N[C@@H](C(C)CCc2ccccc2)C=Cc2c1cn(C)c2C(=O)Nc1cc(F)nc(C#N)c1] | 507 | Peak2 (HPLC) |
| 50o1 | 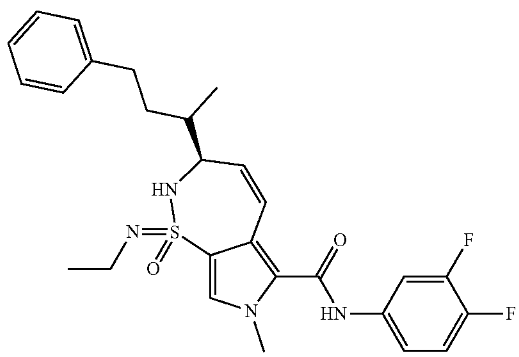 [SMILES: CCN=S1(=O)N[C@@H](C(C)CCc2ccccc2)C=Cc2c1cn(C)c2C(=O)Nc1ccc(F)c(F)c1] | 513 | Peak1 (HPLC) |
| 50o2 | 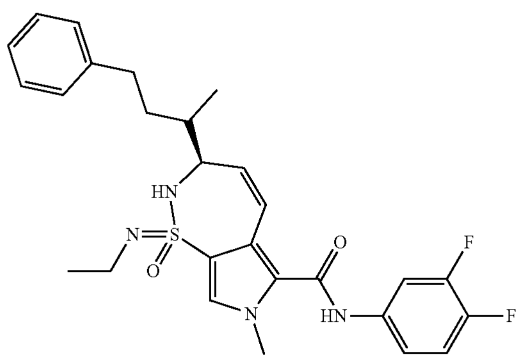 [SMILES: CCN=S1(=O)N[C@@H](C(C)CCc2ccccc2)C=Cc2c1cn(C)c2C(=O)Nc1ccc(F)c(F)c1] | 513 | Peak2 (HPLC) |
| 50p1 | 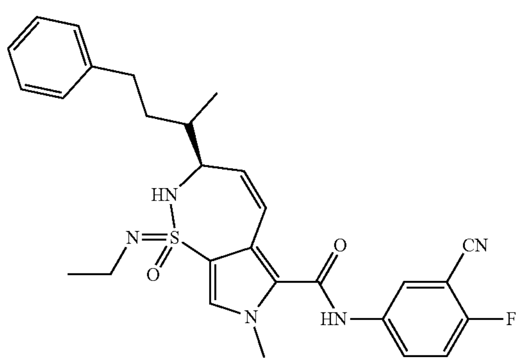 [SMILES: CCN=S1(=O)N[C@@H](C(C)CCc2ccccc2)C=Cc2c1cn(C)c2C(=O)Nc1ccc(F)c(C#N)c1] | 520 | Peak1 (HPLC) |

TABLE 1-continued
| No. | Structure | Mass Spectrum ESI-MS, (M + H) | Remark |
|---|---|---|---|
| 50p2 | 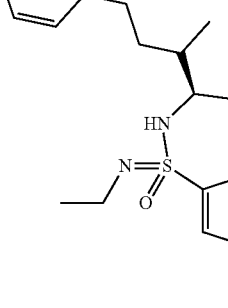 | 520 | Peak2 (HPLC) |
| 50q1 | 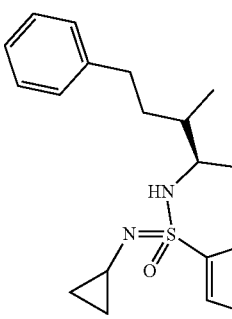 | 525 | Peak1 (HPLC) |
| 50q2 | 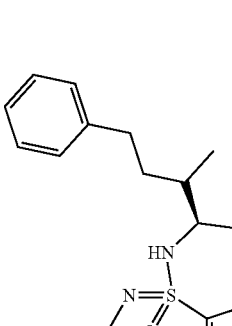 | 525 | Peak2 (HPLC) |
| 50r1 | 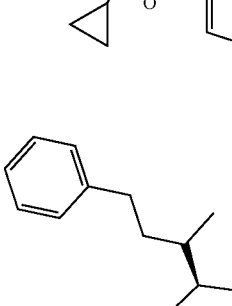 | 532 | Peak1 (HPLC) |

TABLE 1-continued
| No. | Structure | Mass Spectrum ESI-MS, (M + H) | Remark |
|---|---|---|---|
| 50r2 | 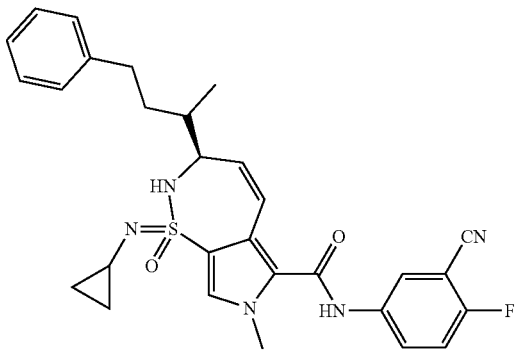 | 532 | Peak2 (HPLC) |
| 50s1 | 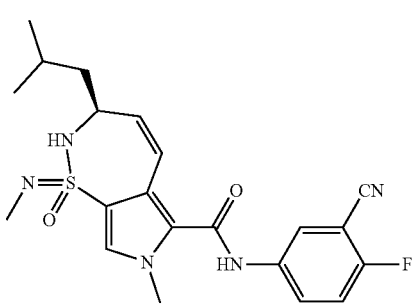 [SMILES: CN=S1(=O)N[C@@H](CC(C)C)C=Cc2c1cn(C)c2C(=O)Nc1ccc(F)c(C#N)c1] | 430 | Peak1 (HPLC) |
| 50s2 | 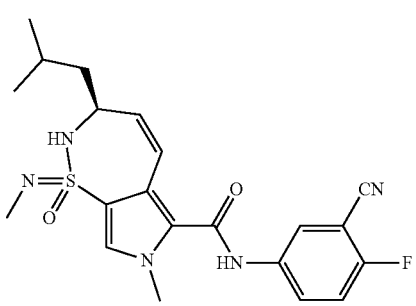 [SMILES: CN=S1(=O)N[C@@H](CC(C)C)C=Cc2c1cn(C)c2C(=O)Nc1ccc(F)c(C#N)c1] | 430 | Peak2 (HPLC) |
| 50t1 | 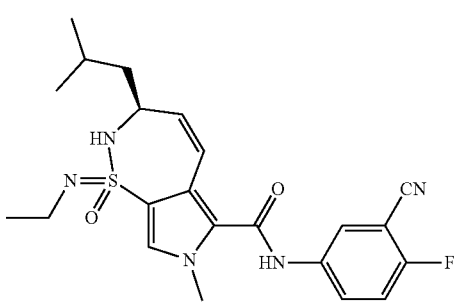 [SMILES: CCN=S1(=O)N[C@@H](CC(C)C)C=Cc2c1cn(C)c2C(=O)Nc1ccc(F)c(C#N)c1] | 444 | Peak1 (HPLC) |
| 50t2 | 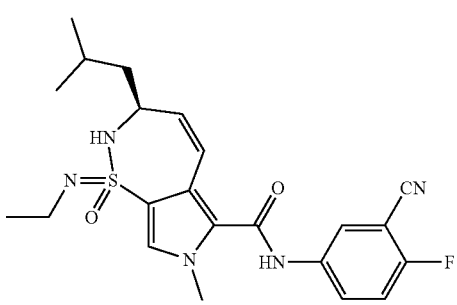 [SMILES: CCN=S1(=O)N[C@@H](CC(C)C)C=Cc2c1cn(C)c2C(=O)Nc1ccc(F)c(C#N)c1] | 444 | Peak2 (HPLC) |

TABLE 1-continued
| No. | Structure | Mass Spectrum ESI-MS, (M + H) | Remark |
|---|---|---|---|
| 50u1 | 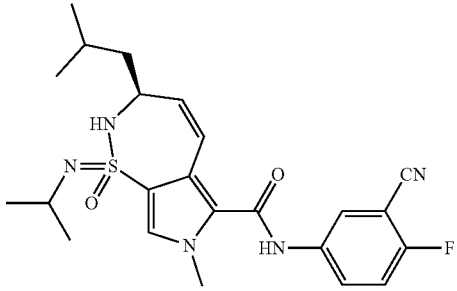 [SMILES: CC(C)C[C@H]1C=Cc2c(cn(C)c2C(=O)Nc2ccc(F)c(C#N)c2)S(=O)(=NC(C)C)N1] | 458 | Peak1 (HPLC) |
| 50u2 | 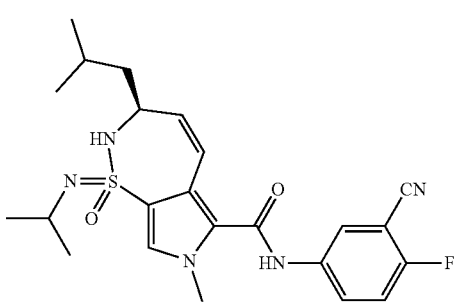 [SMILES: CC(C)C[C@H]1C=Cc2c(cn(C)c2C(=O)Nc2ccc(F)c(C#N)c2)S(=O)(=NC(C)C)N1] | 458 | Peak2 (HPLC) |
| 50v1 | 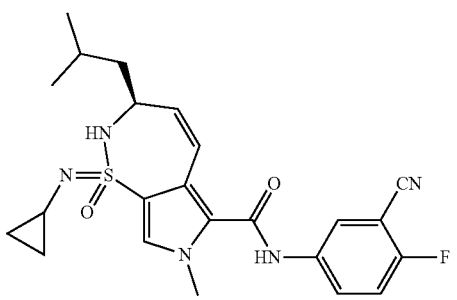 [SMILES: CC(C)C[C@H]1C=Cc2c(cn(C)c2C(=O)Nc2ccc(F)c(C#N)c2)S(=O)(=NC2CC2)N1] | 456 | Peak1 (HPLC) |
| 50v2 | 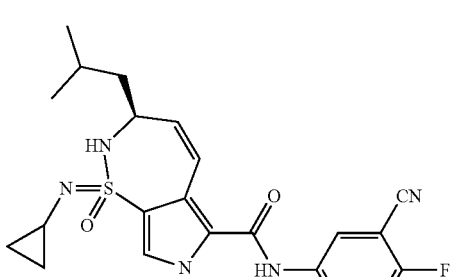 | 456 | Peak2 (HPLC) |
| 50w1 | 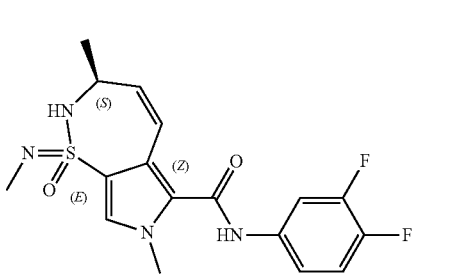 | 381 | Peak1 (HPLC) |

TABLE 1-continued

| No. | Structure | Mass Spectrum ESI-MS, (M + H) | Remark |
|---|---|---|---|
| 50w2 | 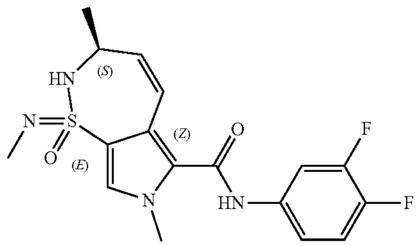 | 381 | Peak2 (HPLC) |
| 50x1 | 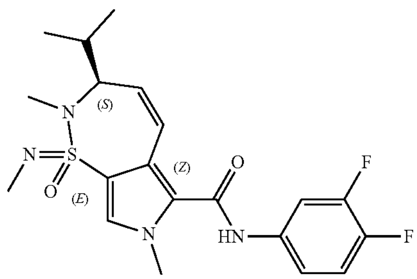 | 423 | Peak1 (HPLC) |
| 50x2 | 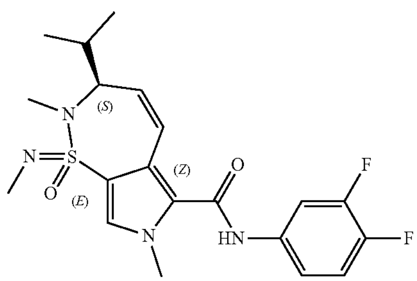 | 423 | Peak2 (HPLC) |
| 60a1 | 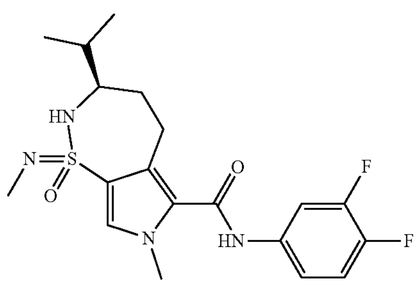 [SMILES: CN=S1(=O)N[C@@H](C(C)C)CCc2c1cn(C)c2C(=O)Nc1ccc(F)c(F)c1] | 411 | Peak1 (HPLC) |
| 60a2 | 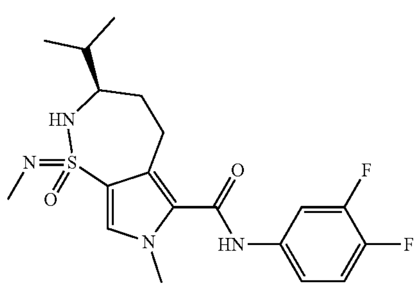 [SMILES: CN=S1(=O)N[C@@H](C(C)C)CCc2c1cn(C)c2C(=O)Nc1ccc(F)c(F)c1] | 411 | Peak2 (HPLC) |

TABLE 1-continued

| No. | Structure | Mass Spectrum ESI-MS, (M + H) | Remark |
|---|---|---|---|
| 60b1 | 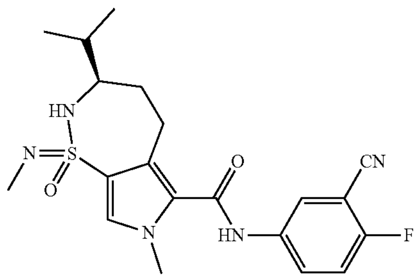 [SMILES: CN=S1(=O)N[C@@H](C(C)C)CCc2c1cn(C)c2C(=O)Nc1ccc(F)c(C#N)c1] | 418 | Peak1 (HPLC) |
| 60b2 | 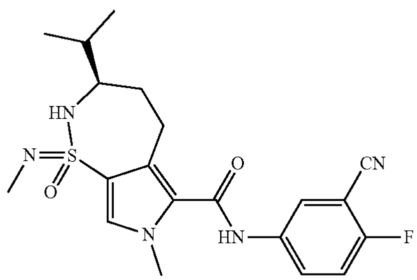 [SMILES: CN=S1(=O)N[C@@H](C(C)C)CCc2c1cn(C)c2C(=O)Nc1ccc(F)c(C#N)c1] | 418 | Peak2 (HPLC) |
| 60c1 | 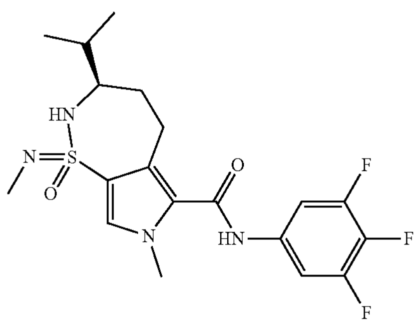 [SMILES: CN=S1(=O)N[C@@H](C(C)C)CCc2c1cn(C)c2C(=O)Nc1cc(F)c(F)c(F)c1] | 429 | Peak1 (HPLC) |
| 60c2 | 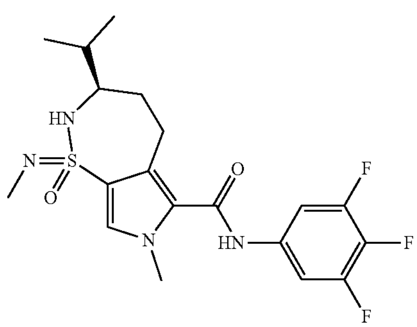 [SMILES: CN=S1(=O)N[C@@H](C(C)C)CCc2c1cn(C)c2C(=O)Nc1cc(F)c(F)c(F)c1] | 429 | Peak2 (HPLC) |
| 60d1 | 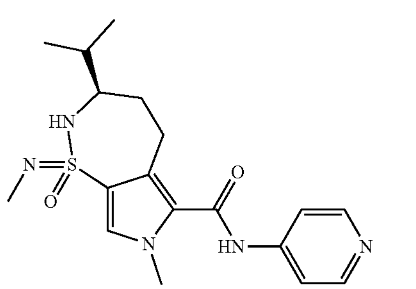 [SMILES: CN=S1(=O)N[C@@H](C(C)C)CCc2c1cn(C)c2C(=O)Nc1ccncc1] | 376 | Peak1 (HPLC) |

TABLE 1-continued

| No. | Structure | Mass Spectrum ESI-MS, (M + H) | Remark |
|---|---|---|---|
| 60d2 | 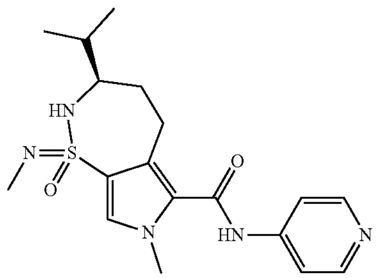 [SMILES: CN=S1(=O)N[C@@H](C(C)C)CCc2c1cn(C)c2C(=O)Nc1ccncc1] | 376 | Peak2 (HPLC) |
| 60e1 | 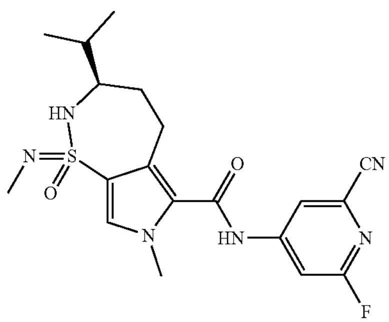 [SMILES: CN=S1(=O)N[C@@H](C(C)C)CCc2c1cn(C)c2C(=O)Nc1cc(F)nc(C#N)c1] | 419 | Peak1 (HPLC) |
| 60e2 | 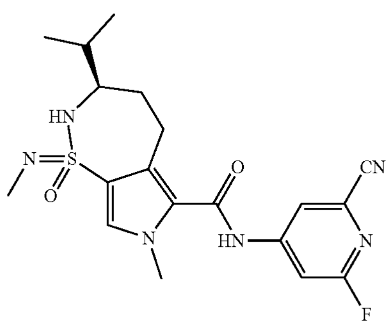 [SMILES: CN=S1(=O)N[C@@H](C(C)C)CCc2c1cn(C)c2C(=O)Nc1cc(F)nc(C#N)c1] | 419 | Peak2 (HPLC) |
| 60f1 | 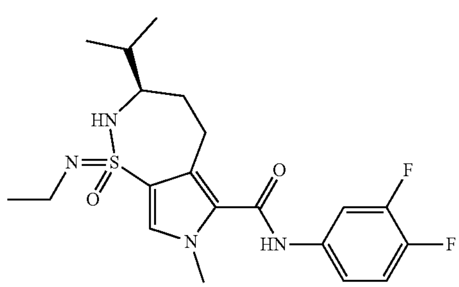 [SMILES: CCN=S1(=O)N[C@@H](C(C)C)CCc2c1cn(C)c2C(=O)Nc1ccc(F)c(F)c1] | 425 | Peak1 (HPLC) |
| 60f2 | 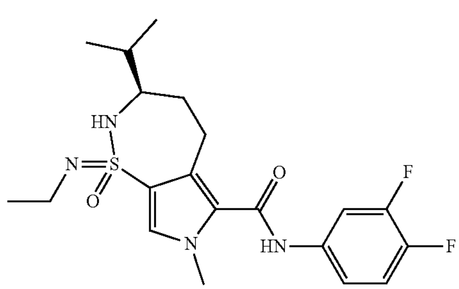 [SMILES: CCN=S1(=O)N[C@@H](C(C)C)CCc2c1cn(C)c2C(=O)Nc1ccc(F)c(F)c1] | 425 | Peak2 (HPLC) |

TABLE 1-continued
| No. | Structure | Mass Spectrum ESI-MS, (M + H) | Remark |
|---|---|---|---|
| 60g1 | 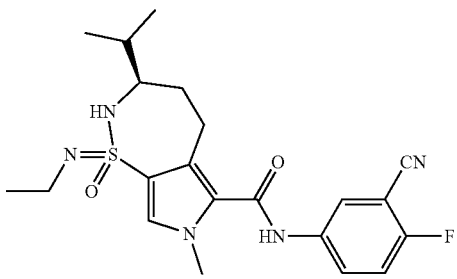 [SMILES: CCN=S1(=O)N[C@@H](C(C)C)CCc2c1cn(C)c2C(=O)Nc1ccc(F)c(C#N)c1] | 432 | Peak1 (HPLC) |
| 60g2 | 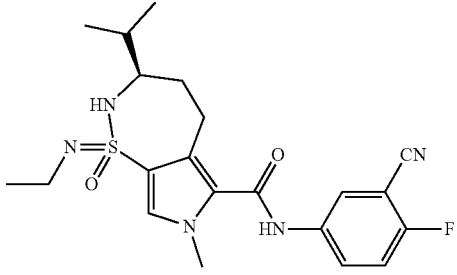 [SMILES: CCN=S1(=O)N[C@@H](C(C)C)CCc2c1cn(C)c2C(=O)Nc1ccc(F)c(C#N)c1] | 432 | Peak2 (HPLC) |
| 60h1 | 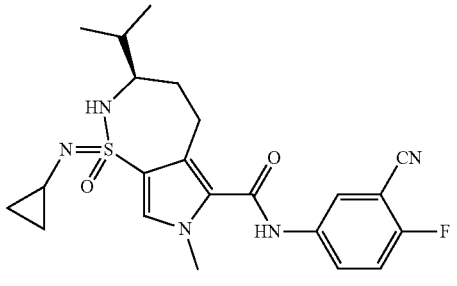 [SMILES: CC(C)[C@H]1CCc2c(cn(C)c2C(=O)Nc2ccc(F)c(C#N)c2)S(=O)(=NC2CC2)N1] | 446 | Peak1 (HPLC) |
| 60h2 | 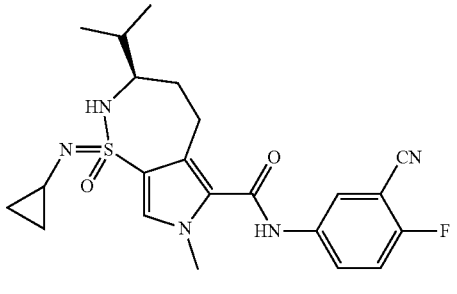 [SMILES: CC(C)[C@H]1CCc2c(cn(C)c2C(=O)Nc2ccc(F)c(C#N)c2)S(=O)(=NC2CC2)N1] | 446 | Peak2 (HPLC) |
| 60i1 | 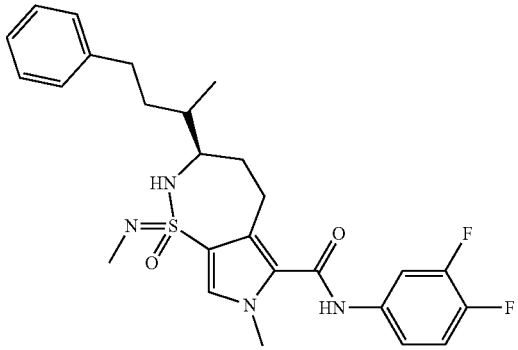 [SMILES: CN=S1(=O)N[C@@H](C(C)CCc2ccccc2)CCc2c1cn(C)c2C(=O)Nc1ccc(F)c(F)c1] | 501 | Peak1 (HPLC) |

TABLE 1-continued
| No. | Structure | Mass Spectrum ESI-MS, (M + H) | Remark |
|---|---|---|---|
| 60i2 | 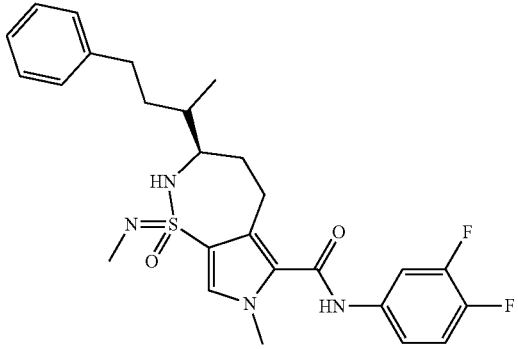 [SMILES: CN=S1(=O)N[C@@H](C(C)CCc2ccccc2)CCc2c1cn(C)c2C(=O)Nc1ccc(F)c(F)c1] | 501 | Peak2 (HPLC) |
| 60j1 | 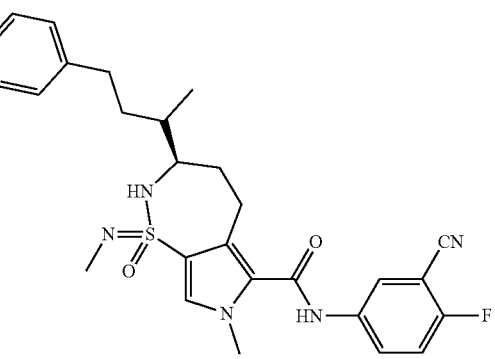 | 508 | Peak1 (HPLC) |
| 60j2 | 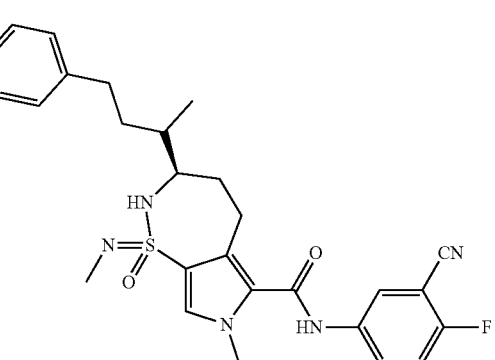 | 508 | Peak2 (HPLC) |
| 60k1 | 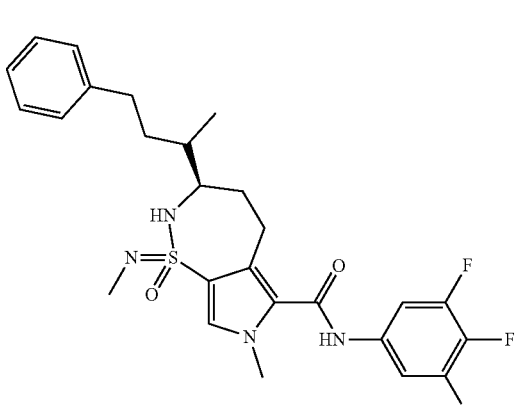 | 519 | Peak1 (HPLC) |

TABLE 1-continued

| No. | Structure | Mass Spectrum ESI-MS, (M + H) | Remark |
|---|---|---|---|
| 60k2 | 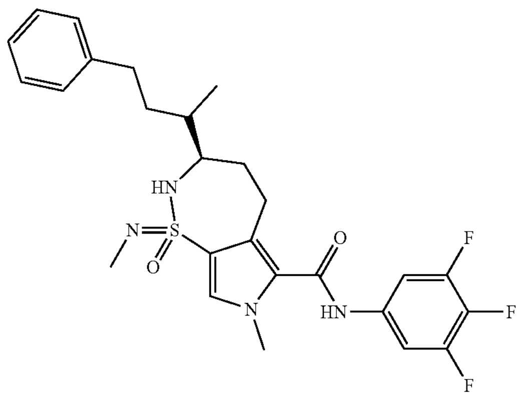 [SMILES: CN=S1(=O)N[C@@H](C(C)CCc2ccccc2)CCc2c1cn(C)c2C(=O)Nc1cc(F)c(F)c(F)c1] | 519 | Peak2 (HPLC) |
| 60m1 | 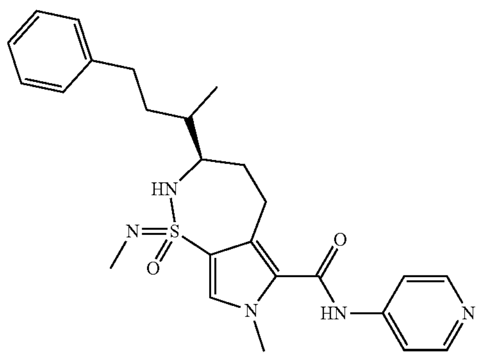 [SMILES: CN=S1(=O)N[C@@H](C(C)CCc2ccccc2)CCc2c1cn(C)c2C(=O)Nc1ccncc1] | 466 | Peak1 (HPLC) |
| 60m2 | 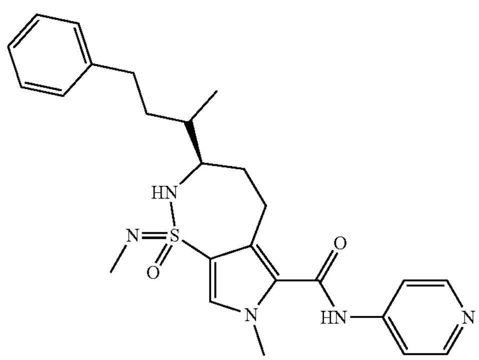 [SMILES: CN=S1(=O)N[C@@H](C(C)CCc2ccccc2)CCc2c1cn(C)c2C(=O)Nc1ccncc1] | 466 | Peak2 (HPLC) |
| 60n1 | 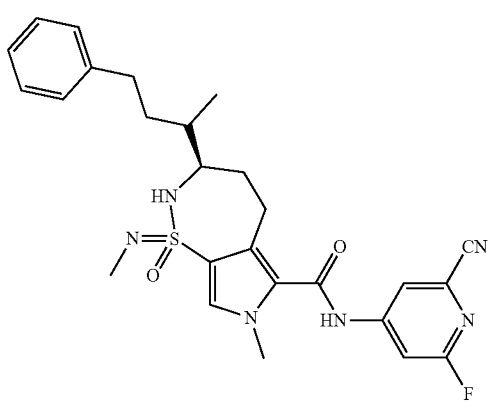 [SMILES: CN=S1(=O)N[C@@H](C(C)CCc2ccccc2)CCc2c1cn(C)c2C(=O)Nc1cc(F)nc(C#N)c1] | 509 | Peak1 (HPLC) |

TABLE 1-continued
| No. | Structure | Mass Spectrum ESI-MS, (M + H) | Remark |
|---|---|---|---|
| 60n2 | 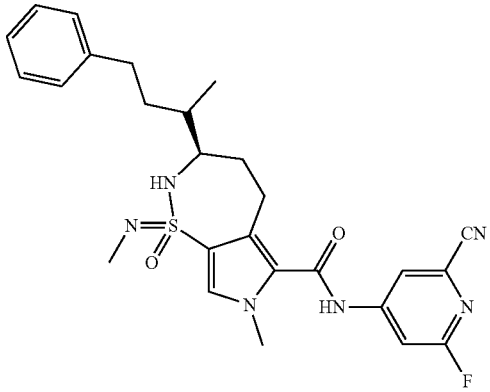 [SMILES: CN=S1(=O)N[C@@H](C(C)CCc2ccccc2)CCc2c1cn(C)c2C(=O)Nc1cc(F)nc(C#N)c1] | 509 | Peak2 (HPLC) |
| 60o1 | 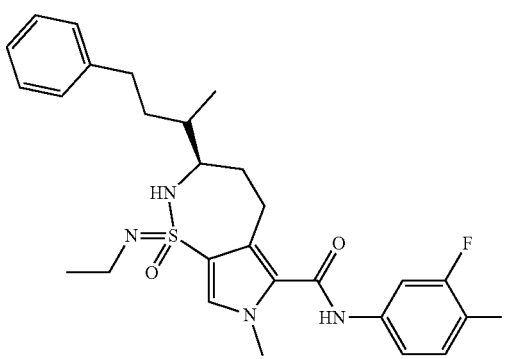 | 515 | Peak1 (HPLC) |
| 60o2 | 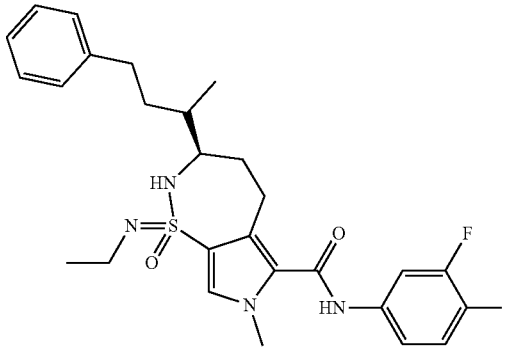 | 515 | Peak2 (HPLC) |
| 60p1 | 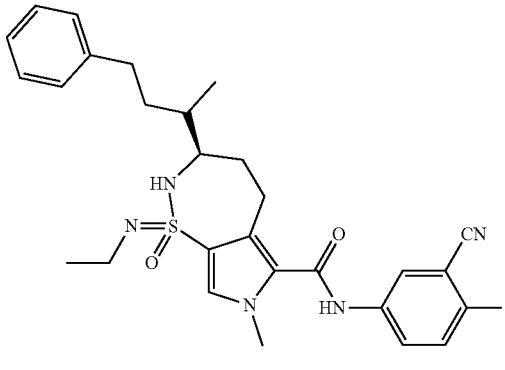 | 522 | Peak1 (HPLC) |

TABLE 1-continued

| No. | Structure | Mass Spectrum ESI-MS, (M + H) | Remark |
| --- | --- | --- | --- |
| 60p2 | 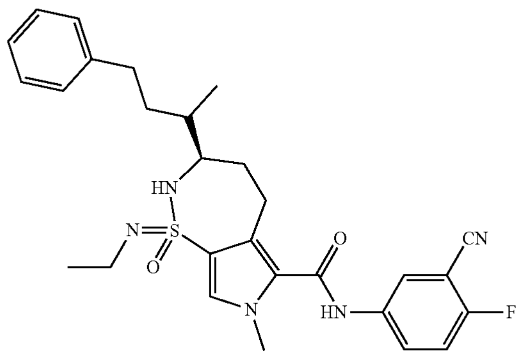 | 522 | Peak2 (HPLC) |
| 60q1 | 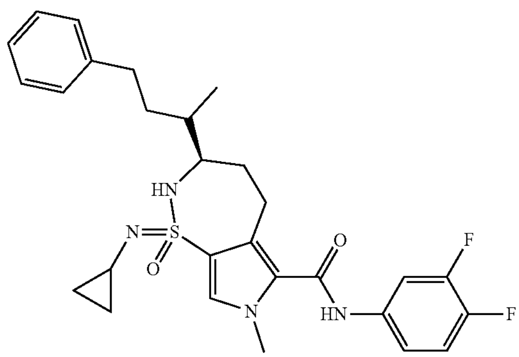 | 527 | Peak1 (HPLC) |
| 60q2 | 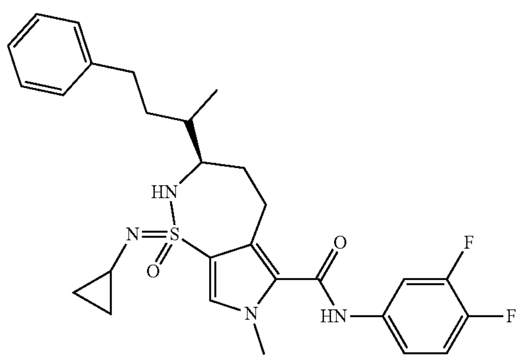 | 527 | Peak2 (HPLC) |
| 60r1 | 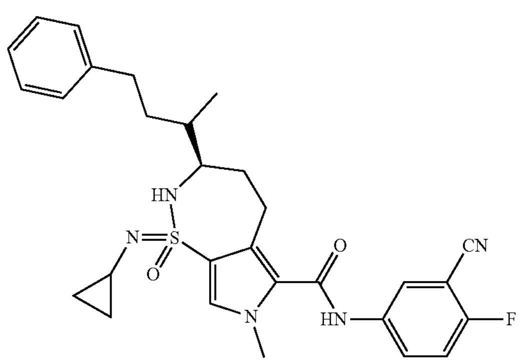 | 534 | Peak1 (HPLC) |

TABLE 1-continued

| No. | Structure | Mass Spectrum ESI-MS, (M + H) | Remark |
|---|---|---|---|
| 60r2 | 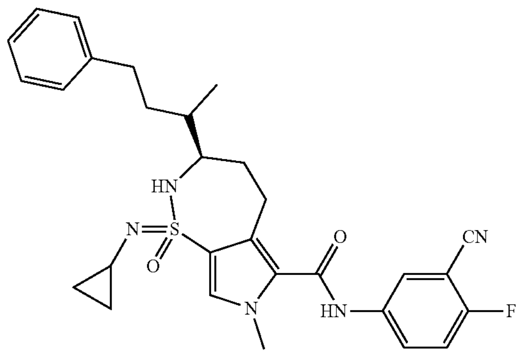 | 534 | Peak2 (HPLC) |
| 60s1 | 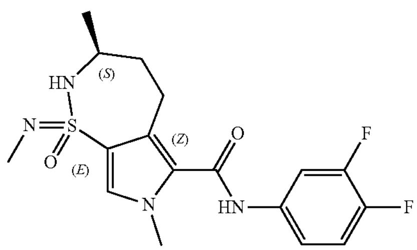 | 383 | Peak1 (HPLC) |
| 60s2 | 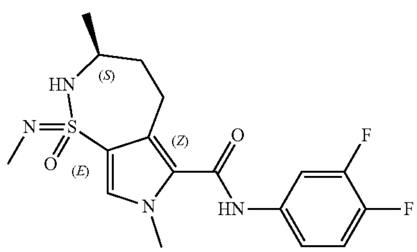 | 383 | Peak2 (HPLC) |
| 60t1 | 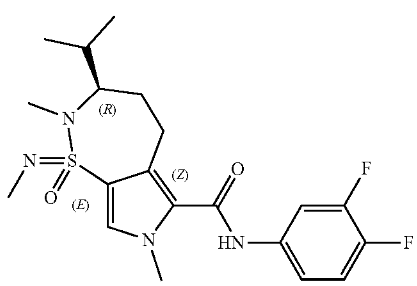 | 425 | Peak1 (HPLC) |
| 60t2 | 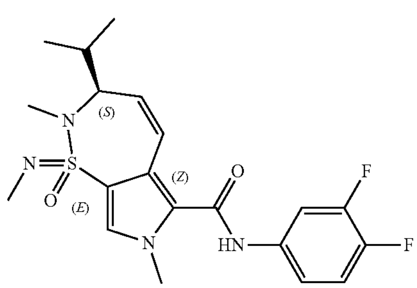 | 425 | Peak2 (HPLC) |

TABLE 1-continued

| No. | Structure | Mass Spectrum ESI-MS, (M + H) | Remark |
| --- | --- | --- | --- |
| 60u1 | 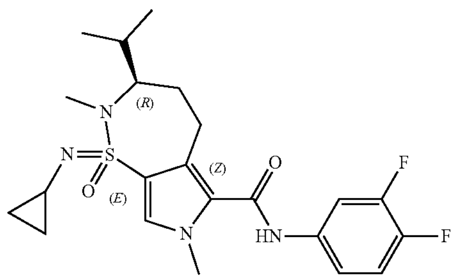 | 451 | Peak1 (HPLC) |
| 60u2 | 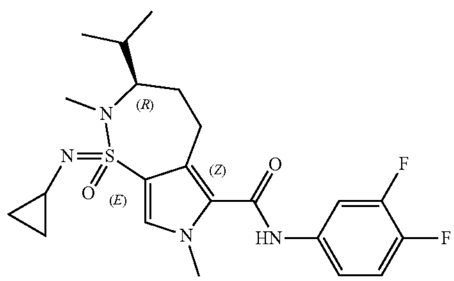 | 451 | Peak2 (HPLC) |
| 60v1 | 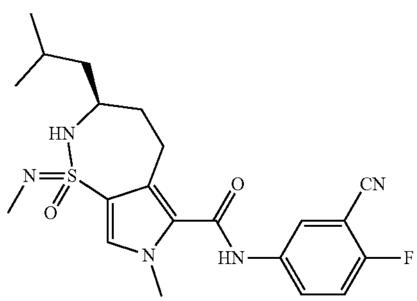 | 432 | Peak1 (HPLC) |
| 60v2 | 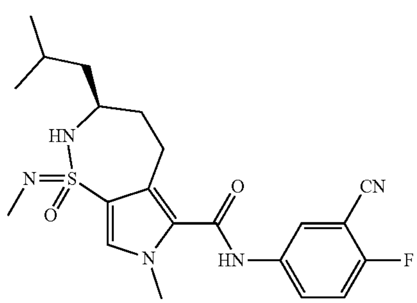 [SMILES: CN=S1(=O)N[C@@H](CC(C)C)CCc2c1cn(C)c2C(=O)Nc1ccc(F)c(C#N)c1] | 432 | Peak2 (HPLC) |
| 60w1 | 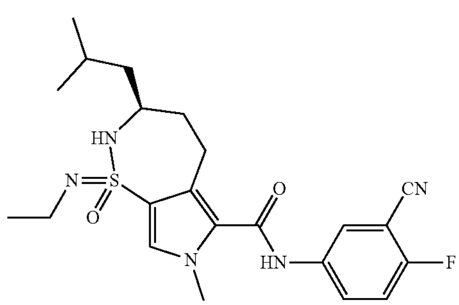 [SMILES: CCN=S1(=O)N[C@@H](CC(C)C)CCc2c1cn(C)c2C(=O)Nc1ccc(F)c(C#N)c1] | 446 | Peak1 (HPLC) |

TABLE 1-continued
| No. | Structure | Mass Spectrum ESI-MS, (M + H) | Remark |
|---|---|---|---|
| 60w2 | 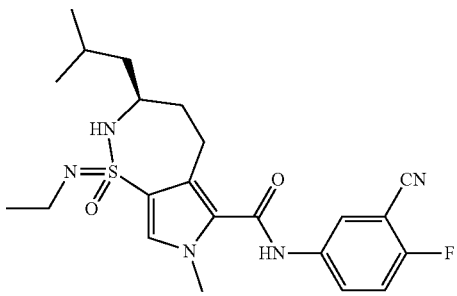 [SMILES: CCN=S1(=O)N[C@@H](CC(C)C)CCc2c1cn(C)c2C(=O)Nc1ccc(F)c(C#N)c1] | 446 | Peak2 (HPLC) |
| 60x1 | 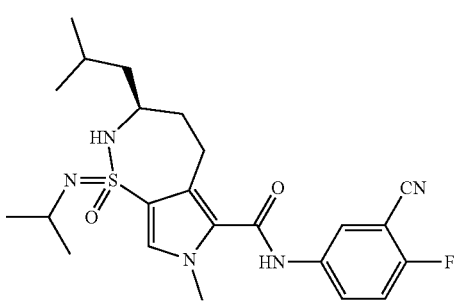 [SMILES: CC(C)C[C@H]1CCc2c(cn(C)c2C(=O)Nc2ccc(F)c(C#N)c2)S(=O)(=NC(C)C)N1] | 460 | Peak1 (HPLC) |
| 60x2 | 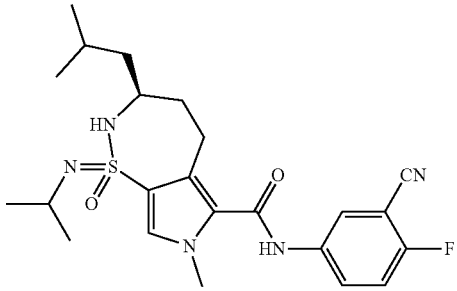 [SMILES: CC(C)C[C@H]1CCc2c(cn(C)c2C(=O)Nc2ccc(F)c(C#N)c2)S(=O)(=NC(C)C)N1] | 460 | Peak2 (HPLC) |
| 60y1 | 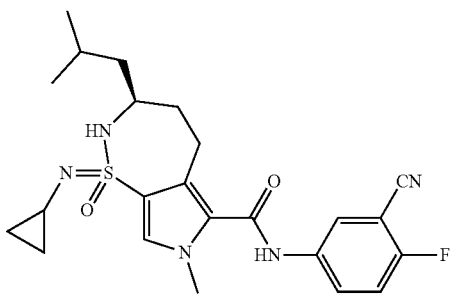 | 458 | Peak1 (HPLC) |
| 60y2 | 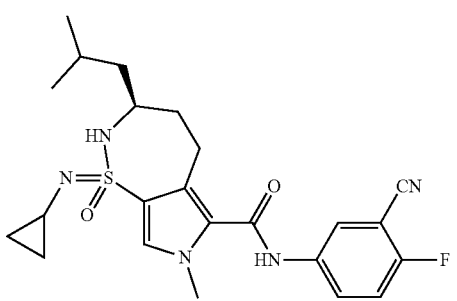 | 458 | Peak2 (HPLC) |

TABLE 1-continued

| No. | Structure | Mass Spectrum ESI-MS, (M + H) | Remark |
|---|---|---|---|
| 70a1 | 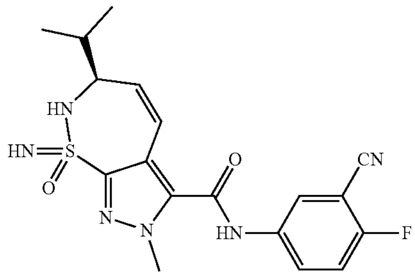 [SMILES: CC(C)[C@H]1C=Cc2c(nn(C)c2C(=O)Nc2ccc(F)c(C#N)c2)S(=N)(=O)N1] | 403 | Peak1 (HPLC) |
| 70a2 | 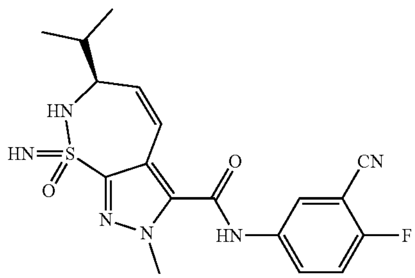 [SMILES: CC(C)[C@H]1C=Cc2c(nn(C)c2C(=O)Nc2ccc(F)c(C#N)c2)S(=N)(=O)N1] | 403 | Peak2 (HPLC) |
| 70b1 | 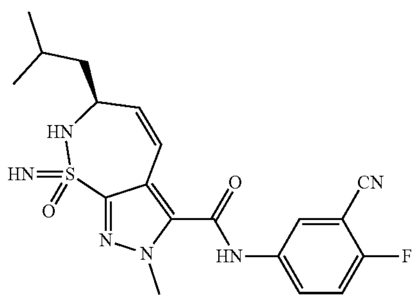 | 417 | Peak1 (HPLC) |
| 70b2 | 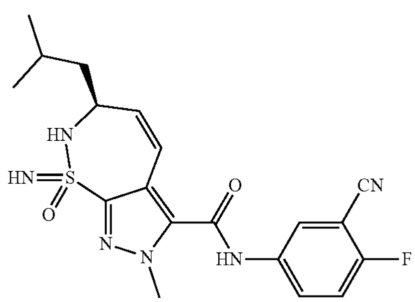 | 417 | Peak2 (HPLC) |
| 80a1 | 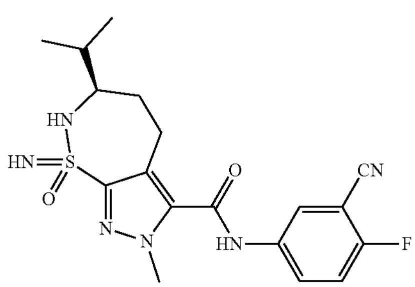 [SMILES: CC(C)[C@H]1CCc2c(nn(C)c2C(=O)Nc2ccc(F)c(C#N)c2)S(=N)(=O)N1] | 405 | Peak1 (HPLC) |

TABLE 1-continued

| No. | Structure | Mass Spectrum ESI-MS, (M + H) | Remark |
| --- | --- | --- | --- |
| 80a2 | 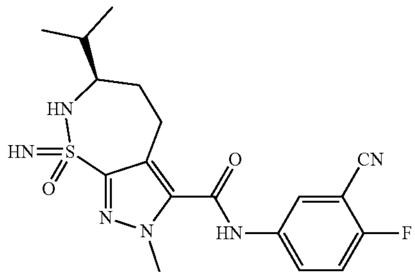 | 405 | Peak2 (HPLC) |
| 80b1 | 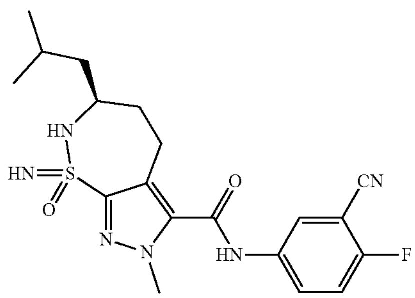 | 419 | Peak1 (HPLC) |
| 80b2 | 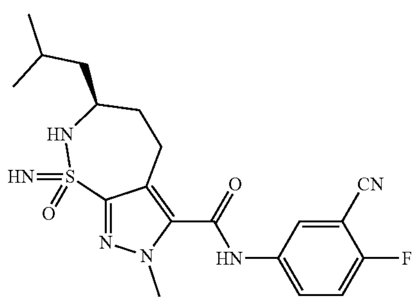 [SMILES: CC(C)C[C@H]1CCc2c(nn(C)c2C(=O)Nc2ccc(F)c(C#N)c2)S(=N)(=O)N1] | 419 | Peak2 (HPLC) |
| 90a1 | 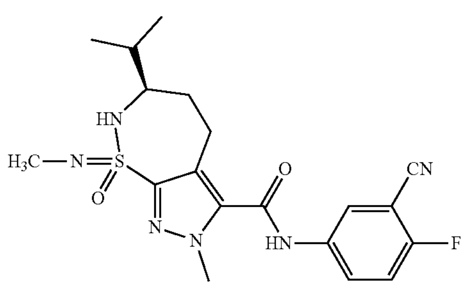 [SMILES: CN=S1(=O)N[C@@H](C(C)C)CCc2c1nn(C)c2C(=O)Nc1ccc(F)c(C#N)c1] | 419 | Peak1 (HPLC) |
| 90a2 | 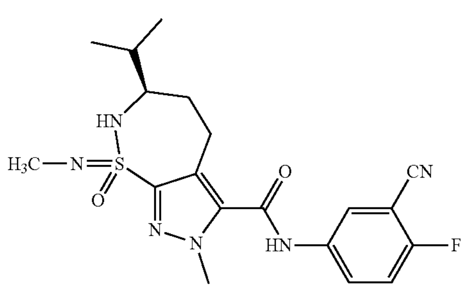 [SMILES: CN=S1(=O)N[C@@H](C(C)C)CCc2c1nn(C)c2C(=O)Nc1ccc(F)c(C#N)c1] | 419 | Peak2 (HPLC) |

TABLE 1-continued

| No. | Structure | Mass Spectrum ESI-MS, (M + H) | Remark |
|---|---|---|---|
| 90b1 | 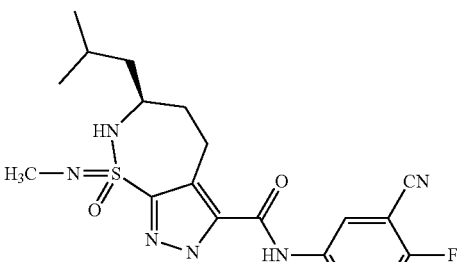 | 433 | Peak1 (HPLC) |
| 90b2 | 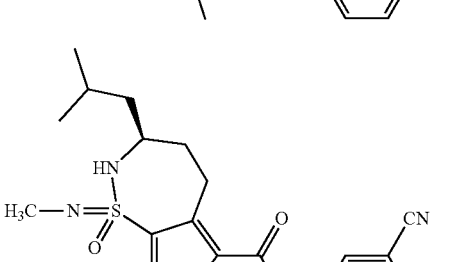 | 433 | Peak2 (HPLC) |

Pharmaceutical Composition and Administration Mode

Since the compounds of the present invention have excellent inhibitory activity against hepatitis B virus (HBV), the various compounds of the present invention, pharmaceutically acceptable inorganic or organic salts, hydrates or solvates thereof, and a pharmaceutical composition containing a compound of the present invention as a main active ingredient can be used for the prevention and/or treatment (stabilization, alleviation or cure) of hepatitis B virus infection or for prevention and/or treatment (stabilization, alleviation or cure) hepatitis B virus-related diseases (for example, hepatitis B, progressive liver fibrosis, inflammation and necrosis which cause cirrhosis, end-stage liver disease, hepatitis B cancer).

The pharmaceutical composition of the invention comprises the compound of the present invention in a safe and effective dosage range and a pharmaceutically acceptable excipient or carrier. The term "safe and effective dosage" means that the amount of compound is sufficient to significantly improve the condition without causing serious side effects. Generally, the pharmaceutical composition contains 1-2000 mg compound of the invention per dose, preferably, 10-200 mg compound of the invention per dose. Preferably, the "one dose" is one capsule or one tablet.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation on administration mode for the compound or pharmaceutical composition of the present invention, and the representative administration mode includes (but is not limited to): oral, parenteral (intravenous, intramuscular or subcutaneous) administration.

Solid dosage forms for oral administration include capsules, tablets, pills, powders and granules. In these solid dosage forms, the active compounds are mixed with at least one conventional inert excipient (or carrier), such as sodium citrate or CaHPO4, or mixed with any of the following components: (a) fillers or compatibilizer, such as starch, lactose, sucrose, glucose, mannitol and silicic acid; (b) binders, such as hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) sorbefacientsabsorption-, such asquaternary ammonium compounds; (g) wetting agents, such as cetyl alcohol and glyceryl monostearate; (h) adsorbents, such askaolin; and (i) lubricants such as talc, calcium stearate, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizes and emulsifiers, such as ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agents, such as ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable combination thereof.

The compounds of the present invention can be administrated alone, or in combination with any other pharmaceutically acceptable compounds (such as anti-HBV agents).

In the case of co-administration, the pharmaceutical composition can also include one or more (2, 3, 4, or more) other pharmaceutically acceptable compounds (such as anti-HBV agents). One or more (2, 3, 4, or more) other pharmaceutically acceptable compounds (e.g., anti-HBV agents) may be used simultaneously, separately or sequentially with the compound of the present invention so as to prevent and/or treat HBV infection or HBV related diseases.

When the pharmaceutical composition is used, a safe and effective amount of compound of the present invention is administered to a mammal (such as human) in need of, wherein the dose of administration is a pharmaceutically effective dose. For a person weighed 60 kg, the daily dose is usually 1-2000 mg, preferably 20-500 mg. Of course, the particular dose should also depend on various factors, such as the route of administration, patient healthy status, which are well within the skills of an experienced physician.

The main advantages of the present invention include:

(1) The compounds of the present invention are novel in structure and have an excellent anti-hepatitis B virus infection effect. In this application, the existing endocyclic sulfoxide amide-arylamide compounds are transformed into endocyclic sulfonimid amide-arylamide compounds in order to better interfering with the assembly process of the capsid protein, thus inhibiting the activity or expression of HBV.

(2) The compounds of the present invention have very low toxicity to normal cells, and therefore can be applied to a subject in a large dose range.

(3) The compounds of the present invention have good drug ability. Compared with the existing compounds, the compounds of the present invention have better solubility and have shown good bioavailability in in vivo experiments. The bioavailability of some compounds has reached 70% or above. Meanwhile, the compounds of the present invention are extremely easy to make into pharmaceutically acceptable salts compared to existing compounds, and thus contribute to the further formation of formulations.

(4) The compound of the present invention and a pharmaceutical composition containing the compound of the present invention as a main active ingredient can be used for prevention and/or treatment of hepatitis B virus-related diseases (for example, hepatitis B, progressive liver fibrosis, inflammation and necrosis leading to liver cirrhosis, end-stage liver diseases, hepatitis B liver cancer).

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight. Unless otherwise specified, the raw materials or instruments used in the embodiments of the present invention are commercially available.

The following are the synthesis of 10 types of compounds:

Example 1: Synthesis of Compound 10a

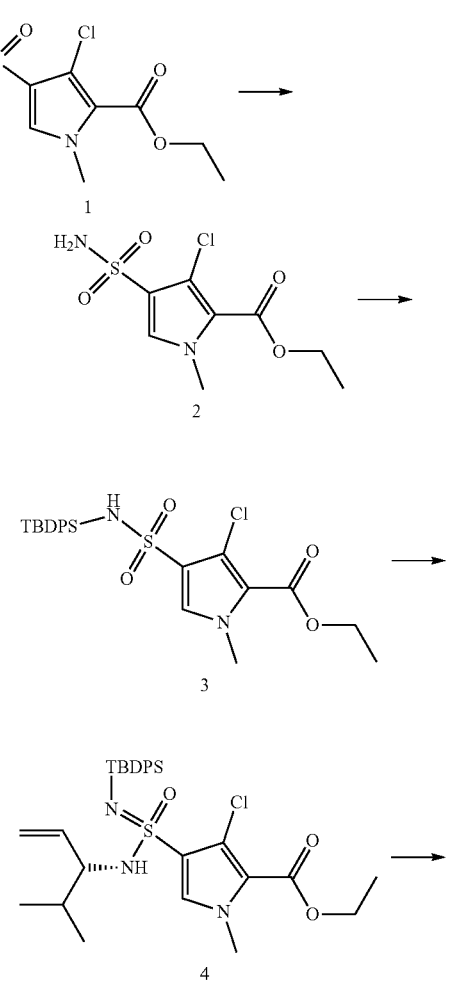

219

-continued

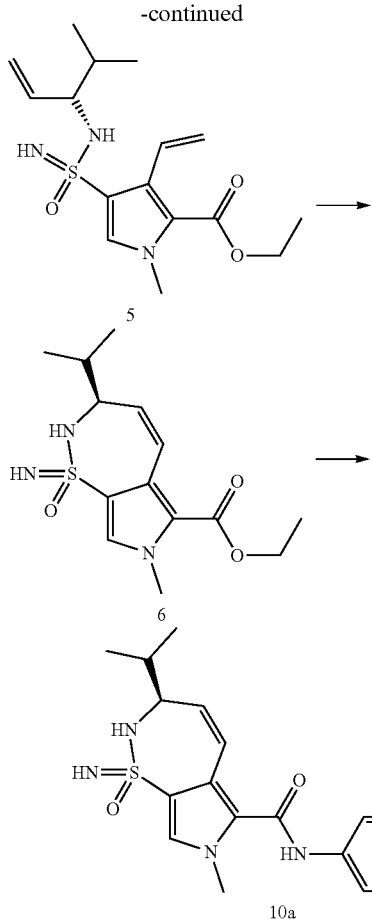

Step 1: Synthesis of Compound 2

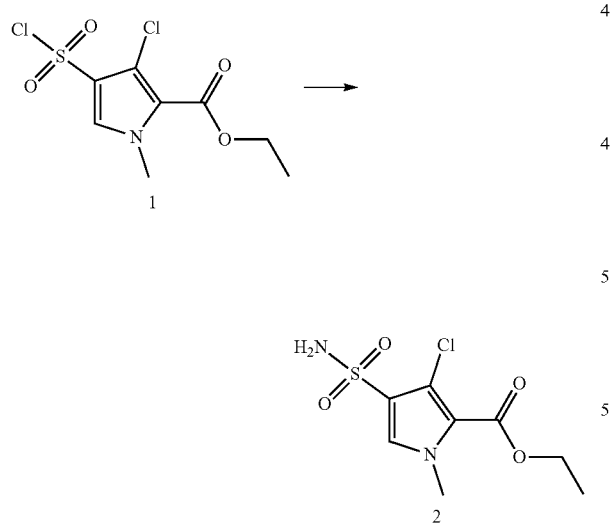

Compound 1 (10 g) was dissolved in dichloromethane (40 mL), and ammonia water (30 mL) was added dropwise to the reaction system at room temperature. The reaction was carried out for 5 h at room temperature, then vacuum filtrated, and the filter cake was s washed with water (5 mL) to provide 5 g of light yellow solid, MS (M+1=267).

220

Step 2: Synthesis of Compound 3

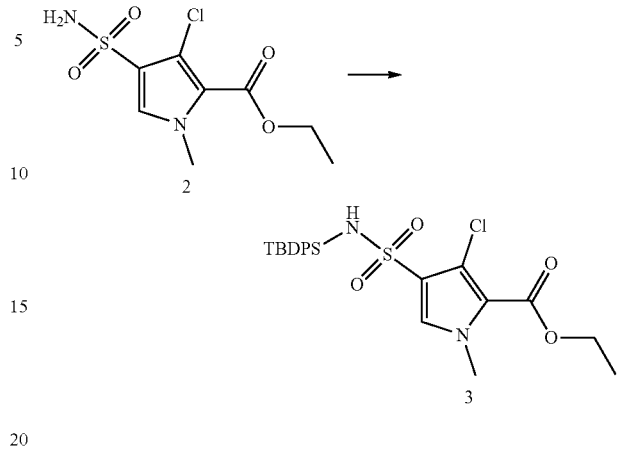

The substrate 2 (5 g) was dissolved in DMF (10 mL), sodium hydride (1.5 g) was added into the reaction system at 0° C., and stirred for 15 min TBDPSCl was then added to the reaction system, and reacted for 18 h. The reaction system was poured into ice water, and extracted with ethyl acetate (3*30 mL), and the organic phase was dried, the solvent was evaporated in vacuum. Crude product was purified via column chromatography (n-heptane:ethyl acetate=1:4) to provide the product 3 (3 g). MS (M+1=505).

Step 3: Synthesis of Compound 4

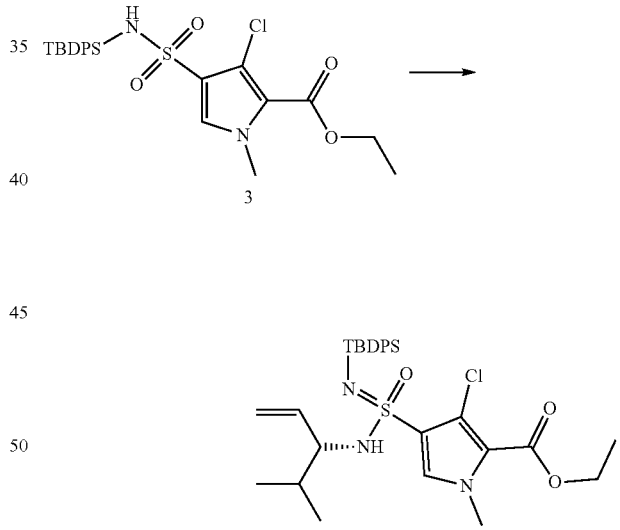

The PPh$_3$Cl$_2$ chloroform solution (80 mL) was cooled to 0° C., and then triethylamine (7 mL) was added, stirred for 10 minutes and then compound 3 was added at 0° C. After stirred for 20 minutes, 2-isopropyl-3-prop enylamine was added to the reaction system and reacted at room temperature for 18 h. Water (20 mL) and ethyl acetate (3*25 mL) were added to the reaction system for extraction. The organic phase was dried and the solvent was evaporated in vacuum. Crude product was purified via column chromatography (n-heptane:ethyl acetate=1:5) to provide the product 4 (1.9 g). MS (M+1=586).

Step 4: Synthesis of Compound 5

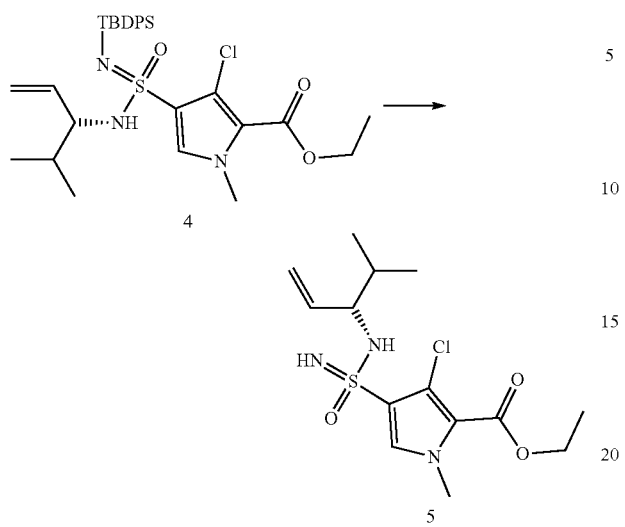

Compound 4 (1.8 g), Tetrakis (triphenylphosphine) palladium (100 mg), pinacol vinylboronate (900 mg), and cesium carbonate (2.7 g) were dissolved in DMF (410 mL), and the mixture was reacted at 100° C. under nitrogen for 15 h. The reaction was quenched with aqueous solution, extracted with ethyl acetate, and the organic phase was dried and the solvent was evaporated in vacuum. The resulting crude product was purified by column chromatography (n-heptane:ethyl acetate=1:5) to provide compound 5 (1.0 g). MS (M+1=340).

Step 5: Synthesis of Compound 6

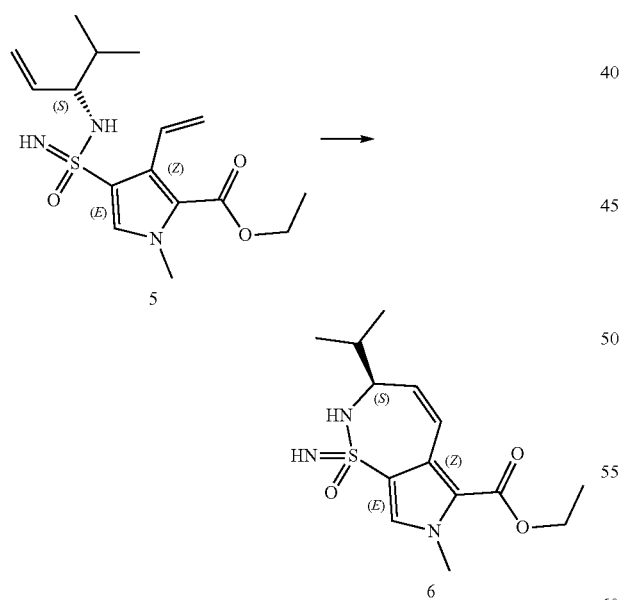

Compound 5 (1.0 g) was dissolved in dichloromethane (500 ml), and then the Zhan Catalyst (0.1 g) was added to the reaction system and stirred overnight. The solvent of reaction solution was evaporated in vacuum and crude product was purified via column chromatography (n-heptane:ethyl acetate=1:3) to provide compound 6. The lower point indicated by TLC was 6-1 (0.22 g), and the upper point indicated by TLC was 6-2 (0.27 g), MS (M+1=312).

Step 6: Synthesis of Compound 10a1

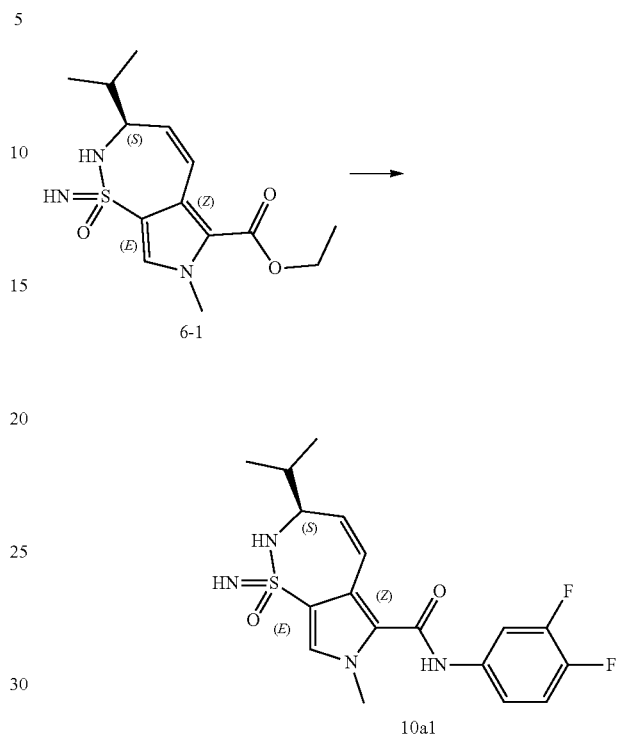

Compound 6-1 (30 mg) and 4-fluoro-3-cyanoaniline (20 mg) were dissolved in THF (5 mL), the solution was cooled to 0° C., and then NaHMDS (0.2 mL) solution was added to the reaction system. The reaction was stirred at room temperature for 16 h, and water was added to the reaction system. The mixture was extracted with ethyl acetate (3*15 mL). The organic phase was dried over anhydrous sodium sulfate and the solvent was evaporated in vacuum. The crude product was subjected to column chromatography (n-heptane:ethyl acetate=1:3) to provide target product 10a1 (11 mg). $^1$H NMR (400 MHz, DMSO-$d_6$) δ 10.78 (s, 1H), 7.89-7.83 (m, 1H), 7.71 (s, 1H), 7.44 (qd, J=4.7, 4.2, 2.5 Hz, 2H), 6.54 (dd, J=12.4, 2.7 Hz, 1H), 5.75 (dd, J=12.4, 2.8 Hz, 1H), 4.0 (dq, J=7.8, 2.6 Hz, 1H), 3.74 (s, 3H), 1.97-1.89 (m, 1H), 0.98 (dd, J=12.6, 6.7 Hz, 6H). MS (M+1=395).

Example 2: Synthesis of Compound 10a2

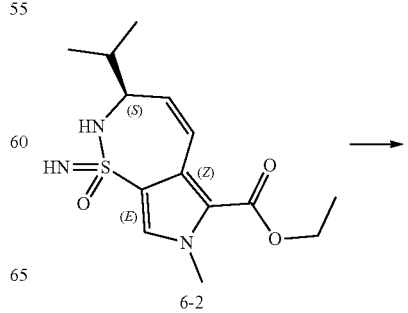

223

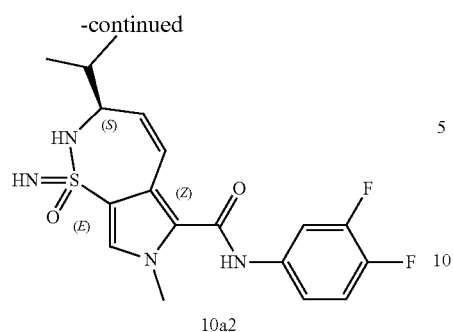

10a2

The reaction was carried out according to the step 6 of example 1, all the conditions were the same except the compound 6-2 was used instead of 6-1, column chromatography (n-heptane:ethyl acetate=1:1) purified to provide target product 10a2 (8 mg). $^1$H NMR (400 MHz, DMSO-$d_6$) δ 10.69 (s, 1H), 7.89-7.83 (m, 1H), 7.51 (s, 1H), 7.44 (qd, J=4.7, 4.2, 2.5 Hz, 2H), 6.53 (dd, J=12.4, 2.7 Hz, 1H), 5.72 (dd, J=12.4, 2.8 Hz, 1H), 3.87 (dq, J=7.8, 2.6 Hz, 1H), 3.72 (s, 3H), 1.91-1.85 (m, 1H), 0.96 (dd, J=12.6, 6.7 Hz, 6H). MS (M+1=395).

Example 3: Synthesis of Compound 10b1

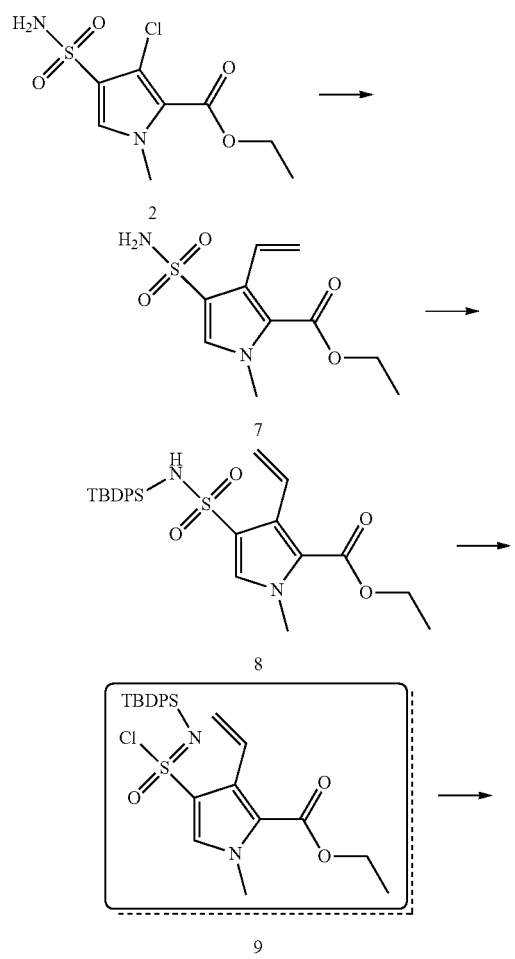

224

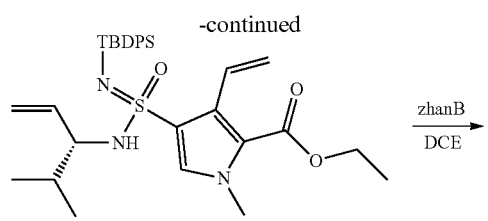

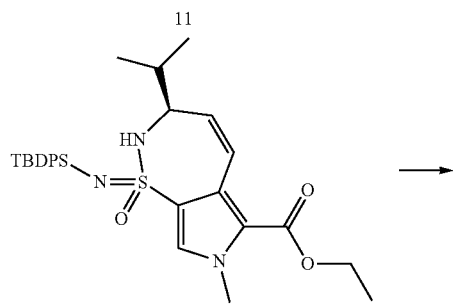

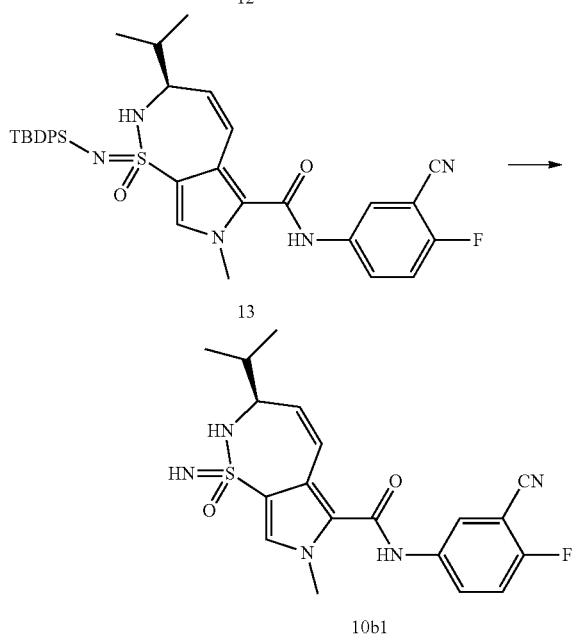

10b1

Step 1: Synthesis of Compound 7

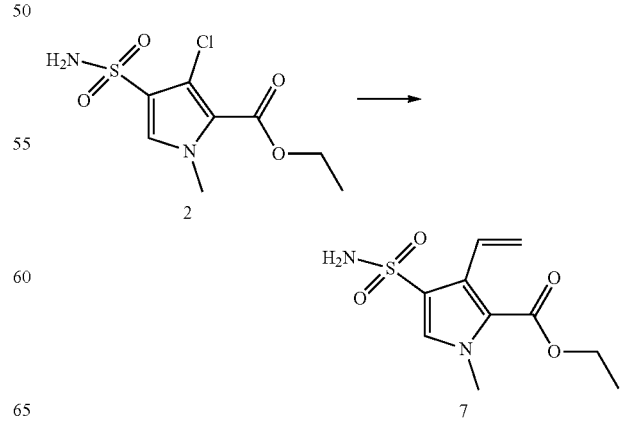

Compound 2 (2.5 g), vinyl borate (1.5 g), sodium carbonate (3.5 g), palladium acetate (120 mg) and Xphos (500 mg) were dissolved in DMF. Under nitrogen protection, the reaction system was placed in a pre-heated 100° C. oil bath to react for 6 hours. Water (50 mL) was added to the reaction system, and extracted with ethyl acetate (3*60 mL), dried over anhydrous sodium sulfate, and the solvent was evaporated in vacuum. Purified via column chromatography to provide 1.2 g of yellow solid. MS (M+1=259).

Step 2: Synthesis of Compound 8

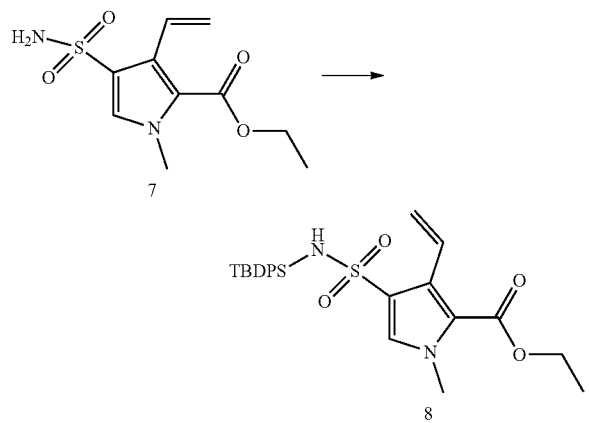

The reaction system was cooled to 0° C., sodium hydride (180 mg) was added to DMF, and then stirred for 10 min. TBDPSCl (2.7 g) and 7 (1.1 g) in DMF was added dropwise to the reaction system at 0° C., and reacted at room temperature for 1.5 h. The reaction liquid was added dropwise to a mixed solution of 1N HCl and saturated ammonium chloride, extracted with ethyl acetate (3*50 mL), dried over anhydrous sodium sulfate, the organic phase was evaporated in vacuum, and 800 mg of white solid was obtained by column chromatography, MS (M+1=497). $^1$H NMR (400 MHz, DMSO-d$_6$) 10.78 (s, 1H), 7.62-7.59 (m, 1H), 7.45-7.41 (m, 1H), 7.33-7.29 (m, 3H), 7.13 (qd, J=4.7, 4.2, 2.5 Hz, 2H), 6.16 (dd, J=12.4, 2.7 Hz, 1H), 5.58 (dd, J=12.4, 2.8 Hz, 1H), 5.09 (s, 1H), 4.35-4.40 (m, 2), 3.56 (s, 3H), 1.45-1.40 (m, 3), 1.04 (s, 9H).

Step 3: Synthesis of Compound 11

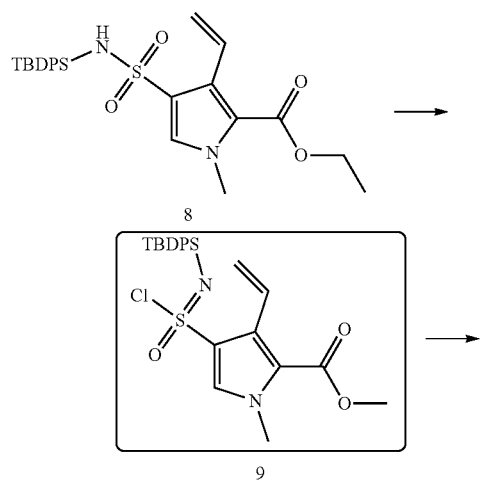

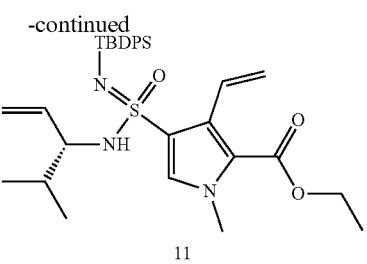

The PPh$_3$Cl$_2$ mixture was cooled to 0° C., and then triethylamine (3 mL) was added into the reaction system. After the addition, the mixture was reacted at 0° C. for 10 minutes, and then solid 8 (500 mg) was added in one batch to the system, and stirred at 0° C. for 20 min. Finally, the chloroform solution of isopropylallylamine (200 mg) was added to the reaction system, and reacted at room temperature for 18 h. The silica gel was directly added to the reaction system, and purified via column chromatography to provide 650 mg of pale yellow oil. MS (M+1=578) $^1$H NMR (400 MHz, DMSO-d$_6$) δ 7.81-7.73 (m, 4H), 7.38-7.32 (m, 7H), 7.06-6.91 (m, 2H), 6.01-5.89 (m, 1H), 5.48-5.33 (m, 2H), 4.92-4.70 (m, 2H), 4.36-4.30 (m, 2H), 3.79 (s, 1.55H), 3.76 (s, 1.36H), 3.50-3.41 (m, 1H), 1.71-1.66 (m, 0.5H), 1.56-1.51 (m, 0.5H), 1.40-1.35 (m, 3), 1.14 (s, 4.2H), 1.12 (s, 4.5H), 0.76-0.73 (m, 3H), 0.68-0.64 (m, 3H).

Step 4: Synthesis of Compound 12

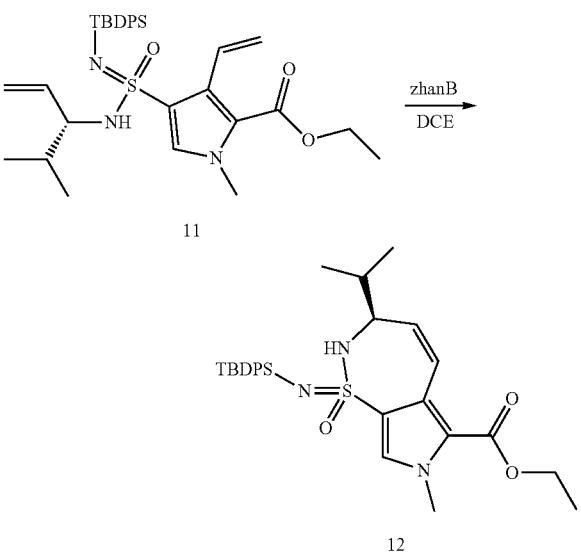

Compound 11 (650 mg) was dissolved in 1,2-dichloroethane, and Zhan 1B was added to the reaction system. Under the protection of nitrogen, the system was warmed to 70° C. and stirred for 24 h. Silica gel was directly added to the reaction system, and purified by column chromatography, after the solvent was evaporated in vacuum to provide pale yellow oil 12: The lower point of the TLC display was 12-1 (0.22 g), and the upper point of the TLC display was 12-2 (0.27 g), MS (M+1=550). $^1$H NMR (400 MHz, DMSO-d$_6$) δ 7.81-7.74 (m, 5H), 7.40-7.37 (m, 7H), 7.28-7.21 (m, 1H), 6.01-5.89 (m, 1H), 6.99 (s, 1H), 5.77-5.73 (m, 1H), 4.42-4.35 (m, 2H), 4.15-4.11 (m, 1H), 3.80 (s, 3H), 1.91-1.86 (m, 1H), 1.43-1.39 (m, 3), 1.14 (s, 9H), 0.87-0.78 (m, 6H).

Step 5: Synthesis of Compound 13

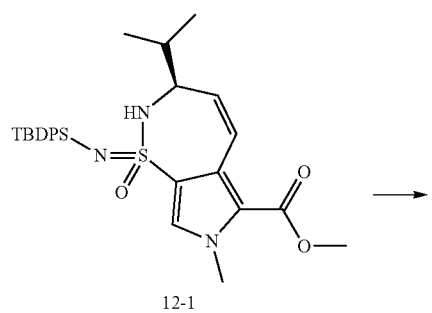

12-1

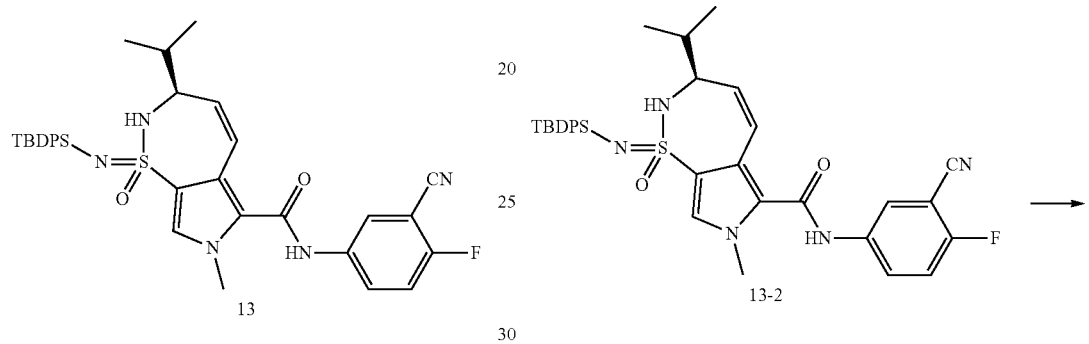

Compound 12-1 (90 mg) (lower point shown by TLC) and 3,4-difluoroaniline (43 mg) was dissolved in THF (8 mL), then the system was cooled to 0° C., and 6 eq of NaHMDS was added to the reaction system to react at 0° C. for 1 h. Water (20 mL) was added to the reaction system, and extracted with ethyl acetate (3*30 mL), dried over anhydrous sodium sulfate, the solvent was evaporated in vacuum, and purified via column chromatography to provide 80 mg of yellow oil. MS (M+1=640).

Step 6: Synthesis of Compound 10b1

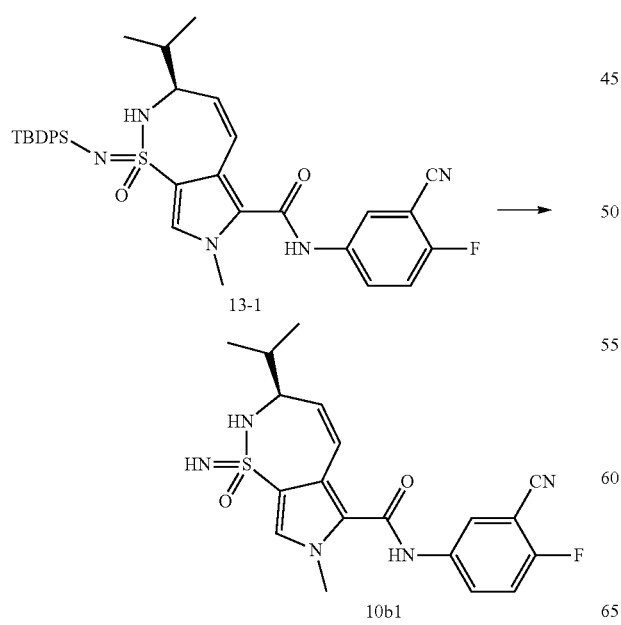

Compound 13-1 (40 mg) (lower point shown by TLC) was dissolved in THF (3 mL), then 120 eq of 3HF.TEA was added dropwise into the reaction system, reacted at room temperature for 3 days, separated by preparation TLC, and freeze-dried to obtain white solid 10b1 (4.5 mg). $^1$H NMR (400 MHz, DMSO-$d_6$) δ 10.90 (s, 1H), 8.18 (dd, J=5.8, 2.7 Hz, 1H), 7.99 (ddd, J=9.2, 4.8, 2.7 Hz, 1H), 7.78-7.70 (m, 2H), 7.57 (d, J=10.3 Hz, 1H), 6.57 (dd, J=12.4, 2.7 Hz, 1H), 5.77 (dd, J=12.4, 2.8 Hz, 1H), 4.07 (ddt, J=10.6, 5.4, 2.7 Hz, 1H), 3.76 (s, 3H), 1.92 (tq, J=12.1, 6.7, 5.6 Hz, 1H), 0.99 (dd, J=12.0, 6.7 Hz, 6H). Ms (ESI) m/z=402 (M+1)

Example 4: Synthesis of Compound-10b2

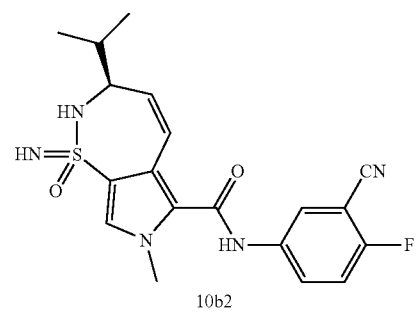

The reaction was carried out according to the step 6 of example 3, all the conditions were the same except the compound 13-2 (upper point shown by TLC) was used instead of compound 13-1 (lower point shown by TLC), purified by column chromatography (n-heptane:ethyl acetate=1:1) to provide target product 10b2 (8 mg). $^1$H NMR (400 MHz, DMSO-$d_6$) δ 10.89 (s, 1H), 8.20 (dd, J=5.8, 2.7 Hz, 1H), 7.97 (ddd, J=9.2, 4.8, 2.7 Hz, 1H), 7.90-7.88 (m, 2H), 7.56 (d, J=10.3 Hz, 1H), 6.65 (dd, J=12.4, 2.7 Hz, 1H), 5.91 (dd, J=12.4, 2.8 Hz, 1H), 3.80 (s, 3H), 3.69-3.63 (m, 1H), 1.95 (tq, J=12.1, 6.7, 5.6 Hz, 1H), 0.99 (dd, J=12.0, 6.7 Hz, 6H). Ms (ESI) m/z=402 (M+1)

The following 10 and 30 series compounds were synthesized according to the method of example 3:

| No. | Structure | Mass Spectrum ESI-MS, (M + H) | Remark |
|---|---|---|---|
| 10c1 | 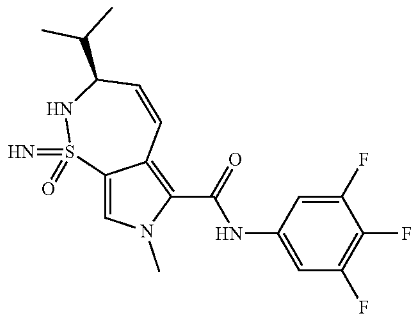 [SMILES: CC(C)[C@H]1C=Cc2c(cn(C)c2C(=O)Nc2cc(F)c(F)c(F)c2)S(=N)(=O)N1] | 413 | Peak1 (HPLC) |
| 10c2 | 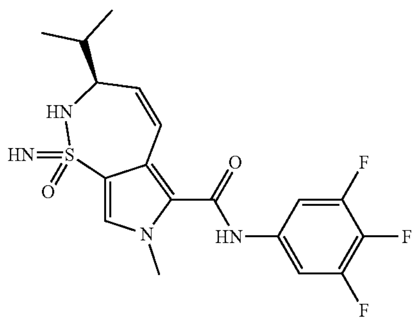 [SMILES: CC(C)[C@H]1C=Cc2c(cn(C)c2C(=O)Nc2cc(F)c(F)c(F)c2)S(=N)(=O)N1] | 413 | Peak2 (HPLC) |
| 10d1 | 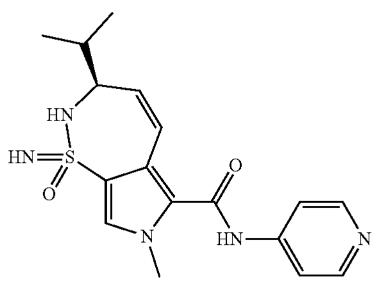 [SMILES: CC(C)[C@H]1C=Cc2c(cn(C)c2C(=O)Nc2ccncc2)S(=N)(=O)N1] | 360 | Peak1 (HPLC) |
| 10d2 | 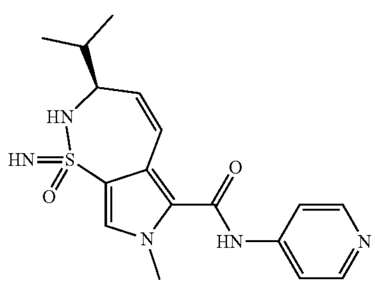 [SMILES: CC(C)[C@H]1C=Cc2c(cn(C)c2C(=O)Nc2ccncc2)S(=N)(=O)N1] | 360 | Peak2 (HPLC) |
| 10e1 | 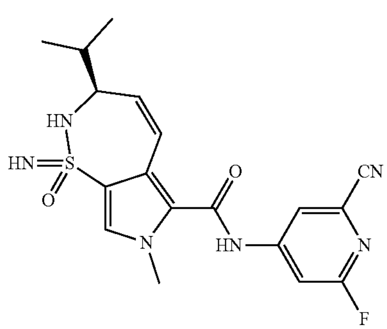 [SMILES: CC(C)[C@H]1C=Cc2c(cn(C)c2C(=O)Nc2cc(F)nc(C#N)c2)S(=N)(=O)N1] | 403 | Peak1 (HPLC) |

| No. | Structure | Mass Spectrum ESI-MS, (M + H) | Remark |
|---|---|---|---|
| 10e2 | 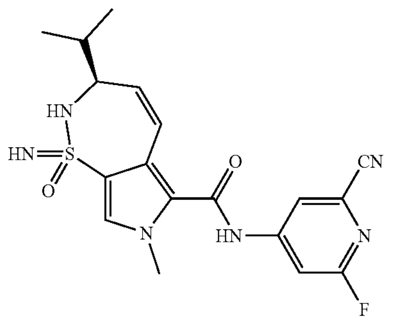 [SMILES: CC(C)[C@H]1C=Cc2c(cn(C)c2C(=O)Nc2cc(F)nc(C#N)c2)S(=N)(=O)N1] | 403 | Peak2 (HPLC) |
| 10f1 | 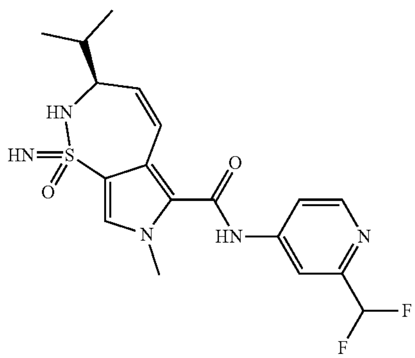 [SMILES: CC(C)[C@H]1C=Cc2c(cn(C)c2C(=O)Nc2ccnc(C(F)F)c2)S(=N)(=O)N1] | 410 | Peak1 (HPLC) |
| 10f2 | 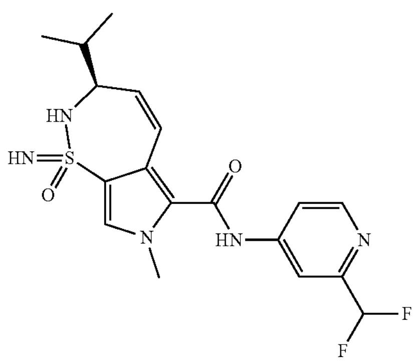 [SMILES: CC(C)[C@H]1C=Cc2c(cn(C)c2C(=O)Nc2ccnc(C(F)F)c2)S(=N)(=O)N1] | 410 | Peak2 (HPLC) |
| 10g1 | 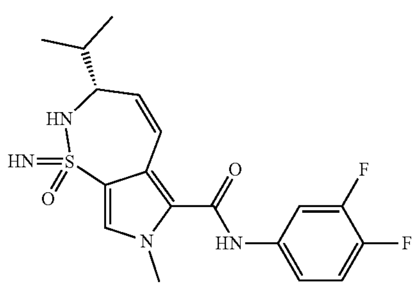 [SMILES: CC(C)[C@@H]1C=Cc2c(cn(C)c2C(=O)Nc2ccc(F)c(F)c2)S(=N)(=O)N1] | 395 | Peak1 (HPLC) |

-continued

| No. | Structure | Mass Spectrum ESI-MS, (M + H) | Remark |
|---|---|---|---|
| 10g2 | 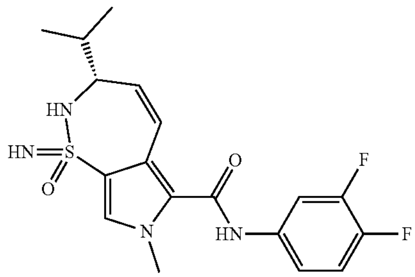 [SMILES: CC(C)[C@@H]1C=Cc2c(cn(C)c2C(=O)Nc2ccc(F)c(F)c2)S(=N)(=O)N1] | 395 | Peak2 (HPLC) |
| 10h1 | 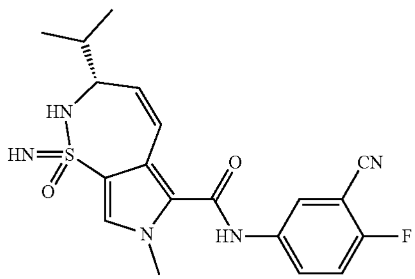 [SMILES: CC(C)[C@@H]1C=Cc2c(cn(C)c2C(=O)Nc2ccc(F)c(C#N)c2)S(=N)(=O)N1] | 402 | Peak1 (HPLC) |
| 10h2 | 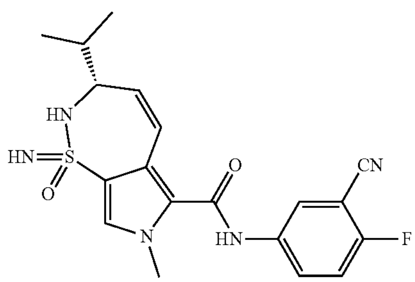 [SMILES: CC(C)[C@@H]1C=Cc2c(cn(C)c2C(=O)Nc2ccc(F)c(C#N)c2)S(=N)(=O)N1] | 402 | Peak2 (HPLC) |
| 10i1 | 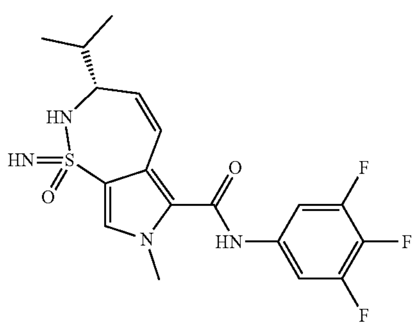 [SMILES: CC(C)[C@@H]1C=Cc2c(cn(C)c2C(=O)Nc2cc(F)c(F)c(F)c2)S(=N)(=O)N1] | 413 | Peak1 (HPLC) |
| 10i2 | 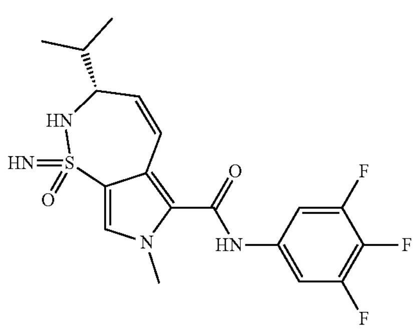 [SMILES: CC(C)[C@@H]1C=Cc2c(cn(C)c2C(=O)Nc2cc(F)c(F)c(F)c2)S(=N)(=O)N1] | 413 | Peak2 (HPLC) |

-continued

| No. | Structure | Mass Spectrum ESI-MS, (M + H) | Remark |
|---|---|---|---|
| 10j1 | 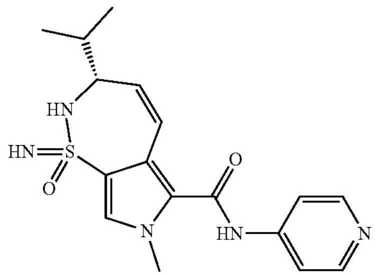 [SMILES: CC(C)[C@@H]1C=Cc2c(cn(C)c2C(=O)Nc2ccncc2)S(=N)(=O)N1] | 360 | Peak1 (HPLC) |
| 10j2 | 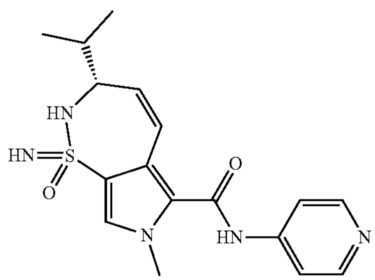 [SMILES: CC(C)[C@@H]1C=Cc2c(cn(C)c2C(=O)Nc2ccncc2)S(=N)(=O)N1] | 360 | Peak2 (HPLC) |
| 10k1 | 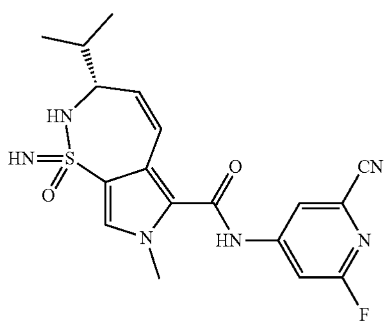 [SMILES: CC(C)[C@@H]1C=Cc2c(cn(C)c2C(=O)Nc2cc(F)nc(C#N)c2)S(=N)(=O)N1] | 403 | Peak1 (HPLC) |
| 10k2 | 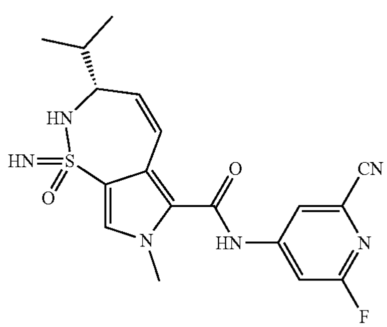 [SMILES: CC(C)[C@@H]1C=Cc2c(cn(C)c2C(=O)Nc2cc(F)nc(C#N)c2)S(=N)(=O)N1] | 403 | Peak2 (HPLC) |

-continued

| No. | Structure | Mass Spectrum ESI-MS, (M + H) | Remark |
|---|---|---|---|
| 10m1 | 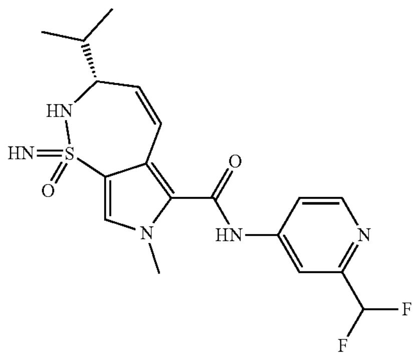 [SMILES: CC(C)[C@@H]1C=Cc2c(cn(C)c2C(=O)Nc2ccnc(C(F)F)c2)S(=N)(=O)N1] | 401 | Peak1 (HPLC) |
| 10m2 | 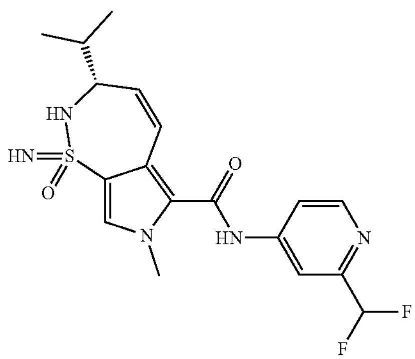 [SMILES: CC(C)[C@@H]1C=Cc2c(cn(C)c2C(=O)Nc2ccnc(C(F)F)c2)S(=N)(=O)N1] | 401 | Peak2 (HPLC) |
| 10n1 | 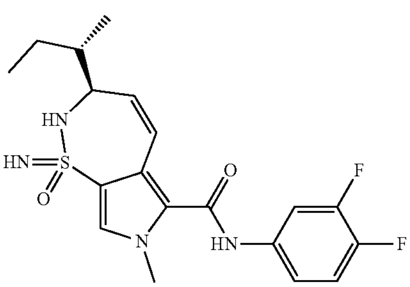 [SMILES: CC[C@H](C)[C@H]1C=Cc2c(cn(C)c2C(=O)Nc2ccc(F)c(F)c2)S(=N)(=O)N1] | 409 | Peak1 (HPLC) |
| 10n2 | 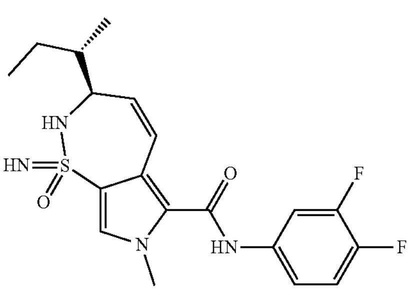 [SMILES: CC[C@H](C)[C@H]1C=Cc2c(cn(C)c2C(=O)Nc2ccc(F)c(F)c2)S(=N)(=O)N1] | 409 | Peak2 (HPLC) |

-continued

| No. | Structure | Mass Spectrum ESI-MS, (M + H) | Remark |
|---|---|---|---|
| 10o1 | 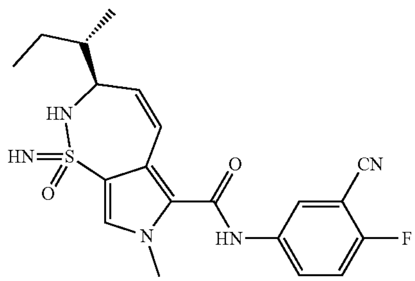 [SMILES: CC[C@H](C)[C@H]1C=Cc2c(cn(C)c2C(=O)Nc2ccc(F)c(C#N)c2)S(=N)(=O)N1] | 416 | Peak1 (HPLC) |
| 10o2 | 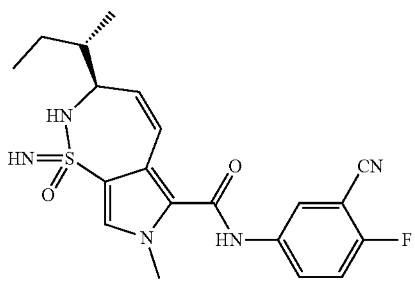 [SMILES: CC[C@H](C)[C@H]1C=Cc2c(cn(C)c2C(=O)Nc2ccc(F)c(C#N)c2)S(=N)(=O)N1] | 416 | Peak2 (HPLC) |
| 10p1 | 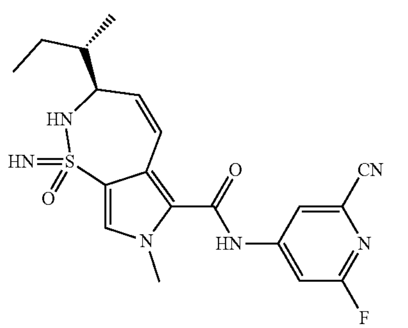 [SMILES: CC[C@H](C)[C@H]1C=Cc2c(cn(C)c2C(=O)Nc2cc(F)nc(C#N)c2)S(=N)(=O)N1] | 417 | Peak1 (HPLC) |
| 10p2 | 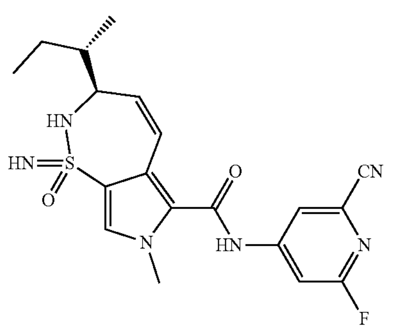 [SMILES: CC[C@H](C)[C@H]1C=Cc2c(cn(C)c2C(=O)Nc2cc(F)nc(C#N)c2)S(=N)(=O)N1] | 417 | Peak2 (HPLC) |

-continued

| No. | Structure | Mass Spectrum ESI-MS, (M + H) | Remark |
|---|---|---|---|
| 10q1 | 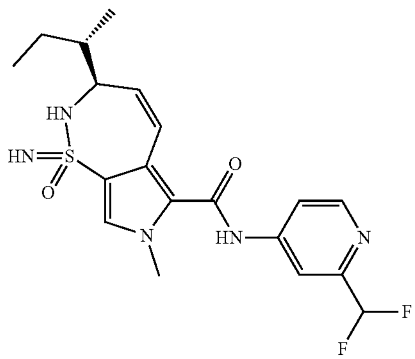 [SMILES: CC[C@H](C)[C@H]1C=Cc2c(cn(C)c2C(=O)Nc2ccnc(C(F)F)c2)S(=N)(=O)N1] | 424 | Peak1 (HPLC) |
| 10q2 | 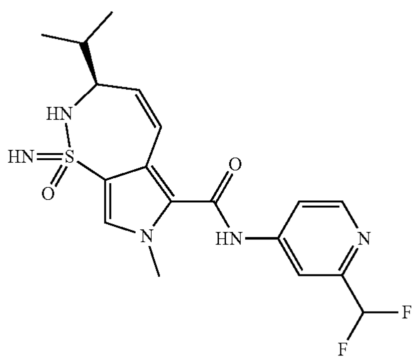 [SMILES: CC(C)[C@H]1C=Cc2c(cn(C)c2C(=O)Nc2ccnc(C(F)F)c2)S(=N)(=O)N1] | 424 | Peak2 (HPLC) |
| 10r1 | 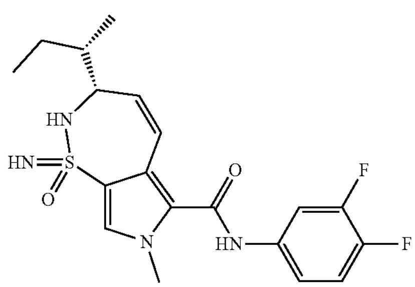 [SMILES: CC[C@H](C)[C@@H]1C=Cc2c(cn(C)c2C(=O)Nc2ccc(F)c(F)c2)S(=N)(=O)N1] | 409 | Peak1 (HPLC) |
| 10r2 | 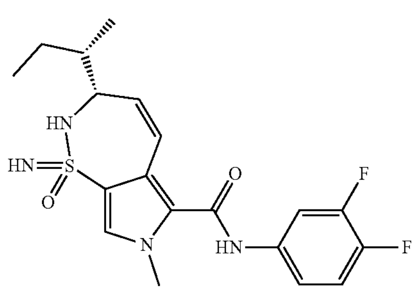 [SMILES: CC[C@H](C)[C@@H]1C=Cc2c(cn(C)c2C(=O)Nc2ccc(F)c(F)c2)S(=N)(=O)N1] | 409 | Peak2 (HPLC) |

-continued

| No. | Structure | Mass Spectrum ESI-MS, (M + H) | Remark |
|---|---|---|---|
| 10s1 | 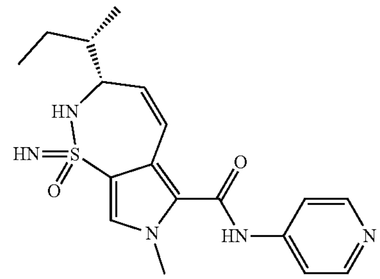 [SMILES: CC[C@H](C)[C@@H]1C=Cc2c(cn(C)c2C(=O)Nc2ccncc2)S(=N)(=O)N1] | 374 | Peak1 (HPLC) |
| 10s2 | 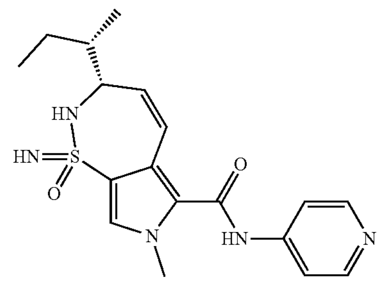 [SMILES: CC[C@H](C)[C@@H]1C=Cc2c(cn(C)c2C(=O)Nc2ccncc2)S(=N)(=O)N1] | 374 | Peak2 (HPLC) |
| 10t1 | 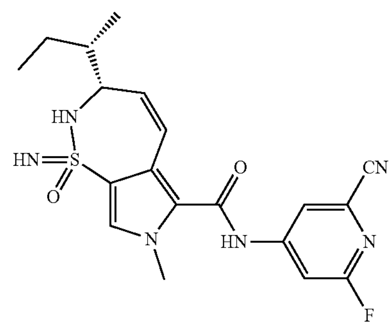 [SMILES: CC[C@H](C)[C@@H]1C=Cc2c(cn(C)c2C(=O)Nc2cc(F)nc(C#N)c2)S(=N)(=O)N1] | 417 | Peak1 (HPLC) |
| 10t2 | 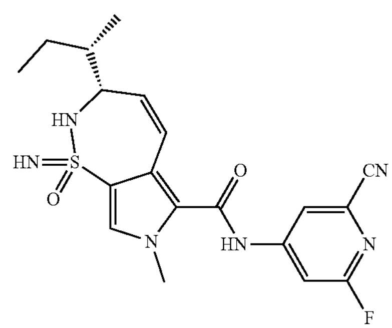 [SMILES: CC[C@H](C)[C@@H]1C=Cc2c(cn(C)c2C(=O)Nc2cc(F)nc(C#N)c2)S(=N)(=O)N1] | 417 | Peak2 (HPLC) |
| 10u1 | 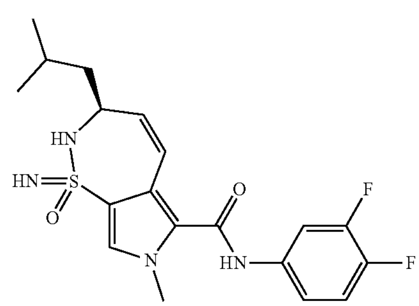 [SMILES: CC(C)C[C@H]1C=Cc2c(cn(C)c2C(=O)Nc2ccc(F)c(F)c2)S(=N)(=O)N1] | 409 | Peak1 (HPLC) |

-continued
| No. | Structure | Mass Spectrum ESI-MS, (M + H) | Remark |
|---|---|---|---|
| 10u2 | 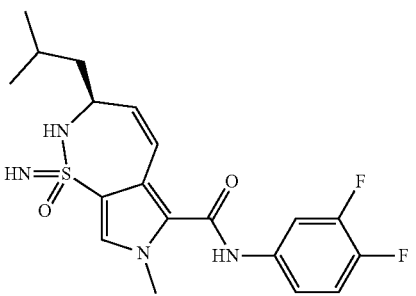 | 409 | Peak2 (HPLC) |
| 10v1 | 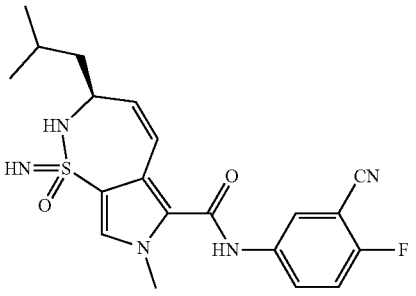 | 416 | Peak1 (HPLC) |
| 10v2 | 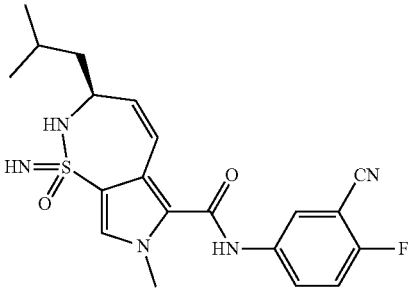 | 416 | Peak2 (HPLC) |
| 10w1 | 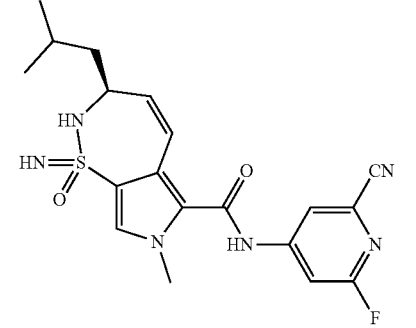 | 417 | Peak1 (HPLC) |

-continued
| No. | Structure | Mass Spectrum ESI-MS, (M + H) | Remark |
|---|---|---|---|
| 10w2 | 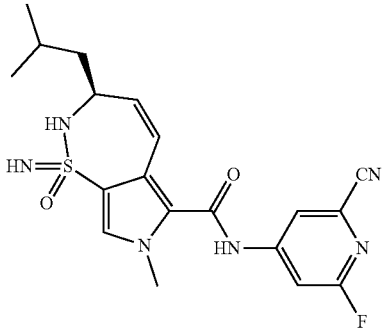 [SMILES: CC(C)C[C@H]1C=Cc2c(cn(C)c2C(=O)Nc2cc(F)nc(C#N)c2)S(=N)(=O)N1] | 417 | Peak2 (HPLC) |
| 10x1 | 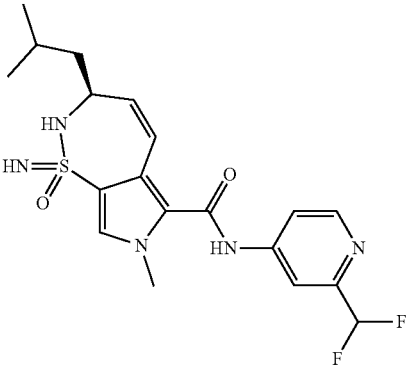 | 424 | Peak1 (HPLC) |
| 10x2 | 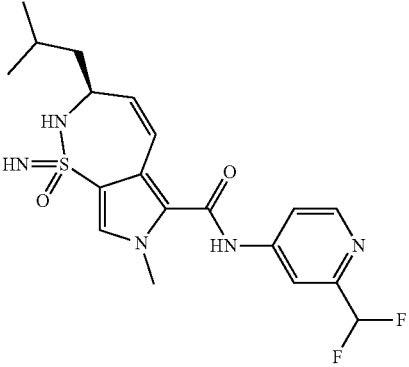 [SMILES: CC(C)C[C@H]1C=Cc2c(cn(C)c2C(=O)Nc2ccnc(C(F)F)c2)S(=N)(=O)N1] | 424 | Peak2 (HPLC) |
| 10y1 | 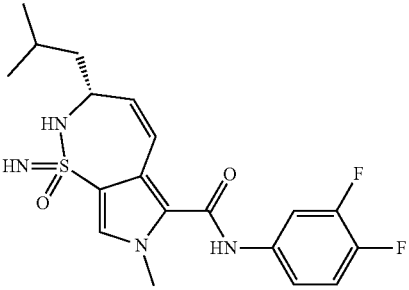 | 409 | Peak1 (HPLC) |

-continued

| No. | Structure | Mass Spectrum ESI-MS, (M + H) | Remark |
|---|---|---|---|
| 10y2 | 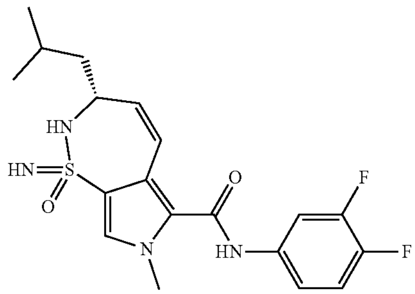 [SMILES: CC(C)C[C@@H]1C=Cc2c(cn(C)c2C(=O)Nc2ccc(F)c(F)c2)S(=N)(=O)N1] | 409 | Peak2 (HPLC) |
| 10z1 | 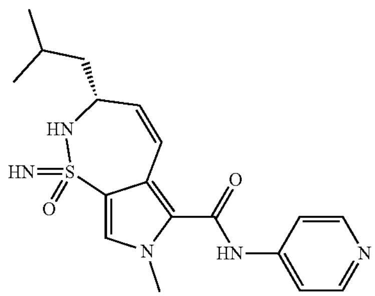 [SMILES: CC(C)C[C@@H]1C=Cc2c(cn(C)c2C(=O)Nc2ccncc2)S(=N)(=O)N1] | 374 | Peak1 (HPLC) |
| 10z2 | 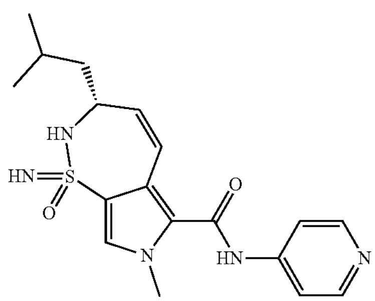 [SMILES: CC(C)C[C@@H]1C=Cc2c(cn(C)c2C(=O)Nc2ccncc2)S(=N)(=O)N1] | 374 | Peak2 (HPLC) |
| 10aa1 | 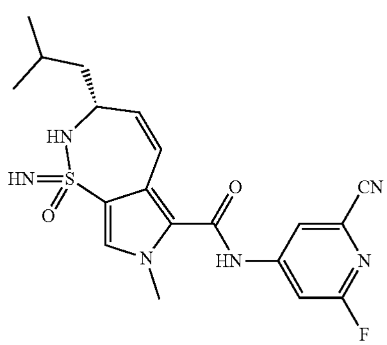 [SMILES: CC(C)C[C@@H]1C=Cc2c(cn(C)c2C(=O)Nc2cc(F)nc(C#N)c2)S(=N)(=O)N1] | 417 | Peak1 (HPLC) |

-continued

| No. | Structure | Mass Spectrum ESI-MS, (M + H) | Remark |
|---|---|---|---|
| 10aa2 | 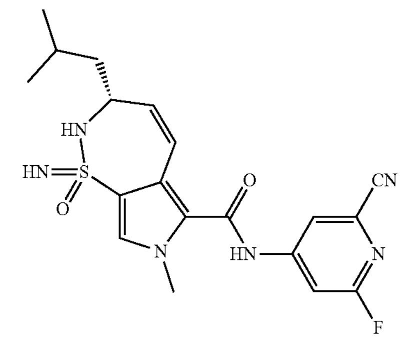 [SMILES: CC(C)C[C@@H]1C=Cc2c(cn(C)c2C(=O)Nc2cc(F)nc(C#N)c2)S(=N)(=O)N1] | 417 | Peak2 (HPLC) |
| 10bb1 | 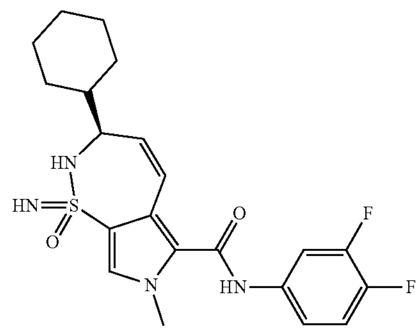 [SMILES: Cn1cc2c(c1C(=O)Nc1ccc(F)c(F)c1)C=C[C@H](C1CCCCC1)NS2(=N)=O] | 435 | Peak1 (HPLC) |
| 10bb2 | 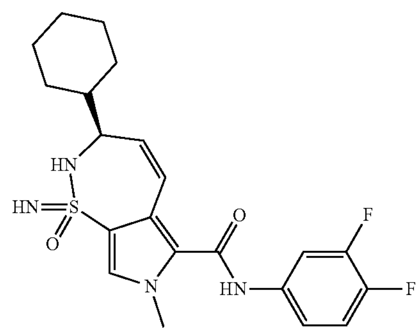 [SMILES: Cn1cc2c(c1C(=O)Nc1ccc(F)c(F)c1)C=C[C@H](C1CCCCC1)NS2(=N)=O] | 435 | Peak2 (HPLC) |
| 10cc1 | 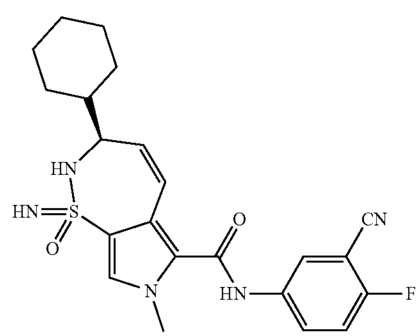 [SMILES: Cn1cc2c(c1C(=O)Nc1ccc(F)c(C#N)c1)C=C[C@H](C1CCCCC1)NS2(=N)=O] | 442 | Peak1 (HPLC) |

-continued

| No. | Structure | Mass Spectrum ESI-MS, (M + H) | Remark |
|---|---|---|---|
| 10cc2 | 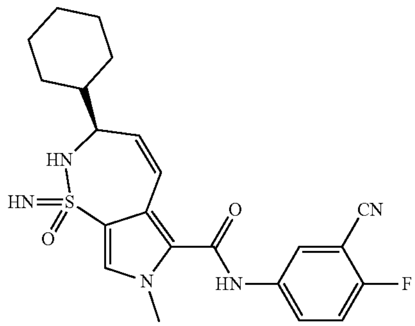 [SMILES: Cn1cc2c(c1C(=O)Nc1ccc(F)c(C#N)c1)C=C[C@H](C1CCCCC1)NS2(=N)=O] | 442 | Peak2 (HPLC) |
| 10dd1 | 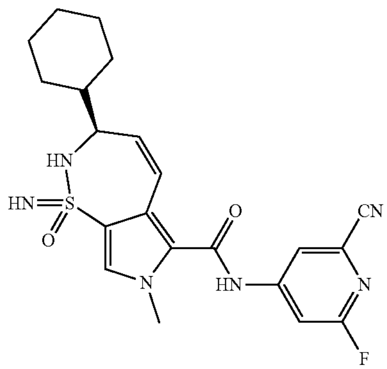 [SMILES: Cn1cc2c(c1C(=O)Nc1cc(F)nc(C#N)c1)C=C[C@H](C1CCCCC1)NS2(=N)=O] | 443 | Peak1 (HPLC) |
| 10dd2 | 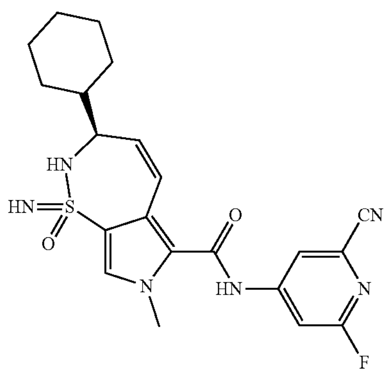 [SMILES: Cn1cc2c(c1C(=O)Nc1cc(F)nc(C#N)c1)C=C[C@H](C1CCCCC1)NS2(=N)=O] | 443 | Peak2 (HPLC) |
| 10ee1 | 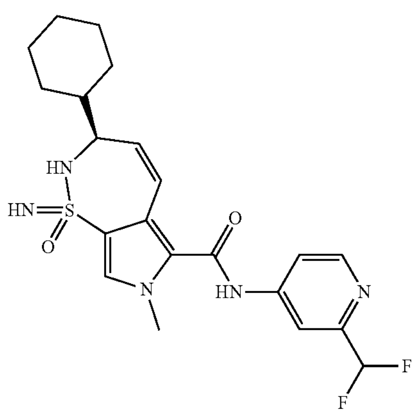 [SMILES: Cn1cc2c(c1C(=O)Nc1ccnc(C(F)F)c1)C=C[C@H](C1CCCCC1)NS2(=N)=O] | 450 | Peak1 (HPLC) |

-continued

| No. | Structure | Mass Spectrum ESI-MS, (M + H) | Remark |
|---|---|---|---|
| 10ee2 | 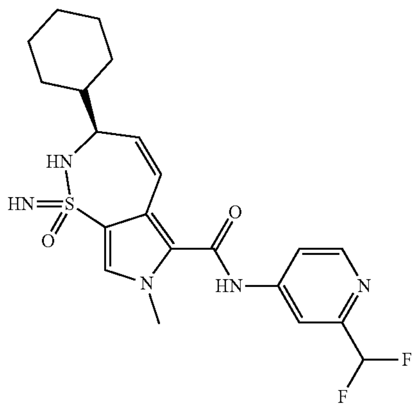 [SMILES: Cn1cc2c(c1C(=O)Nc1ccnc(C(F)F)c1)C=C[C@H](C1CCCCC1)NS2(=N)=O] | 450 | Peak2 (HPLC) |
| 10ff1 | 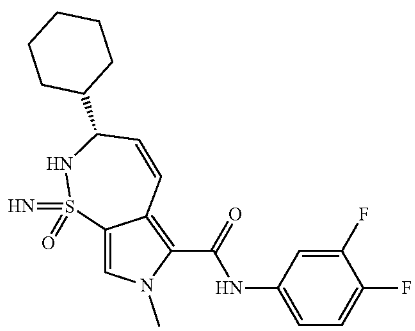 [SMILES: Cn1cc2c(c1C(=O)Nc1ccc(F)c(F)c1)C=C[C@@H](C1CCCCC1)NS2(=N)=O] | 435 | Peak1 (HPLC) |
| 10ff2 | 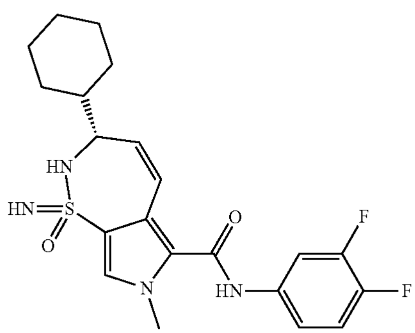 [SMILES: Cn1cc2c(c1C(=O)Nc1ccc(F)c(F)c1)C=C[C@@H](C1CCCCC1)NS2(=N)=O] | 435 | Peak2 (HPLC) |
| 10gg1 | 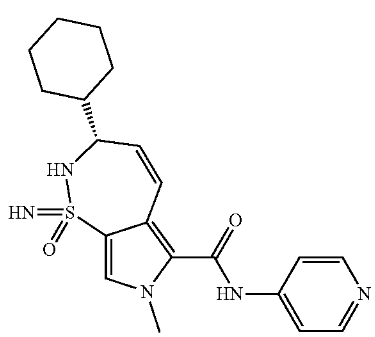 [SMILES: Cn1cc2c(c1C(=O)Nc1ccncc1)C=C[C@@H](C1CCCCC1)NS2(=N)=O] | 400 | Peak1 (HPLC) |

-continued

| No. | Structure | Mass Spectrum ESI-MS, (M + H) | Remark |
|---|---|---|---|
| 10gg2 | 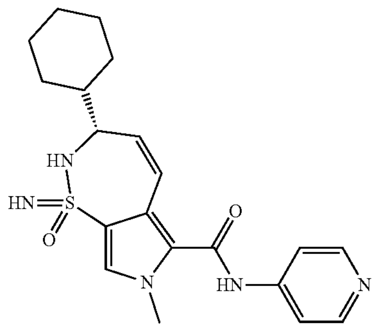 [SMILES: Cn1cc2c(c1C(=O)Nc1ccncc1)C=C[C@@H](C1CCCCC1)NS2(=N)=O] | 400 | Peak2 (HPLC) |
| 10hh1 | 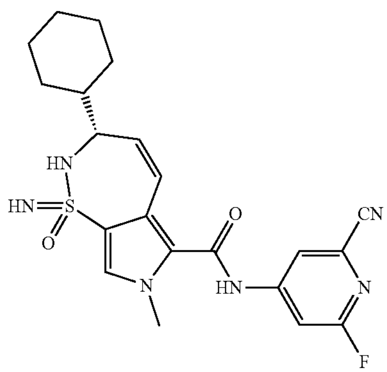 [SMILES: Cn1cc2c(c1C(=O)Nc1cc(F)nc(C#N)c1)C=C[C@@H](C1CCCCC1)NS2(=N)=O] | 443 | Peak1 (HPLC) |
| 10hh2 | 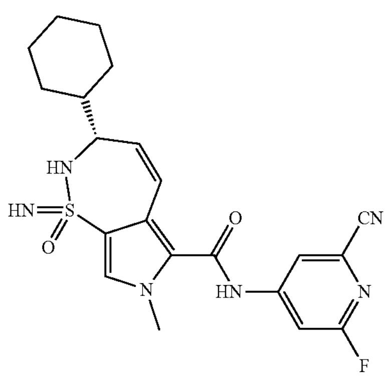 [SMILES: Cn1cc2c(c1C(=O)Nc1cc(F)nc(C#N)c1)C=C[C@@H](C1CCCCC1)NS2(=N)=O] | 443 | Peak2 (HPLC) |
| 10ii1 | 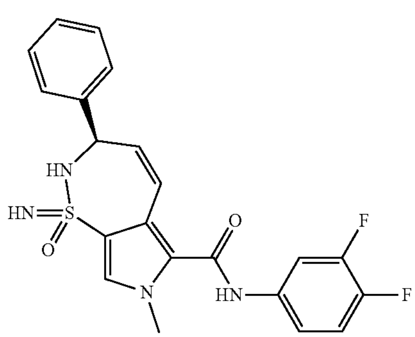 [SMILES: Cn1cc2c(c1C(=O)Nc1ccc(F)c(F)c1)C=C[C@H](c1ccccc1)NS2(=N)=O] | 429 | Peak1 (HPLC) |

-continued

| No. | Structure | Mass Spectrum ESI-MS, (M + H) | Remark |
|---|---|---|---|
| 10ii2 | 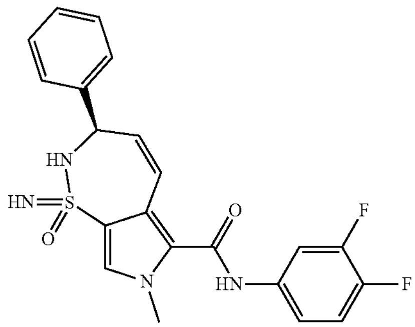 [SMILES: Cn1cc2c(c1C(=O)Nc1ccc(F)c(F)c1)C=C[C@H](c1ccccc1)NS2(=N)=O] | 429 | Peak2 (HPLC) |
| 10jj1 | 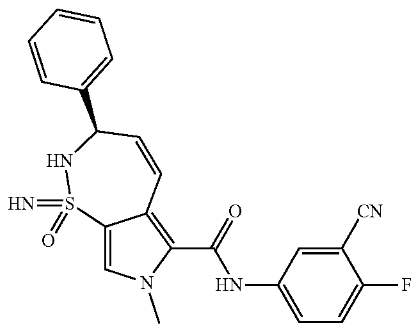 [SMILES: Cn1cc2c(c1C(=O)Nc1ccc(F)c(C#N)c1)C=C[C@H](c1ccccc1)NS2(=N)=O] | 436 | Peak1 (HPLC) |
| 10jj2 | 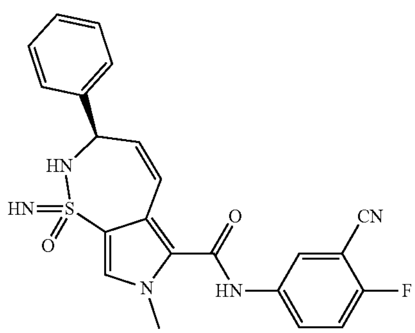 [SMILES: Cn1cc2c(c1C(=O)Nc1ccc(F)c(C#N)c1)C=C[C@H](c1ccccc1)NS2(=N)=O] | 436 | Peak2 (HPLC) |
| 10kk1 | 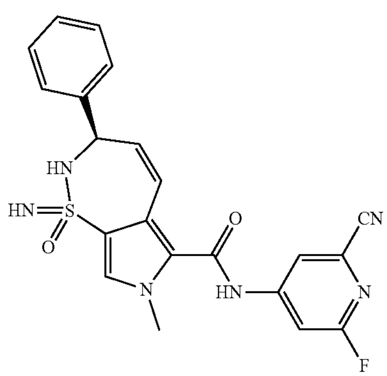 [SMILES: Cn1cc2c(c1C(=O)Nc1cc(F)nc(C#N)c1)C=C[C@H](c1ccccc1)NS2(=N)=O] | 437 | Peak1 (HPLC) |

-continued
| No. | Structure | Mass Spectrum ESI-MS, (M + H) | Remark |
|---|---|---|---|
| 10kk2 | 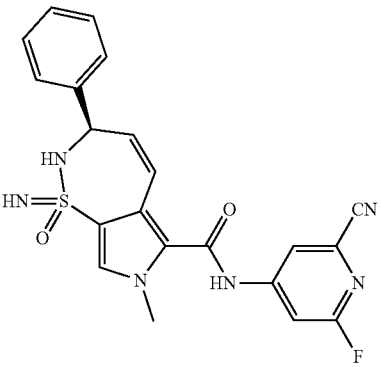 | 437 | Peak2 (HPLC) |
| 10mm1 | 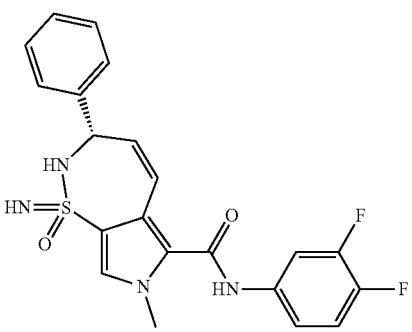 | 429 | Peak1 (HPLC) |
| 10mm2 | 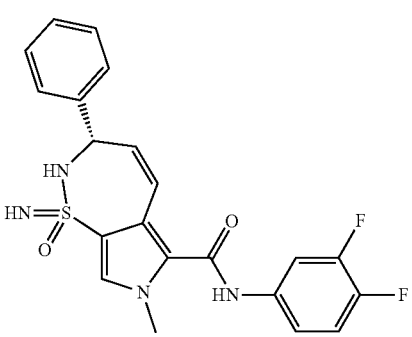 [SMILES: Cn1cc2c(c1C(=O)Nc1ccc(F)c(F)c1)C=C[C@@H](c1ccccc1)NS2(=N)=O] | 429 | Peak2 (HPLC) |
| 10nn1 | 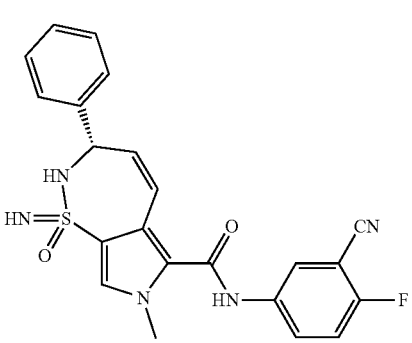 | 436 | Peak1 (HPLC) |

-continued

| No. | Structure | Mass Spectrum ESI-MS, (M + H) | Remark |
|---|---|---|---|
| 10nn2 | 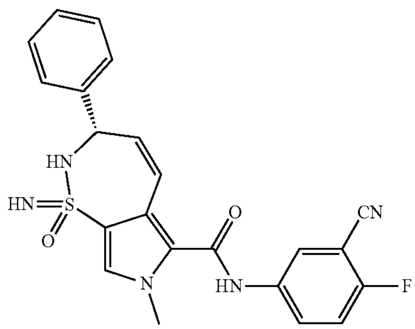 [SMILES: Cn1cc2c(c1C(=O)Nc1ccc(F)c(C#N)c1)C=C[C@@H](c1ccccc1)NS2(=N)=O] | 436 | Peak2 (HPLC) |
| 10oo1 | 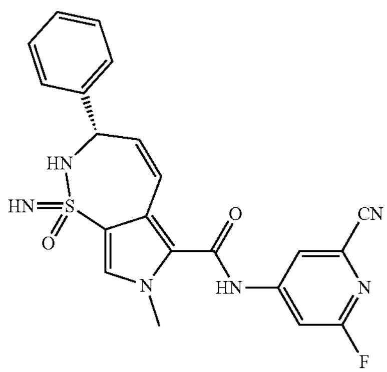 [SMILES: Cn1cc2c(c1C(=O)Nc1cc(F)nc(C#N)c1)C=C[C@@H](c1ccccc1)NS2(=N)=O] | 437 | Peak1 (HPLC) |
| 10oo2 | 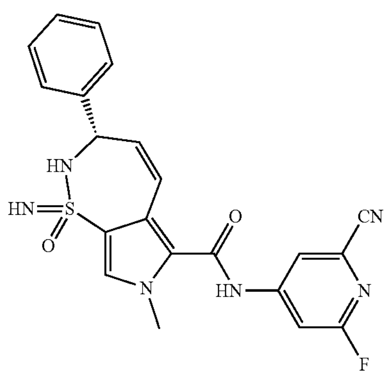 [SMILES: Cn1cc2c(c1C(=O)Nc1cc(F)nc(C#N)c1)C=C[C@@H](c1ccccc1)NS2(=N)=O] | 437 | Peak2 (HPLC) |
| 10pp1 | 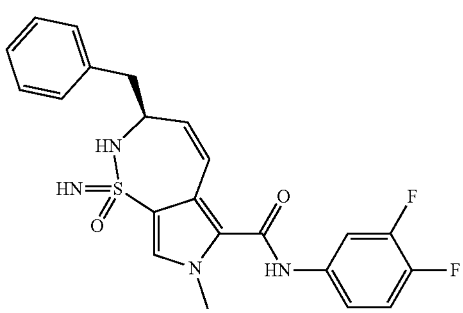 [SMILES: Cn1cc2c(c1C(=O)Nc1ccc(F)c(F)c1)C=C[C@H](Cc1ccccc1)NS2(=N)=O] | 443 | Peak1 (HPLC) |

-continued
| No. | Structure | Mass Spectrum ESI-MS, (M + H) | Remark |
|---|---|---|---|
| 10pp2 | 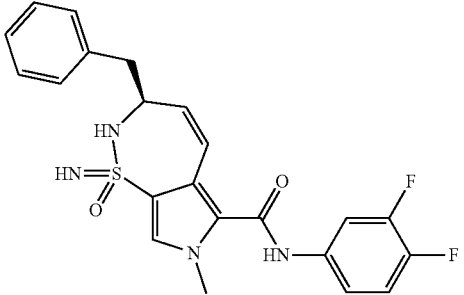 [SMILES: Cn1cc2c(c1C(=O)Nc1ccc(F)c(F)c1)C=C[C@H](Cc1ccccc1)NS2(=N)=O] | 443 | Peak2 (HPLC) |
| 10qq1 | 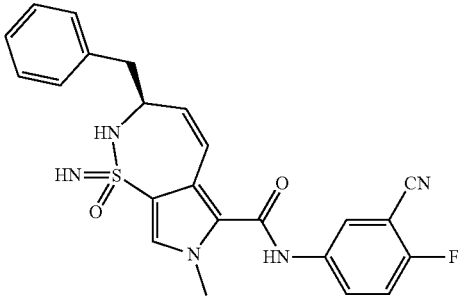 | 450 | Peak1 (HPLC) |
| 10qq2 | 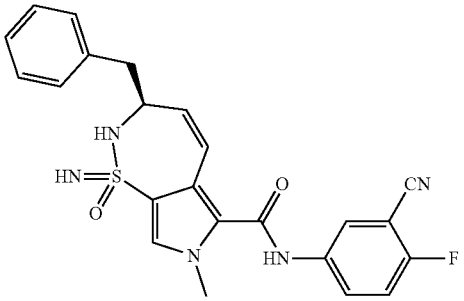 | 450 | Peak2 (HPLC) |
| 10rr1 | 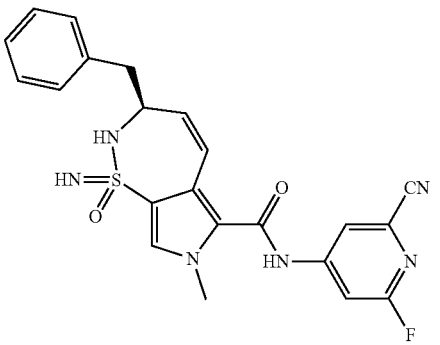 [SMILES: Cn1cc2c(c1C(=O)Nc1cc(F)nc(C#N)c1)C=C[C@H](Cc1ccccc1)NS2(=N)=O] | 451 | Peak1 (HPLC) |

-continued
| No. | Structure | Mass Spectrum ESI-MS, (M + H) | Remark |
|---|---|---|---|
| 10rr2 | 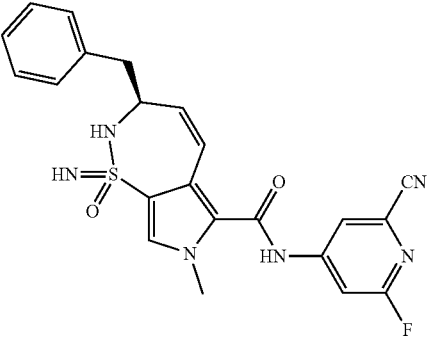 [SMILES: Cn1cc2c(c1C(=O)Nc1cc(F)nc(C#N)c1)C=C[C@H](Cc1ccccc1)NS2(=N)=O] | 451 | Peak2 (HPLC) |
| 10ss1 | 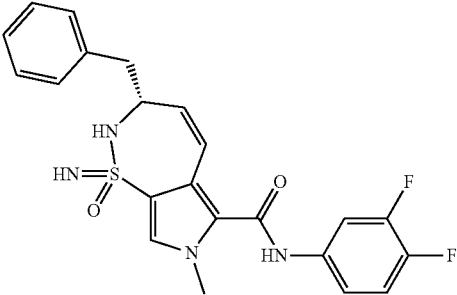 [SMILES: Cn1cc2c(c1C(=O)Nc1ccc(F)c(F)c1)C=C[C@@H](Cc1ccccc1)NS2(=N)=O] | 443 | Peak1 (HPLC) |
| 10ss2 | 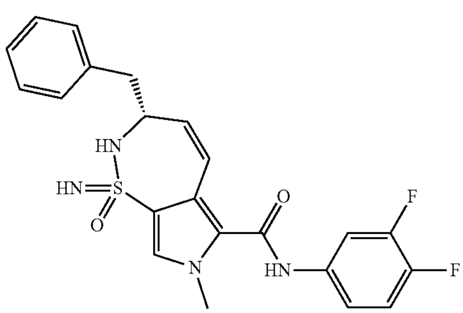 [SMILES: Cn1cc2c(c1C(=O)Nc1ccc(F)c(F)c1)C=C[C@@H](Cc1ccccc1)NS2(=N)=O] | 443 | Peak2 (HPLC) |
| 10tt1 | 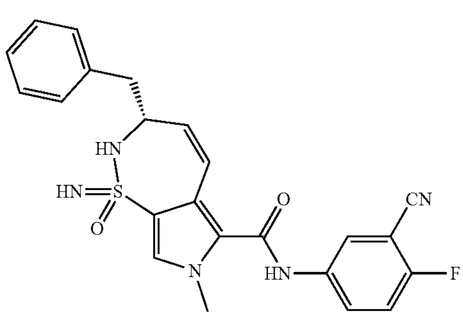 [SMILES: Cn1cc2c(c1C(=O)Nc1ccc(F)c(C#N)c1)C=C[C@@H](Cc1ccccc1)NS2(=N)=O] | 450 | Peak1 (HPLC) |

-continued
| No. | Structure | Mass Spectrum ESI-MS, (M + H) | Remark |
|---|---|---|---|
| 10tt2 | 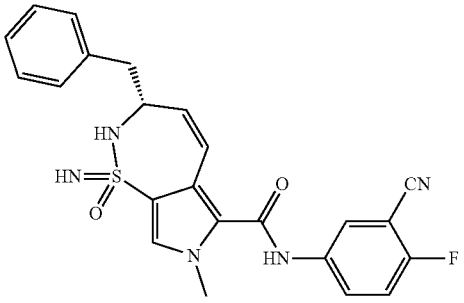 [SMILES: Cn1cc2c(c1C(=O)Nc1ccc(F)c(C#N)c1)C=C[C@@H](Cc1ccccc1)NS2(=N)=O] | 450 | Peak2 (HPLC) |
| 10uu1 | 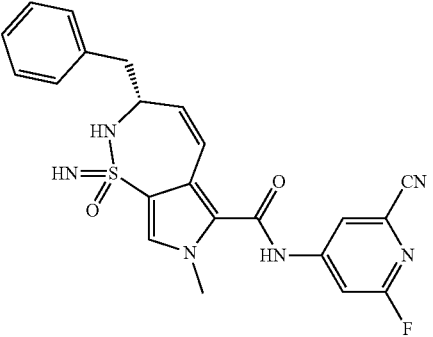 [SMILES: Cn1cc2c(c1C(=O)Nc1cc(F)nc(C#N)c1)C=C[C@@H](Cc1ccccc1)NS2(=N)=O] | 451 | Peak1 (HPLC) |
| 10uu2 | 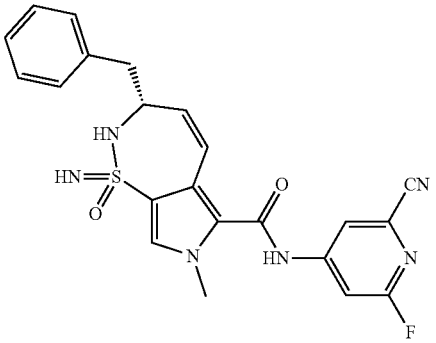 [SMILES: Cn1cc2c(c1C(=O)Nc1cc(F)nc(C#N)c1)C=C[C@@H](Cc1ccccc1)NS2(=N)=O] | 451 | Peak2 (HPLC) |
| 10vv1 | 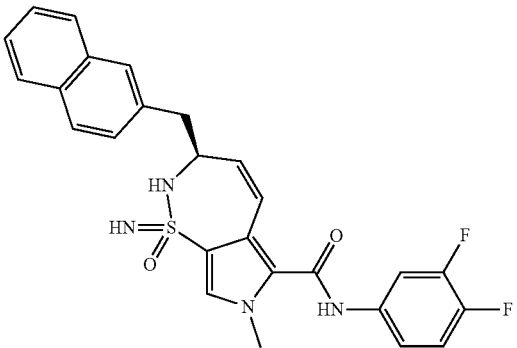 [SMILES: Cn1cc2c(c1C(=O)Nc1ccc(F)c(F)c1)C=C[C@H](Cc1ccc3ccccc3c1)NS2(=N)=O] | 493 | Peak1 (HPLC) |

-continued
| No. | Structure | Mass Spectrum ESI-MS, (M + H) | Remark |
|---|---|---|---|
| 10vv2 | 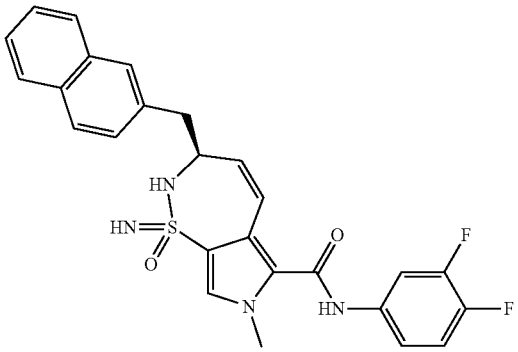 [SMILES: Cn1cc2c(c1C(=O)Nc1ccc(F)c(F)c1)C=C[C@H](Cc1ccc3ccccc3c1)NS2(=N)=O] | 493 | Peak2 (HPLC) |
| 10ww1 | 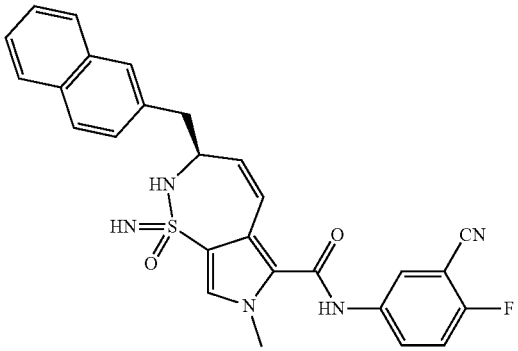 [SMILES: Cn1cc2c(c1C(=O)Nc1ccc(F)c(C#N)c1)C=C[C@H](Cc1ccc3ccccc3c1)NS2(=N)=O] | 500 | Peak1 (HPLC) |
| 10ww2 | 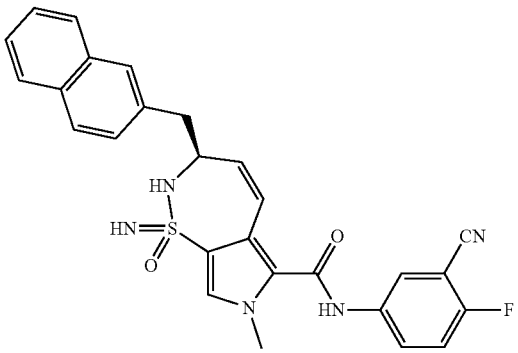 [SMILES: Cn1cc2c(c1C(=O)Nc1ccc(F)c(C#N)c1)C=C[C@H](Cc1ccc3ccccc3c1)NS2(=N)=O] | 500 | Peak2 (HPLC) |
| 10xx1 | 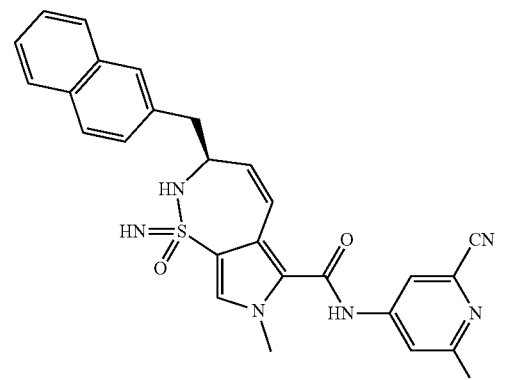 | 501 | Peak1 (HPLC) |

-continued
| No. | Structure | Mass Spectrum ESI-MS, (M + H) | Remark |
|---|---|---|---|
| 10xx2 | 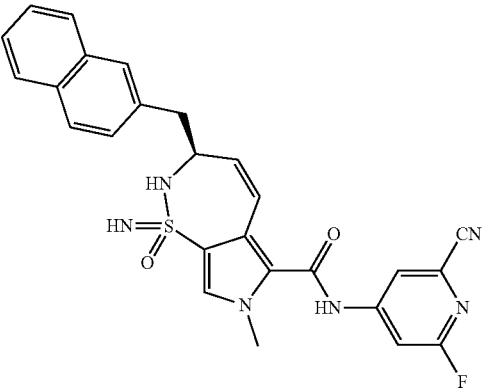 [SMILES: Cn1cc2c(c1C(=O)Nc1cc(F)nc(C#N)c1)C=C[C@H](Cc1ccc3ccccc3c1)NS2(=N)=O] | 501 | Peak2 (HPLC) |
| 10yy1 | 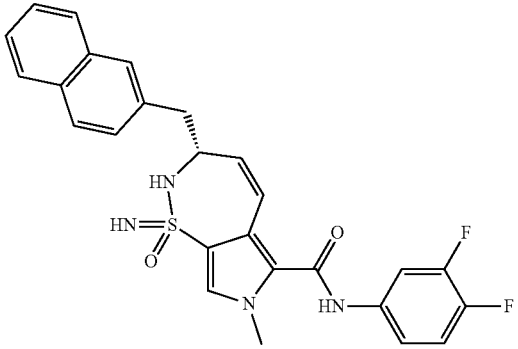 [SMILES: Cn1cc2c(c1C(=O)Nc1ccc(F)c(F)c1)C=C[C@@H](Cc1ccc3ccccc3c1)NS2(=N)=O] | 493 | Peak1 (HPLC) |
| 10yy2 | 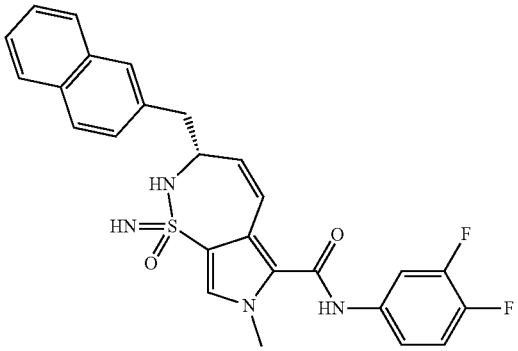 [SMILES: Cn1cc2c(c1C(=O)Nc1ccc(F)c(F)c1)C=C[C@@H](Cc1ccc3ccccc3c1)NS2(=N)=O] | 493 | Peak2 (HPLC) |
| 10zz1 | 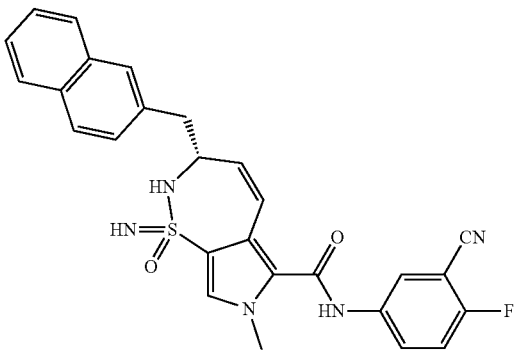 [SMILES: Cn1cc2c(c1C(=O)Nc1ccc(F)c(C#N)c1)C=C[C@@H](Cc1ccc3ccccc3c1)NS2(=N)=O] | 500 | Peak1 (HPLC) |

-continued

| No. | Structure | Mass Spectrum ESI-MS, (M + H) | Remark |
|---|---|---|---|
| 10zz2 | 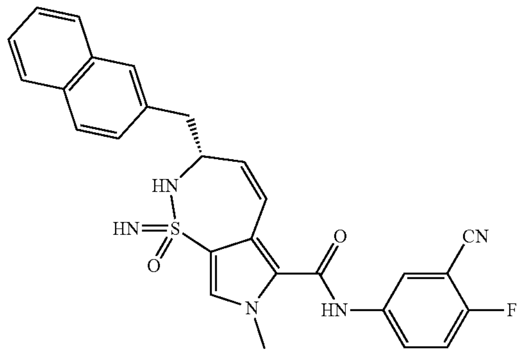 [SMILES: Cn1cc2c(c1C(=O)Nc1ccc(F)c(C#N)c1)C=C[C@@H](Cc1ccc3ccccc3c1)NS2(=N)=O] | 500 | Peak2 (HPLC) |
| 10aaa1 | 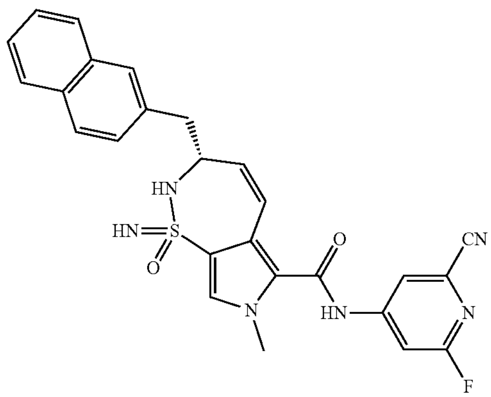 [SMILES: Cn1cc2c(c1C(=O)Nc1cc(F)nc(C#N)c1)C=C[C@@H](Cc1ccc3ccccc3c1)NS2(=N)=O] | 501 | Peak1 (HPLC) |
| 10aaa2 | 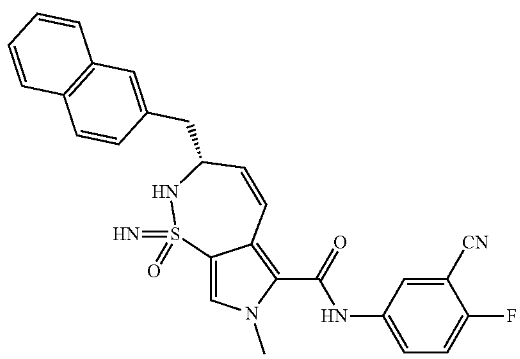 [SMILES: Cn1cc2c(c1C(=O)Nc1ccc(F)c(C#N)c1)C=C[C@@H](Cc1ccc3ccccc3c1)NS2(=N)=O] | 501 | Peak2 (HPLC) |
| 10bbb1 | 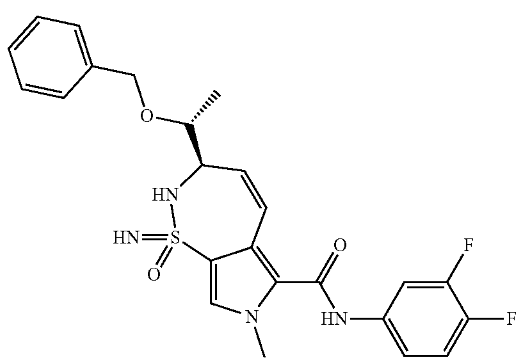 | 487 | Peak1 (HPLC) |

-continued

| No. | Structure | Mass Spectrum ESI-MS, (M + H) | Remark |
|---|---|---|---|
| 10bbb2 | 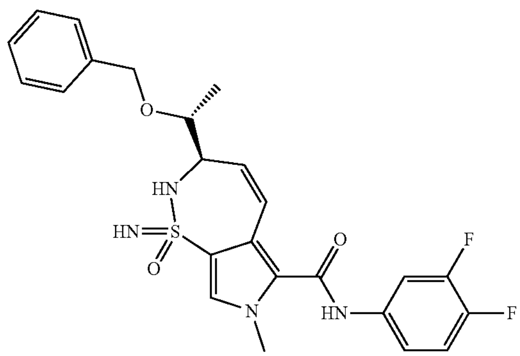 [SMILES: C[C@@H](OCc1ccccc1)[C@H]1C=Cc2c(cn(C)c2C(=O)Nc2ccc(F)c(F)c2)S(=N)(=O)N1] | 487 | Peak2 (HPLC) |
| 10ccc1 | 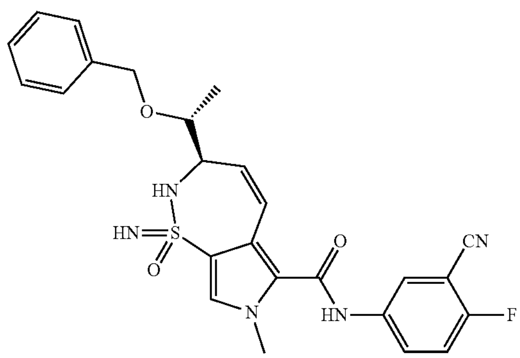 [SMILES: C[C@@H](OCc1ccccc1)[C@H]1C=Cc2c(cn(C)c2C(=O)Nc2ccc(F)c(C#N)c2)S(=N)(=O)N1] | 494 | Peak1 (HPLC) |
| 10ccc2 | 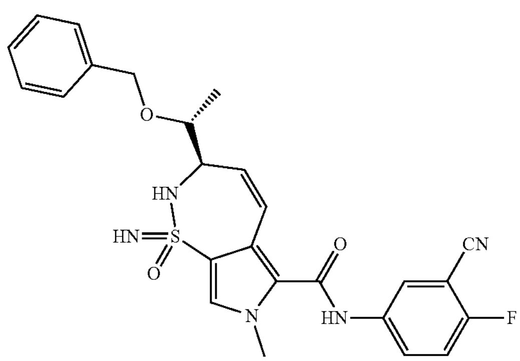 | 494 | Peak2 (HPLC) |
| 10ddd1 | 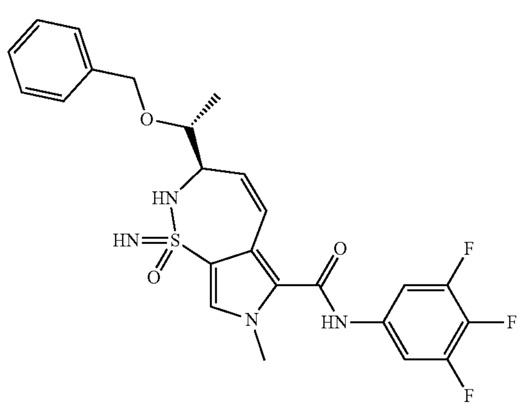 | 505 | Peak1 (HPLC) |

-continued
| No. | Structure | Mass Spectrum ESI-MS, (M + H) | Remark |
|---|---|---|---|
| 10ddd2 | 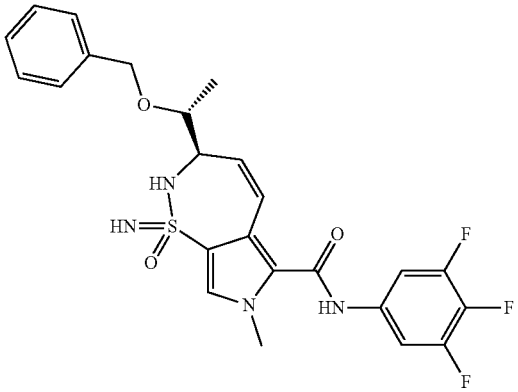 | 505 | Peak2 (HPLC) |
| 10eee1 | 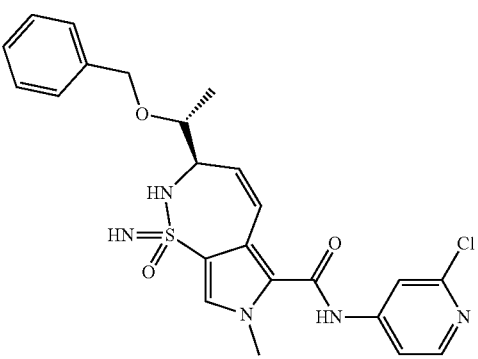 [SMILES: C[C@@H](OCc1ccccc1)[C@H]1C=Cc2c(cn(C)c2C(=O)Nc2ccnc(Cl)c2)S(=N)(=O)N1] | 486 | Peak1 (HPLC) |
| 10eee2 | 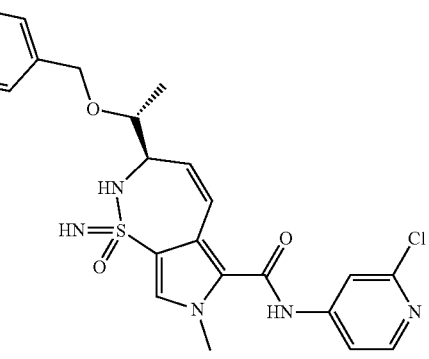 | 486 | Peak2 (HPLC) |
| 10fff1 | 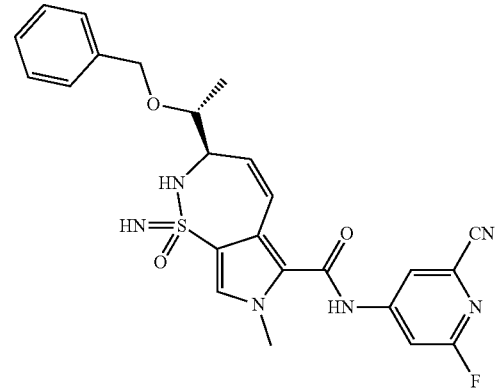 | 495 | Peak1 (HPLC) |

-continued

| No. | Structure | Mass Spectrum ESI-MS, (M + H) | Remark |
|---|---|---|---|
| 10fff2 | 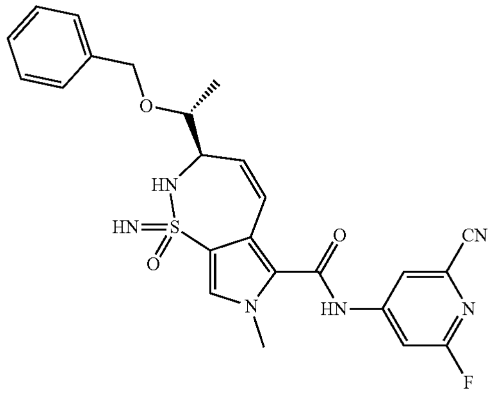 [SMILES: C[C@@H](OCc1ccccc1)[C@H]1C=Cc2c(cn(C)c2C(=O)Nc2cc(F)nc(C#N)c2)S(=N)(=O)N1] | 495 | Peak2 (HPLC) |
| 10ggg1 | 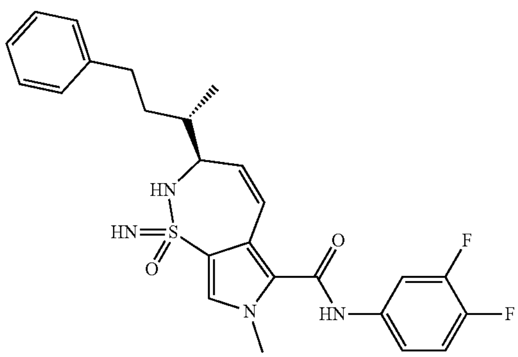 [SMILES: C[C@@H](CCc1ccccc1)[C@H]1C=Cc2c(cn(C)c2C(=O)Nc2ccc(F)c(F)c2)S(=N)(=O)N1] | 485 | Peak1 (HPLC) |
| 10ggg2 | 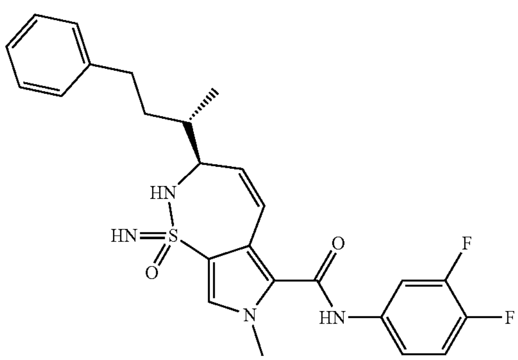 [SMILES: C[C@@H](CCc1ccccc1)[C@H]1C=Cc2c(cn(C)c2C(=O)Nc2ccc(F)c(F)c2)S(=N)(=O)N1] | 485 | Peak2 (HPLC) |
| 10hhh1 | 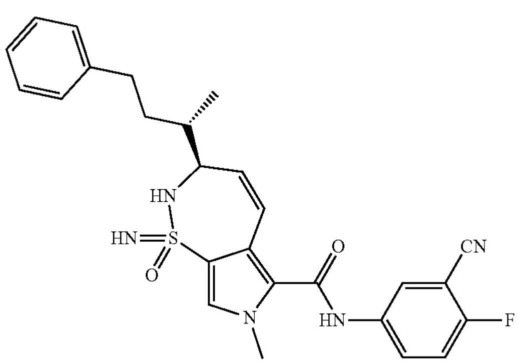 [SMILES: C[C@@H](CCc1ccccc1)[C@H]1C=Cc2c(cn(C)c2C(=O)Nc2ccc(F)c(C#N)c2)S(=N)(=O)N1] | 492 | Peak1 (HPLC) |

| No. | Structure | Mass Spectrum ESI-MS, (M + H) | Remark |
|---|---|---|---|
| 10hhh2 | 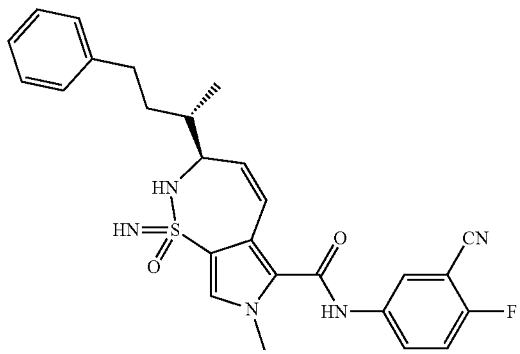 [SMILES: C[C@@H](CCc1ccccc1)[C@H]1C=Cc2c(cn(C)c2C(=O)Nc2ccc(F)c(C#N)c2)S(=N)(=O)N1] | 492 | Peak2 (HPLC) |
| 10iii1 | 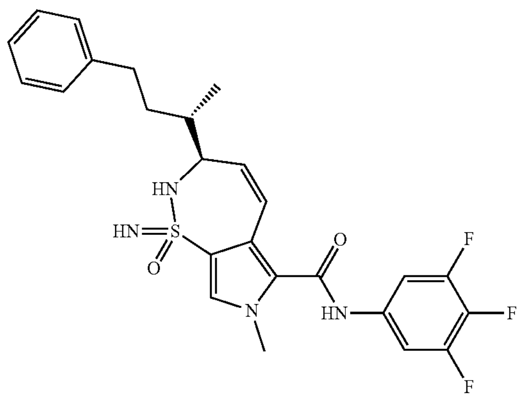 [SMILES: C[C@@H](CCc1ccccc1)[C@H]1C=Cc2c(cn(C)c2C(=O)Nc2cc(F)c(F)c(F)c2)S(=N)(=O)N1] | 503 | Peak1 (HPLC) |
| 10iii2 | 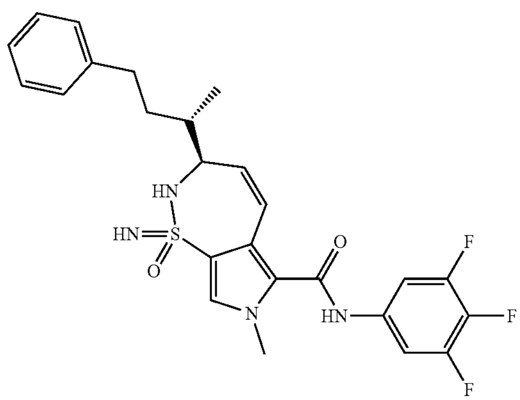 [SMILES: C[C@@H](CCc1ccccc1)[C@H]1C=Cc2c(cn(C)c2C(=O)Nc2cc(F)c(F)c(F)c2)S(=N)(=O)N1] | 503 | Peak2 (HPLC) |
| 10jjj1 | 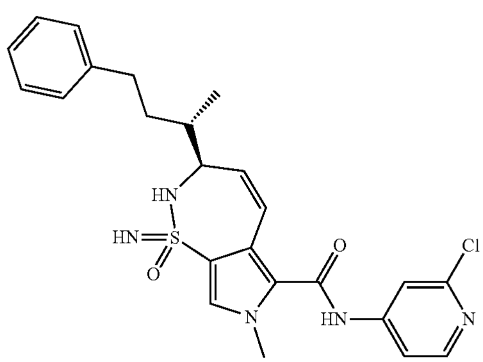 [SMILES: C[C@@H](CCc1ccccc1)[C@H]1C=Cc2c(cn(C)c2C(=O)Nc2ccnc(Cl)c2)S(=N)(=O)N1] | 484 | Peak1 (HPLC) |

-continued
| No. | Structure | Mass Spectrum ESI-MS, (M + H) | Remark |
|---|---|---|---|
| 10jjj2 | 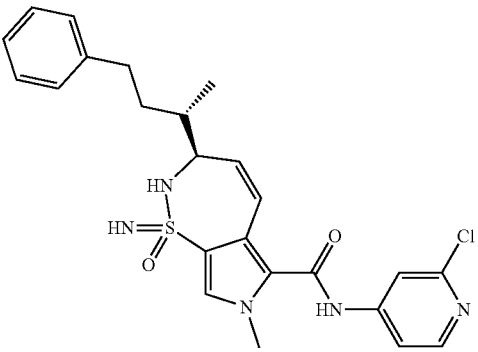 | 484 | Peak2 (HPLC) |
| 10kkk1 | 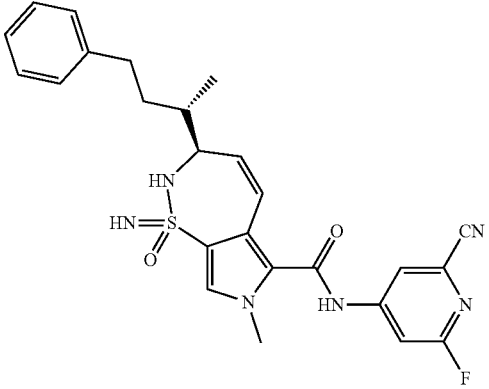 | 493 | Peak1 (HPLC) |
| 10kkk2 | 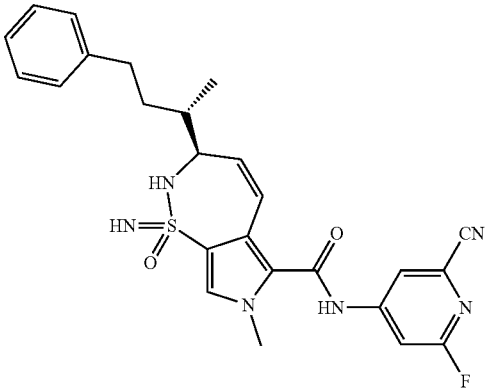 [SMILES: C[C@@H](CCc1ccccc1)[C@H]1C=Cc2c(cn(C)c2C(=O)Nc2cc(F)nc(C#N)c2)S(=N)(=O)N1] | 493 | Peak2 (HPLC) |
| 10mmm1 | 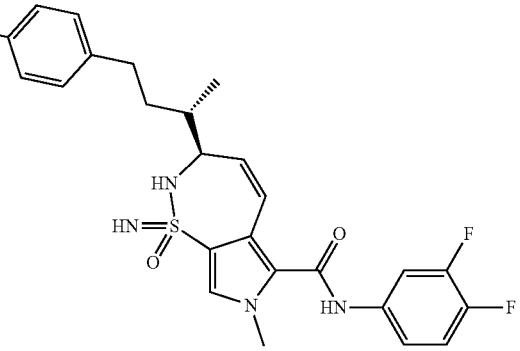 | 503 | Peak1 (HPLC) |

| No. | Structure | Mass Spectrum ESI-MS, (M + H) | Remark |
|---|---|---|---|
| 10mmm2 | 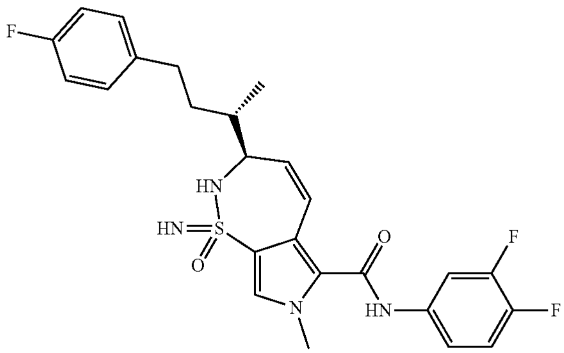 [SMILES: C[C@@H](CCc1ccc(F)cc1)[C@H]1C=Cc2c(cn(C)c2C(=O)Nc2ccc(F)c(F)c2)S(=N)(=O)N1] | 503 | Peak2 (HPLC) |
| 10nnn1 | 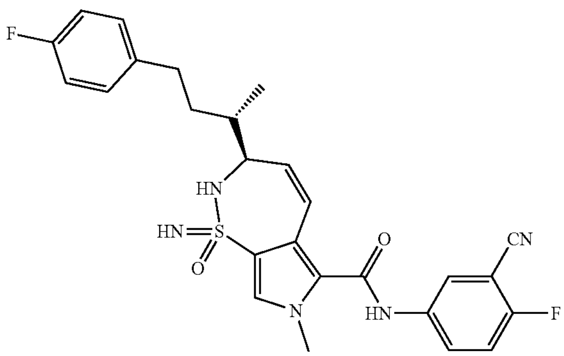 [SMILES: C[C@@H](CCc1ccc(F)cc1)[C@H]1C=Cc2c(cn(C)c2C(=O)Nc2ccc(F)c(C#N)c2)S(=N)(=O)N1] | 510 | Peak1 (HPLC) |
| 10nnn2 | 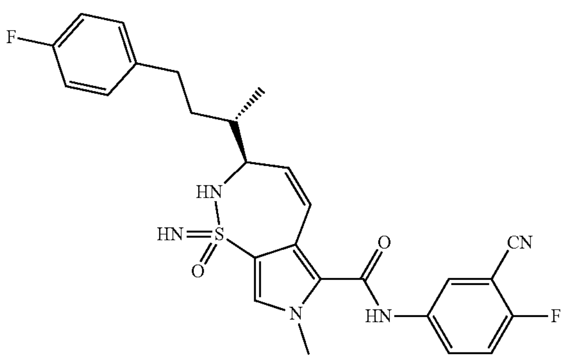 [SMILES: C[C@@H](CCc1ccc(F)cc1)[C@H]1C=Cc2c(cn(C)c2C(=O)Nc2ccc(F)c(C#N)c2)S(=N)(=O)N1] | 510 | Peak2 (HPLC) |
| 10ooo1 | 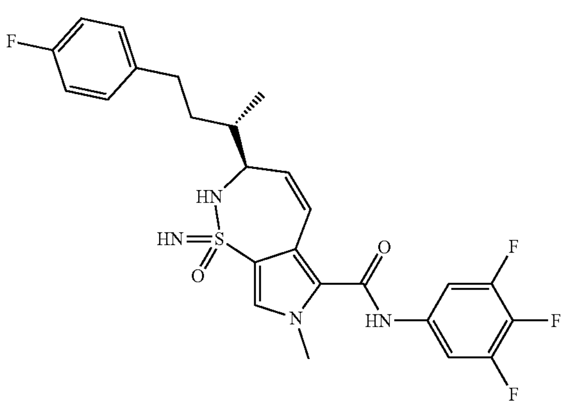 [SMILES: C[C@@H](CCc1ccc(F)cc1)[C@H]1C=Cc2c(cn(C)c2C(=O)Nc2cc(F)c(F)c(F)c2)S(=N)(=O)N1] | 521 | Peak1 (HPLC) |

-continued

| No. | Structure | Mass Spectrum ESI-MS, (M + H) | Remark |
|---|---|---|---|
| 10ooo2 | 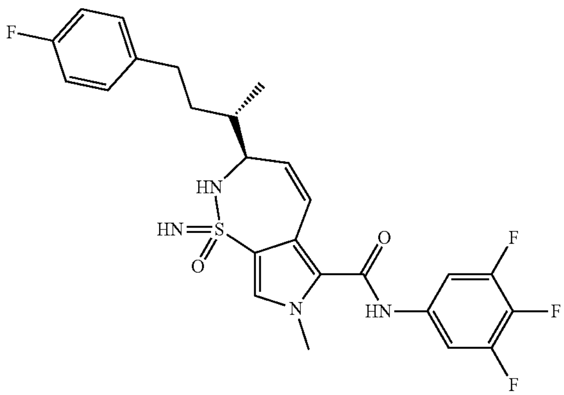 [SMILES: C[C@@H](CCc1ccc(F)cc1)[C@H]1C=Cc2c(cn(C)c2C(=O)Nc2cc(F)c(F)c(F)c2)S(=N)(=O)N1] | 521 | Peak2 (HPLC) |
| 10ppp1 | 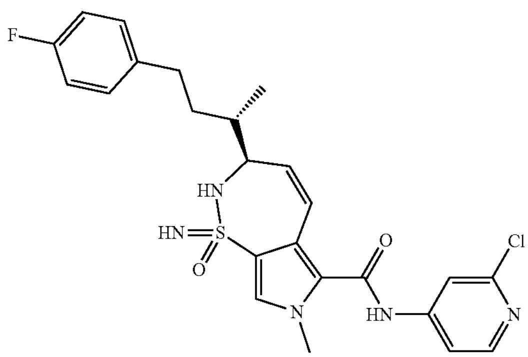 [SMILES: C[C@@H](CCc1ccc(F)cc1)[C@H]1C=Cc2c(cn(C)c2C(=O)Nc2ccnc(Cl)c2)S(=N)(=O)N1] | 502 | Peak1 (HPLC) |
| 10ppp2 | 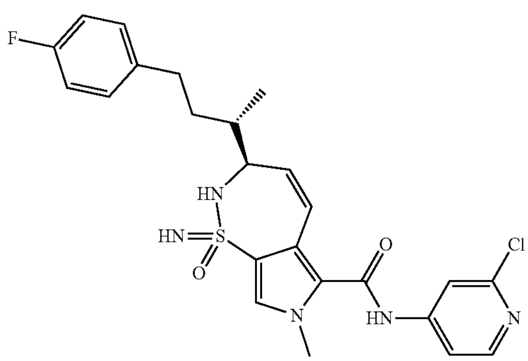 [SMILES: C[C@@H](CCc1ccc(F)cc1)[C@H]1C=Cc2c(cn(C)c2C(=O)Nc2ccnc(Cl)c2)S(=N)(=O)N1] | 502 | Peak2 (HPLC) |
| 10qqq1 | 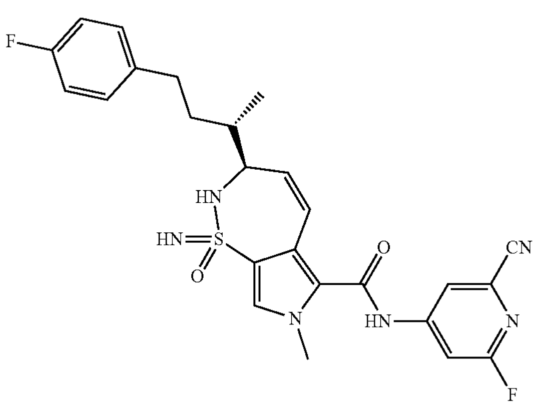 [SMILES: C[C@@H](CCc1ccc(F)cc1)[C@H]1C=Cc2c(cn(C)c2C(=O)Nc2cc(F)nc(C#N)c2)S(=N)(=O)N1] | 511 | Peak1 (HPLC) |

-continued
| No. | Structure | Mass Spectrum ESI-MS, (M + H) | Remark |
|---|---|---|---|
| 10qqq2 | 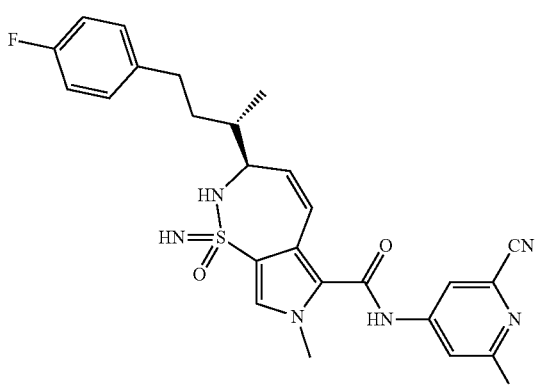 | 511 | Peak2 (HPLC) |
| 10rrr1 | 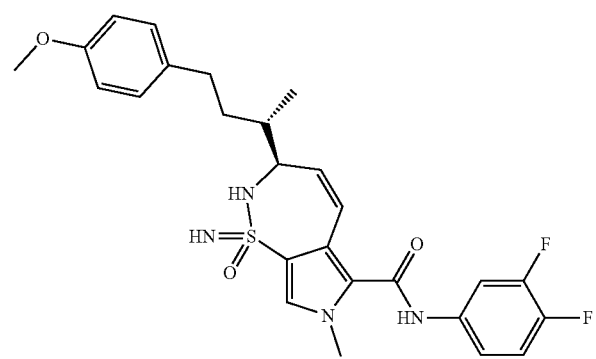 [SMILES: COc1ccc(CC[C@H](C)[C@H]2C=Cc3c(cn(C)c3C(=O)Nc3ccc(F)c(F)c3)S(=N)(=O)N2)cc1] | 515 | Peak1 (HPLC) |
| 10rrr2 | 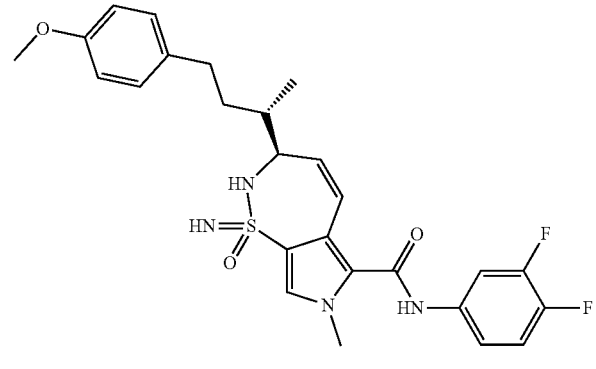 [SMILES: COc1ccc(CC[C@H](C)[C@H]2C=Cc3c(cn(C)c3C(=O)Nc3ccc(F)c(F)c3)S(=N)(=O)N2)cc1] | 515 | Peak2 (HPLC) |
| 10sss1 | 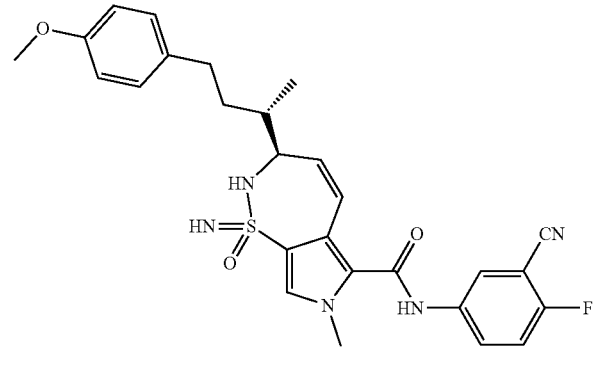 [SMILES: COc1ccc(CC[C@H](C)[C@H]2C=Cc3c(cn(C)c3C(=O)Nc3ccc(F)c(C#N)c3)S(=N)(=O)N2)cc1] | 522 | Peak1 (HPLC) |

-continued
| No. | Structure | Mass Spectrum ESI-MS, (M + H) | Remark |
|---|---|---|---|
| 10sss2 | 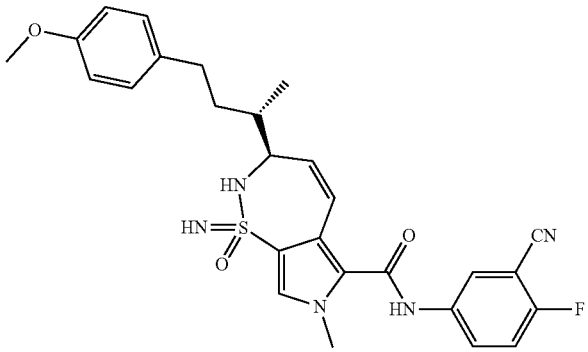 [SMILES: COc1ccc(CC[C@H](C)[C@H]2C=Cc3c(cn(C)c3C(=O)Nc3ccc(F)c(C#N)c3)S(=N)(=O)N2)cc1] | 522 | Peak2 (HPLC) |
| 10ttt1 | 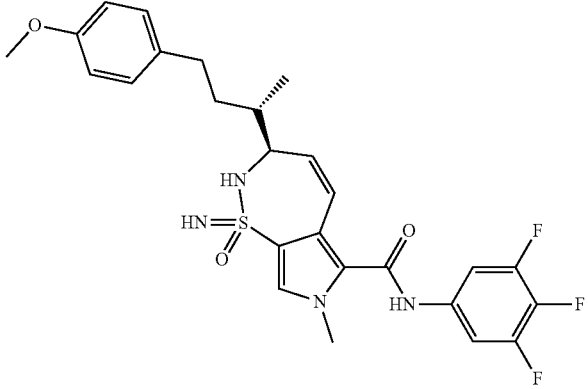 [SMILES: COc1ccc(CC[C@H](C)[C@H]2C=Cc3c(cn(C)c3C(=O)Nc3cc(F)c(F)c(F)c3)S(=N)(=O)N2)cc1] | 533 | Peak1 (HPLC) |
| 10ttt2 | 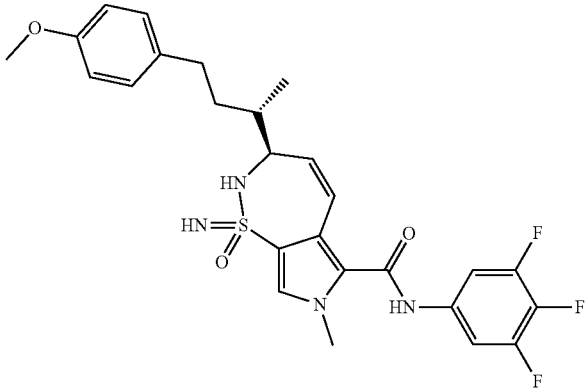 [SMILES: COc1ccc(CC[C@H](C)[C@H]2C=Cc3c(cn(C)c3C(=O)Nc3cc(F)c(F)c(F)c3)S(=N)(=O)N2)cc1] | 533 | Peak2 (HPLC) |
| 10uuu1 | 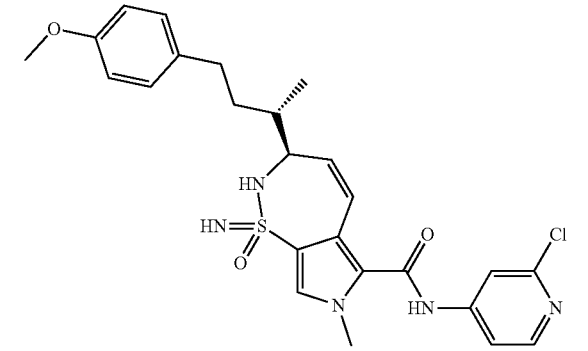 [SMILES: COc1ccc(CC[C@H](C)[C@H]2C=Cc3c(cn(C)c3C(=O)Nc3ccnc(Cl)c3)S(=N)(=O)N2)cc1] | 514 | Peak1 (HPLC) |

| No. | Structure | Mass Spectrum ESI-MS, (M + H) | Remark |
|---|---|---|---|
| 10uuu2 | 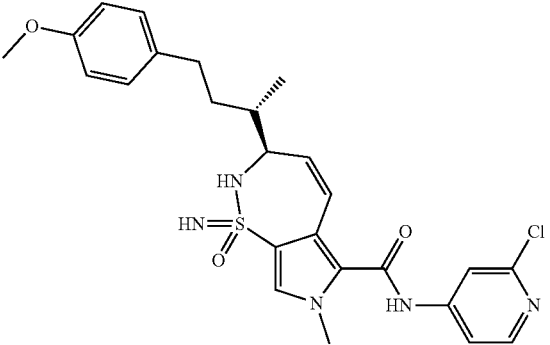 [SMILES: COc1ccc(CC[C@H](C)[C@H]2C=Cc3c(cn(C)c3C(=O)Nc3ccnc(Cl)c3)S(=N)(=O)N2)cc1] | 514 | Peak2 (HPLC) |
| 10vvv1 | 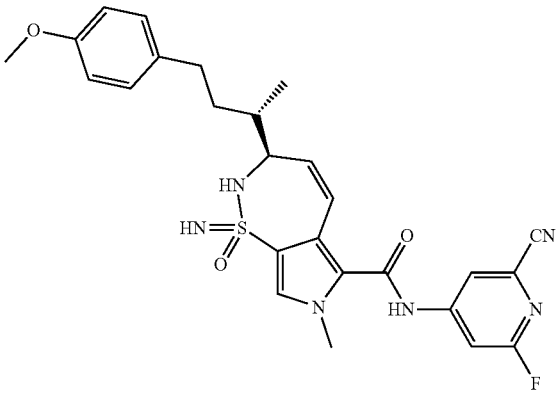 [SMILES: COc1ccc(CC[C@H](C)[C@H]2C=Cc3c(cn(C)c3C(=O)Nc3cc(F)nc(C#N)c3)S(=N)(=O)N2)cc1] | 523 | Peak1 (HPLC) |
| 10vvv2 | 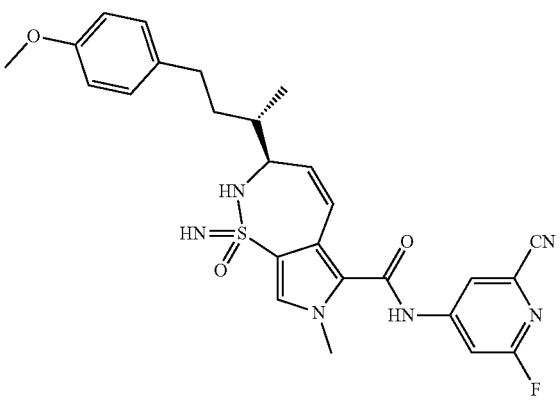 [SMILES: COc1ccc(CC[C@H](C)[C@H]2C=Cc3c(cn(C)c3C(=O)Nc3cc(F)nc(C#N)c3)S(=N)(=O)N2)cc1] | 523 | Peak2 (HPLC) |
| 10www1 | 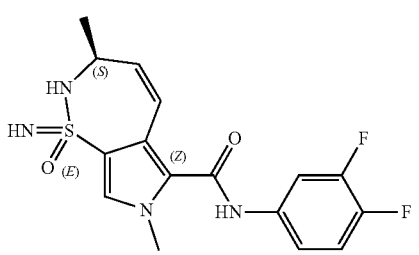 | 367 | Peak1 (HPLC) |

| No. | Structure | Mass Spectrum ESI-MS, (M + H) | Remark |
|---|---|---|---|
| 10www2 | 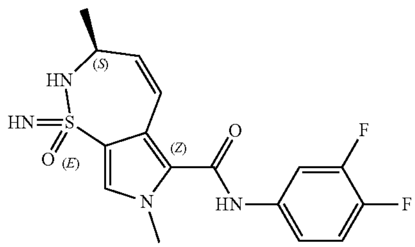 | 367 | Peak2 (HPLC) |
| 10xxx1 | 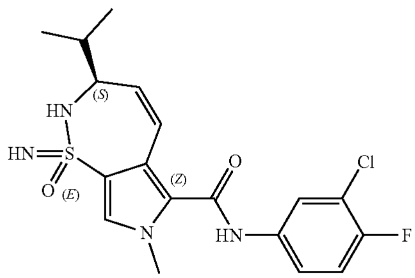 | 411 | Peak1 (HPLC) |
| 10xxx2 | 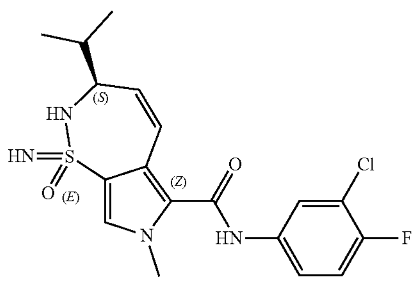 | 411 | Peak2 (HPLC) |
| 30a1 | 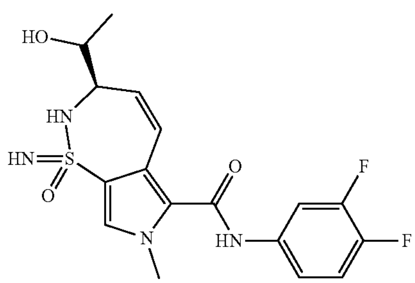 [SMILES: CC(O)[C@H]1C=Cc2c(cn(C)c2C(=O)Nc2ccc(F)c(F)c2)S(=N)(=O)N1] | 397 | Peak1 (HPLC) |
| 30a2 | 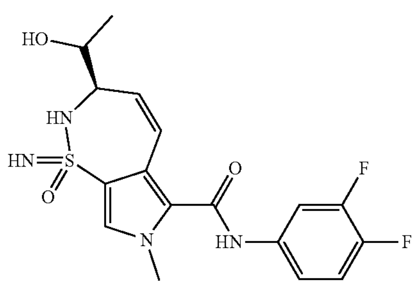 [SMILES: CC(O)[C@H]1C=Cc2c(cn(C)c2C(=O)Nc2ccc(F)c(F)c2)S(=N)(=O)N1] | 397 | Peak2 (HPLC) |

-continued

| No. | Structure | Mass Spectrum ESI-MS, (M + H) | Remark |
|---|---|---|---|
| 30b1 | 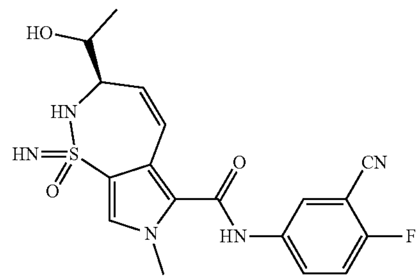 [SMILES: CC(O)[C@H]1C=Cc2c(cn(C)c2C(=O)Nc2ccc(F)c(C#N)c2)S(=N)(=O)N1] | 404 | Peak1 (HPLC) |
| 30b2 | 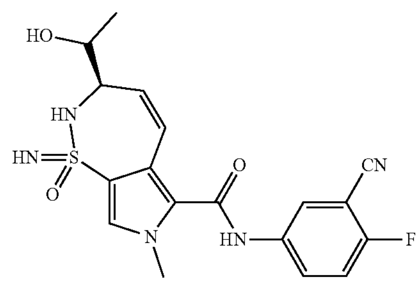 [SMILES: CC(O)[C@H]1C=Cc2c(cn(C)c2C(=O)Nc2ccc(F)c(C#N)c2)S(=N)(=O)N1] | 404 | Peak2 (HPLC) |
| 30c1 | 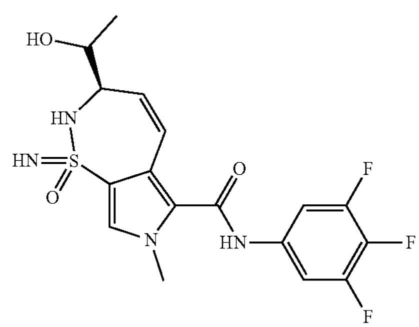 [SMILES: CC(O)[C@H]1C=Cc2c(cn(C)c2C(=O)Nc2cc(F)c(F)c(F)c2)S(=N)(=O)N1] | 415 | Peak1 (HPLC) |
| 30c2 | 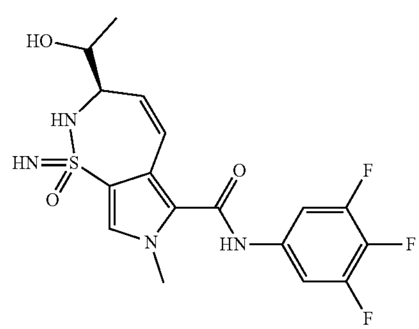 [SMILES: CC(O)[C@H]1C=Cc2c(cn(C)c2C(=O)Nc2cc(F)c(F)c(F)c2)S(=N)(=O)N1] | 415 | Peak2 (HPLC) |
| 30d1 | 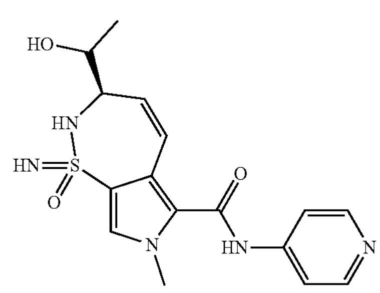 [SMILES: CC(O)[C@H]1C=Cc2c(cn(C)c2C(=O)Nc2ccncc2)S(=N)(=O)N1] | 362 | Peak1 (HPLC) |

-continued

| No. | Structure | Mass Spectrum ESI-MS, (M + H) | Remark |
|---|---|---|---|
| 30d2 | 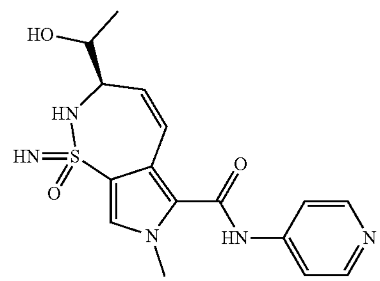 [SMILES: CC(O)[C@H]1C=Cc2c(cn(C)c2C(=O)Nc2ccncc2)S(=N)(=O)N1] | 362 | Peak2 (HPLC) |
| 30e1 | 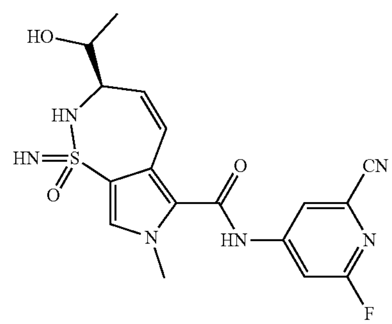 [SMILES: CC(O)[C@H]1C=Cc2c(cn(C)c2C(=O)Nc2cc(F)nc(C#N)c2)S(=N)(=O)N1] | 405 | Peak1 (HPLC) |
| 30e2 | 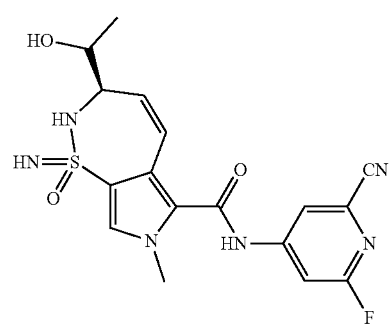 [SMILES: CC(O)[C@H]1C=Cc2c(cn(C)c2C(=O)Nc2cc(F)nc(C#N)c2)S(=N)(=O)N1] | 405 | Peak2 (HPLC) |
| 30f1 | 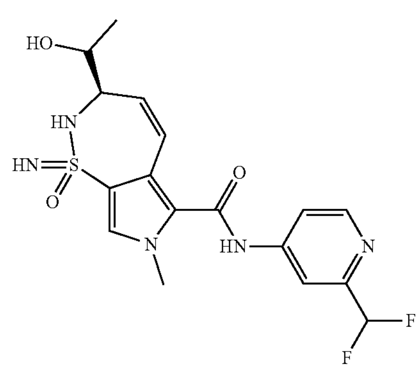 [SMILES: CC(O)[C@H]1C=Cc2c(cn(C)c2C(=O)Nc2ccnc(C(F)F)c2)S(=N)(=O)N1] | 412 | Peak1 (HPLC) |

-continued

| No. | Structure | Mass Spectrum ESI-MS, (M + H) | Remark |
|---|---|---|---|
| 30f2 | 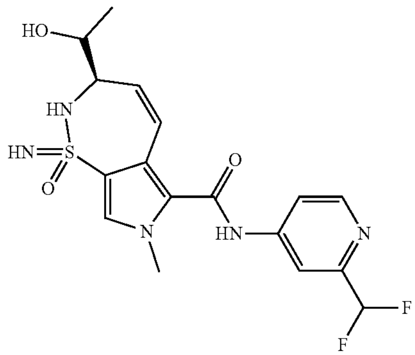 [SMILES: CC(O)[C@H]1C=Cc2c(cn(C)c2C(=O)Nc2ccnc(C(F)F)c2)S(=N)(=O)N1] | 412 | Peak2 (HPLC) |
| 30g1 | 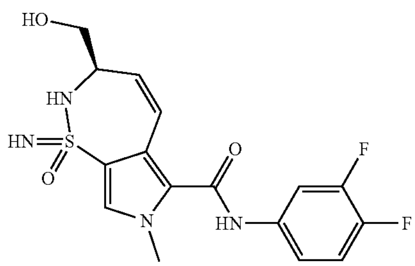 [SMILES: Cn1cc2c(c1C(=O)Nc1ccc(F)c(F)c1)C=C[C@H](CO)NS2(=N)=O] | 383 | Peak1 (HPLC) |
| 30g2 | 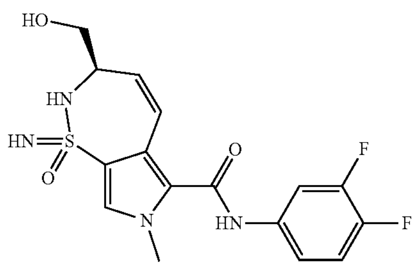 [SMILES: Cn1cc2c(c1C(=O)Nc1ccc(F)c(F)c1)C=C[C@H](CO)NS2(=N)=O] | 383 | Peak2 (HPLC) |
| 30h1 | 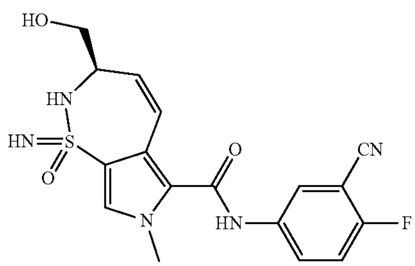 [SMILES: Cn1cc2c(c1C(=O)Nc1ccc(F)c(C#N)c1)C=C[C@H](CO)NS2(=N)=O] | 390 | Peak1 (HPLC) |
| 30h2 | 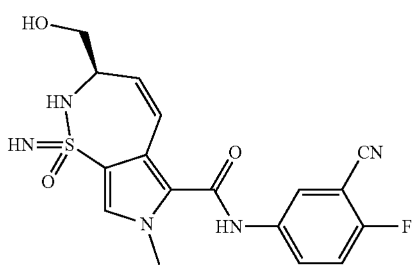 [SMILES: Cn1cc2c(c1C(=O)Nc1ccc(F)c(C#N)c1)C=C[C@H](CO)NS2(=N)=O] | 390 | Peak2 (HPLC) |

-continued

| No. | Structure | Mass Spectrum ESI-MS, (M + H) | Remark |
|---|---|---|---|
| 30i1 | 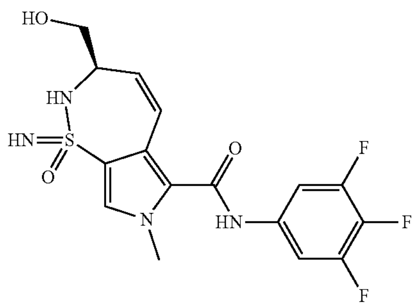 [SMILES: Cn1cc2c(c1C(=O)Nc1cc(F)c(F)c(F)c1)C=C[C@H](CO)NS2(=N)=O] | 401 | Peak1 (HPLC) |
| 30i2 | 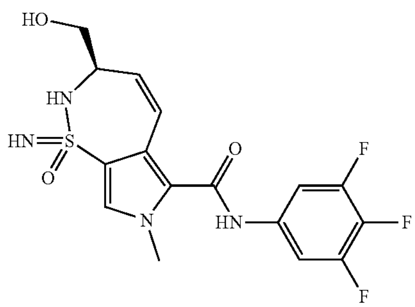 [SMILES: Cn1cc2c(c1C(=O)Nc1cc(F)c(F)c(F)c1)C=C[C@H](CO)NS2(=N)=O] | 401 | Peak2 (HPLC) |
| 30j1 | 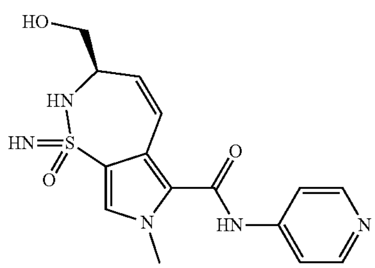 [SMILES: Cn1cc2c(c1C(=O)Nc1ccncc1)C=C[C@H](CO)NS2(=N)=O] | 348 | Peak1 (HPLC) |
| 30j2 | 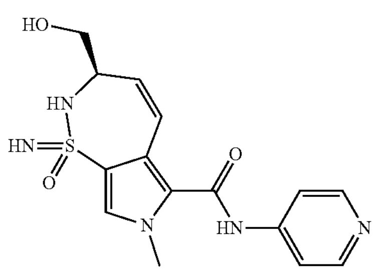 [SMILES: Cn1cc2c(c1C(=O)Nc1ccncc1)C=C[C@H](CO)NS2(=N)=O] | 348 | Peak2 (HPLC) |
| 30k1 | 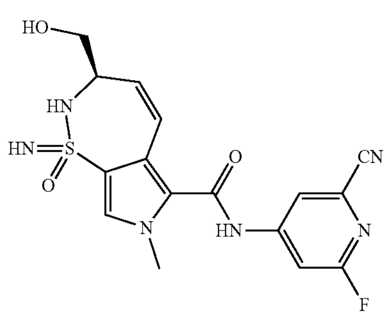 [SMILES: Cn1cc2c(c1C(=O)Nc1cc(F)nc(C#N)c1)C=C[C@H](CO)NS2(=N)=O] | 391 | Peak1 (HPLC) |

-continued
| No. | Structure | Mass Spectrum ESI-MS, (M + H) | Remark |
|---|---|---|---|
| 30k2 | 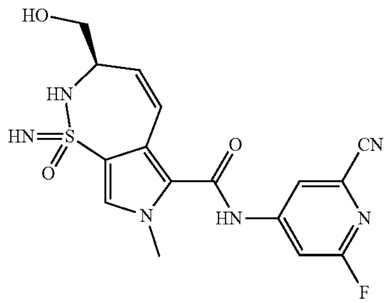 [SMILES: Cn1cc2c(c1C(=O)Nc1cc(F)nc(C#N)c1)C=C[C@H](CO)NS2(=N)=O] | 391 | Peak2 (HPLC) |
| 30m1 | 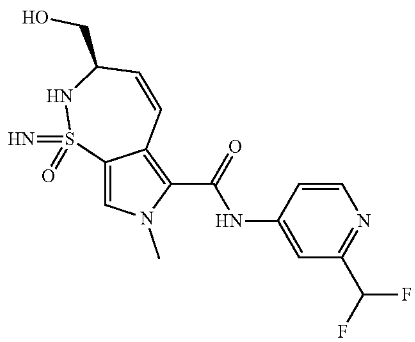 [SMILES: Cn1cc2c(c1C(=O)Nc1ccnc(C(F)F)c1)C=C[C@H](CO)NS2(=N)=O] | 398 | Peak1 (HPLC) |
| 30m2 | 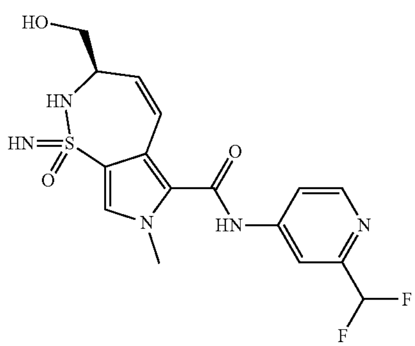 [SMILES: Cn1cc2c(c1C(=O)Nc1ccnc(C(F)F)c1)C=C[C@H](CO)NS2(=N)=O] | 398 | Peak2 (HPLC) |
The following are the synthesis of 20 series compounds:
Example 72: Synthesis of Compound 20a1
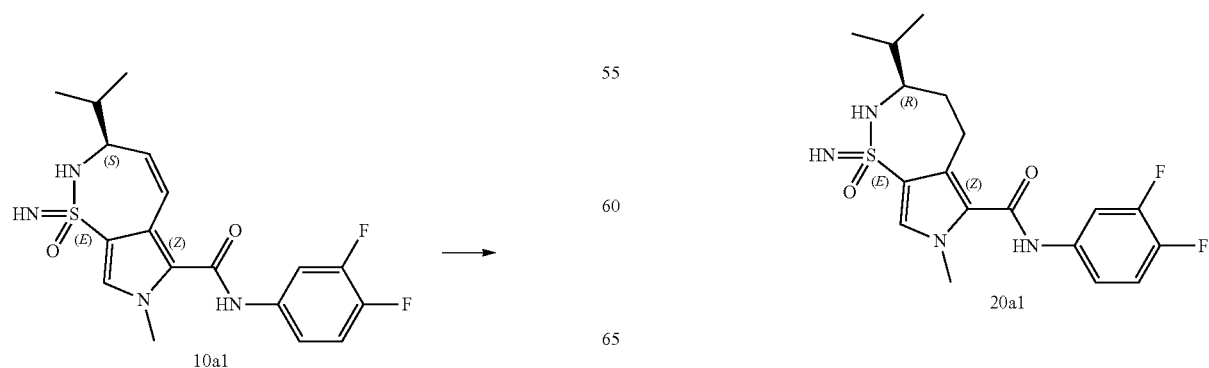

Step 1

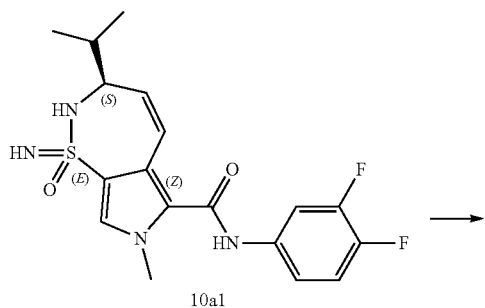

Compound 10a1 (20 mg) was dissolved in methanol (5 mL), and then Pd/C (5 mg) was added to the reaction system. The reaction was performed in hydrogen atmophile at room temperature for 6 h. The crude product was column chromatography (n-heptane:ethyl acetate=1:3) purified to provide the target product 20a1 (11 mg). $^1$H NMR (400 MHz, DMSO-d$_6$) δ 10.56 (s, 1H), 7.88-7.83 (m, 1H), 7.63 (s, 2H), 7.46-7.42 (m, 1H), 7.21-6.96 (m, 1H), 3.72 (s, 3H), 3.12-3.09 (m, 1H), 3.00 (dd, J=15.0, 6.7 Hz, 1H), 2.89-2.78 (m, 1H), 1.89-1.85 (m, 1H), 1.69-1.50 (m, 1H), 1.43 (q, J=12.0 Hz, 1H), 0.92 (dd, J=6.8, 3.5 Hz, 6H). MS (M+1=397).

Example 73: Synthesis of Compound 20a2

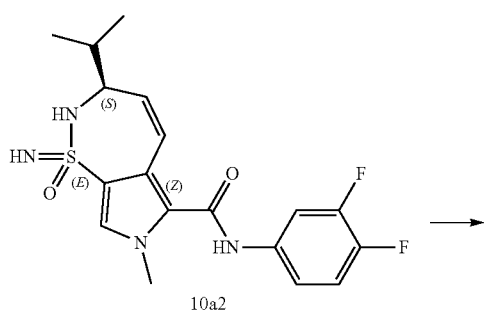

The reaction was carried out according to the step 6 of example 1, all the conditions were the same except the compound 10a2 was used instead of 10a1, purified via column chromatography (n-heptane:ethyl acetate=1:1) to provide target product 20a2 (8 mg). $^1$H NMR (400 MHz, DMSO-d$_6$) δ 10.67 (s, 1H), 8.20-8.18 (m, 1H), 7.97 (d, J=3.7 Hz, 1H), 7.68-7.59 (m, 1H), 7.55 (d, J=10.3 Hz, 1H), 3.76 (s, 3H), 3.04-2.92 (m, 2H), 2.85 (dd, J=15.0, 6.7 Hz, 1H), 1.90-1.83 (m, 1H), 1.73 (dd, J=14.3, 6.7 Hz, 1H), 1.69-1.50 (m, 1H), 1.45 (q, J=12.0 Hz, 1H), 0.89 (dd, J=6.8, 3.5 Hz, 6H). MS (M+1=397).

Example 74: Synthesis of Compound 20b1

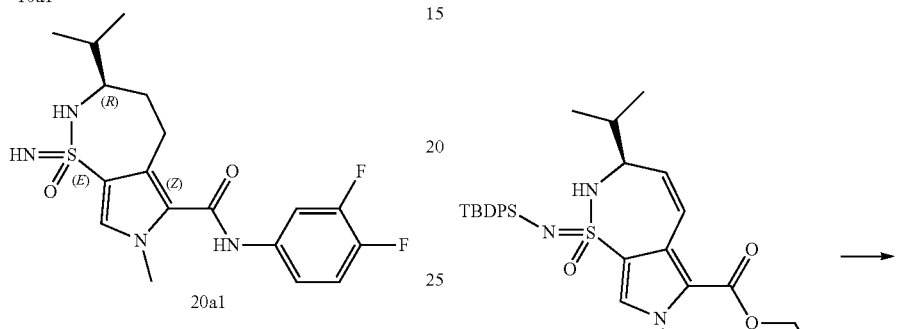

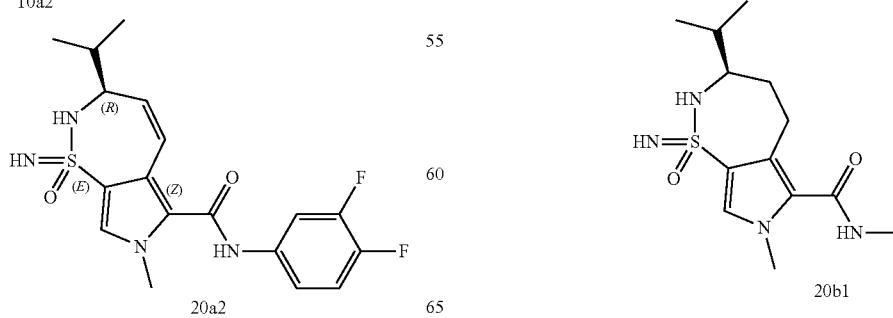

Step 1

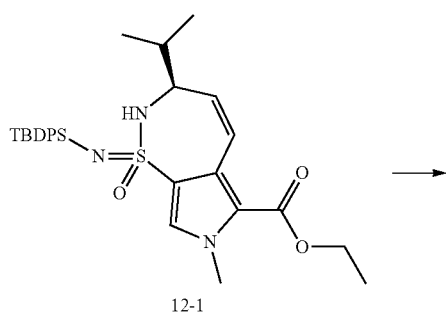

12-1

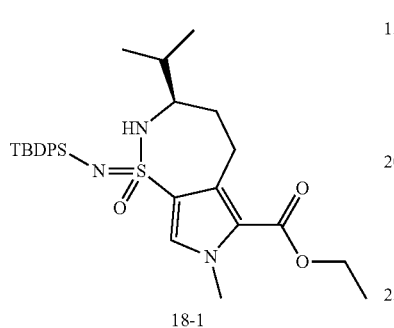

18-1

Compound 1 (150 mg) was dissolved in methanol (8 mL), and Pd/C (30 mg) was added to the reaction system, and purged with nitrogen for three times, then purged with hydrogen for three times. The reaction was carried out at room temperature (25° C.) for 18 h with a hydrogen balloon, and the raw material was monitored to have been consumed with TLC. The reaction was suction filtrated, and the solvent was evaporated in vacuum, and purified via column chromatography (n-heptane:ethyl acetate=5:1) to obtain the target product 130 mg.

MS (M+1=552).

Step 2

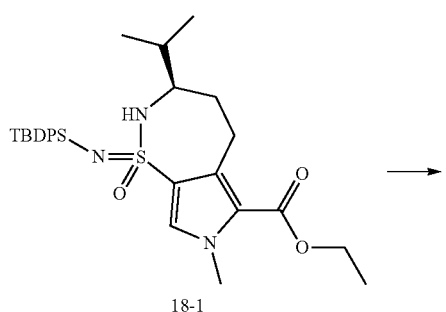

18-1

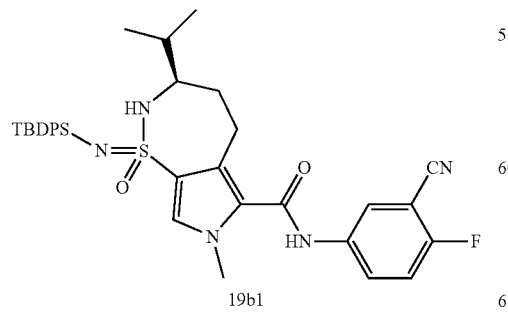

19b1

Compound 12-1 (45 mg) (lower point shown by TLC) and 3-cyano-4-fluoroaniline (23 mg) was dissolved in THF (6 mL), then the system was cooled to 0° C. 8 eq of NaHMDS was added to the reaction system to react at 0° C. for 1 h. Water (20 mL) was added to the reaction system, and extracted with ethyl acetate (3*30 mL), dried over anhydrous sodium sulfate, the solvent was evaporated in vacuum, and purified by column chromatography to provide 18 mg of yellow oil. MS (M+1=640).

Step 3: Synthesis of Compound 20b1

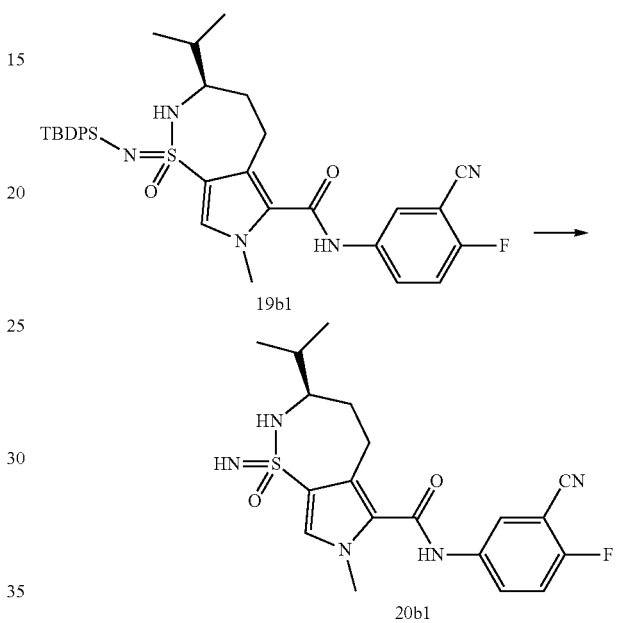

Compound 2 (18 mg) was dissolved in THF (3 mL), and 50 eq of 3HF.TEA was added dropwise to the reaction system. The reaction was performed at room temperature for 3 days. The mixture was purified by preparation TLC and freeze-dried to obtain 4.0 mg of the target product as a white solid. $^1$H NMR (400 MHz, DMSO-$d_6$) δ 10.77 (s, 1H), 8.20 (dd, J=5.8, 2.7 Hz, 1H), 7.98 (ddd, J=9.2, 4.9, 2.7 Hz, 1H), 7.90 (s, 1H), 7.51 (t, J=9.1 Hz, 1H), 3.77 (s, 3H), 3.11-3.02 (m, 2H), 2.89-2.87 (n, 1H), 1.97-1.92 (m, 1H), 1.78-1.73 (m, 1H), 1.60-1.51 (m, 1H), 0.96 (dd, J=6.8, 3.4 Hz, 6H). Ms (ESI) m/z=404 (M+1)

Example 75: Synthesis of Compounds 20b2

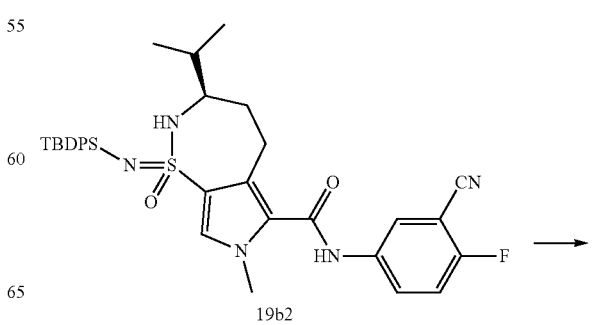

19b2

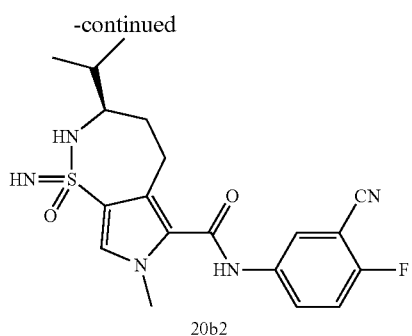

20b2

The reaction was carried out according to the step 3 of example 74, all the conditions were the same except the compound 19b2 was used instead of 19b1, column chromatography (n-heptane:ethyl acetate=1:1) purified to provide target product 20b2 (8 mg). $^1$H NMR (400 MHz, DMSO-d$_6$) 10.67 (s, 1H), 8.19 (dd, J=5.8, 2.7 Hz, 1H), 7.97 (ddd, J=9.2, 4.9, 2.7 Hz, 1H), 7.68 (s, 1H), 7.57 (t, J=9.1 Hz, 1H), 3.76 (s, 3H), 3.04-2.92 (m, 2H), 2.85-2.83 (m, 1H), 1.90-1.83 (m, 1H), 1.74-1.69 (n, 1H), 1.67-1.46 (n, 1H), 0.89 (dd, J=6.8, 3.4 Hz, 6H). Ms (ESI) m/z=404 (M+1)

The following 20 and 40 series compounds are synthesized according to the method of example 72 or 74:

| No. | Structure | Mass Spectrum ESI-MS, (M + H) | Remark |
|---|---|---|---|
| 20c1 | 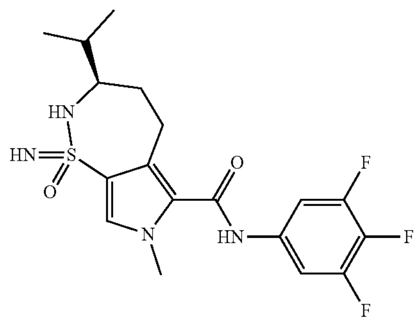 [SMILES: CC(C)[C@H]1CCc2c(cn(C)c2C(=O)Nc2cc(F)c(F)c(F)c2)S(=N)(=O)N1] | 415 | Peak1 (HPLC) |
| 20c2 | 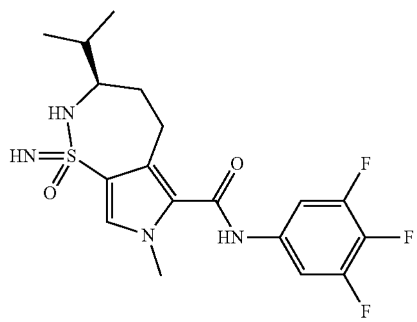 [SMILES: CC(C)[C@H]1CCc2c(cn(C)c2C(=O)Nc2cc(F)c(F)c(F)c2)S(=N)(=O)N1] | 415 | Peak2 (HPLC) |
| 20d1 | 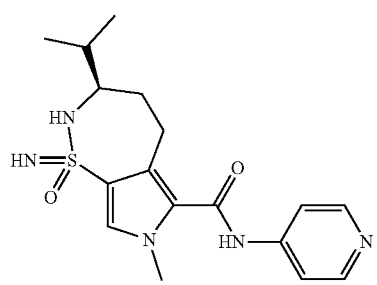 [SMILES: CC(C)[C@H]1CCc2c(cn(C)c2C(=O)Nc2ccncc2)S(=N)(=O)N1] | 362 | Peak1 (HPLC) |
| 20d2 | 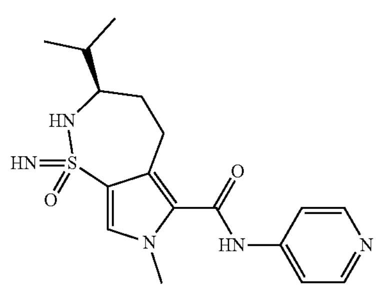 [SMILES: CC(C)[C@H]1CCc2c(cn(C)c2C(=O)Nc2ccncc2)S(=N)(=O)N1] | 362 | Peak2 (HPLC) |

-continued

| No. | Structure | Mass Spectrum ESI-MS, (M + H) | Remark |
|---|---|---|---|
| 20e1 | 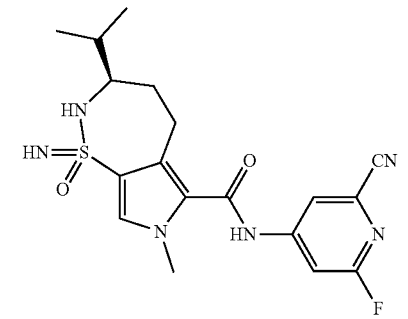 [SMILES: CC(C)[C@H]1CCc2c(cn(C)c2C(=O)Nc2cc(F)nc(C#N)c2)S(=N)(=O)N1] | 405 | Peak1 (HPLC) |
| 20e2 | 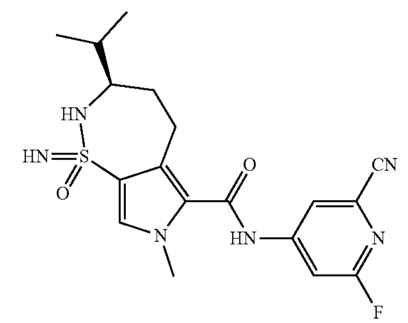 [SMILES: CC(C)[C@H]1CCc2c(cn(C)c2C(=O)Nc2cc(F)nc(C#N)c2)S(=N)(=O)N1] | 405 | Peak2 (HPLC) |
| 20f1 | 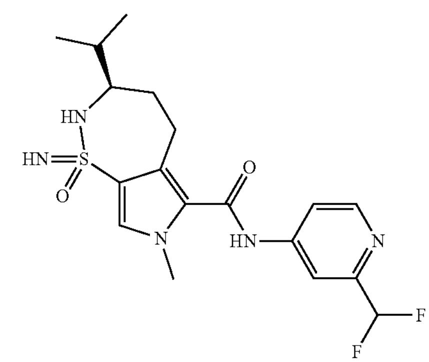 [SMILES: CC(C)[C@H]1CCc2c(cn(C)c2C(=O)Nc2ccnc(C(F)F)c2)S(=N)(=O)N1] | 412 | Peak1 (HPLC) |
| 20f2 | 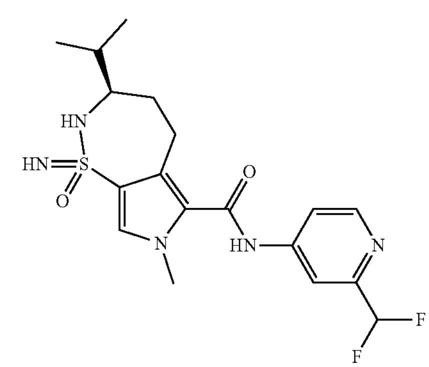 [SMILES: CC(C)[C@H]1CCc2c(cn(C)c2C(=O)Nc2ccnc(C(F)F)c2)S(=N)(=O)N1] | 412 | Peak2 (HPLC) |

-continued
| No. | Structure | Mass Spectrum ESI-MS, (M + H) | Remark |
|---|---|---|---|
| 20g1 | 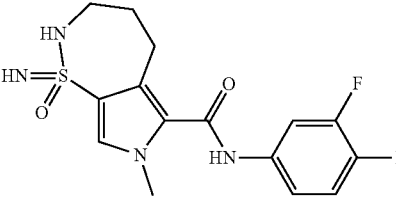 | 397 | Peak1 (HPLC) |
| 20g2 | 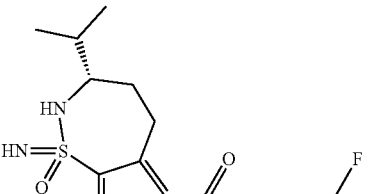 | 397 | Peak2 (HPLC) |
| 20h1 | 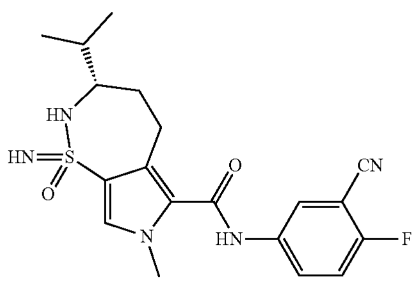 [SMILES: CC(C)[C@@H]1CCc2c(cn(C)c2C(=O)Nc2ccc(F)c(C#N)c2)S(=N)(=O)N1] | 404 | Peak1 (HPLC) |
| 20h2 | 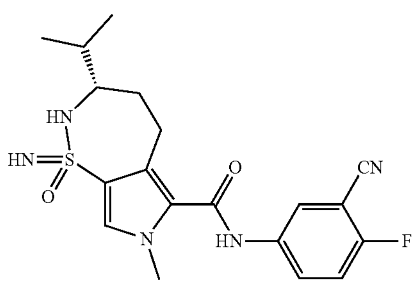 [SMILES: CC(C)[C@@H]1CCc2c(cn(C)c2C(=O)Nc2ccc(F)c(C#N)c2)S(=N)(=O)N1] | 404 | Peak2 (HPLC) |
| 20i1 | 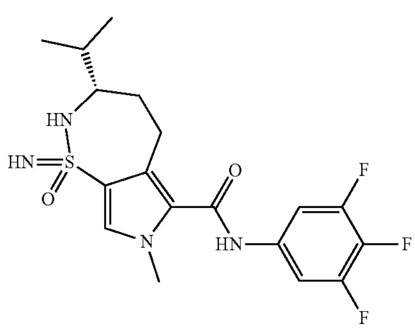 [SMILES: CC(C)[C@@H]1CCc2c(cn(C)c2C(=O)Nc2cc(F)c(F)c(F)c2)S(=N)(=O)N1] | 415 | Peak1 (HPLC) |

-continued
| No. | Structure | Mass Spectrum ESI-MS, (M + H) | Remark |
|---|---|---|---|
| 20i2 | 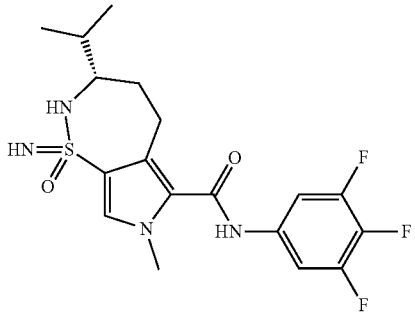 [SMILES: CC(C)[C@@H]1CCc2c(cn(C)c2C(=O)Nc2cc(F)c(F)c(F)c2)S(=N)(=O)N1] | 415 | Peak2 (HPLC) |
| 20j1 | 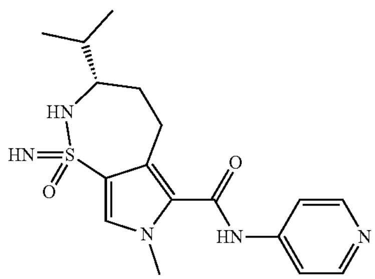 [SMILES: CC(C)[C@@H]1CCc2c(cn(C)c2C(=O)Nc2ccncc2)S(=N)(=O)N1] | 362 | Peak1 (HPLC) |
| 20j2 | 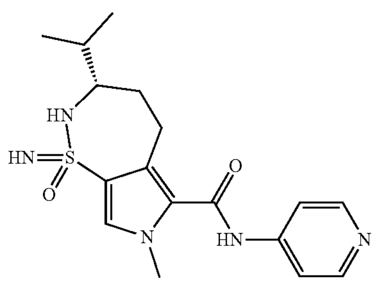 [SMILES: CC(C)[C@@H]1CCc2c(cn(C)c2C(=O)Nc2ccncc2)S(=N)(=O)N1] | 362 | Peak2 (HPLC) |
| 20k1 | 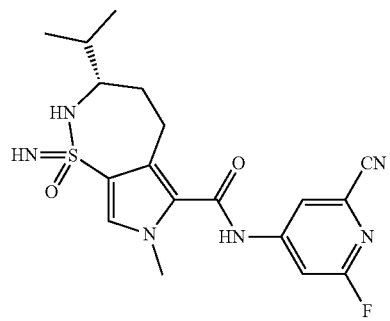 [SMILES: CC(C)[C@@H]1CCc2c(cn(C)c2C(=O)Nc2cc(F)nc(C#N)c2)S(=N)(=O)N1] | 405 | Peak1 (HPLC) |
| 20k2 | 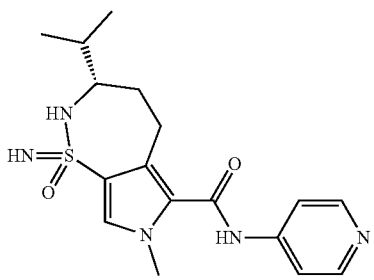 | 405 | Peak2 (HPLC) |

-continued

| No. | Structure | Mass Spectrum ESI-MS, (M + H) | Remark |
|---|---|---|---|
| 20m1 | 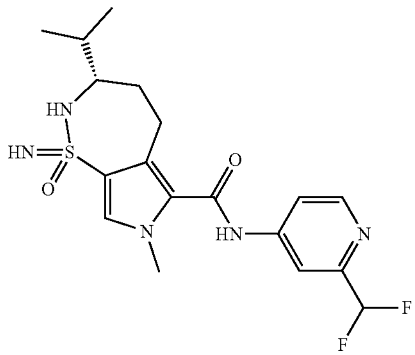 [SMILES: CC(C)[C@@H]1CCc2c(cn(C)c2C(=O)Nc2ccnc(C(F)F)c2)S(=N)(=O)N1] | 412 | Peak1 (HPLC) |
| 10m2 | 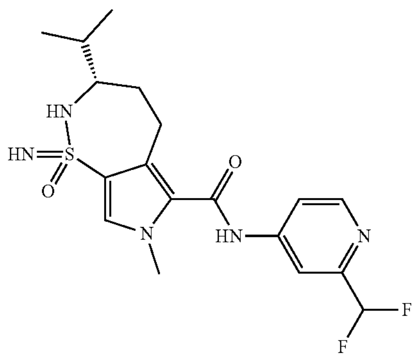 [SMILES: CC(C)[C@@H]1CCc2c(cn(C)c2C(=O)Nc2ccnc(C(F)F)c2)S(=N)(=O)N1] | 412 | Peak2 (HPLC) |
| 20n1 | 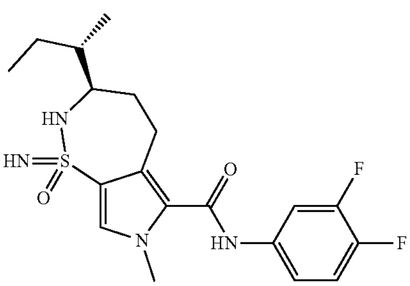 [SMILES: CC[C@H](C)[C@H]1CCc2c(cn(C)c2C(=O)Nc2ccc(F)c(F)c2)S(=N)(=O)N1] | 411 | Peak1 (HPLC) |
| 20n2 | 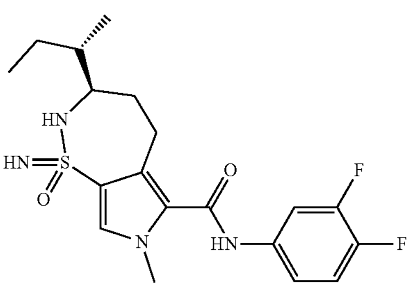 [SMILES: CC[C@H](C)[C@H]1CCc2c(cn(C)c2C(=O)Nc2ccc(F)c(F)c2)S(=N)(=O)N1] | 411 | Peak2 (HPLC) |
| 20o1 | 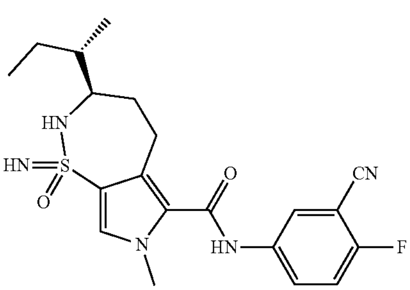 [SMILES: CC[C@H](C)[C@H]1CCc2c(cn(C)c2C(=O)Nc2ccc(F)c(C#N)c2)S(=N)(=O)N1] | 418 | Peak1 (HPLC) |

-continued

| No. | Structure | Mass Spectrum ESI-MS, (M + H) | Remark |
|---|---|---|---|
| 20o2 | 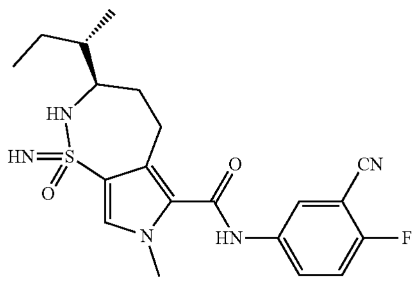 [SMILES: CC[C@H](C)[C@H]1CCc2c(cn(C)c2C(=O)Nc2ccc(F)c(C#N)c2)S(=N)(=O)N1] | 418 | Peak2 (HPLC) |
| 20p1 | 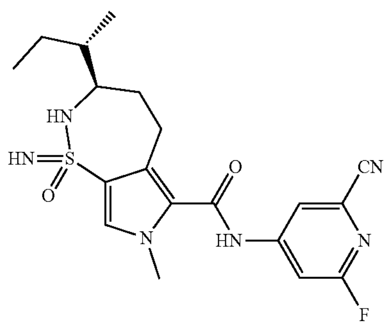 [SMILES: CC[C@H](C)[C@H]1CCc2c(cn(C)c2C(=O)Nc2cc(F)nc(C#N)c2)S(=N)(=O)N1] | 419 | Peak1 (HPLC) |
| 20p2 | 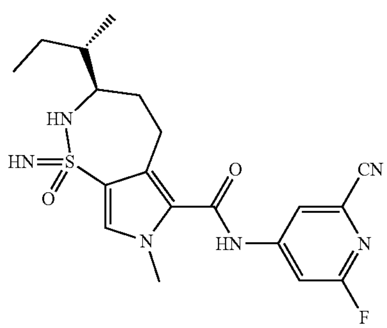 [SMILES: CC[C@H](C)[C@H]1CCc2c(cn(C)c2C(=O)Nc2cc(F)nc(C#N)c2)S(=N)(=O)N1] | 419 | Peak2 (HPLC) |
| 20q1 | 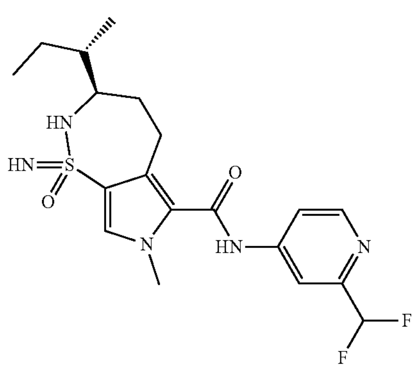 [SMILES: CC[C@H](C)[C@H]1CCc2c(cn(C)c2C(=O)Nc2ccnc(C(F)F)c2)S(=N)(=O)N1] | 426 | Peak1 (HPLC) |

-continued

| No. | Structure | Mass Spectrum ESI-MS, (M + H) | Remark |
|---|---|---|---|
| 20q2 | 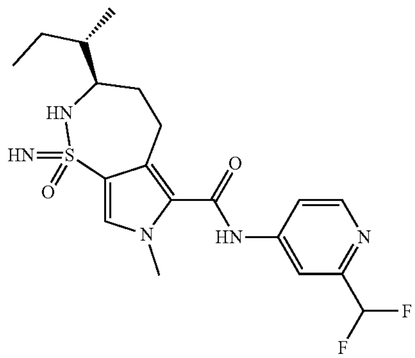 | 426 | Peak2 (HPLC) |
| 20r1 | 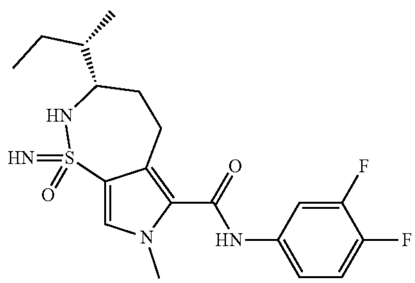 [SMILES: CC[C@H](C)[C@@H]1CCc2c(cn(C)c2C(=O)Nc2ccc(F)c(F)c2)S(=N)(=O)N1] | 411 | Peak1 (HPLC) |
| 20r2 | 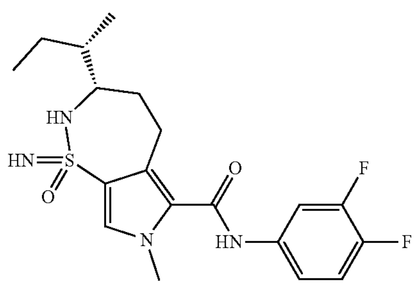 [SMILES: CC[C@H](C)[C@@H]1CCc2c(cn(C)c2C(=O)Nc2ccc(F)c(F)c2)S(=N)(=O)N1] | 411 | Peak2 (HPLC) |
| 20s1 | 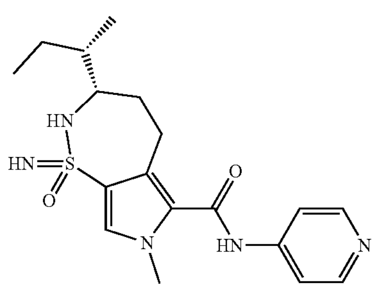 [SMILES: CC[C@H](C)[C@@H]1CCc2c(cn(C)c2C(=O)Nc2ccncc2)S(=N)(=O)N1] | 376 | Peak1 (HPLC) |
| 20s2 | 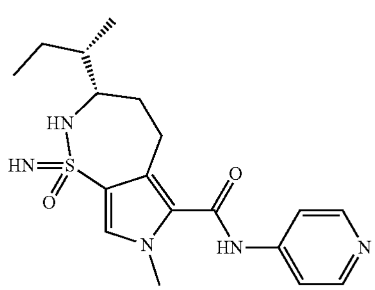 | 376 | Peak2 (HPLC) |

| No. | Structure | Mass Spectrum ESI-MS, (M + H) | Remark |
|---|---|---|---|
| 20t1 | 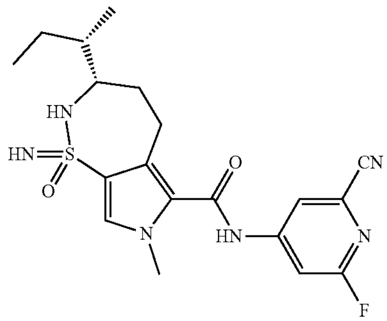 [SMILES: CC[C@H](C)[C@@H]1CCc2c(cn(C)c2C(=O)Nc2cc(F)nc(C#N)c2)S(=N)(=O)N1] | 419 | Peak1 (HPLC) |
| 20t2 | 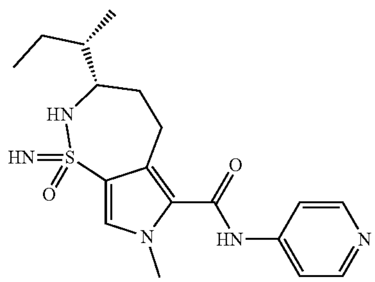 [SMILES: CC[C@H](C)[C@@H]1CCc2c(cn(C)c2C(=O)Nc2ccncc2)S(=N)(=O)N1] | 419 | Peak2 (HPLC) |
| 20u1 | 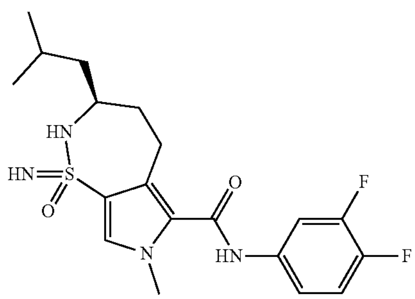 | 411 | Peak1 (HPLC) |
| 20u2 | 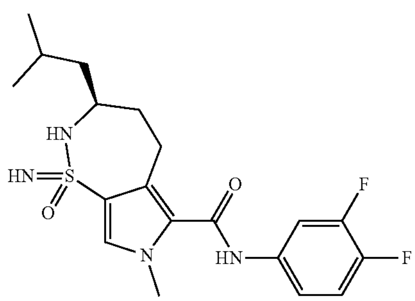 | 411 | Peak2 (HPLC) |
| 20v1 | 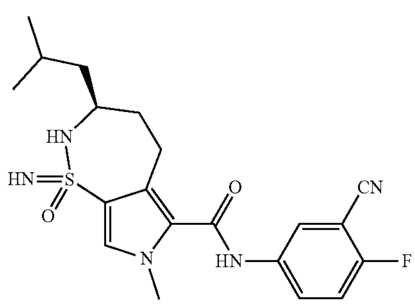 | 418 | Peak1 (HPLC) |

-continued

| No. | Structure | Mass Spectrum ESI-MS, (M + H) | Remark |
|---|---|---|---|
| 20v2 | 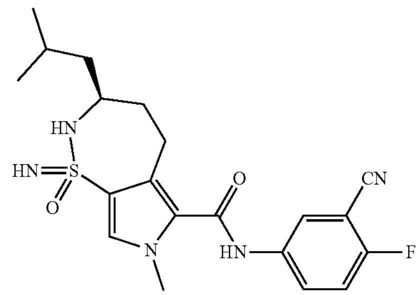 | 418 | Peak2 (HPLC) |
| 20w1 | 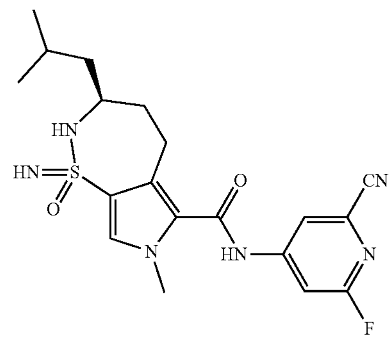 | 419 | Peak1 (HPLC) |
| 20w2 | 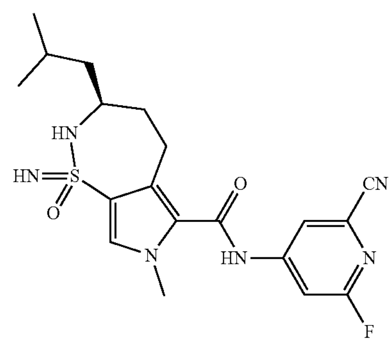 [SMILES: CC(C)C[C@H]1CCc2c(cn(C)c2C(=O)Nc2cc(F)nc(C#N)c2)S(=N)(=O)N1] | 419 | Peak2 (HPLC) |
| 20x1 | 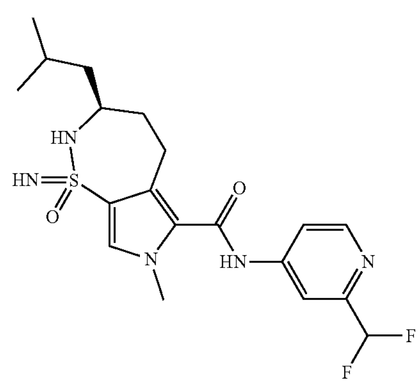 [SMILES: CC(C)C[C@H]1CCc2c(cn(C)c2C(=O)Nc2ccnc(C(F)F)c2)S(=N)(=O)N1] | 426 | Peak1 (HPLC) |

-continued

| No. | Structure | Mass Spectrum ESI-MS, (M + H) | Remark |
|---|---|---|---|
| 20x2 | 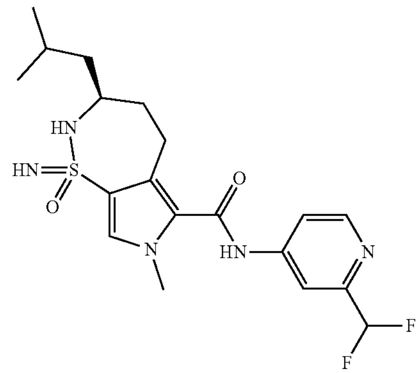 [SMILES: CC(C)C[C@H]1CCc2c(cn(C)c2C(=O)Nc2ccnc(C(F)F)c2)S(=N)(=O)N1] | 426 | Peak2 (HPLC) |
| 20y1 | 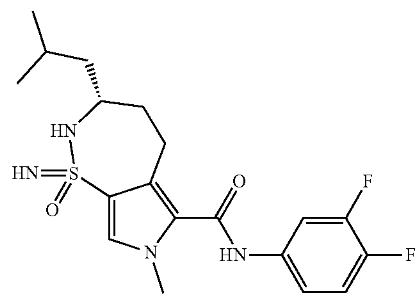 | 411 | Peak1 (HPLC) |
| 20y2 | 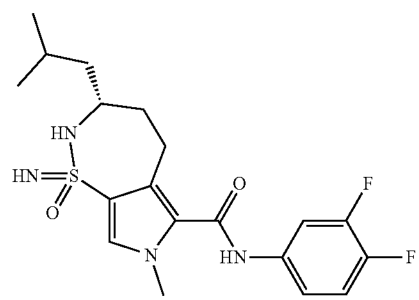 | 411 | Peak2 (HPLC) |
| 20z1 | 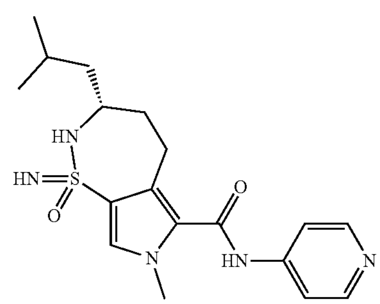 | 376 | Peak1 (HPLC) |
| 20z2 | 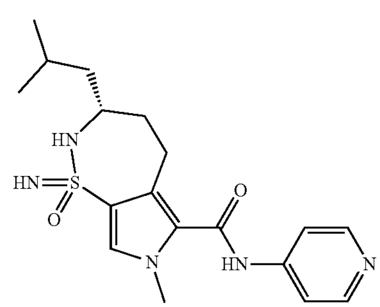 [SMILES: CC(C)C[C@@H]1CCc2c(cn(C)c2C(=O)Nc2ccncc2)S(=N)(=O)N1] | 376 | Peak2 (HPLC) |

| No. | Structure | Mass Spectrum ESI-MS, (M + H) | Remark |
|---|---|---|---|
| 20aa1 | 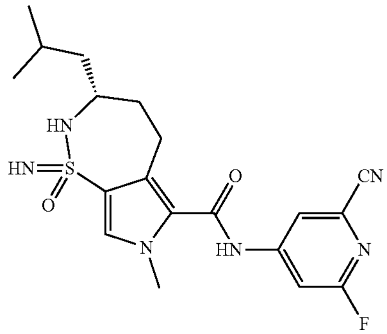 [SMILES: CC(C)C[C@@H]1CCc2c(cn(C)c2C(=O)Nc2cc(F)nc(C#N)c2)S(=N)(=O)N1] | 419 | Peak1 (HPLC) |
| 20aa2 | 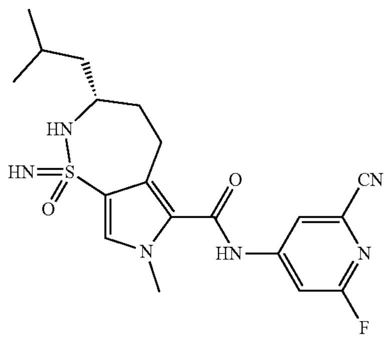 [SMILES: CC(C)C[C@@H]1CCc2c(cn(C)c2C(=O)Nc2cc(F)nc(C#N)c2)S(=N)(=O)N1] | 419 | Peak2 (HPLC) |
| 20bb1 | 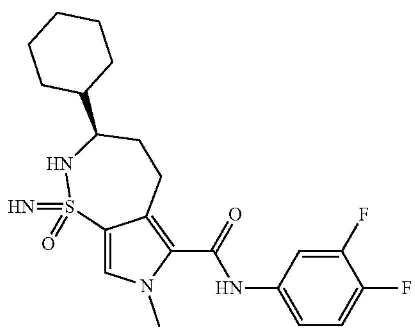 [SMILES: Cn1cc2c(c1C(=O)Nc1ccc(F)c(F)c1)CC[C@H](C1CCCCC1)NS2(=N)=O] | 437 | Peak1 (HPLC) |
| 20bb2 | 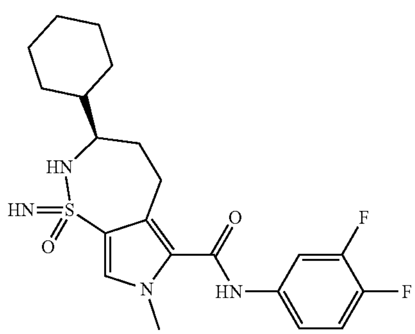 [SMILES: Cn1cc2c(c1C(=O)Nc1ccc(F)c(F)c1)CC[C@H](C1CCCCC1)NS2(=N)=O] | 437 | Peak2 (HPLC) |

-continued

| No. | Structure | Mass Spectrum ESI-MS, (M + H) | Remark |
|---|---|---|---|
| 20cc1 | 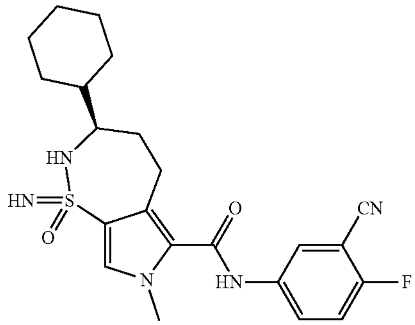 [SMILES: Cn1cc2c(c1C(=O)Nc1ccc(F)c(C#N)c1)CC[C@H](C1CCCCC1)NS2(=N)=O] | 444 | Peak1 (HPLC) |
| 20cc2 | 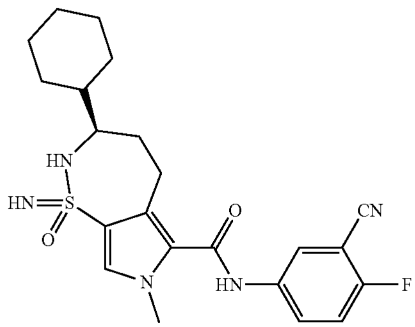 [SMILES: Cn1cc2c(c1C(=O)Nc1ccc(F)c(C#N)c1)CC[C@H](C1CCCCC1)NS2(=N)=O] | 444 | Peak2 (HPLC) |
| 20dd1 | 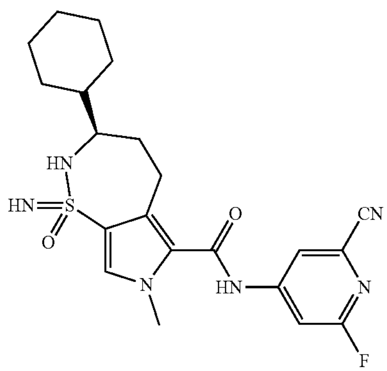 [SMILES: Cn1cc2c(c1C(=O)Nc1cc(F)nc(C#N)c1)CC[C@H](C1CCCCC1)NS2(=N)=O] | 445 | Peak1 (HPLC) |
| 20dd2 | 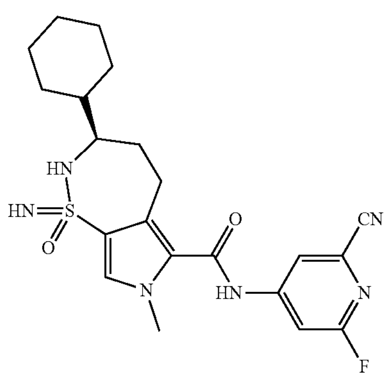 [SMILES: Cn1cc2c(c1C(=O)Nc1cc(F)nc(C#N)c1)CC[C@H](C1CCCCC1)NS2(=N)=O] | 445 | Peak2 (HPLC) |

-continued

| No. | Structure | Mass Spectrum ESI-MS, (M + H) | Remark |
|---|---|---|---|
| 20ee1 | 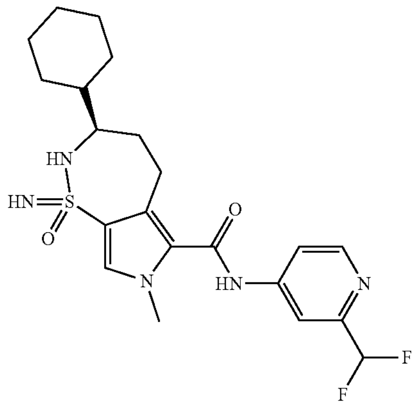 [SMILES: Cn1cc2c(c1C(=O)Nc1ccnc(C(F)F)c1)CC[C@H](C1CCCCC1)NS2(=N)=O] | 452 | Peak1 (HPLC) |
| 20ee2 | 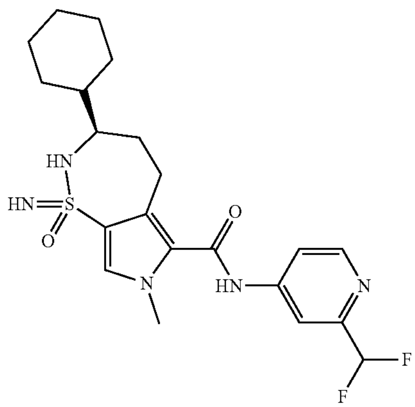 [SMILES: Cn1cc2c(c1C(=O)Nc1ccnc(C(F)F)c1)CC[C@H](C1CCCCC1)NS2(=N)=O] | 452 | Peak2 (HPLC) |
| 20ff1 | 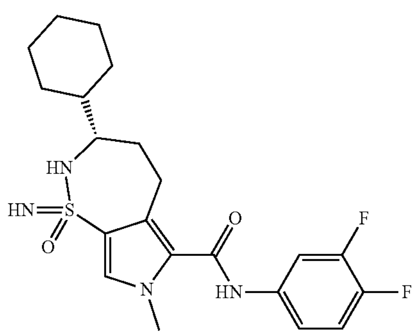 [SMILES: Cn1cc2c(c1C(=O)Nc1ccc(F)c(F)c1)CC[C@@H](C1CCCCC1)NS2(=N)=O] | 437 | Peak1 (HPLC) |
| 20ff2 | 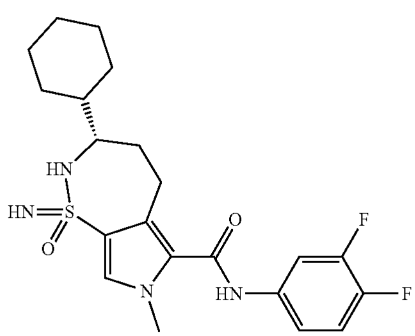 [SMILES: Cn1cc2c(c1C(=O)Nc1ccc(F)c(F)c1)CC[C@@H](C1CCCCC1)NS2(=N)=O] | 437 | Peak2 (HPLC) |

-continued

| No. | Structure | Mass Spectrum ESI-MS, (M + H) | Remark |
|---|---|---|---|
| 20gg1 | 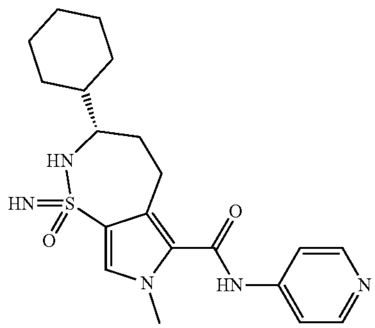 [SMILES: Cn1cc2c(c1C(=O)Nc1ccncc1)CC[C@@H](C1CCCCC1)NS2(=N)=O] | 402 | Peak1 (HPLC) |
| 20gg2 | 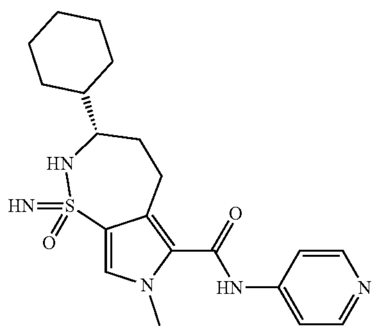 [SMILES: Cn1cc2c(c1C(=O)Nc1ccncc1)CC[C@@H](C1CCCCC1)NS2(=N)=O] | 402 | Peak2 (HPLC) |
| 20hh1 | 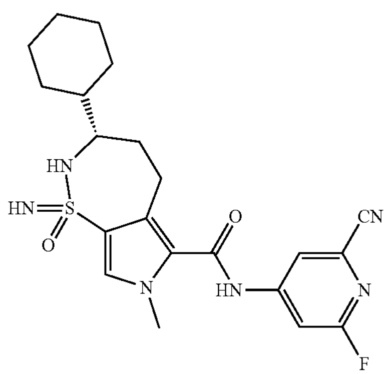 [SMILES: Cn1cc2c(c1C(=O)Nc1cc(F)nc(C#N)c1)CC[C@@H](C1CCCCC1)NS2(=N)=O] | 445 | Peak1 (HPLC) |
| 20hh2 | 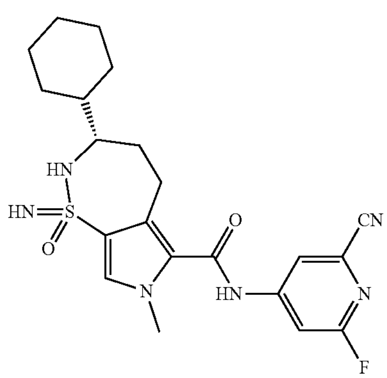 [SMILES: Cn1cc2c(c1C(=O)Nc1cc(F)nc(C#N)c1)CC[C@@H](C1CCCCC1)NS2(=N)=O] | 445 | Peak2 (HPLC) |

-continued

| No. | Structure | Mass Spectrum ESI-MS, (M + H) | Remark |
|---|---|---|---|
| 20ii1 | 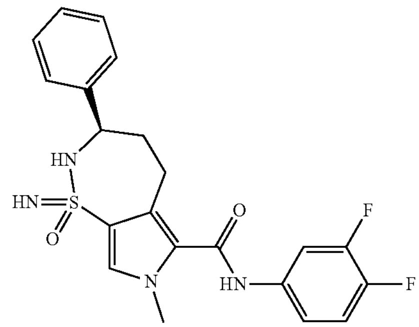 [SMILES: Cn1cc2c(c1C(=O)Nc1ccc(F)c(F)c1)CC[C@H](c1ccccc1)NS2(=N)=O] | 431 | Peak1 (HPLC) |
| 20ii2 | 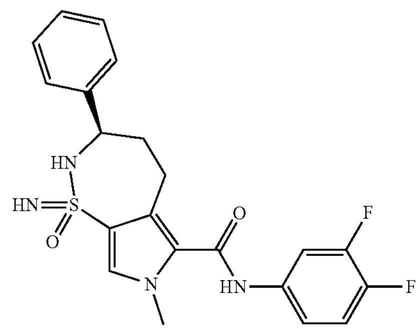 [SMILES: Cn1cc2c(c1C(=O)Nc1ccc(F)c(F)c1)CC[C@H](c1ccccc1)NS2(=N)=O] | 431 | Peak2 (HPLC) |
| 20jj1 | 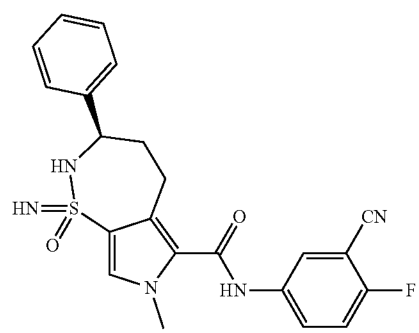 [SMILES: Cn1cc2c(c1C(=O)Nc1ccc(F)c(C#N)c1)CC[C@H](c1ccccc1)NS2(=N)=O] | 438 | Peak1 (HPLC) |
| 20jj2 | 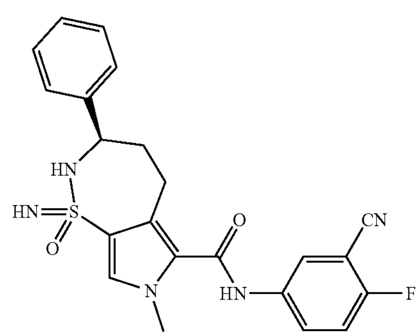 [SMILES: Cn1cc2c(c1C(=O)Nc1ccc(F)c(C#N)c1)CC[C@H](c1ccccc1)NS2(=N)=O] | 438 | Peak2 (HPLC) |

-continued

| No. | Structure | Mass Spectrum ESI-MS, (M + H) | Remark |
|---|---|---|---|
| 20kk1 | 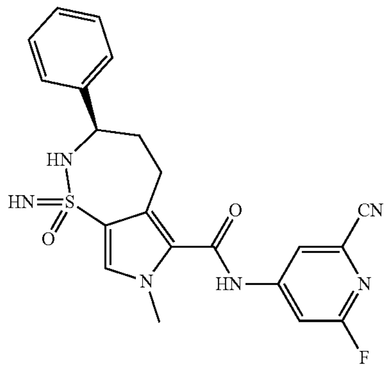 [SMILES: Cn1cc2c(c1C(=O)Nc1cc(F)nc(C#N)c1)CC[C@H](c1ccccc1)NS2(=N)=O] | 439 | Peak1 (HPLC) |
| 20kk2 | 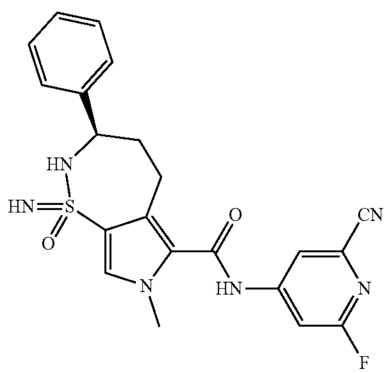 [SMILES: Cn1cc2c(c1C(=O)Nc1cc(F)nc(C#N)c1)CC[C@H](c1ccccc1)NS2(=N)=O] | 439 | Peak2 (HPLC) |
| 20mm1 | 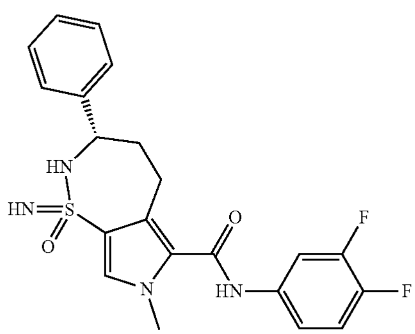 [SMILES: Cn1cc2c(c1C(=O)Nc1ccc(F)c(F)c1)CC[C@@H](c1ccccc1)NS2(=N)=O] | 431 | Peak1 (HPLC) |
| 20mm2 | 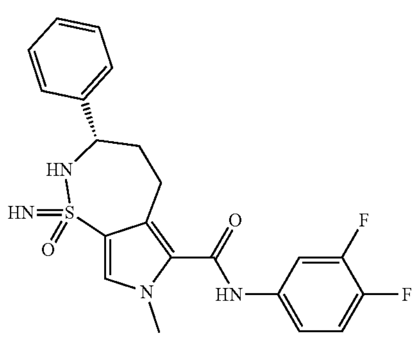 [SMILES: Cn1cc2c(c1C(=O)Nc1ccc(F)c(F)c1)CC[C@@H](c1ccccc1)NS2(=N)=O] | 431 | Peak2 (HPLC) |

-continued

| No. | Structure | Mass Spectrum ESI-MS, (M + H) | Remark |
|---|---|---|---|
| 20nn1 | 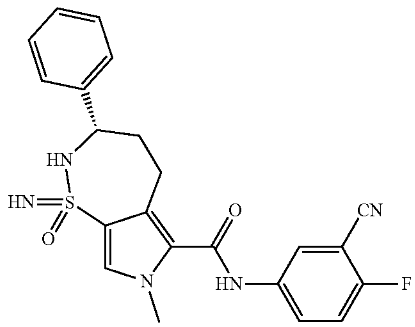 [SMILES: Cn1cc2c(c1C(=O)Nc1ccc(F)c(C#N)c1)CC[C@@H](c1ccccc1)NS2(=N)=O] | 438 | Peak1 (HPLC) |
| 20nn2 | 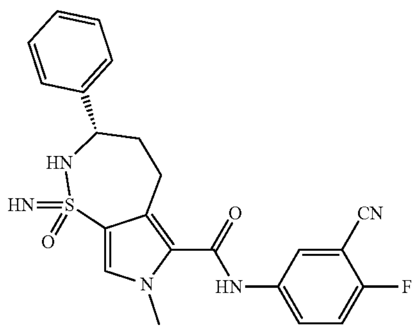 [SMILES: Cn1cc2c(c1C(=O)Nc1ccc(F)c(C#N)c1)CC[C@@H](c1ccccc1)NS2(=N)=O] | 438 | Peak2 (HPLC) |
| 20oo1 | 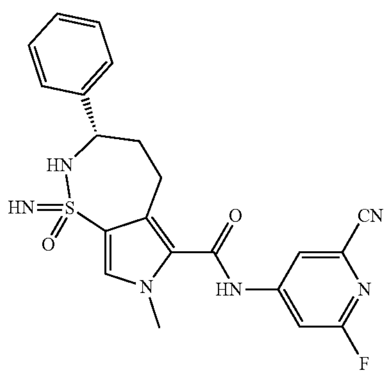 [SMILES: Cn1cc2c(c1C(=O)Nc1cc(F)nc(C#N)c1)CC[C@@H](c1ccccc1)NS2(=N)=O] | 439 | Peak1 (HPLC) |
| 20oo2 | 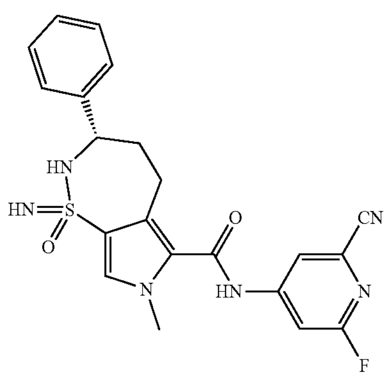 [SMILES: Cn1cc2c(c1C(=O)Nc1cc(F)nc(C#N)c1)CC[C@@H](c1ccccc1)NS2(=N)=O] | 439 | Peak2 (HPLC) |

-continued
| No. | Structure | Mass Spectrum ESI-MS, (M + H) | Remark |
|---|---|---|---|
| 20pp1 | 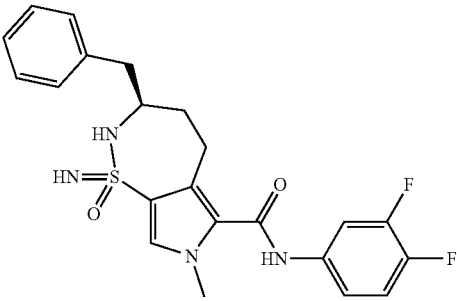 [SMILES: Cn1cc2c(c1C(=O)Nc1ccc(F)c(F)c1)CC[C@H](Cc1ccccc1)NS2(=N)=O] | 445 | Peak1 (HPLC) |
| 20pp2 | 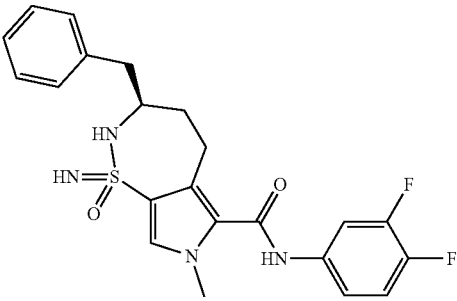 [SMILES: Cn1cc2c(c1C(=O)Nc1ccc(F)c(F)c1)CC[C@H](Cc1ccccc1)NS2(=N)=O] | 445 | Peak2 (HPLC) |
| 20qq1 | 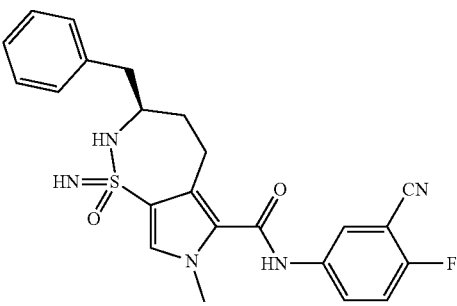 [SMILES: Cn1cc2c(c1C(=O)Nc1ccc(F)c(C#N)c1)CC[C@H](Cc1ccccc1)NS2(=N)=O] | 452 | Peak1 (HPLC) |
| 20qq2 | 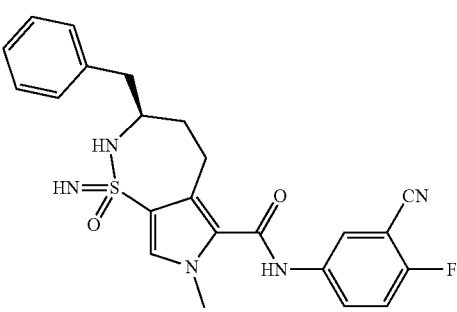 [SMILES: Cn1cc2c(c1C(=O)Nc1ccc(F)c(C#N)c1)CC[C@H](Cc1ccccc1)NS2(=N)=O] | 452 | Peak2 (HPLC) |
| 20rr1 | 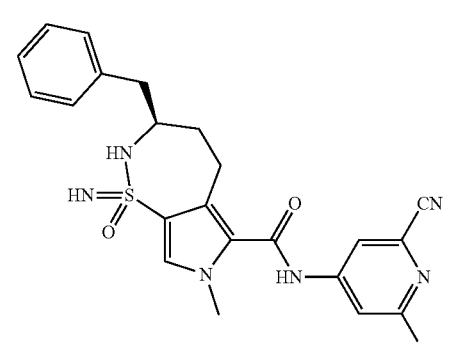 | 453 | Peak1 (HPLC) |

| No. | Structure | Mass Spectrum ESI-MS, (M + H) | Remark |
|---|---|---|---|
| 20rr2 | 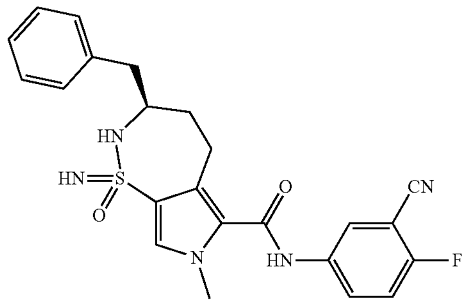 [SMILES: Cn1cc2c(c1C(=O)Nc1ccc(F)c(C#N)c1)CC[C@H](Cc1ccccc1)NS2(=N)=O] | 453 | Peak2 (HPLC) |
| 20ss1 | 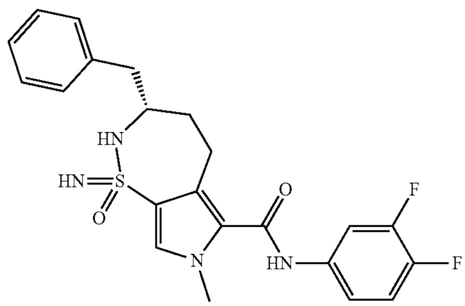 [SMILES: Cn1cc2c(c1C(=O)Nc1ccc(F)c(F)c1)CC[C@@H](Cc1ccccc1)NS2(=N)=O] | 445 | Peak1 (HPLC) |
| 20ss2 | 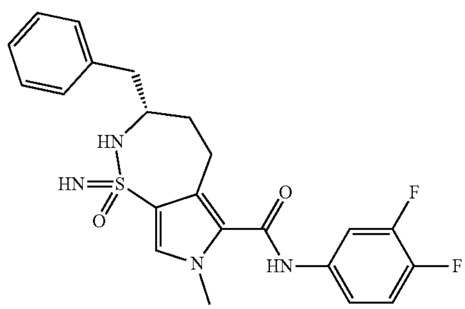 [SMILES: Cn1cc2c(c1C(=O)Nc1ccc(F)c(F)c1)CC[C@@H](Cc1ccccc1)NS2(=N)=O] | 445 | Peak2 (HPLC) |
| 20tt1 | 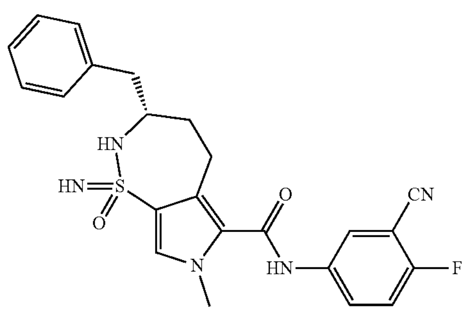 [SMILES: Cn1cc2c(c1C(=O)Nc1ccc(F)c(C#N)c1)CC[C@@H](Cc1ccccc1)NS2(=N)=O] | 452 | Peak1 (HPLC) |
| 20tt2 | 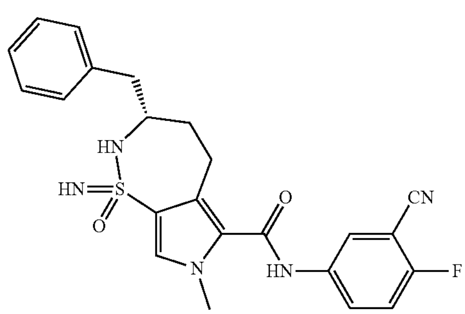 [SMILES: Cn1cc2c(c1C(=O)Nc1ccc(F)c(C#N)c1)CC[C@@H](Cc1ccccc1)NS2(=N)=O] | 452 | Peak2 (HPLC) |

-continued
| No. | Structure | Mass Spectrum ESI-MS, (M + H) | Remark |
|---|---|---|---|
| 20uu1 | 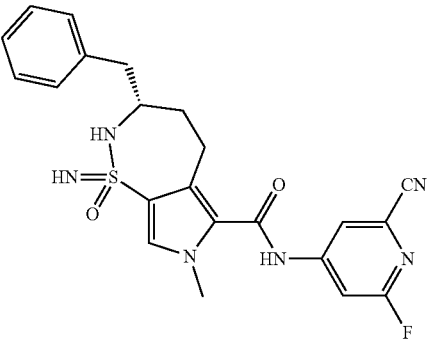 [SMILES: Cn1cc2c(c1C(=O)Nc1cc(F)nc(C#N)c1)CC[C@@H](Cc1ccccc1)NS2(=N)=O] | 453 | Peak1 (HPLC) |
| 20uu2 | 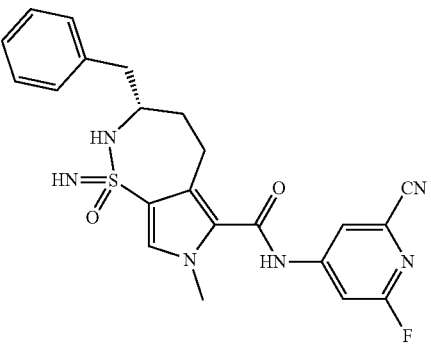 [SMILES: Cn1cc2c(c1C(=O)Nc1cc(F)nc(C#N)c1)CC[C@@H](Cc1ccccc1)NS2(=N)=O] | 453 | Peak2 (HPLC) |
| 20vv1 | 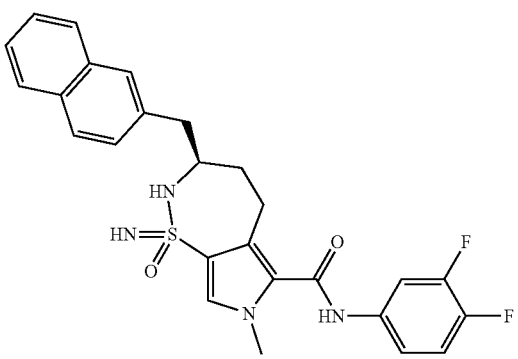 | 495 | Peak1 (HPLC) |
| 20vv2 | 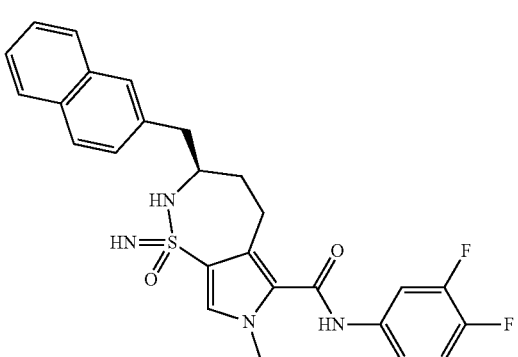 | 495 | Peak2 (HPLC) |

-continued

| No. | Structure | Mass Spectrum ESI-MS, (M + H) | Remark |
|---|---|---|---|
| 20ww1 | 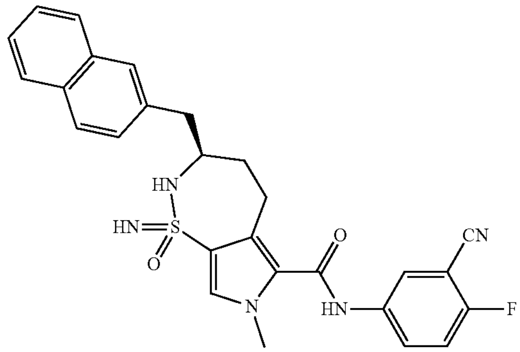 [SMILES: Cn1cc2c(c1C(=O)Nc1ccc(F)c(C#N)c1)CC[C@H](Cc1ccc3ccccc3c1)NS2(=N)=O] | 502 | Peak1 (HPLC) |
| 20ww2 | 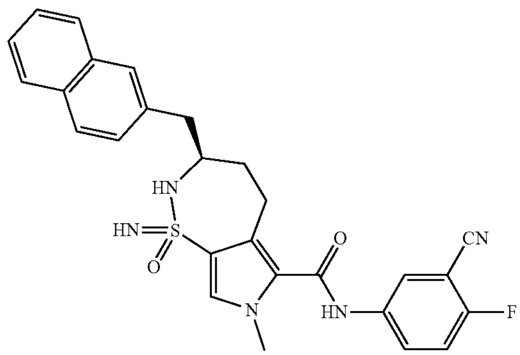 [SMILES: Cn1cc2c(c1C(=O)Nc1ccc(F)c(C#N)c1)CC[C@H](Cc1ccc3ccccc3c1)NS2(=N)=O] | 502 | Peak2 (HPLC) |
| 20xx1 | 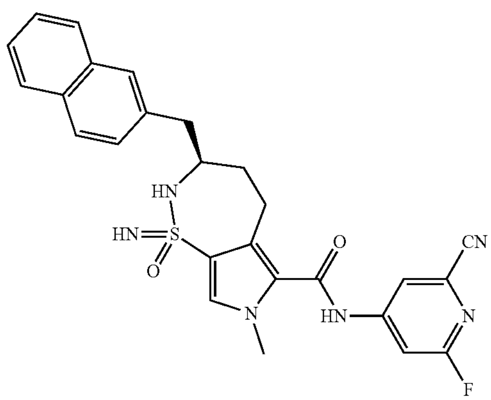 [SMILES: Cn1cc2c(c1C(=O)Nc1cc(F)nc(C#N)c1)CC[C@H](Cc1ccc3ccccc3c1)NS2(=N)=O] | 503 | Peak1 (HPLC) |
| 20xx2 | 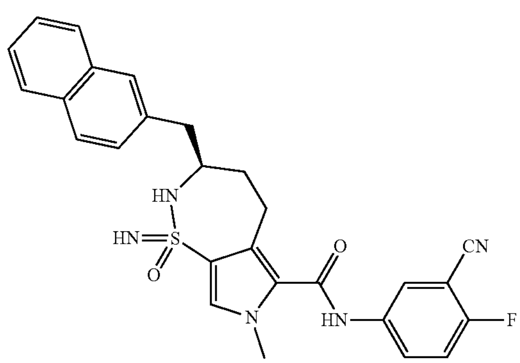 [SMILES: Cn1cc2c(c1C(=O)Nc1ccc(F)c(C#N)c1)CC[C@H](Cc1ccc3ccccc3c1)NS2(=N)=O] | 503 | Peak2 (HPLC) |

| No. | Structure | Mass Spectrum ESI-MS, (M + H) | Remark |
|---|---|---|---|
| 20yy1 | 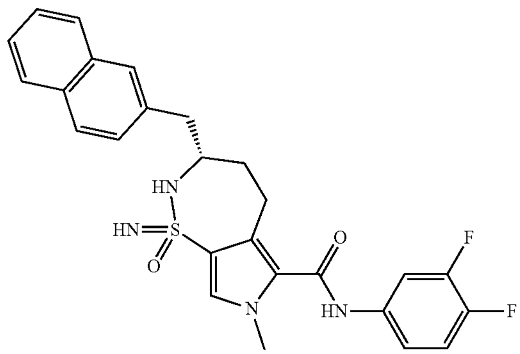 [SMILES: Cn1cc2c(c1C(=O)Nc1ccc(F)c(F)c1)CC[C@@H](Cc1ccc3ccccc3c1)NS2(=N)=O] | 495 | Peak1 (HPLC) |
| 20yy2 | 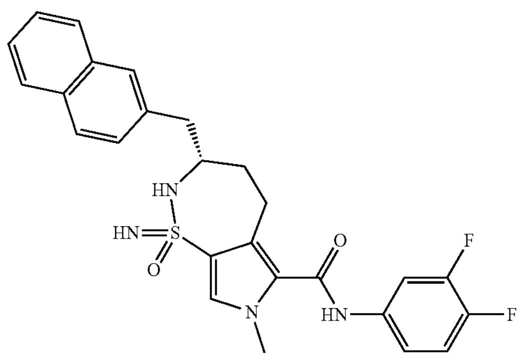 [SMILES: Cn1cc2c(c1C(=O)Nc1ccc(F)c(F)c1)CC[C@@H](Cc1ccc3ccccc3c1)NS2(=N)=O] | 495 | Peak2 (HPLC) |
| 20zz1 | 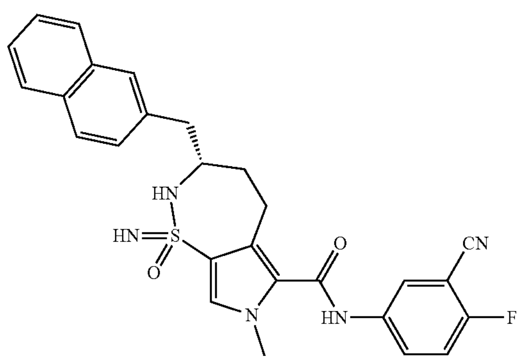 [SMILES: Cn1cc2c(c1C(=O)Nc1ccc(F)c(C#N)c1)CC[C@@H](Cc1ccc3ccccc3c1)NS2(=N)=O] | 502 | Peak1 (HPLC) |
| 20zz2 | 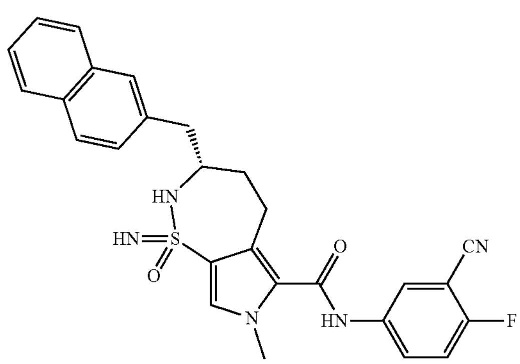 [SMILES: Cn1cc2c(c1C(=O)Nc1ccc(F)c(C#N)c1)CC[C@@H](Cc1ccc3ccccc3c1)NS2(=N)=O] | 502 | Peak2 (HPLC) |

-continued

| No. | Structure | Mass Spectrum ESI-MS, (M + H) | Remark |
|---|---|---|---|
| 20aaa1 | 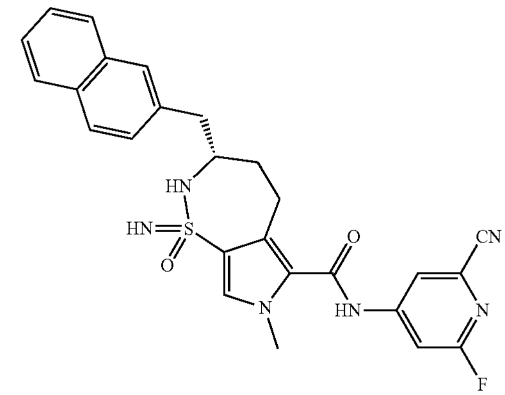 [SMILES: Cn1cc2c(c1C(=O)Nc1cc(F)nc(C#N)c1)CC[C@@H](Cc1ccc3ccccc3c1)NS2(=N)=O] | 503 | Peak1 (HPLC) |
| 20aaa2 | 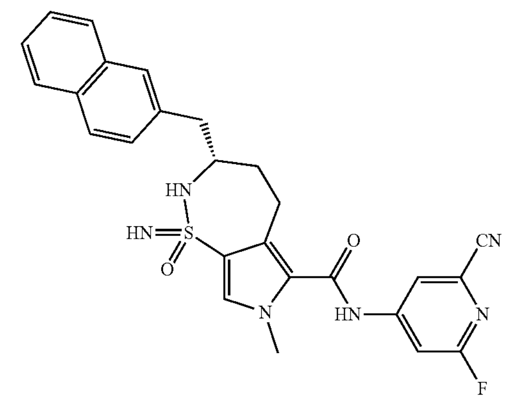 [SMILES: Cn1cc2c(c1C(=O)Nc1cc(F)nc(C#N)c1)CC[C@@H](Cc1ccc3ccccc3c1)NS2(=N)=O] | 503 | Peak2 (HPLC) |
| 20bbb1 | 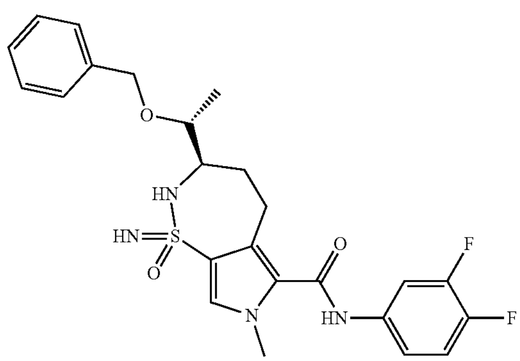 [SMILES: C[C@@H](OCc1ccccc1)[C@H]1CCc2c(cn(C)c2C(=O)Nc2ccc(F)c(F)c2)S(=N)(=O)N1] | 489 | Peak1 (HPLC) |
| 20bbb2 | 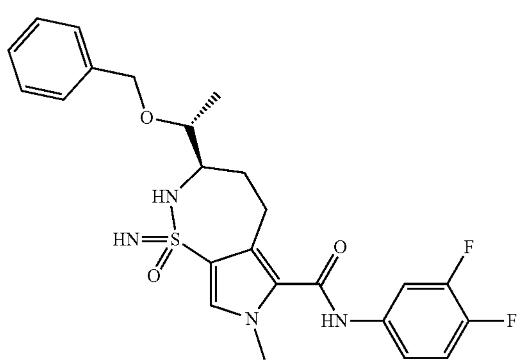 | 489 | Peak2 (HPLC) |

-continued
| No. | Structure | Mass Spectrum ESI-MS, (M + H) | Remark |
|---|---|---|---|
| 20ccc1 | 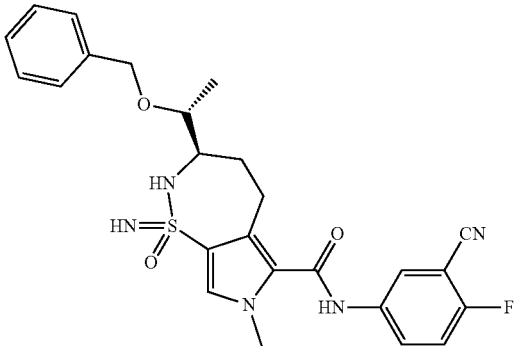 | 496 | Peak1 (HPLC) |
| 20ccc2 | 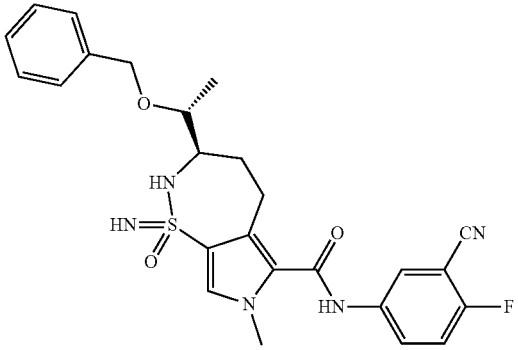 | 496 | Peak2 (HPLC) |
| 20ddd1 | 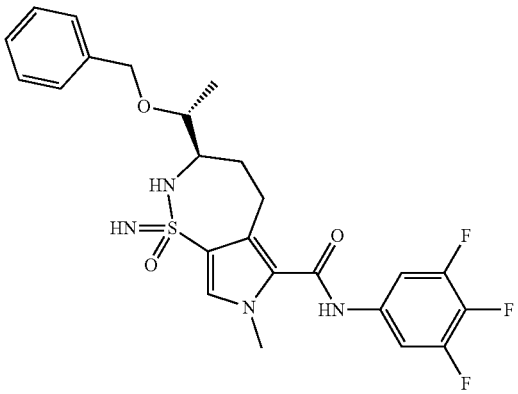 | 507 | Peak1 (HPLC) |
| 20ddd2 | 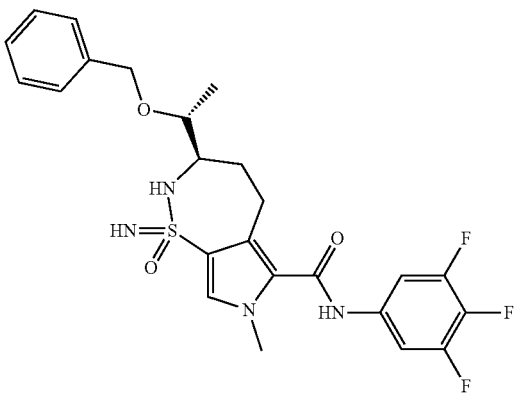 [SMILES: C[C@@H](OCc1ccccc1)[C@H]1CCc2c(cn(C)c2C(=O)Nc2cc(F)c(F)c(F)c2)S(=N)(=O)N1] | 507 | Peak2 (HPLC) |

-continued
| No. | Structure | Mass Spectrum ESI-MS, (M + H) | Remark |
|---|---|---|---|
| 20eee1 | 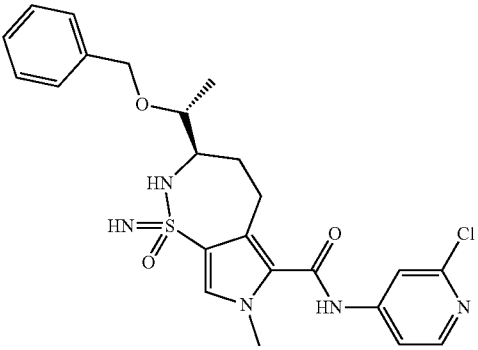 | 488 | Peak1 (HPLC) |
| 20eee2 | 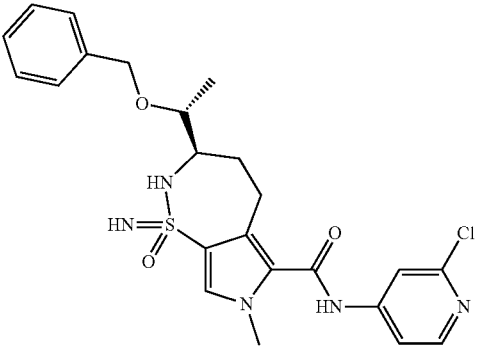 | 488 | Peak2 (HPLC) |
| 20fff1 | 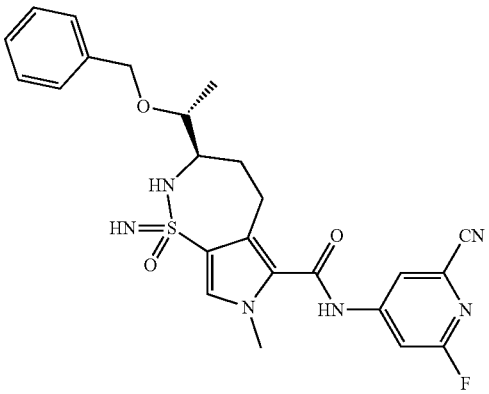 | 497 | Peak1 (HPLC) |
| 20fff2 | 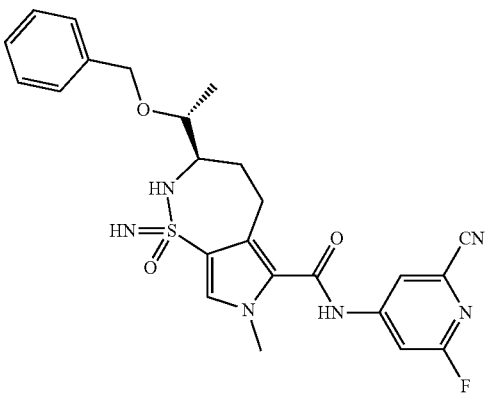 | 497 | Peak2 (HPLC) |

-continued

| No. | Structure | Mass Spectrum ESI-MS, (M + H) | Remark |
|---|---|---|---|
| 20ggg1 | 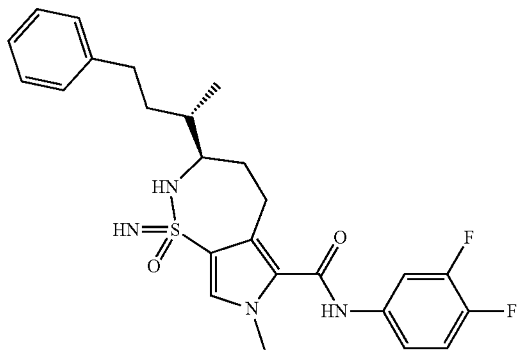 | 486 | Peak1 (HPLC) |
| 20ggg2 | 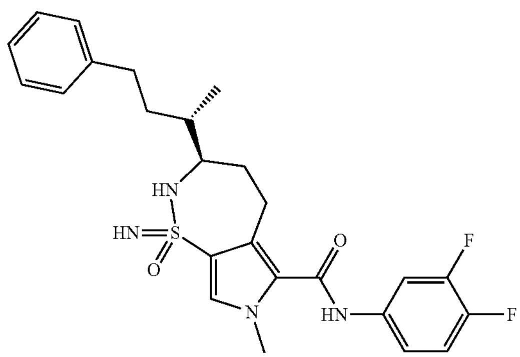 [SMILES: C[C@@H](CCc1ccccc1)[C@H]1CCc2c(cn(C)c2C(=O)Nc2ccc(F)c(F)c2)S(=N)(=O)N1] | 486 | Peak2 (HPLC) |
| 20hhh1 | 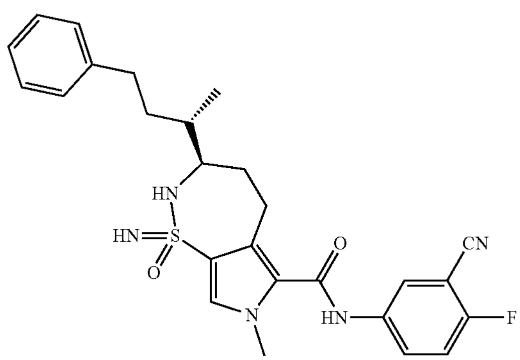 [SMILES: C[C@@H](CCc1ccccc1)[C@H]1CCc2c(cn(C)c2C(=O)Nc2ccc(F)c(C#N)c2)S(=N)(=O)N1] | 494 | Peak1 (HPLC) |
| 20hhh2 | 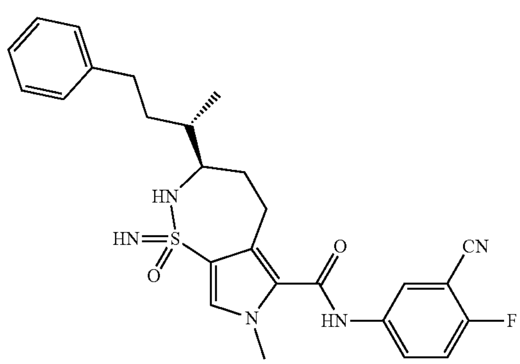 | 494 | Peak2 (HPLC) |

-continued

| No. | Structure | Mass Spectrum ESI-MS, (M + H) | Remark |
|---|---|---|---|
| 20iii1 | 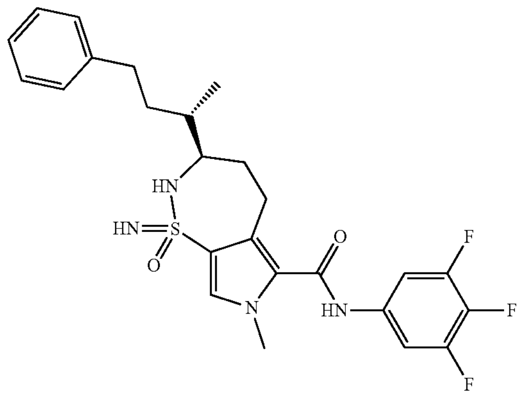 [SMILES: C[C@@H](CCc1ccccc1)[C@H]1CCc2c(cn(C)c2C(=O)Nc2cc(F)c(F)c(F)c2)S(=N)(=O)N1] | 505 | Peak1 (HPLC) |
| 20iii2 | 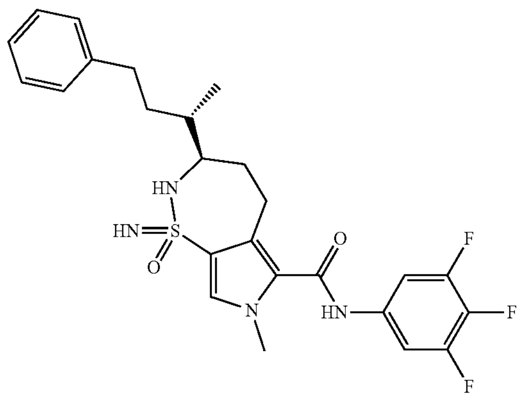 [SMILES: C[C@@H](CCc1ccccc1)[C@H]1CCc2c(cn(C)c2C(=O)Nc2cc(F)c(F)c(F)c2)S(=N)(=O)N1] | 505 | Peak2 (HPLC) |
| 20jjj1 | 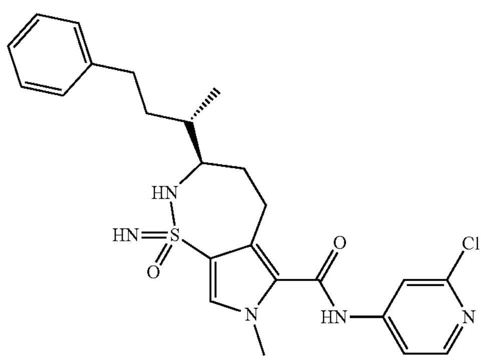 [SMILES: C[C@@H](CCc1ccccc1)[C@H]1CCc2c(cn(C)c2C(=O)Nc2ccnc(Cl)c2)S(=N)(=O)N1] | 486 | Peak1 (HPLC) |
| 20jjj2 | 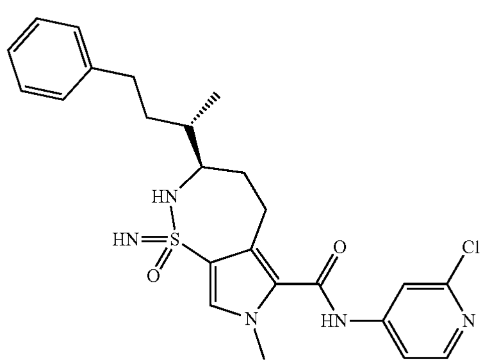 [SMILES: C[C@@H](CCc1ccccc1)[C@H]1CCc2c(cn(C)c2C(=O)Nc2ccnc(Cl)c2)S(=N)(=O)N1] | 486 | Peak2 (HPLC) |

-continued
| No. | Structure | Mass Spectrum ESI-MS, (M + H) | Remark |
|---|---|---|---|
| 20kkk1 | 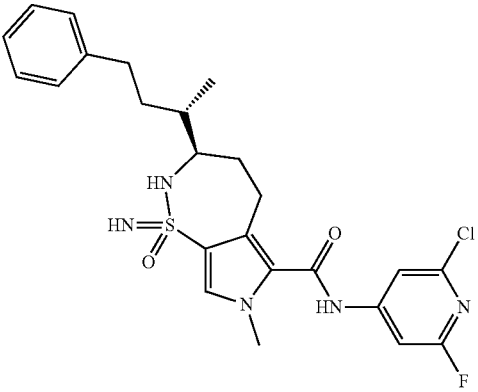 [SMILES: C[C@@H](CCc1ccccc1)[C@H]1CCc2c(cn(C)c2C(=O)Nc2cc(F)nc(Cl)c2)S(=N)(=O)N1] | 495 | Peak1 (HPLC) |
| 20kkk2 | 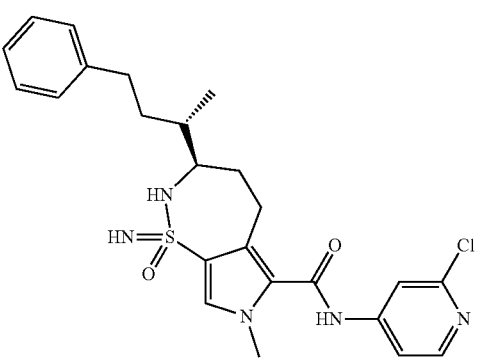 [SMILES: C[C@@H](CCc1ccccc1)[C@H]1CCc2c(cn(C)c2C(=O)Nc2ccnc(Cl)c2)S(=N)(=O)N1] | 495 | Peak2 (HPLC) |
| 20mmm1 | 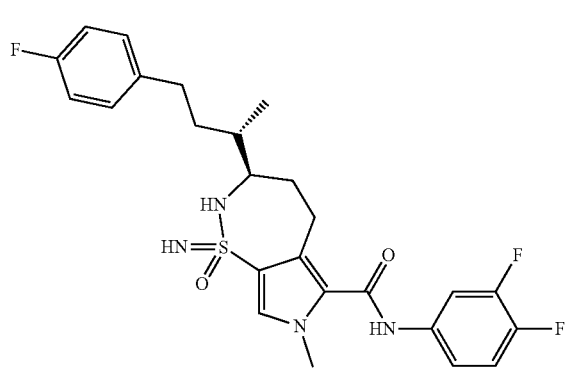 | 505 | Peak1 (HPLC) |
| 20mmm2 | 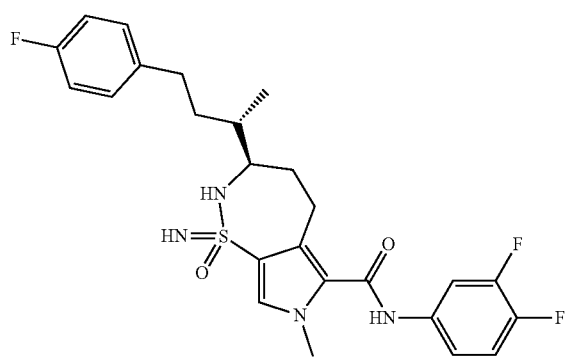 | 505 | Peak2 (HPLC) |

-continued

| No. | Structure | Mass Spectrum ESI-MS, (M + H) | Remark |
|---|---|---|---|
| 20nnn1 | 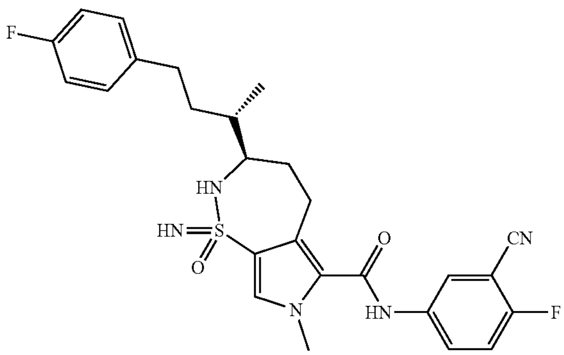 [SMILES: C[C@@H](CCc1ccc(F)cc1)[C@H]1CCc2c(cn(C)c2C(=O)Nc2ccc(F)c(C#N)c2)S(=N)(=O)N1] | 512 | Peak1 (HPLC) |
| 20nnn2 | 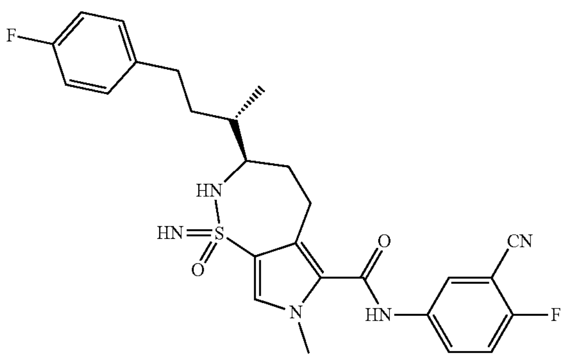 [SMILES: C[C@@H](CCc1ccc(F)cc1)[C@H]1CCc2c(cn(C)c2C(=O)Nc2ccc(F)c(C#N)c2)S(=N)(=O)N1] | 512 | Peak2 (HPLC) |
| 20ooo1 | 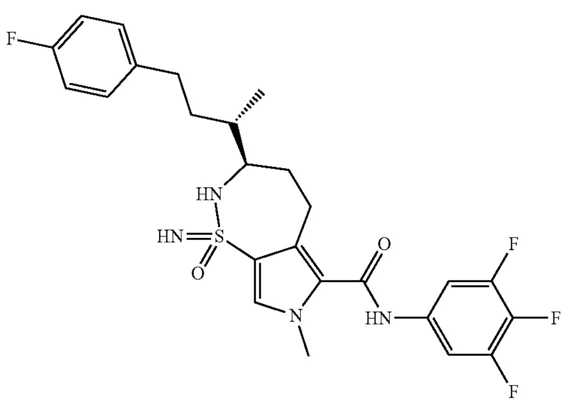 [SMILES: C[C@@H](CCc1ccc(F)cc1)[C@H]1CCc2c(cn(C)c2C(=O)Nc2cc(F)c(F)c(F)c2)S(=N)(=O)N1] | 523 | Peak1 (HPLC) |
| 20ooo2 | 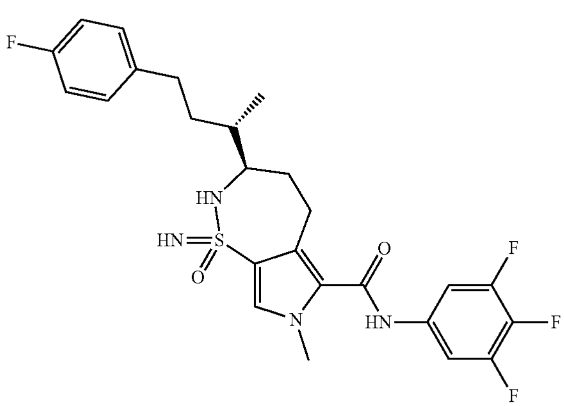 [SMILES: C[C@@H](CCc1ccc(F)cc1)[C@H]1CCc2c(cn(C)c2C(=O)Nc2cc(F)c(F)c(F)c2)S(=N)(=O)N1] | 523 | Peak2 (HPLC) |

-continued
| No. | Structure | Mass Spectrum ESI-MS, (M + H) | Remark |
|---|---|---|---|
| 20ppp1 | 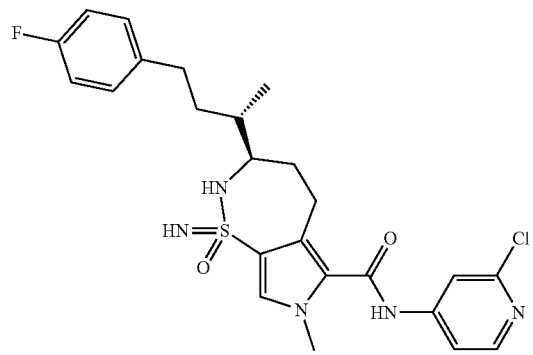 [SMILES: C[C@@H](CCc1ccc(F)cc1)[C@H]1CCc2c(cn(C)c2C(=O)Nc2ccnc(Cl)c2)S(=N)(=O)N1] | 504 | Peak1 (HPLC) |
| 20ppp2 | 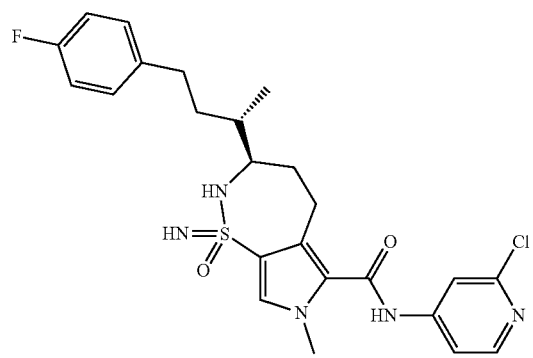 [SMILES: C[C@@H](CCc1ccc(F)cc1)[C@H]1CCc2c(cn(C)c2C(=O)Nc2ccnc(Cl)c2)S(=N)(=O)N1] | 504 | Peak2 (HPLC) |
| 20qqq1 | 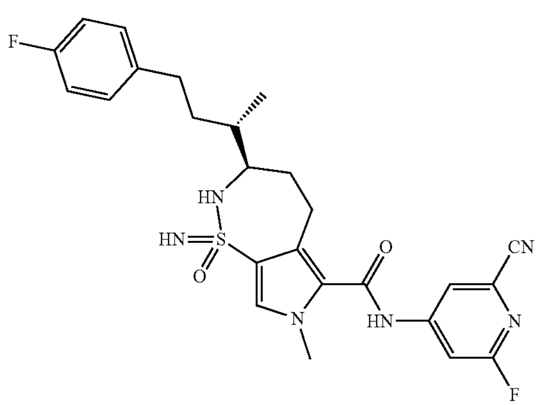 [SMILES: C[C@@H](CCc1ccc(F)cc1)[C@H]1CCc2c(cn(C)c2C(=O)Nc2cc(F)nc(C#N)c2)S(=N)(=O)N1] | 513 | Peak1 (HPLC) |
| 20qqq2 | 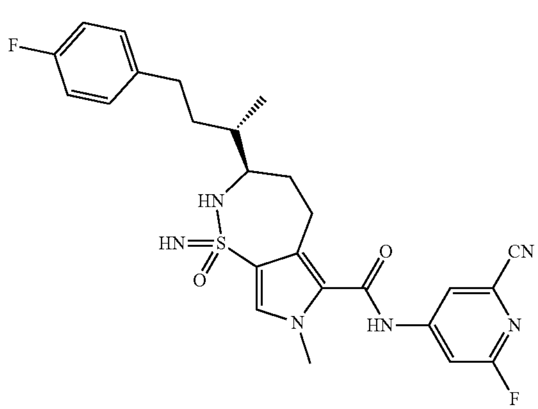 [SMILES: C[C@@H](CCc1ccc(F)cc1)[C@H]1CCc2c(cn(C)c2C(=O)Nc2cc(F)nc(C#N)c2)S(=N)(=O)N1] | 513 | Peak2 (HPLC) |

-continued
| No. | Structure | Mass Spectrum ESI-MS, (M + H) | Remark |
|---|---|---|---|
| 20rrr1 | 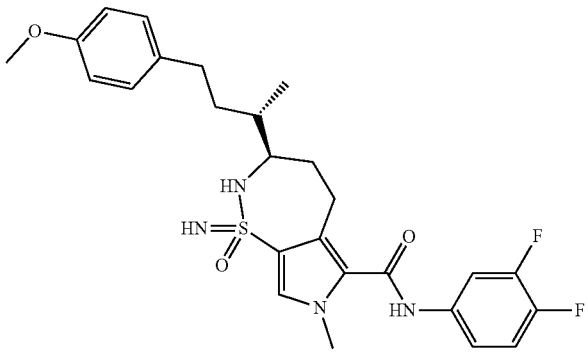 [SMILES: COc1ccc(CC[C@H](C)[C@H]2CCc3c(cn(C)c3C(=O)Nc3ccc(F)c(F)c3)S(=N)(=O)N2)cc1] | 517 | Peak1 (HPLC) |
| 20rrr2 | 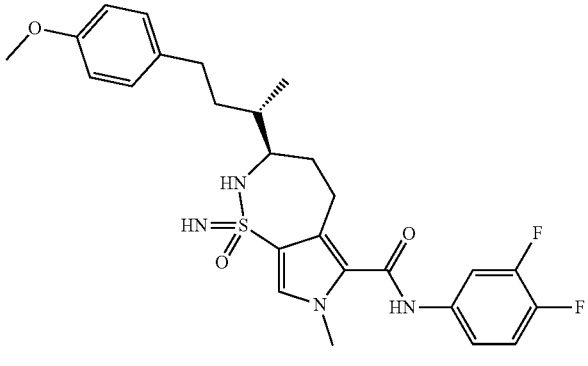 [SMILES: COc1ccc(CC[C@H](C)[C@H]2CCc3c(cn(C)c3C(=O)Nc3ccc(F)c(F)c3)S(=N)(=O)N2)cc1] | 517 | Peak2 (HPLC) |
| 20sss1 | 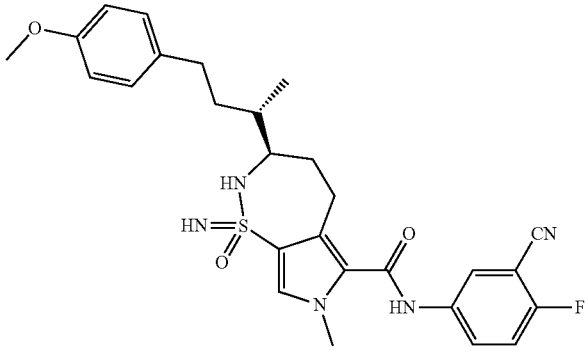 [SMILES: COc1ccc(CC[C@H](C)[C@H]2CCc3c(cn(C)c3C(=O)Nc3ccc(F)c(C#N)c3)S(=N)(=O)N2)cc1] | 524 | Peak1 (HPLC) |
| 20sss2 | 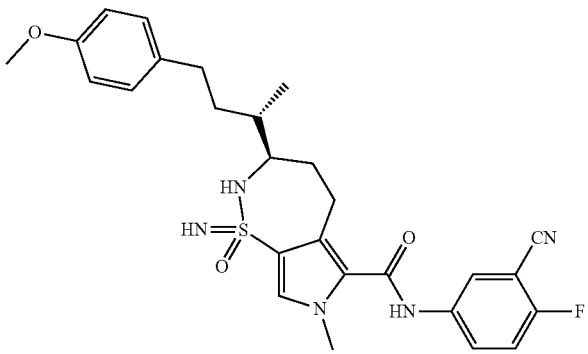 | 524 | Peak2 (HPLC) |

-continued

| No. | Structure | Mass Spectrum ESI-MS, (M + H) | Remark |
|---|---|---|---|
| 20ttt1 | 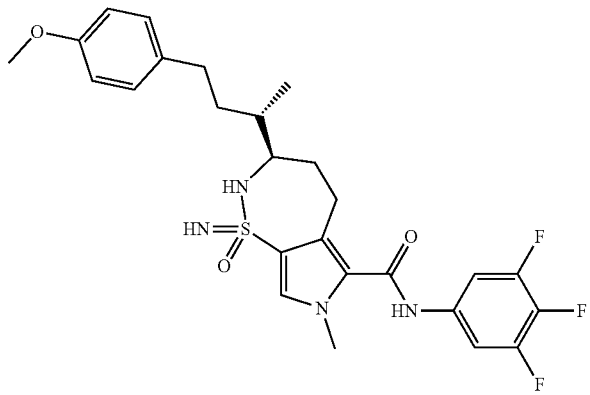 | 535 | Peak1 (HPLC) |
| 20ttt2 | 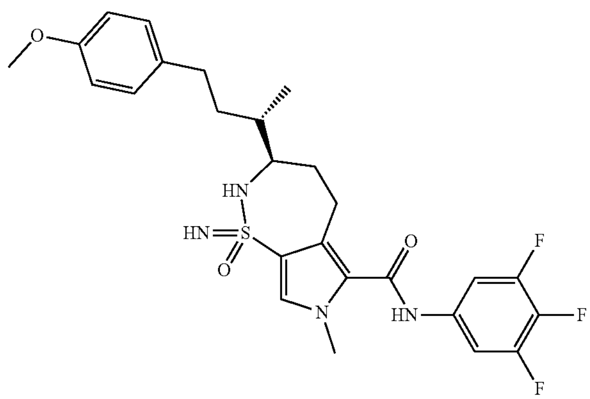 | 535 | Peak2 (HPLC) |
| 20uuu1 | 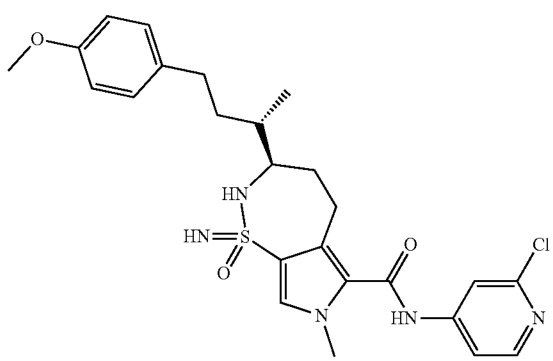 [SMILES: COc1ccc(CC[C@H](C)[C@H]2CCc3c(cn(C)c3C(=O)Nc3ccnc(Cl)c3)S(=N)(=O)N2)cc1] | 516 | Peak1 (HPLC) |
| 20uuu2 | 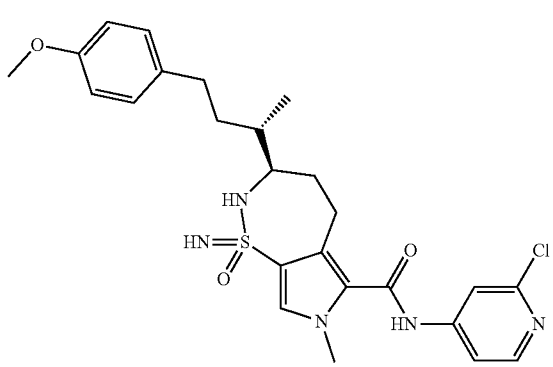 [SMILES: COc1ccc(CC[C@H](C)[C@H]2CCc3c(cn(C)c3C(=O)Nc3ccnc(Cl)c3)S(=N)(=O)N2)cc1] | 516 | Peak2 (HPLC) |

-continued

| No. | Structure | Mass Spectrum ESI-MS, (M + H) | Remark |
|---|---|---|---|
| 20vvv1 | 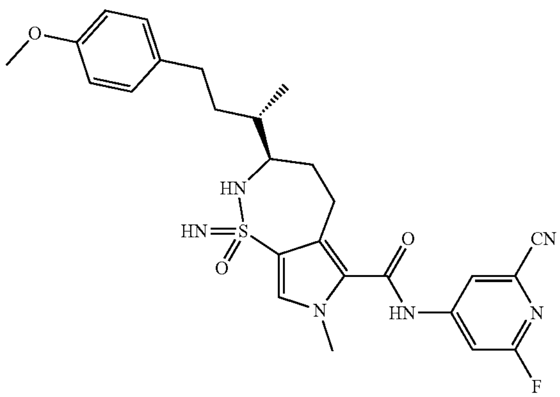 [SMILES: COc1ccc(CC[C@H](C)[C@H]2CCc3c(cn(C)c3C(=O)Nc3cc(F)nc(C#N)c3)S(=N)(=O)N2)cc1] | 525 | Peak1 (HPLC) |
| 20vvv2 | 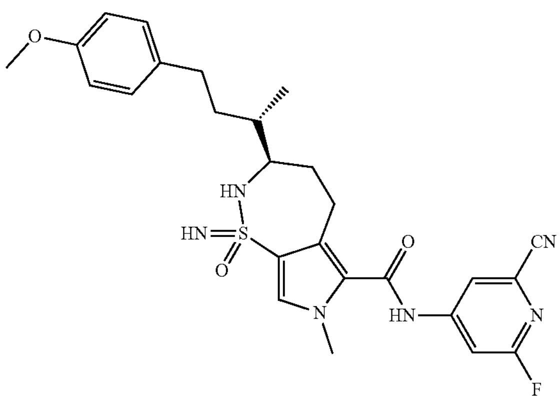 [SMILES: COc1ccc(CC[C@H](C)[C@H]2CCc3c(cn(C)c3C(=O)Nc3cc(F)nc(C#N)c3)S(=N)(=O)N2)cc1] | 525 | Peak2 (HPLC) |
| 20www1 | 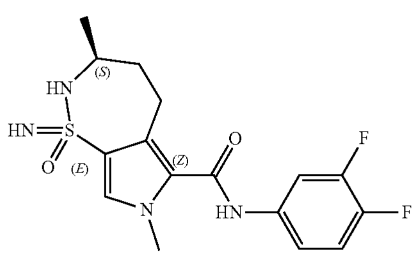 | 369 | Peak1 (HPLC) |
| 20www2 | 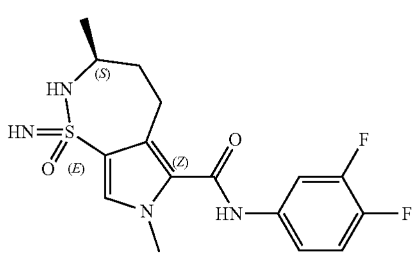 | 369 | Peak2 (HPLC) |
| 20xxx1 | 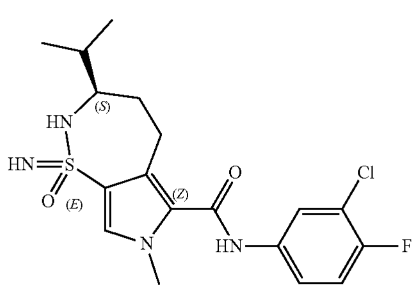 | 413 | Peak1 (HPLC) |

-continued

| No. | Structure | Mass Spectrum ESI-MS, (M + H) | Remark |
|---|---|---|---|
| 20xxx2 | 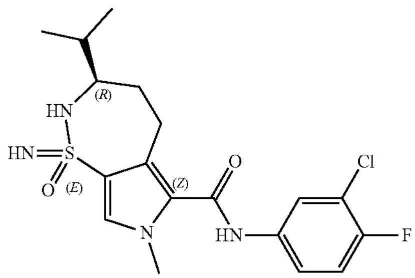 | 413 | Peak2 (HPLC) |
| 40a1 | 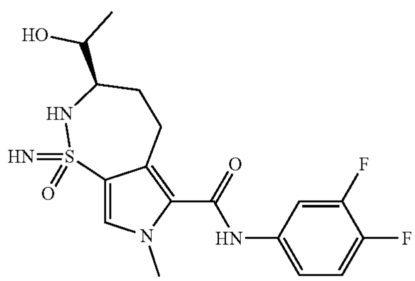 [SMILES: CC(O)[C@H]1CCc2c(cn(C)c2C(=O)Nc2ccc(F)c(F)c2)S(=N)(=O)N1] | 399 | Peak1 (HPLC) |
| 40a2 | 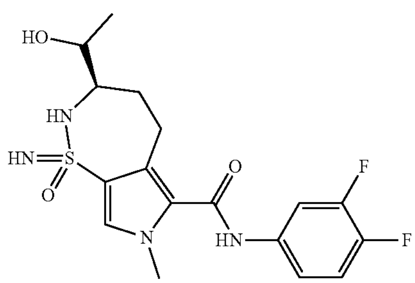 [SMILES: CC(O)[C@H]1CCc2c(cn(C)c2C(=O)Nc2ccc(F)c(F)c2)S(=N)(=O)N1] | 399 | Peak2 (HPLC) |
| 40b1 | 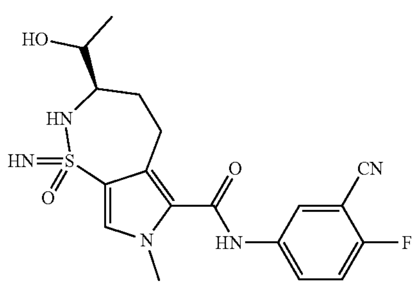 [SMILES: CC(O)[C@H]1CCc2c(cn(C)c2C(=O)Nc2ccc(F)c(C#N)c2)S(=N)(=O)N1] | 406 | Peak1 (HPLC) |
| 40b2 | 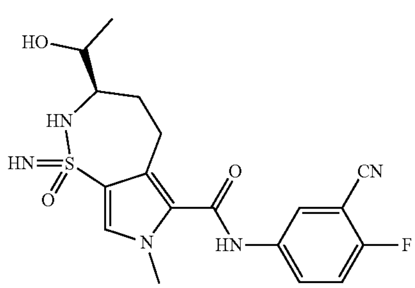 [SMILES: CC(O)[C@H]1CCc2c(cn(C)c2C(=O)Nc2ccc(F)c(C#N)c2)S(=N)(=O)N1] | 406 | Peak2 (HPLC) |

-continued

| No. | Structure | Mass Spectrum ESI-MS, (M + H) | Remark |
|---|---|---|---|
| 40c1 | 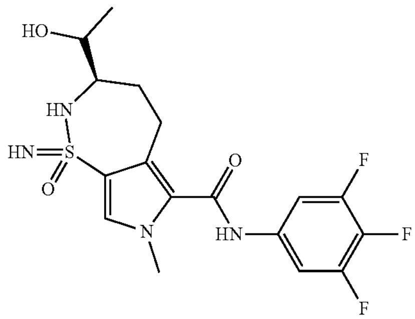 [SMILES: CC(O)[C@H]1CCc2c(cn(C)c2C(=O)Nc2cc(F)c(F)c(F)c2)S(=N)(=O)N1] | 417 | Peak1 (HPLC) |
| 40c2 | 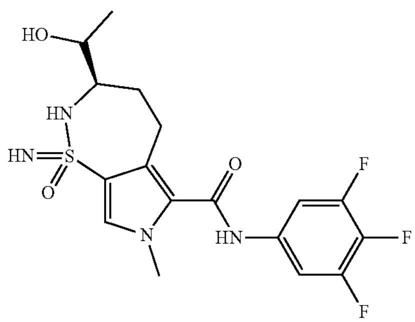 [SMILES: CC(O)[C@H]1CCc2c(cn(C)c2C(=O)Nc2cc(F)c(F)c(F)c2)S(=N)(=O)N1] | 417 | Peak2 (HPLC) |
| 40d1 | 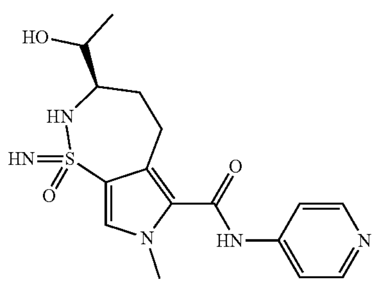 [SMILES: CC(O)[C@H]1CCc2c(cn(C)c2C(=O)Nc2ccncc2)S(=N)(=O)N1] | 364 | Peak1 (HPLC) |
| 40d2 | 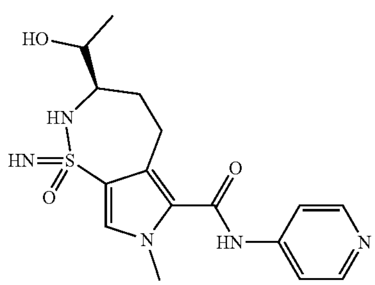 [SMILES: CC(O)[C@H]1CCc2c(cn(C)c2C(=O)Nc2ccncc2)S(=N)(=O)N1] | 364 | Peak2 (HPLC) |
| 40e1 | 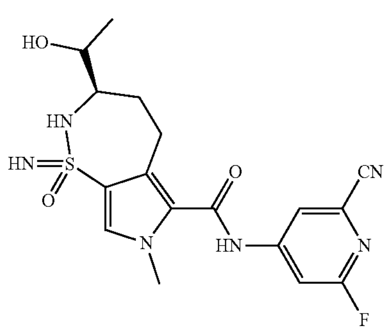 [SMILES: CC(O)[C@H]1CCc2c(cn(C)c2C(=O)Nc2cc(F)nc(C#N)c2)S(=N)(=O)N1] | 407 | Peak1 (HPLC) |

-continued

| No. | Structure | Mass Spectrum ESI-MS, (M + H) | Remark |
|---|---|---|---|
| 40e2 | 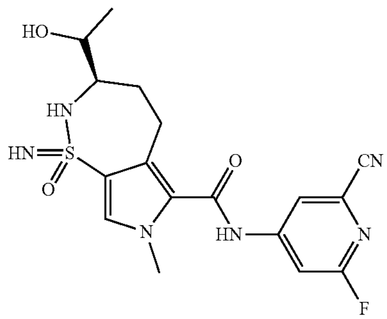 [SMILES: CC(O)[C@H]1CCc2c(cn(C)c2C(=O)Nc2cc(F)nc(C#N)c2)S(=N)(=O)N1] | 407 | Peak2 (HPLC) |
| 40f1 | 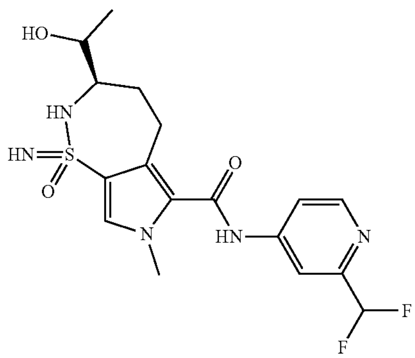 [SMILES: CC(O)[C@H]1CCc2c(cn(C)c2C(=O)Nc2ccnc(C(F)F)c2)S(=N)(=O)N1] | 414 | Peak1 (HPLC) |
| 40f2 | 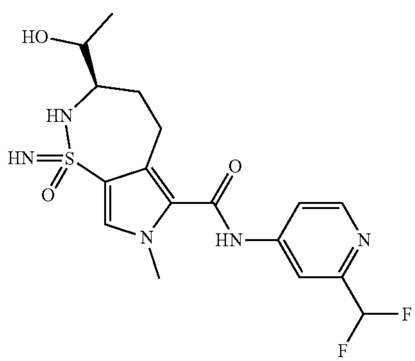 [SMILES: CC(O)[C@H]1CCc2c(cn(C)c2C(=O)Nc2ccnc(C(F)F)c2)S(=N)(=O)N1] | 414 | Peak2 (HPLC) |
| 40g1 | 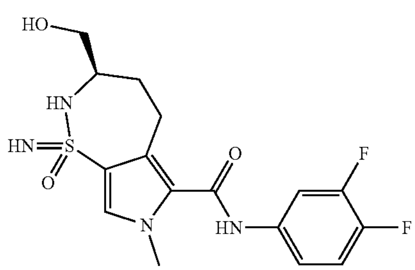 [SMILES: Cn1cc2c(c1C(=O)Nc1ccc(F)c(F)c1)CC[C@H](CO)NS2(=N)=O] | 385 | Peak1 (HPLC) |
| 40g2 | 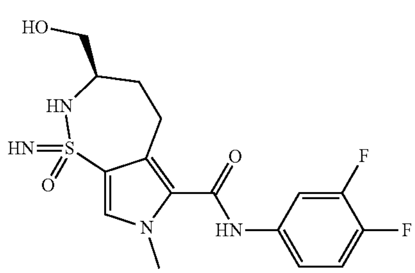 [SMILES: Cn1cc2c(c1C(=O)Nc1ccc(F)c(F)c1)CC[C@H](CO)NS2(=N)=O] | 385 | Peak2 (HPLC) |

-continued

| No. | Structure | Mass Spectrum ESI-MS, (M + H) | Remark |
|---|---|---|---|
| 40h1 | 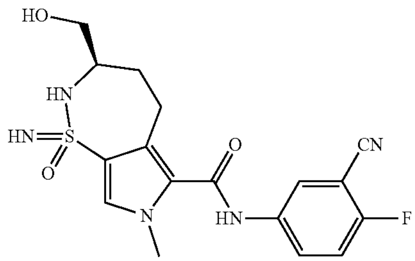 [SMILES: Cn1cc2c(c1C(=O)Nc1ccc(F)c(C#N)c1)CC[C@H](CO)NS2(=N)=O] | 392 | Peak1 (HPLC) |
| 40h2 | 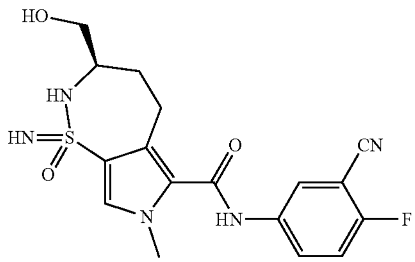 | 392 | Peak2 (HPLC) |
| 40i1 | 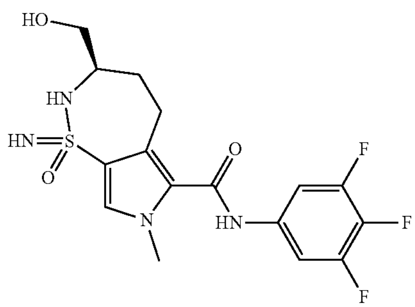 [SMILES: Cn1cc2c(c1C(=O)Nc1cc(F)c(F)c(F)c1)CC[C@H](CO)NS2(=N)=O] | 403 | Peak1 (HPLC) |
| 40i2 | 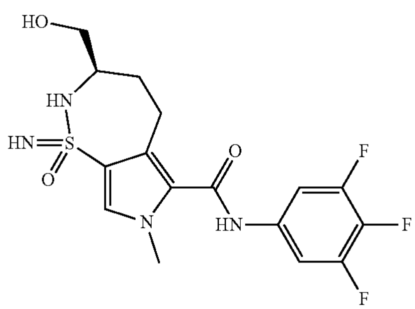 [SMILES: Cn1cc2c(c1C(=O)Nc1cc(F)c(F)c(F)c1)CC[C@H](CO)NS2(=N)=O] | 403 | Peak2 (HPLC) |
| 40j1 | 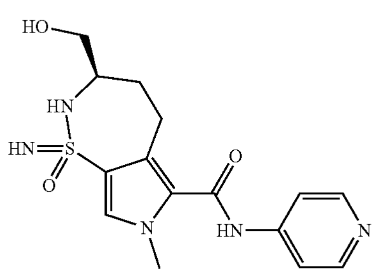 [SMILES: Cn1cc2c(c1C(=O)Nc1ccncc1)CC[C@H](CO)NS2(=N)=O] | 350 | Peak1 (HPLC) |

-continued

| No. | Structure | Mass Spectrum ESI-MS, (M + H) | Remark |
|---|---|---|---|
| 40j2 | 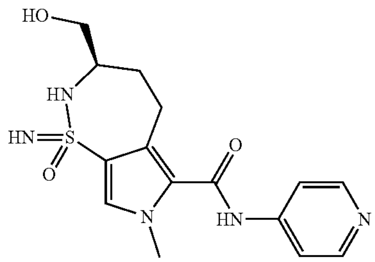 [SMILES: Cn1cc2c(c1C(=O)Nc1ccncc1)CC[C@H](CO)NS2(=N)=O] | 350 | Peak2 (HPLC) |
| 40k1 | 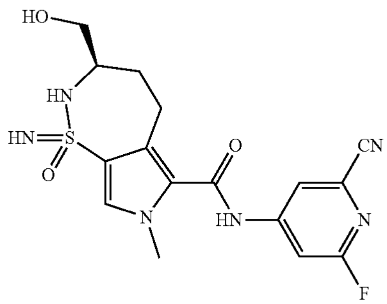 [SMILES: Cn1cc2c(c1C(=O)Nc1cc(F)nc(C#N)c1)CC[C@H](CO)NS2(=N)=O] | 393 | Peak1 (HPLC) |
| 40k2 | 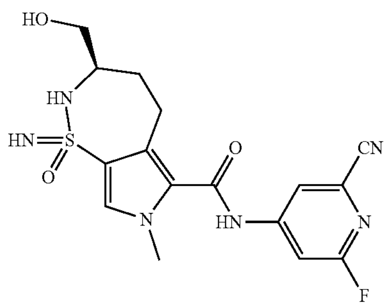 [SMILES: Cn1cc2c(c1C(=O)Nc1cc(F)nc(C#N)c1)CC[C@H](CO)NS2(=N)=O] | 393 | Peak2 (HPLC) |
| 40m1 | 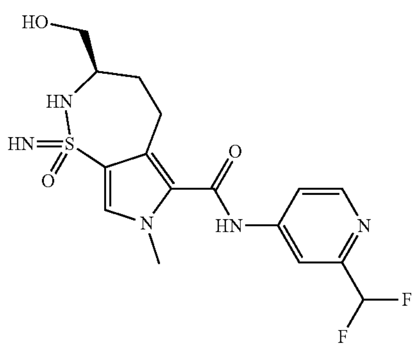 | 400 | Peak1 (HPLC) |
| 40m2 | 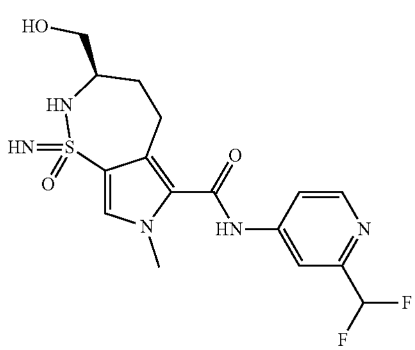 [SMILES: Cn1cc2c(c1C(=O)Nc1ccnc(C(F)F)c1)CC[C@H](CO)NS2(=N)=O] | 400 | Peak2 (HPLC) |

The following are the synthesis of 50 series compounds:

Example 167: Synthesis of Compound 50a1

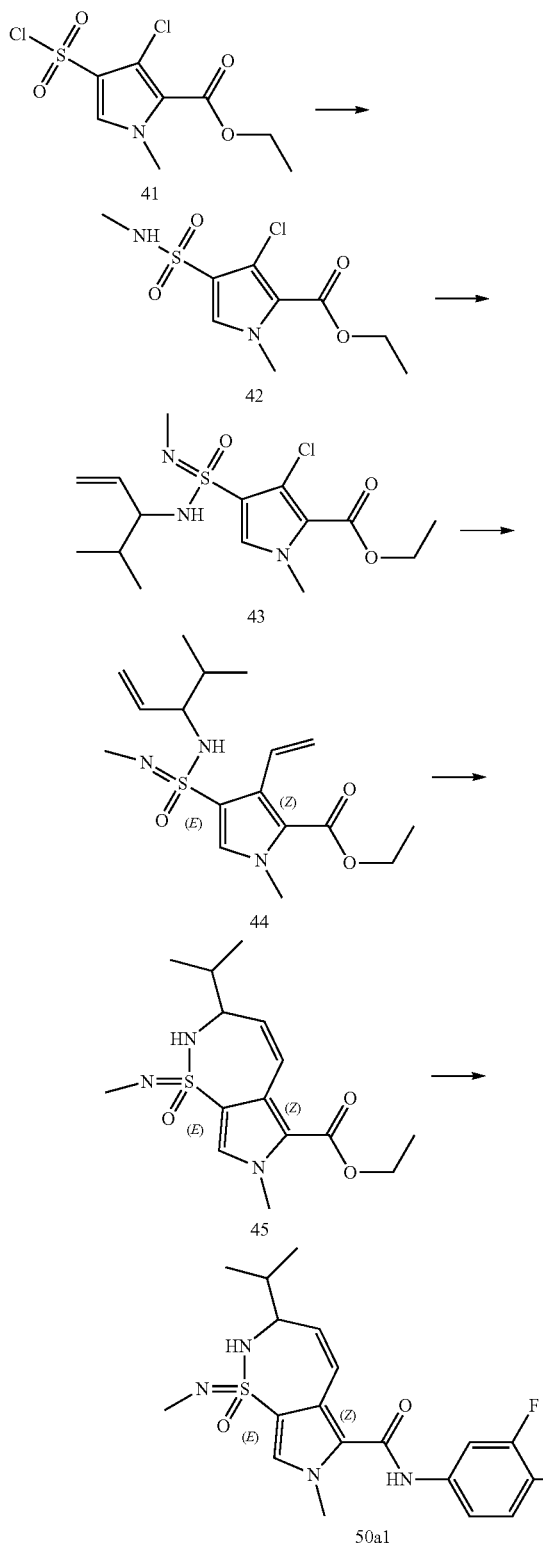

Step 1: Synthesis of Compound 42

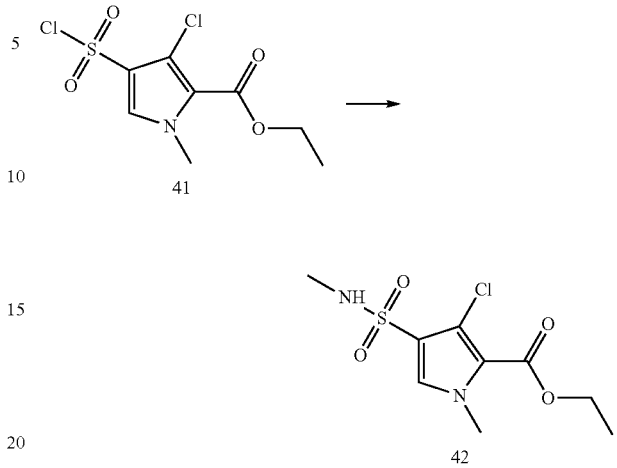

Compound 41 (10 g) was dissolved in dichloromethane (40 mL), and methylamine aqueous solution (30 mL) was added dropwise to the reaction system at room temperature. The reaction was carried out for 5 h at room temperature, then suction filtrated, and the filter cake was washed with water (5 mL) to provide 5 g of light yellow solid 42, MS (M+1=281).

Step 2: Synthesis of Compound 43

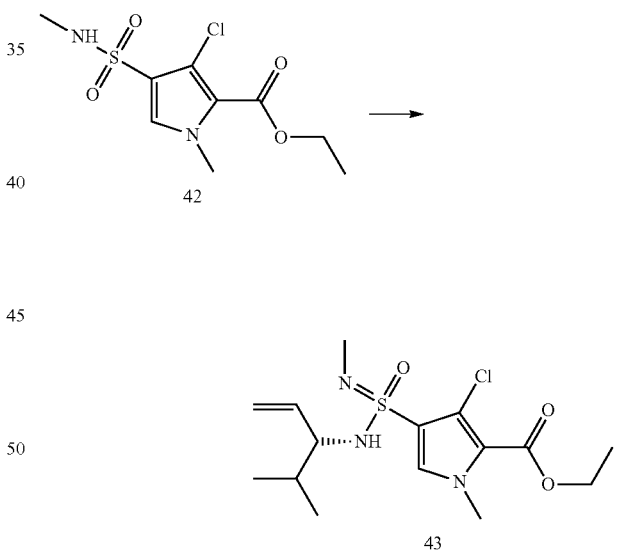

The PPh$_3$Cl$_2$ chloroform solution (80 mL) was cooled to 0° C., and then triethylamine (7 mL) was added, stirred for 10 minutes and then compound 42 (5.0 g) was added at 0° C. After stirred for 20 minutes, 2-isopropyl-3-propenylamine (5 g) was added to the reaction system and reacted at room temperature for 18 h. Water (20 mL) and ethyl acetate (3*25 mL) were added to the reaction system for extraction. The organic phase was dried and the solvent was evaporated in vacuum. Crude product was purified by column chromatography (n-heptane:ethyl acetate=1:5) to provide the product 43 (400 mg). MS (M+1=362).

Step 3: Synthesis of Compound 44

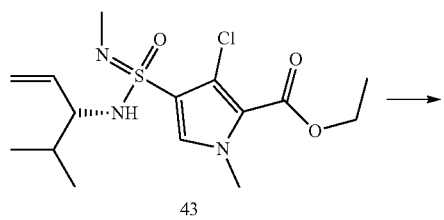

43

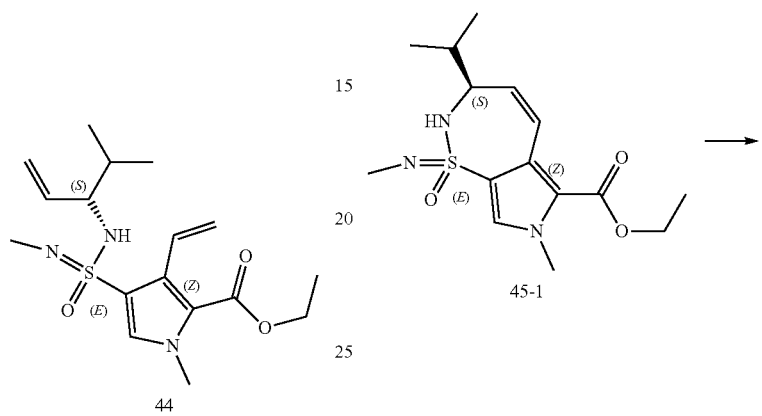

Compound 43 (1.8 g), tetrakis (triphenylphosphine) palladium (100 mg), vinyl borate (900 mg), and cesium carbonate (2.7 g) were dissolved in DMF (410 mL), and the mixture was reacted at 100° C. under the protection of nitrogen for 15 h. The reaction was quenched with an aqueous solution, extracted with ethyl acetate, and the organic phase was dried and the solvent was evaporated in vacuum. The resulting crude product was purified by column chromatography (n-heptane:ethyl acetate=1:5) to provide compound 44 (0.5 g). MS (M+1=354).

Step 4: Synthesis of Compound 45

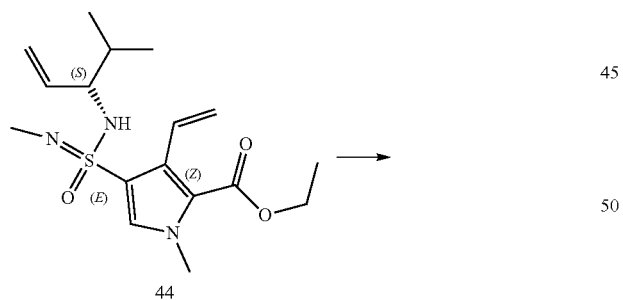

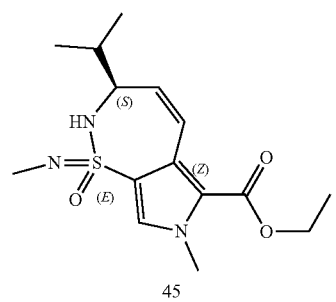

Compound 44 (1.0 g) was dissolved in dichloromethane (500 ml), and then the Zhan Catalyst (0.1 g) was added to the reaction system and stirred overnight. The reaction solution was evaporated in vacuum and crude product was column chromatography (n-heptane:ethyl acetate=1:3) purified to provide compound 45. The lower point of the TLC display was 45-1 (0.22 g), and the upper point of the TLC display was 45-2 (0.27 g), MS (M+1=312).

Step 5: Synthesis of Compound 50a1

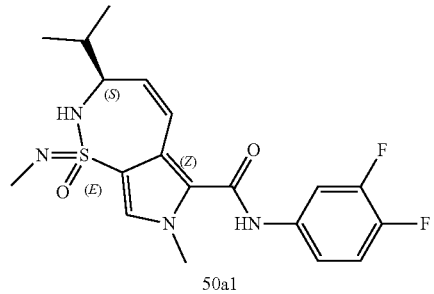

Compound 45-1 (30 mg) and 4-fluoro-3-cyanoaniline (20 mg) were dissolved in THF (5 mL), the system was cooled to 0° C., and then NaHMDS (0.2 mL) was added to the reaction system. The reaction was stirred at room temperature for 16 h, and water was added to the reaction system. The mixture was extracted with ethyl acetate (3*15 mL). The organic phase was dried over anhydrous sodium sulfate and the solvent was evaporated in vacuum. The crude product was subjected to column chromatography (n-heptane:ethyl acetate=1:3) to provide target product 50a1 (11 mg). MS (M+1=409).

The following 50 series compounds are synthesized according to the method of example 167:

| No. | Structure | Mass Spectrum ESI-MS, (M + H) | Remark |
| --- | --- | --- | --- |
| 50b1 | 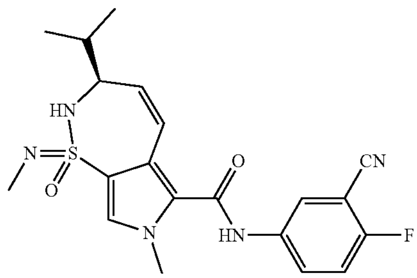 | 416 | Peak1 (HPLC) |
| 50b2 | 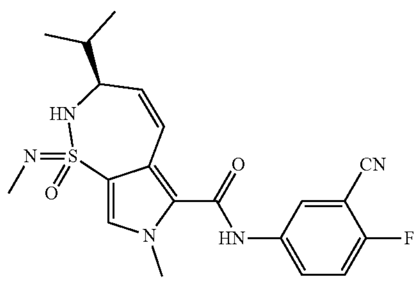 | 416 | Peak2 (HPLC) |
| 50c1 | 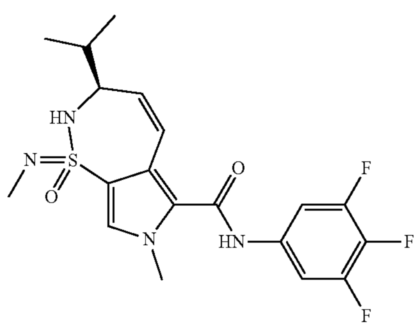 [SMILES: CN=S1(=O)N[C@@H](C(C)C)C=Cc2c1cn(C)c2C(=O)Nc1cc(F)c(F)c(F)c1] | 413 | Peak1 (HPLC) |
| 50c2 | 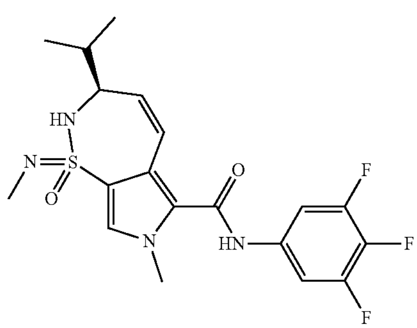 [SMILES: CN=S1(=O)N[C@@H](C(C)C)C=Cc2c1cn(C)c2C(=O)Nc1cc(F)c(F)c(F)c1] | 427 | Peak2 (HPLC) |
| 50d1 | 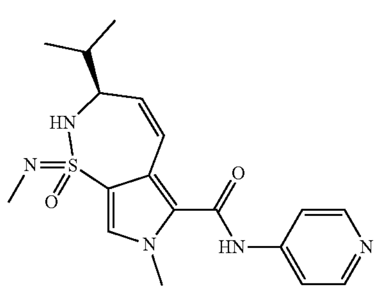 [SMILES: CN=S1(=O)N[C@@H](C(C)C)C=Cc2c1cn(C)c2C(=O)Nc1ccncc1] | 374 | Peak1 (HPLC) |

-continued

| No. | Structure | Mass Spectrum ESI-MS, (M + H) | Remark |
|---|---|---|---|
| 50d2 | 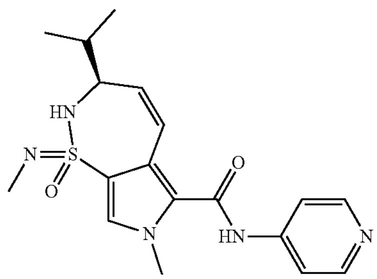 [SMILES: CN=S1(=O)N[C@@H](C(C)C)C=Cc2c1cn(C)c2C(=O)Nc1ccncc1] | 360 | Peak2 (HPLC) |
| 50e1 | 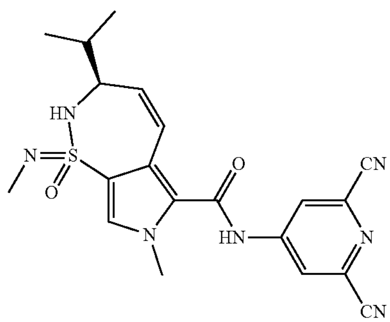 [SMILES: CN=S1(=O)N[C@@H](C(C)C)C=Cc2c1cn(C)c2C(=O)Nc1cc(C#N)nc(C#N)c1] | 417 | Peak1 (HPLC) |
| 50e2 | 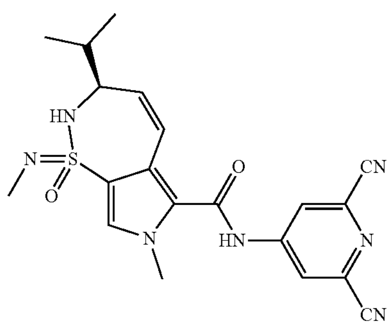 [SMILES: CN=S1(=O)N[C@@H](C(C)C)C=Cc2c1cn(C)c2C(=O)Nc1cc(C#N)nc(C#N)c1] | 417 | Peak2 (HPLC) |
| 50f1 | 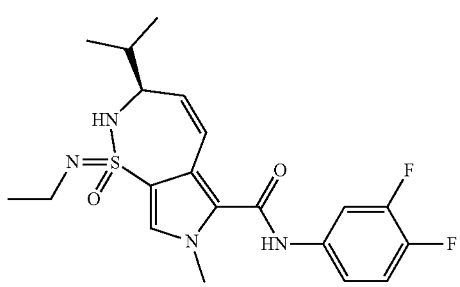 [SMILES: CCN=S1(=O)N[C@@H](C(C)C)C=Cc2c1cn(C)c2C(=O)Nc1ccc(F)c(F)c1] | 423 | Peak1 (HPLC) |
| 50f2 | 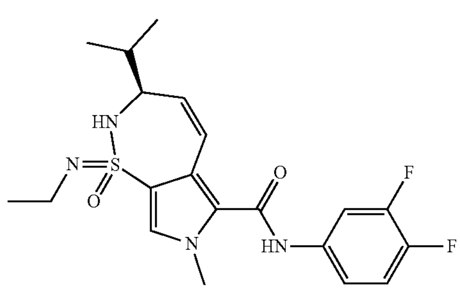 [SMILES: CCN=S1(=O)N[C@@H](C(C)C)C=Cc2c1cn(C)c2C(=O)Nc1ccc(F)c(F)c1] | 423 | Peak2 (HPLC) |

-continued

| No. | Structure | Mass Spectrum ESI-MS, (M + H) | Remark |
|---|---|---|---|
| 50g1 | 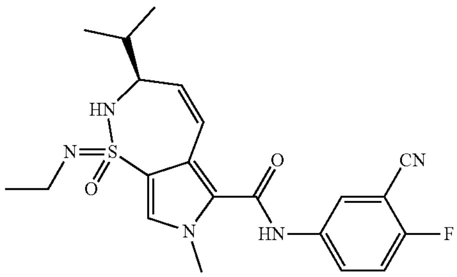 [SMILES: CCN=S1(=O)N[C@@H](C(C)C)C=Cc2c1cn(C)c2C(=O)Nc1ccc(F)c(C#N)c1] | 430 | Peak1 (HPLC) |
| 50g2 | 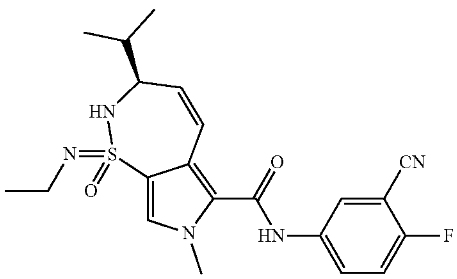 [SMILES: CCN=S1(=O)N[C@@H](C(C)C)C=Cc2c1cn(C)c2C(=O)Nc1ccc(F)c(C#N)c1] | 430 | Peak2 (HPLC) |
| 50h1 | 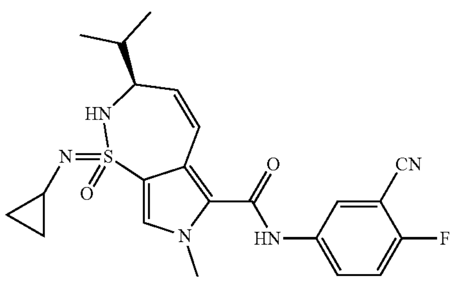 [SMILES: CC(C)[C@H]1C=Cc2c(cn(C)c2C(=O)Nc2ccc(F)c(C#N)c2)S(=O)(=NC2CC2)N1] | 442 | Peak1 (HPLC) |
| 50h2 | 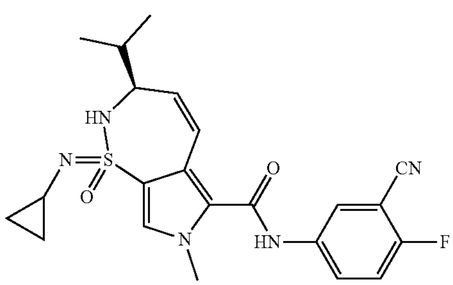 | 442 | Peak2 (HPLC) |
| 50i1 | 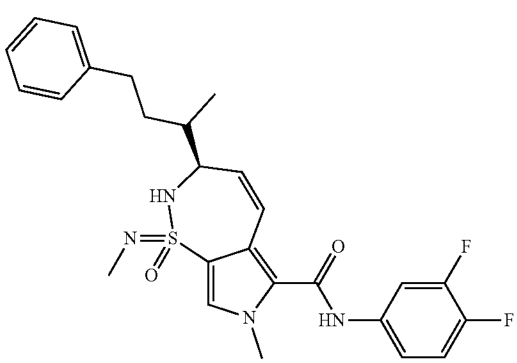 [SMILES: CN=S1(=O)N[C@@H](C(C)CCc2ccccc2)C=Cc2c1cn(C)c2C(=O)Nc1ccc(F)c(F)c1] | 499 | Peak1 (HPLC) |

-continued

| No. | Structure | Mass Spectrum ESI-MS, (M + H) | Remark |
|---|---|---|---|
| 50i2 | 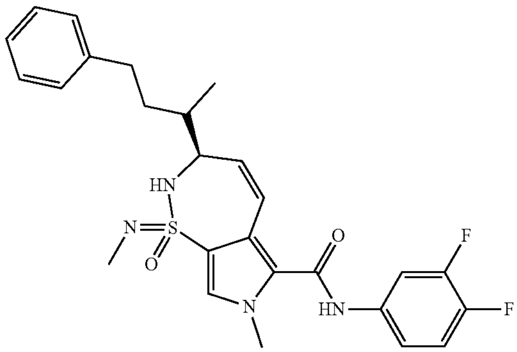 [SMILES: CN=S1(=O)N[C@@H](C(C)CCc2ccccc2)C=Cc2c1cn(C)c2C(=O)Nc1ccc(F)c(F)c1] | 499 | Peak2 (HPLC) |
| 50j1 | 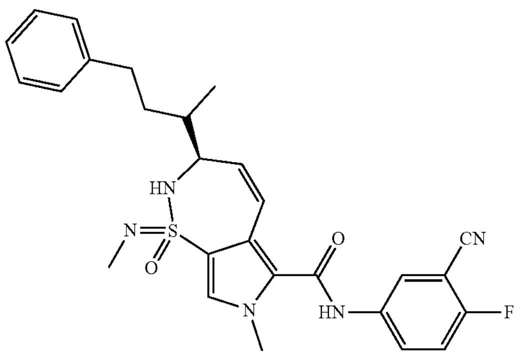 [SMILES: CN=S1(=O)N[C@@H](C(C)CCc2ccccc2)C=Cc2c1cn(C)c2C(=O)Nc1ccc(F)c(C#N)c1] | 506 | Peak1 (HPLC) |
| 50j2 | 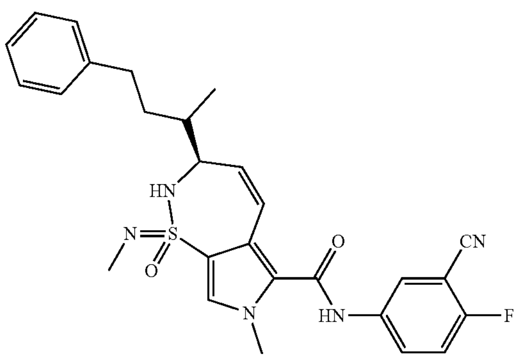 [SMILES: CN=S1(=O)N[C@@H](C(C)CCc2ccccc2)C=Cc2c1cn(C)c2C(=O)Nc1ccc(F)c(C#N)c1] | 506 | Peak2 (HPLC) |
| 50k1 | 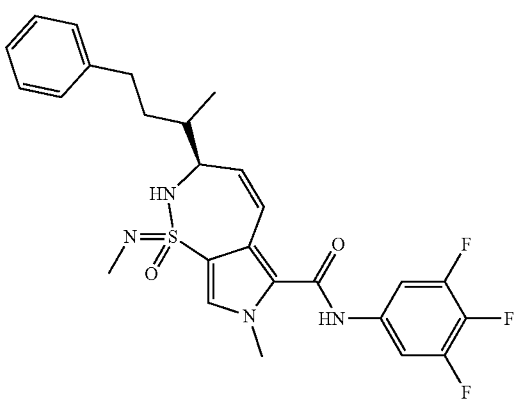 [SMILES: CN=S1(=O)N[C@@H](C(C)CCc2ccccc2)C=Cc2c1cn(C)c2C(=O)Nc1cc(F)c(F)c(F)c1] | 517 | Peak1 (HPLC) |

-continued

| No. | Structure | Mass Spectrum ESI-MS, (M + H) | Remark |
|---|---|---|---|
| 50k2 | 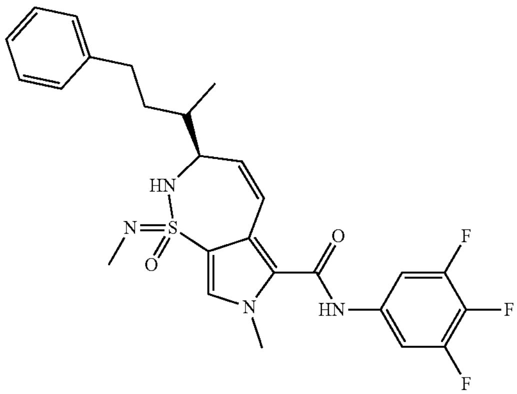 [SMILES: CN=S1(=O)N[C@@H](C(C)CCc2ccccc2)C=Cc2c1cn(C)c2C(=O)Nc1cc(F)c(F)c(F)c1] | 427 | Peak2 (HPLC) |
| 50m1 | 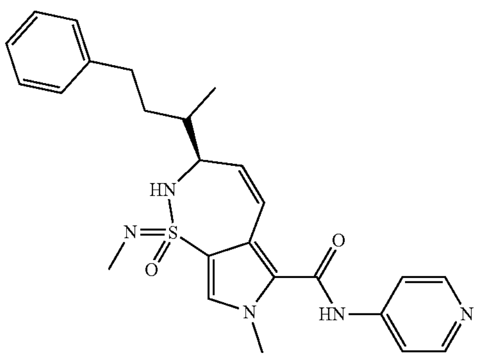 [SMILES: CN=S1(=O)N[C@@H](C(C)CCc2ccccc2)C=Cc2c1cn(C)c2C(=O)Nc1ccncc1] | 464 | Peak1 (HPLC) |
| 50m2 | 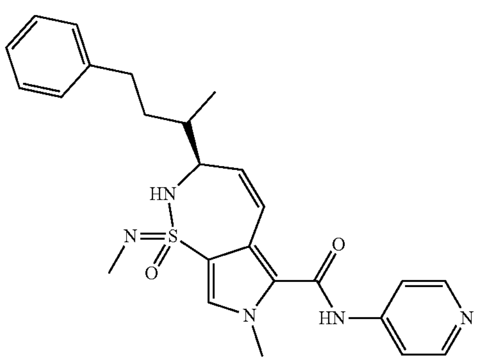 [SMILES: CN=S1(=O)N[C@@H](C(C)CCc2ccccc2)C=Cc2c1cn(C)c2C(=O)Nc1ccncc1] | 464 | Peak2 (HPLC) |
| 50n1 | 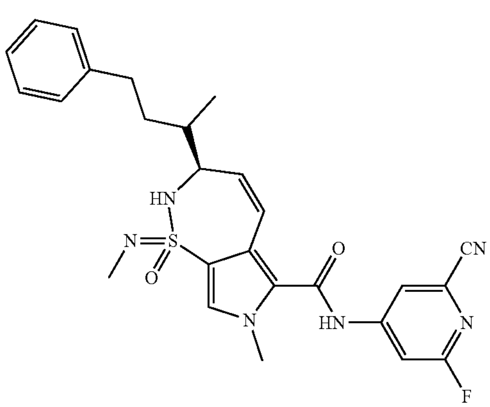 [SMILES: CN=S1(=O)N[C@@H](C(C)CCc2ccccc2)C=Cc2c1cn(C)c2C(=O)Nc1cc(F)nc(C#N)c1] | 507 | Peak1 (HPLC) |

-continued
| No. | Structure | Mass Spectrum ESI-MS, (M + H) | Remark |
|---|---|---|---|
| 50n2 | 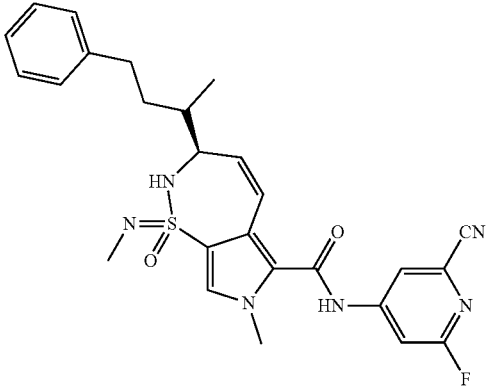 [SMILES: CN=S1(=O)N[C@@H](C(C)CCc2ccccc2)C=Cc2c1cn(C)c2C(=O)Nc1cc(F)nc(C#N)c1] | 507 | Peak2 (HPLC) |
| 50o1 | 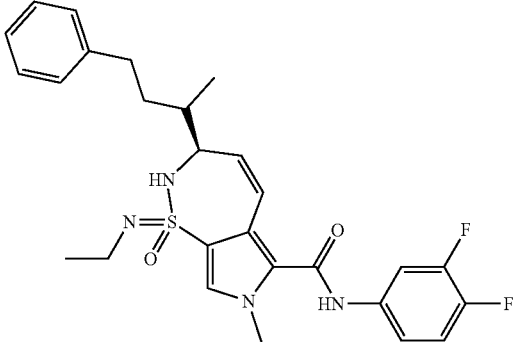 [SMILES: CCN=S1(=O)N[C@@H](C(C)CCc2ccccc2)C=Cc2c1cn(C)c2C(=O)Nc1ccc(F)c(F)c1] | 513 | Peak1 (HPLC) |
| 50o2 | 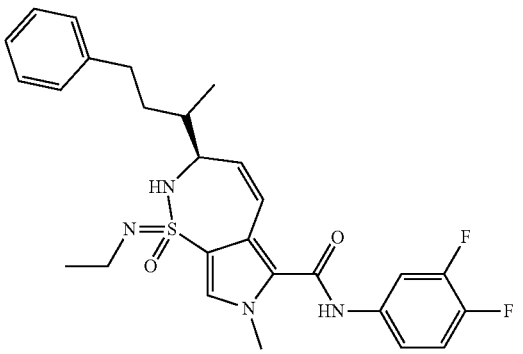 [SMILES: CCN=S1(=O)N[C@@H](C(C)CCc2ccccc2)C=Cc2c1cn(C)c2C(=O)Nc1ccc(F)c(F)c1] | 513 | Peak2 (HPLC) |
| 50p1 | 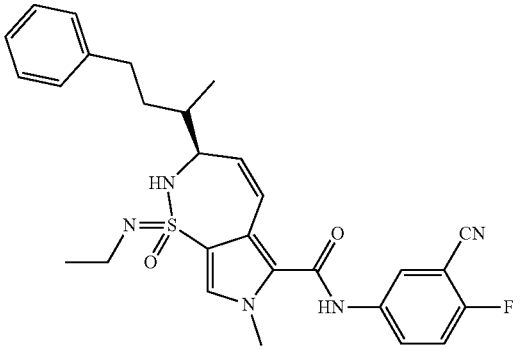 [SMILES: CCN=S1(=O)N[C@@H](C(C)CCc2ccccc2)C=Cc2c1cn(C)c2C(=O)Nc1ccc(F)c(C#N)c1] | 520 | Peak1 (HPLC) |

-continued

| No. | Structure | Mass Spectrum ESI-MS, (M + H) | Remark |
|---|---|---|---|
| 50p2 | 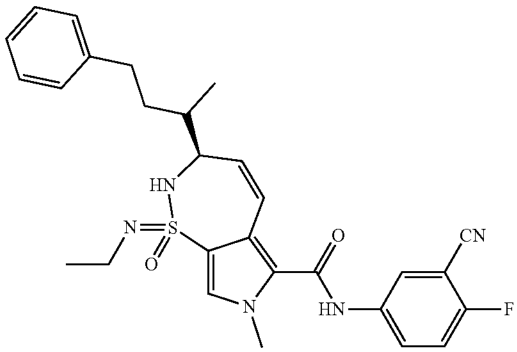 [SMILES: CCN=S1(=O)N[C@@H](C(C)CCc2ccccc2)C=Cc2c1cn(C)c2C(=O)Nc1ccc(F)c(C#N)c1] | 520 | Peak2 (HPLC) |
| 50q1 | 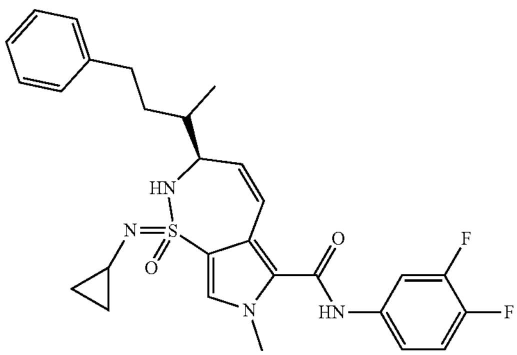 [SMILES: CC(CCc1ccccc1)[C@H]1C=Cc2c(cn(C)c2C(=O)Nc2ccc(F)c(F)c2)S(=O)(=NC2CC2)N1] | 525 | Peak1 (HPLC) |
| 50q2 | 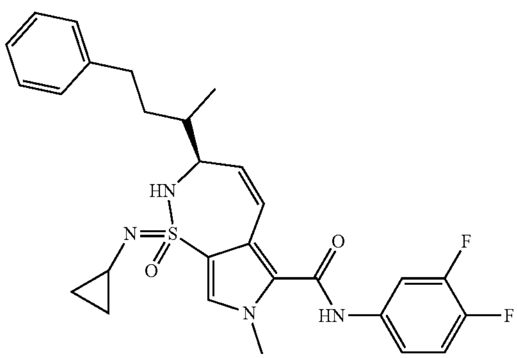 [SMILES: CC(CCc1ccccc1)[C@H]1C=Cc2c(cn(C)c2C(=O)Nc2ccc(F)c(F)c2)S(=O)(=NC2CC2)N1] | 525 | Peak2 (HPLC) |
| 50r1 | 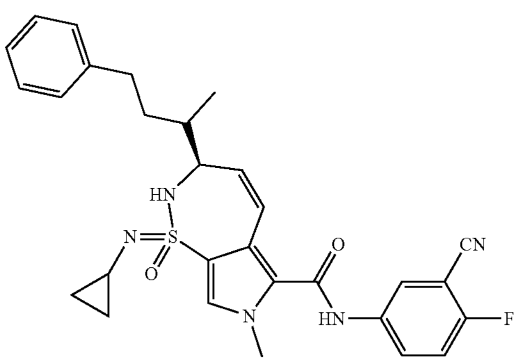 [SMILES: CC(CCc1ccccc1)[C@H]1C=Cc2c(cn(C)c2C(=O)Nc2ccc(F)c(C#N)c2)S(=O)(=NC2CC2)N1] | 532 | Peak1 (HPLC) |

-continued
| No. | Structure | Mass Spectrum ESI-MS, (M + H) | Remark |
|---|---|---|---|
| 50r2 | 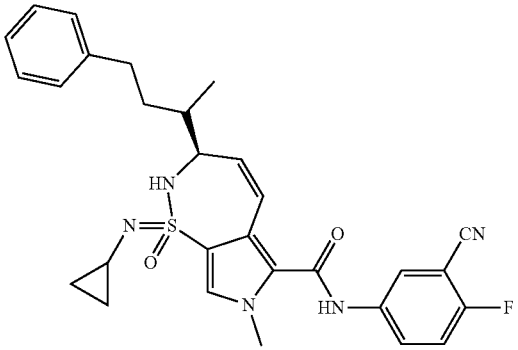 [SMILES: CC(CCc1ccccc1)[C@H]1C=Cc2c(cn(C)c2C(=O)Nc2ccc(F)c(C#N)c2)S(=O)(=NC2CC2)N1] | 532 | Peak2 (HPLC) |
| 50s1 | 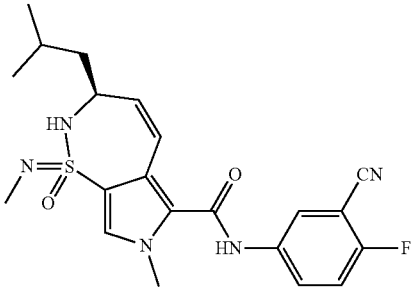 [SMILES: CN=S1(=O)N[C@@H](CC(C)C)C=Cc2c1cn(C)c2C(=O)Nc1ccc(F)c(C#N)c1] | 430 | Peak1 (HPLC) |
| 50s2 | 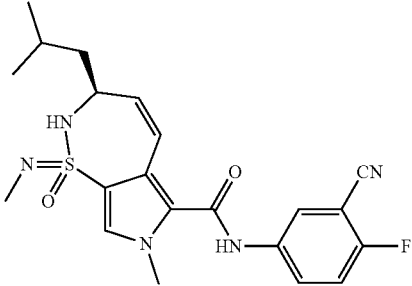 [SMILES: CN=S1(=O)N[C@@H](CC(C)C)C=Cc2c1cn(C)c2C(=O)Nc1ccc(F)c(C#N)c1] | 430 | Peak2 (HPLC) |
| 50t1 | 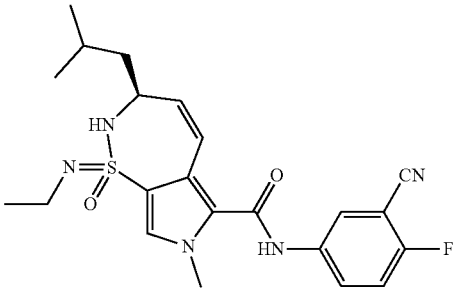 [SMILES: CCN=S1(=O)N[C@@H](CC(C)C)C=Cc2c1cn(C)c2C(=O)Nc1ccc(F)c(C#N)c1] | 444 | Peak1 (HPLC) |
| 50t2 | 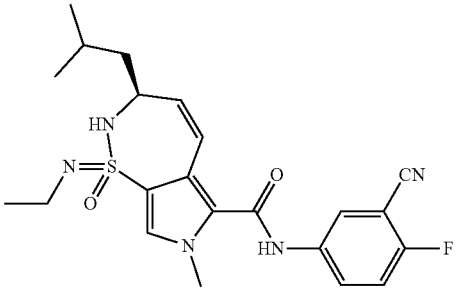 | 444 | Peak2 (HPLC) |

-continued

| No. | Structure | Mass Spectrum ESI-MS, (M + H) | Remark |
|---|---|---|---|
| 50u1 | 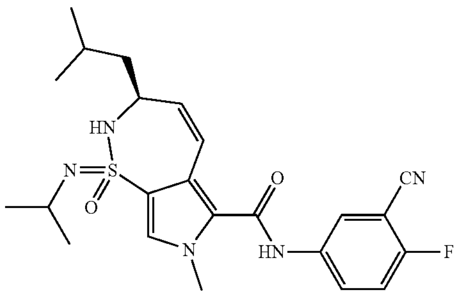 [SMILES: CC(C)C[C@H]1C=Cc2c(cn(C)c2C(=O)Nc2ccc(F)c(C#N)c2)S(=O)(=NC(C)C)N1] | 458 | Peak1 (HPLC) |
| 50u2 | 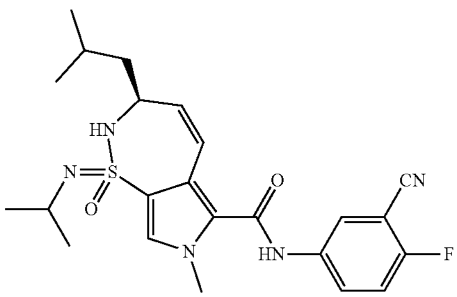 [SMILES: CC(C)C[C@H]1C=Cc2c(cn(C)c2C(=O)Nc2ccc(F)c(C#N)c2)S(=O)(=NC(C)C)N1] | 458 | Peak2 (HPLC) |
| 50v1 | 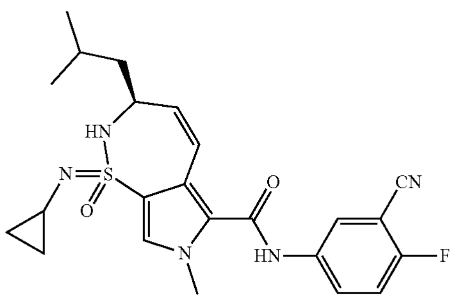 [SMILES: CC(C)C[C@H]1C=Cc2c(cn(C)c2C(=O)Nc2ccc(F)c(C#N)c2)S(=O)(=NC2CC2)N1] | 456 | Peak1 (HPLC) |
| 50v2 | 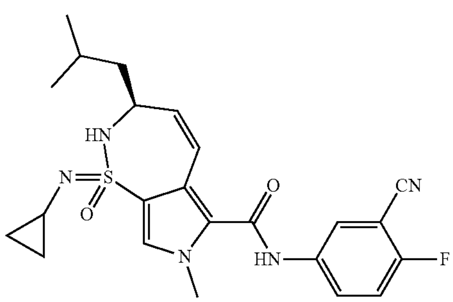 [SMILES: CC(C)C[C@H]1C=Cc2c(cn(C)c2C(=O)Nc2ccc(F)c(C#N)c2)S(=O)(=NC2CC2)N1] | 456 | Peak2 (HPLC) |
| 50w1 | 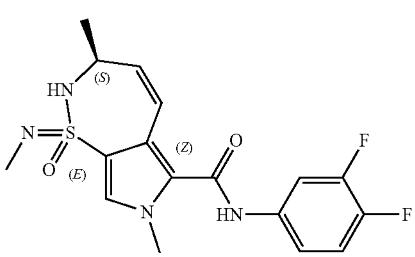 | 381 | Peak1 (HPLC) |

-continued
| No. | Structure | Mass Spectrum ESI-MS, (M + H) | Remark |
|---|---|---|---|
| 50w2 | 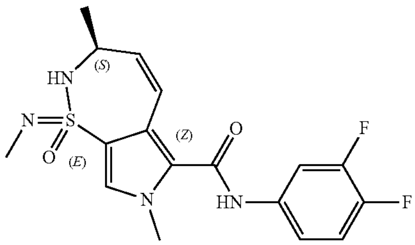 | 381 | Peak2 (HPLC) |
| 50x1 | 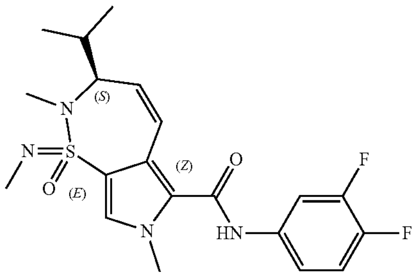 | 423 | Peak1 (HPLC) |
| 50x2 | 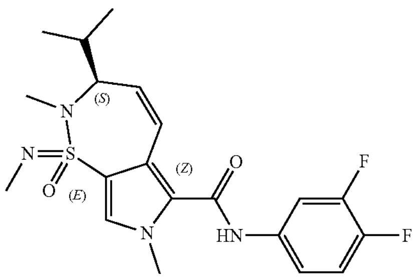 | 423 | Peak2 (HPLC) |
The following are the synthesis of 60 series compounds:
Example 186: Synthesis of Compound 60a1
Step 1
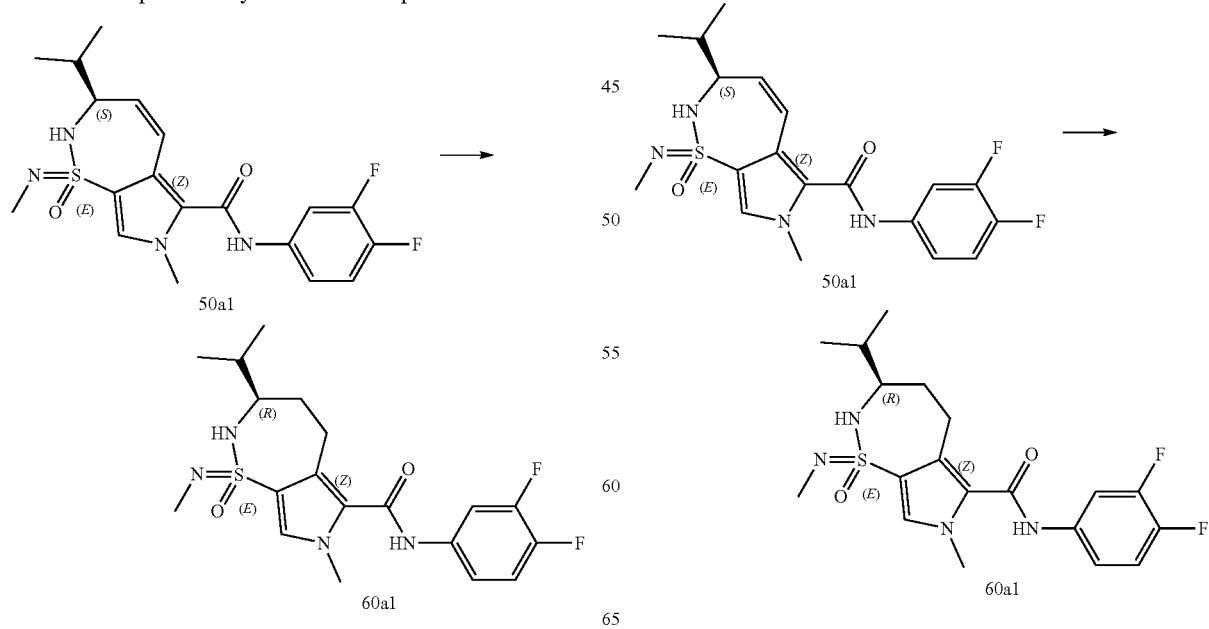

Compound 50a1 (20 mg) was dissolved in methanol (5 mL), and then palladium carbon (5 mg) was added to the reaction system. The reaction was performed at room temperature for 6 h under hydrogen. The crude product was purified by column chromatography (n-heptane:ethyl acetate=1:3) to provide the target product 60a1 (11 mg). MS (M+1=411)

The following 60 series compounds are synthesized according to the method of example 186:

| No. | Structure | Mass Spectrum ESI-MS, (M + H) | Remark |
|---|---|---|---|
| 60a2 | 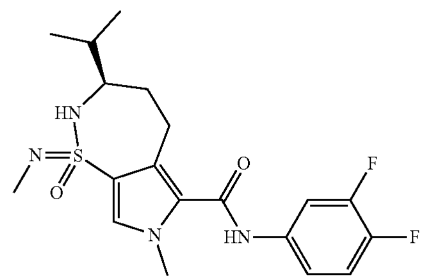 | 411 | Peak2 (HPLC) |
| 60b1 | 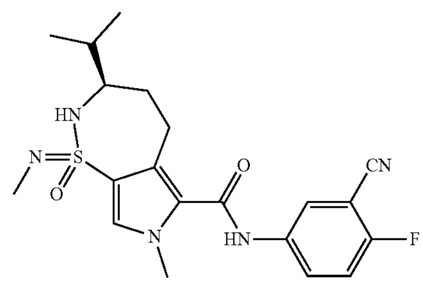 | 418 | Peak1 (HPLC) |
| 60b2 | 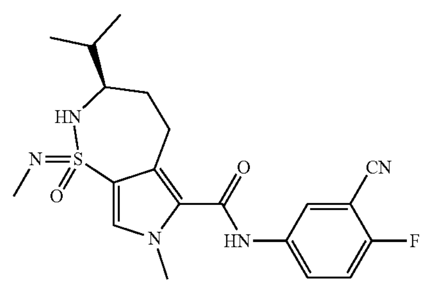 [SMILES: CN=S1(=O)N[C@@H](C(C)C)CCc2c1cn(C)c2C(=O)Nc1ccc(F)c(C#N)c1] | 418 | Peak2 (HPLC) |
| 60c1 | 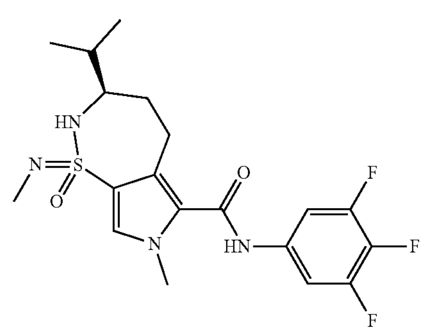 | 429 | Peak1 (HPLC) |

| No. | Structure | Mass Spectrum ESI-MS, (M + H) | Remark |
|---|---|---|---|
| 60c2 | 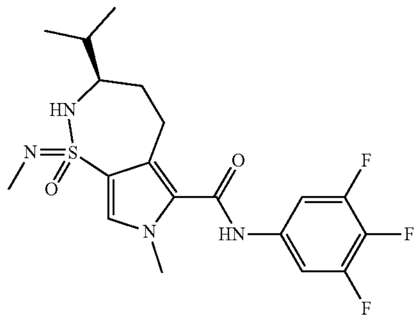 | 429 | Peak2 (HPLC) |
| 60d1 | 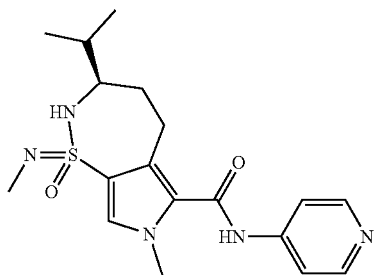 [SMILES: CN=S1(=O)N[C@@H](C(C)C)CCc2c1cn(C)c2C(=O)Nc1ccncc1] | 376 | Peak1 (HPLC) |
| 60d2 | 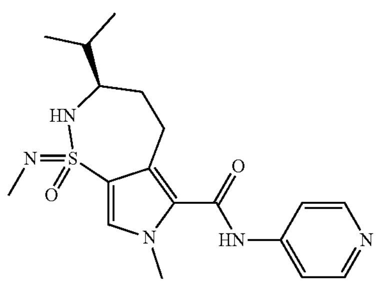 [SMILES: CN=S1(=O)N[C@@H](C(C)C)CCc2c1cn(C)c2C(=O)Nc1ccncc1] | 376 | Peak2 (HPLC) |
| 60e1 | 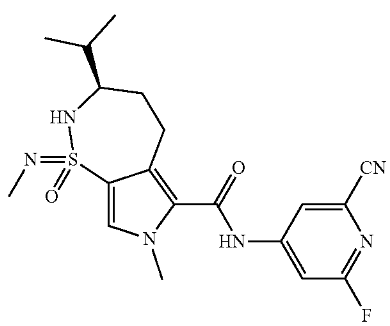 [SMILES: CN=S1(=O)N[C@@H](C(C)C)CCc2c1cn(C)c2C(=O)Nc1cc(F)nc(C#N)c1] | 419 | Peak1 (HPLC) |
| 60e2 | 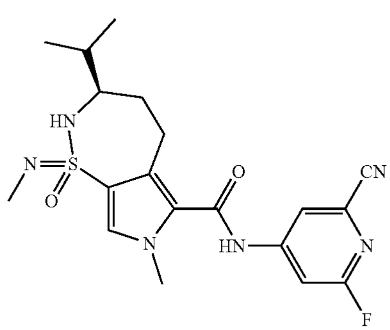 [SMILES: CN=S1(=O)N[C@@H](C(C)C)CCc2c1cn(C)c2C(=O)Nc1cc(F)nc(C#N)c1] | 419 | Peak2 (HPLC) |

-continued
| No. | Structure | Mass Spectrum ESI-MS, (M + H) | Remark |
|---|---|---|---|
| 60f1 | 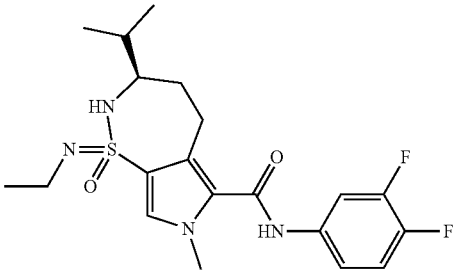 | 425 | Peak1 (HPLC) |
| 60f2 | 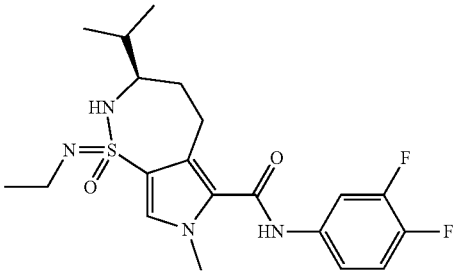 [SMILES: CCN=S1(=O)N[C@@H](C(C)C)CCc2c1cn(C)c2C(=O)Nc1ccc(F)c(F)c1] | 425 | Peak2 (HPLC) |
| 60g1 | 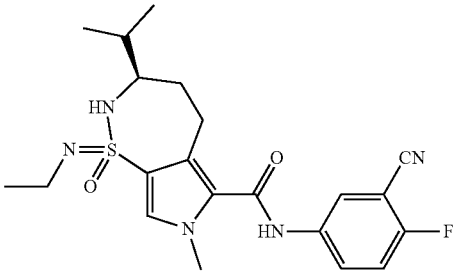 | 432 | Peak1 (HPLC) |
| 60g2 | 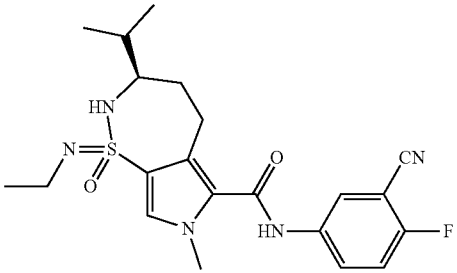 | 432 | Peak2 (HPLC) |
| 60h1 | 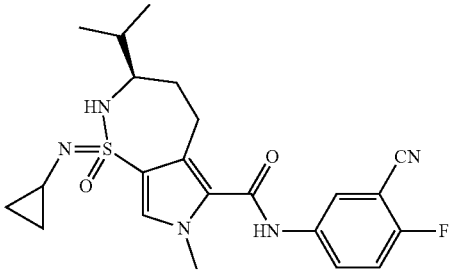 [SMILES: CC(C)[C@H]1CCc2c(cn(C)c2C(=O)Nc2ccc(F)c(C#N)c2)S(=O)(=NC2CC2)N1] | 446 | Peak1 (HPLC) |

-continued

| No. | Structure | Mass Spectrum ESI-MS, (M + H) | Remark |
|---|---|---|---|
| 60h2 | 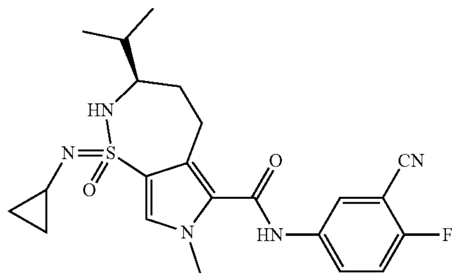 [SMILES: CC(C)[C@H]1CCc2c(cn(C)c2C(=O)Nc2ccc(F)c(C#N)c2)S(=O)(=NC2CC2)N1] | 446 | Peak2 (HPLC) |
| 60i1 | 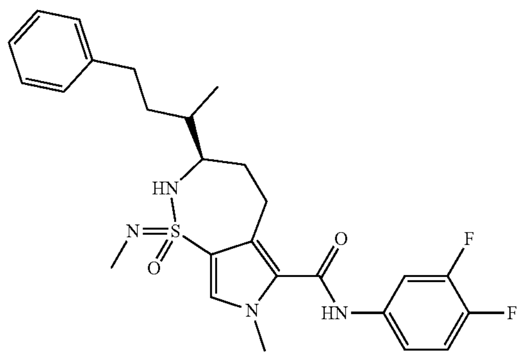 [SMILES: CN=S1(=O)N[C@@H](C(C)CCc2ccccc2)CCc2c1cn(C)c2C(=O)Nc1ccc(F)c(F)c1] | 501 | Peak1 (HPLC) |
| 60i2 | 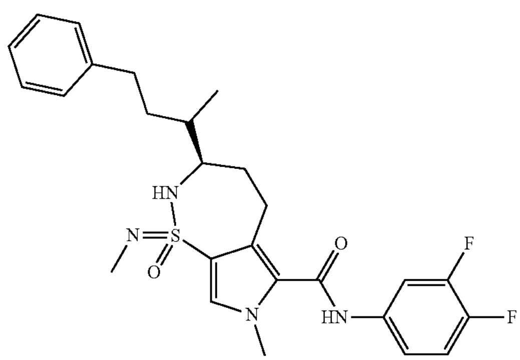 [SMILES: CN=S1(=O)N[C@@H](C(C)CCc2ccccc2)CCc2c1cn(C)c2C(=O)Nc1ccc(F)c(F)c1] | 501 | Peak2 (HPLC) |
| 60j1 | 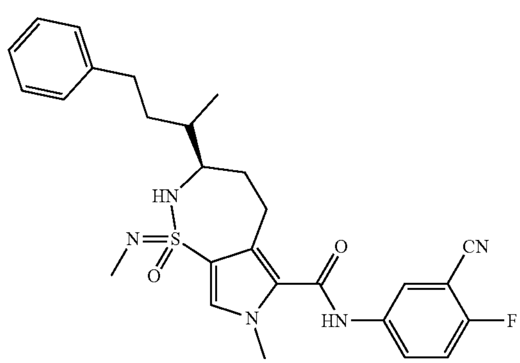 [SMILES: CN=S1(=O)N[C@@H](C(C)CCc2ccccc2)CCc2c1cn(C)c2C(=O)Nc1ccc(F)c(C#N)c1] | 508 | Peak1 (HPLC) |

-continued

| No. | Structure | Mass Spectrum ESI-MS, (M + H) | Remark |
|---|---|---|---|
| 60j2 | 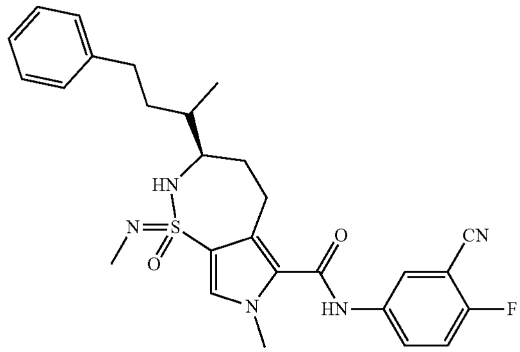 [SMILES: CN=S1(=O)N[C@@H](C(C)CCc2ccccc2)CCc2c1cn(C)c2C(=O)Nc1ccc(F)c(C#N)c1] | 508 | Peak2 (HPLC) |
| 60k1 | 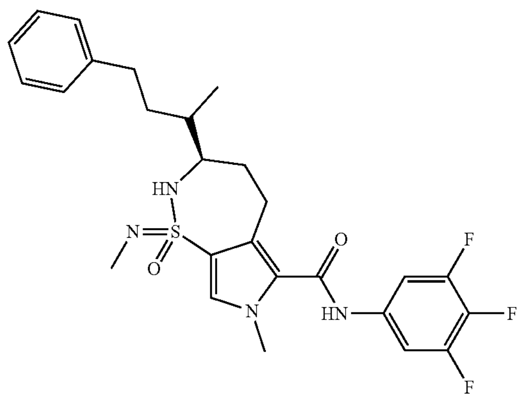 [SMILES: CN=S1(=O)N[C@@H](C(C)CCc2ccccc2)CCc2c1cn(C)c2C(=O)Nc1cc(F)c(F)c(F)c1] | 519 | Peak1 (HPLC) |
| 60k2 | 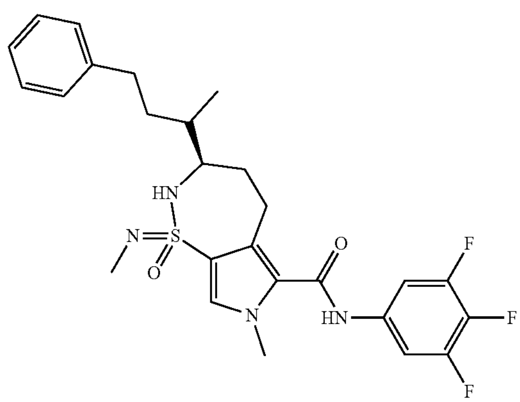 [SMILES: CN=S1(=O)N[C@@H](C(C)CCc2ccccc2)CCc2c1cn(C)c2C(=O)Nc1cc(F)c(F)c(F)c1] | 519 | Peak2 (HPLC) |
| 60m1 | 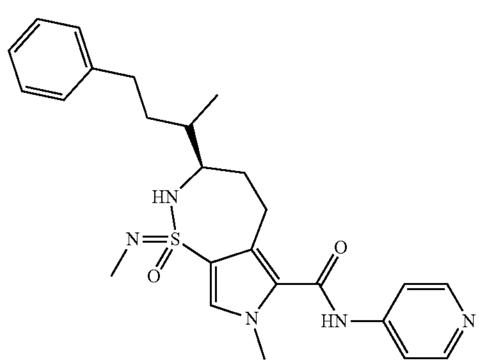 [SMILES: CN=S1(=O)N[C@@H](C(C)CCc2ccccc2)CCc2c1cn(C)c2C(=O)Nc1ccncc1] | 466 | Peak1 (HPLC) |

-continued

| No. | Structure | Mass Spectrum ESI-MS, (M + H) | Remark |
|---|---|---|---|
| 60m2 | 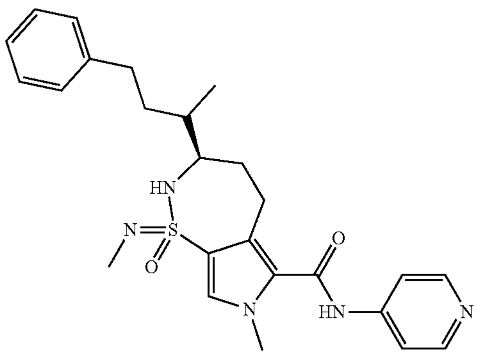 [SMILES: CN=S1(=O)N[C@@H](C(C)CCc2ccccc2)CCc2c1cn(C)c2C(=O)Nc1ccncc1] | 466 | Peak2 (HPLC) |
| 60n1 | 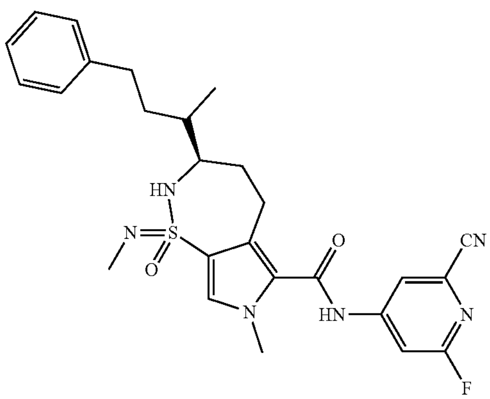 [SMILES: CN=S1(=O)N[C@@H](C(C)CCc2ccccc2)CCc2c1cn(C)c2C(=O)Nc1cc(F)nc(C#N)c1] | 509 | Peak1 (HPLC) |
| 60n2 | 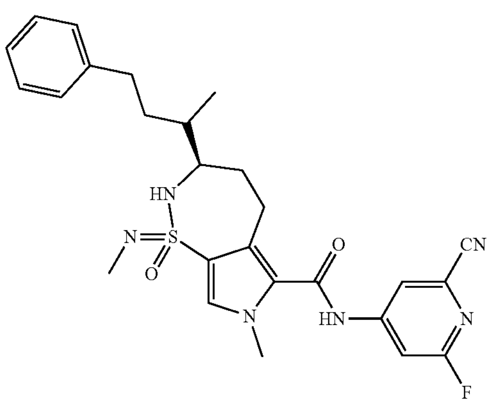 [SMILES: CN=S1(=O)N[C@@H](C(C)CCc2ccccc2)CCc2c1cn(C)c2C(=O)Nc1cc(F)nc(C#N)c1] | 509 | Peak2 (HPLC) |
| 60o1 | 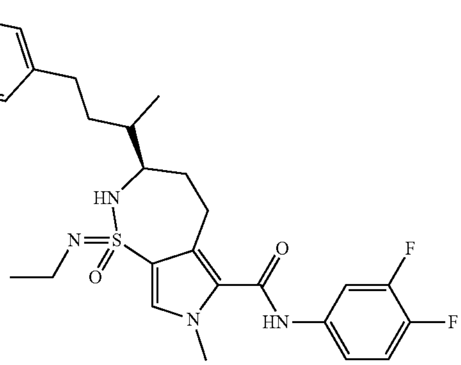 | 515 | Peak1 (HPLC) |

-continued

| No. | Structure | Mass Spectrum ESI-MS, (M + H) | Remark |
|-----|-----------|-------------------------------|--------|
| 60o2 | 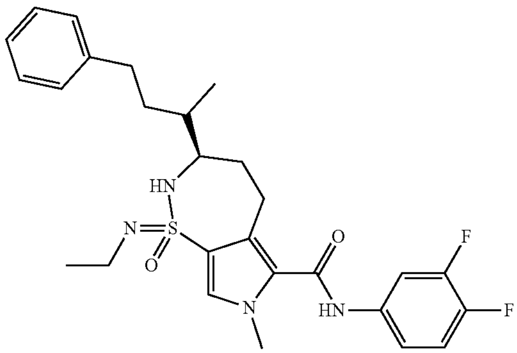 [SMILES: CCN=S1(=O)N[C@@H](C(C)CCc2ccccc2)CCc2c1cn(C)c2C(=O)Nc1ccc(F)c(F)c1] | 515 | Peak2 (HPLC) |
| 60p1 | 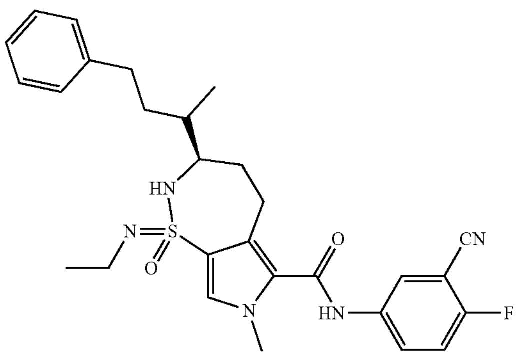 | 522 | Peak1 (HPLC) |
| 60p2 | 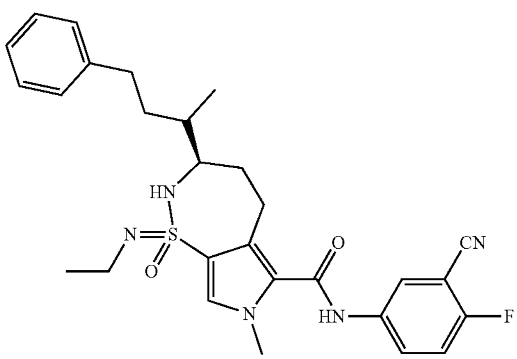 [SMILES: CCN=S1(=O)N[C@@H](C(C)CCc2ccccc2)CCc2c1cn(C)c2C(=O)Nc1ccc(F)c(C#N)c1] | 522 | Peak2 (HPLC) |
| 60q1 | 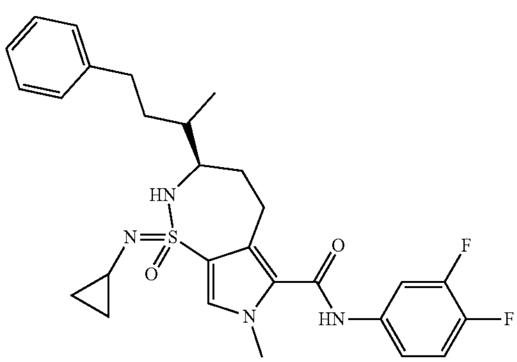 | 527 | Peak1 (HPLC) |

-continued

| No. | Structure | Mass Spectrum ESI-MS, (M + H) | Remark |
|---|---|---|---|
| 60q2 | 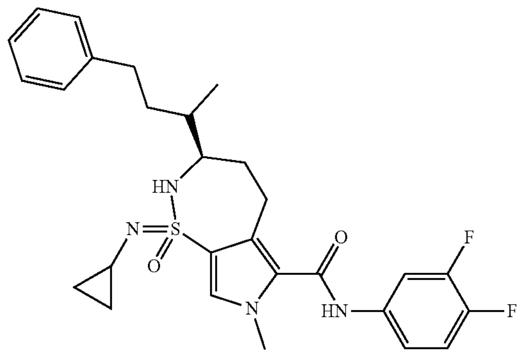 | 527 | Peak2 (HPLC) |
| 60r1 | 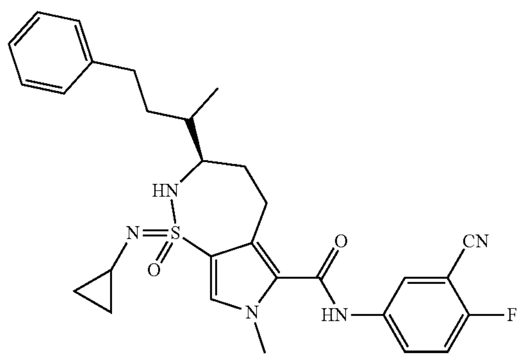 | 534 | Peak1 (HPLC) |
| 60r2 | 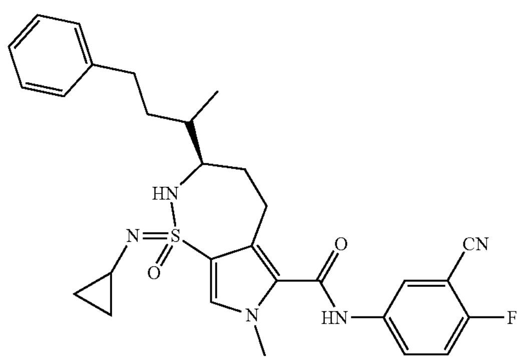 | 534 | Peak2 (HPLC) |
| 60s1 | 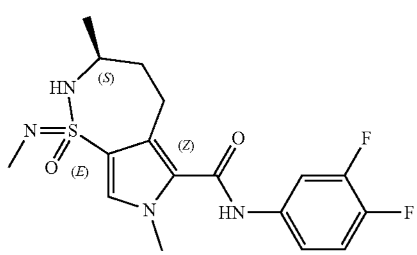 | 383 | Peak1 (HPLC) |
| 60s2 | 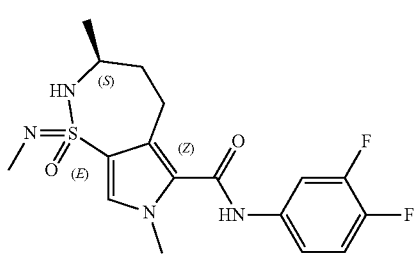 | 383 | Peak2 (HPLC) |

-continued

| No. | Structure | Mass Spectrum ESI-MS, (M + H) | Remark |
|---|---|---|---|
| 60t1 | 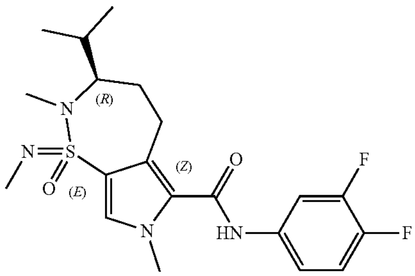 | 425 | Peak1 (HPLC) |
| 60t2 | 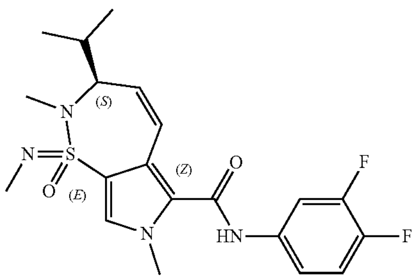 | 425 | Peak2 (HPLC) |
| 60u1 | 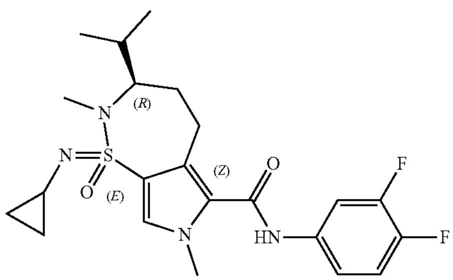 | 451 | Peak1 (HPLC) |
| 60u2 | 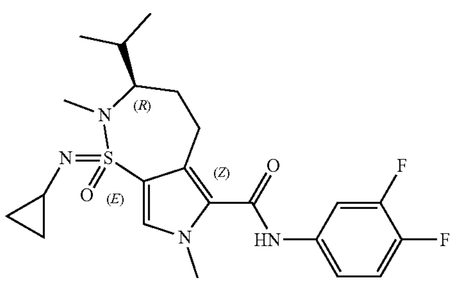 | 451 | Peak2 (HPLC) |
| 60v1 | 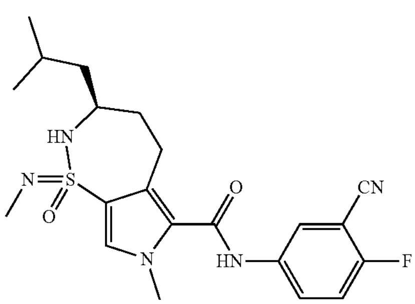 | 432 | Peak1 (HPLC) |

| No. | Structure | Mass Spectrum ESI-MS, (M + H) | Remark |
|---|---|---|---|
| 60v2 | 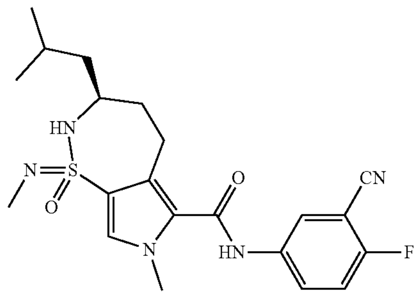 | 432 | Peak2 (HPLC) |
| 60w1 | 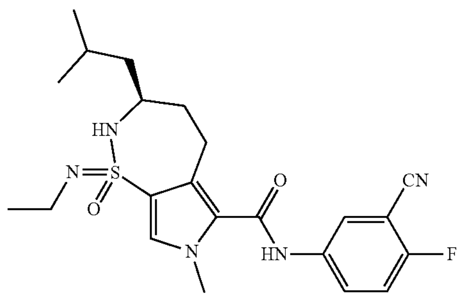 | 446 | Peak1 (HPLC) |
| 60w2 | 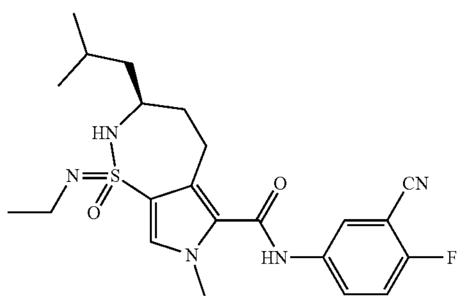 | 446 | Peak2 (HPLC) |
| 60x1 | 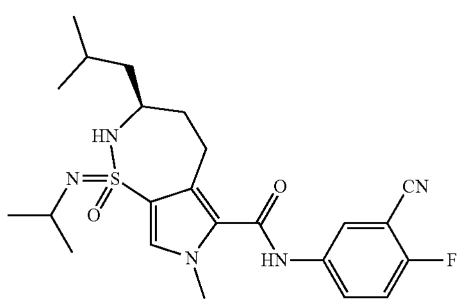 [SMILES: CC(C)C[C@H]1CCc2c(cn(C)c2C(=O)Nc2ccc(F)c(C#N)c2)S(=O)(=NC(C)C)N1] | 460 | Peak1 (HPLC) |
| 60x2 | 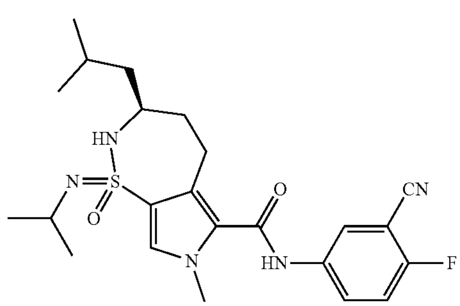 [SMILES: CC(C)C[C@H]1CCc2c(cn(C)c2C(=O)Nc2ccc(F)c(C#N)c2)S(=O)(=NC(C)C)N1] | 460 | Peak2 (HPLC) |

| No. | Structure | Mass Spectrum ESI-MS, (M + H) | Remark |
|---|---|---|---|
| 60y1 | 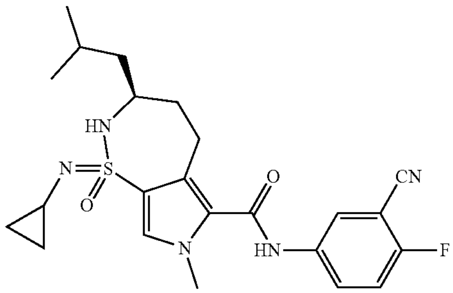 [SMILES: CC(C)C[C@H]1CCc2c(cn(C)c2C(=O)Nc2ccc(F)c(C#N)c2)S(=O)(=NC2CC2)N1] | 458 | Peak1 (HPLC) |
| 60y2 | 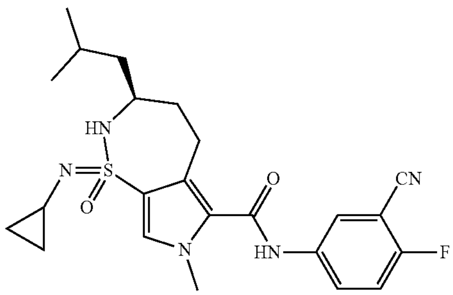 | 458 | Peak2 (HPLC) |

The following are the synthesis of 70, 80 and 90 series compounds:

Example 234: Synthesis of Compound 70a1

The reaction was carried out according to the example 74 and example 167, while the pyrrole compounds were replaced with pyrazole compounds to obtain the compounds in the

| | | | |
|---|---|---|---|
| 70a1 | | 403 | Peak1 (HPLC) |
| 70a2 | | 403 | Peak2 (HPLC) |

| | | |
|---|---|---|
| 70b1 | 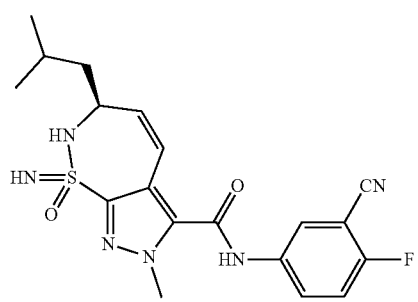 | 417 Peak1 (HPLC) |
| 70b2 | 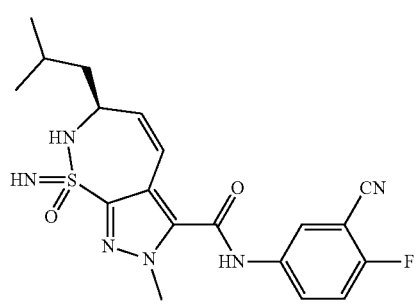 [SMILES: CC(C)C[C@H]1C=Cc2c(nn(C)c2C(=O)Nc2ccc(F)c(C#N)c2)S(=N)(=O)N1] | 417 Peak2 (HPLC) |
| 80a1 | 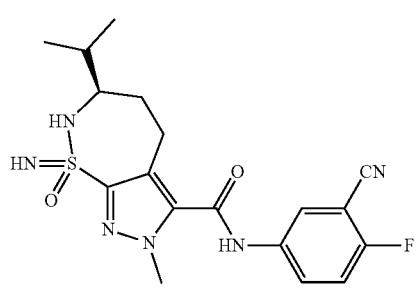 | 405 Peak1 (HPLC) |
| 80a2 | 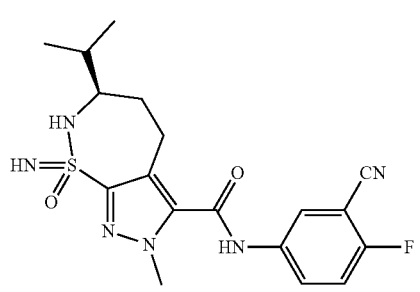 | 405 Peak2 (HPLC) |
| 80b1 | 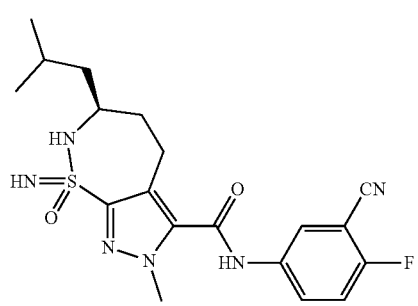 | 419 Peak1 (HPLC) |

-continued
| | | |
|---|---|---|
| 80b2 | 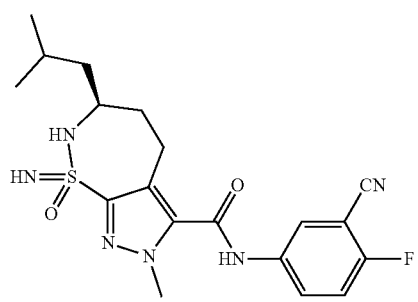 | 419 Peak2 (HPLC) |
| 90a1 | 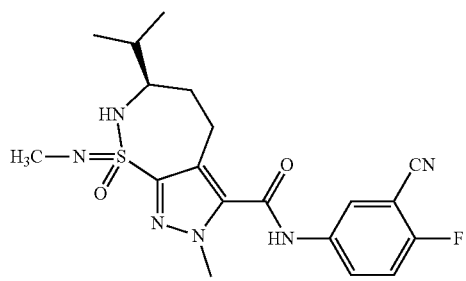 | 419 Peak1 (HPLC) |
| 90a2 | 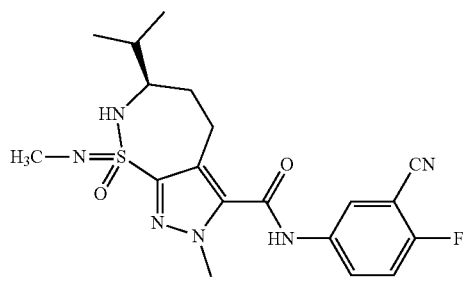 | 419 Peak2 (HPLC) |
| 90b1 | 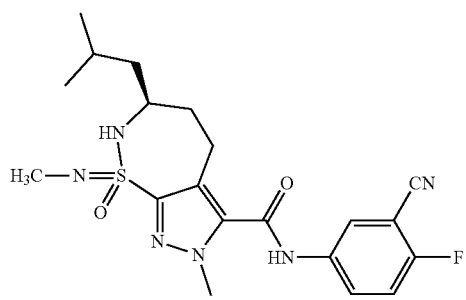 [SMILES: CN=S1(=O)N[C@@H](CC(C)C)CCc2c1nn(C)c2C(=O)Nc1ccc(F)c(C#N)c1] | 433 Peak1 (HPLC) |
| 90b2 | 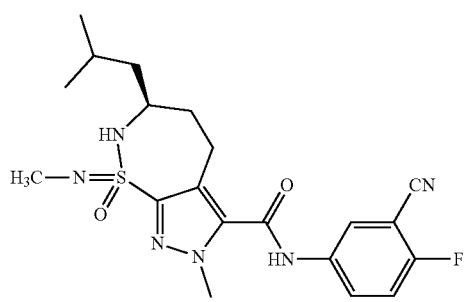 [SMILES: CN=S1(=O)N[C@@H](CC(C)C)CCc2c1nn(C)c2C(=O)Nc1ccc(F)c(C#N)c1] | 433 Peak2 (HPLC) |

BIOLOGICAL EXAMPLE—ANTI-HBV ACTIVITY EXPERIMENT

Experiment 1: In Vitro Anti-HBV Nucleocapsid Assembly Activity Test

Main Reagents and Raw Materials:

C150 protein was expressed and purified by WuXi Apptec Co., Ltd;

BoDIPY® FL was purchased from Thermo Fisher Scientific.

Protein Fluorescent Label:

150 μL of 2% w/v skimmed milk was added into each well of 96-well plate, and incubated at room temperature for 2 hours. The skimmed milk was aspirated. The plate was washed with deionized water and dried, and stored at room temperature. C150 protein (3 mg per tube) was desalted with 5 ml Hitrap desalting column. The desalted C150 protein of each tube was added with 50 mM BoDIPY® FL Fluorescent Dye (20 μl), and incubated under 4° C. overnight in the dark after well mixed. Sephadex G-25 gel was used for filtration to remove fluorescent dyes that were not bounded onto C150. The C150 fluorescent labeling efficiency was calculated according to the following equation:

$$[BoDIPY®FL] = A504/78{,}000\ M^{-1};$$

$$[C150Bo] = (A280 - [BoDIPY®FL] \times 1300\ M^{-1})/60{,}900\ M^{-1};$$

$$\text{Fluorescent Labeling Efficiency} = [BoDIPY®FL]/[C150Bo];$$

wherein,

[BoDIPY®FL] represents the concentration of the fluorescent label;

[C150Bo] represents the concentration of fluorescently labeled protein;

A504 represents the absorbance value at 504 nM wavelength;

A280 represents the absorbance value at 280 nM wavelength;

$M^{-1}$ represents the reciprocal of the molar concentration.

Compound Dilution:

The mother liquor of compound was diluted with DMSO to 6 mM, then diluted to 600 μM with 50 mM HEPES, and then further 3-fold diluted with 10 DMSO/50 mM HEPES to 8 concentrations.

C150Bo was diluted to 2 μM with 50 mM HEPES. 37.5 μL of C150Bo and 2.5 μL of compound at each concentration were added into a 96 well plate and well mixed, then incubated at room temperature for 15 minutes. 10 μl of 750 mM NaCl/50 mM HEPES were added into the each reaction well, and the final concentration of NaCl was 150 mM.

Into the control wells in the 0% protein group 10 μL of 50 mM HEPES was added, and the final concentration of NaCl was 0 mM.

Into the control wells in the 100% protein group 10 μL of 5 M/50 mM HEPES was added, and the final concentration of NaCl was 1 M.

The final concentration of DMSO was 0.5%, the maximum final concentration of the compound was 30 μM, and final concentration of C150Bo was 1.5 μM. The mixture was incubated at room temperature for 1 hour. Fluorescence signal was measured (excitation light was 485 nm; emission light was 535 nm).

Data Analysis

% protein assembly=[1−(Sample fluorescence value−1 M NaCl fluorescence value)/(0 M NaCl fluorescence value−1 M NaCl fluorescence value)]×100.

$IC_{50}$ value was calculated by prism software, and the equation was as follows:

$$Y = \text{Bottom} + (\text{Top} - \text{Bottom})/(1 + 10^{((Log\ IC50-X)*Hillslope)});$$

wherein,

X represents the logarithm of the concentration, Y represents the effect value, and Y starts from the bottom and fits to the top by S type fitting.

Bottom represents the bottom of the curve;

Top represents the top of the curve;

HillSlope represents the absolute value of the maximum slope of the curve.

Experiment 2: Determination of Anti-HBV Activity in HepG2.2.15 Cell

Main Reagents:

QIAamp 96 DNA Blood Kit (12) (Qiagen, Item No. 51162);

FastStart Universal Probe Master (Roche, Item No. 04914058001);

Cell-titer Glo Testing Reagent (Promega, Item No. G7573).

Compound dilution: all the compounds for in vitro anti-HBV activity assay and cytotoxicity assay were 3-fold diluted into 8 concentrations. The final starting concentration of the tested compound was 30 μM, the final starting concentration of reference compound GLS4 was 1 μM, and the final concentration of DMSO was 0.5%.

HepG2.2.15 cells ($4 \times 10^4$ cells/well) was inoculated into 96-well plates and cultured overnight at 37° C., 5% $CO_2$. On the second day, fresh culture medium containing different concentrations of compounds was added into the culture wells. On the fifth day, the old culture solution in the culture well was aspirated and fresh culture medium containing different concentrations of the compound was added.

On the eighth day, the supernatant in the culture well was collected for extraction of HBV DNA, and the content of HBV DNA in the supernatant of HepG2.2.15 was detected by qPCR. After the supernatant was collected, the medium and Cell-titer Glo reagent were added into the culture well, and the chemiluminescence value of each well was measured by microplate reader.

The activity calculation formula was as follows:

$$Y = \text{Bottom} + (\text{Top} - \text{Bottom})/(1 + 10^{((Log\ IC50-X*Hillslope)});$$

wherein,

X represents the logarithm of the concentration, Y represents the effect value, and Y starts from the bottom and fits to the top by S type fitting.

Bottom represents the bottom of the curve;

Top represents the top of the curve;

HillSlope represents the absolute value of the maximum slope of the curve.

Experiment 3: Determination of Cytotoxicity

The cytotoxicity of the test compound was tested using HepG2 cells. The cells were incubated for 4 days in the presence of the test compound. Cell activity was assessed using the resazurin assay.

The results showed that the compound of the present invention had good anti-HBV nucleocapsid assembly activity and anti-HBV activity in vitro, and had low cytotoxicity.

The activity data of experiment 1 to 3 are shown in Table 13:

TABLE 13

| Compound No. | Experiment 1 Protein experiment IC$_{50}$ (μM) | Experiment 2 Cell experiment EC$_{50}$ (nM) | Experiment 3 Cytotoxicity CC$_{50}$ (nM) |
|---|---|---|---|
| 10a1 | ++ | ++ | >30000 |
| 10a2 | ++ | +++ | >30000 |
| 10b1 | ++ | ++ | >30000 |
| 10b2 | ++ | +++ | >30000 |
| 10c1 | ++ | ++ | >30000 |
| 10c2 | ++ | +++ | >30000 |
| 10e1 | ++ | ++ | >30000 |
| 10e2 | ++ | +++ | >30000 |
| 10f1 | ++ | ++ | >30000 |
| 10f2 | ++ | +++ | >30000 |
| 10g1 | ++ | ++ | >30000 |
| 10g2 | ++ | +++ | >30000 |
| 10h1 | ++ | + | >30000 |
| 10h2 | ++ | + | >30000 |
| 10n1 | ++ | ++ | >30000 |
| 10n2 | ++ | +++ | >30000 |
| 10o1 | ++ | ++ | >30000 |
| 10o2 | ++ | +++ | >30000 |
| 10w1 | ++ | ++ | >30000 |
| 10w2 | ++ | +++ | >30000 |
| 10bb1 | ++ | ++ | >30000 |
| 10bb2 | ++ | +++ | >30000 |
| 10cc1 | ++ | ++ | >30000 |
| 10cc2 | ++ | +++ | >30000 |
| 10ccc1 | ++ | ++ | >30000 |
| 10ccc2 | ++ | +++ | >30000 |
| 10ddd1 | ++ | ++ | >30000 |
| 10ddd2 | ++ | +++ | >30000 |
| 10vvv1 | ++ | ++ | >30000 |
| 10vvv2 | ++ | +++ | >30000 |
| 20a1 | ++ | ++ | >30000 |
| 20a2 | ++ | +++ | >30000 |
| 20b1 | ++ | ++ | >30000 |
| 20b2 | ++ | +++ | >30000 |
| 20c1 | ++ | ++ | >30000 |
| 20c2 | ++ | +++ | >30000 |
| 20dd1 | ++ | ++ | >30000 |
| 20dd2 | ++ | +++ | >30000 |
| 20ee1 | ++ | ++ | >30000 |
| 20ee2 | ++ | +++ | >30000 |
| 20ccc1 | ++ | +++ | >30000 |
| 20ccc2 | ++ | +++ | >30000 |
| 20ttt1 | ++ | ++ | >30000 |
| 20ttt2 | ++ | +++ | >30000 |
| 30a1 | ++ | ++ | >30000 |
| 30a2 | ++ | ++ | >30000 |
| 30b1 | ++ | ++ | >30000 |
| 30b2 | ++ | ++ | >30000 |
| 30c1 | ++ | ++ | >30000 |
| 30c2 | ++ | ++ | >30000 |
| 30g1 | ++ | ++ | >30000 |
| 30g2 | ++ | ++ | >30000 |
| 40a1 | ++ | ++ | >30000 |
| 40a2 | ++ | ++ | >30000 |
| 40b1 | ++ | ++ | >30000 |
| 40b2 | ++ | ++ | >30000 |
| 40g1 | ++ | ++ | >30000 |
| 40g2 | ++ | ++ | >30000 |
| 50a1 | ++ | ++ | >30000 |
| 50a2 | ++ | +++ | >30000 |
| 50s1 | ++ | ++ | >30000 |
| 50s2 | ++ | +++ | >30000 |
| 50t1 | ++ | ++ | >30000 |
| 50t2 | ++ | +++ | >30000 |
| 50u1 | ++ | ++ | >30000 |
| 50u2 | ++ | +++ | >30000 |
| 50v1 | ++ | ++ | >30000 |
| 50v2 | ++ | +++ | >30000 |
| 60a1 | ++ | ++ | >30000 |
| 60a2 | ++ | +++ | >30000 |
| 60g1 | ++ | ++ | >30000 |
| 60g2 | ++ | +++ | >30000 |
| 60h1 | ++ | ++ | >30000 |
| 60h2 | ++ | +++ | >30000 |
| 60v1 | ++ | ++ | >30000 |
| 60v2 | ++ | +++ | >30000 |
| 60w1 | ++ | ++ | >30000 |
| 60w2 | ++ | +++ | >30000 |
| 60x1 | ++ | ++ | >30000 |
| 60x2 | ++ | +++ | >30000 |
| 60y1 | ++ | ++ | >30000 |
| 60y2 | ++ | +++ | >30000 |
| 70a1 | ++ | ++ | >30000 |
| 70a2 | ++ | +++ | >30000 |
| 70b1 | ++ | ++ | >30000 |
| 70b2 | ++ | +++ | >30000 |
| 80a1 | ++ | ++ | >30000 |
| 80a2 | ++ | +++ | >30000 |
| 80b1 | ++ | ++ | >30000 |
| 80b2 | ++ | +++ | >30000 |
| 90a1 | ++ | ++ | >30000 |
| 90a2 | ++ | +++ | >30000 |
| 90b1 | ++ | ++ | >30000 |
| 90b2 | ++ | +++ | >30000 |

In the table:
+++ indicates IC$_{50}$ <1 μM;
++ indicates that IC$_{50}$ is 1~100 μM;
+ indicates that IC$_{50}$ is >100 μM.
++++ indicates EC$_{50}$ <0.1 nM;
+++ indicates EC$_{50}$ is 0.1~100 nM;
++ indicates that EC$_{50}$ is 100~1000 nM;
+ indicates that EC$_{50}$ is >1000 nM.

Therefore, the compounds of the present application have excellent anti-HBV activity.

Meanwhile, for the compound of the present invention, after being separated by HPLC, the two configuration of compounds based on the chiral sulfur atom center (that is, the S atom in O=S=N—R6) can be effectively separated. The inventors have unexpectedly founded that, between the two configuration compounds based on the chiral sulfur atom center, the enantiomer with less polarity has significantly higher activity against HBV nucleocapsid than the enantiomer with greater polarity, and in some embodiments, and the difference in activity can reach up to several times.

Experiment 4 Example of Mouse PK Experiment 18 male C57 mice (9 intravenously administrated and 9 orally administrated) were randomly grouped according to body weight, and were administered with the test compounds at 2 mg/kg (intravenous) and 50 mg/kg (oral). 3 mice were taken at each time point in each group for a total of 8 time points (5 minutes, 15 minutes, 30 minutes, 1 hour, 2 hours, 4 hours, 8 hours, and 24 hours). The calculation method of oral bioavailability F was AUC$_{po}$/Dose$_{po}$/AUC$_{iv}$/Dose$_{iv}$.

The compound of the present invention was administrated, and the result showed that each compound showed good bioavailability in in vivo experiments, and the bioavailability of some compounds have reached or exceeded 70%.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:
1. A compound represented by formula L, or a stereoisomer or tautomer thereof, or a pharmaceutically acceptable salt, hydrate or solvate thereof,

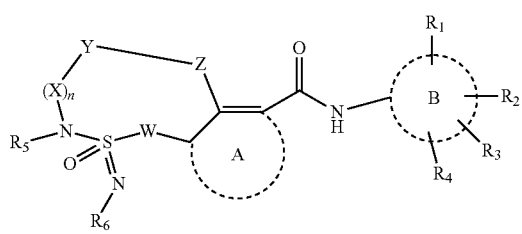

wherein n is 1, 2, 3, 4, 5, 6, 7, 8, 9, or 10;

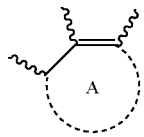

is a substituted or unsubstituted five or six membered ring, wherein the five or six membered ring optionally contains one or more heteroatoms selected from the group consisting of O, S, N or P; the substituted means that the hydrogen atoms on the group are substituted by one or more substituents selected from the group consisting of C1-C3 alkyl, C3-C4 cycloalkyl, cyano, or halogen;

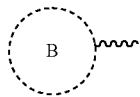

is a substituted or unsubstituted five- or six-membered aromatic ring, or a substituted or unsubstituted five- or six-membered heteroaromatic ring;
X is —$CR^aR^b$—;
Y is substituted or unsubstituted C1-C7 alkylene, or substituted or unsubstituted C2-C7 alkenylene, wherein the substituent is selected from the group consisting of C1-C4 alkyl, hydroxyl;
Z is selected from the group consisting of O, S, N, and P, or Z is a C—C single bond;
W is NRc or none;
$R_1$, $R_2$, $R_3$ and $R_4$ are each independently selected from the group consisting of H, halogen, cyano, substituted or unsubstituted C3-C4 cycloalkyl, substituted or unsubstituted C1-C4 alkyl, substituted or unsubstituted C1-C4 alkoxy; wherein the substituted means that hydrogen atoms on the group are substituted by one or more substituents selected from the group consisting of halogen and C1-C4 alkyl;
$R_5$ and $R_6$ are each independently selected from the group consisting of H, halogen, —CN, hydroxyl, amino, carboxyl, —(C=O)-substituted or unsubstituted $C_1$-$C_8$ alkyl, substituted or unsubstituted $C_1$-$C_8$ alkyl, substituted or unsubstituted $C_2$-$C_6$ alkenyl, substituted or unsubstituted $C_2$-$C_6$ alkynyl, substituted or unsubstituted $C_1$-$C_8$ alkylamino, substituted or unsubstituted $C_1$-$C_8$ alkoxy, substituted or unsubstituted $C_3$-$C_{10}$ cycloalkyl, substituted or unsubstituted 3-10 membered heterocycloalkyl having 1-3 heteroatoms selected from the group consisting of N, S and O, substituted or unsubstituted $C_6$-$C_{10}$ aryl, and substituted or unsubstituted 5-10 membered heteroaryl having 1-3 heteroatoms selected from the group consisting of N, S and O;
$R^a$ and $R^b$ are each independently H, halogen, —CN, hydroxyl, amino, carboxyl, —(C=O)— substituted or unsubstituted $C_1$-$C_8$ alkyl, substituted or unsubstituted $C_1$-$C_8$ alkyl, substituted or unsubstituted $C_2$-$C_6$ alkenyl, substituted or unsubstituted $C_2$-$C_6$ alkynyl, substituted or unsubstituted $C_1$-$C_8$ alkylamino, substituted or unsubstituted $C_1$-$C_8$ alkoxy, substituted or unsubstituted $C_1$-$C_6$ alkoxy-alkyl, substituted or unsubstituted $C_3$-$C_{10}$ cycloalkyl, substituted or unsubstituted 3-10 membered heterocycloalkyl having 1-3 heteroatoms selected from the group consisting of N, S and O, substituted or unsubstituted $C_6$-$C_{10}$ aryl, or substituted or unsubstituted 5-10 membered heteroaryl having 1-3 heteroatoms selected from the group consisting of N, S and O;
Rc is H, halogen, —CN, hydroxyl, amino, carboxyl, —(C=O)-substituted or unsubstituted $C_1$-$C_8$ alkyl, substituted or unsubstituted $C_1$-$C_8$ alkyl, substituted or unsubstituted $C_2$-$C_6$ alkenyl, substituted or unsubstituted $C_2$-$C_6$ alkynyl, substituted or unsubstituted $C_1$-$C_8$ alkylamino, substituted or unsubstituted $C_1$-$C_8$ alkoxy, substituted or unsubstituted $C_3$-$C_{10}$ cycloalkyl, substituted or unsubstituted 3-10 membered heterocycloalkyl having 1-3 heteroatoms selected from the group consisting of N, S and O, substituted or unsubstituted $C_6$-$C_{10}$ aryl, or substituted or unsubstituted 5-10 membered heteroaryl having 1-3 heteroatoms selected from the group consisting of N, S and O;
"substituted" means that the group substituted by one or more substituents selected from the group consisting of halogen, C1-C6 alkyl, halogenated C1-C6 alkyl, C1-C6 alkoxy, halogenated C1-C6 alkoxy, C3-C8 cycloalkyl, halogenated C3-C8 cycloalkyl, oxo, —CN, hydroxyl, amino, carboxyl, and the following groups unsubstituted or substituted by one or more substituents: C6-C10 aryl, halogenated C6-C10 aryl, 5-10 membered heteroaryl having 1-3 heteroatoms selected from the group consisting of N, S and O, halogenated 5-10 membered heteroaryl having 1-3 heteroatoms selected from N, S and O; and
the substituent is selected from the group consisting of halogen and C1-C6 alkoxy.
2. The compound of claim 1, or a stereoisomer or tautomer thereof, or a pharmaceutically acceptable salt, hydrate or solvate thereof, wherein the compound is of a formula selected from the group consisting of L-1, L-2, L-3 and L-4:

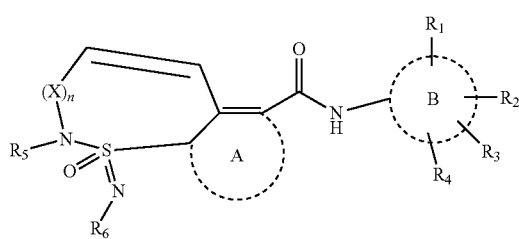

-continued

L-2

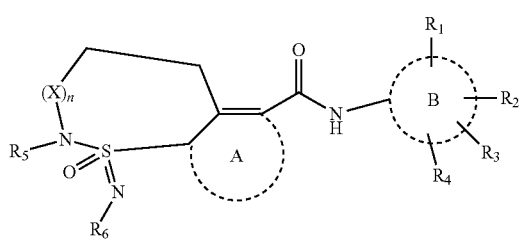

L-3

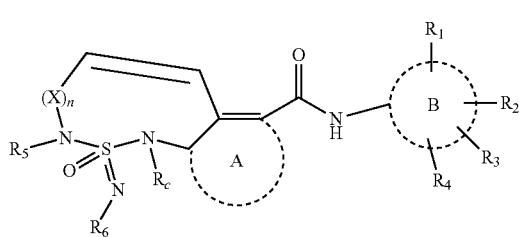

L-4

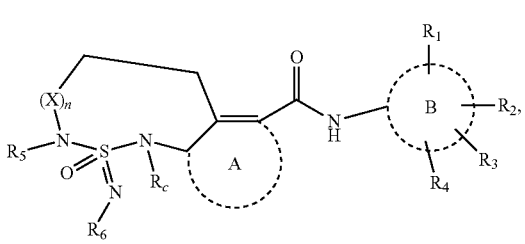

in each formula, n is 1, 2, 3, 4, 5, 6, 7, 8, 9, or 10;

the definitions of A ring, B ring, X, $R_1$, $R_2$, $R_3$, $R_4$, $R_5$, and $R_6$ are as described in claim 1.

3. The compound of claim 1, or a stereoisomer or tautomer thereof, or a pharmaceutically acceptable salt, hydrate or solvate thereof, wherein the compound of formula I has a structure shown in the following formula II:

II

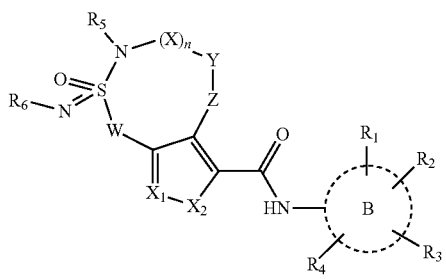

wherein $X_1$ is —CR= or —N=, $X_2$ is —NR—; and R is H or C1-C4 alkyl.

4. The compound of claim 1, or a stereoisomer or tautomer thereof, or a pharmaceutically acceptable salt, hydrate or solvate thereof, wherein the $X_2$ is —$NCH_3$—.

5. The compound of claim 1, or a stereoisomer or tautomer thereof, or a pharmaceutically acceptable salt, hydrate or solvate thereof, wherein the compound of formula I has the following structure:

III

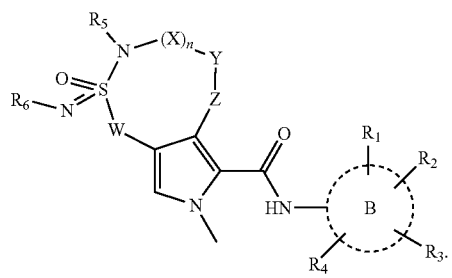

6. The compound of claim 1, or a stereoisomer or tautomer thereof, or a pharmaceutically acceptable salt, hydrate or solvate thereof, wherein the compound of formula I has a structure shown by the following formula IV-1 or IV-2:

IV-1

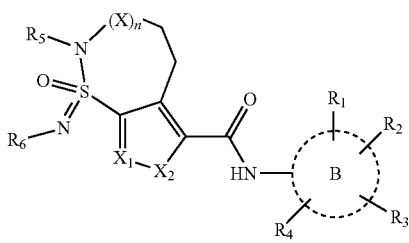

IV-2

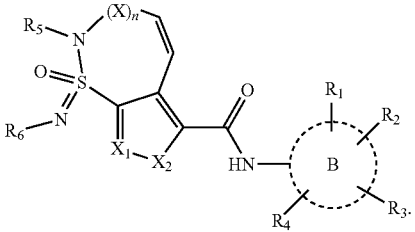

7. The compound of claim 1, or a stereoisomer or tautomer thereof, or a pharmaceutically acceptable salt, hydrate or solvate thereof, wherein $R^a$ is selected from the group consisting of substituted or unsubstituted $C_1$-$C_8$ alkyl, substituted or unsubstituted $C_1$-$C_8$ alkoxy, and substituted or unsubstituted C1-C6 alkoxy-alkyl; and $R^b$ is H.

8. The compound of claim 1, or a stereoisomer or tautomer thereof, or a pharmaceutically acceptable salt, hydrate or solvate thereof, wherein the compound is selected from the following:

| No. | Structure | Remark |
|---|---|---|
| 10a1 | 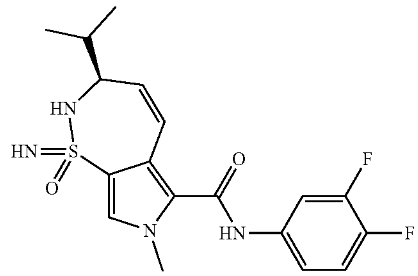 | Peak1 (HPLC) |
| 10a2 | 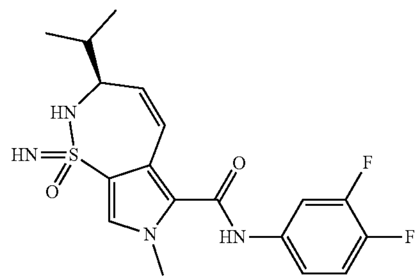 [SMILES: CC(C)[C@H]1C=Cc2c(cn(C)c2C(=O)Nc2ccc(F)c(F)c2)S(=N)(=O)N1] | Peak2 (HPLC) |
| 10b1 | 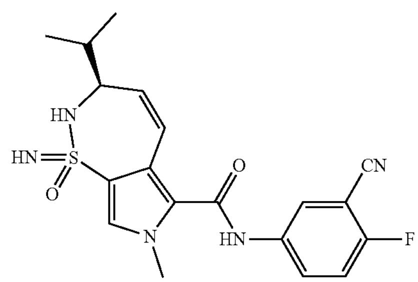 [SMILES: CC(C)[C@H]1C=Cc2c(cn(C)c2C(=O)Nc2ccc(F)c(C#N)c2)S(=N)(=O)N1] | Peak1 (HPLC) |
| 10b2 | 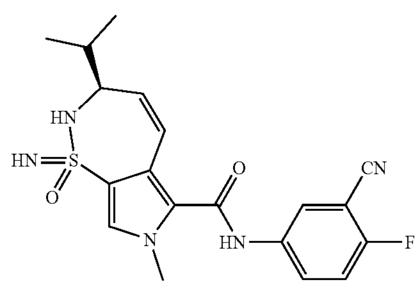 [SMILES: CC(C)[C@H]1C=Cc2c(cn(C)c2C(=O)Nc2ccc(F)c(C#N)c2)S(=N)(=O)N1] | Peak2 (HPLC) |
| 10c1 | 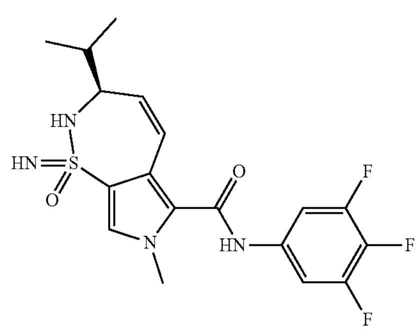 [SMILES: CC(C)[C@H]1C=Cc2c(cn(C)c2C(=O)Nc2cc(F)c(F)c(F)c2)S(=N)(=O)N1] | Peak1 (HPLC) |

-continued

| No. | Structure | Remark |
|---|---|---|
| 10c2 | 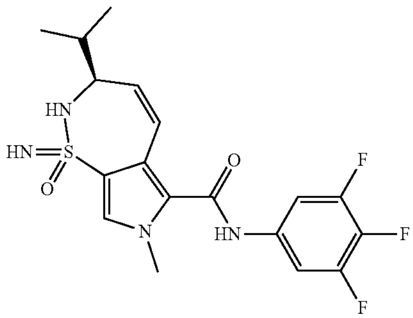 [SMILES: CC(C)[C@H]1C=Cc2c(cn(C)c2C(=O)Nc2cc(F)c(F)c(F)c2)S(=N)(=O)N1] | Peak2 (HPLC) |
| 10d1 | 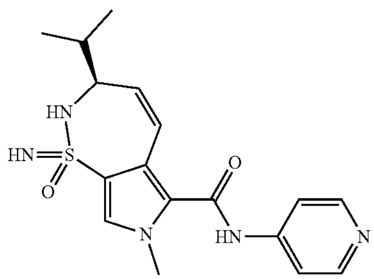 [SMILES: CC(C)[C@H]1C=Cc2c(cn(C)c2C(=O)Nc2ccncc2)S(=N)(=O)N1] | Peak1 (HPLC) |
| 10d2 | 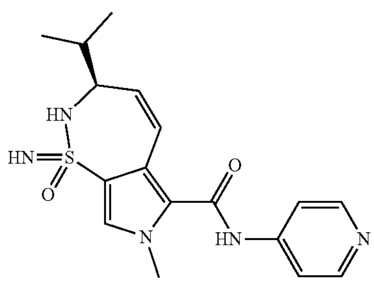 | Peak2 (HPLC) |
| 10e1 | 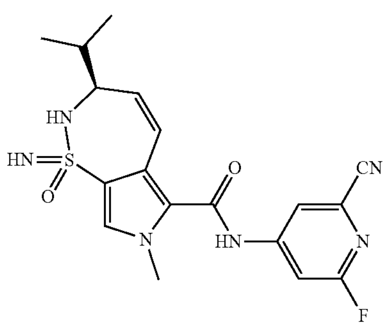 [SMILES: CC(C)[C@H]1C=Cc2c(cn(C)c2C(=O)Nc2cc(F)nc(C#N)c2)S(=N)(=O)N1] | Peak1 (HPLC) |
| 10e2 | 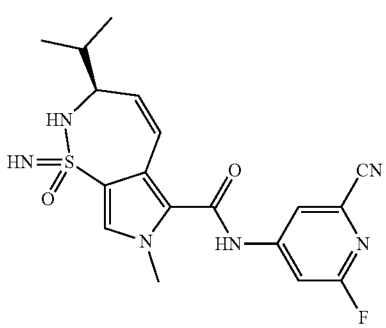 [SMILES: CC(C)[C@H]1C=Cc2c(cn(C)c2C(=O)Nc2cc(F)nc(C#N)c2)S(=N)(=O)N1] | Peak2 (HPLC) |

-continued
| No. | Structure | Remark |
|---|---|---|
| 10f1 | 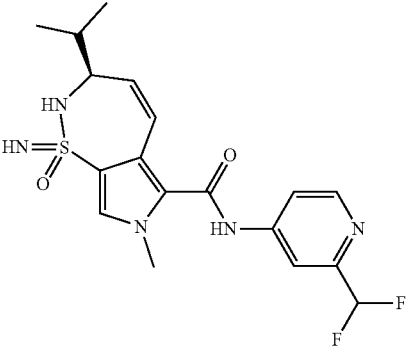 [SMILES: CC(C)[C@H]1C=Cc2c(cn(C)c2C(=O)Nc2ccnc(C(F)F)c2)S(=N)(=O)N1] | Peak1 (HPLC) |
| 10f2 | 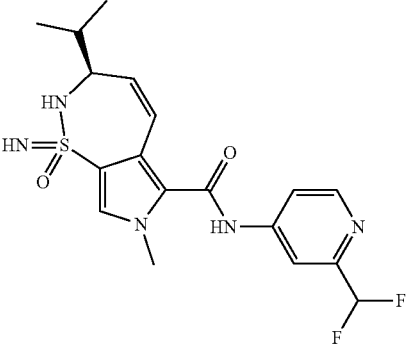 [SMILES: CC(C)[C@H]1C=Cc2c(cn(C)c2C(=O)Nc2ccnc(C(F)F)c2)S(=N)(=O)N1] | Peak2 (HPLC) |
| 10g1 | 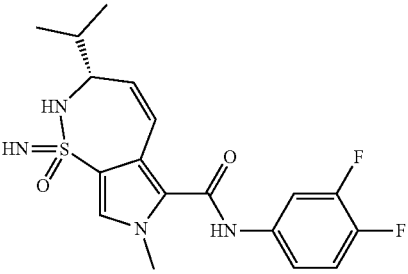 [SMILES: CC(C)[C@@H]1C=Cc2c(cn(C)c2C(=O)Nc2ccc(F)c(F)c2)S(=N)(=O)N1] | Peak1 (HPLC) |
| 10g2 | 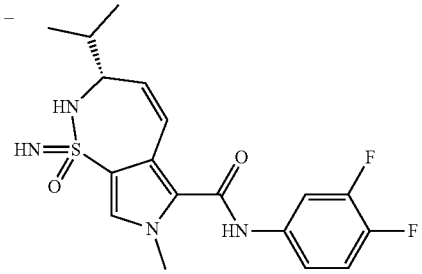 | Peak2 (HPLC) |
| 10h1 | 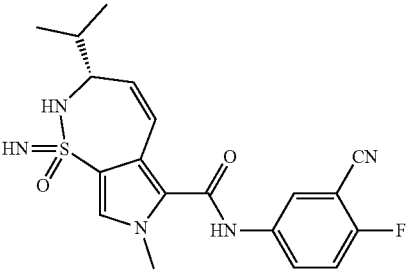 [SMILES: CC(C)[C@@H]1C=Cc2c(cn(C)c2C(=O)Nc2ccc(F)c(C#N)c2)S(=N)(=O)N1] | Peak1 (HPLC) |

| No. | Structure | Remark |
|---|---|---|
| 10h2 | 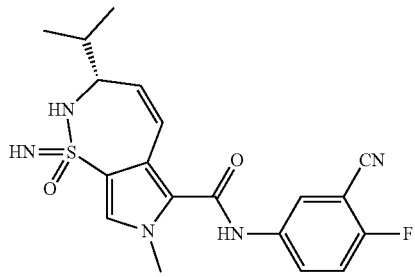 | Peak2 (HPLC) |
| 10i1 | 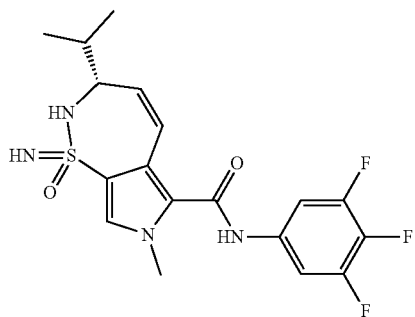 [SMILES: CC(C)[C@@H]1C=Cc2c(cn(C)c2C(=O)Nc2cc(F)c(F)c(F)c2)S(=N)(=O)N1] | Peak1 (HPLC) |
| 10i2 | 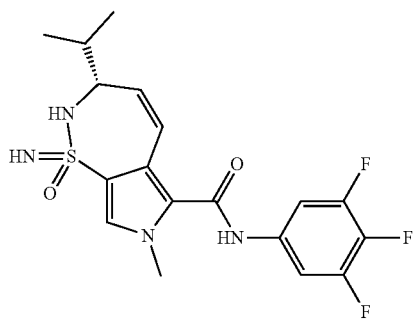 [SMILES: CC(C)[C@@H]1C=Cc2c(cn(C)c2C(=O)Nc2cc(F)c(F)c(F)c2)S(=N)(=O)N1] | Peak2 (HPLC) |
| 10j1 | 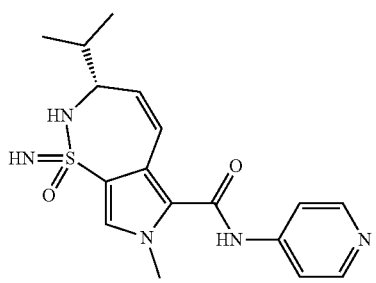 [SMILES: CC(C)[C@@H]1C=Cc2c(cn(C)c2C(=O)Nc2ccncc2)S(=N)(=O)N1] | Peak1 (HPLC) |
| 10j2 | 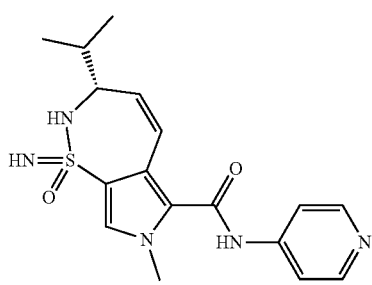 [SMILES: CC(C)[C@@H]1C=Cc2c(cn(C)c2C(=O)Nc2ccncc2)S(=N)(=O)N1] | Peak2 (HPLC) |

-continued
| No. | Structure | Remark |
|---|---|---|
| 10k1 | 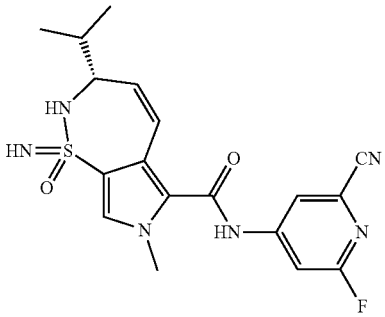 [SMILES: CC(C)[C@@H]1C=Cc2c(cn(C)c2C(=O)Nc2cc(F)nc(C#N)c2)S(=N)(=O)N1] | Peak1 (HPLC) |
| 10k2 | 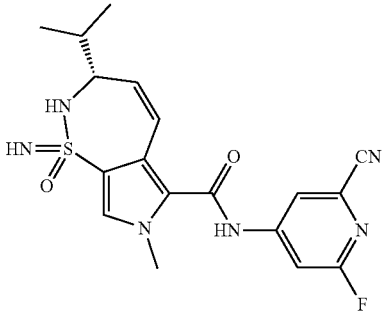 [SMILES: CC(C)[C@@H]1C=Cc2c(cn(C)c2C(=O)Nc2cc(F)nc(C#N)c2)S(=N)(=O)N1] | Peak2 (HPLC) |
| 10m1 | 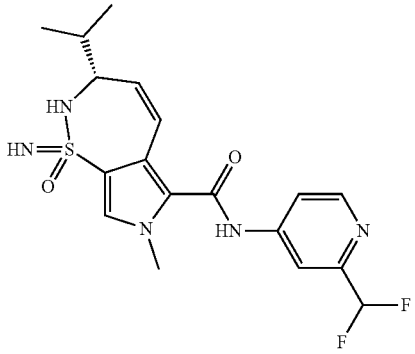 [SMILES: CC(C)[C@@H]1C=Cc2c(cn(C)c2C(=O)Nc2ccnc(C(F)F)c2)S(=N)(=O)N1] | Peak1 (HPLC) |
| 10m2 | 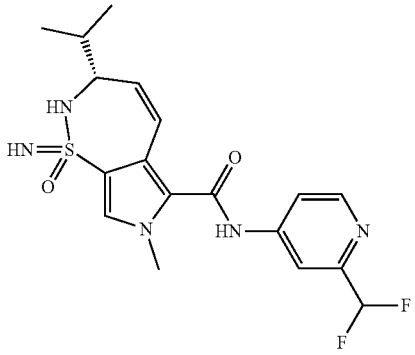 [SMILES: CC(C)[C@@H]1C=Cc2c(cn(C)c2C(=O)Nc2ccnc(C(F)F)c2)S(=N)(=O)N1] | Peak2 (HPLC) |

-continued

| No. | Structure | Remark |
|---|---|---|
| 10n1 | 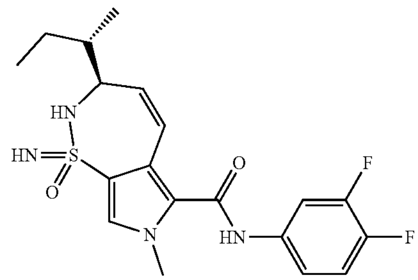 [SMILES: CC[C@H](C)[C@H]1C=Cc2c(cn(C)c2C(=O)Nc2ccc(F)c(F)c2)S(=N)(=O)N1] | Peak1 (HPLC) |
| 10n2 | 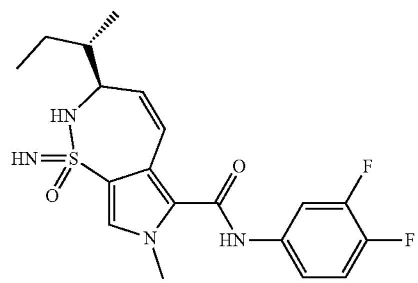 [SMILES: CC[C@H](C)[C@H]1C=Cc2c(cn(C)c2C(=O)Nc2ccc(F)c(F)c2)S(=N)(=O)N1] | Peak2 (HPLC) |
| 10o1 | 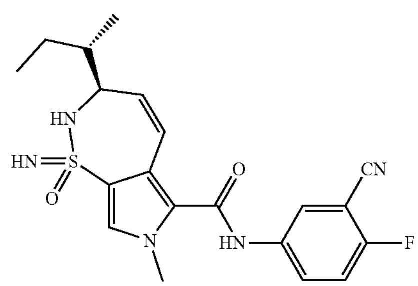 [SMILES: CC[C@H](C)[C@H]1C=Cc2c(cn(C)c2C(=O)Nc2ccc(F)c(C#N)c2)S(=N)(=O)N1] | Peak1 (HPLC) |
| 10o2 | 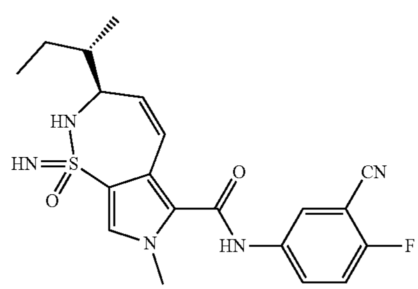 [SMILES: CC[C@H](C)[C@H]1C=Cc2c(cn(C)c2C(=O)Nc2ccc(F)c(C#N)c2)S(=N)(=O)N1] | Peak2 (HPLC) |
| 10p1 | 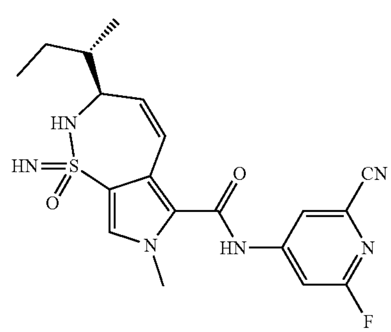 [SMILES: CC[C@H](C)[C@H]1C=Cc2c(cn(C)c2C(=O)Nc2cc(F)nc(C#N)c2)S(=N)(=O)N1] | Peak1 (HPLC) |

| No. | Structure | Remark |
|---|---|---|
| 10p2 | 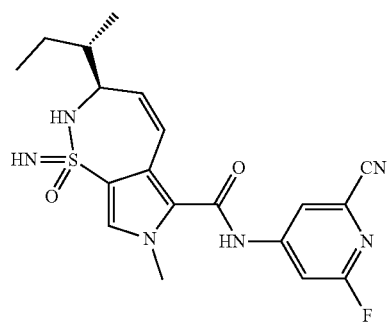 [SMILES: CC[C@H](C)[C@H]1C=Cc2c(cn(C)c2C(=O)Nc2cc(F)nc(C#N)c2)S(=N)(=O)N1] | Peak2 (HPLC) |
| 10q1 | 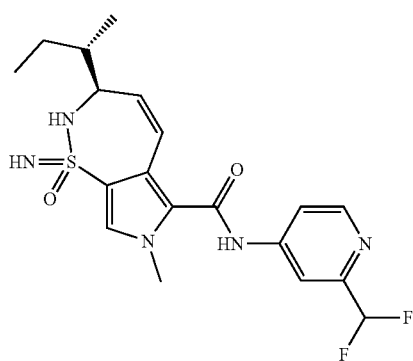 [SMILES: CC[C@H](C)[C@H]1C=Cc2c(cn(C)c2C(=O)Nc2ccnc(C(F)F)c2)S(=N)(=O)N1] | Peak1 (HPLC) |
| 10q2 | 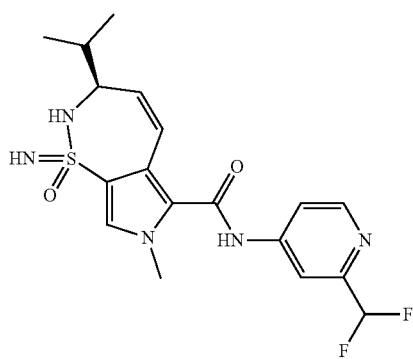 [SMILES: CC(C)[C@H]1C=Cc2c(cn(C)c2C(=O)Nc2ccnc(C(F)F)c2)S(=N)(=O)N1] | Peak2 (HPLC) |
| 10r1 | 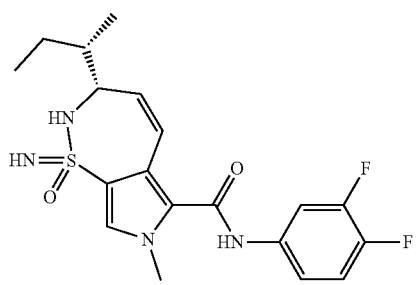 [SMILES: CC[C@H](C)[C@@H]1C=Cc2c(cn(C)c2C(=O)Nc2ccc(F)c(F)c2)S(=N)(=O)N1] | Peak1 (HPLC) |

-continued

| No. | Structure | Remark |
|---|---|---|
| 10r2 | 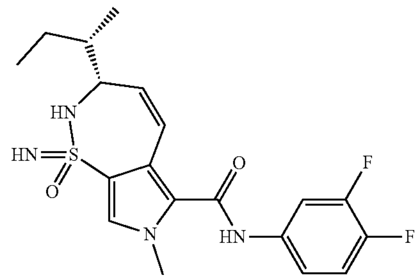 [SMILES: CC[C@H](C)[C@@H]1C=Cc2c(cn(C)c2C(=O)Nc2ccc(F)c(F)c2)S(=N)(=O)N1] | Peak2 (HPLC) |
| 10s1 | 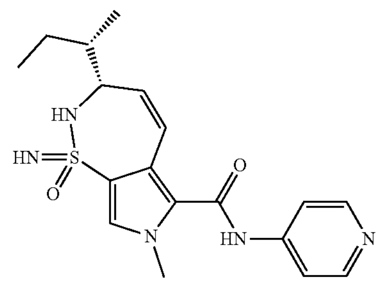 [SMILES: CC[C@H](C)[C@@H]1C=Cc2c(cn(C)c2C(=O)Nc2ccncc2)S(=N)(=O)N1] | Peak1 (HPLC) |
| 10s2 | 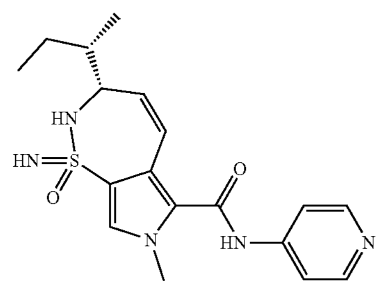 [SMILES: CC[C@H](C)[C@@H]1C=Cc2c(cn(C)c2C(=O)Nc2ccncc2)S(=N)(=O)N1] | Peak2 (HPLC) |
| 10t1 | 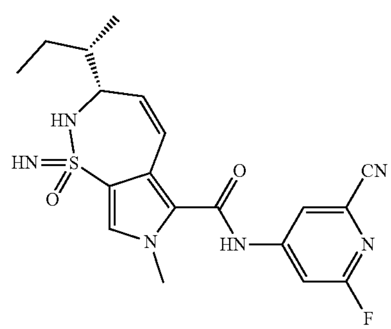 [SMILES: CC[C@H](C)[C@@H]1C=Cc2c(cn(C)c2C(=O)Nc2cc(F)nc(C#N)c2)S(=N)(=O)N1] | Peak1 (HPLC) |
| 10t2 | 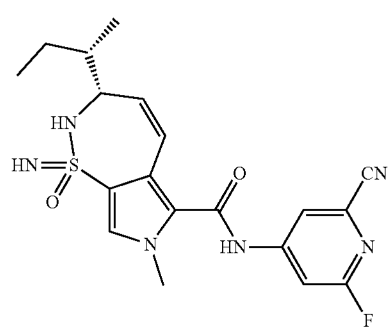 [SMILES: CC[C@H](C)[C@@H]1C=Cc2c(cn(C)c2C(=O)Nc2cc(F)nc(C#N)c2)S(=N)(=O)N1] | Peak2 (HPLC) |

-continued

| No. | Structure | Remark |
|---|---|---|
| 10u1 | 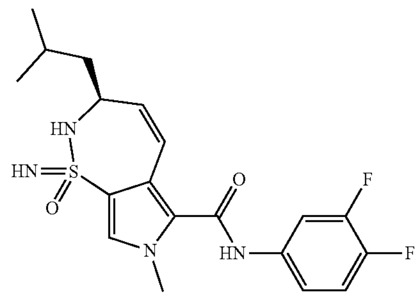 [SMILES: CC(C)C[C@H]1C=Cc2c(cn(C)c2C(=O)Nc2ccc(F)c(F)c2)S(=N)(=O)N1] | Peak1 (HPLC) |
| 10u2 | 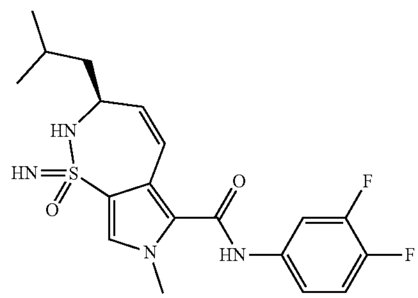 [SMILES: CC(C)C[C@H]1C=Cc2c(cn(C)c2C(=O)Nc2ccc(F)c(F)c2)S(=N)(=O)N1] | Peak2 (HPLC) |
| 10v1 | 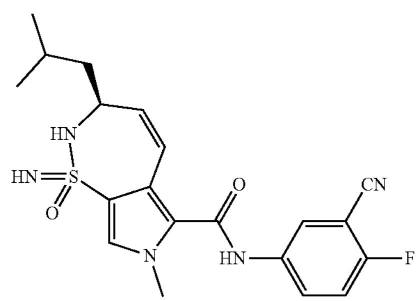 [SMILES: CC(C)C[C@H]1C=Cc2c(cn(C)c2C(=O)Nc2ccc(F)c(C#N)c2)S(=N)(=O)N1] | Peak1 (HPLC) |
| 10v2 | 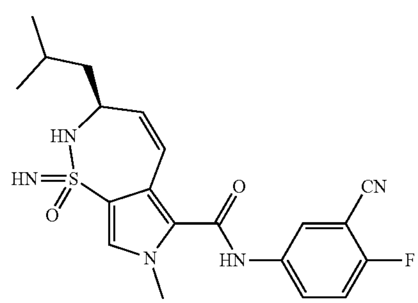 [SMILES: CC(C)C[C@H]1C=Cc2c(cn(C)c2C(=O)Nc2ccc(F)c(C#N)c2)S(=N)(=O)N1] | Peak2 (HPLC) |
| 10w1 | 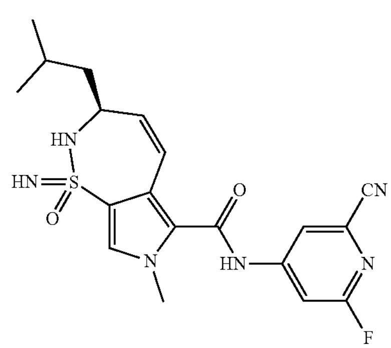 [SMILES: CC(C)C[C@H]1C=Cc2c(cn(C)c2C(=O)Nc2cc(F)nc(C#N)c2)S(=N)(=O)N1] | Peak1 (HPLC) |

| No. | Structure | Remark |
| --- | --- | --- |
| 10w2 | 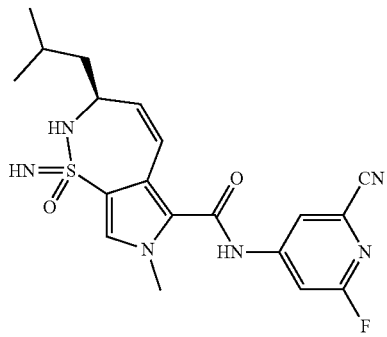 [SMILES: CC(C)C[C@H]1C=Cc2c(cn(C)c2C(=O)Nc2cc(F)nc(C#N)c2)S(=N)(=O)N1] | Peak2 (HPLC) |
| 10x1 | 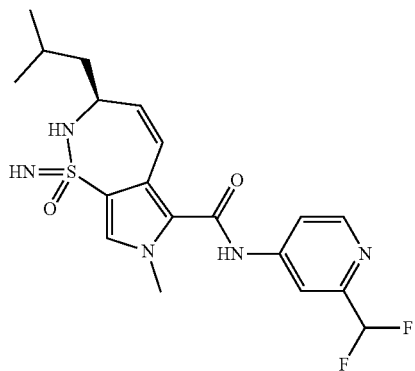 [SMILES: CC(C)C[C@H]1C=Cc2c(cn(C)c2C(=O)Nc2ccnc(C(F)F)c2)S(=N)(=O)N1] | Peak1 (HPLC) |
| 10x2 | 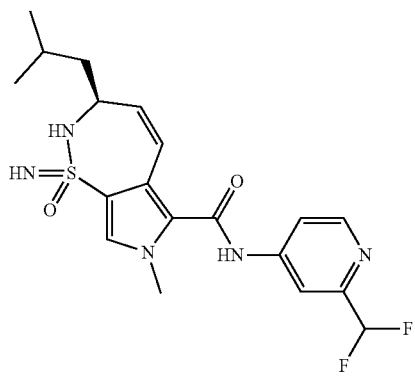 [SMILES: CC(C)C[C@H]1C=Cc2c(cn(C)c2C(=O)Nc2ccnc(C(F)F)c2)S(=N)(=O)N1] | Peak2 (HPLC) |
| 10y1 | 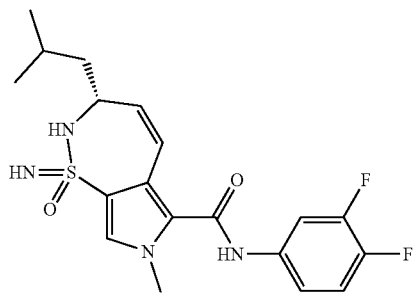 [SMILES: CC(C)C[C@@H]1C=Cc2c(cn(C)c2C(=O)Nc2ccc(F)c(F)c2)S(=N)(=O)N1] | Peak1 (HPLC) |

-continued
| No. | Structure | Remark |
|---|---|---|
| 10y2 | 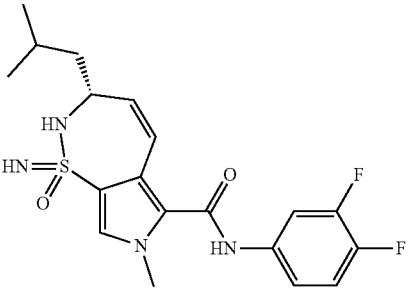 [SMILES: CC(C)C[C@@H]1C=Cc2c(cn(C)c2C(=O)Nc2ccc(F)c(F)c2)S(=N)(=O)N1] | Peak2 (HPLC) |
| 10z1 | 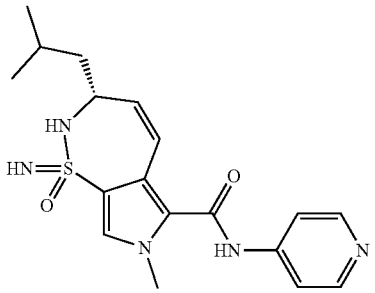 [SMILES: CC(C)C[C@@H]1C=Cc2c(cn(C)c2C(=O)Nc2ccncc2)S(=N)(=O)N1] | Peak1 (HPLC) |
| 10z2 | 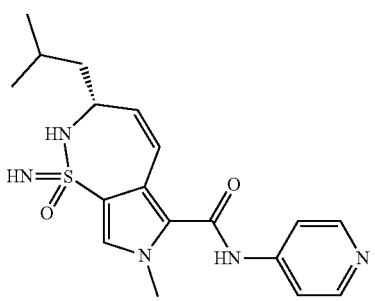 [SMILES: CC(C)C[C@@H]1C=Cc2c(cn(C)c2C(=O)Nc2ccncc2)S(=N)(=O)N1] | Peak2 (HPLC) |
| 10aa1 | 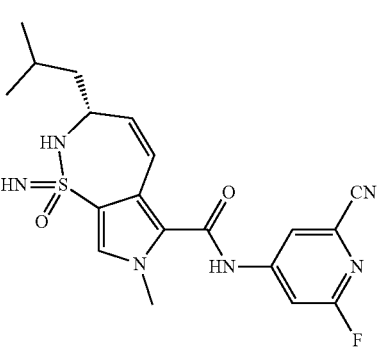 [SMILES: CC(C)C[C@@H]1C=Cc2c(cn(C)c2C(=O)Nc2cc(F)nc(C#N)c2)S(=N)(=O)N1] | Peak1 (HPLC) |
| 10aa2 | 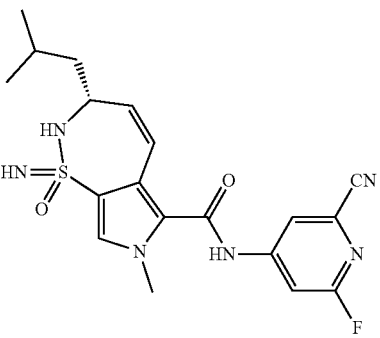 [SMILES: CC(C)C[C@@H]1C=Cc2c(cn(C)c2C(=O)Nc2cc(F)nc(C#N)c2)S(=N)(=O)N1] | Peak2 (HPLC) |

-continued
| No. | Structure | Remark |
|---|---|---|
| 10bb1 | 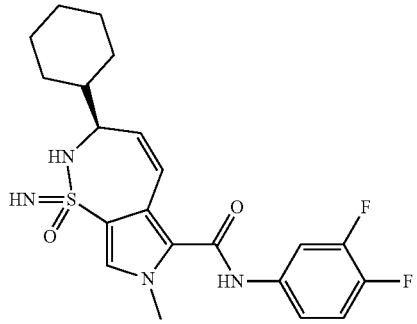 [SMILES: Cn1cc2c(c1C(=O)Nc1ccc(F)c(F)c1)C=C[C@H](C1CCCCC1)NS2(=N)=O] | Peak1 (HPLC) |
| 10bb2 | 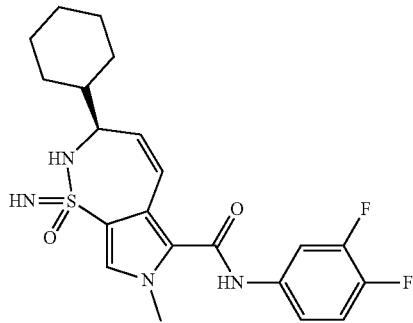 [SMILES: Cn1cc2c(c1C(=O)Nc1ccc(F)c(F)c1)C=C[C@H](C1CCCCC1)NS2(=N)=O] | Peak2 (HPLC) |
| 10cc1 | 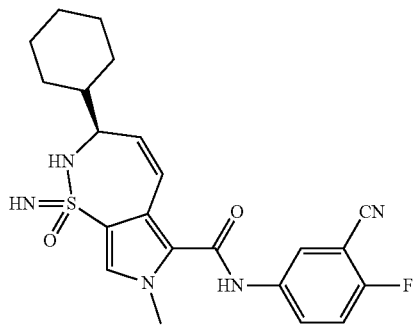 [SMILES: Cn1cc2c(c1C(=O)Nc1ccc(F)c(C#N)c1)C=C[C@H](C1CCCCC1)NS2(=N)=O] | Peak1 (HPLC) |
| 10cc2 | 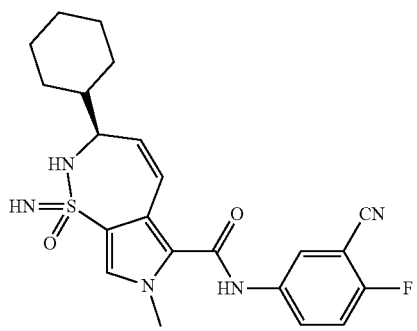 [SMILES: Cn1cc2c(c1C(=O)Nc1ccc(F)c(C#N)c1)C=C[C@H](C1CCCCC1)NS2(=N)=O] | Peak2 (HPLC) |

-continued

| No. | Structure | Remark |
|---|---|---|
| 10dd1 | 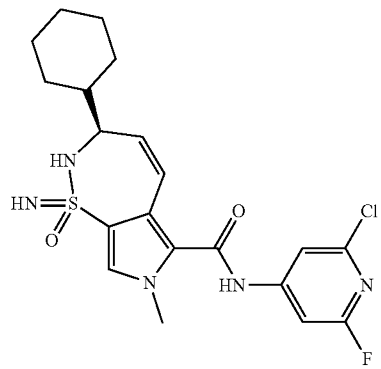 [SMILES: Cn1cc2c(c1C(=O)Nc1cc(F)nc(Cl)c1)C=C[C@H](C1CCCCC1)NS2(=N)=O] | Peak1 (HPLC) |
| 10dd2 | 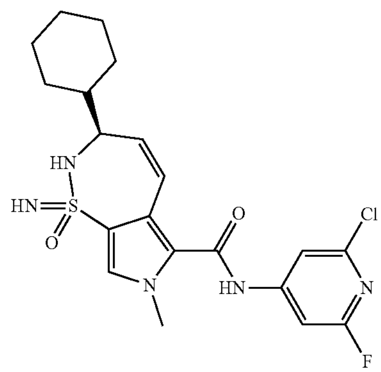 [SMILES: Cn1cc2c(c1C(=O)Nc1cc(F)nc(Cl)c1)C=C[C@H](C1CCCCC1)NS2(=N)=O] | Peak2 (HPLC) |
| 10ee1 | 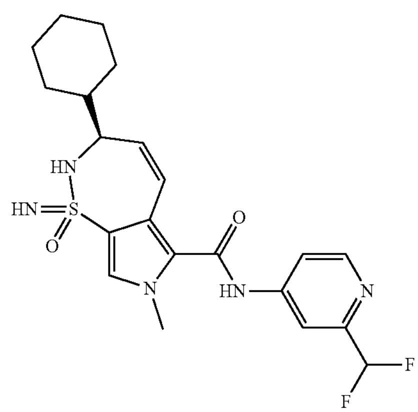 [SMILES: Cn1cc2c(c1C(=O)Nc1ccnc(C(F)F)c1)C=C[C@H](C1CCCCC1)NS2(=N)=O] | Peak1 (HPLC) |
| 10ee2 | 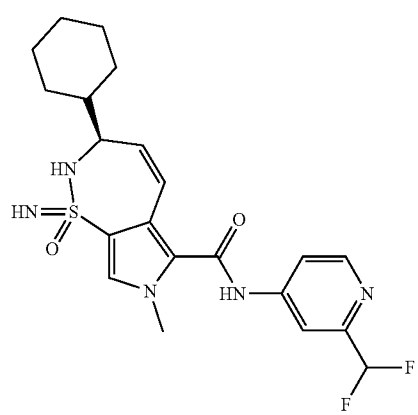 [SMILES: Cn1cc2c(c1C(=O)Nc1ccnc(C(F)F)c1)C=C[C@H](C1CCCCC1)NS2(=N)=O] | Peak2 (HPLC) |

|No.|Structure|Remark|
|---|---|---|
|10ff1|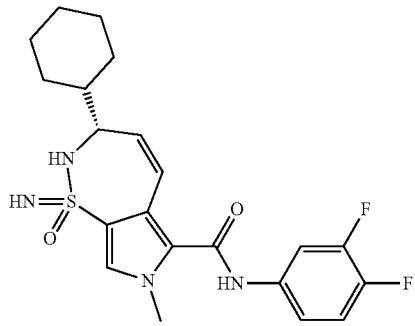 [SMILES: Cn1cc2c(c1C(=O)Nc1ccc(F)c(F)c1)C=C[C@@H](C1CCCCC1)NS2(=N)=O]|Peak1 (HPLC)|
|10ff2|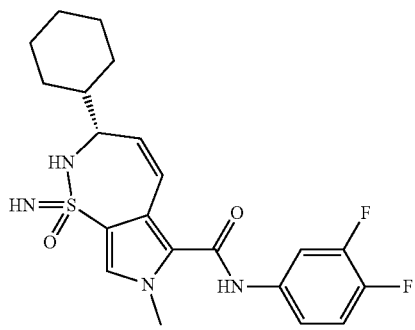 [SMILES: Cn1cc2c(c1C(=O)Nc1ccc(F)c(F)c1)C=C[C@@H](C1CCCCC1)NS2(=N)=O]|Peak2 (HPLC)|
|10gg1|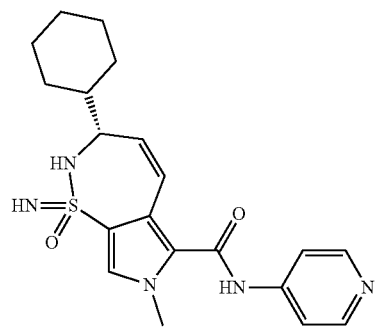 [SMILES: Cn1cc2c(c1C(=O)Nc1ccncc1)C=C[C@@H](C1CCCCC1)NS2(=N)=O]|Peak1 (HPLC)|
|10gg2|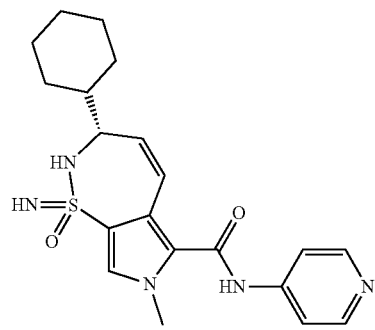 [SMILES: Cn1cc2c(c1C(=O)Nc1ccncc1)C=C[C@@H](C1CCCCC1)NS2(=N)=O]|Peak2 (HPLC)|

| No. | Structure | Remark |
|---|---|---|
| 10hh1 | 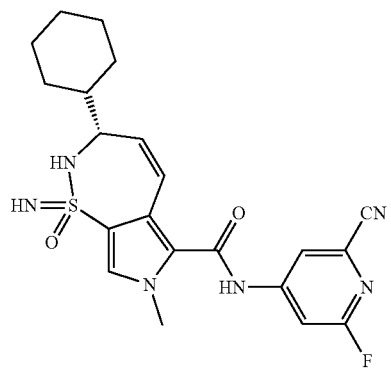 [SMILES: Cn1cc2c(c1C(=O)Nc1cc(F)nc(C#N)c1)C=C[C@@H](C1CCCCC1)NS2(=N)=O] | Peak1 (HPLC) |
| 10hh2 | 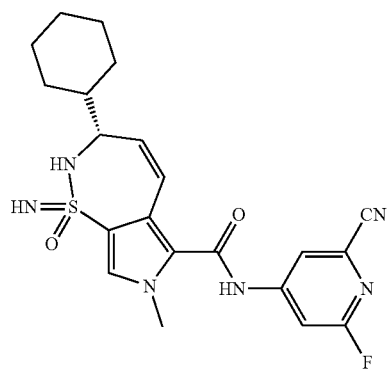 [SMILES: Cn1cc2c(c1C(=O)Nc1cc(F)nc(C#N)c1)C=C[C@@H](C1CCCCC1)NS2(=N)=O] | Peak2 (HPLC) |
| 10ii1 | 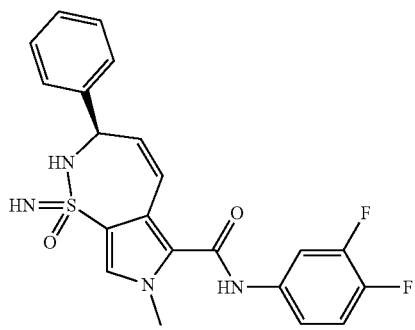 [SMILES: Cn1cc2c(c1C(=O)Nc1ccc(F)c(F)c1)C=C[C@H](c1ccccc1)NS2(=N)=O] | Peak1 (HPLC) |
| 10ii2 | 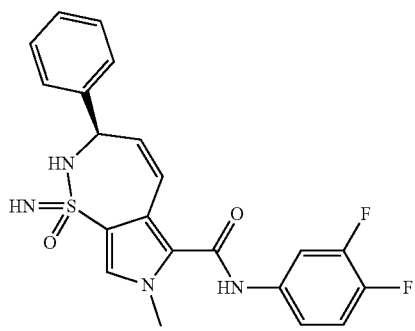 [SMILES: Cn1cc2c(c1C(=O)Nc1ccc(F)c(F)c1)C=C[C@H](c1ccccc1)NS2(=N)=O] | Peak2 (HPLC) |

-continued

| No. | Structure | Remark |
|---|---|---|
| 10ji1 | 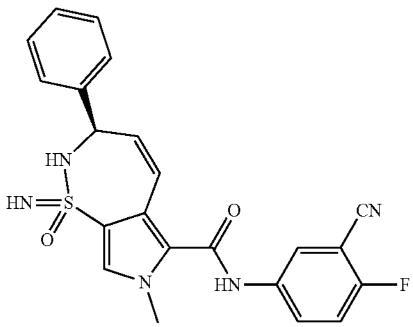 [SMILES: Cn1cc2c(c1C(=O)Nc1ccc(F)c(C#N)c1)C=C[C@H](c1ccccc1)NS2(=N)=O] | Peak1 (HPLC) |
| 10jj2 | 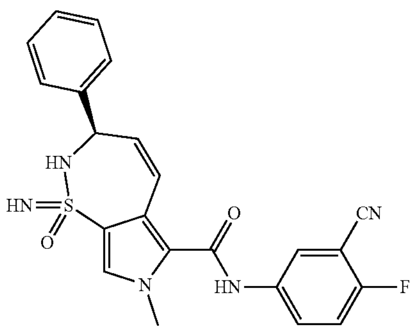 | Peak2 (HPLC) |
| 10kk1 | 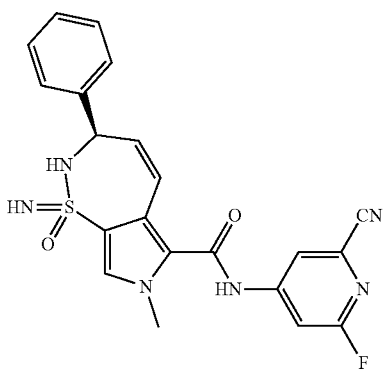 [SMILES: Cn1cc2c(c1C(=O)Nc1cc(F)nc(C#N)c1)C=C[C@H](c1ccccc1)NS2(=N)=O] | Peak1 (HPLC) |
| 10kk2 | 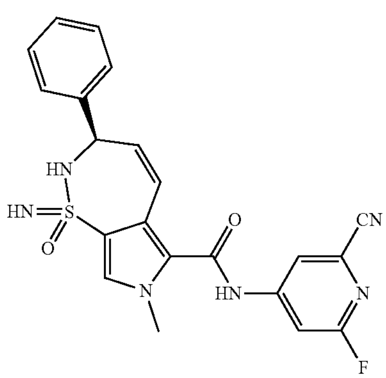 [SMILES: Cn1cc2c(c1C(=O)Nc1cc(F)nc(C#N)c1)C=C[C@H](c1ccccc1)NS2(=N)=O] | Peak2 (HPLC) |

| No. | Structure | Remark |
|---|---|---|
| 10mm1 | 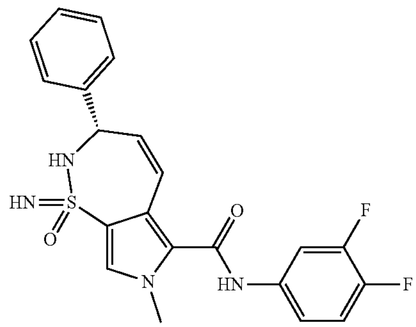 | Peak1 (HPLC) |
| 10mm2 | 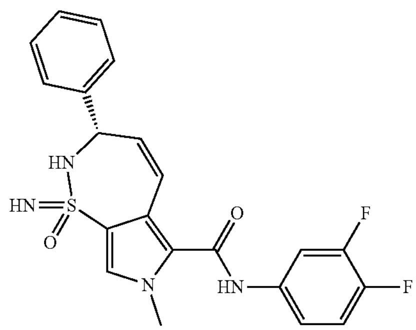 | Peak2 (HPLC) |
| 10nn1 | 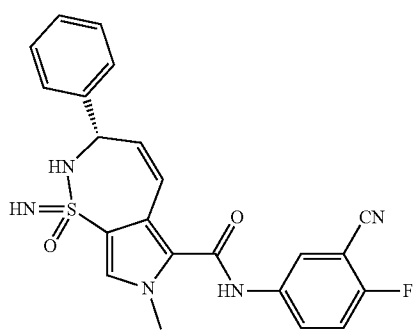 | Peak1 (HPLC) |
| 10nn2 | 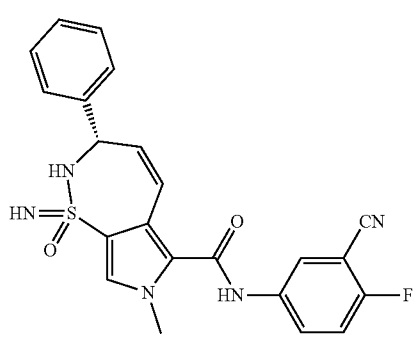 | Peak2 (HPLC) |

| No. | Structure | Remark |
|---|---|---|
| 10oo1 | 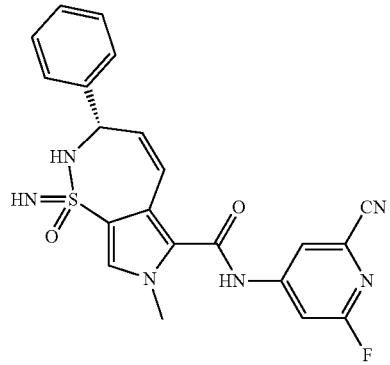 [SMILES: Cn1cc2c(c1C(=O)Nc1cc(F)nc(C#N)c1)C=C[C@@H](c1ccccc1)NS2(=N)=O] | Peak1 (HPLC) |
| 10oo2 | 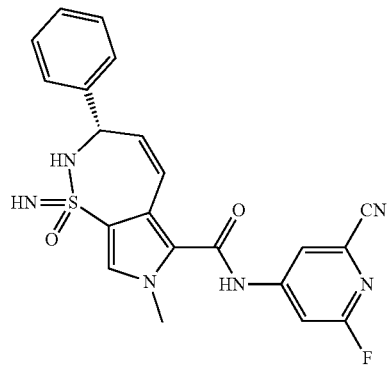 [SMILES: Cn1cc2c(c1C(=O)Nc1cc(F)nc(C#N)c1)C=C[C@@H](c1ccccc1)NS2(=N)=O] | Peak2 (HPLC) |
| 10pp1 | 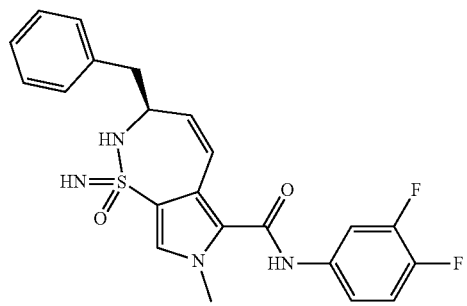 [SMILES: Cn1cc2c(c1C(=O)Nc1ccc(F)c(F)c1)C=C[C@H](Cc1ccccc1)NS2(=N)=O] | Peak1 (HPLC) |
| 10pp2 | 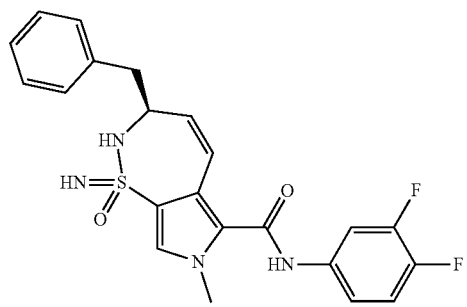 [SMILES: Cn1cc2c(c1C(=O)Nc1ccc(F)c(F)c1)C=C[C@H](Cc1ccccc1)NS2(=N)=O] | Peak2 (HPLC) |

| No. | Structure | Remark |
|---|---|---|
| 10qq1 | 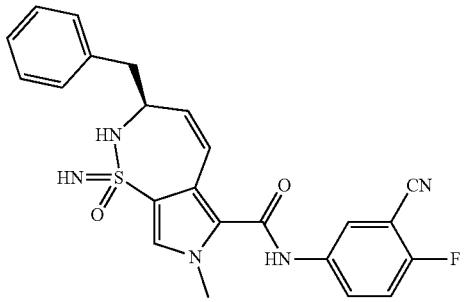 | Peak1 (HPLC) |
| 10qq2 | 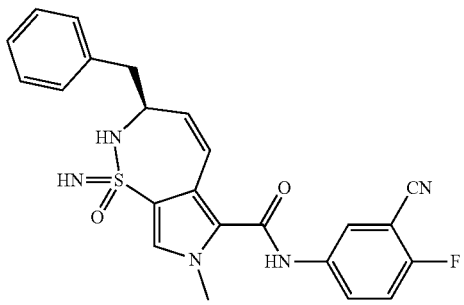 [SMILES: Cn1cc2c(c1C(=O)Nc1ccc(F)c(C#N)c1)C=C[C@H](Cc1ccccc1)NS2(=N)=O] | Peak2 (HPLC) |
| 10rr1 | 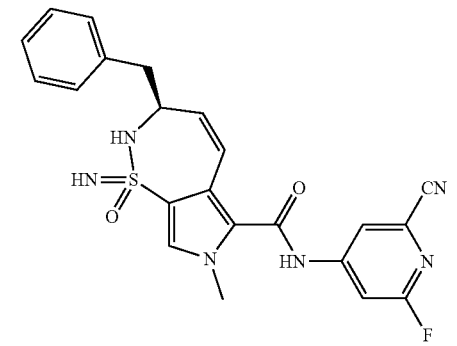 [SMILES: Cn1cc2c(c1C(=O)Nc1cc(F)nc(C#N)c1)C=C[C@H](Cc1ccccc1)NS2(=N)=O] | Peak 1 (HPLC) |
| 10rr2 | 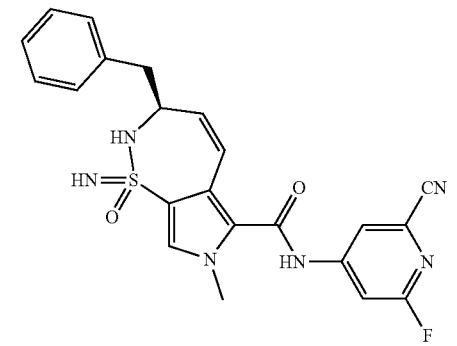 [SMILES: Cn1cc2c(c1C(=O)Nc1cc(F)nc(C#N)c1)C=C[C@H](Cc1ccccc1)NS2(=N)=O] | Peak2 (HPLC) |

-continued

| No. | Structure | Remark |
|---|---|---|
| 10ss1 | 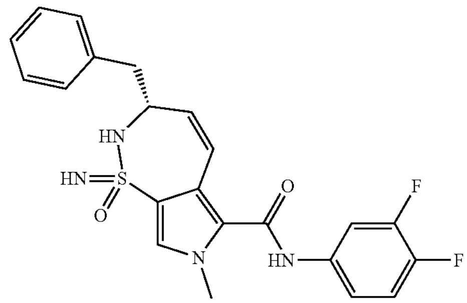 | Peak 1 (HPLC) |
| 10ss2 | 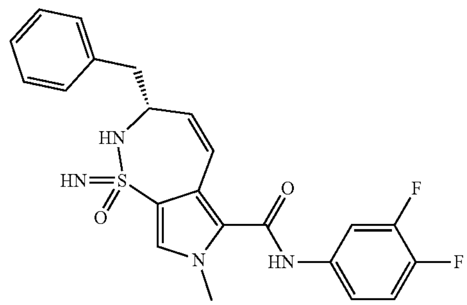 [SMILES: Cn1cc2c(c1C(=O)Nc1ccc(F)c(F)c1)C=C[C@@H](Cc1ccccc1)NS2(=N)=O] | Peak2 (HPLC) |
| 10tt1 | 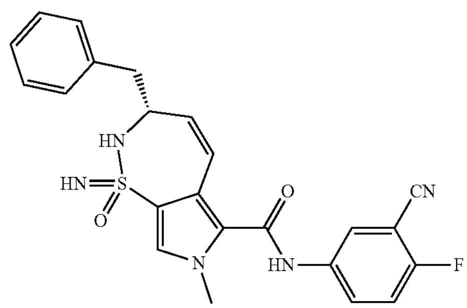 [SMILES: Cn1cc2c(c1C(=O)Nc1ccc(F)c(C#N)c1)C=C[C@@H](Cc1ccccc1)NS2(=N)=O] | Peak1 (HPLC) |
| 10tt2 | 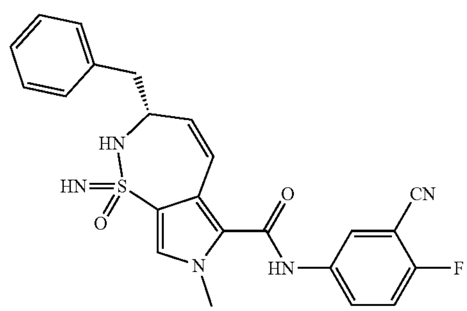 [SMILES: Cn1cc2c(c1C(=O)Nc1ccc(F)c(C#N)c1)C=C[C@@H](Cc1ccccc1)NS2(=N)=O] | Peak2 (HPLC) |
| 10uu1 | 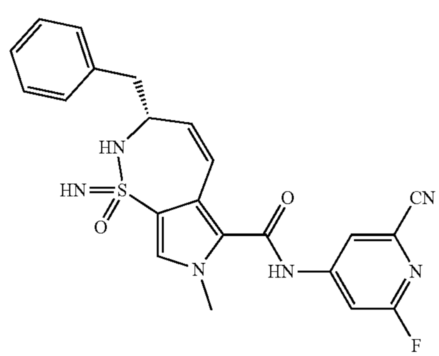 [SMILES: Cn1cc2c(c1C(=O)Nc1cc(F)nc(C#N)c1)C=C[C@@H](Cc1ccccc1)NS2(=N)=O] | Peak1 (HPLC) |

-continued
| No. | Structure | Remark |
| --- | --- | --- |
| 10uu2 | 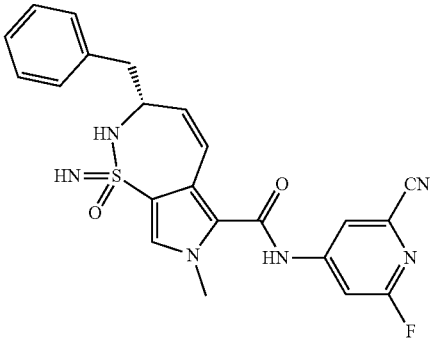 [SMILES: Cn1cc2c(c1C(=O)Nc1cc(F)nc(C#N)c1)C=C[C@@H](Cc1ccccc1)NS2(=N)=O] | Peak2 (HPLC) |
| 10vv1 | 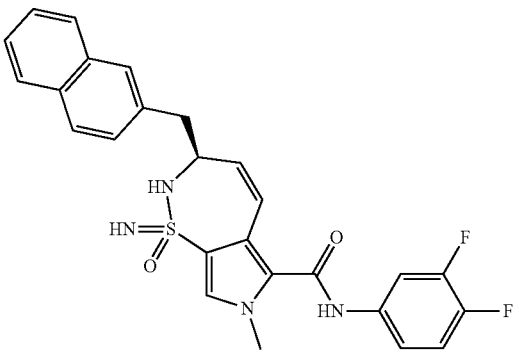 [SMILES: Cn1cc2c(c1C(=O)Nc1ccc(F)c(F)c1)C=C[C@H](Cc1ccc3ccccc3c1)NS2(=N)=O] | Peak1 (HPLC) |
| 10vv2 | 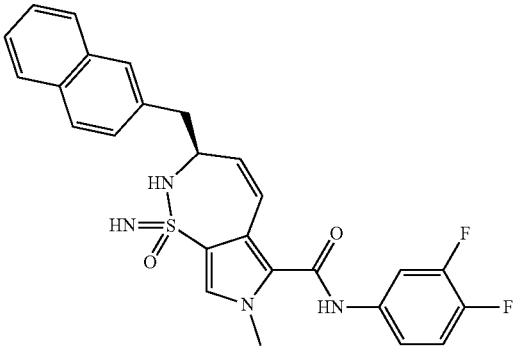 [SMILES: Cn1cc2c(c1C(=O)Nc1ccc(F)c(F)c1)C=C[C@H](Cc1ccc3ccccc3c1)NS2(=N)=O] | Peak2 (HPLC) |
| 10ww1 | 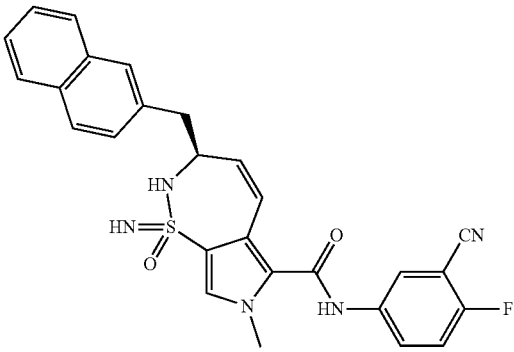 [SMILES: Cn1cc2c(c1C(=O)Nc1ccc(F)c(C#N)c1)C=C[C@H](Cc1ccc3ccccc3c1)NS2(=N)=O] | Peak1 (HPLC) |

-continued

| No. | Structure | Remark |
|---|---|---|
| 10ww2 | 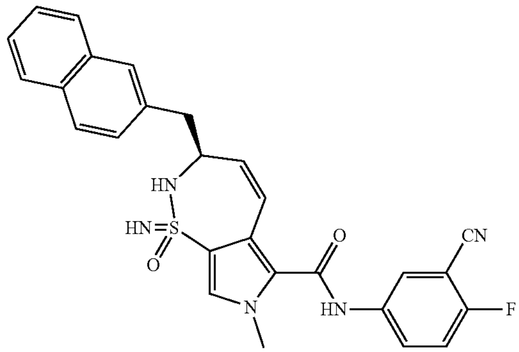 [SMILES: Cn1cc2c(c1C(=O)Nc1ccc(F)c(C#N)c1)C=C[C@H](Cc1ccc3ccccc3c1)NS2(=N)=O] | Peak2 (HPLC) |
| 10xx1 | 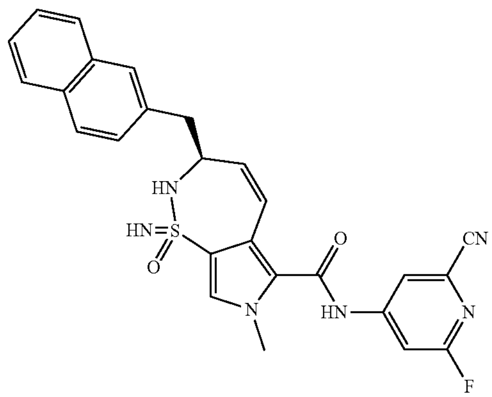 [SMILES: Cn1cc2c(c1C(=O)Nc1cc(F)nc(C#N)c1)C=C[C@H](Cc1ccc3ccccc3c1)NS2(=N)=O] | Peak1 (HPLC) |
| 10xx2 | 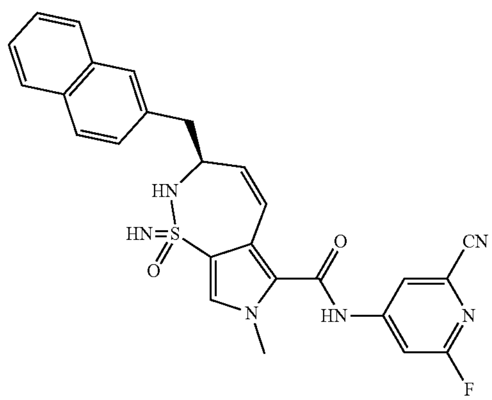 [SMILES: Cn1cc2c(c1C(=O)Nc1cc(F)nc(C#N)c1)C=C[C@H](Cc1ccc3ccccc3c1)NS2(=N)=O] | Peak2 (HPLC) |
| 10yy1 | 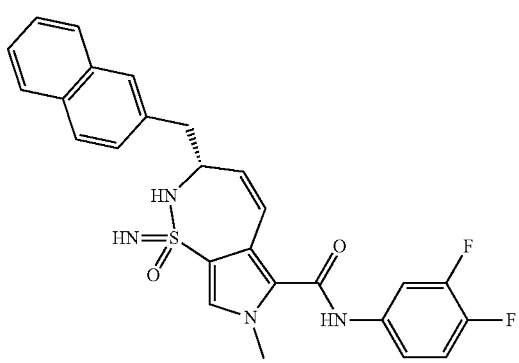 [SMILES: Cn1cc2c(c1C(=O)Nc1ccc(F)c(F)c1)C=C[C@@H](Cc1ccc3ccccc3c1)NS2(=N)=O] | Peak1 (HPLC) |

-continued
| No. | Structure | Remark |
|---|---|---|
| 10yy2 | 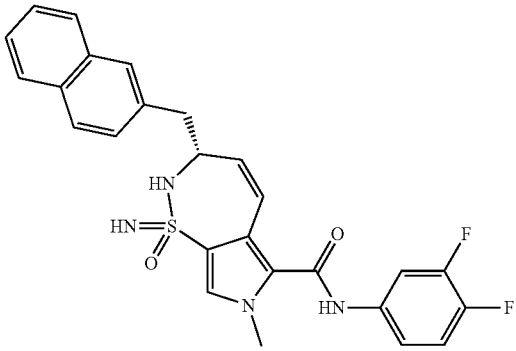 [SMILES: Cn1cc2c(c1C(=O)Nc1ccc(F)c(F)c1)C=C[C@@H](Cc1ccc3ccccc3c1)NS2(=N)=O] | Peak2 (HPLC) |
| 10zz1 | 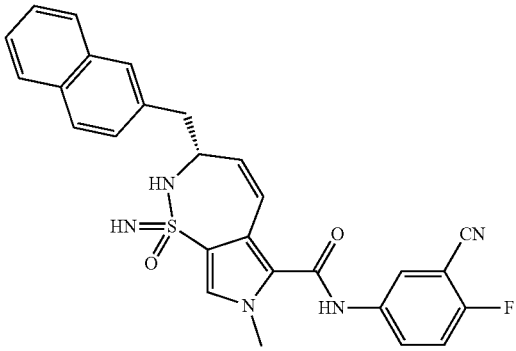 [SMILES: Cn1cc2c(c1C(=O)Nc1ccc(F)c(C#N)c1)C=C[C@@H](Cc1ccc3ccccc3c1)NS2(=N)=O] | Peak1 (HPLC) |
| 10zz2 | 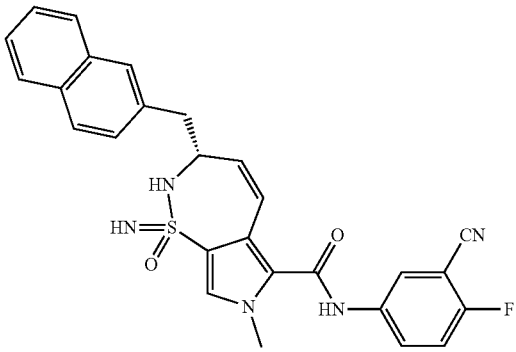 [SMILES: Cn1cc2c(c1C(=O)Nc1ccc(F)c(C#N)c1)C=C[C@@H](Cc1ccc3ccccc3c1)NS2(=N)=O] | Peak2 (HPLC) |
| 10aaa1 | 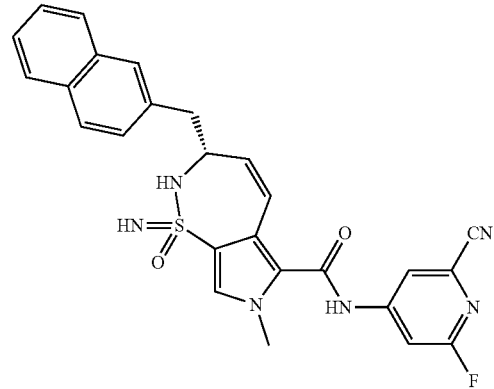 [SMILES: Cn1cc2c(c1C(=O)Nc1cc(F)nc(C#N)c1)C=C[C@@H](Cc1ccc3ccccc3c1)NS2(=N)=O] | Peak1 (HPLC) |

| No. | Structure | Remark |
|---|---|---|
| 10aaa2 | 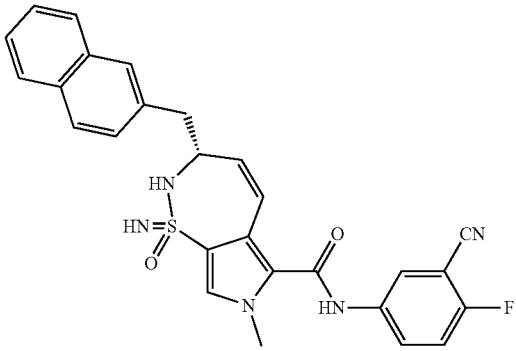 [SMILES: Cn1cc2c(c1C(=O)Nc1ccc(F)c(C#N)c1)C=C[C@@H](Cc1ccc3ccccc3c1)NS2(=N)=O] | Peak2 (HPLC) |
| 10bbb1 | 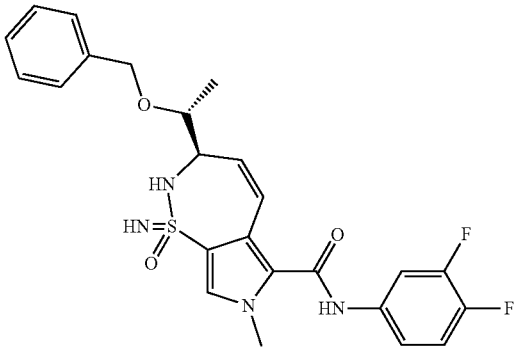 [SMILES: C[C@@H](OCc1ccccc1)[C@H]1C=Cc2c(cn(C)c2C(=O)Nc2ccc(F)c(F)c2)S(=N)(=O)N1] | Peak1 (HPLC) |
| 10bbb2 | 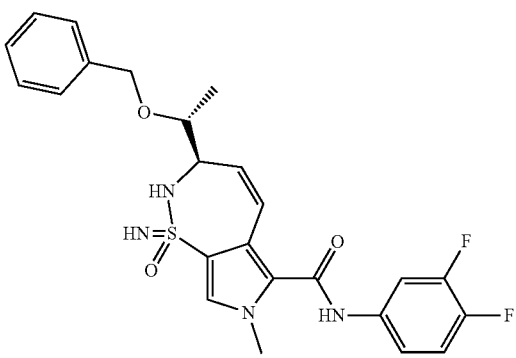 [SMILES: C[C@@H](OCc1ccccc1)[C@H]1C=Cc2c(cn(C)c2C(=O)Nc2ccc(F)c(F)c2)S(=N)(=O)N1] | Peak2 (HPLC) |
| 10ccc1 | 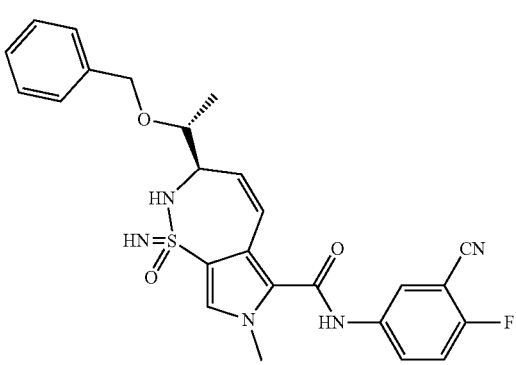 [SMILES: C[C@@H](OCc1ccccc1)[C@H]1C=Cc2c(cn(C)c2C(=O)Nc2ccc(F)c(C#N)c2)S(=N)(=O)N1] | Peak1 (HPLC) |

| No. | Structure | Remark |
|---|---|---|
| 10ccc2 | 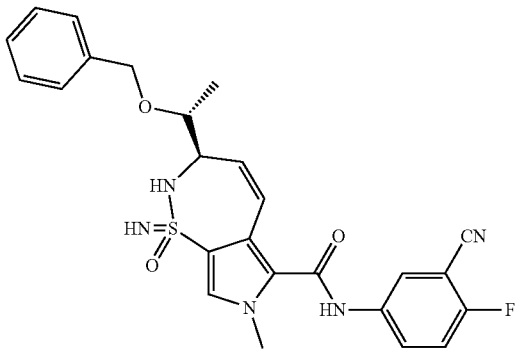 [SMILES: C[C@@H](OCc1ccccc1)[C@H]1C=Cc2c(cn(C)c2C(=O)Nc2ccc(F)c(C#N)c2)S(=N)(=O)N1] | Peak2 (HPLC) |
| 10ddd1 | 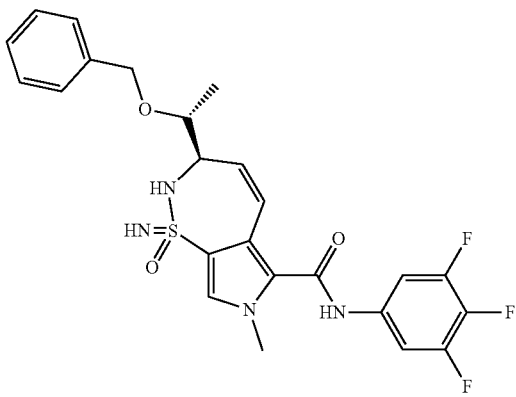 | Peak1 (HPLC) |
| 10ddd2 | 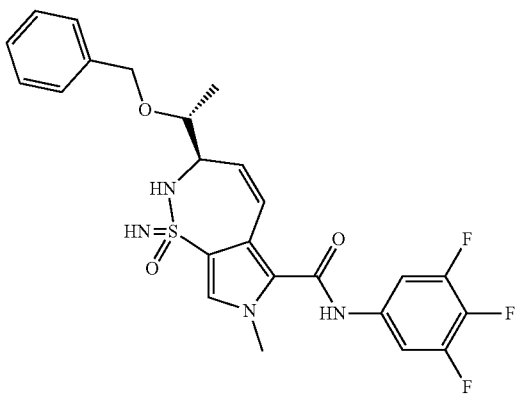 [SMILES: C[C@@H](OCc1ccccc1)[C@H]1C=Cc2c(cn(C)c2C(=O)Nc2cc(F)c(F)c(F)c2)S(=N)(=O)N1] | Peak2 (HPLC) |
| 10eee1 | 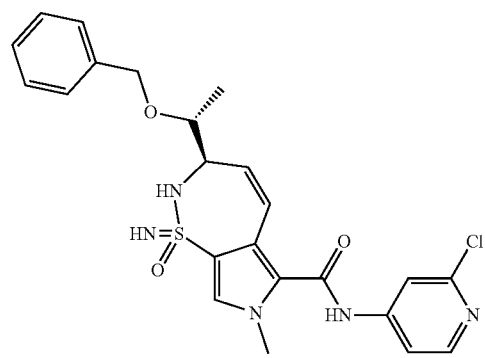 [SMILES: C[C@@H](OCc1ccccc1)[C@H]1C=Cc2c(cn(C)c2C(=O)Nc2ccnc(Cl)c2)S(=N)(=O)N1] | Peak1 (HPLC) |

-continued
| No. | Structure | Remark |
|---|---|---|
| 10eee2 | 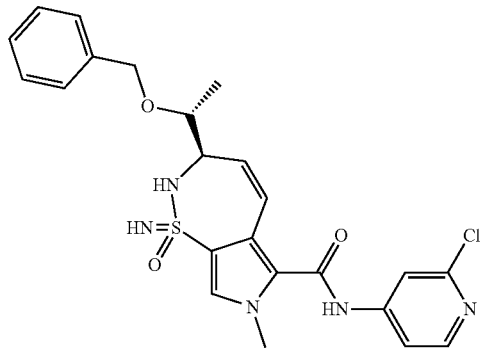 [SMILES: C[C@@H](OCc1ccccc1)[C@H]1C=Cc2c(cn(C)c2C(=O)Nc2ccnc(Cl)c2)S(=N)(=O)N1] | Peak2 (HPLC) |
| 10fff1 | 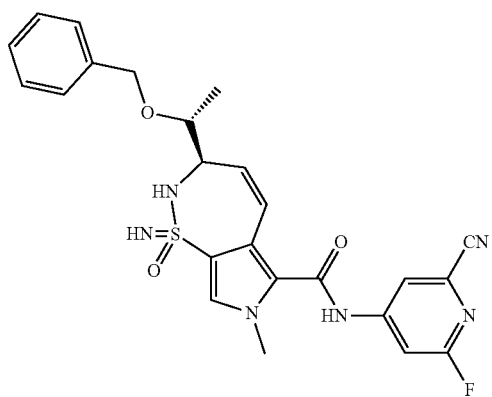 [SMILES: C[C@@H](OCc1ccccc1)[C@H]1C=Cc2c(cn(C)c2C(=O)Nc2cc(F)nc(C#N)c2)S(=N)(=O)N1] | Peak1 (HPLC) |
| 10fff2 | 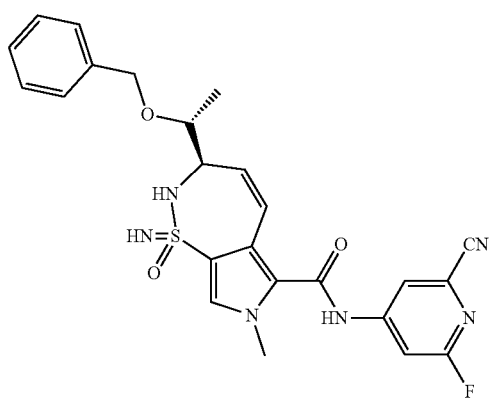 [SMILES: C[C@@H](OCc1ccccc1)[C@H]1C=Cc2c(cn(C)c2C(=O)Nc2cc(F)nc(C#N)c2)S(=N)(=O)N1] | Peak2 (HPLC) |
| 10ggg1 | 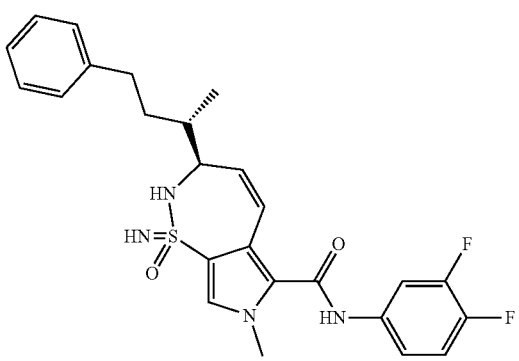 [SMILES: C[C@@H](CCc1ccccc1)[C@H]1C=Cc2c(cn(C)c2C(=O)Nc2ccc(F)c(F)c2)S(=N)(=O)N1] | Peak1 (HPLC) |

| No. | Structure | Remark |
|---|---|---|
| 10ggg2 | 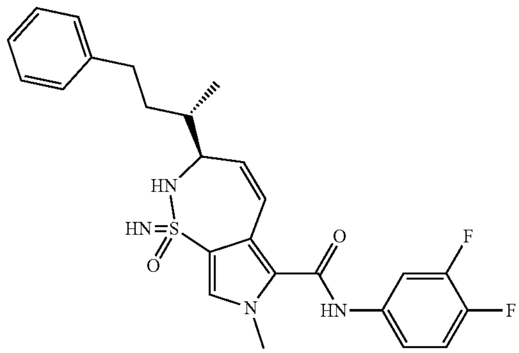 [SMILES: C[C@@H](CCc1ccccc1)[C@H]1C=Cc2c(cn(C)c2C(=O)Nc2ccc(F)c(F)c2)S(=N)(=O)N1] | Peak2 (HPLC) |
| 10hhh1 | 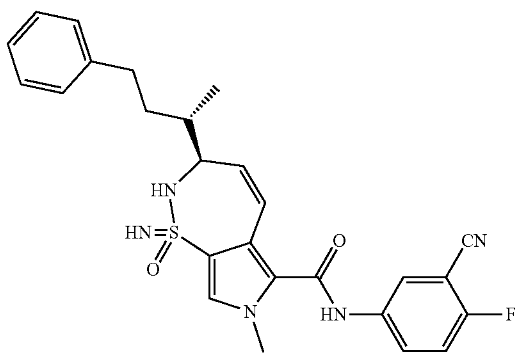 [SMILES: C[C@@H](CCc1ccccc1)[C@H]1C=Cc2c(cn(C)c2C(=O)Nc2ccc(F)c(C#N)c2)S(=N)(=O)N1] | Peak1 (HPLC) |
| 10hhh2 | 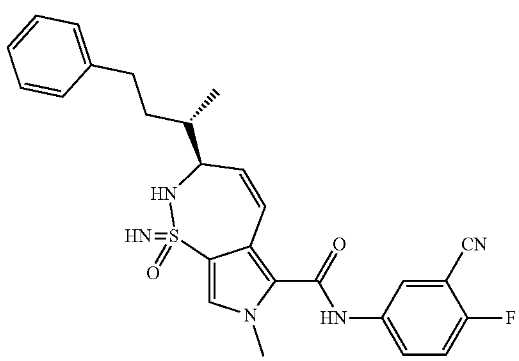 [SMILES: C[C@@H](CCc1ccccc1)[C@H]1C=Cc2c(cn(C)c2C(=O)Nc2ccc(F)c(C#N)c2)S(=N)(=O)N1] | Peak2 (HPLC) |
| 10iii1 | 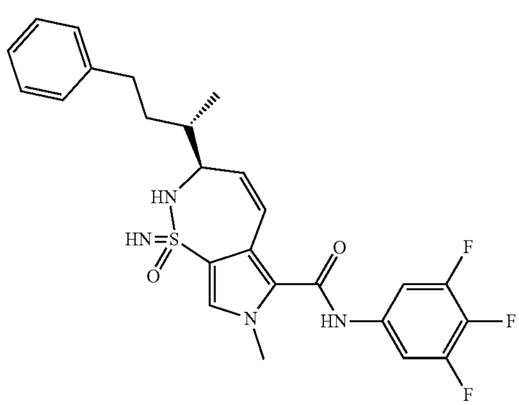 | Peak1 (HPLC) |

| No. | Structure | Remark |
|---|---|---|
| 10iii2 | 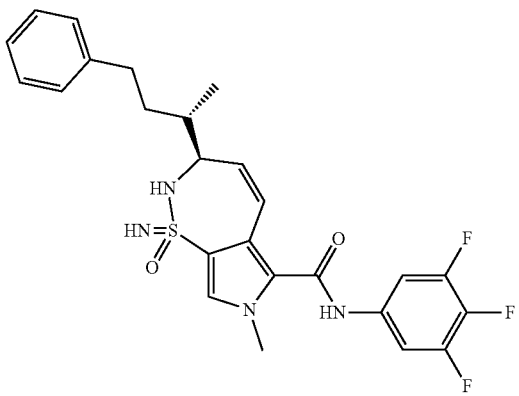 [SMILES: C[C@@H](CCc1ccccc1)[C@H]1C=Cc2c(cn(C)c2C(=O)Nc2cc(F)c(F)c(F)c2)S(=N)(=O)N1] | Peak2 (HPLC) |
| 10jjj1 | 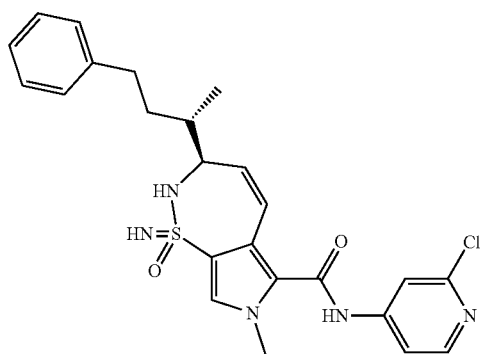 [SMILES: C[C@@H](CCc1ccccc1)[C@H]1C=Cc2c(cn(C)c2C(=O)Nc2ccnc(Cl)c2)S(=N)(=O)N1] | Peak1 (HPLC) |
| 10jjj2 | 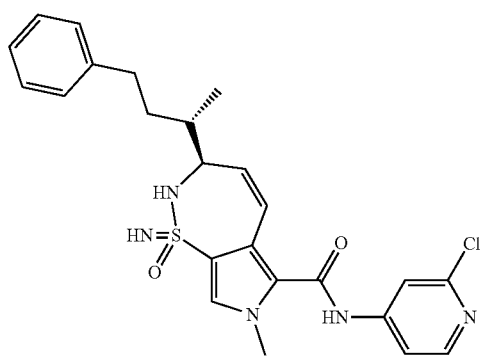 | Peak2 (HPLC) |
| 10kkk1 | 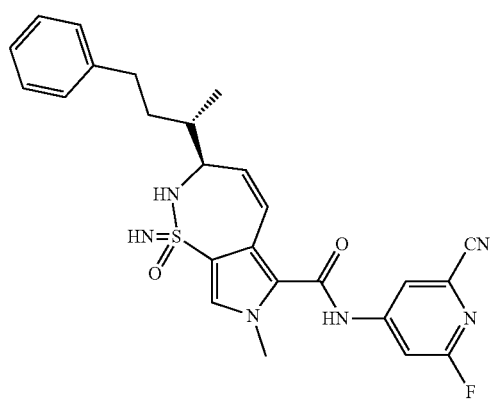 [SMILES: C[C@@H](CCc1ccccc1)[C@H]1C=Cc2c(cn(C)c2C(=O)Nc2cc(F)nc(C#N)c2)S(=N)(=O)N1] | Peak1 (HPLC) |

-continued
| No. | Structure | Remark |
|---|---|---|
| 10kkk2 | 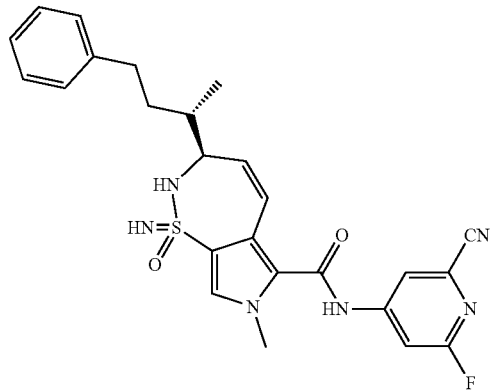 [SMILES: C[C@@H](CCc1ccccc1)[C@H]1C=Cc2c(cn(C)c2C(=O)Nc2cc(F)nc(C#N)c2)S(=N)(=O)N1] | Peak2 (HPLC) |
| 10mmm1 | 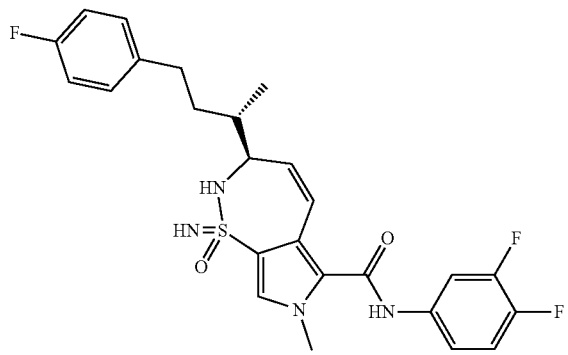 [SMILES: C[C@@H](CCc1ccc(F)cc1)[C@H]1C=Cc2c(cn(C)c2C(=O)Nc2ccc(F)c(F)c2)S(=N)(=O)N1] | Peak1 (HPLC) |
| 10mmm2 | 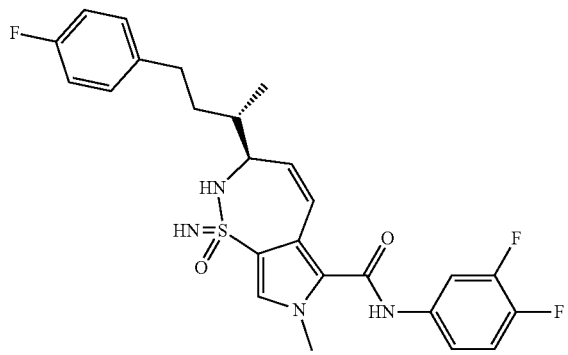 [SMILES: C[C@@H](CCc1ccc(F)cc1)[C@H]1C=Cc2c(cn(C)c2C(=O)Nc2ccc(F)c(F)c2)S(=N)(=O)N1] | Peak2 (HPLC) |
| 10nnn1 | 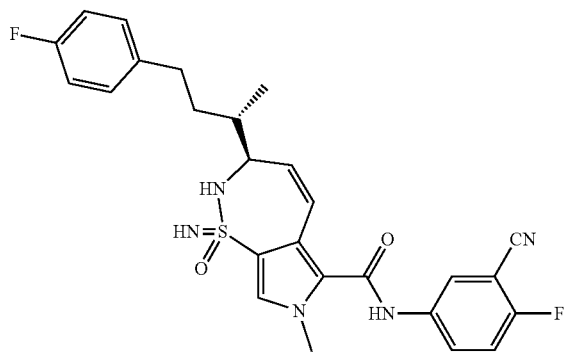 [SMILES: C[C@@H](CCc1ccc(F)cc1)[C@H]1C=Cc2c(cn(C)c2C(=O)Nc2ccc(F)c(C#N)c2)S(=N)(=O)N1] | Peak1 (HPLC) |

-continued
| No. | Structure | Remark |
|---|---|---|
| 10nnn2 | 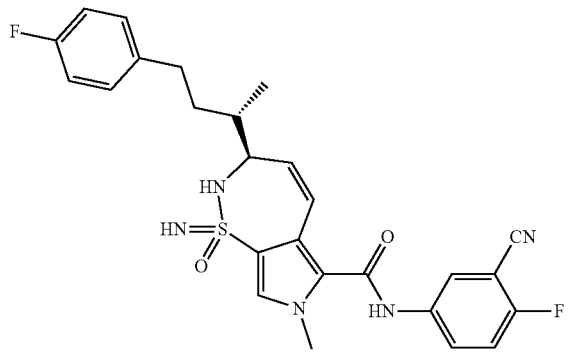 | Peak2 (HPLC) |
| 10ooo1 | 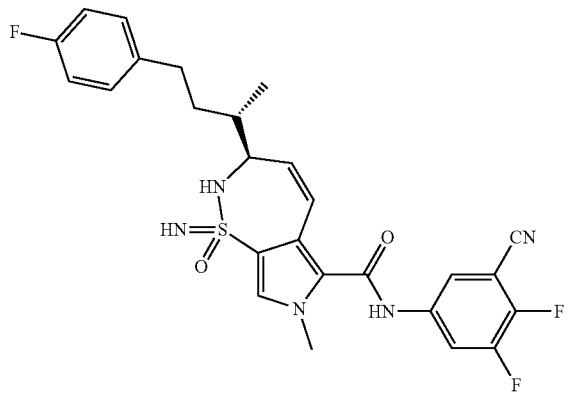 [SMILES: C[C@@H](CCc1ccc(F)cc1)[C@H]1C=Cc2c(cn(C)c2C(=O)Nc2cc(F)c(F)c(C#N)c2)S(=N)(=O)N1] | Peak 1 (HPLC) |
| 10ooo2 | 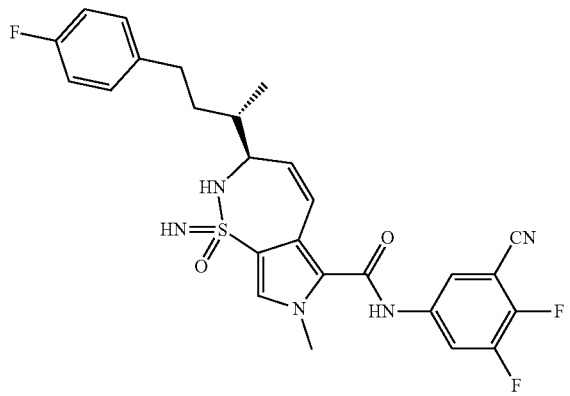 [SMILES: C[C@@H](CCc1ccc(F)cc1)[C@H]1C=Cc2c(cn(C)c2C(=O)Nc2cc(F)c(F)c(C#N)c2)S(=N)(=O)N1] | Peak2 (HPLC) |
| 10ppp1 | 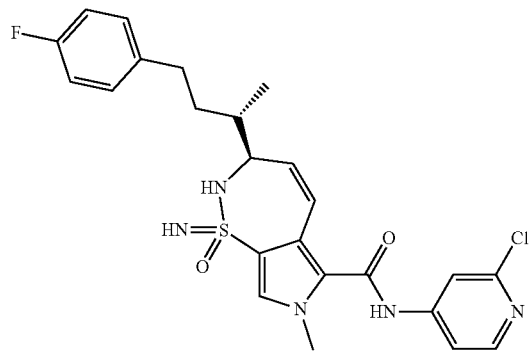 [SMILES: C[C@@H](CCc1ccc(F)cc1)[C@H]1C=Cc2c(cn(C)c2C(=O)Nc2ccnc(Cl)c2)S(=N)(=O)N1] | Peak 1 (HPLC) |

-continued

| No. | Structure | Remark |
|---|---|---|
| 10ppp2 | 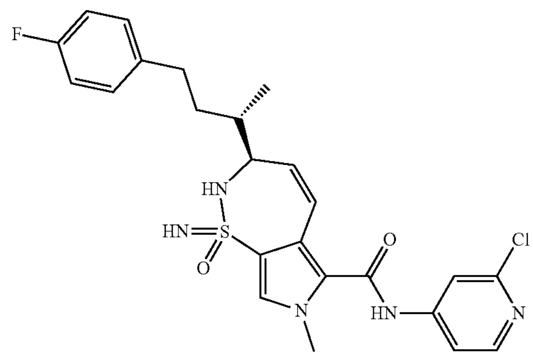 [SMILES: C[C@@H](CCc1ccc(F)cc1)[C@H]1C=Cc2c(cn(C)c2C(=O)Nc2ccnc(Cl)c2)S(=N)(=O)N1] | Peak2 (HPLC) |
| 10qqq1 | 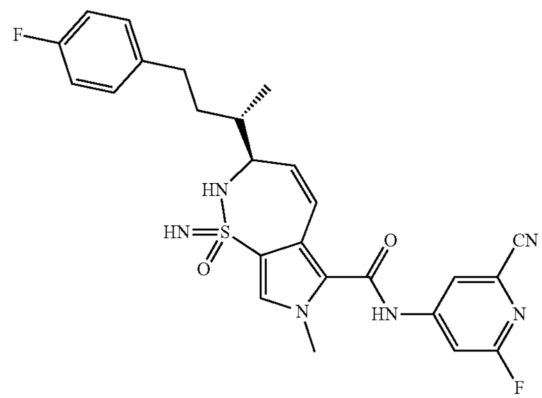 [SMILES: C[C@@H](CCc1ccc(F)cc1)[C@H]1C=Cc2c(cn(C)c2C(=O)Nc2cc(F)nc(C#N)c2)S(=N)(=O)N1] | Peak 1 (HPLC) |
| 10qqq2 | 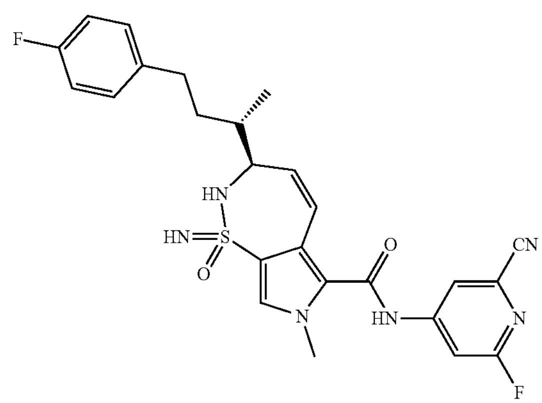 [SMILES: C[C@@H](CCc1ccc(F)cc1)[C@H]1C=Cc2c(cn(C)c2C(=O)Nc2cc(F)nc(C#N)c2)S(=N)(=O)N1] | Peak2 (HPLC) |
| 10rrr1 | 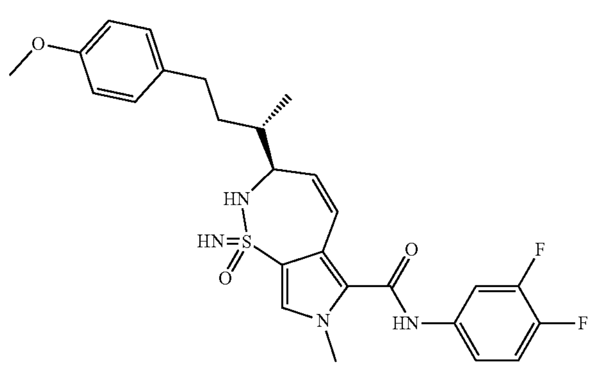 [SMILES: COc1ccc(CC[C@H](C)[C@H]2C=Cc3c(cn(C)c3C(=O)Nc3ccc(F)c(F)c3)S(=N)(=O)N2)cc1] | Peak 1 (HPLC) |

| No. | Structure | Remark |
|---|---|---|
| 10rrr2 | 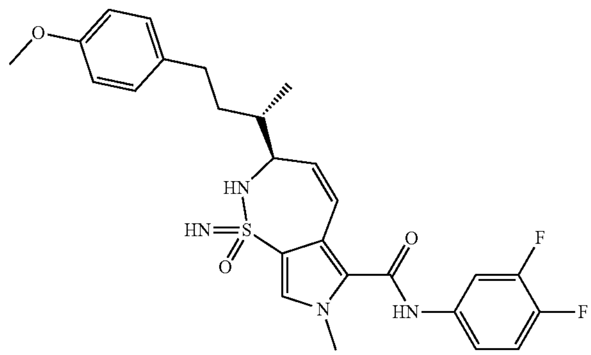 [SMILES: COc1ccc(CC[C@H](C)[C@H]2C=Cc3c(cn(C)c3C(=O)Nc3ccc(F)c(F)c3)S(=N)(=O)N2)cc1] | Peak2 (HPLC) |
| 10sss1 | 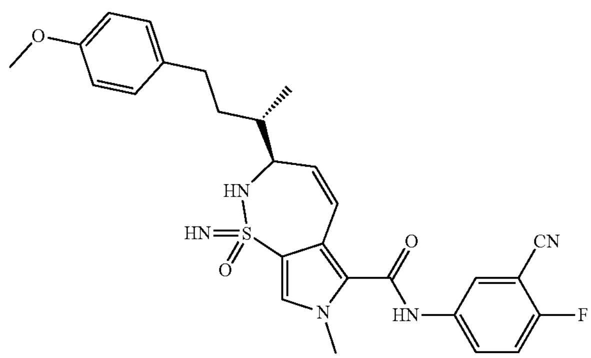 [SMILES: COc1ccc(CC[C@H](C)[C@H]2C=Cc3c(cn(C)c3C(=O)Nc3ccc(F)c(C#N)c3)S(=N)(=O)N2)cc1] | Peak1 (HPLC) |
| 10sss2 | 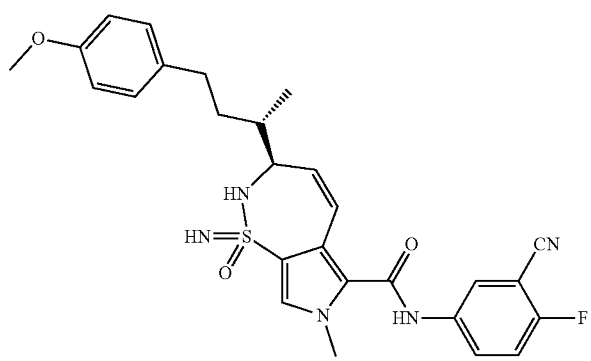 [SMILES: COc1ccc(CC[C@H](C)[C@H]2C=Cc3c(cn(C)c3C(=O)Nc3ccc(F)c(C#N)c3)S(=N)(=O)N2)cc1] | Peak2 (HPLC) |
| 10ttt1 | 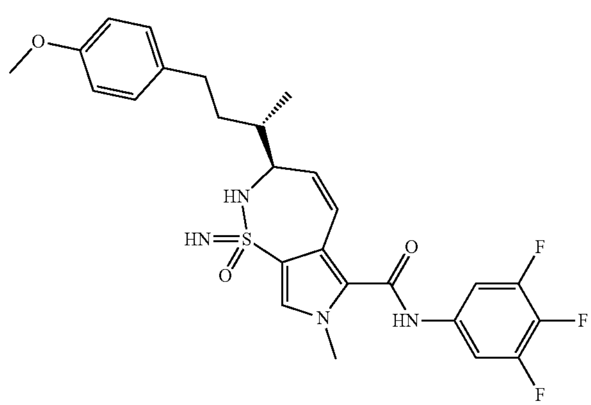 [SMILES: COc1ccc(CC[C@H](C)[C@H]2C=Cc3c(cn(C)c3C(=O)Nc3cc(F)c(F)c(F)c3)S(=N)(=O)N2)cc1] | Peak1 (HPLC) |

| No. | Structure | Remark |
|---|---|---|
| 10ttt2 | 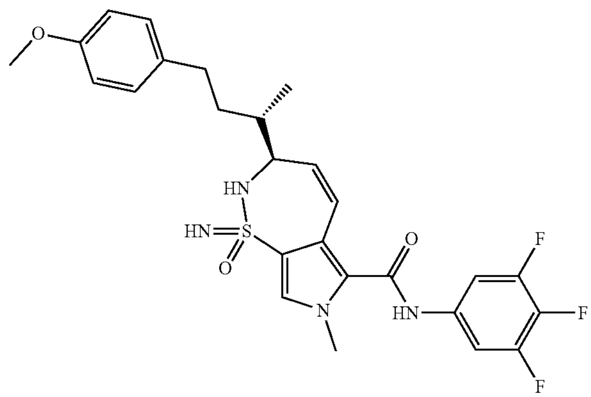 [SMILES: COc1ccc(CC[C@H](C)[C@H]2C=Cc3c(cn(C)c3C(=O)Nc3cc(F)c(F)c(F)c3)S(=N)(=O)N2)cc1] | Peak2 (HPLC) |
| 10uuu1 | 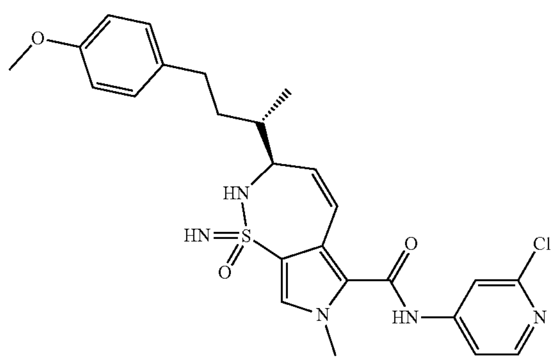 [SMILES: COc1ccc(CC[C@H](C)[C@H]2C=Cc3c(cn(C)c3C(=O)Nc3ccnc(Cl)c3)S(=N)(=O)N2)cc1] | Peak1 (HPLC) |
| 10uuu2 | 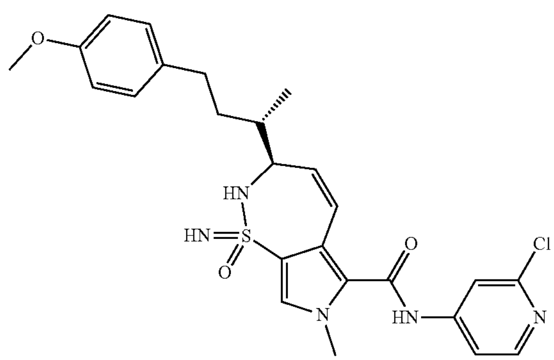 [SMILES: COc1ccc(CC[C@H](C)[C@H]2C=Cc3c(cn(C)c3C(=O)Nc3ccnc(Cl)c3)S(=N)(=O)N2)cc1] | Peak2 (HPLC) |
| 10vvv1 | 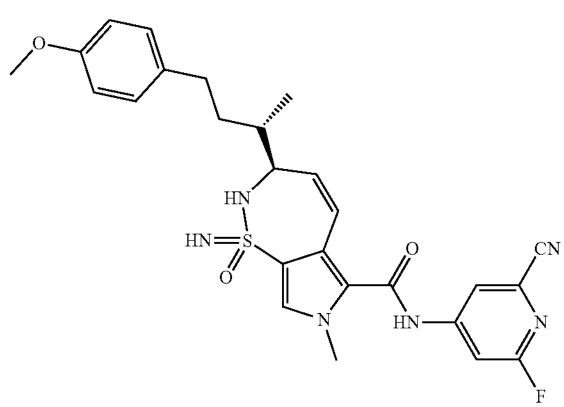 [SMILES: COc1ccc(CC[C@H](C)[C@H]2C=Cc3c(cn(C)c3C(=O)Nc3cc(F)nc(C#N)c3)S(=N)(=O)N2)cc1] | Peak1 (HPLC) |

| No. | Structure | Remark |
|---|---|---|
| 10vvv2 | 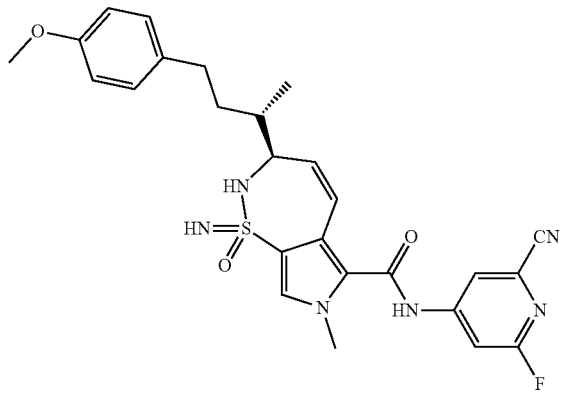 [SMILES: COc1ccc(CC[C@H](C)[C@H]2C=Cc3c(cn(C)c3C(=O)Nc3cc(F)nc(C#N)c3)S(=N)(=O)N2)cc1] | Peak2 (HPLC) |
| 10www1 | 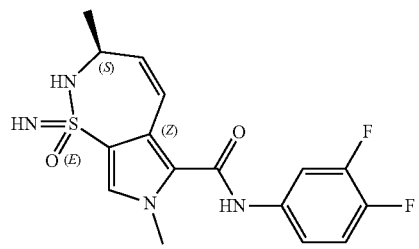 | Peak1 (HPLC) |
| 10www2 | 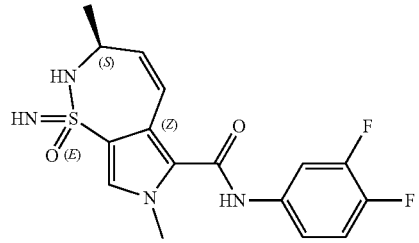 | Peak2 (HPLC) |
| 10xxx1 | 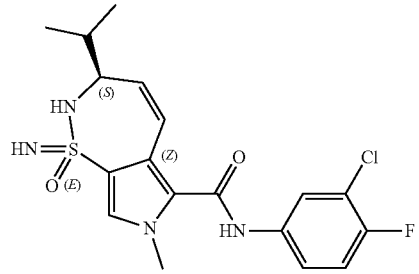 | Peak1 (HPLC) |
| 10xxx2 | 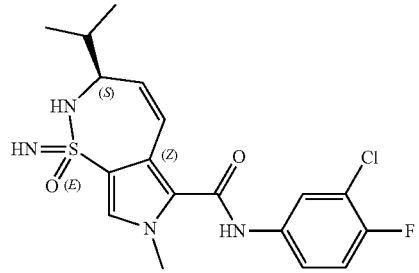 | Peak2 (HPLC) |

-continued

| No. | Structure | Remark |
|---|---|---|
| 20a1 | 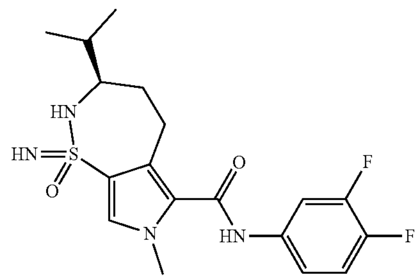 [SMILES: CC(C)[C@H]1CCc2c(cn(C)c2C(=O)Nc2ccc(F)c(F)c2)S(=N)(=O)N1] | Peak1 (HPLC) |
| 20a2 | 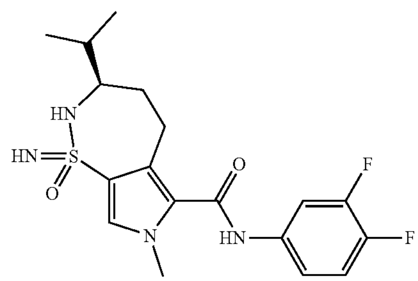 [SMILES: CC(C)[C@H]1CCc2c(cn(C)c2C(=O)Nc2ccc(F)c(F)c2)S(=N)(=O)N1] | Peak2 (HPLC) |
| 20b1 | 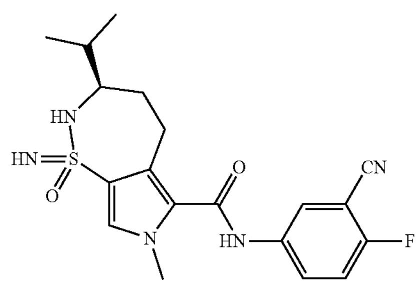 [SMILES: CC(C)[C@H]1CCc2c(cn(C)c2C(=O)Nc2ccc(F)c(C#N)c2)S(=N)(=O)N1] | Peak1 (HPLC) |
| 20b2 | 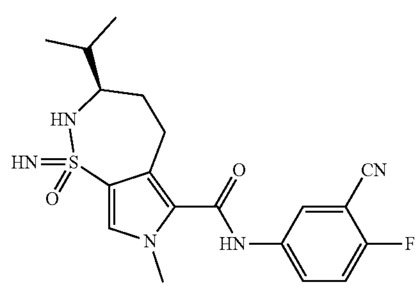 [SMILES: CC(C)[C@H]1CCc2c(cn(C)c2C(=O)Nc2ccc(F)c(C#N)c2)S(=N)(=O)N1] | Peak2 (HPLC) |
| 20c1 | 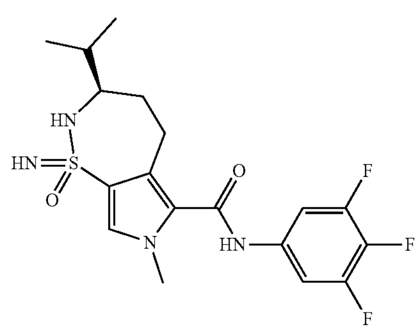 [SMILES: CC(C)[C@H]1CCc2c(cn(C)c2C(=O)Nc2cc(F)c(F)c(F)c2)S(=N)(=O)N1] | Peak1 (HPLC) |

-continued
| No. | Structure | Remark |
|---|---|---|
| 20c2 | 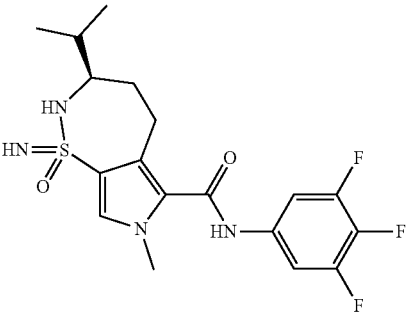 [SMILES: CC(C)[C@H]1CCc2c(cn(C)c2C(=O)Nc2cc(F)c(F)c(F)c2)S(=N)(=O)N1] | Peak2 (HPLC) |
| 20d1 | 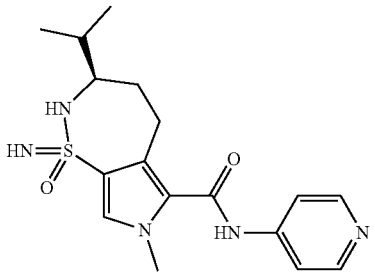 [SMILES: CC(C)[C@H]1CCc2c(cn(C)c2C(=O)Nc2ccncc2)S(=N)(=O)N1] | Peak1 (HPLC) |
| 20d2 | 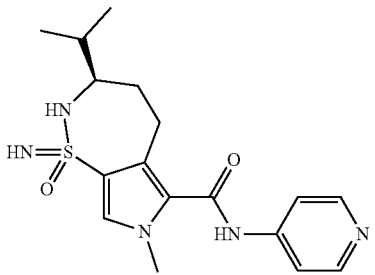 [SMILES: CC(C)[C@H]1CCc2c(cn(C)c2C(=O)Nc2ccncc2)S(=N)(=O)N1] | Peak2 (HPLC) |
| 20e1 | 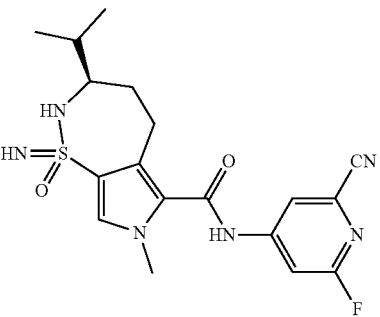 [SMILES: CC(C)[C@H]1CCc2c(cn(C)c2C(=O)Nc2cc(F)nc(C#N)c2)S(=N)(=O)N1] | Peak1 (HPLC) |
| 20e2 | 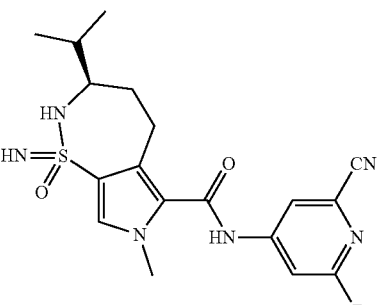 | Peak2 (HPLC) |

-continued
| No. | Structure | Remark |
|---|---|---|
| 20f1 | 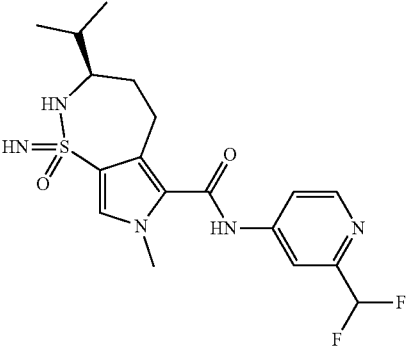 [SMILES: CC(C)[C@H]1CCc2c(cn(C)c2C(=O)Nc2ccnc(C(F)F)c2)S(=N)(=O)N1] | Peak1 (HPLC) |
| 20f2 | 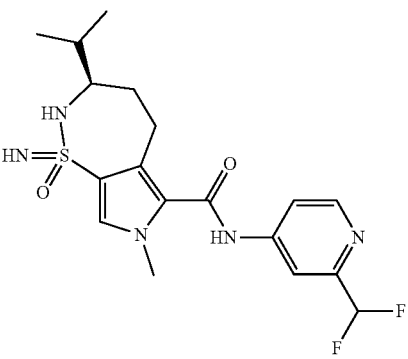 [SMILES: CC(C)[C@H]1CCc2c(cn(C)c2C(=O)Nc2ccnc(C(F)F)c2)S(=N)(=O)N1] | Peak2 (HPLC) |
| 20g1 | 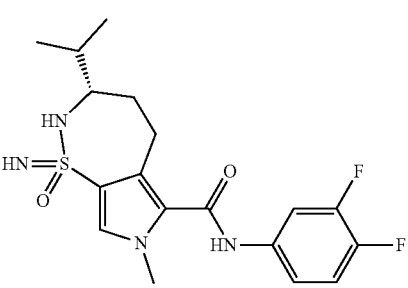 [SMILES: CC(C)[C@@H]1CCc2c(cn(C)c2C(=O)Nc2ccc(F)c(F)c2)S(=N)(=O)N1] | Peak1 (HPLC) |
| 20g2 | 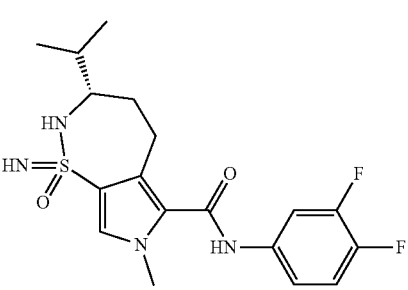 [SMILES: CC(C)[C@@H]1CCc2c(cn(C)c2C(=O)Nc2ccc(F)c(F)c2)S(=N)(=O)N1] | Peak2 (HPLC) |
| 20h1 | 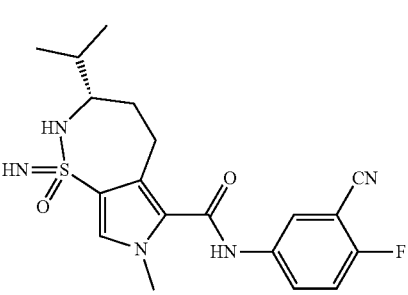 [SMILES: CC(C)[C@@H]1CCc2c(cn(C)c2C(=O)Nc2ccc(F)c(C#N)c2)S(=N)(=O)N1] | Peak1 (HPLC) |

-continued

| No. | Structure | Remark |
|---|---|---|
| 20h2 | 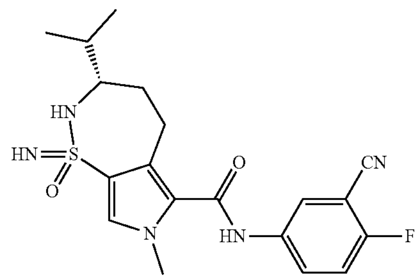 [SMILES: CC(C)[C@@H]1CCc2c(cn(C)c2C(=O)Nc2ccc(F)c(C#N)c2)S(=N)(=O)N1] | Peak2 (HPLC) |
| 20i1 | 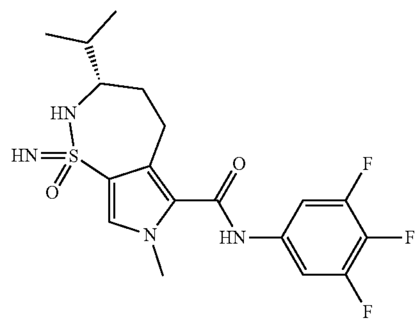 [SMILES: CC(C)[C@@H]1CCc2c(cn(C)c2C(=O)Nc2cc(F)c(F)c(F)c2)S(=N)(=O)N1] | Peak1 (HPLC) |
| 20i2 | 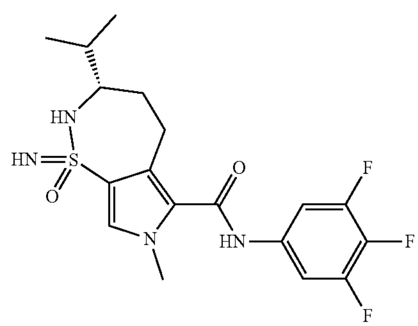 [SMILES: CC(C)[C@@H]1CCc2c(cn(C)c2C(=O)Nc2cc(F)c(F)c(F)c2)S(=N)(=O)N1] | Peak2 (HPLC) |
| 20j1 | 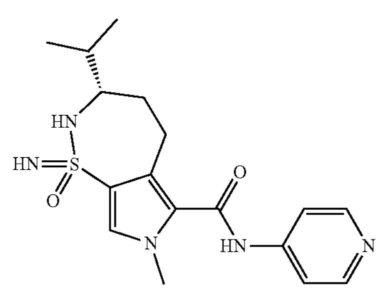 [SMILES: CC(C)[C@@H]1CCc2c(cn(C)c2C(=O)Nc2ccncc2)S(=N)(=O)N1] | Peak1 (HPLC) |
| 20j2 | 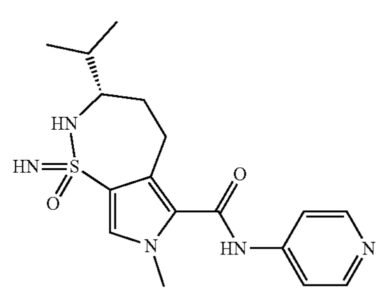 [SMILES: CC(C)[C@@H]1CCc2c(cn(C)c2C(=O)Nc2ccncc2)S(=N)(=O)N1] | Peak2 (HPLC) |

-continued

| No. | Structure | Remark |
|---|---|---|
| 20k1 | 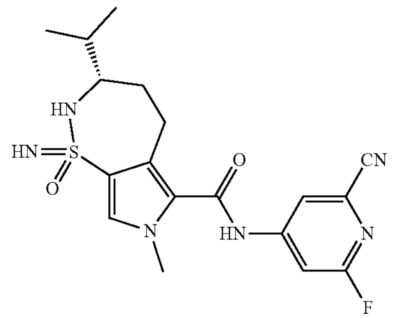 [SMILES: CC(C)[C@@H]1CCc2c(cn(C)c2C(=O)Nc2cc(F)nc(C#N)c2)S(=N)(=O)N1] | Peak1 (HPLC) |
| 20k2 | 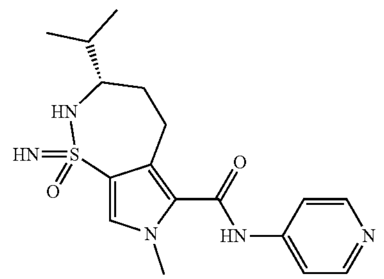 [SMILES: CC(C)[C@@H]1CCc2c(cn(C)c2C(=O)Nc2ccncc2)S(=N)(=O)N1] | Peak2 (HPLC) |
| 20m1 | 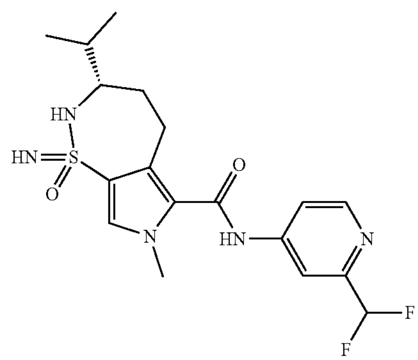 [SMILES: CC(C)[C@@H]1CCc2c(cn(C)c2C(=O)Nc2ccnc(C(F)F)c2)S(=N)(=O)N1] | Peak1 (HPLC) |
| 10m2 | 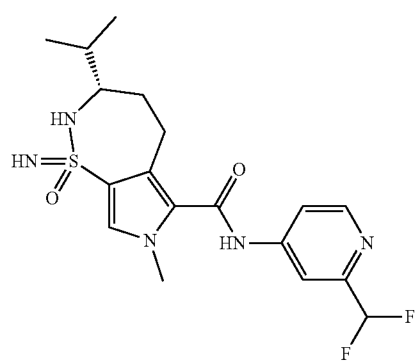 [SMILES: CC(C)[C@@H]1CCc2c(cn(C)c2C(=O)Nc2ccnc(C(F)F)c2)S(=N)(=O)N1] | Peak2 (HPLC) |
| 20n1 | 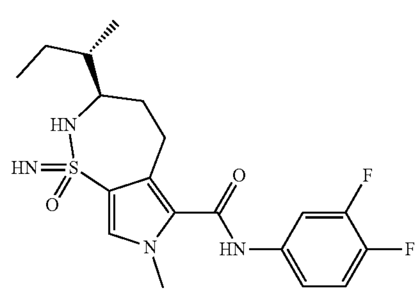 [SMILES: CC[C@H](C)[C@H]1CCc2c(cn(C)c2C(=O)Nc2ccc(F)c(F)c2)S(=N)(=O)N1] | Peak1 (HPLC) |

| No. | Structure | Remark |
|---|---|---|
| 20n2 | 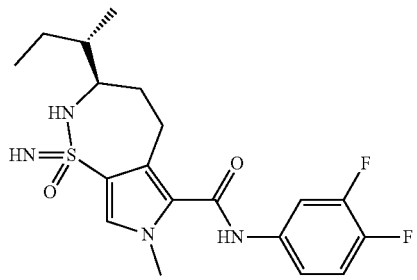 [SMILES: CC[C@H](C)[C@H]1CCc2c(cn(C)c2C(=O)Nc2ccc(F)c(F)c2)S(=N)(=O)N1] | Peak2 (HPLC) |
| 20o1 | 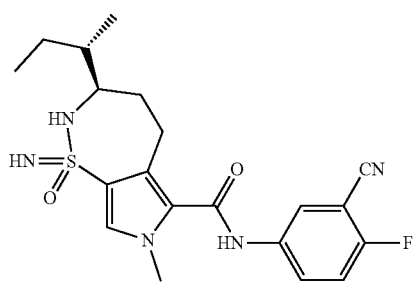 [SMILES: CC[C@H](C)[C@H]1CCc2c(cn(C)c2C(=O)Nc2ccc(F)c(C#N)c2)S(=N)(=O)N1] | Peak1 (HPLC) |
| 20o2 | 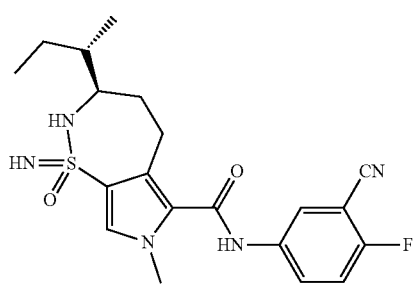 [SMILES: CC[C@H](C)[C@H]1CCc2c(cn(C)c2C(=O)Nc2ccc(F)c(C#N)c2)S(=N)(=O)N1] | Peak2 (HPLC) |
| 20p1 | 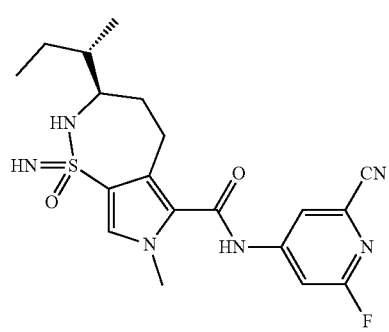 [SMILES: CC[C@H](C)[C@H]1CCc2c(cn(C)c2C(=O)Nc2cc(F)nc(C#N)c2)S(=N)(=O)N1] | Peak1 (HPLC) |
| 20p2 | 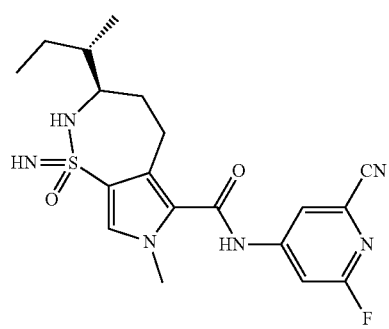 [SMILES: CC[C@H](C)[C@H]1CCc2c(cn(C)c2C(=O)Nc2cc(F)nc(C#N)c2)S(=N)(=O)N1] | Peak2 (HPLC) |

-continued
| No. | Structure | Remark |
|---|---|---|
| 20q1 | 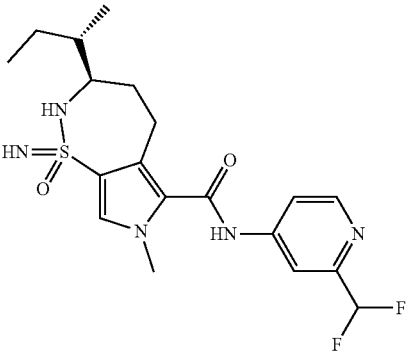 [SMILES: CC[C@H](C)[C@H]1CCc2c(cn(C)c2C(=O)Nc2ccnc(C(F)F)c2)S(=N)(=O)N1] | Peak1 (HPLC) |
| 20q2 | 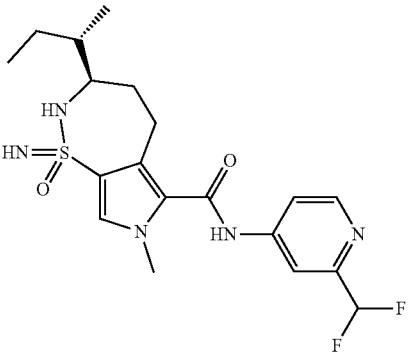 [SMILES: CC[C@H](C)[C@H]1CCc2c(cn(C)c2C(=O)Nc2ccnc(C(F)F)c2)S(=N)(=O)N1] | Peak2 (HPLC) |
| 20r1 | 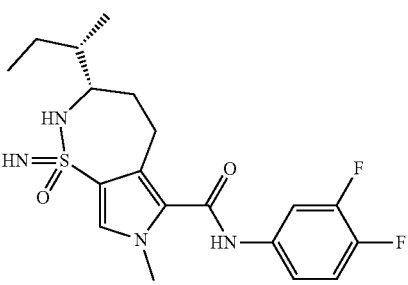 | Peak1 (HPLC) |
| 20r2 | 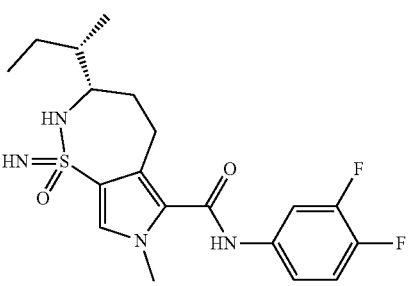 | Peak2 (HPLC) |
| 20s1 | 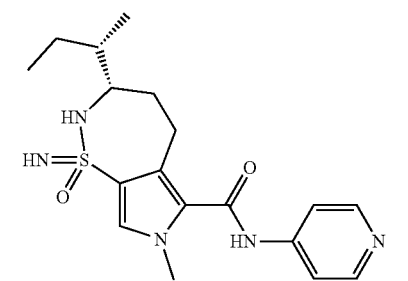 | Peak1 (HPLC) |

-continued
| No. | Structure | Remark |
|---|---|---|
| 20s2 | 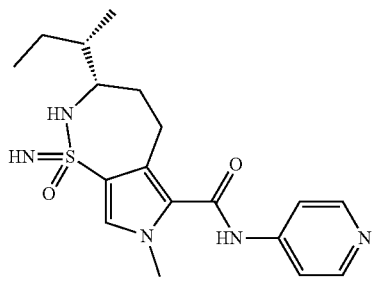 | Peak2 (HPLC) |
| 20t1 | 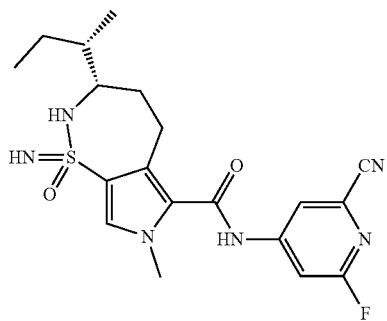 | Peak1 (HPLC) |
| 20t2 | 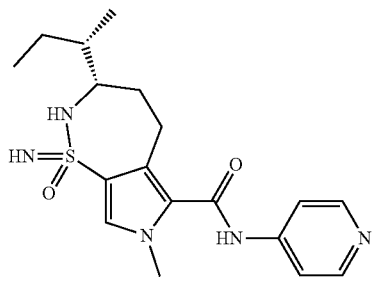 | Peak2 (HPLC) |
| 20u1 | 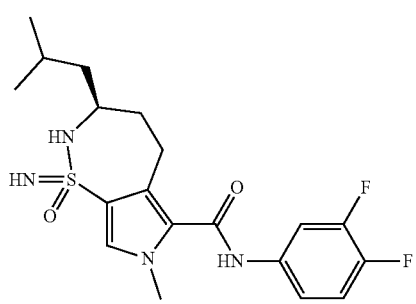 | Peak1 (HPLC) |
| 20u2 | 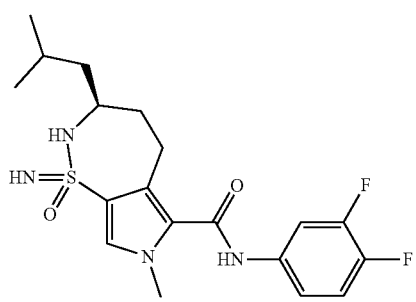 | Peak2 (HPLC) |

-continued
| No. | Structure | Remark |
|---|---|---|
| 20v1 | 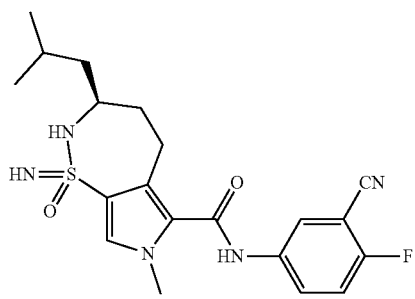 | Peak1 (HPLC) |
| 20v2 | 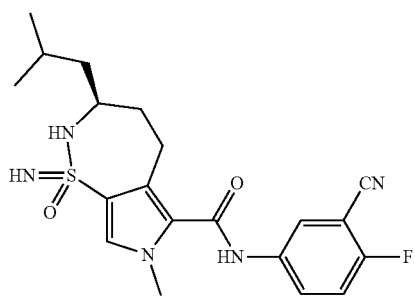 | Peak2 (HPLC) |
| 20w1 | 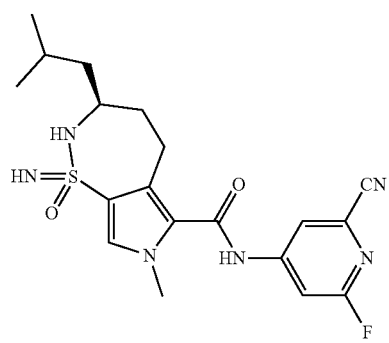 | Peak1 (HPLC) |
| 20w2 | 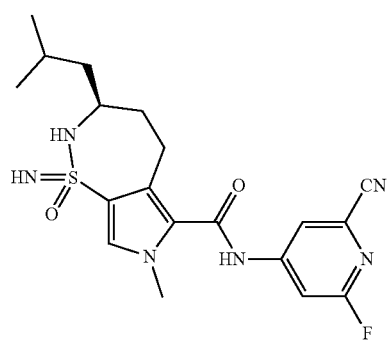 | Peak2 (HPLC) |

-continued
| No. | Structure | Remark |
|---|---|---|
| 20x1 | 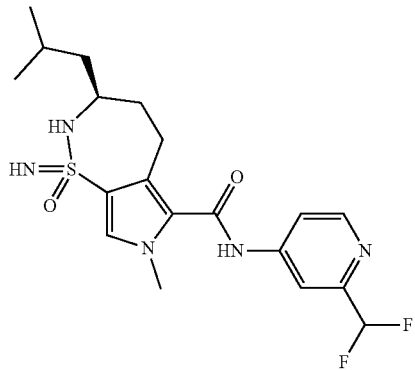 | Peak1 (HPLC) |
| 20x2 | 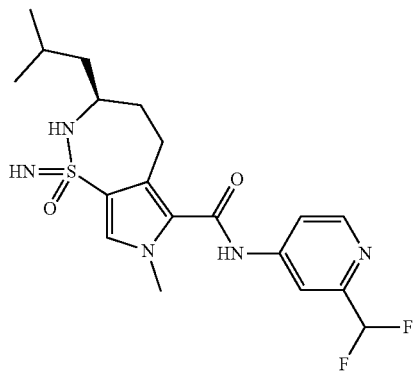 [SMILES: CC(C)C[C@H]1CCc2c(cn(C)c2C(=O)Nc2ccnc(C(F)F)c2)S(=N)(=O)N1] | Peak2 (HPLC) |
| 20y1 | 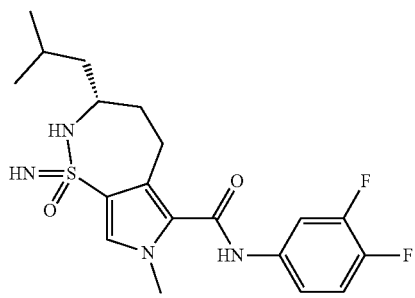 | Peak1 (HPLC) |
| 20y2 | 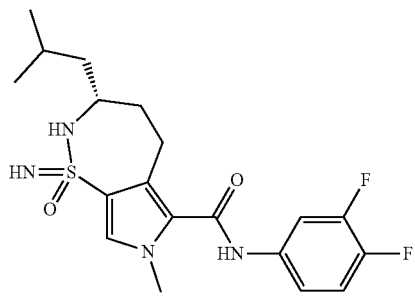 | Peak2 (HPLC) |

-continued

| No. | Structure | Remark |
|---|---|---|
| 20z1 | 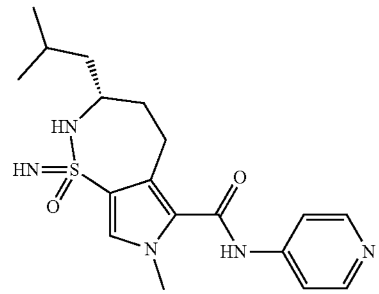 | Peak1 (HPLC) |
| 20z2 | 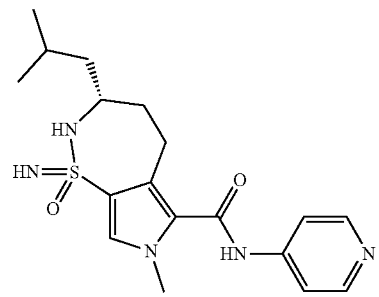 | Peak2 (HPLC) |
| 20aa1 | 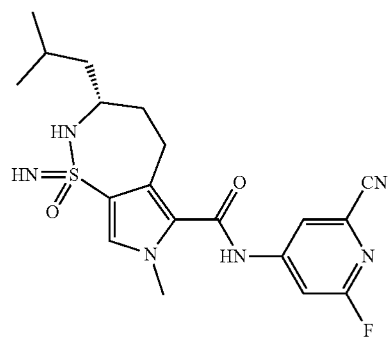 | Peak1 (HPLC) |
| 20aa2 | 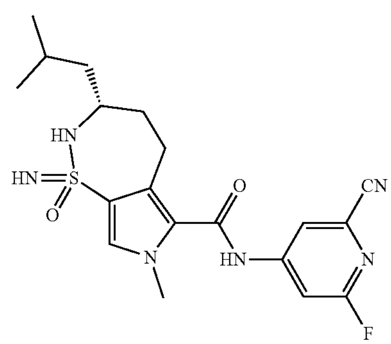 [SMILES: CC(C)C[C@@H]1CCc2c(cn(C)c2C(=O)Nc2cc(F)nc(C#N)c2)S(=N)(=O)N1] | Peak2 (HPLC) |
| 20bb1 | 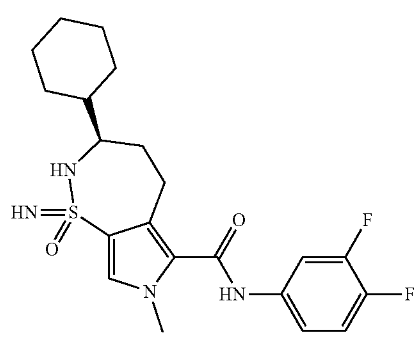 [SMILES: Cn1cc2c(c1C(=O)Nc1ccc(F)c(F)c1)CC[C@H](C1CCCCC1)NS2(=N)=O] | Peak1 (HPLC) |

-continued
| No. | Structure | Remark |
|---|---|---|
| 20bb2 | 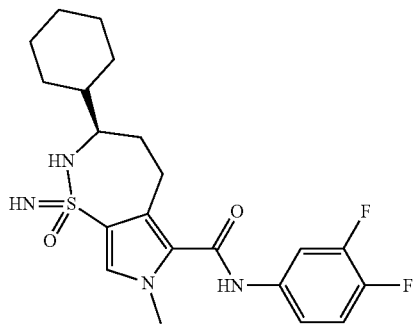 [SMILES: Cn1cc2c(c1C(=O)Nc1ccc(F)c(F)c1)CC[C@H](C1CCCCC1)NS2(=N)=O] | Peak2 (HPLC) |
| 20cc1 | 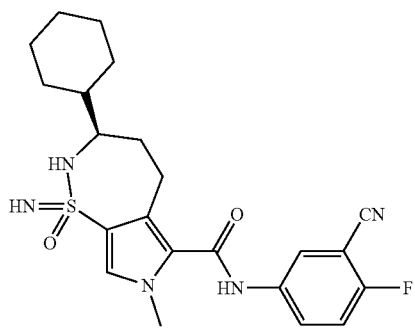 [SMILES: Cn1cc2c(c1C(=O)Nc1ccc(F)c(C#N)c1)CC[C@H](C1CCCCC1)NS2(=N)=O] | Peak1 (HPLC) |
| 20cc2 | 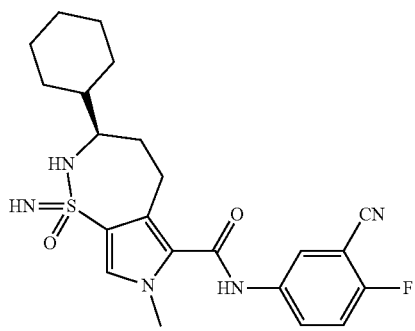 [SMILES: Cn1cc2c(c1C(=O)Nc1ccc(F)c(C#N)c1)CC[C@H](C1CCCCC1)NS2(=N)=O] | Peak2 (HPLC) |
| 20dd1 | 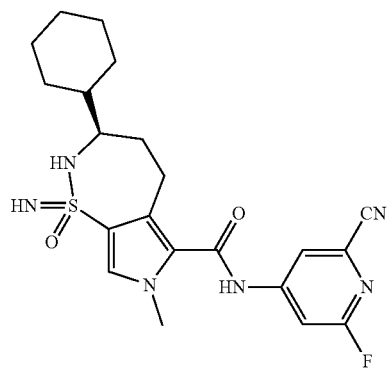 [SMILES: Cn1cc2c(c1C(=O)Nc1cc(F)nc(C#N)c1)CC[C@H](C1CCCCC1)NS2(=N)=O] | Peak1 (HPLC) |

-continued
| No. | Structure | Remark |
|---|---|---|
| 20dd2 | 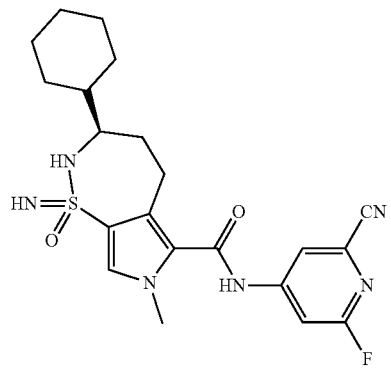 [SMILES: Cn1cc2c(c1C(=O)Nc1cc(F)nc(C#N)c1)CC[C@H](C1CCCCC1)NS2(=N)=O] | Peak2 (HPLC) |
| 20ee1 | 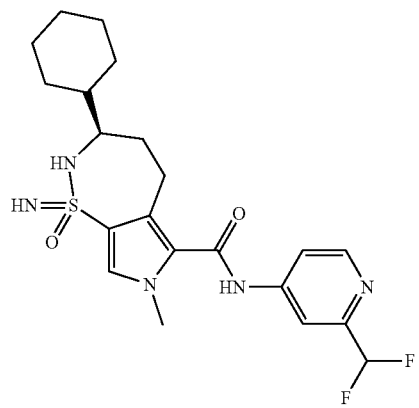 [SMILES: Cn1cc2c(c1C(=O)Nc1ccnc(C(F)F)c1)CC[C@H](C1CCCCC1)NS2(=N)=O] | Peak1 (HPLC) |
| 20ee2 | 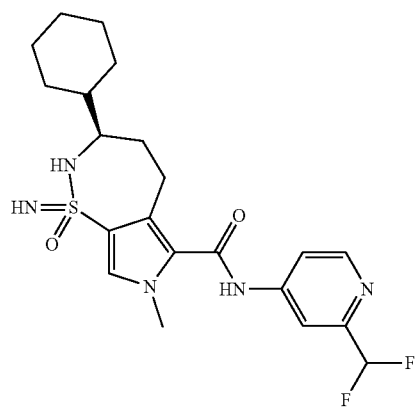 [SMILES: Cn1cc2c(c1C(=O)Nc1ccnc(C(F)F)c1)CC[C@H](C1CCCCC1)NS2(=N)=O] | Peak2 (HPLC) |
| 20ff1 | 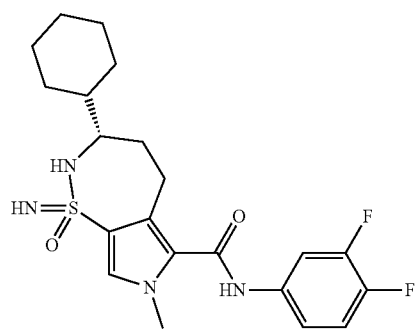 | Peak1 (HPLC) |

| No. | Structure | Remark |
|---|---|---|
| 20ff2 | 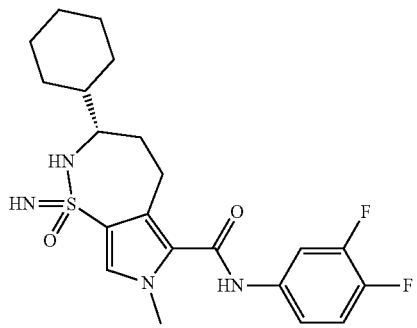 | Peak2 (HPLC) |
| 20gg1 | 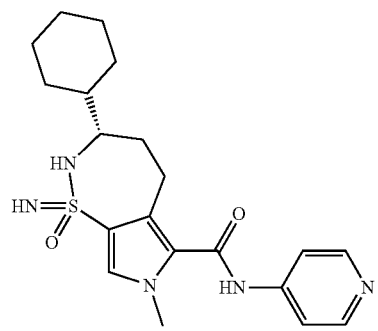 [SMILES: Cn1cc2c(c1C(=O)Nc1ccncc1)CC[C@@H](C1CCCCC1)NS2(=N)=O] | Peak1 (HPLC) |
| 20gg2 | 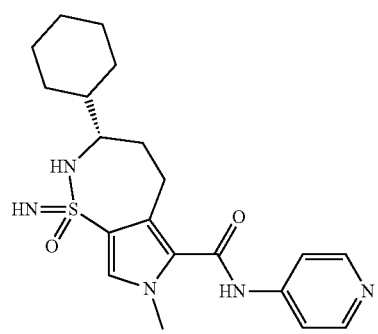 | Peak2 (HPLC) |
| 20hh1 | 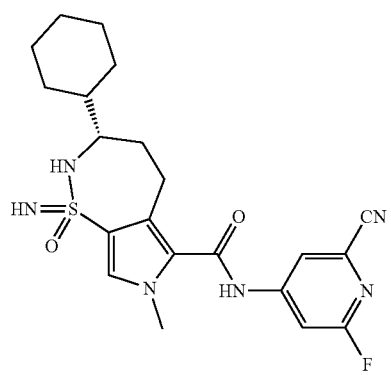 [SMILES: Cn1cc2c(c1C(=O)Nc1cc(F)nc(C#N)c1)CC[C@@H](C1CCCCC1)NS2(=N)=O] | Peak1 (HPLC) |

|No.|Structure|Remark|
|---|---|---|
|20hh2|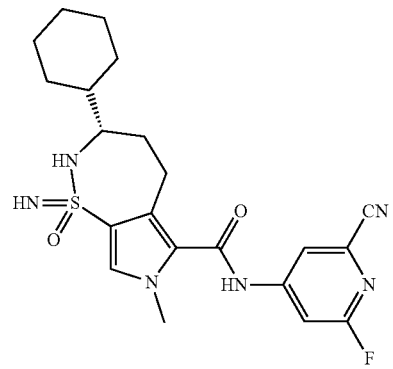 [SMILES: Cn1cc2c(c1C(=O)Nc1cc(F)nc(C#N)c1)CC[C@@H](C1CCCCC1)NS2(=N)=O]|Peak2 (HPLC)|
|20ii1|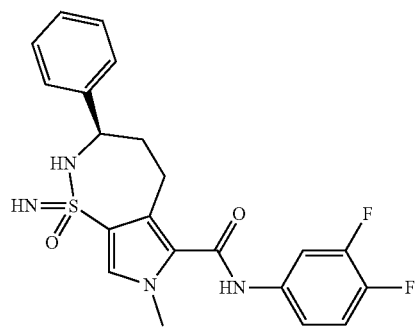|Peak1 (HPLC)|
|20ii2|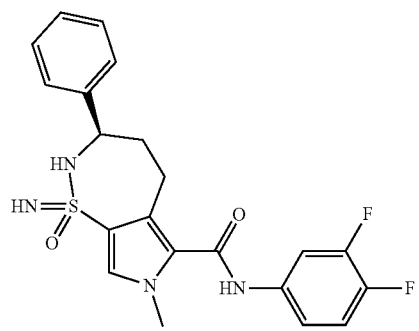 [SMILES: Cn1cc2c(c1C(=O)Nc1ccc(F)c(F)c1)CC[C@H](c1ccccc1)NS2(=N)=O]|Peak2 (HPLC)|
|20jj1|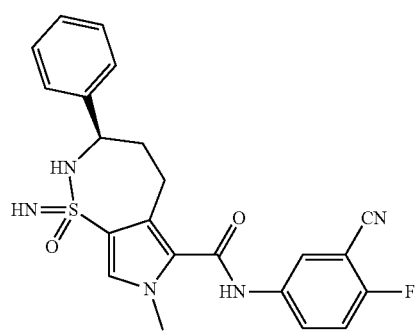|Peak1 (HPLC)|

| No. | Structure | Remark |
|---|---|---|
| 20jj2 | 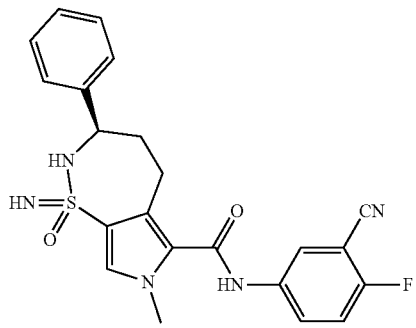 [SMILES: Cn1cc2c(c1C(=O)Nc1ccc(F)c(C#N)c1)CC[C@H](c1ccccc1)NS2(=N)=O] | Peak2 (HPLC) |
| 20kk1 | 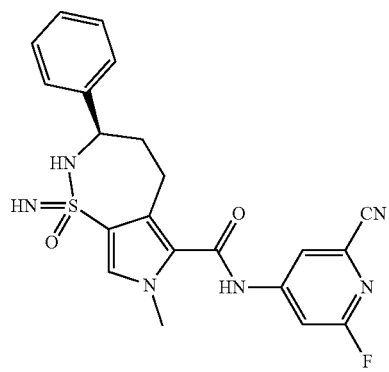 [SMILES: Cn1cc2c(c1C(=O)Nc1cc(F)nc(C#N)c1)CC[C@H](c1ccccc1)NS2(=N)=O] | Peak1 (HPLC) |
| 20kk2 | 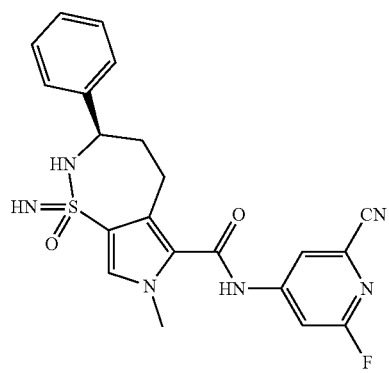 [SMILES: Cn1cc2c(c1C(=O)Nc1cc(F)nc(C#N)c1)CC[C@H](c1ccccc1)NS2(=N)=O] | Peak2 (HPLC) |
| 20mm1 | 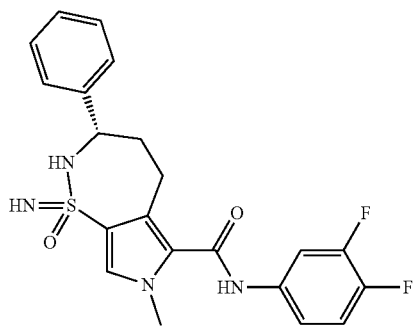 | Peak1 (HPLC) |

| No. | Structure | Remark |
| --- | --- | --- |
| 20mm2 | 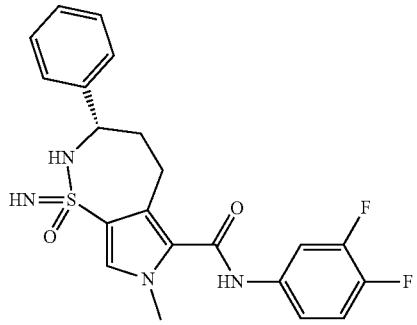 [SMILES: Cn1cc2c(c1C(=O)Nc1ccc(F)c(F)c1)CC[C@@H](c1ccccc1)NS2(=N)=O] | Peak2 (HPLC) |
| 20nn1 | 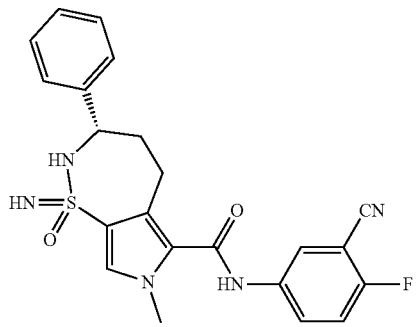 [SMILES: Cn1cc2c(c1C(=O)Nc1ccc(F)c(C#N)c1)CC[C@@H](c1ccccc1)NS2(=N)=O] | Peak1 (HPLC) |
| 20nn2 | 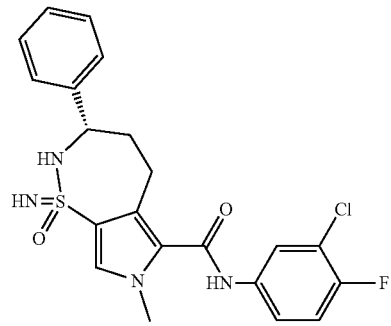 [SMILES: Cn1cc2c(c1C(=O)Nc1ccc(F)c(Cl)c1)CC[C@@H](c1ccccc1)NS2(=N)=O] | Peak2 (HPLC) |
| 20oo1 | 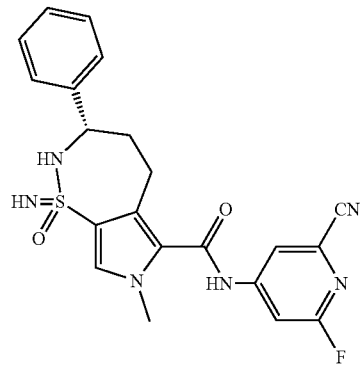 [SMILES: Cn1cc2c(c1C(=O)Nc1cc(F)nc(C#N)c1)CC[C@@H](c1ccccc1)NS2(=N)=O] | Peak1 (HPLC) |

-continued

| No. | Structure | Remark |
|---|---|---|
| 20oo2 | 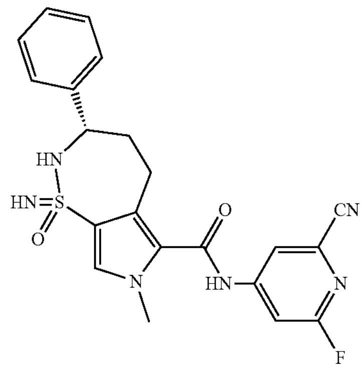 [SMILES: Cn1cc2c(c1C(=O)Nc1cc(F)nc(C#N)c1)CC[C@@H](c1ccccc1)NS2(=N)=O] | Peak2 (HPLC) |
| 20pp1 | 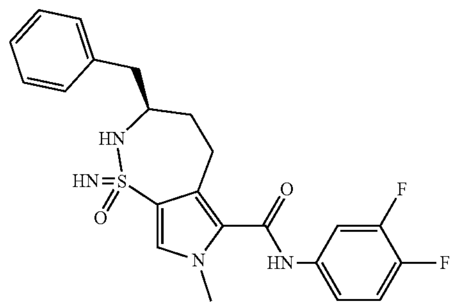 [SMILES: Cn1cc2c(c1C(=O)Nc1ccc(F)c(F)c1)CC[C@H](Cc1ccccc1)NS2(=N)=O] | Peak1 (HPLC) |
| 20pp2 | 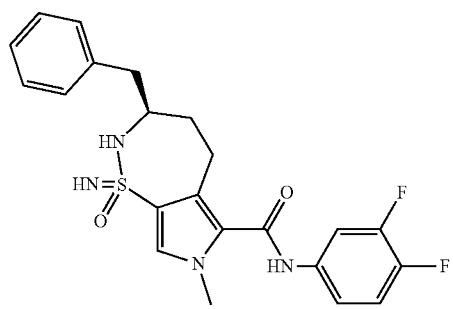 [SMILES: Cn1cc2c(c1C(=O)Nc1ccc(F)c(F)c1)CC[C@H](Cc1ccccc1)NS2(=N)=O] | Peak2 (HPLC) |
| 20qq1 | 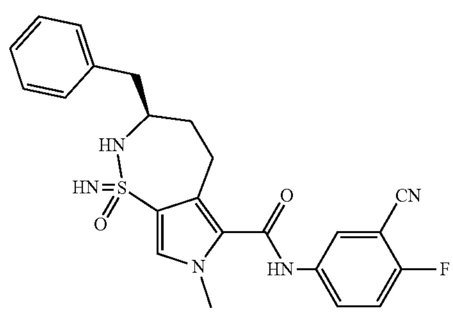 [SMILES: Cn1cc2c(c1C(=O)Nc1ccc(F)c(C#N)c1)CC[C@H](Cc1ccccc1)NS2(=N)=O] | Peak1 (HPLC) |
| 20qq2 | 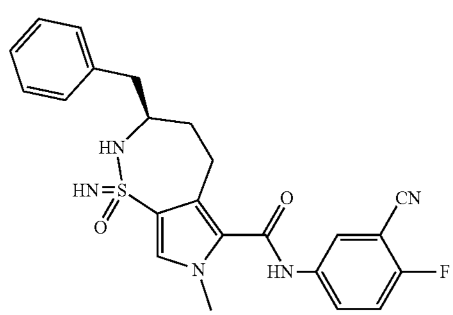 [SMILES: Cn1cc2c(c1C(=O)Nc1ccc(F)c(C#N)c1)CC[C@H](Cc1ccccc1)NS2(=N)=O] | Peak2 (HPLC) |

-continued
| No. | Structure | Remark |
|---|---|---|
| 20rr1 | 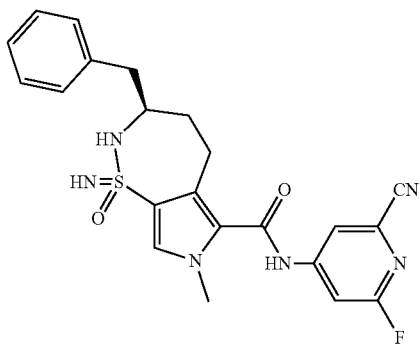 [SMILES: Cn1cc2c(c1C(=O)Nc1cc(F)nc(C#N)c1)CC[C@H](Cc1ccccc1)NS2(=N)=O] | Peak1 (HPLC) |
| 20rr2 | 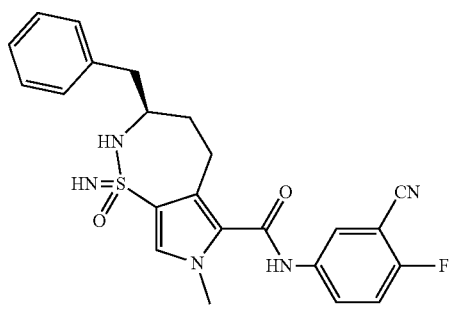 [SMILES: Cn1cc2c(c1C(=O)Nc1ccc(F)c(C#N)c1)CC[C@H](Cc1ccccc1)NS2(=N)=O] | Peak2 (HPLC) |
| 20ss1 | 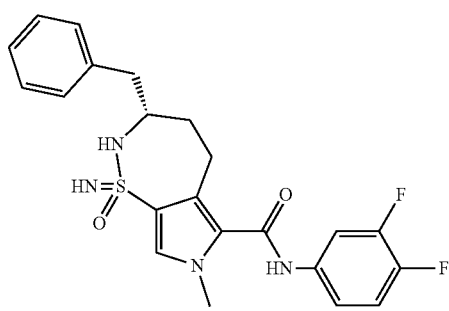 [SMILES: Cn1cc2c(c1C(=O)Nc1ccc(F)c(F)c1)CC[C@@H](Cc1ccccc1)NS2(=N)=O] | Peak1 (HPLC) |
| 20ss2 | 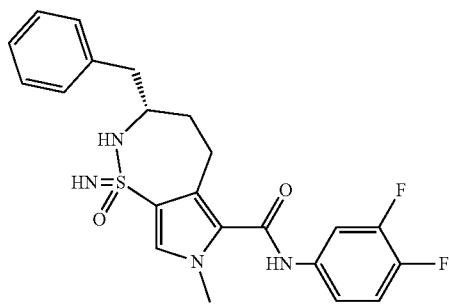 [SMILES: Cn1cc2c(c1C(=O)Nc1ccc(F)c(F)c1)CC[C@@H](Cc1ccccc1)NS2(=N)=O] | Peak2 (HPLC) |

-continued

| No. | Structure | Remark |
|---|---|---|
| 20tt1 | 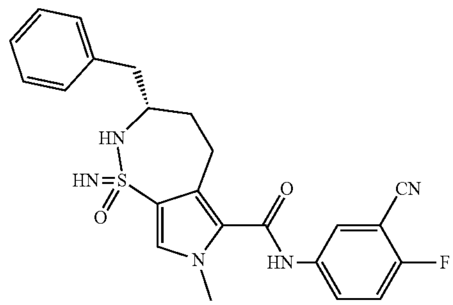 [SMILES: Cn1cc2c(c1C(=O)Nc1ccc(F)c(C#N)c1)CC[C@@H](Cc1ccccc1)NS2(=N)=O] | Peak1 (HPLC) |
| 20tt2 | 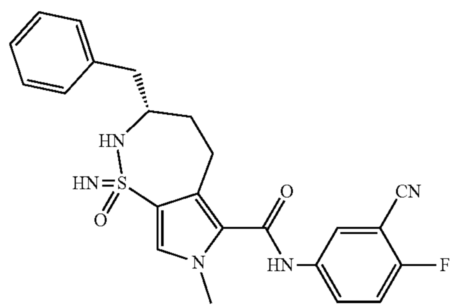 [SMILES: Cn1cc2c(c1C(=O)Nc1ccc(F)c(C#N)c1)CC[C@@H](Cc1ccccc1)NS2(=N)=O] | Peak2 (HPLC) |
| 20uu1 | 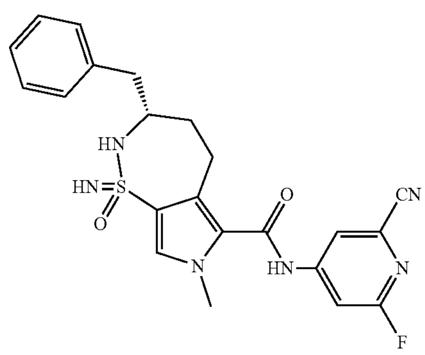 [SMILES: Cn1cc2c(c1C(=O)Nc1cc(F)nc(C#N)c1)CC[C@@H](Cc1ccccc1)NS2(=N)=O] | Peak1 (HPLC) |
| 20uu2 | 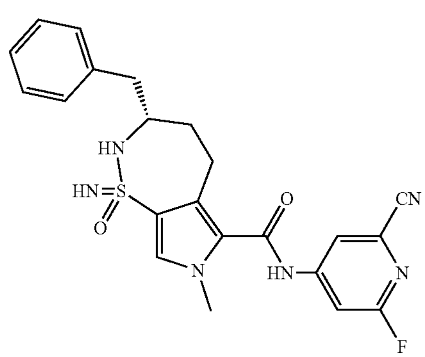 [SMILES: Cn1cc2c(c1C(=O)Nc1cc(F)nc(C#N)c1)CC[C@@H](Cc1ccccc1)NS2(=N)=O] | Peak2 (HPLC) |

| No. | Structure | Remark |
|---|---|---|
| 20vv1 | 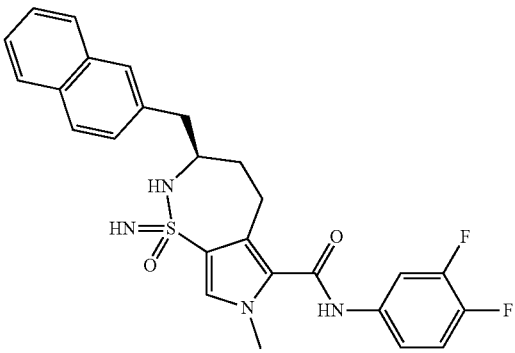 [SMILES: Cn1cc2c(c1C(=O)Nc1ccc(F)c(F)c1)CC[C@H](Cc1ccc3ccccc3c1)NS2(=N)=O] | Peak1 (HPLC) |
| 20vv2 | 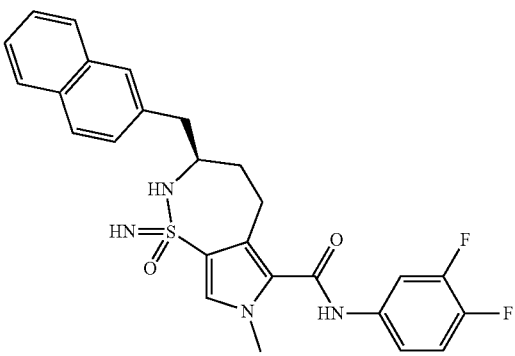 [SMILES: Cn1cc2c(c1C(=O)Nc1ccc(F)c(F)c1)CC[C@H](Cc1ccc3ccccc3c1)NS2(=N)=O] | Peak2 (HPLC) |
| 20ww1 | 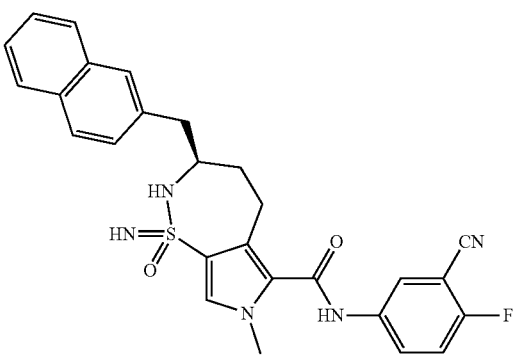 [SMILES: Cn1cc2c(c1C(=O)Nc1ccc(F)c(C#N)c1)CC[C@H](Cc1ccc3ccccc3c1)NS2(=N)=O] | Peak1 (HPLC) |
| 20ww2 | 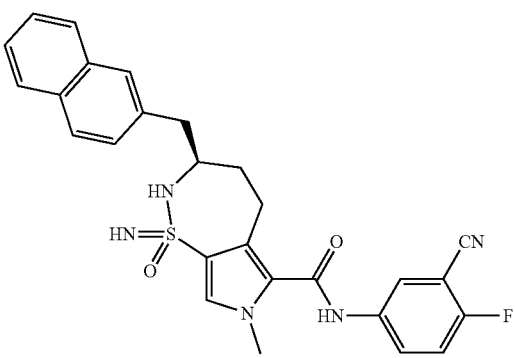 [SMILES: Cn1cc2c(c1C(=O)Nc1ccc(F)c(C#N)c1)CC[C@H](Cc1ccc3ccccc3c1)NS2(=N)=O] | Peak2 (HPLC) |

| No. | Structure | Remark |
|---|---|---|
| 20xx1 | 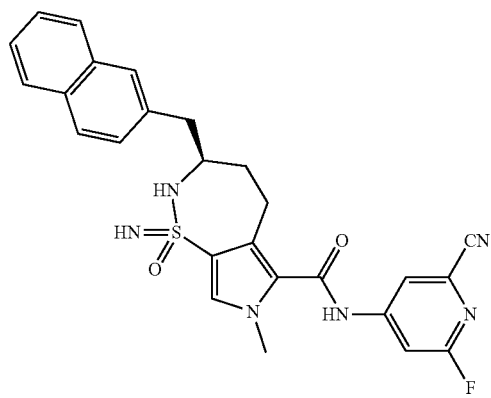 [SMILES: Cn1cc2c(c1C(=O)Nc1cc(F)nc(C#N)c1)CC[C@H](Cc1ccc3ccccc3c1)NS2(=N)=O] | Peak1 (HPLC) |
| 20xx2 | 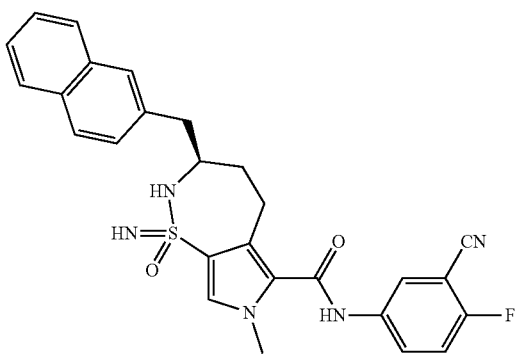 [SMILES: Cn1cc2c(c1C(=O)Nc1ccc(F)c(C#N)c1)CC[C@H](Cc1ccc3ccccc3c1)NS2(=N)=O] | Peak2 (HPLC) |
| 20yy1 | 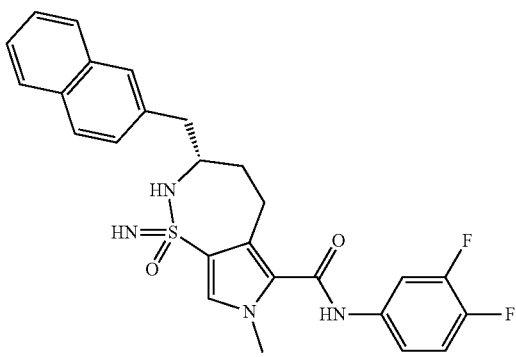 [SMILES: Cn1cc2c(c1C(=O)Nc1ccc(F)c(F)c1)CC[C@@H](Cc1ccc3ccccc3c1)NS2(=N)=O] | Peak1 (HPLC) |
| 20yy2 | 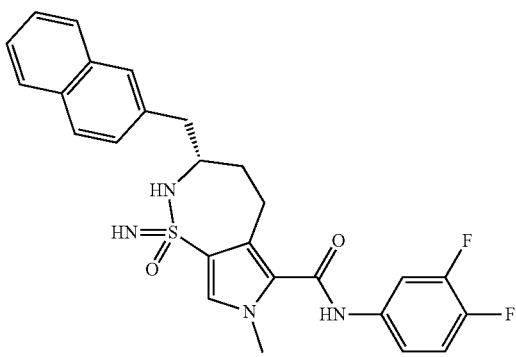 [SMILES: Cn1cc2c(c1C(=O)Nc1ccc(F)c(F)c1)CC[C@@H](Cc1ccc3ccccc3c1)NS2(=N)=O] | Peak2 (HPLC) |

| No. | Structure | Remark |
|---|---|---|
| 20zz1 | 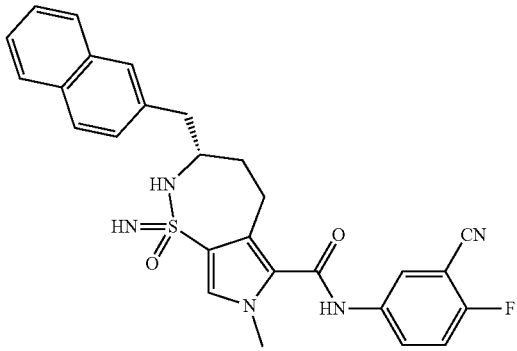 [SMILES: Cn1cc2c(c1C(=O)Nc1ccc(F)c(C#N)c1)CC[C@@H](Cc1ccc3ccccc3c1)NS2(=N)=O] | Peak1 (HPLC) |
| 20zz2 | 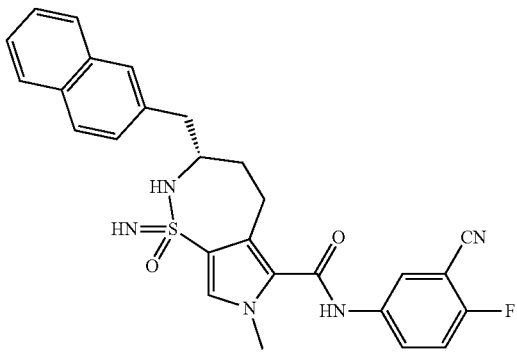 [SMILES: Cn1cc2c(c1C(=O)Nc1ccc(F)c(C#N)c1)CC[C@@H](Cc1ccc3ccccc3c1)NS2(=N)=O] | Peak2 (HPLC) |
| 20aaa1 | 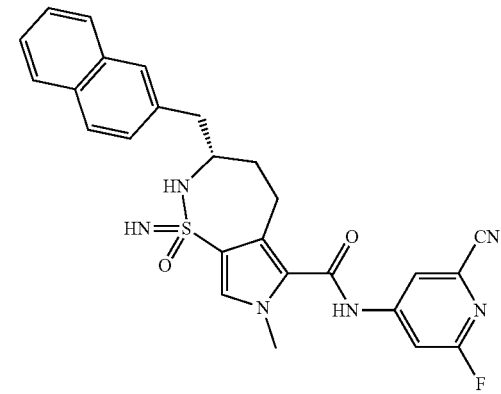 [SMILES: Cn1cc2c(c1C(=O)Nc1cc(F)nc(C#N)c1)CC[C@@H](Cc1ccc3ccccc3c1)NS2(=N)=O] | Peak1 (HPLC) |
| 20aaa2 | 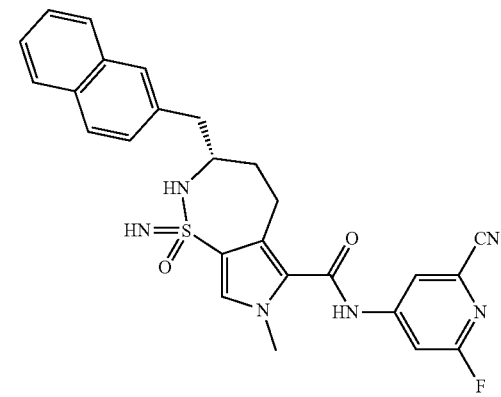 | Peak2 (HPLC) |

| No. | Structure | Remark |
|---|---|---|
| 20bbb1 | 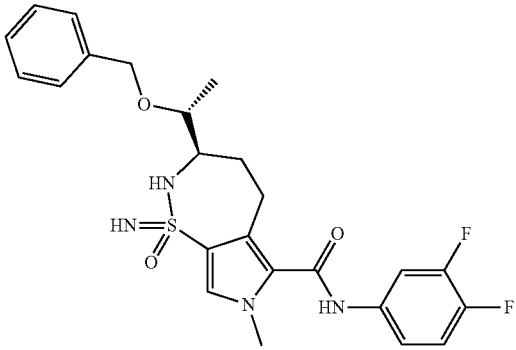 [SMILES: C[C@@H](OCc1ccccc1)[C@H]1CCc2c(cn(C)c2C(=O)Nc2ccc(F)c(F)c2)S(=N)(=O)N1] | Peak1 (HPLC) |
| 20bbb2 | 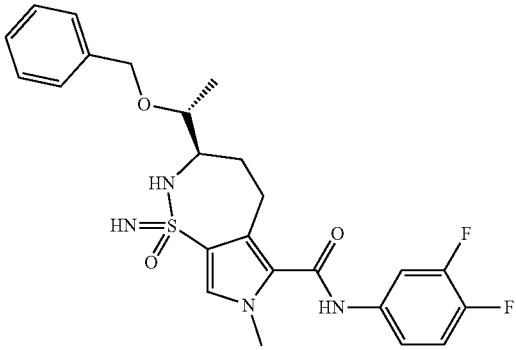 [SMILES: C[C@@H](OCc1ccccc1)[C@H]1CCc2c(cn(C)c2C(=O)Nc2ccc(F)c(F)c2)S(=N)(=O)N1] | Peak2 (HPLC) |
| 20ccc1 | 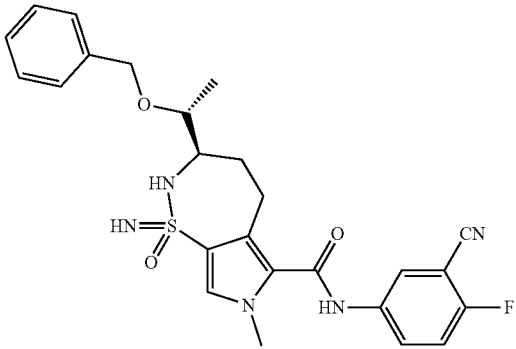 [SMILES: C[C@@H](OCc1ccccc1)[C@H]1CCc2c(cn(C)c2C(=O)Nc2ccc(F)c(C#N)c2)S(=N)(=O)N1] | Peak1 (HPLC) |
| 20ccc2 | 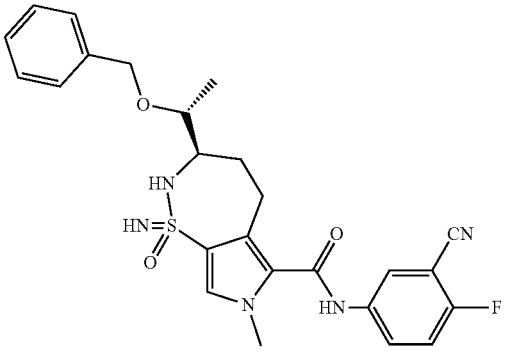 [SMILES: C[C@@H](OCc1ccccc1)[C@H]1CCc2c(cn(C)c2C(=O)Nc2ccc(F)c(C#N)c2)S(=N)(=O)N1] | Peak2 (HPLC) |

-continued

| No. | Structure | Remark |
|---|---|---|
| 20ddd1 | 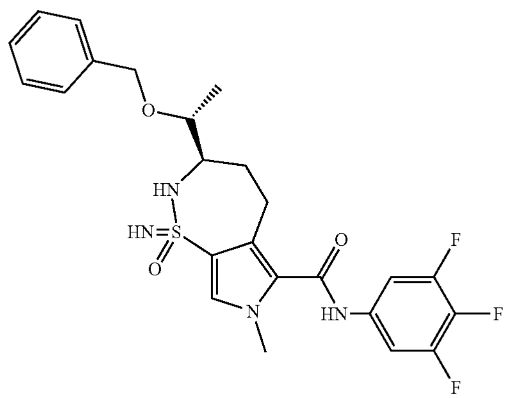 [SMILES: C[C@@H](OCc1ccccc1)[C@H]1CCc2c(cn(C)c2C(=O)Nc2cc(F)c(F)c(F)c2)S(=N)(=O)N1] | Peak1 (HPLC) |
| 20ddd2 | 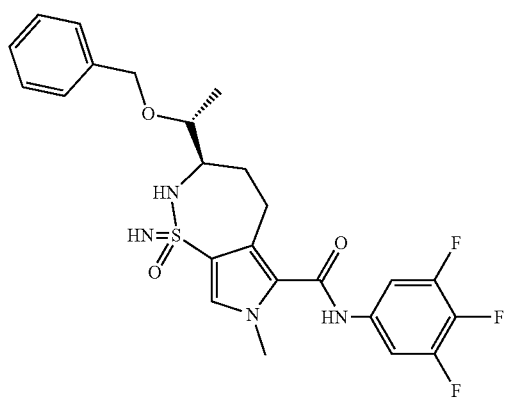 | Peak2 (HPLC) |
| 20eee1 | 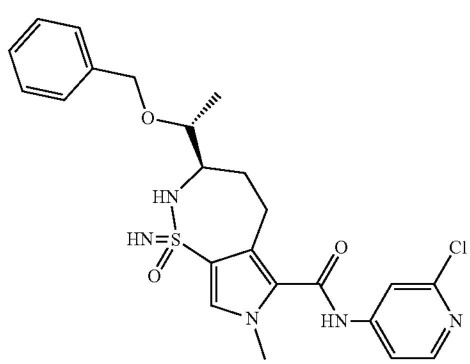 [SMILES: C[C@@H](OCc1ccccc1)[C@H]1CCc2c(cn(C)c2C(=O)Nc2ccnc(Cl)c2)S(=N)(=O)N1] | Peak1 (HPLC) |
| 20eee2 | 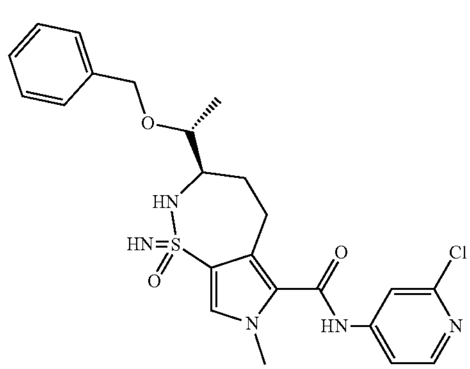 [SMILES: C[C@@H](OCc1ccccc1)[C@H]1CCc2c(cn(C)c2C(=O)Nc2ccnc(Cl)c2)S(=N)(=O)N1] | Peak2 (HPLC) |

| No. | Structure | Remark |
|---|---|---|
| 20fff1 | 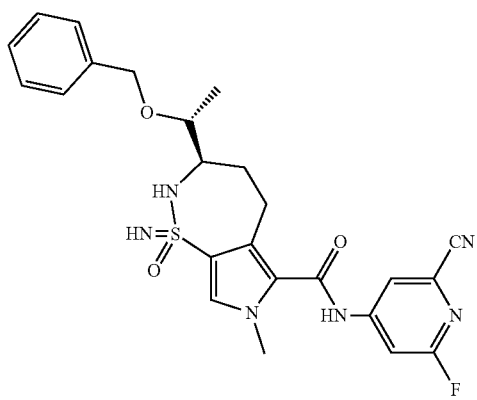 [SMILES: C[C@@H](OCc1ccccc1)[C@H]1CCc2c(cn(C)c2C(=O)Nc2cc(F)nc(C#N)c2)S(=N)(=O)N1] | Peak1 (HPLC) |
| 20fff2 | 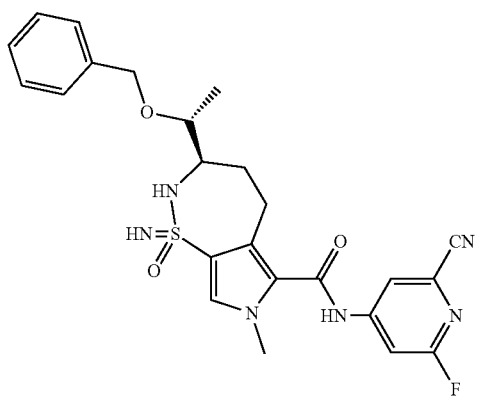 [SMILES: C[C@@H](OCc1ccccc1)[C@H]1CCc2c(cn(C)c2C(=O)Nc2cc(F)nc(C#N)c2)S(=N)(=O)N1] | Peak2 (HPLC) |
| 20ggg1 | 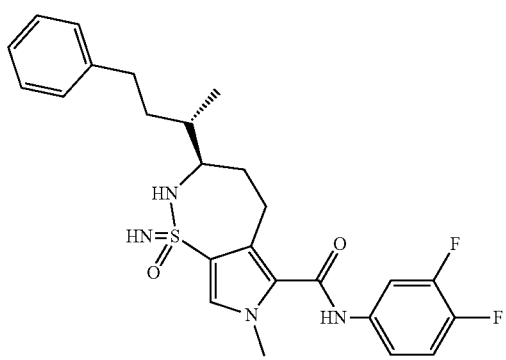 [SMILES: C[C@@H](CCc1ccccc1)[C@H]1CCc2c(cn(C)c2C(=O)Nc2ccc(F)c(F)c2)S(=N)(=O)N1] | Peak1 (HPLC) |
| 20ggg2 | 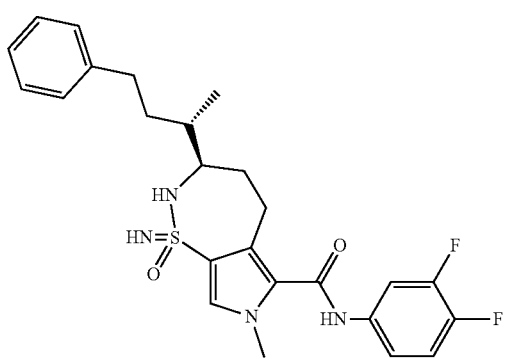 | Peak2 (HPLC) |

| No. | Structure | Remark |
|---|---|---|
| 20hhh1 | 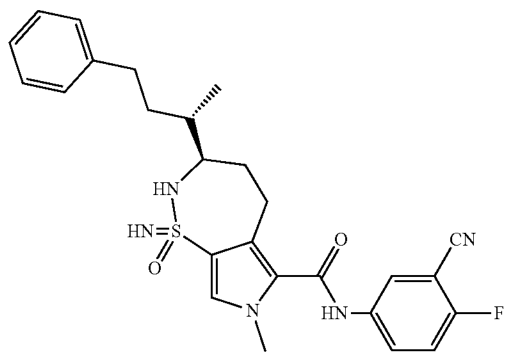 [SMILES: C[C@@H](CCc1ccccc1)[C@H]1CCc2c(cn(C)c2C(=O)Nc2ccc(F)c(C#N)c2)S(=N)(=O)N1] | Peak1 (HPLC) |
| 20hhh2 | 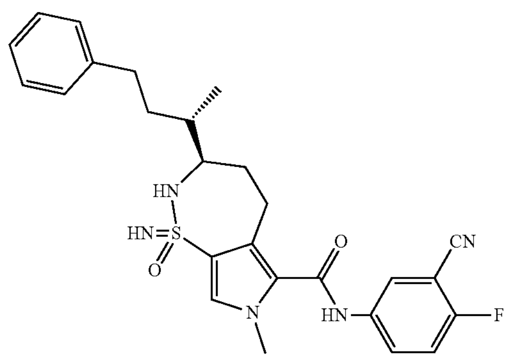 [SMILES: C[C@@H](CCc1ccccc1)[C@H]1CCc2c(cn(C)c2C(=O)Nc2ccc(F)c(C#N)c2)S(=N)(=O)N1] | Peak2 (HPLC) |
| 20iii1 | 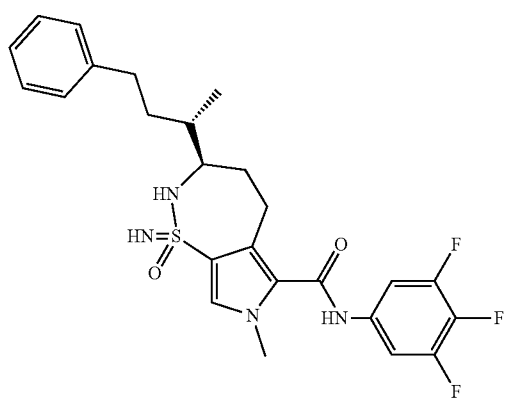 | Peak1 (HPLC) |
| 20iii2 | 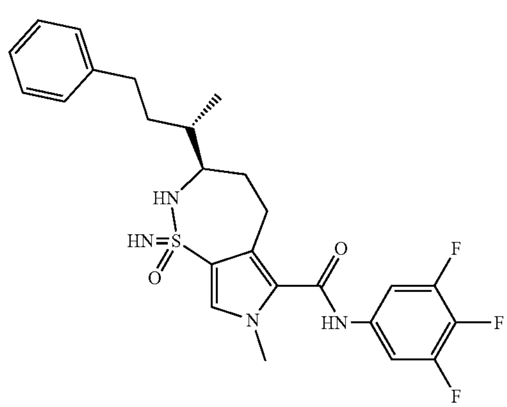 [SMILES: C[C@@H](CCc1ccccc1)[C@H]1CCc2c(cn(C)c2C(=O)Nc2cc(F)c(F)c(F)c2)S(=N)(=O)N1] | Peak2 (HPLC) |

| No. | Structure | Remark |
| --- | --- | --- |
| 20jjj1 | 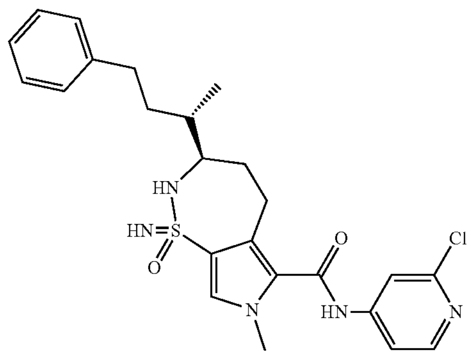 [SMILES: C[C@@H](CCc1ccccc1)[C@H]1CCc2c(cn(C)c2C(=O)Nc2ccnc(Cl)c2)S(=N)(=O)N1] | Peak1 (HPLC) |
| 20jjj2 | 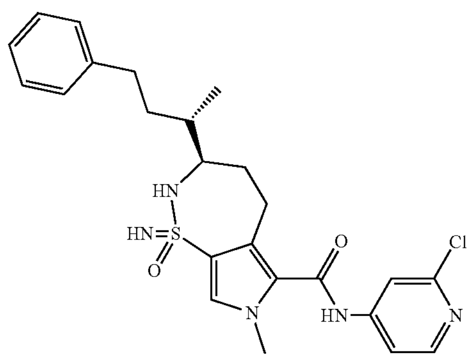 [SMILES: C[C@@H](CCc1ccccc1)[C@H]1CCc2c(cn(C)c2C(=O)Nc2ccnc(Cl)c2)S(=N)(=O)N1] | Peak2 (HPLC) |
| 20kkk1 | 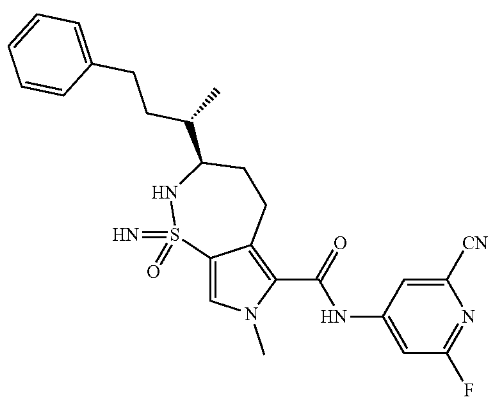 [SMILES: C[C@@H](CCc1ccccc1)[C@H]1CCc2c(cn(C)c2C(=O)Nc2cc(F)nc(C#N)c2)S(=N)(=O)N1] | Peak1 (HPLC) |
| 20kkk2 | 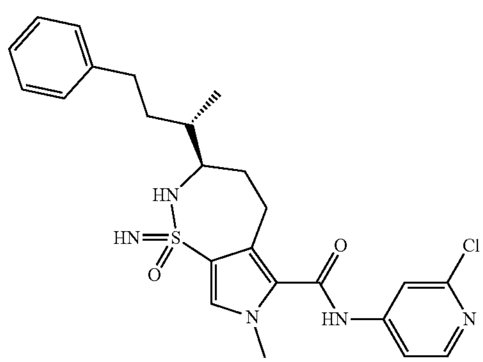 [SMILES: C[C@@H](CCc1ccccc1)[C@H]1CCc2c(cn(C)c2C(=O)Nc2ccnc(Cl)c2)S(=N)(=O)N1] | Peak2 (HPLC) |

| No. | Structure | Remark |
|---|---|---|
| 20mmm1 | 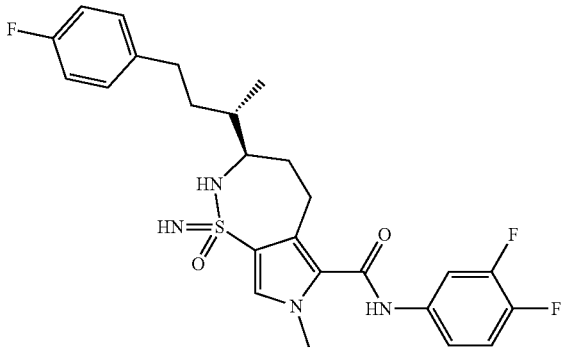 | Peak1 (HPLC) |
| 20mmm2 | 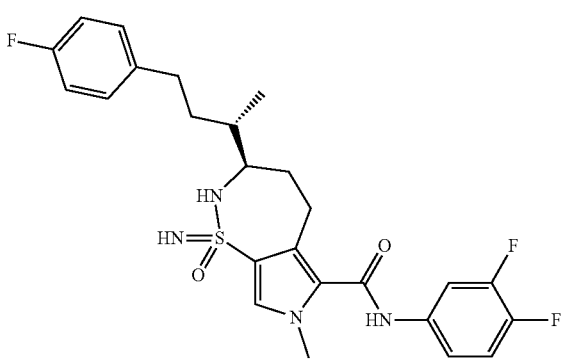 | Peak2 (HPLC) |
| 20nnn1 | 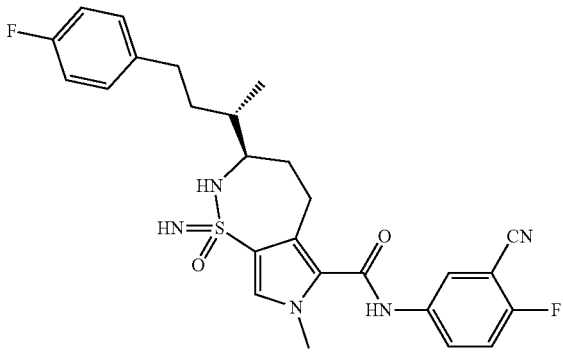 | Peak1 (HPLC) |
| 20nnn2 | 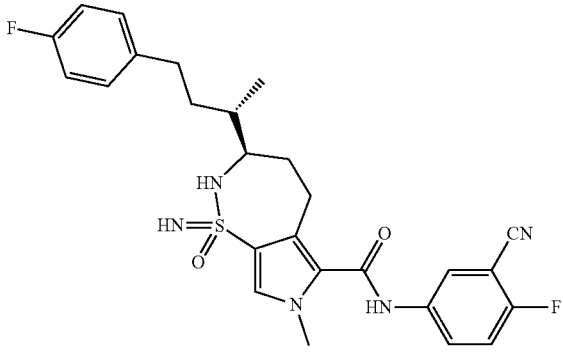 | Peak2 (HPLC) |

| No. | Structure | Remark |
|---|---|---|
| 20ooo1 | 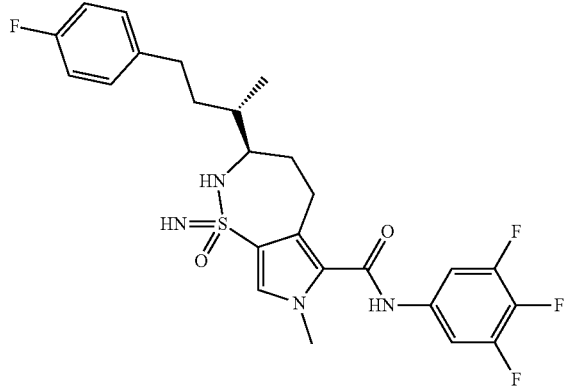 | Peak1 (HPLC) |
| 20ooo2 | 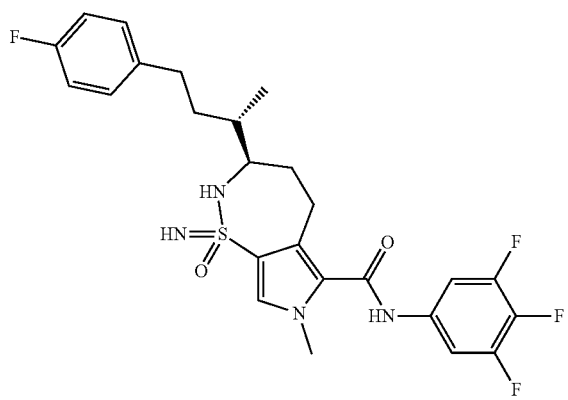 [SMILES: C[C@@H](CCc1ccc(F)cc1)[C@H]1CCc2c(cn(C)c2C(=O)Nc2cc(F)c(F)c(F)c2)S(=N)(=O)N1] | Peak2 (HPLC) |
| 20ppp1 | 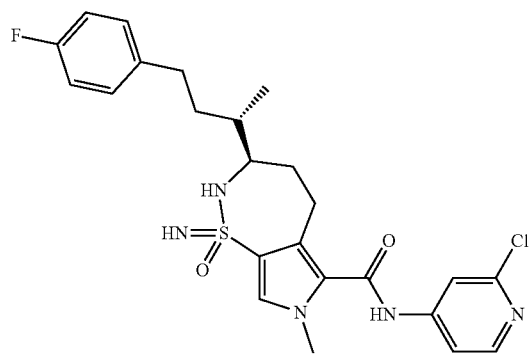 [SMILES: C[C@@H](CCc1ccc(F)cc1)[C@H]1CCc2c(cn(C)c2C(=O)Nc2ccnc(Cl)c2)S(=N)(=O)N1] | Peak1 (HPLC) |
| 20ppp2 | 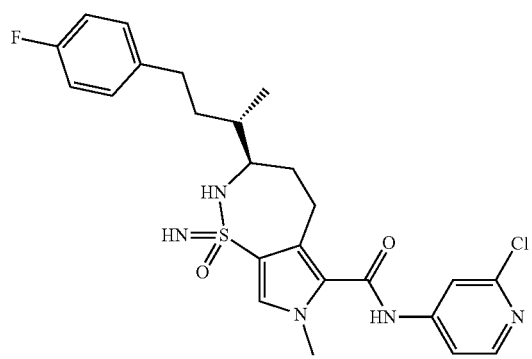 [SMILES: C[C@@H](CCc1ccc(F)cc1)[C@H]1CCc2c(cn(C)c2C(=O)Nc2ccnc(Cl)c2)S(=N)(=O)N1] | Peak2 (HPLC) |

| No. | Structure | Remark |
|---|---|---|
| 20qqq1 | 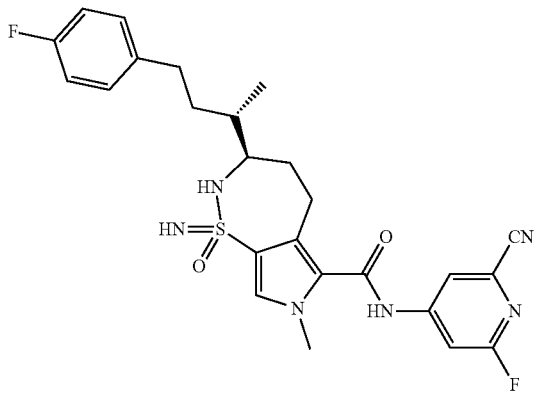 [SMILES: C[C@@H](CCc1ccc(F)cc1)[C@H]1CCc2c(cn(C)c2C(=O)Nc2cc(F)nc(C#N)c2)S(=N)(=O)N1] | Peak1 (HPLC) |
| 20qqq2 | 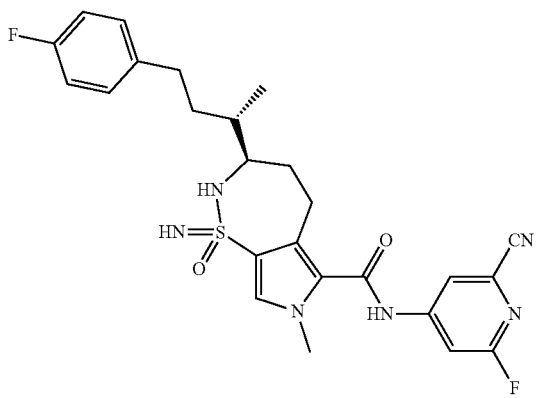 [SMILES: C[C@@H](CCc1ccc(F)cc1)[C@H]1CCc2c(cn(C)c2C(=O)Nc2cc(F)nc(C#N)c2)S(=N)(=O)N1] | Peak2 (HPLC) |
| 20rrr1 | 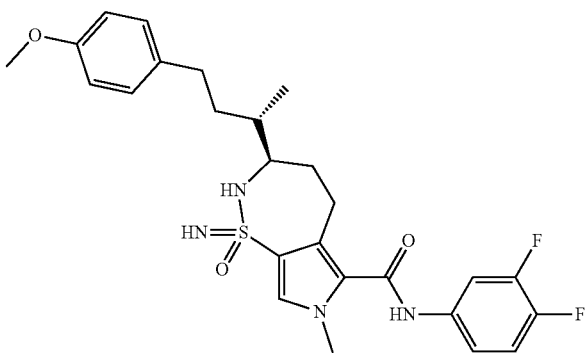 | Peak1 (HPLC) |
| 20rrr2 | 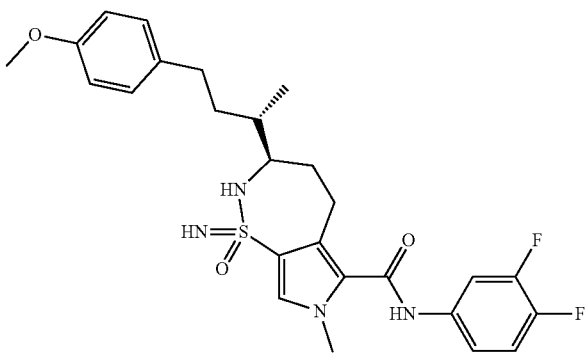 | Peak2 (HPLC) |

-continued
| No. | Structure | Remark |
|---|---|---|
| 20sss1 | 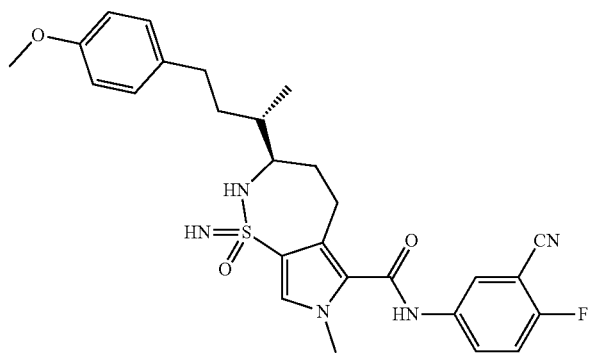 | Peak1 (HPLC) |
| 20sss2 | 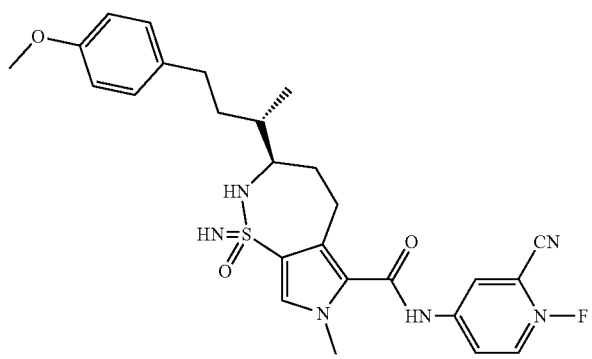 | Peak2 (HPLC) |
| 20ttt1 | 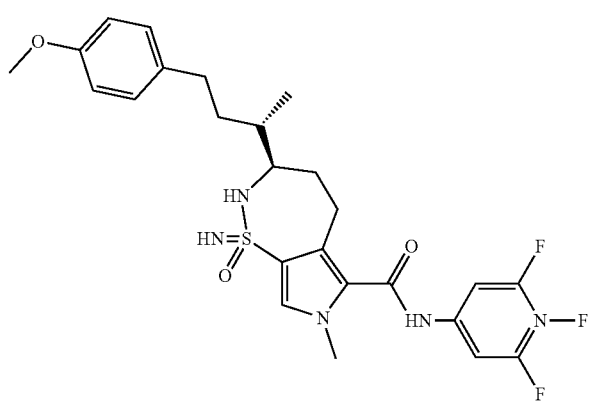 | Peak1 (HPLC) |
| 20ttt2 | 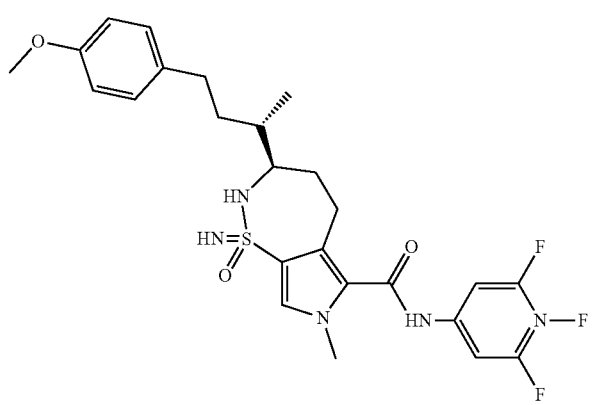 | Peak2 (HPLC) |

-continued

| No. | Structure | Remark |
|---|---|---|
| 20uuu1 | 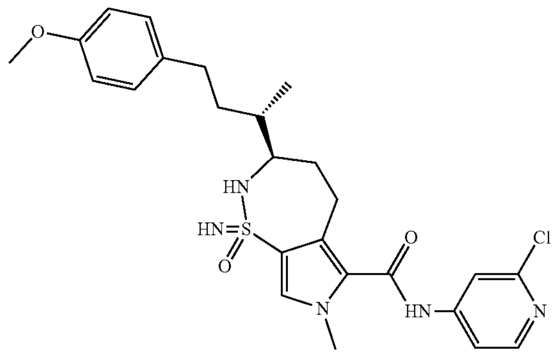 [SMILES: COc1ccc(CC[C@H](C)[C@H]2CCc3c(cn(C)c3C(=O)Nc3ccnc(Cl)c3)S(=N)(=O)N2)cc1] | Peak1 (HPLC) |
| 20uuu2 | 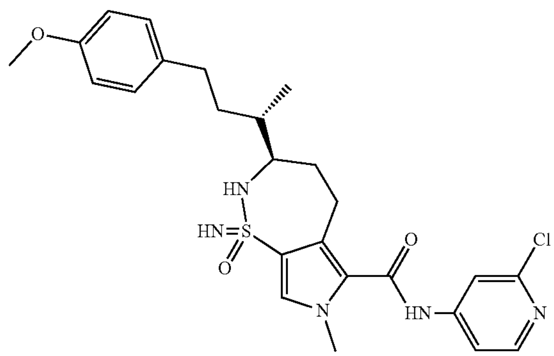 [SMILES: COc1ccc(CC[C@H](C)[C@H]2CCc3c(cn(C)c3C(=O)Nc3ccnc(Cl)c3)S(=N)(=O)N2)cc1] | Peak2 (HPLC) |
| 20vvv1 | 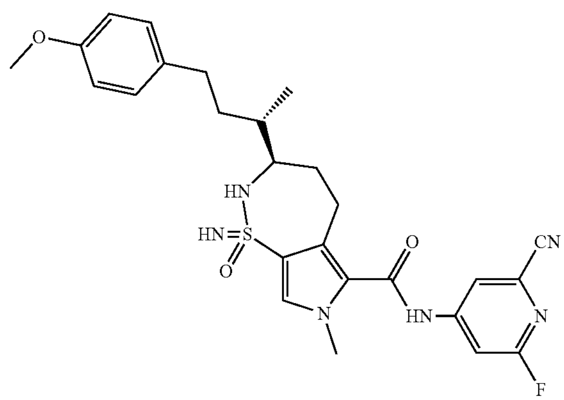 [SMILES: COc1ccc(CC[C@H](C)[C@H]2CCc3c(cn(C)c3C(=O)Nc3cc(F)nc(C#N)c3)S(=N)(=O)N2)cc1] | Peak1 (HPLC) |
| 20vvv2 | 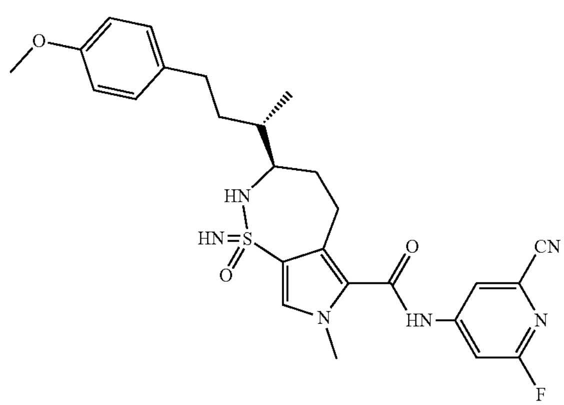 [SMILES: COc1ccc(CC[C@H](C)[C@H]2CCc3c(cn(C)c3C(=O)Nc3cc(F)nc(C#N)c3)S(=N)(=O)N2)cc1] | Peak2 (HPLC) |

-continued
| No. | Structure | Remark |
|---|---|---|
| 20www1 | 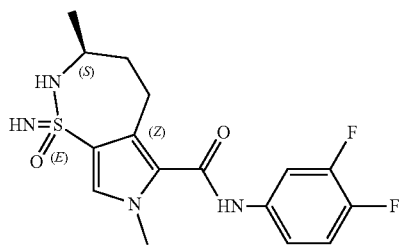 | Peak1 (HPLC) |
| 20www2 | 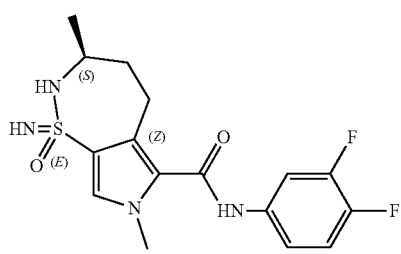 | Peak2 (HPLC) |
| 20xxx1 | 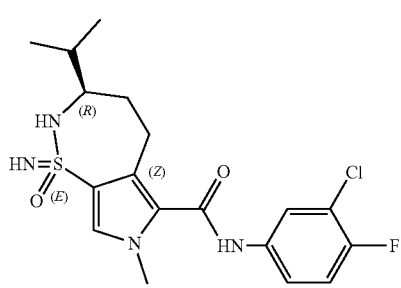 | Peak1 (HPLC) |
| 20xxx2 | 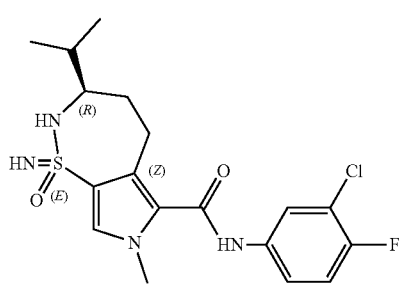 | Peak2 (HPLC) |
| 30a1 | 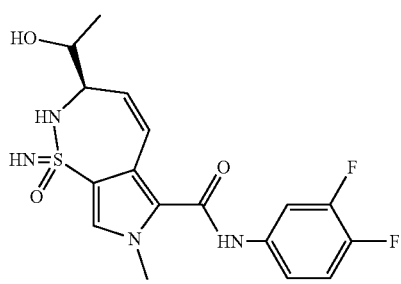 [SMILES: CC(O)[C@H]1C=Cc2c(cn(C)c2C(=O)Nc2ccc(F)c(F)c2)S(=N)(=O)N1] | Peak1 (HPLC) |

-continued
| No. | Structure | Remark |
|---|---|---|
| 30a2 | 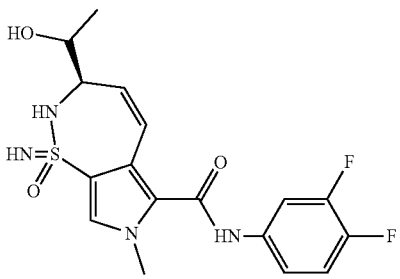 | Peak2 (HPLC) |
| 30b1 | 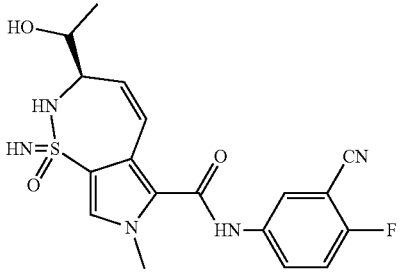 [SMILES: CC(O)[C@H]1C=Cc2c(cn(C)c2C(=O)Nc2ccc(F)c(C#N)c2)S(=N)(=O)N1] | Peak1 (HPLC) |
| 30b2 | 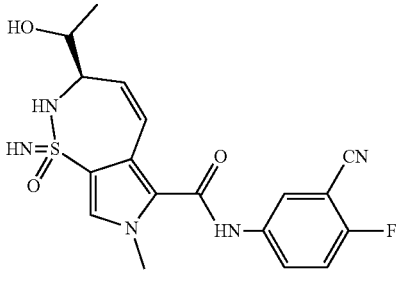 [SMILES: CC(O)[C@H]1C=Cc2c(cn(C)c2C(=O)Nc2ccc(F)c(C#N)c2)S(=N)(=O)N1] | Peak2 (HPLC) |
| 30c1 | 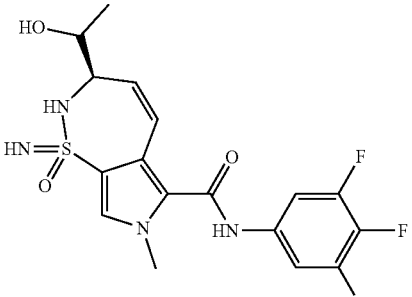 | Peak1 (HPLC) |
| 30c2 | 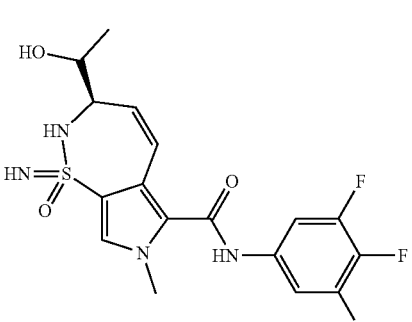 | Peak2 (HPLC) |

-continued

| No. | Structure | Remark |
|---|---|---|
| 30d1 | 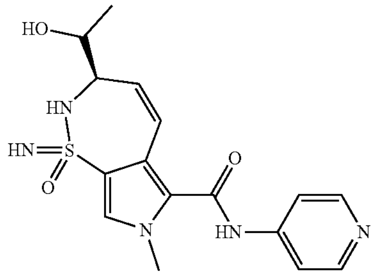 [SMILES: CC(O)[C@H]1C=Cc2c(cn(C)c2C(=O)Nc2ccncc2)S(=N)(=O)N1] | Peak1 (HPLC) |
| 30d2 | 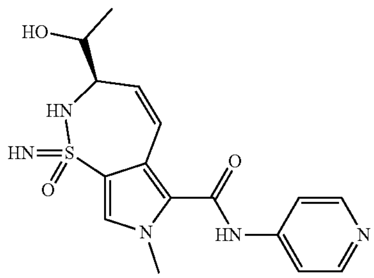 [SMILES: CC(O)[C@H]1C=Cc2c(cn(C)c2C(=O)Nc2ccncc2)S(=N)(=O)N1] | Peak2 (HPLC) |
| 30e1 | 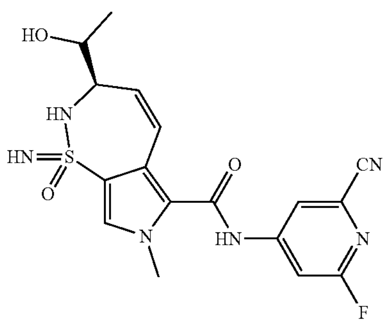 [SMILES: CC(O)[C@H]1C=Cc2c(cn(C)c2C(=O)Nc2cc(F)nc(C#N)c2)S(=N)(=O)N1] | Peak1 (HPLC) |
| 30e2 | 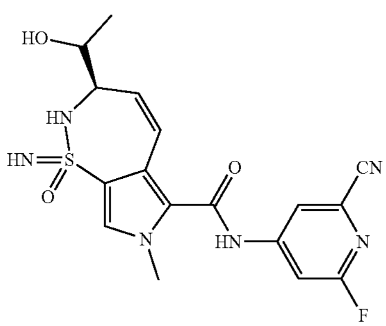 [SMILES: CC(O)[C@H]1C=Cc2c(cn(C)c2C(=O)Nc2cc(F)nc(C#N)c2)S(=N)(=O)N1] | Peak2 (HPLC) |
| 30f1 | 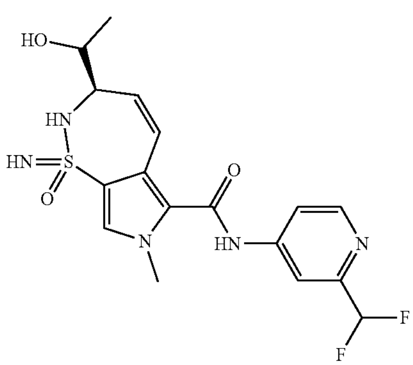 [SMILES: CC(O)[C@H]1C=Cc2c(cn(C)c2C(=O)Nc2ccnc(C(F)F)c2)S(=N)(=O)N1] | Peak1 (HPLC) |

-continued

| No. | Structure | Remark |
|---|---|---|
| 30f2 | 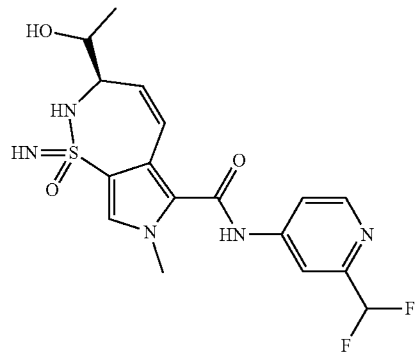 [SMILES: CC(O)[C@H]1C=Cc2c(cn(C)c2C(=O)Nc2ccnc(C(F)F)c2)S(=N)(=O)N1] | Peak2 (HPLC) |
| 30g1 | 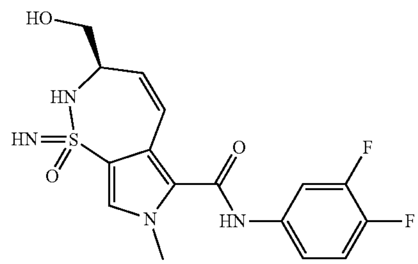 [SMILES: Cn1cc2c(c1C(=O)Nc1ccc(F)c(F)c1)C=C[C@H](CO)NS2(=N)=O] | Peak1 (HPLC) |
| 30g2 | 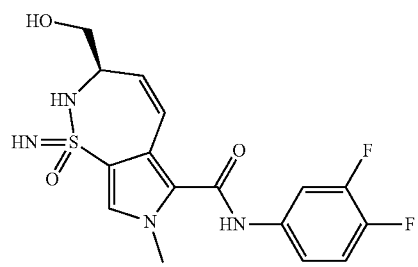 [SMILES: Cn1cc2c(c1C(=O)Nc1ccc(F)c(F)c1)C=C[C@H](CO)NS2(=N)=O] | Peak2 (HPLC) |
| 30h1 | 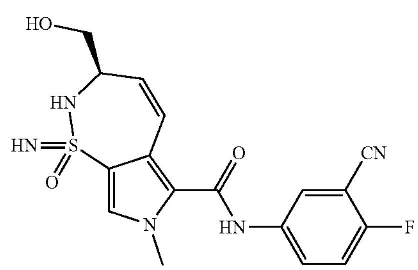 [SMILES: Cn1cc2c(c1C(=O)Nc1ccc(F)c(C#N)c1)C=C[C@H](CO)NS2(=N)=O] | Peak1 (HPLC) |
| 30h2 | 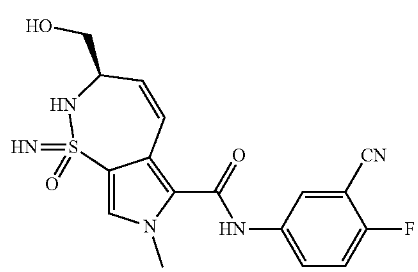 [SMILES: Cn1cc2c(c1C(=O)Nc1ccc(F)c(C#N)c1)C=C[C@H](CO)NS2(=N)=O] | Peak2 (HPLC) |

-continued

| No. | Structure | Remark |
|---|---|---|
| 30i1 | 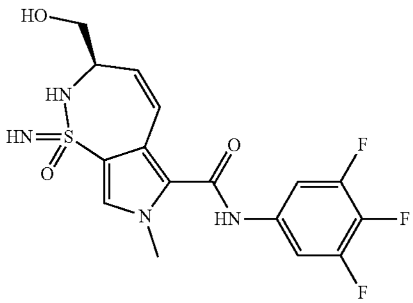 [SMILES: Cn1cc2c(c1C(=O)Nc1cc(F)c(F)c(F)c1)C=C[C@H](CO)NS2(=N)=O] | Peak1 (HPLC) |
| 30i2 | 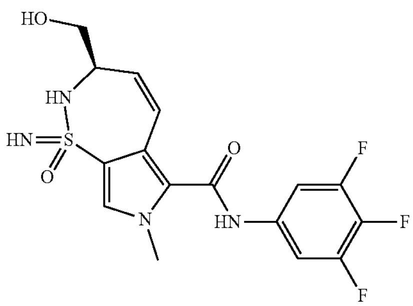 [SMILES: Cn1cc2c(c1C(=O)Nc1cc(F)c(F)c(F)c1)C=C[C@H](CO)NS2(=N)=O] | Peak2 (HPLC) |
| 30j1 | 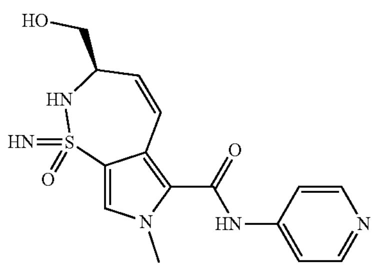 [SMILES: Cn1cc2c(c1C(=O)Nc1ccncc1)C=C[C@H](CO)NS2(=N)=O] | Peak1 (HPLC) |
| 30j2 | 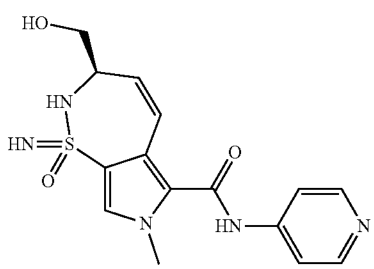 [SMILES: Cn1cc2c(c1C(=O)Nc1ccncc1)C=C[C@H](CO)NS2(=N)=O] | Peak2 (HPLC) |
| 30k1 | 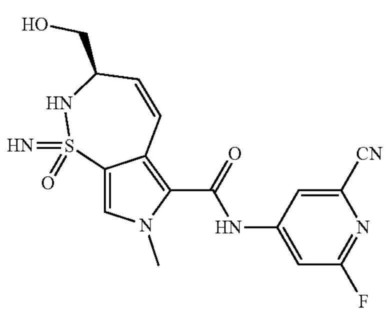 [SMILES: Cn1cc2c(c1C(=O)Nc1cc(F)nc(C#N)c1)C=C[C@H](CO)NS2(=N)=O] | Peak1 (HPLC) |

| No. | Structure | Remark |
|---|---|---|
| 30k2 | 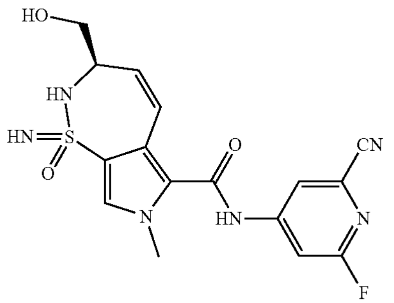 [SMILES: Cn1cc2c(c1C(=O)Nc1cc(F)nc(C#N)c1)C=C[C@H](CO)NS2(=N)=O] | Peak2 (HPLC) |
| 30m1 | 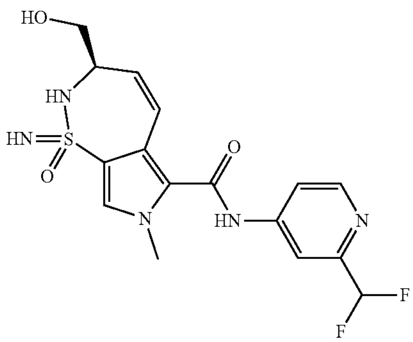 [SMILES: Cn1cc2c(c1C(=O)Nc1ccnc(C(F)F)c1)C=C[C@H](CO)NS2(=N)=O] | Peak1 (HPLC) |
| 30m2 | 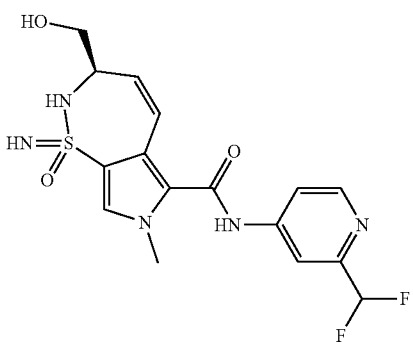 [SMILES: Cn1cc2c(c1C(=O)Nc1ccnc(C(F)F)c1)C=C[C@H](CO)NS2(=N)=O] | Peak2 (HPLC) |
| 40a1 | 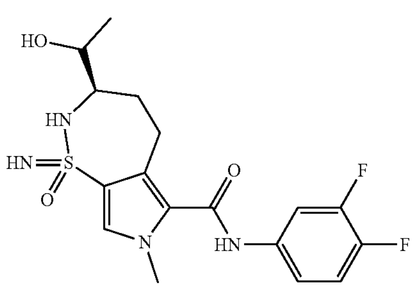 | Peak1 (HPLC) |
| 40a2 | 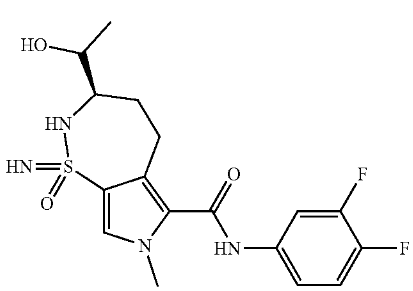 | Peak2 (HPLC) |

| No. | Structure | Remark |
|---|---|---|
| 40b1 | 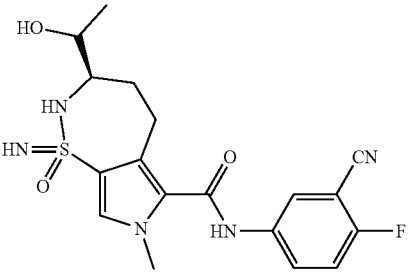 | Peak1 (HPLC) |
| 40b2 | 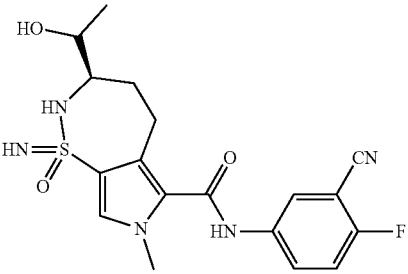 | Peak2 (HPLC) |
| 40c1 | 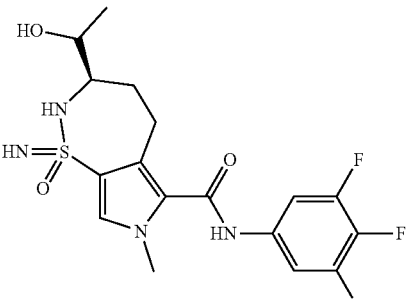 | Peak1 (HPLC) |
| 40c2 | 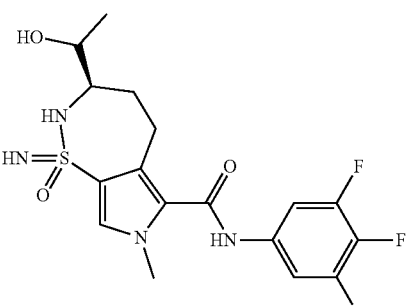 | Peak2 (HPLC) |
| 40d1 | 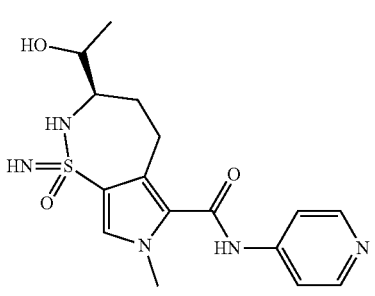 | Peak1 (HPLC) |

| No. | Structure | Remark |
|---|---|---|
| 40d2 | 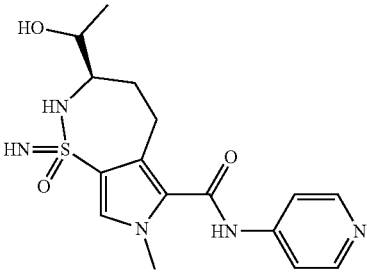 | Peak2 (HPLC) |
| 40e1 | 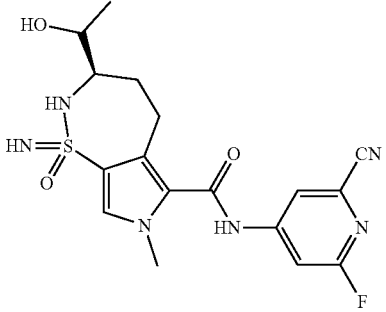 [SMILES: CC(O)[C@H]1CCc2c(cn(C)c2C(=O)Nc2cc(F)nc(C#N)c2)S(=N)(=O)N1] | Peak1 (HPLC) |
| 40e2 | 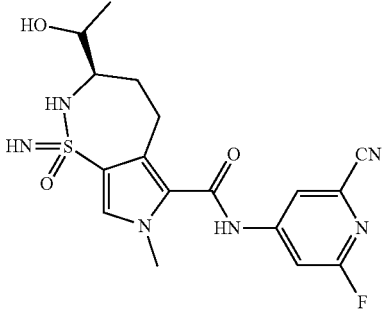 [SMILES: CC(O)[C@H]1CCc2c(cn(C)c2C(=O)Nc2cc(F)nc(C#N)c2)S(=N)(=O)N1] | Peak2 (HPLC) |
| 40f1 | 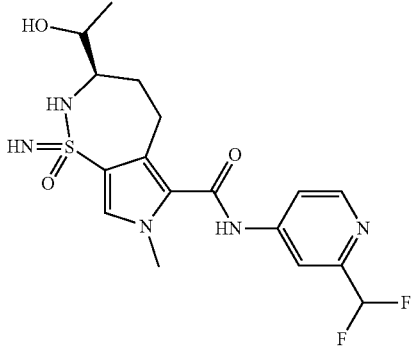 | Peak1 (HPLC) |

| No. | Structure | Remark |
|---|---|---|
| 40f2 | 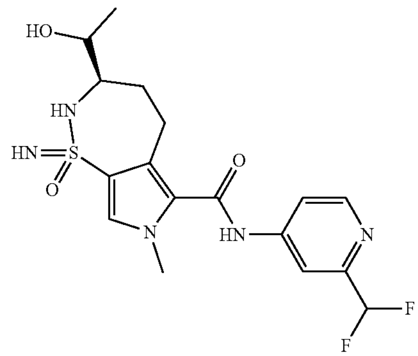 | Peak2 (HPLC) |
| 40g1 | 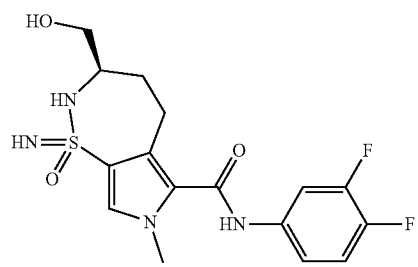 [SMILES: Cn1cc2c(c1C(=O)Nc1ccc(F)c(F)c1)CC[C@H](CO)NS2(=N)=O] | Peak1 (HPLC) |
| 40g2 | 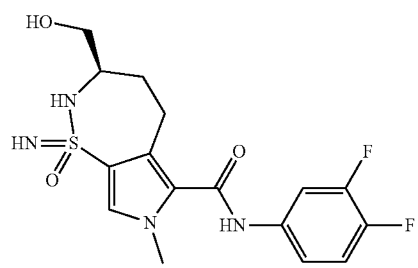 [SMILES: Cn1cc2c(c1C(=O)Nc1ccc(F)c(F)c1)CC[C@H](CO)NS2(=N)=O] | Peak2 (HPLC) |
| 40h1 | 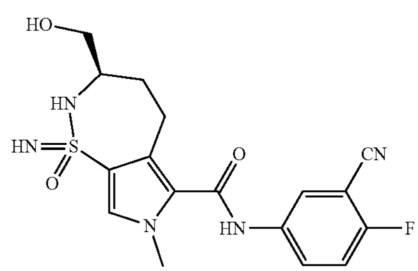 [SMILES: Cn1cc2c(c1C(=O)Nc1ccc(F)c(C#N)c1)CC[C@H](CO)NS2(=N)=O] | Peak1 (HPLC) |
| 40h2 | 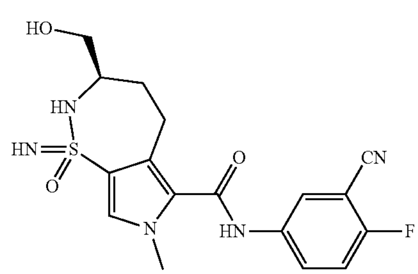 [SMILES: Cn1cc2c(c1C(=O)Nc1ccc(F)c(C#N)c1)CC[C@H](CO)NS2(=N)=O] | Peak2 (HPLC) |

-continued

| No. | Structure | Remark |
|---|---|---|
| 40i1 | 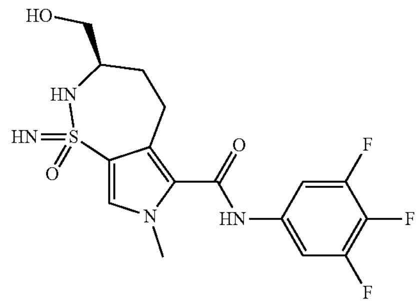 [SMILES: Cn1cc2c(c1C(=O)Nc1cc(F)c(F)c(F)c1)CC[C@H](CO)NS2(=N)=O] | Peak1 (HPLC) |
| 40i2 | 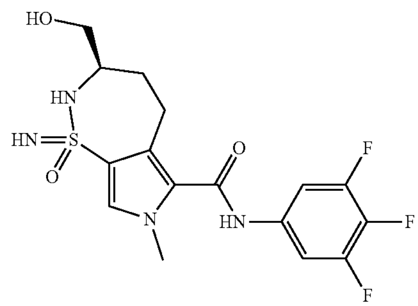 [SMILES: Cn1cc2c(c1C(=O)Nc1cc(F)c(F)c(F)c1)CC[C@H](CO)NS2(=N)=O] | Peak2 (HPLC) |
| 40j1 | 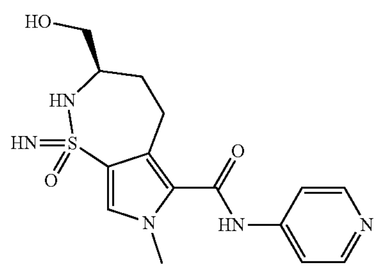 | Peak1 (HPLC) |
| 40j2 | 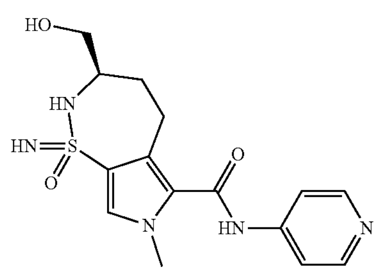 | Peak2 (HPLC) |
| 40k1 | 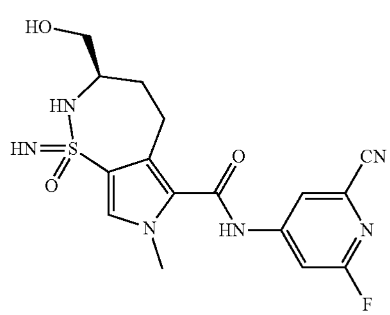 | Peak1 (HPLC) |

-continued

| No. | Structure | Remark |
|---|---|---|
| 40k2 | 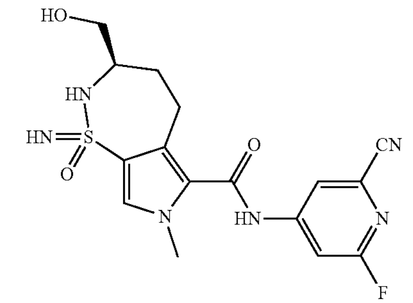 [SMILES: Cn1cc2c(c1C(=O)Nc1cc(F)nc(C#N)c1)CC[C@H](CO)NS2(=N)=O] | Peak2 (HPLC) |
| 40m1 | 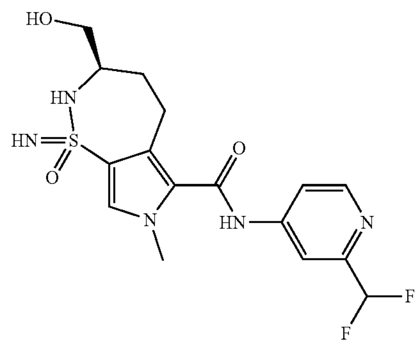 [SMILES: Cn1cc2c(c1C(=O)Nc1ccnc(C(F)F)c1)CC[C@H](CO)NS2(=N)=O] | Peak1 (HPLC) |
| 40m2 | 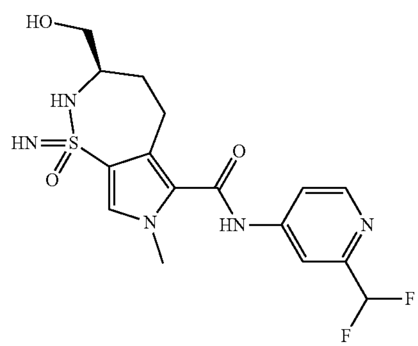 [SMILES: Cn1cc2c(c1C(=O)Nc1ccnc(C(F)F)c1)CC[C@H](CO)NS2(=N)=O] | Peak2 (HPLC) |
| 50a1 | 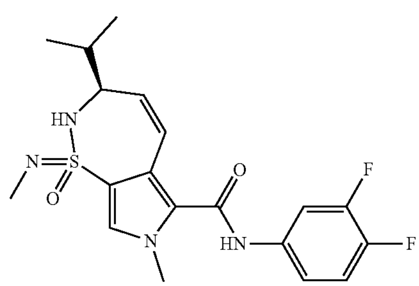 [SMILES: CN=S1(=O)N[C@@H](C(C)C)C=Cc2c1cn(C)c2C(=O)Nc1ccc(F)c(F)c1] | Peak1 (HPLC) |
| 50a2 | 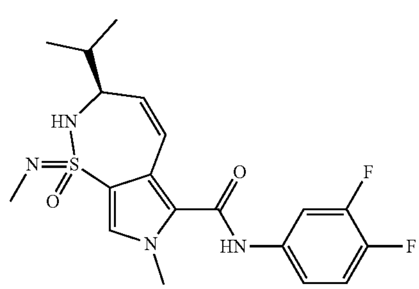 | Peak2 (HPLC) |

-continued
| No. | Structure | Remark |
|---|---|---|
| 50b1 | 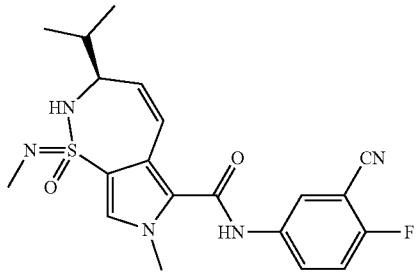 [SMILES: CN=S1(=O)N[C@@H](C(C)C)C=Cc2c1cn(C)c2C(=O)Nc1ccc(F)c(C#N)c1] | Peak1 (HPLC) |
| 50b2 | 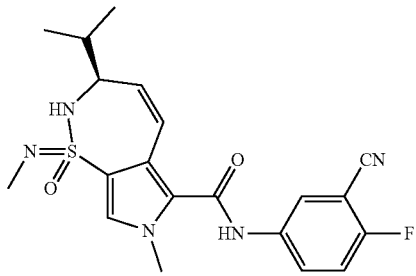 [SMILES: CN=S1(=O)N[C@@H](C(C)C)C=Cc2c1cn(C)c2C(=O)Nc1ccc(F)c(C#N)c1] | Peak2 (HPLC) |
| 50c1 | 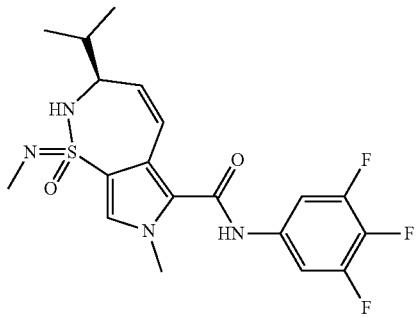 [SMILES: CN=S1(=O)N[C@@H](C(C)C)C=Cc2c1cn(C)c2C(=O)Nc1cc(F)c(F)c(F)c1] | Peak1 (HPLC) |
| 50c2 | 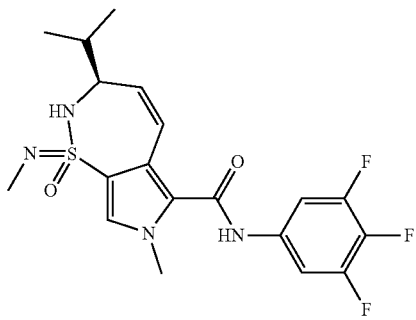 [SMILES: CN=S1(=O)N[C@@H](C(C)C)C=Cc2c1cn(C)c2C(=O)Nc1cc(F)c(F)c(F)c1] | Peak2 (HPLC) |
| 50d1 | 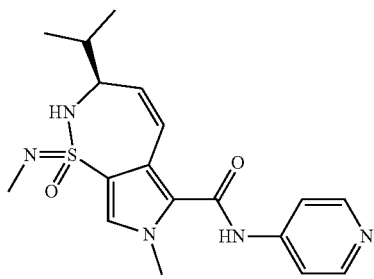 [SMILES: CN=S1(=O)N[C@@H](C(C)C)C=Cc2c1cn(C)c2C(=O)Nc1ccncc1] | Peak1 (HPLC) |

-continued
| No. | Structure | Remark |
|---|---|---|
| 50d2 | 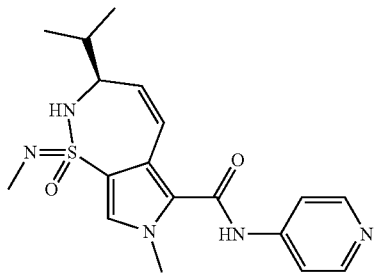 | Peak2 (HPLC) |
| 50e1 | 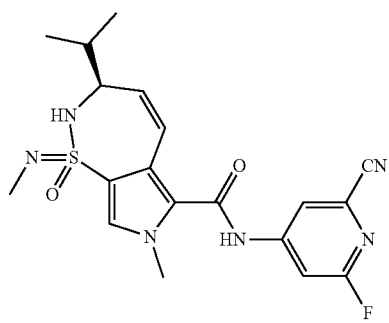 [SMILES: CN=S1(=O)N[C@@H](C(C)C)C=Cc2c1cn(C)c2C(=O)Nc1cc(F)nc(C#N)c1] | Peak1 (HPLC) |
| 50e2 | 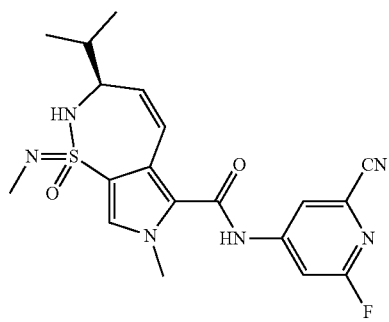 [SMILES: CN=S1(=O)N[C@@H](C(C)C)C=Cc2c1cn(C)c2C(=O)Nc1cc(F)nc(C#N)c1] | Peak2 (HPLC) |
| 50f1 | 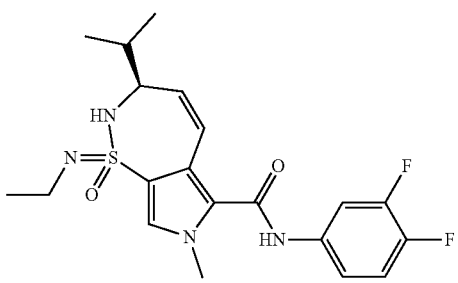 [SMILES: CCN=S1(=O)N[C@@H](C(C)C)C=Cc2c1cn(C)c2C(=O)Nc1ccc(F)c(F)c1] | Peak1 (HPLC) |
| 50f2 | 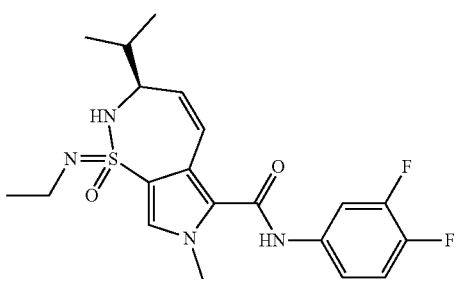 [SMILES: CCN=S1(=O)N[C@@H](C(C)C)C=Cc2c1cn(C)c2C(=O)Nc1ccc(F)c(F)c1] | Peak2 (HPLC) |

-continued
| No. | Structure | Remark |
|---|---|---|
| 50g1 | 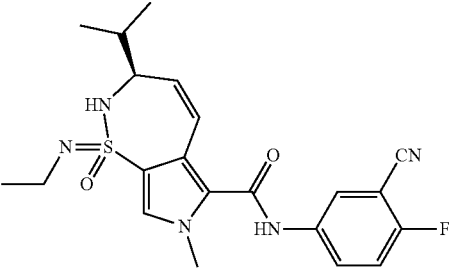 [SMILES: CCN=S1(=O)N[C@@H](C(C)C)C=Cc2c1cn(C)c2C(=O)Nc1ccc(F)c(C#N)c1] | Peak1 (HPLC) |
| 50g2 | 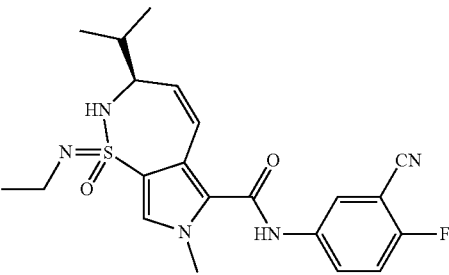 [SMILES: CCN=S1(=O)N[C@@H](C(C)C)C=Cc2c1cn(C)c2C(=O)Nc1ccc(F)c(C#N)c1] | Peak2 (HPLC) |
| 50h1 | 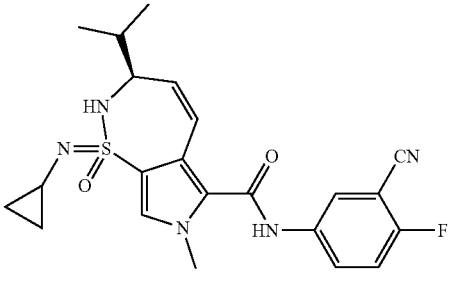 [SMILES: CC(C)[C@H]1C=Cc2c(cn(C)c2C(=O)Nc2ccc(F)c(C#N)c2)S(=O)(=NC2CC2)N1] | Peak1 (HPLC) |
| 50h2 | 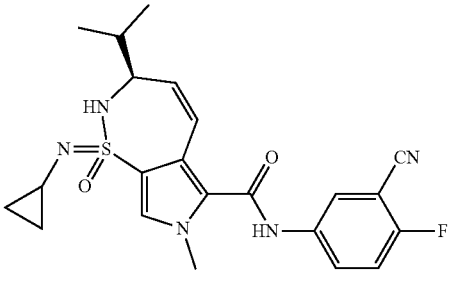 [SMILES: CC(C)[C@H]1C=Cc2c(cn(C)c2C(=O)Nc2ccc(F)c(C#N)c2)S(=O)(=NC2CC2)N1] | Peak2 (HPLC) |
| 50i1 | 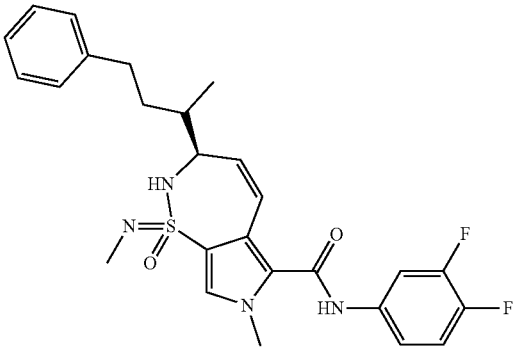 [SMILES: CN=S1(=O)N[C@@H](C(C)CCc2ccccc2)C=Cc2c1cn(C)c2C(=O)Nc1ccc(F)c(F)c1] | Peak1 (HPLC) |

-continued
| No. | Structure | Remark |
|---|---|---|
| 50i2 | 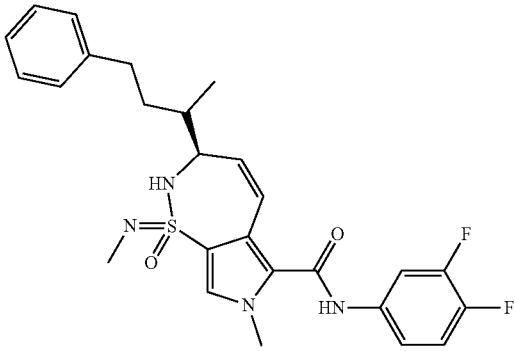 [SMILES: CN=S1(=O)N[C@@H](C(C)CCc2ccccc2)C=Cc2c1cn(C)c2C(=O)Nc1ccc(F)c(F)c1] | Peak2 (HPLC) |
| 50j1 | 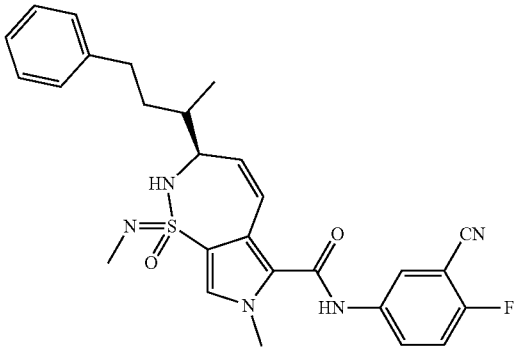 [SMILES: CN=S1(=O)N[C@@H](C(C)CCc2ccccc2)C=Cc2c1cn(C)c2C(=O)Nc1ccc(F)c(C#N)c1] | Peak1 (HPLC) |
| 50j2 | 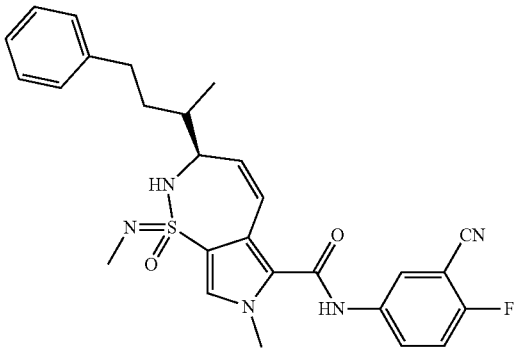 [SMILES: CN=S1(=O)N[C@@H](C(C)CCc2ccccc2)C=Cc2c1cn(C)c2C(=O)Nc1ccc(F)c(C#N)c1] | Peak2 (HPLC) |
| 50k1 | 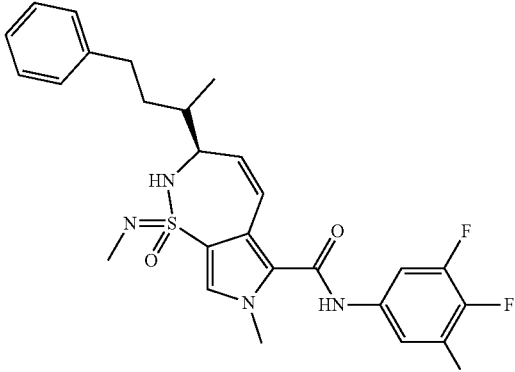 | Peak1 (HPLC) |

| No. | Structure | Remark |
|---|---|---|
| 50k2 | 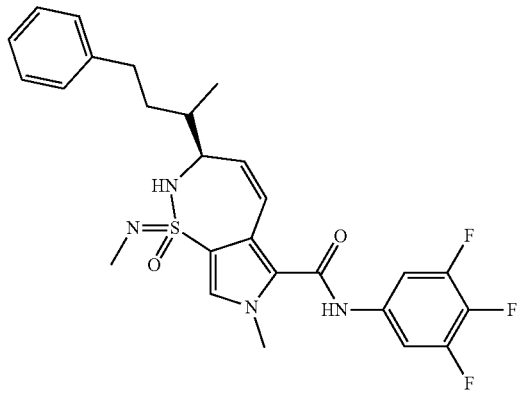 [SMILES: CN=S1(=O)N[C@@H](C(C)CCc2ccccc2)C=Cc2c1cn(C)c2C(=O)Nc1cc(F)c(F)c(F)c1] | Peak2 (HPLC) |
| 50m1 | 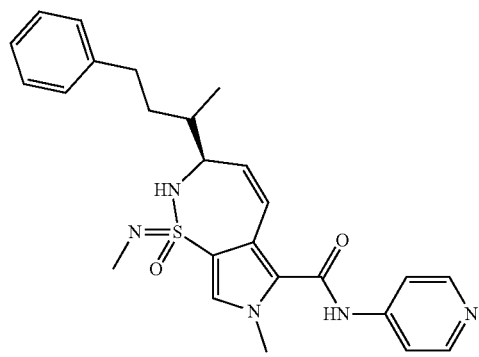 [SMILES: CN=S1(=O)N[C@@H](C(C)CCc2ccccc2)C=Cc2c1cn(C)c2C(=O)Nc1ccncc1] | Peak1 (HPLC) |
| 50m2 | 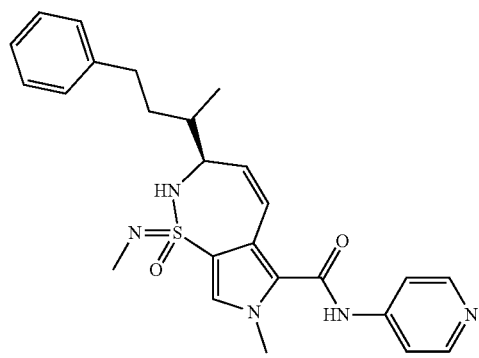 [SMILES: CN=S1(=O)N[C@@H](C(C)CCc2ccccc2)C=Cc2c1cn(C)c2C(=O)Nc1ccncc1] | Peak2 (HPLC) |
| 50n1 | 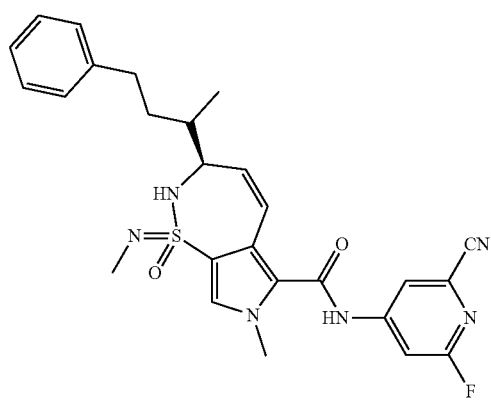 [SMILES: CN=S1(=O)N[C@@H](C(C)CCc2ccccc2)C=Cc2c1cn(C)c2C(=O)Nc1cc(F)nc(C#N)c1] | Peak1 (HPLC) |

-continued

| No. | Structure | Remark |
|---|---|---|
| 50n2 | 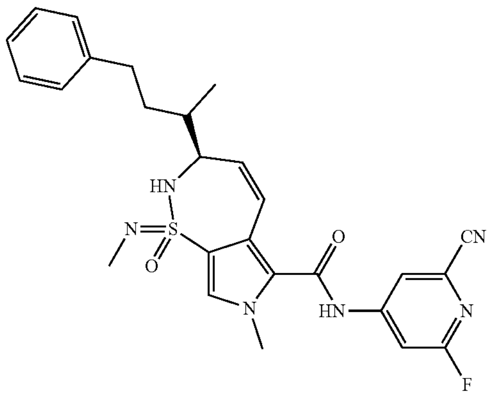 [SMILES: CN=S1(=O)N[C@@H](C(C)CCc2ccccc2)C=Cc2c1cn(C)c2C(=O)Nc1cc(F)nc(C#N)c1] | Peak2 (HPLC) |
| 50o1 | 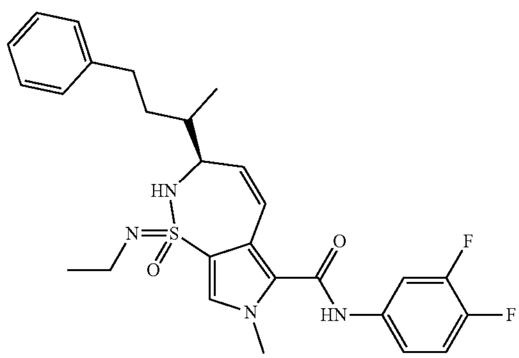 [SMILES: CCN=S1(=O)N[C@@H](C(C)CCc2ccccc2)C=Cc2c1cn(C)c2C(=O)Nc1ccc(F)c(F)c1] | Peak1 (HPLC) |
| 50o2 | 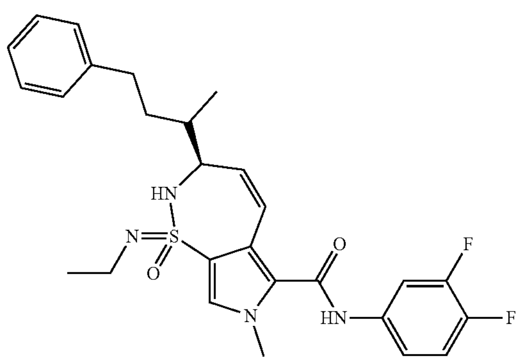 [SMILES: CCN=S1(=O)N[C@@H](C(C)CCc2ccccc2)C=Cc2c1cn(C)c2C(=O)Nc1ccc(F)c(F)c1] | Peak2 (HPLC) |
| 50p1 | 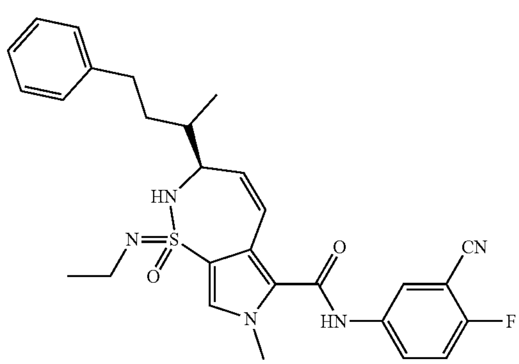 | Peak1 (HPLC) |

| No. | Structure | Remark |
|---|---|---|
| 50p2 | 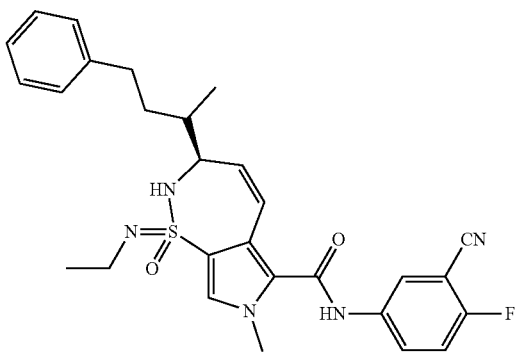 [SMILES: CCN=S1(=O)N[C@@H](C(C)CCc2ccccc2)C=Cc2c1cn(C)c2C(=O)Nc1ccc(F)c(C#N)c1] | Peak2 (HPLC) |
| 50q1 | 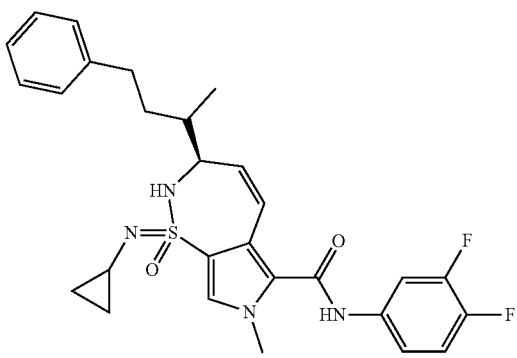 [SMILES: CC(CCc1ccccc1)[C@H]1C=Cc2c(cn(C)c2C(=O)Nc2ccc(F)c(F)c2)S(=O)(=NC2CC2)N1] | Peak1 (HPLC) |
| 50q2 | 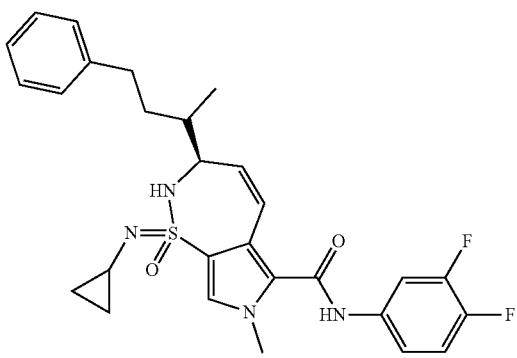 [SMILES: CC(CCc1ccccc1)[C@H]1C=Cc2c(cn(C)c2C(=O)Nc2ccc(F)c(F)c2)S(=O)(=NC2CC2)N1] | Peak2 (HPLC) |
| 50r1 | 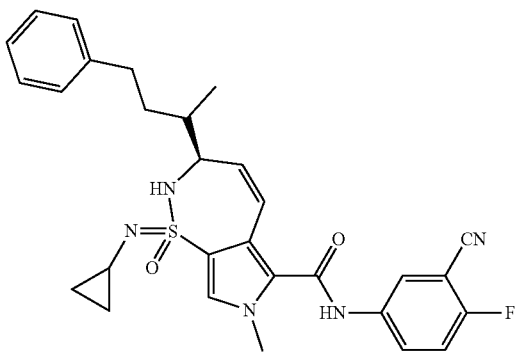 | Peak1 (HPLC) |

| No. | Structure | Remark |
|---|---|---|
| 50r2 | 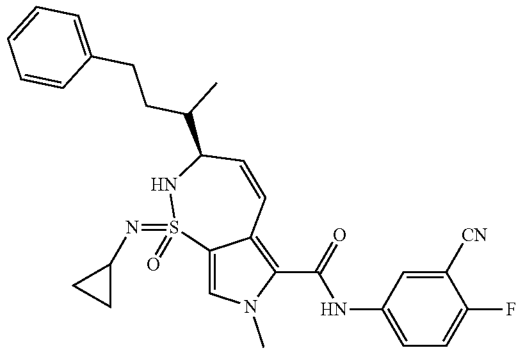 | Peak2 (HPLC) |
| 50s1 | 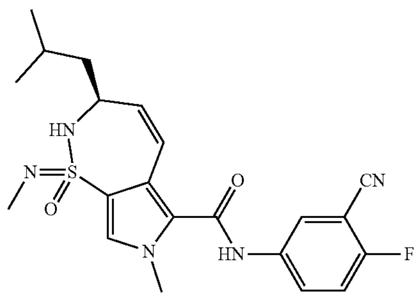 [SMILES: CN=S1(=O)N[C@@H](CC(C)C)C=Cc2c1cn(C)c2C(=O)Nc1ccc(F)c(C#N)c1] | Peak1 (HPLC) |
| 50s2 | 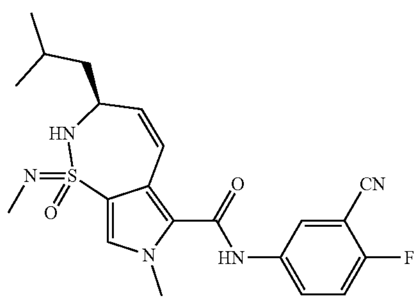 [SMILES: CN=S1(=O)N[C@@H](CC(C)C)C=Cc2c1cn(C)c2C(=O)Nc1ccc(F)c(C#N)c1] | Peak2 (HPLC) |
| 50t1 | 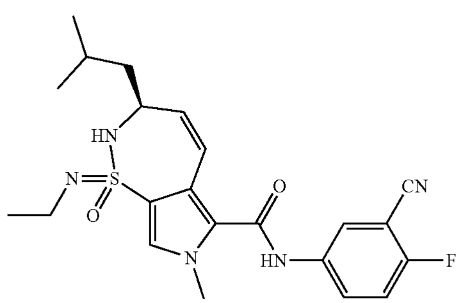 [SMILES: CCN=S1(=O)N[C@@H](CC(C)C)C=Cc2c1cn(C)c2C(=O)Nc1ccc(F)c(C#N)c1] | Peak1 (HPLC) |
| 50t2 | 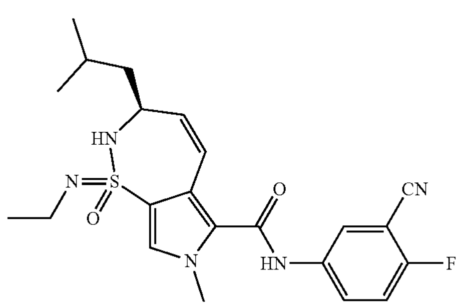 [SMILES: CCN=S1(=O)N[C@@H](CC(C)C)C=Cc2c1cn(C)c2C(=O)Nc1ccc(F)c(C#N)c1] | Peak2 (HPLC) |

| No. | Structure | Remark |
|---|---|---|
| 50u1 | 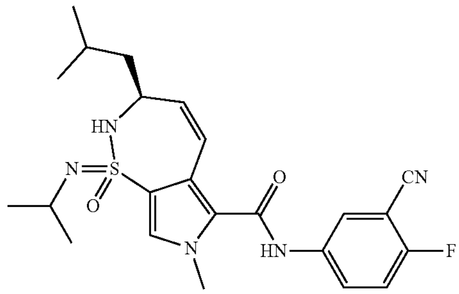 [SMILES: CC(C)C[C@H]1C=Cc2c(cn(C)c2C(=O)Nc2ccc(F)c(C#N)c2)S(=O)(=NC(C)C)N1] | Peak1 (HPLC) |
| 50u2 | 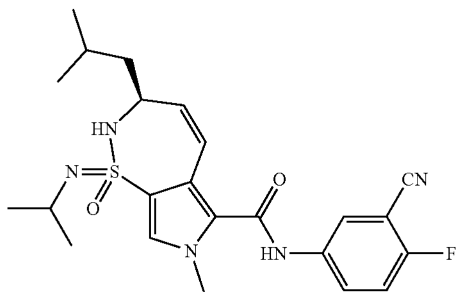 [SMILES: CC(C)C[C@H]1C=Cc2c(cn(C)c2C(=O)Nc2ccc(F)c(C#N)c2)S(=O)(=NC(C)C)N1] | Peak2 (HPLC) |
| 50v1 | 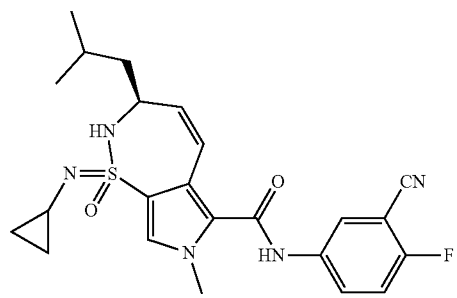 [SMILES: CC(C)C[C@H]1C=Cc2c(cn(C)c2C(=O)Nc2ccc(F)c(C#N)c2)S(=O)(=NC2CC2)N1] | Peak1 (HPLC) |
| 50v2 | 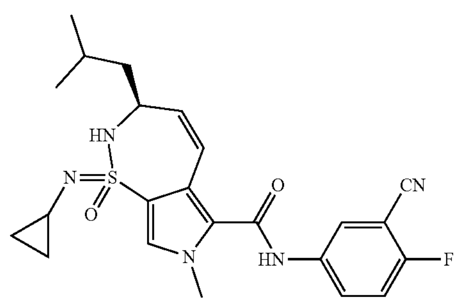 [SMILES: CC(C)C[C@H]1C=Cc2c(cn(C)c2C(=O)Nc2ccc(F)c(C#N)c2)S(=O)(=NC2CC2)N1] | Peak2 (HPLC) |
| 50w1 | 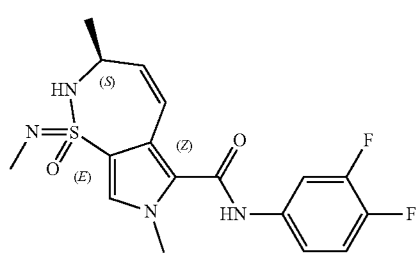 | Peak1 (HPLC) |

| No. | Structure | Remark |
|---|---|---|
| 50w2 | 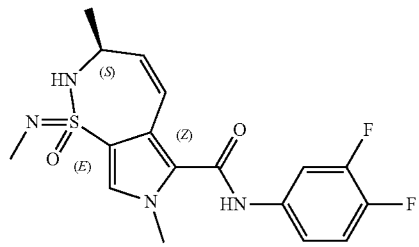 | Peak2 (HPLC) |
| 50x1 | 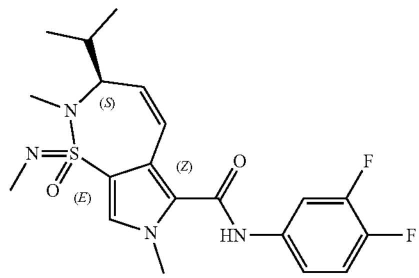 | Peak1 (HPLC) |
| 50x2 | 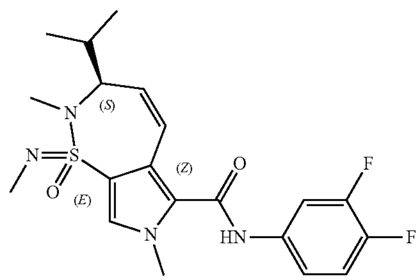 | Peak2 (HPLC) |
| 60a1 | 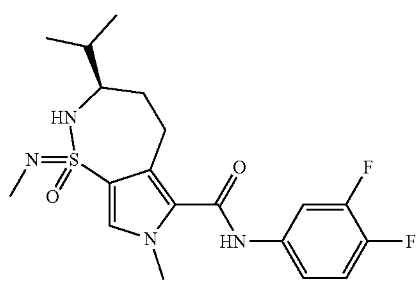 [SMILES: CN=S1(=O)N[C@@H](C(C)C)CCc2c1cn(C)c2C(=O)Nc1ccc(F)c(F)c1] | Peak1 (HPLC) |
| 60a2 | 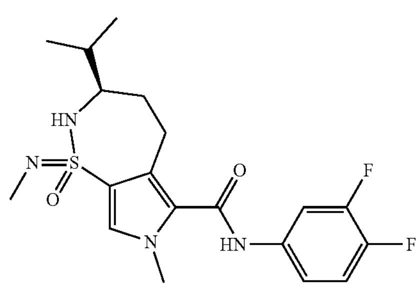 [SMILES: CN=S1(=O)N[C@@H](C(C)C)CCc2c1cn(C)c2C(=O)Nc1ccc(F)c(F)c1] | Peak2 (HPLC) |

-continued

| No. | Structure | Remark |
|---|---|---|
| 60b1 | 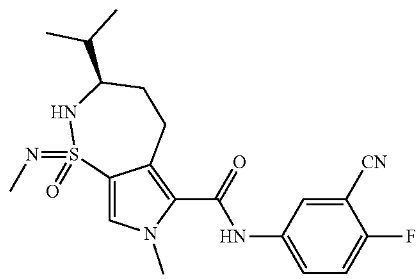 [SMILES: CN=S1(=O)N[C@@H](C(C)C)CCc2c1cn(C)c2C(=O)Nc1ccc(F)c(C#N)c1] | Peak1 (HPLC) |
| 60b2 | 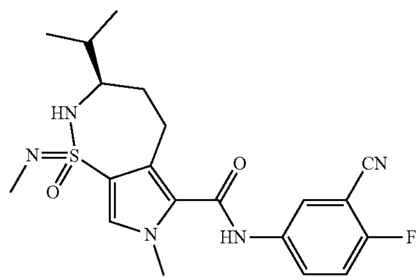 [SMILES: CN=S1(=O)N[C@@H](C(C)C)CCc2c1cn(C)c2C(=O)Nc1ccc(F)c(C#N)c1] | Peak2 (HPLC) |
| 60c1 | 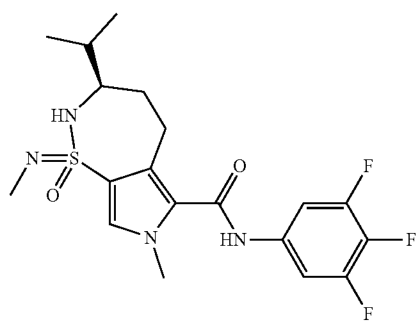 [SMILES: CN=S1(=O)N[C@@H](C(C)C)CCc2c1cn(C)c2C(=O)Nc1cc(F)c(F)c(F)c1] | Peak1 (HPLC) |
| 60c2 | 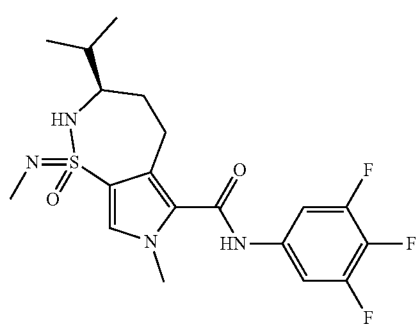 [SMILES: CN=S1(=O)N[C@@H](C(C)C)CCc2c1cn(C)c2C(=O)Nc1cc(F)c(F)c(F)c1] | Peak2 (HPLC) |
| 60d1 | 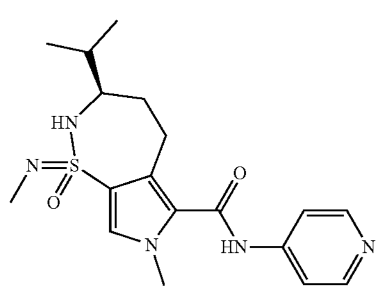 [SMILES: CN=S1(=O)N[C@@H](C(C)C)CCc2c1cn(C)c2C(=O)Nc1ccncc1] | Peak1 (HPLC) |

| No. | Structure | Remark |
|---|---|---|
| 60d2 | 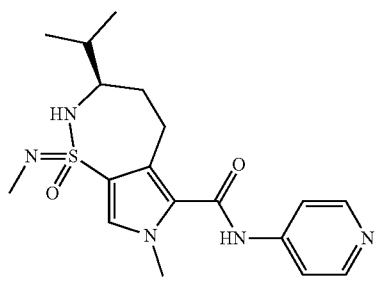 [SMILES: CN=S1(=O)N[C@@H](C(C)C)CCc2c1cn(C)c2C(=O)Nc1ccncc1] | Peak2 (HPLC) |
| 60e1 | 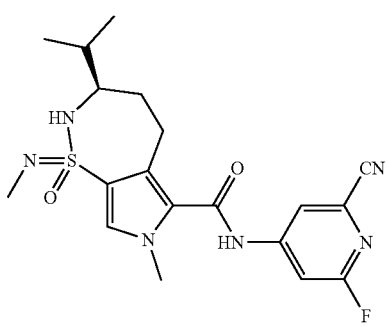 [SMILES: CN=S1(=O)N[C@@H](C(C)C)CCc2c1cn(C)c2C(=O)Nc1cc(F)nc(C#N)c1] | Peak1 (HPLC) |
| 60e2 | 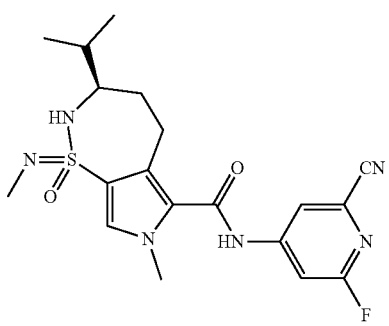 [SMILES: CN=S1(=O)N[C@@H](C(C)C)CCc2c1cn(C)c2C(=O)Nc1cc(F)nc(C#N)c1] | Peak2 (HPLC) |
| 60f1 | 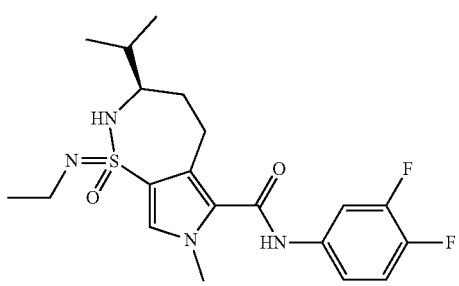 | Peak1 (HPLC) |
| 60f2 | 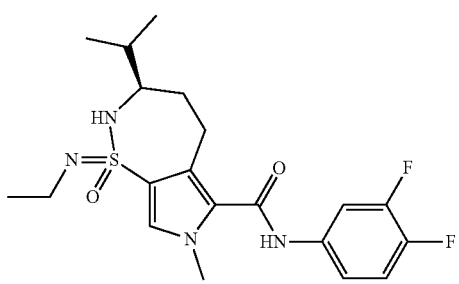 | Peak2 (HPLC) |

-continued
| No. | Structure | Remark |
|---|---|---|
| 60g1 | 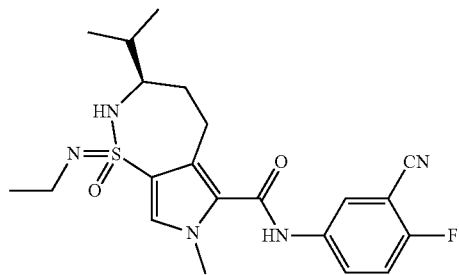 | Peak1 (HPLC) |
| 60g2 | 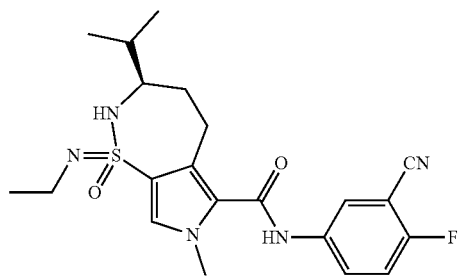 [SMILES: CCN=S1(=O)N[C@@H](C(C)C)CCc2c1cn(C)c2C(=O)Nc1ccc(F)c(C#N)c1] | Peak2 (HPLC) |
| 60h1 | 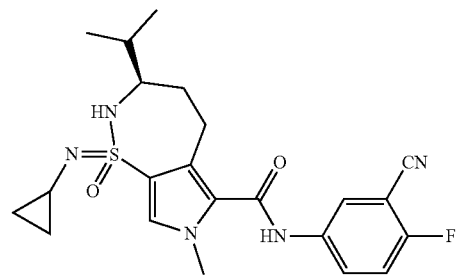 | Peak1 (HPLC) |
| 60h2 | 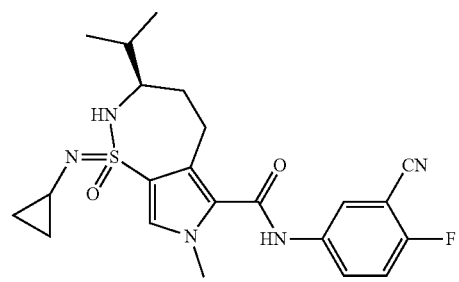 [SMILES: CC(C)[C@H]1CCc2c(cn(C)c2C(=O)Nc2ccc(F)c(C#N)c2)S(=O)(=NC2CC2)N1] | Peak2 (HPLC) |
| 60i1 | 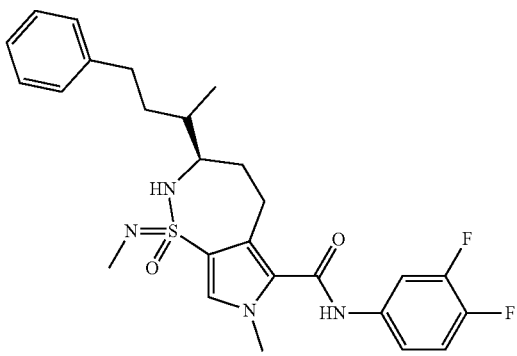 | Peak1 (HPLC) |

-continued
| No. | Structure | Remark |
|---|---|---|
| 60i2 | 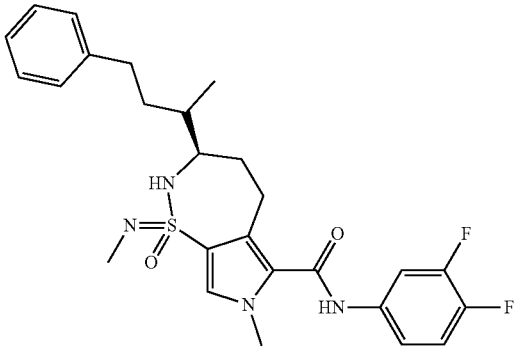 | Peak2 (HPLC) |
| 60j1 | 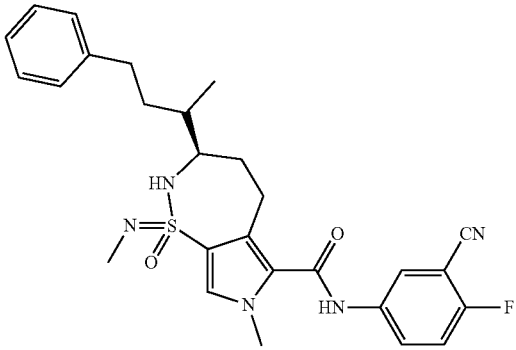 | Peak1 (HPLC) |
| 60j2 | 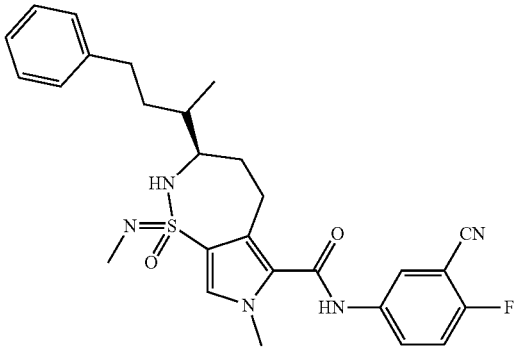 | Peak2 (HPLC) |
| 60k1 | 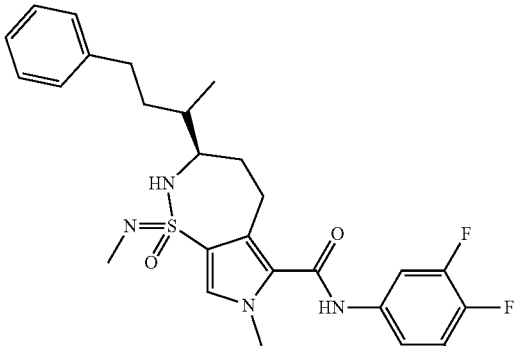 | Peak1 (HPLC) |

-continued
| No. | Structure | Remark |
|---|---|---|
| 60k2 | 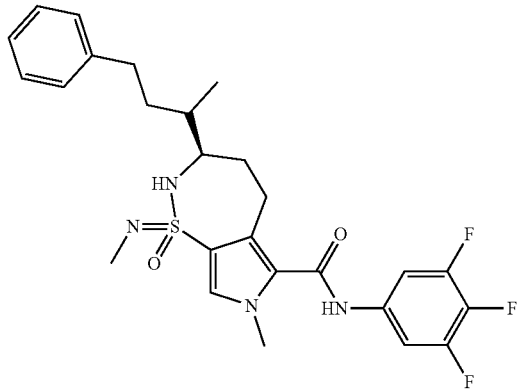 [SMILES: CN=S1(=O)N[C@@H](C(C)CCc2ccccc2)CCc2c1cn(C)c2C(=O)Nc1cc(F)c(F)c(F)c1] | Peak2 (HPLC) |
| 60m1 | 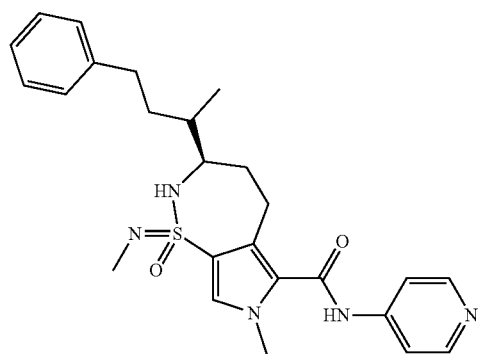 [SMILES: CN=S1(=O)N[C@@H](C(C)CCc2ccccc2)CCc2c1cn(C)c2C(=O)Nc1ccncc1] | Peak1 (HPLC) |
| 60m2 | 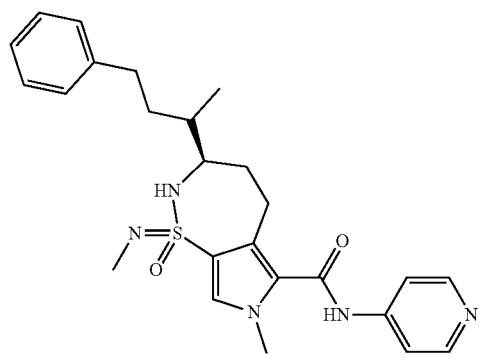 [SMILES: CN=S1(=O)N[C@@H](C(C)CCc2ccccc2)CCc2c1cn(C)c2C(=O)Nc1ccncc1] | Peak2 (HPLC) |
| 60n1 | 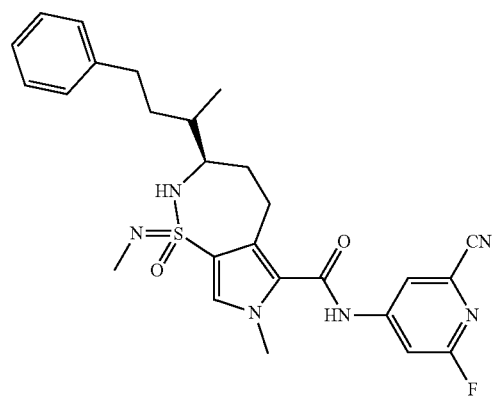 [SMILES: CN=S1(=O)N[C@@H](C(C)CCc2ccccc2)CCc2c1cn(C)c2C(=O)Nc1cc(F)nc(C#N)c1] | Peak1 (HPLC) |

| No. | Structure | Remark |
|---|---|---|
| 60n2 | 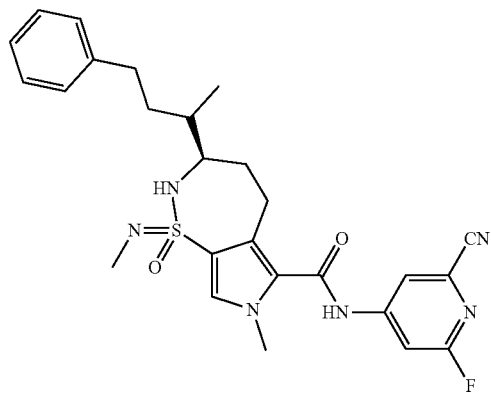 [SMILES: CN=S1(=O)N[C@@H](C(C)CCc2ccccc2)CCc2c1cn(C)c2C(=O)Nc1cc(F)nc(C#N)c1] | Peak2 (HPLC) |
| 60o1 | 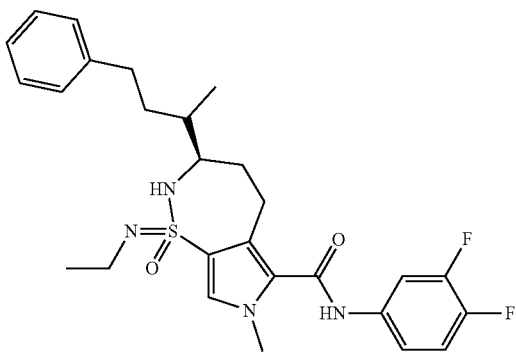 [SMILES: CCN=S1(=O)N[C@@H](C(C)CCc2ccccc2)CCc2c1cn(C)c2C(=O)Nc1ccc(F)c(F)c1] | Peak1 (HPLC) |
| 60o2 | 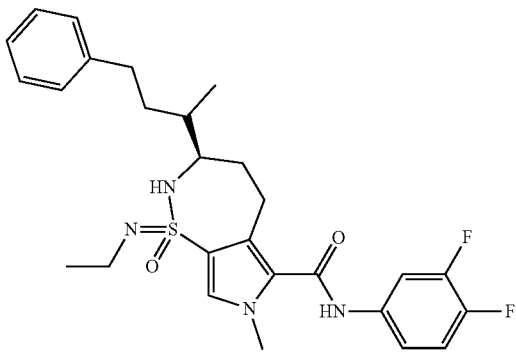 [SMILES: CCN=S1(=O)N[C@@H](C(C)CCc2ccccc2)CCc2c1cn(C)c2C(=O)Nc1ccc(F)c(F)c1] | Peak2 (HPLC) |
| 60p1 | 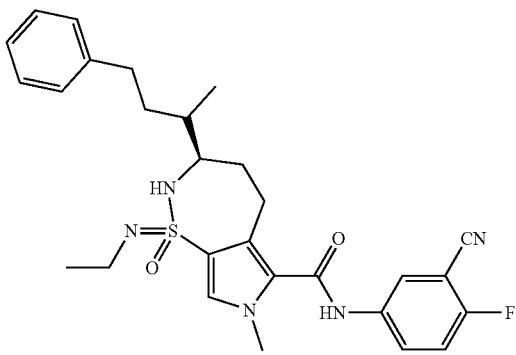 [SMILES: CCN=S1(=O)N[C@@H](C(C)CCc2ccccc2)CCc2c1cn(C)c2C(=O)Nc1ccc(F)c(C#N)c1] | Peak1 (HPLC) |

| No. | Structure | Remark |
|---|---|---|
| 60p2 | 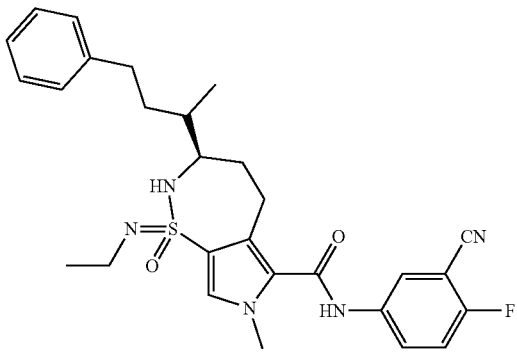 [SMILES: CCN=S1(=O)N[C@@H](C(C)CCc2ccccc2)CCc2c1cn(C)c2C(=O)Nc1ccc(F)c(C#N)c1] | Peak2 (HPLC) |
| 60q1 | 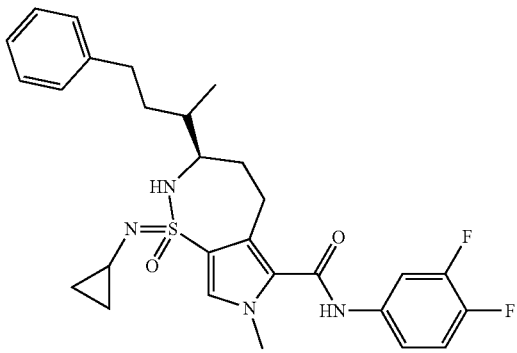 [SMILES: CC(CCc1ccccc1)[C@H]1CCc2c(cn(C)c2C(=O)Nc2ccc(F)c(F)c2)S(=O)(=NC2CC2)N1] | Peak1 (HPLC) |
| 60q2 | 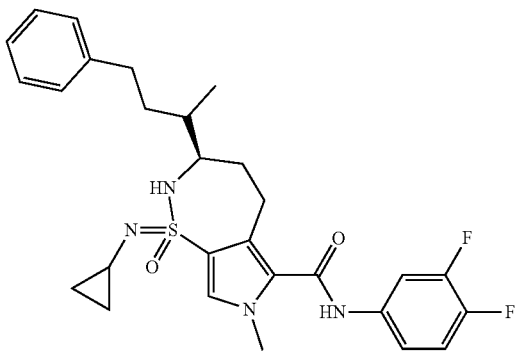 [SMILES: CC(CCc1ccccc1)[C@H]1CCc2c(cn(C)c2C(=O)Nc2ccc(F)c(F)c2)S(=O)(=NC2CC2)N1] | Peak2 (HPLC) |
| 60r1 | 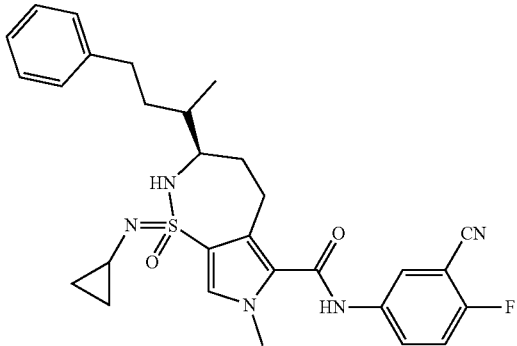 [SMILES: CC(CCc1ccccc1)[C@H]1CCc2c(cn(C)c2C(=O)Nc2ccc(F)c(C#N)c2)S(=O)(=NC2CC2)N1] | Peak1 (HPLC) |

-continued
| No. | Structure | Remark |
|---|---|---|
| 60r2 | 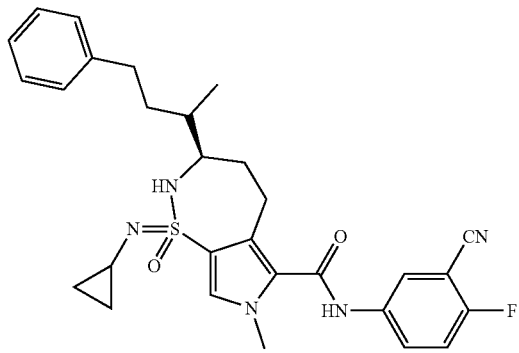 [SMILES: CC(CCc1ccccc1)[C@H]1CCc2c(cn(C)c2C(=O)Nc2ccc(F)c(C#N)c2)S(=O)(=NC2CC2)N1] | Peak2 (HPLC) |
| 60s1 | 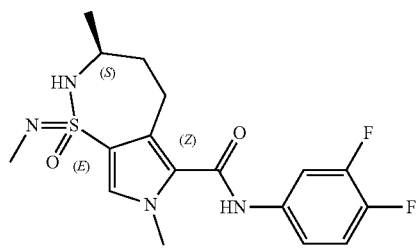 | Peak1 (HPLC) |
| 60s2 | 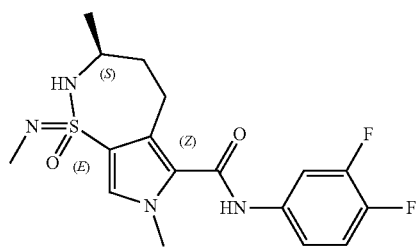 | Peak2 (HPLC) |
| 60t1 | 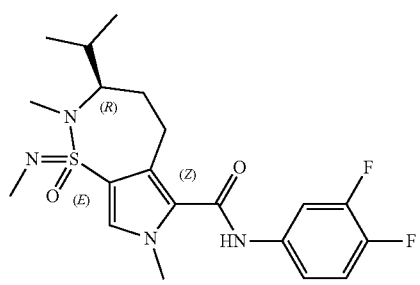 | Peak1 (HPLC) |
| 60t2 | 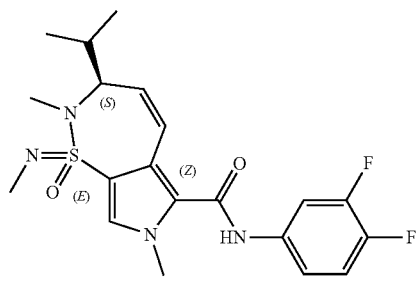 | Peak2 (HPLC) |

| No. | Structure | Remark |
|---|---|---|
| 60u1 | 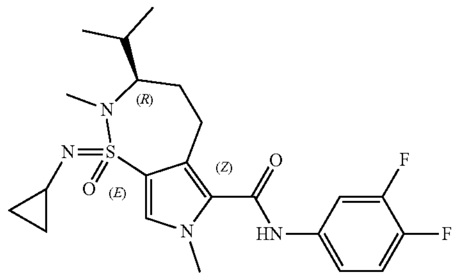 | Peak1 (HPLC) |
| 60u2 | 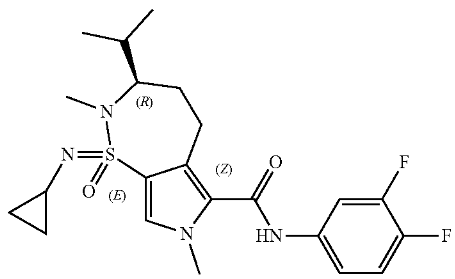 | Peak2 (HPLC) |
| 60v1 | 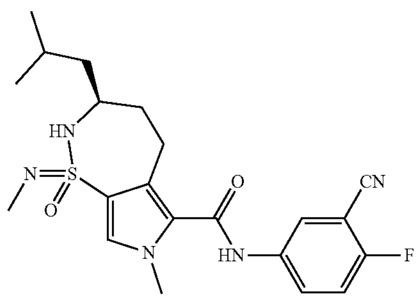 [SMILES: CN=S1(=O)N[C@@H](CC(C)C)CCc2c1cn(C)c2C(=O)Nc1ccc(F)c(C#N)c1] | Peak1 (HPLC) |
| 60v2 | 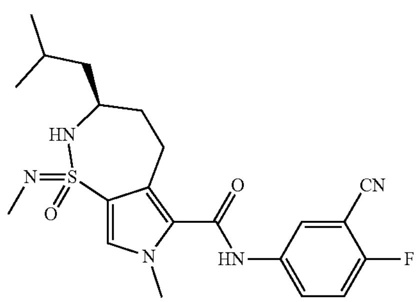 [SMILES: CN=S1(=O)N[C@@H](CC(C)C)CCc2c1cn(C)c2C(=O)Nc1ccc(F)c(C#N)c1] | Peak2 (HPLC) |
| 60w1 | 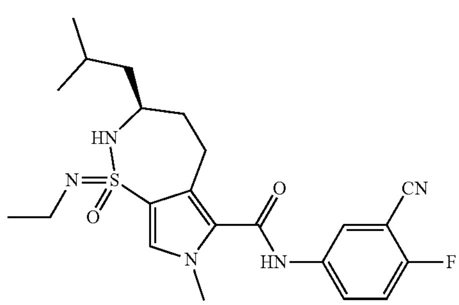 [SMILES: CCN=S1(=O)N[C@@H](CC(C)C)CCc2c1cn(C)c2C(=O)Nc1ccc(F)c(C#N)c1] | Peak1 (HPLC) |

-continued

| No. | Structure | Remark |
|---|---|---|
| 60w2 | 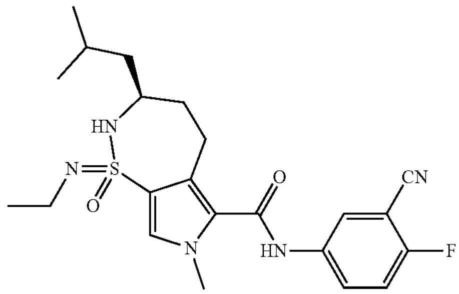 [SMILES: CCN=S1(=O)N[C@@H](CC(C)C)CCc2c1cn(C)c2C(=O)Nc1ccc(F)c(C#N)c1] | Peak2 (HPLC) |
| 60x1 | 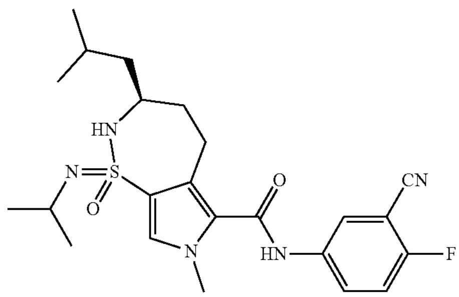 [SMILES: CC(C)C[C@H]1CCc2c(cn(C)c2C(=O)Nc2ccc(F)c(C#N)c2)S(=O)(=NC(C)C)N1] | Peak1 (HPLC) |
| 60x2 | 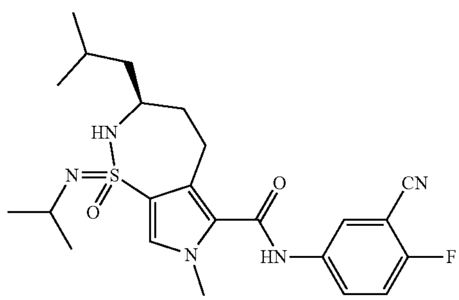 [SMILES: CC(C)C[C@H]1CCc2c(cn(C)c2C(=O)Nc2ccc(F)c(C#N)c2)S(=O)(=NC(C)C)N1] | Peak2 (HPLC) |
| 60y1 | 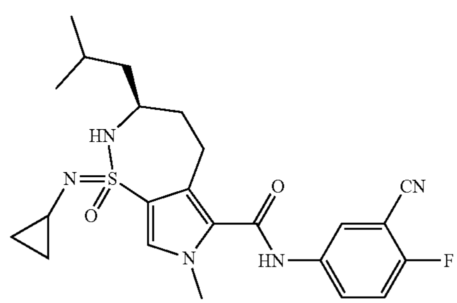 [SMILES: CC(C)C[C@H]1CCc2c(cn(C)c2C(=O)Nc2ccc(F)c(C#N)c2)S(=O)(=NC2CC2)N1] | Peak1 (HPLC) |
| 60y2 | 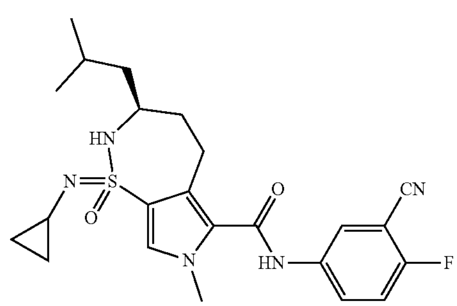 [SMILES: CC(C)C[C@H]1CCc2c(cn(C)c2C(=O)Nc2ccc(F)c(C#N)c2)S(=O)(=NC2CC2)N1] | Peak2 (HPLC) |

-continued

| No. | Structure | Remark |
|---|---|---|
| 70a1 | 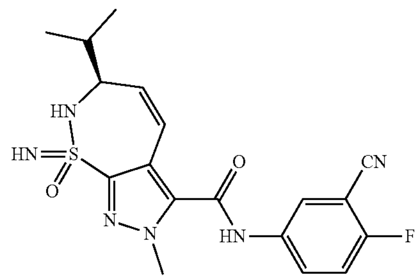 [SMILES: CC(C)[C@H]1C=Cc2c(nn(C)c2C(=O)Nc2ccc(F)c(C#N)c2)S(=N)(=O)N1] | Peak1 (HPLC) |
| 70a2 | 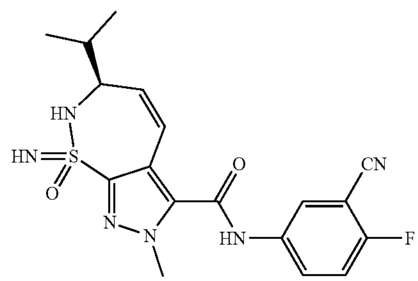 | Peak2 (HPLC) |
| 70b1 | 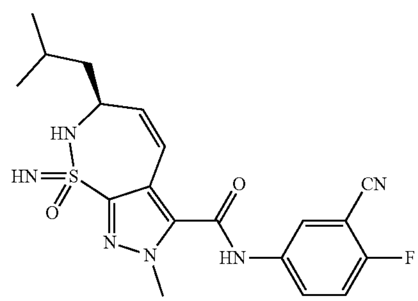 | Peak1 (HPLC) |
| 70b2 | 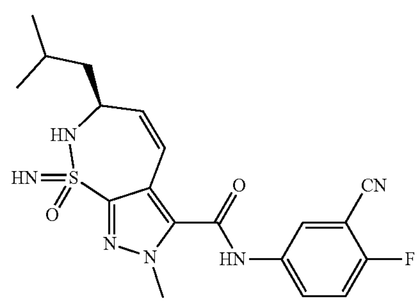 | Peak2 (HPLC) |
| 80a1 | 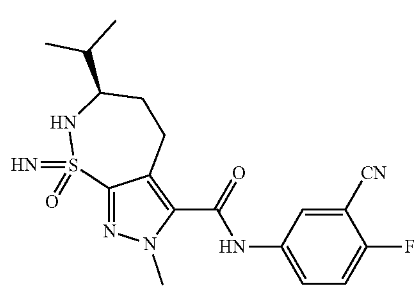 | Peak1 (HPLC) |

-continued

| No. | Structure | Remark |
|---|---|---|
| 80a2 | 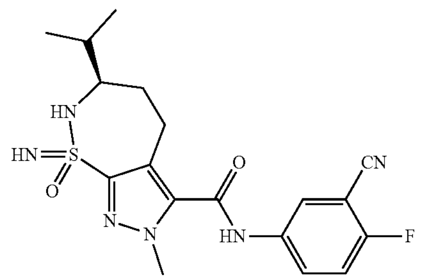 [SMILES: CC(C)[C@H]1CCc2c(nn(C)c2C(=O)Nc2ccc(F)c(C#N)c2)S(=N)(=O)N1] | Peak2 (HPLC) |
| 80b1 | 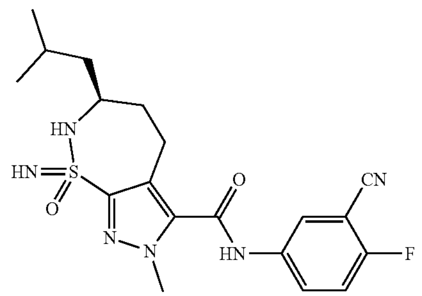 [SMILES: CC(C)C[C@H]1CCc2c(nn(C)c2C(=O)Nc2ccc(F)c(C#N)c2)S(=N)(=O)N1] | Peak1 (HPLC) |
| 80b2 | 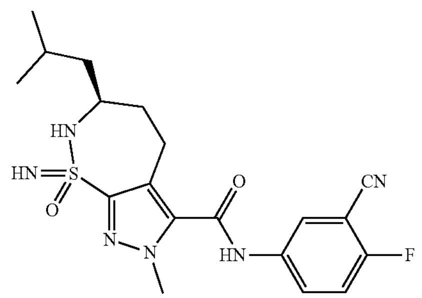 [SMILES: CC(C)C[C@H]1CCc2c(nn(C)c2C(=O)Nc2ccc(F)c(C#N)c2)S(=N)(=O)N1] | Peak2 (HPLC) |
| 90a1 | 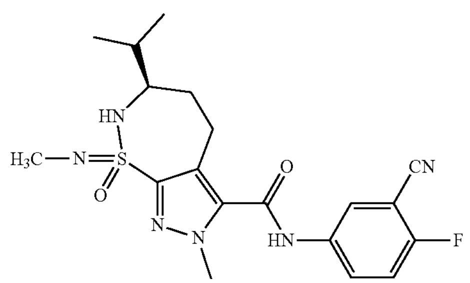 [SMILES: CN=S1(=O)N[C@@H](C(C)C)CCc2c1nn(C)c2C(=O)Nc1ccc(F)c(C#N)c1] | Peak1 (HPLC) |
| 90a2 | 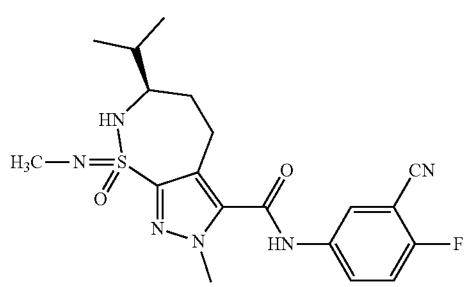 [SMILES: CN=S1(=O)N[C@@H](C(C)C)CCc2c1nn(C)c2C(=O)Nc1ccc(F)c(C#N)c1] | Peak2 (HPLC) |

| No. | Structure | Remark |
|---|---|---|
| 90b1 | 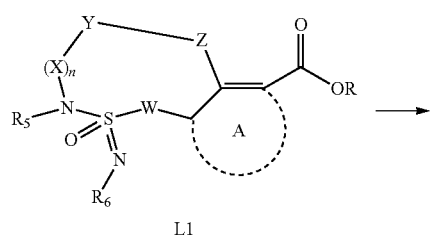 | Peak1 (HPLC) |
| 90b2 | | Peak2 (HPLC) | wherein Peak 1 and Peak 2 refer to the order of the enantiomers' peaks in reversed-phase HPLC, wherein Peak 1 is the first peak in the enantiomer, and Peak 2 is the latter peak of the enantiomer.

9. A method for preparation of compound of claim 1, or a stereoisomer or tautomer thereof, or a pharmaceutically acceptable salt, hydrate or solvate thereof, wherein the formula L compound is a compound represented by formula VII-1, and the method comprises the following steps:

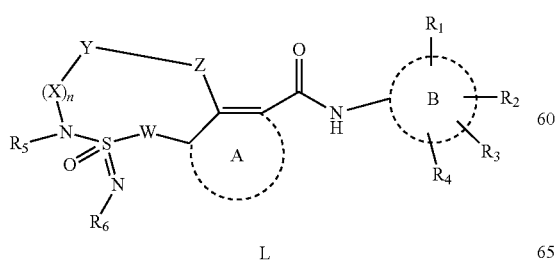

in an inert solvent, reacting formula L1 compound with

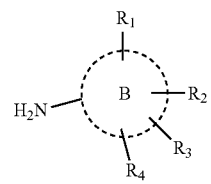

to provide compound L;

wherein R is a leaving group, and the definitions of the remaining groups are as described in claim 1.

10. A compound selected from the group consisting of:

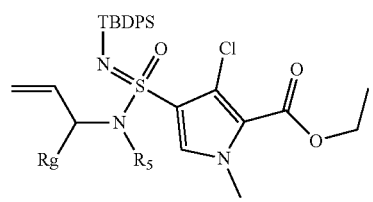

IV-1

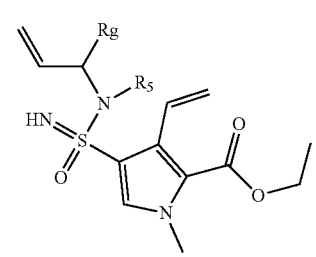

V-1

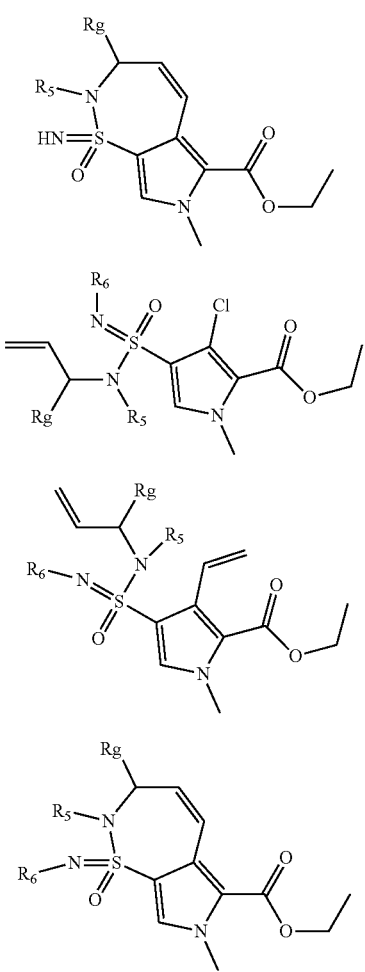

in each formula, Rg is selected from the group consisting of H, halogen, —CN, hydroxyl, amino, carboxyl, —(C=O)-substituted or unsubstituted $C_1$-$C_8$ alkyl, substituted or unsubstituted $C_1$-$C_8$ alkyl, substituted or unsubstituted $C_2$-$C_6$ alkenyl, substituted or unsubstituted $C_2$-$C_6$ alkynyl, substituted or unsubstituted $C_1$-$C_8$ alkylamino, substituted or unsubstituted $C_1$-$C_8$ alkoxy, substituted or unsubstituted $C_3$-$C_{10}$ cycloalkyl, substituted or unsubstituted 3-10 membered heterocycloalkyl having 1-3 heteroatoms selected from the group consisting of N, S and O, substituted or unsubstituted $C_6$-$C_{10}$ aryl, and substituted or unsubstituted 5-10 membered heteroaryl having 1-3 heteroatoms selected from the group consisting of N, S and O;

the definition of each group is as described in claim 1.

11. A pharmaceutical composition, wherein comprises (1) the compound, or the stereoisomer thereof, tautomer thereof, or a pharmaceutically acceptable salt, hydrate or solvate of claim 1 and (2) pharmaceutically acceptable carriers.

12. A method for treating hepatitis B virus infection comprising administering the compound, or a stereoisomer or tautomer thereof, or a pharmaceutically acceptable salt, hydrate or solvate thereof of claim 1 to a subject in need thereof.

13. A hepatitis B virus inhibitor which comprises a compound, or a stereoisomer or a tautomer thereof, or a pharmaceutically acceptable salt, hydrate or solvate thereof of claim 1.

14. A method for in vitro inhibiting hepatitis B virus, which comprises the step: contacting the compound, or a stereoisomer or tautomer thereof, or a pharmaceutically acceptable salt, hydrate or solvate thereof of claim 1 with hepatitis B virus so as to inhibit the replication of hepatitis B virus.

15. The compound of claim 1, wherein

is a substituted or unsubstituted five or six membered ring, wherein the five or six membered ring optionally contains one or more heteroatoms selected from the group consisting of O, S, N or P; the substituted means that the hydrogen atoms on the group are substituted by one or more substituents of methyl.

16. The compound of claim 1, wherein $R_1$, $R_2$, $R_3$, and $R_4$ are each independently selected from the group consisting of H, halogen, cyano, difluoromethyl, difluoroethyl, monofluoromethyl, trifluoromethyl, and trifluoromethoxy.

17. A method for treating hepatitis B virus infection comprising administering the pharmaceutical composition of claim 11 to a subject in need thereof.

* * * * *